(12) United States Patent
Betschmann et al.

(10) Patent No.: US 7,202,363 B2
(45) Date of Patent: Apr. 10, 2007

(54) THIENOPYRIDINE AND FUROPYRIDINE KINASE INHIBITORS

(75) Inventors: Patrick Betschmann, Shrewsbury, MA (US); Andrew F. Burchat, Shrewsbury, MA (US); David J. Calderwood, Framingham, MA (US); Michael L. Curtin, Pleasant Prairie, WI (US); Steven K. Davidsen, Libertyville, IL (US); Heather M. Davis, Oxford, MA (US); Robin R. Frey, Libertyville, IL (US); Howard R. Heyman, Deerfield, IL (US); Gavin C. Hirst, Princeton, MA (US); Peter Hrnciar, Hamden, CT (US); Michael R. Michaelides, Libertyville, IL (US); Melanie A. Muckey, Trevor, WI (US); Kelly D. Mullen, Charlton, MA (US); Paul Rafferty, Westborough, MA (US); Carol K. Wada, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/899,168

(22) Filed: Jul. 26, 2004

(65) Prior Publication Data

US 2005/0043347 A1 Feb. 24, 2005

Related U.S. Application Data

(60) Provisional application No. 60/567,703, filed on May 3, 2004, provisional application No. 60/489,734, filed on Jul. 24, 2003.

(51) Int. Cl.
*C07D 491/04* (2006.01)
*C07D 421/04* (2006.01)
(52) U.S. Cl. ..................... 546/114; 514/299
(58) Field of Classification Search ............ 546/114; 514/299
See application file for complete search history.

(56) References Cited

U.S. PATENT DOCUMENTS

| 3,470,183 | A | 9/1969 | Roth et al. | |
|---|---|---|---|---|
| 2001/0044538 | A1 | 11/2001 | Cheng et al. | 544/238 |
| 2002/0004511 | A1 | 1/2002 | Luzzio et al. | |
| 2002/0013354 | A1 | 1/2002 | Cheng et al. | 514/374 |
| 2002/0151544 | A1 | 10/2002 | Hayakawa et al. | 514/224.2 |

FOREIGN PATENT DOCUMENTS

| EP | 0 438 261 | 7/1991 |
|---|---|---|
| WO | 97/13771 | 4/1997 |
| WO | 00/39108 | 6/2000 |
| WO | 01/19828 | 3/2001 |
| WO | 03/22852 | 3/2003 |
| WO | 2004100947 | * 11/2004 |

OTHER PUBLICATIONS

Abdelraek et al., "Synthesis of novel thieno[2,3-d]pyrimidine, thieno[2,3-b]pyridine and thiazolo[3,2-a]pyrimidine derivates and their effect on the production of mycotoxins", Arch. Pharm. (Weinheim) 325:301-305 (1992).

Abdelrazek et al., "Heterocyclic synthesis with nitriles: a new approach to thiophene and tieno-[2,3-d]-pyrimidine derivates", Journal f. prakt. Chemie. Band 330(4):585-589 (1988).

Abdelrazek et al., "Heterocyclic synthesis with nitriles: a novel synthesis of some thiophene and thieno[2,3-d]pyrimidine derivates, II [1]", Z. Naturforsch, B.: Chemical Sci. 44(4):488-492 (1989).

Abdelrazek et al., "Heterocyclic synthesis with nitriles: synthesis of some new thiophene and thieno[2,3-d]pyrimidine derivates IV", Phosphorus, Sulfur, and Silicon 1:271-277 (1996).

Abdelrazek et al., "Heterocyclic Synthesis with Nitriles: synthesis of some novel thiophene and thieno[2,3-d]pyrimidine derivates", Phosphorus. Sulfur, and Silicon 71:93-97 (1992).

Dave et al., "Gold-Jacob type of reaction in the synthesis of thieno[3,2-e]pyrimido{1,2-c]pyrimidines: a comparison of classical heating vs solvent-free microwave irradiation", Heterocycles 51(8):1819-1826 (1999).

Kandeel et al., "Nitriles in heterocyclic synthesis: a novel synthesis of some thieno[2,3-d]pyrimidine and thieno[2,3-b]pyridine derivates", Heteroatom Chemistry 7(1):29-33 (1996).

Nelson et al., "Dicyclic and Tricyclic Diaminopyrimidine derivates as potent inhibitors of cryptosporidium parvum dihydrofolate reductase: structure-activity and structure-selectivity correlations", Antimicrobial Agents and Chemotherapy 45(12):3293-3303 (2001).

Rosowsky et al., "2,4-diaminothieno[2,3-d]pyrimidines as antifolates and antimalarials. 3. Synthesis of 5,6-disubstituted deriviates and related tetracyclic analogs", Journal of Medicinal Chemistry 16(3):191-194 (1973).

(Continued)

*Primary Examiner*—Rita Desai
(74) *Attorney, Agent, or Firm*—B. Gregory Donner

(57) ABSTRACT

Compounds having the formula

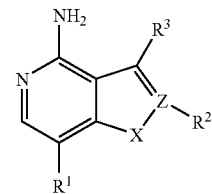

are useful for inhibiting protein tyrosine kinases. The present invention also discloses methods of making the compounds, compositions containing the compounds, and methods of treatment using the compounds.

9 Claims, No Drawings

OTHER PUBLICATIONS

Roth et al., "2,4-diaminopyrimidines. The cyclization of 6-phenacylthio and related derivates to thieno[2,3-d]pyrimidines and thiazolo[3,2-c]pyrimidines", J Med. Chemical 12(2):227-232 (1969).

Roth et al., "The protonation of 2,4-diaminopyrimidines. I. Dissociation constants and substituent effects", J. Organic Chemical 34(4):821-836 (1969).

Sherif et al., "Syntheses with heterocyclic beta-enaminonitriles: an expeditious synthetic approach to polyfunctionally substituted 5-phenyl-sulfonylthiophenes and their fused derivates", Monatshefte fur Chemie 128:687-696 (1997).

Taylor et al., "Synthesis of thieno[2,3-d]pyrimidine analogues of the potent antitumor agent N-{4-[2-[(2-amino-4(3H)-oxo-7H-pyrrolo[2,3-d]pyrimidin-5-yl)ethyl]-benzoyl}-1-glutamic acid (LY231514)," Heterocycles 43(2):349-365 (1996).

* cited by examiner

THIENOPYRIDINE AND FUROPYRIDINE KINASE INHIBITORS

This application claims priority from U.S. Provisional Patent Application Ser. No. 60/567,703, filed May 3, 2004 and U.S. Provisional Patent Application Ser. No. 60/489,734, filed Jul. 24, 2003, which are both hereby incorporated by reference.

TECHNICAL FIELD

The present invention relates to compounds which are useful for inhibiting protein tyrosine kinases, methods of making the compounds, compositions containing the compounds, and methods of treatment using the compounds.

BACKGROUND OF THE INVENTION

Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation, or differentiation. Aberrant or excessive PTK activity has been observed in many disease states including benign and malignant proliferative disorders as well as diseases resulting from inappropriate activation of the immune system (e.g., autoimmune disorders), allograft rejection, and graft vs. host disease.

Endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

The non-receptor tyrosine kinases represent a collection of cellular enzymes which lack extracellular and transmembrane sequences. At present, over twenty-four individual non-receptor tyrosine kinases, comprising eleven subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and includes Src, Yes, Fyn, Lyn, Lck, Blk, Hck, Fgr and Yrk. The Src subfamily of enzymes has been linked to oncogenesis and immune responses.

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

In its principle embodiment, the present invention provides a compound of formula (I)

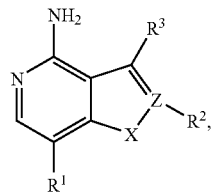

or a therapeutically acceptable salt thereof, wherein
X is selected from the group consisting of O and S;
Z is selected from the group consisting of C and N;
$R^1$ is selected from the group consisting of hydrogen, alkenyl, alkoxyalkynyl, alkoxycarbonyl, alkoxycarbonylalkenyl, alkoxycarbonylalkyl, alkoxycarbonylalkynyl, alkyl, alkynyl, aryl, arylalkenyl, arylalkyl, arylalkynyl, aryloxyalkyl, aryloxyalkynyl, arylsulfanylalkyl, arylsulfanylalkynyl, arylsulfonyloxyalkenyl, carboxy, carboxyalkenyl, carboxyalkyl, carboxyalkynyl, cyano, cyanoalkenyl, cyanoalkyl, cyanoalkynyl, cycloalkyl, cycloalkylalkoxyalkynyl, cycloalkylalkenyl, cycloalkylalkynyl, formylalkenyl, formylalkyl, halo, haloalkyl, heteroaryl, heteroarylalkenyl, heteroarylalkyl, heteroarylalkynyl, heteroarylcarbonyl, heteroarylcarbonylalkenyl, heteroarylcarbonylalkyl, heterocyclyl, heterocyclylalkenyl, heterocyclylalkyl, heterocyclylalkylcarbonyl, heterocyclylalkynyl, heterocyclylcarbonyl, heterocyclylcarbonylalkenyl, heterocyclylcarbonylalkyl, heterocyclyloxyalkenyl, hydroxyalkenyl, hydroxyalkyl, hydroxyalkynyl, $NR^aR^b$, $(NR^aR^b)$alkenyl, $(NR^aR^b)$alkyl, $(NR^aR^b)$alkynyl, $(NR^aR^b)$carbonyl, $(NR^aR^b)$carbonylalkenyl, $(NR^aR^b)$carbonylalkyl, $(NR^aR^b)$carbonylalkynyl, nitro, nitroalkenyl, nitroalkyl, and nitroalkynyl;
$R^2$ is absent or selected from the group consisting of hydrogen and alkyl;
$R^3$ is selected from the group consisting of halo, aryl, heteroaryl, and heterocyclyl, wherein the aryl, the heteroaryl, and the heterocyclyl are optionally substituted with one, two, or three substituents independently selected from the group consisting of alkoxy, alkyl, aryl, cyano, halo, haloalkoxy, haloalkyl, heteroaryl, heterocyclyl, hydroxy, hydroxyalkyl, $LR^4$, and $NR^aR^b$; provided that at least two of the three substituents are other than $LR^4$;
L is selected from the group consisting of O, $(CH_2)_mC(O)NR^5$, $NR^5C(O)(CH_2)_m$, $NR^5SO_2$, $SO_2NR^5$, $(CH_2)_mN(R^5)C(O)N(R^6)(CH_2)_n$, and $(CH_2)_mN(R^5)C(S)N(R^6)(CH_2)_n$, wherein m and n are independently 0 or 1, and wherein each group is drawn with its right end attached to $R^4$;
$R^4$ is selected from the group consisting of aryl, arylalkyl, cycloalkyl, heteroaryl, heteroarylalkyl, heterocyclyl, and heterocyclylalkyl;
$R^5$ and $R^6$ are independently selected from the group consisting of hydrogen and alkyl;
$R^a$ and $R^b$ are independently selected from the group consisting of hydrogen, alkenyl, alkoxyalkyl, alkoxycarbonyl, alkoxycarbonylalkyl, alkyl, alkylcarbonyl, alkylsulfanylalkyl, alkylsulfonyl, aryl, arylalkoxycarbonyl, arylalkoxycarbonylalkyl, arylalkyl, arylcarbonyl, arylsulfonyl, carboxyalkyl, cycloalkyl, cycloalkylalkyl, formylalkyl, heteroaryl, heteroarylalkyl, heteroarylcarbonyl, heteroarylsulfonyl, heterocyclyl, heterocyclylalkyl, heterocyclylalkylcarbonyl, heterocyclylcarbonyl, heterocyclylsulfonyl, hydroxyalkoxyalkyl, hydroxyalkyl, $(NR^cR^d)$alkyl, $(NR^cR^d)$alkylcarbonyl, $(NR^cR^d)$carbonyl, and $(NR^cR^d)$carbonylalkyl, wherein the aryl, the aryl part of the arylalkoxycarbonyl, the arylalkoxycarbonylalkyl, the arylalkyl, the arylcarbonyl, and the arylsulfonyl, the cycloalkyl, the cycloalkyl part of the cycloalkylalkyl, the heteroaryl, the heteroaryl part of the heteroarylalkyl, and the heteroarylcarbonyl, the heterocyclyl, and the heterocyclyl part of the heterocyclylalkyl and the heterocyclylcarbonyl can be further optionally substituted with one, two, three, four, or five substituents independently selected from the group consisting of alkenyl, alkoxy, alkoxycarbonyl, alkyl, alkylcarbonyl, aryl, arylalkyl, halo, haloalkoxy, haloalkyl, hydroxy, nitro, $NR^cR^d$, $(NR^cR^d)$alkyl, $(NR^cR^d)$alkylcarbonyl, $(NR^cR^d)$carbonyl, $(NR^cR^d)$carbonylalkyl, oxo, and spiroheterocyclyl, wherein the aryl and the aryl part of the arylalkyl can be substituted with one, two, three, four, or five substituents independently selected from the group consisting of alkoxy, alkyl, cyano, halo, haloalkoxy, haloalkyl, nitro, and oxo;

$R^c$ and $R^d$ are independently selected from the group consisting of hydrogen, alkoxy, alkyl, aryl, carboxyalkyl, cycloalkyl, haloalkyl, heteroaryl, heterocyclyl, heterocyclylalkyl, hydroxyalkoxyalkyl, hydroxyalkyl, and $(NR^eR^f)$alkyl, wherein the aryl, the heteroaryl, and the heterocyclyl can be optionally substituted with one, two, three, four, or five substituents independently selected from the group consisting of alkenyl, alkoxy, alkyl, halo, haloalkoxy, haloalkyl, hydroxy, and nitro; and $R^e$ and $R^f$ are independently selected from the group consisting of hydrogen and alkyl.

In another embodiment, the present invention provides compounds of formula (I) wherein $R^2$ is hydrogen and $R^1$, $R^3$, Z, and X are as defined in formula (I).

In another embodiment, the present invention provides compounds of formula (I) wherein $R^3$ is selected from the group consisting of halo, heteroaryl, and heterocyclyl; and $R^1$, $R^2$, Z, and X are as defined in formula (I).

In another embodiment, the present invention provides compounds of formula (I) wherein $R^3$ is aryl and $R^1$, $R^2$, Z, and X are as defined in formula (I).

In another embodiment, the present invention provides compounds of formula (I) wherein $R^3$ is aryl wherein the aryl is unsubstituted or substituted with one or two substituents independently selected from the group consisting of alkoxy, alkyl, aryl, cyano, halo, haloalkoxy, haloalkyl, hydroxyalkyl, and $NR^aR^b$; and $R^a$, $R^b$, $R^1$, $R^2$, Z, and X are as defined in formula (I).

In another embodiment, the present invention provides compounds of formula (I) wherein $R^3$ is aryl wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$; and $R^a$, $R^b$, $R^1$, $R^2$, $R^4$, L, Z, and X are as defined in formula (I).

In another embodiment, the present invention provides compounds of formula (I) wherein $R^3$ is aryl wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$; L is O; and and $R^a$, $R^b$, $R^1$, $R^2$, $R^4$, Z, and X are as defined in formula (I).

In another embodiment the present invention provides compounds of formula (I) wherein $R^3$ is aryl wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$; L is O; $R^1$ is selected from the group consisting of heterocyclylalkenyl, heterocyclylcarbonylalkenyl, $(NR^aR^b)$alkenyl, and $(NR^aR^b)$carbonylalkenyl; and $R^a$, $R^b$, $R^2$, $R^4$, Z, and X are as defined in formula (I).

In another embodiment, the present invention provides compounds of formula (I) wherein $R^3$ is aryl wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$; L is O; $R^1$ is selected from the group consisting of hydrogen, alkoxycarbonylalkenyl, carboxyalkenyl, heteroaryl, and hydroxyalkenyl; and $R^a$, $R^b$, $R^2$, $R^4$, Z, and X are as defined in formula (I).

In another embodiment, the present invention provides compounds of formula (I) wherein $R^3$ is aryl wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$; L is selected from the group consisting of $NR^5C(O)(CH_2)_m$ and $NR^5SO_2$; and m, $R^a$, $R^b$, $R^1$, $R^2$, $R^4$, $R^5$, Z, and X are as defined in formula (I).

In another more preferred embodiment the present invention provides the compound of formula (I) wherein $R^3$ is aryl, wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$; L is selected from the group consisting of $NR^5C(O)(CH_2)_m$ and $NR^5SO_2$; $R^1$ is $(NR^aR^b)$alkenyl; and m, $R^a$, $R^b$, $R^2$, $R^4$, $R^5$, Z, and X are as defined in formula (I).

In another embodiment, the present invention provides compounds of formula (I) wherein $R^3$ is aryl wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$; L is selected from the group consisting of $NR^5C(O)(CH_2)_m$ and $NR^5SO_2$; $R^1$ is selected from the group consisting of heterocyclylalkenyl, heterocyclylalkyl, and $(NR^aR^b)$carbonylalkenyl; and m, $R^a$, $R^b$, $R^2$, $R^4$, $R^5$, Z, and X are as defined in formula (I).

In another embodiment the present invention provides compounds of formula (I) wherein $R^3$ is aryl wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$; L is selected from the group consisting of $NR^5C(O)(CH_2)_m$ and $NR^5SO_2$; $R^1$ is selected from the group consisting of hydrogen, alkoxycarbonylalkenyl, carboxyalkenyl, formylalkenyl, and heteroaryl; and m, $R^a$, $R^b$, $R^2$, $R^4$, $R^5$, Z, and X are as defined in formula (I).

In another embodiment, the present invention provides compounds of formula (I) wherein $R^3$ is aryl wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$; L is selected from the group consisting of $NR^5C(O)(CH_2)_m$ and $NR^5SO_2$; $R^1$ is selected from the group consisting of alkoxyalkynyl, arylalkynyl, carboxyalkynyl, cycloalkylalkynyl, halo, heteroarylalkynyl, heterocyclylalkynyl, heterocyclylalkynyl, hydroxyalkynyl, and $(NR^aR^b)$alkynyl; and m, $R^a$, $R^b$, $R^2$, $R^4$, $R^5$, Z, and X are as defined in formula (I).

In another embodiment, the present invention provides compounds of formula (I) wherein $R^3$ is aryl wherein the aryl is substituted with LR⁴ and optionally with one or two additional substituents independently selected from the group consisting of alkoxy, alkyl, aryl, cyano, halo, haloalkoxy, haloalkyl, hydroxyalkyl, and NRᵃRᵇ; L is (CH₂)ₘN(R⁵)C(O)N(R⁶)(CH₂)ₙ; and m, n, Rᵃ, Rᵇ, R¹, R², R⁴, R⁵, R⁶, Z, and X are as defined in formula (I).

In another embodiment, the present invention provides compounds of formula (I) wherein R³ is aryl wherein the aryl is substituted with LR⁴ and optionally with one or two additional substituents independently selected from the group consisting of alkoxy, alkyl, aryl, cyano, halo, haloalkoxy, haloalkyl, hydroxyalkyl, and NRᵃRᵇ; L is (CH₂)ₘN(R⁵)C(O)N(R⁶)(CH₂)ₙ; R¹ is selected from the group consisting of alkynyl, arylalkynyl, aryloxyalkynyl, arylsulfanylalkynyl, cyanoalkynyl, heteroarylalkynyl, hydroxyalkynyl, and (NRᵃRᵇ)alkynyl; and m, n, Rᵃ, Rᵇ, R², R⁴, R⁵, R⁶, Z, and X are as defined in formula (I).

In another embodiment, the present invention provides compounds of formula (I) wherein R³ is aryl wherein the aryl is substituted with LR⁴ and optionally with one or two additional substituents independently selected from the group consisting of alkoxy, alkyl, aryl, cyano, halo, haloalkoxy, haloalkyl, hydroxyalkyl, and NRᵃRᵇ; L is (CH₂)ₘN(R⁵)C(O)N(R⁶)(CH₂)ₙ; R¹ is selected from the group consisting of alkoxycarbonylalkenyl, carboxyalkenyl, heteroarylcarbonylalkenyl, heterocyclylcarbonylalkenyl, and (NRᵃRᵇ)carbonylalkenyl; and m, n, Rᵃ, Rᵇ, R², R⁴, R⁵, R⁶, Z, and X are as defined in formula (I).

In another embodiment, the present invention provides compounds of formula (I) wherein R³ is aryl wherein the aryl is substituted with LR⁴ and optionally with one or two additional substituents independently selected from the group consisting of alkoxy, alkyl, aryl, cyano, halo, haloalkoxy, haloalkyl, hydroxyalkyl, and NRᵃRᵇ; L is (CH₂)ₘN(R⁵)C(O)N(R⁶)(CH₂)ₙ; R¹ is selected from the group consisting of aryl and heteroaryl; and m, n, Rᵃ, Rᵇ, R², R⁴, R⁵, R⁶, Z, and X are as defined in formula (I).

In another embodiment, the present invention provides compounds of formula (I) wherein R³ is aryl wherein the aryl is substituted with LR⁴ and optionally with one or two additional substituents independently selected from the group consisting of alkoxy, alkyl, aryl, cyano, halo, haloalkoxy, haloalkyl, hydroxyalkyl, and NRᵃRᵇ; L is (CH₂)ₘN(R⁵)C(O)N(R⁶)(CH₂)ₙ; R¹ is selected from the group consisting of alkoxycarbonylalkyl, carboxyalkyl, heterocyclylalkyl, hydroxyalkyl, (NRᵃRᵇ)alkyl, and (NRᵃRᵇ)carbonylalkyl; and m, n, Rᵃ, Rᵇ, R², R⁴, R⁵, R⁶, Z, and X are as defined in formula (I).

In another embodiment, the present invention provides compounds of formula (I) wherein R³ is aryl wherein the aryl is substituted with LR⁴ and optionally with one or two additional substituents independently selected from the group consisting of alkoxy, alkyl, aryl, cyano, halo, haloalkoxy, haloalkyl, hydroxyalkyl, and NRᵃRᵇ; L is (CH₂)ₘN(R⁵)C(O)N(R⁶)(CH₂)ₙ; R¹ is selected from the group consisting of hydrogen, halo, nitro, and NRᵃRᵇ; and m, n, Rᵃ, Rᵇ, R², R⁴, R⁵, R⁶, Z, and X are as defined in formula (I).

In another embodiment, the present invention provides compounds of formula (I) wherein R¹ is selected from the group consisting of alkynyl, arylalkynyl, aryloxyalkynyl, arylsulfanylalkynyl, cyanoalkynyl, cycloalkylalkoxyalkynyl, heteroarylalkynyl, hydroxyalkynyl, and (NRᵃRᵇ)alkynyl; R² is hydrogen; R³ is aryl wherein the aryl is phenyl substituted with LR⁴ and optionally with one or two additional substituents independently selected from the group consisting of alkoxy, alkyl, aryl, cyano, halo, haloalkoxy, haloalkyl, hydroxyalkyl, and NRᵃRᵇ; R⁴ is aryl; L is (CH₂)ₘN(R⁵)C(O)N(R⁶)(CH₂)ₙ; X is S, Z is C; and m, n, Rᵃ, Rᵇ, R⁵, and R⁶ are as defined in formula (I).

In another embodiment, the present invention provides compounds of formula (I) wherein R¹ is selected from the group consisting of alkynyl, arylalkynyl, aryloxyalkynyl, arylsulfanylalkynyl, cyanoalkynyl, cycloalkylalkoxyalkynyl, heteroarylalkynyl, hydroxyalkynyl, and (NRᵃRᵇ)alkynyl; R² is hydrogen; R³ is aryl wherein the aryl is phenyl substituted with LR⁴; R⁴ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; L is (CH₂)ₘN(R⁵)C(O)N(R⁶)(CH₂)ₙ; R⁵ and R⁶ are hydrogen; m is 0; n is 0; X is S; Z is C; and Rᵃ and Rᵇ are independently selected from the group consisting of hydrogen, alkyl, alkylcarbonyl, alkylsulfonyl, and heterocyclylcarbonyl wherein the heterocyclyl is pyridinyl.

In another embodiment, the present invention provides compounds of formula (I) wherein R¹ is (NRᵃRᵇ)alkynyl; R² is hydrogen; R³ is aryl wherein the aryl is phenyl substituted with LR⁴; R⁴ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; L is (CH₂)ₘN(R⁵)C(O)N(R⁶)(CH₂)ₙ; R⁵ and R⁶ are hydrogen; m is 0; n is 0; X is S; Z is C; and Rᵃ and Rᵇ are independently selected from the group consisting of hydrogen, alkyl, alkylcarbonyl, alkylsulfonyl, and heterocyclylcarbonyl wherein the heterocyclyl is pyridinyl.

In another embodiment, the present invention provides compounds of formula (I) wherein R¹ is (NRᵃRᵇ)alkynyl; R² is hydrogen; R³ is aryl wherein the aryl is phenyl substituted with LR⁴; R⁴ is aryl wherein the aryl is phenyl optionally substituted with 1 or 2 substituents independently selected from the group consisting of alkyl, alkylcarbonyl, cyano, halogen, and haloalkyl wherein preferred groups are chloro, fluoro, methyl, and trifluoromethyl; L is (CH₂)ₘN(R⁵)C(O)N(R⁶)(CH₂)ₙ; R⁵ and R⁶ are hydrogen; m is 0; n is 0; X is S; Z is C; Rᵃ is selected from the group consisting of hydrogen and alkyl; and Rᵇ is heteroarylcarbonyl.

In another embodiment, the present invention provides compounds of formula (I) wherein R¹ is (NRᵃRᵇ)alkynyl; R² is hydrogen; R³ is aryl wherein the aryl is phenyl substituted with LR⁴; R⁴ is aryl wherein the aryl is phenyl optionally substituted with 1 or 2 substituents independently selected from the group consisting of alkyl, alkylcarbonyl, cyano, halogen, and haloalkyl wherein preferred groups are chloro, fluoro, methyl, and trifluoromethyl; L is (CH₂)ₘN(R⁵)C(O)N(R⁶)(CH₂)ₙ; R⁵ and R⁶ are hydrogen; m is 0; n is 0; is S; Z is C; Rᵃ is selected from the group consisting of hydrogen and alkyl; and Rᵇ is heteroarylcarbonyl wherein the heteroaryl is pyridinyl.

In another embodiment, the present invention provides compounds of formula (I) wherein R¹ is selected from the group consisting of alkynyl, arylalkynyl, aryloxyalkynyl, arylsulfanylalkynyl, cyanoalkynyl, cycloalkylalkoxyalkynyl, heteroarylalkynyl, hydroxyalkynyl, and (NRᵃRᵇ)alkynyl; R² is hydrogen; R³ is aryl wherein the aryl is phenyl substituted with LR⁴ and optionally substituted with 1 alkoxy group; R⁴ is heteroaryl; L is N(R⁵)C(O)(CH₂)ₘ wherein the nitrogen is attached to R³ and the carbonyl is attached to R⁴; R⁵ is hydrogen; m is 0; X is S; Z is C; and Rᵃ and Rᵇ are independently selected from the group consisting of hydrogen, alkyl, alkylsulfonyl, and heteroarylcarbonyl, wherein the heteroaryl is pyridinyl.

In another embodiment, the present invention provides compounds of formula (I) wherein $R^1$ is selected from the group consisting of alkynyl, arylalkynyl, aryloxyalkynyl, arylsulfanylalkynyl, cyanoalkynyl, cycloalkylalkoxyalkynyl, heteroarylalkynyl, hydroxyalkynyl, and $(NR^aR^b)$alkynyl; $R^2$ is hydrogen; $R^3$ is aryl wherein the aryl is phenyl substituted with $LR^4$ and optionally substituted with 1 alkoxy group; $R^4$ is heteroaryl wherein the heteroaryl is selected from the group consisting of indolyl and thienyl wherein the heteroaryl is optionally substituted with 1 alkyl group wherein the preferred heteoaryl is 1-methyl-1H-indol-2-yl; L is $N(R^5)C(O)(CH_2)_m$ wherein the nitrogen is attached to $R^3$ and the carbonyl is attached to $R^4$; $R^5$ is hydrogen; m is 0; X is S; Z is C; and $R^a$ and $R^b$ are independently selected from the group consisting of hydrogen, alkyl, alkylsulfonyl, and heteroarylcarbonyl, wherein the heteroaryl is pyridinyl.

In another embodiment, the present invention provides compounds of formula (I) wherein $R^1$ is selected from the group consisting of alkenyl, arylalkenyl, heterocyclylalkenyl, hydroxyalkenyl, $(NR^aR^b)$carbonylalkenyl, and $(NR^aR^b)$alkenyl; $R^2$ is hydrogen; $R^3$ is aryl wherein the aryl is phenyl substituted with $LR^4$; $R^4$ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; $R^5$ and $R^6$ are hydrogen; L is $(CH_2)_mN(R^5)C(O)N(R^6)(CH_2)_n$; m is 0; n is 0; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is heterocyclylalkenyl wherein the heterocycle is selected from the group consisting of piperazinyl and piperidinyl wherein the heterocycle is optionally substituted with 1 substituent selected from the group consisting of carboxy, hydroxy, hydroxyalkyl, oxo, $NR^aR^b$, and $(NR^aR^b)$alkyl; $R^2$ is hydrogen; $R^3$ is aryl wherein the aryl is phenyl substituted with $LR^4$; $R^4$ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; $R^5$ and $R^6$ are hydrogen; L is $(CH_2)_mN(R^5)C(O)N(R^6)(CH_2)_n$; m is 0; n is 0; is S; Z is C; and $R^a$ and $R^b$ are independently selected from the group consisting of hydrogen, alkyl, and cycloalkyl wherein the cycloalkyl is cyclohexyl optionally substituted with $NH_2$ In another embodiment, the present invention provides compounds of formula (I) wherein $R^1$ is $(NR^aR^b)$alkenyl; $R^2$ is hydrogen; $R^3$ is aryl wherein the aryl is phenyl substituted with $LR^4$; $R^4$ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; $R^5$ and $R^6$ are hydrogen; L is $(CH_2)_mN(R^5)C(O)N(R^6)(CH_2)_n$; m is 0; n is 0; X is S; Z is C; and $R^a$ and $R^b$ are independently selected from the group consisting of hydrogen, alkyl, and cycloalkyl wherein the cycloalkyl is cyclohexyl optionally substituted with $NH_2$ In another embodiment, the present invention provides compounds of formula (I) wherein $R^1$ is selected from the group consisting of alkenyl, arylalkenyl, heterocyclylalkenyl, hydroxyalkenyl, $(NR^aR^b)$carbonylalkenyl, and $(NR^aR^b)$alkenyl; $R^2$ is hydrogen; $R^3$ is aryl wherein the aryl is phenyl substituted with $LR^4$ and optionally substituted with 1 alkoxy group; $R^4$ is heteroaryl; L is $N(R^5)C(O)(CH_2)_m$ wherein the nitrogen is attached to $R^3$ and the carbonyl is attached to $R^4$; $R^5$ is hydrogen; m is 0; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is heterocyclylalkenyl wherein the heterocycle is selected from the group consisting of piperazinyl and piperidinyl wherein the heterocycle is optionally substituted with 1 substituent selected from the group consisting of carboxy, hydroxy, hydroxyalkyl, oxo, $NR^aR^b$, and $(NR^aR^b)$alkyl; $R^2$ is hydrogen; $R^3$ is aryl wherein the aryl is phenyl substituted with $LR^4$ and optionally substituted with 1 alkoxy group; $R^4$ is heteroaryl wherein the heteroaryl is selected from the group consisting of indolyl and thienyl wherein the heteroaryl is optionally substituted with 1 alkyl group wherein the preferred heteoaryl is 1-methyl-1H-indol-2-yl; L is $N(R^5)C(O)(CH_2)_m$ wherein the nitrogen is attached to $R^3$ and the carbonyl is attached to $R^4$; $R^5$ is hydrogen; m is 0; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is $(NR^aR^b)$alkenyl; $R^3$ is aryl wherein the aryl is phenyl substituted with $LR^4$ and optionally substituted with 1 alkoxy group; $R^4$ is heteroaryl wherein the heteroaryl is selected from the group consisting of indolyl and thienyl wherein the heteroaryl is optionally substituted with 1 alkyl group wherein the preferred heteoaryl is 1-methyl-1H-indol-2-yl; L is $N(R^5)C(O)(CH_2)_m$ wherein the nitrogen is attached to $R^3$ and the carbonyl is attached to $R^4$; $R^5$ is hydrogen; m is 0; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is heteroaryl; $R^2$ is hydrogen; $R^3$ is aryl wherein the aryl is phenyl substituted with $LR^4$; $R^4$ is aryl; L is $(CH_2)_mN(R^5)C(O)N(R^6)(CH_2)_n$; $R^5$ and $R^6$ are hydrogen; m is 0; is C; and X is S.

In another embodiment, the present invention provides compounds of formula (I) wherein $R^1$ is heteroaryl wherein the heteroaryl is selected from the group consisting of benzothiazolyl, benzothienyl, benzoxazolyl, furyl, indolyl, pyrazolyl, pyrazinyl, pyridazinyl, pyridinyl, pyrimidinyl, pyrrolyl, and thienyl wherein the heteroaryl is optionally substituted with 1 or 2 substituents selected from the group consisting of alkoxy, alkyl, formyl, halogen, and haloalkyl; $R^2$ is hydrogen; $R^3$ is aryl wherein the aryl is phenyl substituted with LR⁴; R⁴ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; L is $(CH_2)_mN(R^5)C(O)N(R^6)(CH_2)_n$; $R^5$ and $R^6$ are hydrogen; m is 0; n is 0; Z is C; and X is S.

In another embodiment, the present invention provides compounds of formula (I) wherein $R^1$ is heteroaryl wherein the heteroaryl is selected from the group consisting of indolyl, pyridinyl, and pyrimidinyl, wherein the heteroaryl is optionally substituted with 1 or 2 substituents selected from the group consisting of alkoxy, alkyl, halogen, and haloalkyl; $R^2$ is hydrogen; $R^3$ is aryl wherein the aryl is phenyl substituted with LR⁴; R⁴ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; L is $(CH_2)_mN(R^5)C(O)N(R^6)(CH_2)_n$; $R^5$ and $R^6$ are hydrogen; m is 0; n is 0; Z is C; and X is S.

In another embodiment, the present invention provides compounds of formula (I) wherein $R^1$ is heteroaryl; $R^2$ is hydrogen; $R^3$ is aryl wherein the aryl is phenyl substituted with LR⁴; R⁴ is heteroaryl; L is $N(R^5)C(O)(CH_2)_m$ wherein the nitrogen is attached to $R^3$ and the carbonyl is attached to $R^4$; $R^5$ is hydrogen; m is 0; Z is C; and X is S.

In another embodiment, the present invention provides compounds of formula (I) wherein $R^1$ is heteroaryl wherein the heteroaryl is selected from the group consisting of benzothiazolyl, benzothienyl, benzoxazolyl, furyl, indolyl, pyrazolyl, pyrazinyl, pyridazinyl, pyridinyl, pyrimidinyl, pyrrolyl, and thienyl wherein the heteroaryl is optionally substituted with 1 or 2 substituents selected from the group consisting of alkoxy, alkyl, formyl, halogen, and haloalkyl; $R^2$ is hydrogen; $R^3$ is aryl wherein the aryl is phenyl substituted with LR⁴; R⁴ is heteroaryl wherein the heteroaryl is selected from the group consisting of indolyl and thienyl wherein the heteroaryl is optionally substituted with 1 alkyl group wherein the preferred heteoaryl is 1-methyl-1H-indol-2-yl; L is $N(R^5)C(O)(CH_2)_m$ wherein the nitrogen is attached to $R^3$ and the carbonyl is attached to $R^4$; $R^5$ is hydrogen; m is 0; Z is C; and X is S.

In another embodiment, the present invention provides compounds of formula (I) wherein $R^1$ is heteroaryl wherein the heteroaryl is selected from the group consisting of indolyl, pyridinyl, and pyrimidinyl, wherein the heteroaryl is optionally substituted with 1 or 2 substituents selected from the group consisting of alkoxy, alkyl, halogen, and haloalkyl; $R^2$ is hydrogen; $R^3$ is aryl wherein the aryl is phenyl substituted with LR⁴; R⁴ is heteroaryl wherein the heteroaryl is selected from the group consisting of indolyl and thienyl wherein the heteroaryl is optionally substituted with 1 alkyl group wherein the preferred heteoaryl is 1-methyl-1H-indol-2-yl; L is $N(R^5)C(O)(CH_2)_m$ wherein the nitrogen is attached to $R^3$ and the carbonyl is attached to $R^4$; $R^5$ is hydrogen; m is 0; Z is C; and X is S.

In another embodiment, the present invention provides compounds of formula (I) wherein $R^2$ is hydrogen; $R^3$ is heteroaryl; Z is C; X is S; and $R^1$ is as defined in formula (I).

In another embodiment, the present invention provides compounds of formula (I) wherein $R^1$ is selected from the group consisting of alkenyl, arylalkenyl, heterocyclylalkenyl, hydroxyalkenyl, $(NR^aR^b)$carbonylalkenyl, and $(NR^aR^b)$alkenyl; $R^2$ is hydrogen; $R^3$ is heteroaryl; Z is C; X is S; and $R^a$ and $R^b$ are as defined in formula (I).

In another embodiment, the present invention provides compounds of formula (I) wherein $R^1$ is heterocyclylalkenyl wherein the heterocycle is selected from the group consisting of piperazinyl and piperidinyl wherein the heterocycle is optionally substituted with 1 substituent selected from the group consisting of carboxy, hydroxy, hydroxyalkyl, oxo, $NR^aR^b$, and $(NR^aR^b)$alkyl; $R^2$ is hydrogen; $R^3$ is heteroaryl wherein the heteroaryl is selected from the group consisting of benzisoxazolyl, benzofuranyl, benzothiazolyl, benzothienyl, benzoxadiazolyl, benzoxazolyl, indolyl, isoquinolinyl, and quinolinyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is heterocyclylalkenyl wherein the heterocycle is selected from the group consisting of piperazinyl and piperidinyl wherein the heterocycle is optionally substituted with 1 substituent selected from the group consisting of carboxy, hydroxy, hydroxyalkyl, oxo, $NR^aR^b$, and $(NR^aR^b)$alkyl; $R^2$ is hydrogen; $R^3$ is heteroaryl wherein the heteroaryl is selected from the group consisting of benzofuranyl, benzothienyl, and indolyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is $(NR^aR^b)$carbonylalkenyl; $R^2$ is hydrogen; $R^3$ is heteroaryl wherein the heteroaryl is selected from the group consisting of benzisoxazolyl, benzofuranyl, benzothiazolyl, benzothienyl, benzoxadiazolyl, benzoxazolyl, indolyl, isoquinolinyl, and quinolinyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is $(NR^aR^b)$carbonylalkenyl; $R^2$ is hydrogen; $R^3$ is heteroaryl wherein the heteroaryl is selected from the group consisting of benzofuranyl, benzothienyl, and indolyl, wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is $(NR^aR^b)$alkenyl; $R^2$ is hydrogen; $R^3$ is heteroaryl wherein the heteroaryl is selected from the group consisting of benzisoxazolyl, benzofuranyl, benzothiazolyl, benzothienyl, benzoxadiazolyl, benzoxazolyl, indolyl, isoquinolinyl, and quinolinyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is $(NR^aR^b)$alkenyl; $R^2$ is hydrogen; $R^3$ is heteroaryl wherein the heteroaryl is selected from the group consisting of benzofuranyl, benzothienyl, and indolyl, wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; X is S; Z is C; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is selected from the group consisting of alkynyl, arylalkynyl, aryloxyalkynyl, arylsulfanylalkynyl, cyanoalkynyl, heteroarylalkynyl, hydroxyalkynyl, and $(NR^aR^b)$alkynyl; $R^2$ is hydrogen; $R^3$ is heteroaryl; X is S; Z is C; and $R^a$ and $R^b$ are as defined in formula (I).

In another embodiment, the present invention provides compounds of formula (I) wherein $R^1$ is $(NR^aR^b)$alkynyl; $R^2$ is hydrogen; $R^3$ is heteroaryl wherein the heteroaryl is selected from the group consisting of benzisoxazolyl, benzofuranyl, benzothiazolyl, benzothienyl, benzoxadiazolyl, benzoxazolyl, indolyl, isoquinolinyl, and quinolinyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; X is S; Z is C; and $R^a$ and $R^b$ are independently selected from the group consisting of hydrogen, alkyl, alkylcarbonyl, alkylsulfonyl, and heterocyclylcarbonyl wherein the heterocyclyl is pyridinyl.

In another embodiment, the present invention provides compounds of formula (I) wherein $R^1$ is $(NR^aR^b)$alkynyl; $R^2$ is hydrogen; $R^3$ is heteroaryl wherein the heteroaryl is selected from the group consisting of benzofuranyl, benzothienyl, and indolyl, wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; X is S; Z is C; and $R^a$ and $R^b$ are independently selected from the group consisting of hydrogen, alkyl, alkylcarbonyl, alkylsulfonyl, and heterocyclylcarbonyl wherein the heterocyclyl is pyridinyl.

In another embodiment, the present invention provides compounds of formula (I) wherein $R^1$ is heteroaryl; $R^2$ is hydrogen; $R^3$ is heteroaryl; X is S; Z is C; and $R^a$ and $R^b$ are as defined in formula (I).

In another embodiment, the present invention provides compounds of formula (I) wherein $R^1$ is heteroaryl wherein the heteroaryl is selected from the group consisting of benzothiazolyl, benzothienyl, benzoxazolyl, furyl, indolyl, pyrazolyl, pyrazinyl, pyridazinyl, pyridinyl, pyrimidinyl, pyrrolyl, and thienyl wherein the heteroaryl is optionally substituted with 1 or 2 substituents selected from the group consisting of alkoxy, alkyl, formyl, halogen, and haloalkyl; $R^2$ is hydrogen; $R^3$ is heteroaryl wherein the heteroaryl is selected from the group consisting of benzisoxazolyl, benzofuranyl, benzothiazolyl, benzothienyl, benzoxadiazolyl, benzoxazolyl, indolyl, isoquinolinyl, and quinolinyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; Z is C; and X is S.

In another embodiment, the present invention provides compounds of formula (I) wherein $R^1$ is heteroaryl wherein the heteroaryl is selected from the group consisting of indolyl, pyridinyl, and pyrimidinyl wherein the heteroaryl is optionally substituted with 1 or 2 substituents selected from the group consisting of alkoxy, alkyl, formyl, halogen, and haloalkyl; $R^2$ is hydrogen; $R^3$ is heteroaryl wherein the heteroaryl is selected from the group consisting of benzofuranyl, benzothienyl, and indolyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; Z is C; and X is S.

In another embodiment, the present invention provides compounds of formula (I) wherein $R^1$ is heteroaryl; $R^2$ is hydrogen; $R^3$ is heterocyclyl; X is S; Z is C; and $R^a$ and $R^b$ are as defined in formula (I).

In another embodiment, the present invention provides compounds of formula (I) wherein $R^1$ is heteroaryl wherein the heteroaryl is selected from the group consisting of benzothiazolyl, benzothienyl, benzoxazolyl, furyl, indolyl, pyrazolyl, pyrazinyl, pyridazinyl, pyridinyl, pyrimidinyl, pyrrolyl, and thienyl wherein the heteroaryl is optionally substituted with 1 or 2 substituents selected from the group consisting of alkoxy, alkyl, formyl, halogen, and haloalkyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; and X is S.

In another embodiment, the present invention provides compounds of formula (I) wherein $R^1$ is heteroaryl wherein the heteroaryl is selected from the group consisting of indolyl, pyridinyl, and pyrimidinyl wherein the heteroaryl is optionally substituted with 1 or 2 substituents selected from the group consisting of alkoxy, alkyl, formyl, halogen, and haloalkyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; and X is S.

In another embodiment, the present invention provides compounds of formula (I) wherein $R^1$ is selected from the group consisting of alkynyl, arylalkynyl, aryloxyalkynyl, arylsulfanylalkynyl, cyanoalkynyl, heteroarylalkynyl, hydroxyalkynyl, and $(NR^aR^b)$alkynyl; $R^2$ is hydrogen; $R^3$ is heterocyclyl; Z is C; X is S; and $R^a$ and $R^b$ are as defined in formula (I).

In another embodiment, the present invention provides compounds of formula (I) wherein $R^1$ is $(NR^aR^b)$alkynyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; X is S; and $R^a$ and $R^b$ are independently selected from the group consisting of hydrogen, alkyl, alkylcarbonyl, alkylsulfonyl, and heterocyclylcarbonyl wherein the heterocyclyl is pyridinyl.

In another embodiment, the present invention provides compounds of formula (I) wherein $R^1$ is selected from the group consisting of alkenyl, arylalkenyl, heterocyclylalkenyl, hydroxyalkenyl, $(NR^aR^b)$carbonylalkenyl, and $(NR^aR^b)$alkenyl; $R^2$ is hydrogen; $R^3$ is heterocyclyl; Z is C; X is S; and $R^a$ and $R^b$ are as defined in formula (I).

In another embodiment, the present invention provides compounds of formula (I) wherein $R^1$ is heterocyclylalkenyl wherein the heterocycle is selected from the group consisting of piperazinyl and piperidinyl wherein the heterocycle is optionally substituted with 1 substituent selected from the group consisting of carboxy, hydroxy, hydroxyalkyl, oxo, $NR^aR^b$, and $(NR^aR^b)$alkyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; X is S; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is $(NR^aR^b)$carbonylalkenyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; X is S; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is $(NR^aR^b)$alkenyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; X is S; and $R^a$ and $R^b$ are independently selected from the group consisting of hydrogen, alkyl, and cycloalkyl wherein the cycloalkyl is cyclohexyl optionally substituted with $NH_2$.

In another embodiment, the present invention provides compounds of formula (I) wherein $R^1$ is aryl; and Z, X, $R^2$, and $R^3$ are as defined in formula (I).

In another embodiment, the present invention provides compounds of formula (I) wherein $R^1$ is aryl wherein the aryl is phenyl optionally substituted with 1, 2, or 3 substituents selected from the group consisting of alkoxy, alkoxycarbonyl, alkyl, alkylcarbonyl, alkylsulfanyl, alkylsulfonyl, carboxy, cyano, halo, haloalkoxy, haloalkyl, hydroxy, methylenedioxy, 4-methylpiperazin-1-yl, phenoxy, (3-piperidin-1-ylpropanoyl)amino, pyrrolidin-1-ylmethyl, —$NR^aR^b$, $(NR^aR^b)$alkyl, and $(NR^aR^b)$carbonyl; $R^2$ is hydrogen; $R^3$ is aryl wherein the aryl is phenyl substituted with $LR^4$; $R^4$ is aryl wherein the aryl is phenyl optionally substituted with 1 or 2 substituents selected from the group consisting of alkyl, alkylcarbonyl, cyano, halogen, and haloalkyl wherein the preferred groups are chloro, fluoro, methyl, and trifluoromethyl; L is $(CH_2)_mN(R^5)C(O)N(R^6)(CH_2)_n$; $R^5$ and $R^6$ are hydrogen; m is 0; n is 0; Z is C; X is S; $R^a$ and $R^b$ are independently selected from the group consisting of hydrogen, alkyl, alkylcarbonyl, alkylsulfonyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is aryl wherein the aryl is phenyl optionally substituted with 1, 2, or 3 substituents selected from the group consisting of alkoxy, alkoxycarbonyl, alkyl, alkylcarbonyl, alkylsulfanyl, alkylsulfonyl, carboxy, cyano, halo, haloalkoxy, haloalkyl, hydroxy, methylenedioxy, 4-methylpiperazin-1-yl, phenoxy, (3-piperidin-1-ylpropanoyl)amino, pyrrolidin-1-ylmethyl, —$NR^aR^b$, $(NR^aR^b)$alkyl, and $(NR^aR^b)$carbonyl; $R^2$ is hydrogen; $R^3$ is aryl wherein the aryl is phenyl substituted with $NH_2$; Z is C; X is S; $R^a$ and $R^b$ are independently selected from the group consisting of hydrogen, alkyl, alkylcarbonyl, alkylsulfonyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is aryl wherein the aryl is phenyl optionally substituted with 1, 2, or 3 substituents selected from the group consisting of alkoxy, alkoxycarbonyl, alkyl, alkylcarbonyl, alkylsulfanyl, alkylsulfonyl, carboxy, cyano, halo, haloalkoxy, haloalkyl, hydroxy, methylenedioxy, 4-methylpiperazin-1-yl, phenoxy, (3-piperidin-1-ylpropanoyl)amino, pyrrolidin-1-ylmethyl, —$NR^aR^b$, $(NR^aR^b)$alkyl, and $(NR^aR^b)$carbonyl; $R^2$ is hydrogen; $R^3$ is heteroaryl wherein the heteroaryl is selected from the group consisting of benzofuranyl, benzothienyl, and indolyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; Z is C; X is S; $R^a$ and $R^b$ are independently selected from the group consisting of hydrogen, alkyl, alkylcarbonyl, alkylsulfonyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is aryl wherein the aryl is phenyl optionally substituted with 1, 2, or 3 substituents selected from the group consisting of alkoxy, alkoxycarbonyl, alkyl, alkylcarbonyl, alkylsulfanyl, alkylsulfonyl, carboxy, cyano, halo, haloalkoxy, haloalkyl, hydroxy, methylenedioxy, 4-methylpiperazin-1-yl, phenoxy, (3-piperidin-1-ylpropanoyl)amino, pyrrolidin-1-ylmethyl, —$NR^aR^b$, $(NR^aR^b)$alkyl, and $(NR^aR^b)$carbonyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; X is S; $R^a$ and $R^b$ are independently selected from the group consisting of hydrogen, alkyl, alkylcarbonyl, alkylsulfonyl, and $(NR^cR^d)$ alkylcarbonyl; and $R^c$ and $R^d$ are independently selected from the group consisting of hydrogen and alkyl.

In another embodiment, the present invention provides compounds of formula (I) wherein $R^1$ is selected from the group consisting of hydrogen, alkoxycarbonyl, carboxy, and $(NR^aR^b)$carbonyl; and Z, X, $R^a$, $R^b$, $R^2$, and $R^3$ are as defined in formula (I).

In another embodiment, the present invention provides compounds of formula (I) wherein $R^1$ is selected from the group consisting of hydrogen, alkoxycarbonyl, carboxy, and $(NR^aR^b)$carbonyl; $R^2$ is hydrogen; $R^3$ is aryl wherein the aryl is phenyl substituted with $LR^4$; $R^4$ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; L is $(CH_2)_mN(R^5)C(O)N(R^6)(CH_2)_n$; $R^5$ and $R^6$ are hydrogen; m is 0; n is 0; Z is C; X is S; $R^a$ and $R^b$ are independently selected from the group consisting of hydrogen, alkyl, alkylcarbonyl, alkylsulfonyl, heteroarylalkyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is selected from the group consisting of hydrogen, alkoxycarbonyl, carboxy, and $(NR^aR^b)$carbonyl; $R^2$ is hydrogen; $R^3$ is aryl wherein the aryl is phenyl substituted with $NH_2$; Z is C; X is S; $R^a$ and $R^b$ are independently selected from the group consisting of hydrogen, alkyl, alkylcarbonyl, alkylsulfonyl, heteroarylalkyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is selected from the group consisting of hydrogen, alkoxycarbonyl, carboxy, and $(NR^aR^b)$carbonyl; $R^2$ is hydrogen; $R^3$ is heteroaryl wherein the heteroaryl is selected from the group consisting of benzofuranyl, benzothienyl, and indolyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; Z is C; X is S; $R^a$ and $R^b$ are independently selected from the group consisting of hydrogen, alkyl, alkylcarbonyl, alkylsulfonyl, heteroarylalkyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is selected from the group consisting of hydrogen, alkoxycarbonyl, carboxy, and $(NR^aR^b)$carbonyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; X is S; $R^a$ and $R^b$ are independently selected from the group consisting of hydrogen, alkyl, alkylcarbonyl, alkylsulfonyl, heteroarylalkyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is selected from the group consisting of heterocyclyl, heterocyclylalkynyl, heterocyclylcarbonyl, and heterocyclylalkyl; and X, $R^2$, and $R^3$ are as defined in formula (I).

In another embodiment, the present invention provides compounds of formula (I) wherein $R^1$ is selected from the group consisting of heterocyclyl, heterocyclylalkynyl, heterocyclylcarbonyl, and heterocyclylalkyl, wherein the heterocyclyl is selected from the group consisting of morpholinyl, piperazinyl, and piperidinyl, wherein the heterocyclyl is optionally substituted with 1 or 2 substituents selected from the group consisting of alkoxy, alkoxycarbonyl, alkyl, alkylcarbonyl, oxo, phenyl, pyrimidinyl, pyridinyl, and $(NR^aR^b)$ alkyl; $R^2$ is hydrogen; $R^3$ is aryl wherein the aryl is phenyl substituted with $LR^4$; $R^4$ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; L is $(CH_2)_mN(R^5)C(O)N(R^6)(CH_2)_n$; $R^5$ and $R^6$ are hydrogen; m is 0; n is 0; Z is C; X is S; $R^a$ and $R^b$ are independently selected from the group consisting of hydrogen, alkyl, alkylcarbonyl, alkylsulfonyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is selected from the group consisting of heterocyclyl, heterocyclylalkynyl, heterocyclylcarbonyl, and heterocyclylalkyl, wherein the heterocyclyl is selected from the group consisting of morpholinyl, piperazinyl, and piperidinyl, wherein the heterocyclyl is optionally substituted with 1 or 2 substituents selected from the group consisting of alkoxy, alkoxycarbonyl, alkyl, alkylcarbonyl, oxo, phenyl, pyrimidinyl, pyridinyl, and $(NR^aR^b)$ alkyl; $R^2$ is hydrogen; $R^3$ is aryl wherein the aryl is phenyl substituted with $NH_2$; Z is C; X is S; $R^a$ and $R^b$ are independently selected from the group consisting of hydrogen, alkyl, alkylcarbonyl, alkylsulfonyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is selected from the group consisting of heterocyclyl, heterocyclylalkynyl, heterocyclylcarbonyl, and heterocyclylalkyl, wherein the heterocyclyl is selected from the group consisting of morpholinyl, piperazinyl, and piperidinyl, wherein the heterocyclyl is optionally substituted with 1 or 2 substituents selected from the group consisting of alkoxy, alkoxycarbonyl, alkyl, alkylcarbonyl, oxo, phenyl, pyrimidinyl, pyridinyl, and $(NR^aR^b)$ alkyl; $R^2$ is hydrogen; $R^3$ is heteroaryl wherein the heteroaryl is selected from the group consisting of benzofuranyl, benzothienyl, and indolyl wherein the heteroaryl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, cyano, halo, haloalkoxy, haloalkyl, hydroxy, hydroxyalkyl, and nitro; Z is C; X is S; $R^a$ and $R^b$ are independently selected from the group consisting of hydrogen, alkyl, alkylcarbonyl, alkylsulfonyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is selected from the group consisting of heterocyclyl, heterocyclylalkynyl, heterocyclylcarbonyl, and heterocyclylalkyl, wherein the heterocyclyl is selected from the group consisting of morpholinyl, piperazinyl, and piperidinyl, wherein the heterocyclyl is optionally substituted with 1 or 2 substituents selected from the group consisting of alkoxy, alkoxycarbonyl, alkyl, alkylcarbonyl, oxo, phenyl, pyrimidinyl, pyridinyl, and $(NR^aR^b)$alkyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; X is S; $R^a$ and $R^b$ are independently selected from the group consisting of hydrogen, alkyl, alkylcarbonyl, alkylsulfonyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is selected from the group consisting of hydrogen, alkoxycarbonyl, carboxy, and carbonyl; $R^2$ is hydrogen; $R^3$ is aryl wherein the aryl is phenyl substituted with $LR^4$; $R^4$ is heteroaryl wherein the heteroaryl is selected from the group consisting of indolyl and thienyl wherein the heteroaryl is optionally substituted with 1 alkyl group wherein the preferred heteroaryl is 1-methyl-1H-indol-2-yl; L is $(CH_2)_mN(R^5)C(O)N(R^6)(CH_2)_n$; $R^5$ and $R^6$ are hydrogen; m is 0; n is 0; Z is C; X is S; $R^a$ and $R^b$ are independently selected from the group consisting of hydrogen, alkyl, alkylcarbonyl, alkylsulfonyl, heteroarylalkyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is heteroaryl wherein the heteroaryl is selected from the group consisting of benzothiazolyl, benzothienyl, benzoxazolyl, furyl, indolyl, pyrazolyl, pyrazinyl, pyridazinyl, pyridinyl, pyrimidinyl, pyrrolyl, and thienyl wherein the heteroaryl is optionally substituted with 1 or 2 substituents selected from the group consisting of alkoxy, alkyl, formyl, halogen, and haloalkyl; $R^2$ is hydrogen; $R^3$ is aryl wherein the aryl is phenyl substituted with $LR^4$; $R^4$ is heteroaryl wherein the heteroaryl is selected from the group consisting of indolyl and thienyl wherein the heteroaryl is optionally substituted with 1 alkyl group wherein the preferred heteoaryl is 1-methyl-1H-indol-2-yl; L is $(CH_2)_mN(R^5)C(O)N(R^6)(CH_2)_n$; $R^5$ and $R^6$ are hydrogen; m is 0; n is 0; Z is C; X is S; $R^a$ and $R^b$ are independently selected from the group consisting of hydrogen, alkyl, alkylcarbonyl, alkylsulfonyl, heteroarylalkyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is selected from the group consisting of hydrogen, alkoxycarbonyl, carboxy, and $(NR^aR^b)$carbonyl; $R^2$ is hydrogen; $R^3$ is aryl wherein the aryl is phenyl substituted with $LR^4$; $R^4$ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; L is $(CH_2)_mN(R^5)C(O)N(R^6)(CH_2)_n$; $R^5$ and $R^6$ are hydrogen; m is 0; n is 0; Z is C; X is O; $R^a$ and $R^b$ are independently selected from the group consisting of hydrogen, alkyl, alkylcarbonyl, alkylsulfonyl, heteroarylalkyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is aryl wherein the aryl is phenyl optionally substituted with 1, 2, or 3 substituents selected from the group consisting of alkoxy, alkoxycarbonyl, alkyl, alkylcarbonyl, alkylsulfanyl, alkylsulfonyl, carboxy, cyano, halo, haloalkoxy, haloalkyl, hydroxy, methylenedioxy, 4-methylpiperazin-1-yl, phenoxy, (3-piperidin-1-ylpropanoyl)amino, pyrrolidin-1-ylmethyl, $-NR^aR^b$, $(NR^aR^b)$alkyl, and $(NR^aR^b)$carbonyl; $R^2$ is hydrogen; $R^3$ is aryl wherein the aryl is phenyl substituted with $LR^4$; $R^4$ is aryl wherein the aryl is phenyl optionally substituted with 1 or 2 substituents selected from the group consisting of alkyl, alkylcarbonyl, cyano, halogen, and haloalkyl wherein the preferred groups are chloro, fluoro, methyl, and trifluoromethyl; L is $(CH_2)_mN(R^5)C(O)N(R^6)(CH_2)_n$; $R^5$ and $R^6$ are hydrogen; m is 0; n is 0; Z is C; X is O; $R^a$ and $R^b$ are independently selected from the group consisting of hydrogen, alkyl, alkylcarbonyl, alkylsulfonyl, and $(NR^cR^d)$alkylcarbonyl; and $R^c$ and $R^d$ are independently selected from the group consisting of hydrogen and alkyl.

In another embodiment, the present invention provides compounds of formula (I) wherein $R^1$ is heteroaryl wherein the heteroaryl is selected from the group consisting of benzothiazolyl, benzothienyl, benzoxazolyl, furyl, indolyl, pyrazolyl, pyrazinyl, pyridazinyl, pyridinyl, pyrimidinyl, pyrrolyl, and thienyl wherein the heteroaryl is optionally substituted with 1 or 2 substituents selected from the group consisting of alkoxy, alkyl, formyl, halogen, and haloalkyl; $R^2$ is hydrogen; $R^3$ is aryl wherein the aryl is phenyl substituted with $LR^4$; $R^4$ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; L is $(CH_2)_mN(R^5)C(O)N(R^6)(CH_2)_n$; $R^5$ and $R^6$ are hydrogen; m is 0; n is 0; Z is C; and X is O.

In another embodiment, the present invention provides compounds of formula (I) wherein $R^1$ is selected from the group consisting of alkynyl, arylalkynyl, aryloxyalkynyl, arylsulfanylalkynyl, cyanoalkynyl, cycloalkylalkoxyalkynyl, heteroarylalkynyl, hydroxyalkynyl, and $(NR^aR^b)$alkynyl; $R^2$ is hydrogen; $R^3$ is aryl wherein the aryl is phenyl substituted with $LR^4$; $R^4$ is aryl wherein the aryl is phenyl optionally substituted with 1 or 2 substituents independently selected from the group consisting of alkyl, alkylcarbonyl, cyano, halogen, and haloalkyl wherein the preferred groups are chloro, fluoro, methyl, and trifluoromethyl; L is $(CH_2)_mN(R^5)C(O)N(R^6)(CH_2)_n$; $R^5$ and $R^6$ are hydrogen; m is 0; n is 0; Z is C; X is O; and $R^a$ and $R^b$ are independently selected from the group consisting of hydrogen, alkyl, alkylcarbonyl, alkylsulfonyl, and heterocyclylcarbonyl wherein the heterocyclyl is pyridinyl.

In another embodiment, the present invention provides compounds of formula (I) wherein $R^1$ is selected from the group consisting of heterocyclyl, heterocyclylalkynyl, heterocyclylcarbonyl, and heterocyclylalkyl, wherein the heterocyclyl is selected from the group consisting of morpholinyl, piperazinyl, and piperidinyl, wherein the heterocyclyl is optionally substituted with 1 or 2 substituents selected from the group consisting of alkoxy, alkoxycarbonyl, alkyl, alkylcarbonyl, oxo, phenyl, pyrimidinyl, pyridinyl, and $(NR^aR^b)$alkyl; $R^2$ is hydrogen; $R^3$ is heterocyclyl wherein the heterocyclyl is selected from the group consisting of dihydroindolyl and dihydroisoindolyl wherein the heterocyclyl is optionally substituted with 1 or 2 substituents selected from the group consisting of alkenyl, alkoxy, alkoxyalkyl, alkoxycarbonyl, alkyl, alkylcarbonyl, alkylsulfanyl, alkynyl, carboxy, cyano, halo, haloalkoxy, haloalkyl, hydroxy, and hydroxyalkyl; Z is C; X is O; $R^a$ and $R^b$ are independently selected from the group consisting of hydrogen, alkyl, alkylcarbonyl, alkylsulfonyl, and $(NR^cR^d)$alkylcarbonyl;

and $R^c$ and $R^d$ are independently selected from the group consisting of hydrogen and alkyl.

In another embodiment, the present invention provides compounds of formula (I) wherein $R^2$ is hydrogen; $R^3$ is aryl wherein the aryl is phenyl substituted with alkoxy and $LR^4$; $R^4$ is heteroaryl wherein the heteroaryl is indolyl optionally substituted with an alkyl group wherein the preferred alkyl group is methyl; L is $NR^5C(O)(CH_2)_m$; $R^5$ and $R^6$ are hydrogen; m is 0; Z is C; X is S; and $R^1$ is as defined in formula (I).

In another embodiment, the present invention provides compounds of formula (I) wherein $R^1$ is aryl; $R^2$ is hydrogen; $R^3$ is aryl wherein the aryl is phenyl substituted with alkoxy and $LR^4$; $R^4$ is heteroaryl wherein the heteroaryl is indolyl optionally substituted with an alkyl group wherein the preferred alkyl group is methyl; L is $NR^5C(O)(CH_2)_m$; $R^5$ and $R^6$ are hydrogen; m is 0; Z is C; and X is S.

In another embodiment, the present invention provides compounds of formula (I) wherein $R^1$ is aryl wherein the aryl is phenyl optionally substituted with 1, 2, or 3 substituents selected from the group consisting of alkoxy, alkoxycarbonyl, alkyl, alkylcarbonyl, alkylsulfanyl, alkylsulfonyl, carboxy, cyano, halo, haloalkoxy, haloalkyl, hydroxy, methylenedioxy, 4-methylpiperazin-1-yl, phenoxy, (3-piperidin-1-ylpropanoyl)amino, pyrrolidin-1-ylmethyl, —$NR^aR^b$, ($NR^aR^b$)alkyl, and ($NR^aR^b$)carbonyl; $R^2$ is hydrogen; $R^3$ is aryl wherein the aryl is phenyl substituted with alkoxy and $LR^4$; $R^4$ is heteroaryl wherein the heteroaryl is indolyl optionally substituted with an alkyl group wherein the preferred alkyl group is methyl; L is ($NR^5C(O)(CH_2)_m$; $R^5$ and $R^6$ are hydrogen; m is 0; Z is C; X is S; $R^a$ and $R^b$ are independently selected from the group consisting of hydrogen, alkyl, alkylcarbonyl, alkylsulfonyl, and ($NR^cR^d$)alkylcarbonyl; and $R^c$ and $R^d$ are independently selected from the group consisting of hydrogen and alkyl.

In another embodiment, the present invention provides compounds of formula (I) wherein $R^1$ is selected from the group consisting of hydrogen, alkoxycarbonyl, carboxy, cyano, ($NR^aR^b$)alkenyl, and ($NR^aR^b$)carbonyl; $R^2$ is hydrogen; $R^3$ is aryl wherein the aryl is phenyl substituted with alkoxy and $LR^4$; $R^4$ is heteroaryl wherein the heteroaryl is indolyl optionally substituted with an alkyl group wherein the preferred alkyl group is methyl; L is ($NR^5C(O)(CH_2)_m$; $R^5$ and $R^6$ are hydrogen; m is 0; Z is C; X is S; and $R^a$ and $R^b$ are as defined in formula (I).

In another embodiment, the present invention provides compounds of formula (I) wherein $R^1$ is selected from the group consisting of hydrogen, alkoxycarbonyl, carboxy, cyano, ($NR^aR^b$)alkenyl, and ($NR^aR^b$)carbonyl; $R^2$ is hydrogen; $R^3$ is aryl wherein the aryl is phenyl substituted with alkoxy and $LR^4$; $R^4$ is heteroaryl wherein the heteroaryl is indolyl optionally substituted with an alkyl group wherein the preferred alkyl group is methyl; L is ($NR^5C(O)(CH_2)_m$; $R^5$ and $R^6$ are hydrogen; m is 0; Z is C; X is S; $R^a$ and $R^b$ are independently selected from the group consisting of hydrogen, alkyl, alkylcarbonyl, alkylsulfonyl, heteroarylalkyl, heterocyclyl, heterocyclylalkyl, and ($NR^cR^d$)alkylcarbonyl; and $R^c$ and $R^d$ are independently selected from the group consisting of hydrogen and alkyl.

In another embodiment, the present invention provides compounds of formula (I) wherein $R^1$ is selected from the group consisting of heterocyclyl, heterocyclylalkenyl, heterocyclylalkynyl, heterocyclylcarbonyl, and heterocyclylalkyl; $R^2$ is hydrogen; $R^3$ is aryl wherein the aryl is phenyl substituted with alkoxy and $LR^4$; $R^4$ is heteroaryl wherein the heteroaryl is indolyl optionally substituted with an alkyl group wherein the preferred alkyl group is methyl; L is ($NR^5C(O)(CH_2)_m$; $R^5$ and $R^6$ are hydrogen; m is 0; Z is C; and X is S.

In another embodiment, the present invention provides compounds of formula (I) wherein $R^1$ is selected from the group consisting of heterocyclyl, heterocyclylalkenyl, heterocyclylalkynyl, heterocyclylcarbonyl, and heterocyclylalkyl, wherein the heterocyclyl is selected from the group consisting of morpholinyl, piperazinyl, and piperidinyl, wherein the heterocyclyl is optionally substituted with 1 or 2 substituents selected from the group consisting of alkoxy, alkoxycarbonyl, alkyl, alkylcarbonyl, oxo, phenyl, pyrimidinyl, pyridinyl, and ($NR^aR^b$)alkyl; $R^2$ is hydrogen; $R^3$ is aryl wherein the aryl is phenyl substituted with alkoxy and $LR^4$; $R^4$ is heteroaryl wherein the heteroaryl is indolyl optionally substituted with an alkyl group wherein the preferred alkyl group is methyl; L is ($NR^5C(O)(CH_2)_m$; $R^5$ and $R^6$ are hydrogen; m is 0; Z is C; X is S; $R^a$ and $R^b$ are independently selected from the group consisting of hydrogen, alkyl, alkylcarbonyl, alkylsulfonyl, and ($NR^cR^d$)alkylcarbonyl; and $R^c$ and $R^d$ are independently selected from the group consisting of hydrogen and alkyl.

In another embodiment, the present invention provides compounds of formula (I) wherein $R^1$ is selected from the group consisting of heteroaryl, heteroarylalkyl, and heteroarylcarbonyl; $R^2$ is hydrogen; $R^3$ is aryl wherein the aryl is phenyl substituted with alkoxy and $LR^4$; $R^4$ is heteroaryl wherein the heteroaryl is indolyl optionally substituted with an alkyl group wherein the preferred alkyl group is methyl; L is ($NR^5C(O)(CH_2)_m$; $R^5$ and $R^6$ are hydrogen; m is 0; Z is C; and X is S.

In another embodiment, the present invention provides compounds of formula (I) wherein $R^1$ is heteroaryl wherein the heteroaryl is selected from the group consisting of benzothiazolyl, benzothienyl, benzoxazolyl, furyl, indolyl, pyrazolyl, pyrazinyl, pyridazinyl, pyridinyl, pyrimidinyl, pyrrolyl, and thienyl wherein the heteroaryl is optionally substituted with 1 or 2 substituents selected from the group consisting of alkoxy, alkyl, formyl, halogen, haloalkyl, $NR^aR^b$, and ($NR^aR^b$)carbonyl; $R^2$ is hydrogen; $R^3$ is aryl wherein the aryl is phenyl substituted with alkoxy and $LR^4$; $R^4$ is heteroaryl wherein the heteroaryl is indolyl optionally substituted with an alkyl group wherein the preferred alkyl group is methyl; L is ($NR^5C(O)(CH_2)_m$; $R^5$ and $R^6$ are hydrogen; m is 0; Z is C; X is S; $R^a$ and $R^b$ are independently selected from the group consisting of hydrogen, alkyl, alkylcarbonyl, alkylsulfonyl, and ($NR^cR^d$)alkylcarbonyl; and $R^c$ and $R^d$ are independently selected from the group consisting of hydrogen and alkyl.

In another embodiment the present invention provides a pharmaceutical composition comprising a compound of formula (I), or a therapeutically acceptable salt thereof, in combination with a therapeutically acceptable carrier.

In another embodiment the present invention provides a method for inhibiting one or more protein kinases in a patient in recognized need of such treatment comprising administering to the patient a therapeutically acceptable amount of a compound of formula (I), or a therapeutically acceptable salt thereof. Preferably the protein kinases are selected from the group consisting of KDR, Ckit, CSF-1R, PDGFRβ, PDGFRα, Flt-1, Flt-3, Flt-4, Tie-2, Lck, Src, Fyn, Lyn, Blk, Hck, Fgr, Cot, and Yes. More preferably the protein kinases are selected from the group consisting of KDR and Lck.

In another embodiment the present invention provides a method for treating a condition in a patient comprising administering a therapeutically effective amount of a compound of formula (I), or a therapeutically acceptable salt thereof, to the patient, wherein the condition is selected from the group consisting of an ocular condition, a cardiovascular condition, a cancer, Crow-Fukase (POEMS) syndrome, a diabetic condition, sickle cell anemia, chronic inflammation, systemic lupus, glomerulonephritis, synovitis, inflammatory bowel disease, Crohn's disease, rheumatoid arthritis, osteoarthritis, multiple sclerosis, graft rejection, lyme disease, sepsis, von Hippel Lindau disease, pemphigoid, psoriasis, Paget's disease, polycystic kidney disease, fibrosis, sarcoidosis, cirrhosis, thyroditis, hyperviscosity syndrome, Osler-Weber-Rendu disease, chronic occlusive pulmonary disease, asthma or edema following burns, trauma, radiation, stroke, hypoxia, ischemia, overian hyperstimulation syndrome, preecampsia, menometrorrhagia, endometriosis, or infection by Herpes simplex, Herpes Zoster, human immunodeficiency virus, parapoxyvirus, protozoa, and toxoplasmosis. More preferably the condition is a cancer.

DETAILED DESCRIPTION OF THE INVENTION

All publications, issued patents, and patent applications cited herein are hereby incorporated by reference.

As used in the present specification the following terms have the meanings indicated:

As used herein, the singular forms "a", "an", and "the" include plural reference unless the context clearly dictates otherwise.

The term "alkenyl," as used herein, refers to a straight or branched chain group of two to ten carbon atoms containing at least one carbon-carbon double bond. Preferred alkenyl groups of the present invention contain two to three carbon atoms.

The term "alkoxy," as used herein, refers to an alkyl group attached to the parent molecular moiety through an oxygen atom.

The term "alkoxyalkyl," as used herein, refers to an alkyl group substituted with at least one alkoxy group.

The term "alkoxycarbonyl," as used herein, refers to an alkoxy group attached to the parent molecular moiety through a carbonyl group.

The term "alkoxycarbonylalkenyl," as used herein, refers to an alkenyl group substituted with at least one alkoxycarbonyl group.

The term "alkoxycarbonylalkyl," as used herein, refers to an alkyl group substituted with at least one alkoxycarbonyl group.

The term "alkoxycarbonylalkynyl," as used herein, refers to an alkynyl group substituted with at least one alkoxycarbonyl group.

The term "alkyl," as used herein, refers to a group derived from a straight or branched chain saturated hydrocarbon containing from one to ten carbon atoms. Preferred alkyl groups of the present invention contain one to four carbon atoms.

The term "alkylcarbonyl," as used herein, refers to an alkyl group attached to the parent molecular moiety through a carbonyl group.

The term "alkylsulfanyl," as used herein, refers to an alkyl group attached to the parent molecular moiety through a sulfur atom.

The term "alkylsulfanylalkyl," as used herein, refers to an alkyl group substituted with at least one alkylsulfanyl group.

The term "alkylsulfonyl," as used herein, refers to an alkyl group attached to the parent molecular moiety through a sulfonyl group.

The term "alkynyl," as used herein, refers to a straight or branched chain hydrocarbon of two to ten carbon atoms containing at least one carbon-carbon triple bond. Preferred alkynyl groups of the present invention contain between two and six carbon atoms.

The term "aryl," as used herein, refers to a phenyl group, or a bicyclic or tricyclic fused ring system wherein one or more of the fused rings is a phenyl group. Bicyclic fused ring systems are exemplified by a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Representative examples of aryl groups include, but are not limited to, anthracenyl, azulenyl, fluorenyl, indanyl, indenyl, naphthyl, phenyl, and tetrahydronaphthyl. The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylsulfanyl, alkylsulfonyl, alkynyl, a second aryl group, arylalkenyl, arylalkoxy, arylalkyl, aryloxy, carboxy, carboxyalkenyl, carboxyalkyl, cyano, formyl, formylalkenyl, halo, haloalkoxy, haloalkyl, heteroaryl, heteroarylalkyl, heterocyclyl, heterocyclylalkyl, heterocyclylcarbonyl, hydroxy, hydroxyalkyl, methylenedioxy, nitro, $NR^aR^b$, $(NR^aR^b)$alkyl, $(NR^aR^b)$carbonyl, and oxo; wherein the second aryl group, the aryl part of the arylalkenyl, the arylalkoxy, the arylalkyl, and the aryloxy, the heteroaryl, the heteroaryl part of the heteroarylalkyl, the heterocyclyl, and the heterocyclyl part of the heterocyclylalkyl can be further optionally substituted with one, two, three, four, or five substituents independently selected from the group consisting of alkenyl, alkoxy, alkyl, halo, haloalkoxy, haloalkyl, hydroxy, nitro, and heterocyclyl wherein the heterocyclyl can be further optionally substituted with one, two, three, four, or five substituents independently selected from the group consisting of alkenyl, alkoxy, alkyl, halo, haloalkoxy, haloalkyl, hydroxy, and nitro.

The term "arylalkenyl," as used herein, refers to an alkenyl group substituted with at least one aryl group.

The term "arylalkoxy," as used herein, refers to an arylalkyl group attached to the parent molecular moiety through an oxygen atom.

The term "arylalkoxycarbonyl," as used herein, refers to an arylalkoxy group attached to the parent molecular moiety through a carbonyl group.

The term "arylalkoxycarbonylalkyl," as used herein, refers to an alkyl group substituted with at least one arylalkoxycarbonyl group.

The term "arylalkyl," as used herein, refers to an alkyl group substituted with at least one aryl group.

The term "arylalkynyl," as used herein, refers to an alkynyl group substituted with at least one aryl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with at least one aryloxy group.

The term "aryloxyalkynyl," as used herein, refers to an alkynyl group substituted with at least one aryloxy group.

The term "arylsulfanyl," as used herein, refers to an aryl group attached to the parent molecular moiety through a sulfur atom.

The term "arylsulfanylalkyl," as used herein, refers to an alkyl group substituted with at least one arylsulfanyl group.

The term "arylsulfanylalkynyl," as used herein, refers to an alkynyl group substituted with at least one arylsulfanyl group.

The term "arylsulfonyl," as used herein, refers to an aryl group attached to the parent molecular moiety through a sulfonyl group.

The term "arylsulfonyloxy," as used herein, refers to an arylsulfonyl group attached to the parent molecular moiety through an oxygen atom.

The term "arylsulfonyloxyalkenyl," as used herein, refers to an alkenyl group substituted with at least one arylsulfonyloxy group.

The term "carbonyl," as used herein, refers to —C(O)—.

The term "carboxy," as used herein, refers to —CO$_2$H.

The term "carboxyalkenyl," as used herein, refers to an alkenyl group substituted with at least one carboxy group.

The term "carboxyalkyl," as used herein, refers to an alkyl group substituted with at least one carboxy group.

The term "carboxyalkenyl," as used herein, refers to an alkenyl group substituted with at least one carboxy group.

The term "carboxyalkynyl," as used herein, refers to an alkynyl group substituted with at least one carboxy group.

The term "cyano," as used herein, refers to —CN.

The term "cyanoalkynyl," as used herein, refers to an alkynyl group substituted with at least one cyano group.

The term "cycloalkenyl," as used herein, refers to a non-aromatic cyclic or bicyclic ring system having three to ten carbon atoms and one to three rings, wherein each five-membered ring has one double bond, each six-membered ring has one or two double bonds, each seven- and eight-membered ring has one to three double bonds, and each nine-to ten-membered ring has one to four double bonds. Representative examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to twelve carbon atoms. Representative examples of cycloalkyl groups include, but are not limited to, cyclopropyl, cyclopentyl, bicyclo[3.1.1]heptyl, and adamantyl. The cycloalkyl groups of the present invention can be optionally substituted with one, two, three, four, or five substituents independently selected from the group consisting of alkoxy, alkyl, cyano, halo, haloalkoxy, haloalkyl, hydroxy, hydroxyalkyl, nitro, NR$^a$R$^b$, and spiroheterocyclyl. A preferred cycloalkyl group of the present invention is cyclohexyl.

The term "cycloalkylalkoxy," as used herein, refers to an alkoxy group substituted with at least one cycloalkyl group.

The term "cycloalkylalkoxyalkynyl," as used herein, refers to an alkynyl group substituted with at least one cycloalkylalkoxy group.

The term "cycloalkylalkenyl," as used herein, refers to an alkenyl group substituted with at least one cycloalkyl group.

The term "cycloalkylalkyl," as used herein, refers to an alkyl group substituted with at least one cycloalkyl group.

The term "formyl," as used herein, refers to —CHO.

The term "formylalkenyl," as used herein, refers to an alkenyl group substituted with at least one formyl group.

The term "formylalkyl," as used herein, refers to an alkyl group substituted with at least one formyl group.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms. A preferred haloalkyl group of the present invention is trfluoromethyl.

The term "heteroalkylene," as used herein, refers to a divalent group of two to eight atoms derived from a saturated straight or branched chain containing one or two heteroatoms independently selected from the group consisting of nitrogen, oxygen, and sulfur, wherein the remaining atoms are carbon. The heteroalkylene groups of the present invention are attached to the parent molecular moiety through the carbon atoms or the heteroatoms in the chain.

The term "heteroaryl," as used herein, refers to an aromatic five- or six-membered ring where at least one atom is selected from the group consisting of N, O, and S, and the remaining atoms are carbon. The five-membered rings have two double bonds, and the six-membered rings have three double bonds. The heteroaryl groups are connected to the parent molecular moiety through a substitutable carbon or nitrogen atom in the ring. The term "heteroaryl" also includes bicyclic systems where a heteroaryl ring is fused to a phenyl group, a monocyclic cycloalkenyl group, as defined herein, a monocyclic cycloalkyl group, as defined herein, a monocyclic heterocyclyl group, as defined herein, or an additional monocyclic heteroaryl group; and tricyclic systems where a bicyclic system is fused to a phenyl group, a monocyclic cycloalkenyl group, as defined herein, a monocyclic cycloalkyl group, as defined herein, a heterocyclyl group, as defined herein, or an additional monocyclic heteroaryl group. Representative examples of heteroaryl groups include, but are not limited to, benzimidazolyl, benzoxadiazolyl, benzoxazolyl, benzofuranyl, benzisoxazolyl, benzothiazolyl, benzothienyl, cinnolinyl, dibenzofuranyl, furanyl, imidazolyl, indazolyl, indolyl, isoxazolyl, isoquinolinyl, isothiazolyl, naphthyridinyl, oxadiazolyl, oxadiazolyl, oxazolyl, pyridinyl, pyridazinyl, pyrimidinyl, pyrazinyl, pyrazolyl, pyrrolyl, quinolinyl, thiazolyl, thienopyridinyl, thienyl, triazolyl, thiadiazolyl, and triazinyl. Preferred heteroaryl groups of the present invention are benzofuranyl, benzoxazolyl, furyl, imidazolyl, indolyl, isoquinolinyl, isoxazolyl, pyrazinyl, pyrazolyl, pyridinyl, pyrimidinyl, pyrrolyl, and thienyl. The heteroaryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylsulfanyl, alkynyl, aryl, arylalkenyl, arylalkoxy, arylalkyl, cyano, formyl, halo, haloalkoxy, haloalkyl, a second heteroaryl group, heteroarylalkyl, heterocyclyl, heterocyclylalkyl, hydroxy, hydroxyalkyl, nitro, NR$^a$R$^b$, (NR$^a$R$^b$)alkyl, (NR$^a$R$^b$)carbonyl, and oxo; wherein the aryl, the aryl part of the arylalkenyl, the arylalkoxy, and the arylalkyl, the second heteroaryl group, the heteroaryl part of the heteroarylalkyl, the heterocyclyl, and the heterocyclyl part of the heterocyclylalkyl can be further optionally substituted with one, two, three, four, or five substituents independently selected from the group consisting of alkenyl, alkoxy, alkyl, halo, haloalkoxy, haloalkyl, hydroxy, and nitro.

The term "heteroarylalkenyl," as used herein, refers to an alkenyl group substituted with at least one heteroaryl group.

The term "heteroarylalkyl," as used herein, refers to an alkyl group substituted with at least one heteroaryl group.

The term "heteroarylalkynyl," as used herein, refers to an alkynyl group substituted with at least one heteroaryl group.

The term "heteroarylcarbonyl," as used herein, refers to a heteroaryl group attached to the parent molecular moiety through a carbonyl group.

The term "heteroarylcarbonylalkenyl," as used herein, refers to an alkenyl group substituted with at least one heteroarylcarbonyl group.

The term "heteroarylcarbonylalkyl," as used herein, refers to an alkyl group substituted with at least one heteroarylcarbonyl group.

The term "heteroarylsulfonyl," as used herein, refers to a heteroaryl group attached to the parent molecular moiety through a carbonyl group.

The term "heterocyclyl," as used herein, refers to a non-aromatic four-, five-, six-, seven-, or eight-membered monocyclic or bicyclic ring where at least one atom is selected from the group consisting of oxygen, nitrogen, and sulfur. The four- and five-membered rings have zero or one double bonds and the six- and seven-membered rings have zero, one, or two double bonds. The heterocyclyl groups of the invention are connected to the parent molecular group through a substitutable carbon or nitrogen atom in the ring. The term "heterocyclyl" also includes systems where a heterocyclyl ring is fused to a phenyl group, a monocyclic cycloalkenyl group, as defined herein, a monocyclic cycloalkyl group, as defined herein, or an additional monocyclic heterocyclyl group; and tricyclic systems where a bicyclic system is fused to a phenyl group, a monocyclic cycloalkenyl group, as defined herein, a monocyclic cycloalkyl group, as defined herein, or an additional monocyclic heterocyclyl group. Representative examples of heterocyclyl groups include, but are not limited to, azetidinyl, benzodioxolyl, benzothiazolyl, diazepanyl, dihydroindolyl, dihydroisoindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, and thiomorpholinyl. Preferred heterocyclyl groups of the present invention are benzodioxolyl, diazepinyl, imidazolidinyl, morpholinyl, piperazinyl, piperidinyl, pyrrolidinyl, and tetrahydropyranyl. The heterocyclyl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylsulfanyl, alkylsulfonyl, alkynyl, aryl, arylalkenyl, arylalkoxy, arylalkyl, carboxy, carboxyalkyl, cyano, cyanoalkyl, formyl, halo, haloalkoxy, haloalkyl, heteroaryl, heteroarylalkyl, heteroarylcarbonyl, a second heterocyclyl group, heterocyclylalkyl, hydroxy, hydroxyalkyl, nitro, $NR^aR^b$, $(NR^aR^b)$alkyl, $(NR^aR^b)$alkylcarbonyl, $(NR^aR^b)$carbonyl, $(NR^aR^b)$carbonylalkyl, $(NR^aR^b)$sulfonyl,oxo, and spiroheterocyclyl; wherein the aryl group, the aryl part of the arylalkenyl, the arylalkoxy, and the arylalkyl, the heteroaryl, the heteroaryl part of the heteroarylalkyl and the heteroarylcarbonyl, the second heterocyclyl group, and the heterocyclyl part of the heterocylylalkyl can be further optionally substituted with one, two, three, four, or five substituents independently selected from the group consisting of alkenyl, alkoxy, alkyl, halo, haloalkoxy, haloalkyl, hydroxy, and nitro.

The term "heterocyclylalkenyl," as used herein, refers to an alkenyl group substituted with at least one heterocyclyl group.

The term "heterocyclylalkyl," as used herein, refers to an alkyl group substituted with at least one heterocyclyl group.

The term "heterocyclylalkylcarbonyl," as used herein, refers to a heterocyclylalkyl group attached to the parent molecular moiety through a carbonyl group.

The term "heterocyclylalkynyl," as used herein, refers to an alkynyl group substituted with at least one heterocyclyl group.

The term "heterocyclylcarbonyl," as used herein, refers to a heterocyclyl group attached to the parent molecular moiety through a carbonyl group.

The term "heterocyclylcarbonylalkenyl," as used herein, refers to an alkenyl group substituted with at least one heterocyclylcarbonyl group.

The term "heterocyclylcarbonylalkyl," as used herein, refers to an alkyl group substituted with at least one heterocyclylcarbonyl group.

The term "hydroxy," as used herein, refers to —OH.

The term "hydroxyalkenyl," as used herein, refers to an alkenyl group substituted with at least one hydroxy group.

The term "hydroxyalkoxy," as used herein, refers to a hydroxyalkyl group attached to the parent molecular moiety through an oxygen atom.

The term "hydroxyalkoxyalkyl," as used herein, refers to an alkyl group substituted with at least one hydroxyalkoxy group.

The term "hydroxyalkyl," as used herein, refers to an alkyl group substituted with at least one hydroxy group.

The term "hydroxyalkynyl," as used herein, refers to an alkynyl group substituted with at least one hydroxy group.

The term "methylenedioxy" as used herein, means a —OCH$_2$O— group wherein the oxygen atoms of the methylenedioxy are attached to the parent molecular moiety through two adjacent carbon atoms.

The term "nitro," as used herein, refers to —NO$_2$.

The term "nitroalkenyl," as used herein, refers to an alkenyl group substituted with at least one nitro group.

The term "nitroalkyl," as used herein, refers to an alkyl group substituted with at least one nitro group.

The term "nitroalkynyl," as used herein, refers to an alkynyl group substituted with at least one nitro group.

The term "$NR^aR^b$," as used herein, refers to two groups, $R^a$ and $R^b$, which are attached to the parent molecular moiety through a nitrogen atom. $R^a$ and $R^b$ are independently selected from the group consisting of hydrogen, alkenyl, alkoxyalkyl, alkoxycarbonyl, alkoxycarbonylalkyl, alkyl, alkylcarbonyl, alkylsulfanylalkyl, alkylsulfonyl, aryl, arylalkoxycarbonyl, arylalkoxycarbonylalkyl, arylalkyl, arylcarbonyl, arylsulfonyl, carboxyalkyl, cycloalkyl, cycloalkylalkyl, formylalkyl, heteroaryl, heteroarylalkyl, heteroarylcarbonyl, heteroarylsulfonyl, heterocyclyl, heterocyclylalkyl, heterocyclylalkylcarbonyl, heterocyclylcarbonyl, heterocyclylsulfonyl, hydroxyalkoxyalkyl, hydroxyalkyl, $(NR^cR^d)$alkyl, $(NR^cR^d)$alkylcarbonyl, $(NR^cR^d)$carbonyl, and $(NR^cR^d)$carbonylalkyl, wherein the aryl, the aryl part of the arylalkoxycarbonyl, the arylalkoxycarbonylalkyl, the arylalkyl, the arylcarbonyl, and the arylsulfonyl, the cycloalkyl, the cycloalkyl part of the cycloalkylalkyl, the heteroaryl, the heteroaryl part of the heteroarylalkyl, and the heteroarylcarbonyl, the heterocyclyl, and the heterocyclyl part of the heterocyclylalkyl and the heterocyclylcarbonyl can be further optionally substituted with one, two, three, four, or five substituents independently selected from the group consisting of alkenyl, alkoxy, alkoxycarbonyl, alkyl, alkylcarbonyl, aryl, arylalkyl, halo, haloalkoxy, haloalkyl, hydroxy, nitro, $NR^cR^d$, $(NR^cR^d)$alkyl, $(NR^cR^d)$alkylcarbonyl, $(NR^cR^d)$carbonyl, $(NR^cR^d)$carbonylalkyl, oxo, and spiroheterocyclyl, wherein the aryl and the aryl part of the arylalkyl can be substituted with one, two, three, four, or five substituents independently selected from the group consisting of alkoxy, alkyl, cyano, halo, haloalkoxy, haloalkyl, nitro, and oxo.

The term "(NR$^a$R$^b$)alkenyl," as used herein, refers to an alkenyl group substituted with at least one NR$^a$R$^b$ group.

The term "(NR$^a$R$^b$)alkyl," as used herein, refers to an alkyl group substituted with at least one NR$^a$R$^b$ group.

The term "(NR$^a$R$^b$)alkylcarbonyl," as used herein, refers to a (NR$^a$R$^b$)alkyl group attached to the parent molecular moiety through a carbonyl group.

The term "(NR$^a$R$^b$)alkynyl," as used herein, refers to an alkynyl group substituted with at least one NR$^a$R$^b$ group.

The term "(NR$^a$R$^b$)carbonyl," as used herein, refers to an NR$^a$R$^b$ group attached to the parent molecular moiety through a carbonyl group.

The term "(NR$^a$R$^b$)carbonylalkenyl," as used herein, refers to an alkenyl group substituted with at least one (NR$^a$R$^b$)carbonyl group.

The term "(NR$^a$R$^b$)carbonylalkyl," as used herein, refers to an alkyl group substituted with at least one (NR$^a$R$^b$)carbonyl group.

The term "(NR$^a$R$^b$)carbonylalkynyl," as used herein, refers to an alkynyl group substituted with at least one (NR$^a$R$^b$)carbonyl group.

The term "NR$^c$R$^d$," as used herein, refers to two groups, R$^c$ and R$^d$, which are attached to the parent molecular moiety through a nitrogen atom. R$^c$ and R$^d$ are independently selected from the group consisting of hydrogen, alkoxy, alkyl, aryl, carboxyalkyl, cycloalkyl, haloalkyl, heteroaryl, heterocyclyl, heterocyclylalkyl, hydroxyalkoxyalkyl, hydroxyalkyl, and (NR$^e$R$^f$)alkyl, wherein the aryl, the heteroaryl, and the heterocyclyl can be optionally substituted with one, two, three, four, or five substituents independently selected from the group consisting of alkenyl, alkoxy, alkyl, halo, haloalkoxy, haloalkyl, hydroxy, and nitro.

The term "(NR$^c$R$^d$)alkyl," as used herein, refers to an alkyl group substituted with at least one NR$^c$R$^d$ group.

The term "(NR$^c$R$^d$)alkylcarbonyl," as used herein, refers to a (NR$^c$R$^d$)alkyl group attached to the parent molecular moiety through a carbonyl group.

The term "(NR$^c$R$^d$)carbonyl," as used herein, refers to an NR$^c$R$^d$ group attached to the parent molecular moiety through a carbonyl group.

The term "(NR$^c$R$^d$)carbonylalkyl," as used herein refers to an alkyl group substituted with at least one (NR$^c$R$^d$)carbonyl group.

The term "NR$^e$R$^f$," as used herein, refers to two groups, R$^e$ and R$^f$, which are attached to the parent molecular moiety through a nitrogen atom. R$^e$ and R$^f$ are independently selected from the group consisting of hydrogen and alkyl.

The term "(NR$^e$R$^f$)alkyl," as used herein, refers to an alkyl group substituted with at least one NR$^e$R$^f$ group.

The term "oxo," as used herein, refers to (=O).

The term "spiroheterocyclyl," as used herein, refers to a heteroalkylene diradical, each end of which is attached to the same carbon atom of the parent molecular moiety. Examples of spiroheterocyclyl groups include, but are not limited to, dioxanyl, dioxolanyl, tetrahydrofuranyl, and pyrrolidinyl. The spiroheterocyclyl groups of the present invention can be optionally substituted with one, two, three, or four groups independently selected from the group consisting of alkoxy, alkyl, and halo.

The term "sulfonyl," as used herein, refers to —SO$_2$—.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an NR$^a$R$^b$ or NR$^c$R$^d$ group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, NR$^a$R$^b$ and NR$^c$R$^d$ groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

Asymmetric centers exist in the compounds of the present invention. These centers are designated by the symbols "R" or "S," depending on the configuration of substituents around the chiral carbon atom. It should be understood that the invention encompasses all stereochemical isomeric forms, or mixtures thereof, which possess the ability to inhibit one or more protein kinases. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Because carbon-carbon double bonds exist in the present compounds, the invention contemplates various geometric isomers and mixtures thereof resulting from the arrangement of substituents around these carbon-carbon double bonds. It should be understood that the invention encompasses both isomeric forms, or mixtures thereof, which possess the ability to inhibit one or more protein kinases. These substituents are designated as being in the E or Z configuration wherein the term "E" represents higher order substituents on opposite sides of the carbon-carbon double bond, and the term "Z" represents higher order substituents on the same side of the carbon-carbon double bond.

It should be understood that the terms "administering a" and "administering to," refer to providing a compound of the present invention to a patient in need of treatment.

The patient to be treated can be any animal, and is preferably a mammal, such as a domesticated animal or a livestock animal. More preferably, the patient is a human.

When it is possible that, for use in therapy, therapeutically effective amounts of a compound of formula (I), as well as therapeutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I), or therapeutically acceptable salts thereof, and one or more pharmaceutically acceptable carriers, diluents, or excipients. The compounds of formula (I) and therapeutically acceptable salts thereof are as described above. The carrier(s), diluent(s), or excipient(s) must be acceptable in the sense of being compatible with the other ingredients of the formulation and not deleterious to the recepient thereof. In accordance with another aspect of the invention there is also provided a process for the preparation of a pharmaceutical formulation including admixing a compound of formula (I), or a therapeutically acceptable salt thereof, with one or more pharmaceutically acceptable carriers, diluents, or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of formula (I), depending on the condition being treated, the severity of the condition, the time of administration, the route of administration, the rate of excretion of the compound employed, the duration of treatment, and the age, gender, weight, and condition of the patient, or pharmaceutical formulations may be presented in unit dose forms containing a predetermined amount of an active ingredient per dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intramuscular, intravenous, or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical cerrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, wasces, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an altenative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present invention can also be combined ith a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added ot these coatings to distinguis different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxy ethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or susain the release as for example by coating or embedding particulate material in polymers, wax, or the like.

The compounds of formula (I), and therapeutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I), and therapeutically acceptable salts thereof, may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of a protein kinase-mediated condition will generally be in the range of 0.1 to 100 mg/kg body weight of recipient (mammal) per day and more usually in the range of 1 to 10 mg/kg body weight per day.

The compounds of the present invention and therapeutically acceptable salts thereof, may be employed alone or in combination with other therapeutic agents for the treatment of the conditions mentioned herein. For example, in anti-cancer therapy, combination with other chemotherapeutic, hormonal, or antibody agents is envisaged as well as combination with surgical therapy and radiotherapy. Combination therapies according to the present invention thus comprise the administration of at least one compound of formula (I), or a therapeutically acceptable salt thereof, and the use of at least one other cancer treatment method. Preferably, combination therapies according to the present invention comprise the administration of at least one other pharmaceutically active agent, preferably an anti-neoplastic agent. The compound(s) of formula (I) and the other pharmaceutically active agent(s) may be administered together or separately and when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of formula (I), or therapeutically acceptable salts thereof, and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I), or therapeutically acceptable salts thereof, with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may include anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts of formula (I) include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludarabine, methotrexate, cladrabine, cytarabine, mercaptopurine, and thioguanine; and camptothecins such as 9-amino camptothecin, irinotecan, topotecan, CPT-11, and the various optial forms of 7-(-4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumor antibiotics such as doxorubicin, daunomycin, epirubicin, idarubicin, mitomycin-C, dacttainomycin, and mithramycin; and platinum coordination complexes such as cisplatin, carboplatin, and oxaliplatin; and (3) other chemotherapeutic agents including, but not limited to, anti-estrogens such as tomixefen, toremifene, raloxifene, droloxifene, and iodoxyfene; progesterogens such as megastrol acetate; aromatase inhibitors such as anastrozole, letrazole, vorazole, and exemestane; antiandrogens such as flutamide, nilutamide, bicalutamide, and cyproterone acetate; LHRH agonists and antagonists such as goserelin acetate and luprolide, testosterone 5α-dihydroreductase inhibitors such as finasteride; metallopreteinase inhibitors such as marimastat; antiprogestogens; urokinase plasminogen activator receptor function inhibitors; growth factor function inhibitors such as inhibitors of the functions of hepatocyte growth factor; erb-B2, erb-B4, and epidermal growth factor receptor (EGFR).

In the treatment of immunologic disorders, combination with other agents is also envisaged. Examples of other therapeutic agents include the following: ras inhibitors, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, P13 kinase inhibitors, cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal anti-inflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-alpha inhibitors such as tenidap, anti-TNF antibodies or soluble TNF receptor, and rapamycin (sirolimus or Rapamune) or derivatives thereof. The compound(s) of formula (I) and the other pharmaceutically active agent(s) may be administered together or separately and when administered separately this may occur simultaneously or sequentially in any order. The amounts of the compound(s) of formula (I) and the other pharmaceutically active agent(s) and the relative timings of administration will be selected in order to achieve the desired combined therapeutic effect.

Determination of Biological Activity

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., Nature. 373:536–539) by a test compound relative to control.

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing $(His)_6KDR(aa789-1354)$ were lysed by adding 50 ml of Triton X-100 lysis buffer (20 mM Tris, pH 8.0, 137 mM NaCl, 10% glycerol, 1% Triton X-100, 1 mM PMSF, 10 µg/ml aprotinin, 1 µg/ml leupeptin) to the cell pellet from 1 L of cell culture. The lysate was centrifuged at 19,000 rpm in a Sorval SS-34 rotor for 30 min at 4° C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Human Tie-2 Kinase Production and Purification

The coding sequence for the human Tie-2 intra-cellular domain (aa775-1124) was generated through PCR using cDNAs isolated from human placenta as a template. A poly-$His_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (Cat # E-3641; 500 units/50 µL) and the EGF ligand was acquired from Oncogene Research Products/Calbiochem (Cat # PF011-100).

Expression of ZAP70

The baculoviral expression vector used was pVL1393. (Pharmingen, Los Angeles, Calif.) The nucleotide sequence encoding amino acids M(H)6 LVP$_9$S was placed 5' to the region encoding the entirety of ZAP70 (amino acids 1–619). The nucleotide sequence encoding the ZAP70 coding region was generated through PCR using cDNA libraries isolated from Jurkat immortalized T-cells. The histidine residues enabled affinity purification of the protein (vide infra). The LVPR$_9$S bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70

SF-9 cells were lysed in a buffer consisting of 20 mM Tris, pH 8.0, 137 mM NaCl, 10% glycerol, 1% Triton X-100, 1 mM PMSF, 1 µg/ml leupeptin, 10 µg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Protein Kinase Source

Lck, Fyn, Src, Blk, Csk, and Lyn, and truncated forms thereof may be commercially obtained (e.g., from Upstate Biotechnology Inc. (Saranac Lake, N.Y) and Santa Cruz Biotechnology Inc. (Santa Cruz, Calif.)) or purified from known natural or recombinant sources using conventional methods.

Enzyme Linked Immunosorbent Assay (ELISA) For PTKs

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: Manual of Clinical Immunology, 2d ed., edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly(Glu$_4$ Tyr), 20,000–50,000 MW) was employed together with ATP (typically 5 µM) at concentrations approximately twice the apparent Km in the assay.

The following procedure was used to assay the inhibitory effect of compounds of this invention on KDR, Flt-1, Flt-4, Tie-1, Tie-2, EGFR, FGFR, PDGFR, IGF-1-R, c-Met, Lck, hck, Blk, Csk, Src, Lyn, fgr, Fyn and ZAP70 tyrosine kinase activity:

Buffers and Solutions:

PGTPoly (Glu,Tyr) 4:1

Store powder at −20° C. Dissolve powder in phosphate buffered saline (PBS) for 50 mg/ml solution. Store 1 ml aliquots at −20° C. When making plates dilute to 250 µg/ml in Gibco PBS.

Reaction Buffer: 100 mM Hepes, 20 mM MgCl$_2$, 4 mM MnCl$_2$, 5 mM DTT, 0.02% BSA, 200 µM NaVO$_4$, pH 7.10

ATP: Store aliquots of 100 mM at −20° C. Dilute to 20 µM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/ml, frozen) in PBS to a 250 µg/ml. Add 125 µl per well of Corning modified flat bottom high affinity ELISA plates (Corning #25805-96). Add 125 µl PBS to blank wells. Cover with sealing tape and incubate overnight 37° C. Wash 1× with 250 µl washing buffer and dry for about 2 hrs in 37° C. dry incubator.

Store coated plates in sealed bag at 4° C. until used.

2. Tyrosine Kinase Reaction:

Prepare inhibitor solutions at a 4×concentration in 20% DMSO in water.

Prepare reaction buffer

Prepare enzyme solution so that desired units are in 50 µl, e.g. for KDR make to 1 ng/µl for a total of 50 ng per well in the reactions. Store on ice.

Make 4× ATP solution to 20 µM from 100 mM stock in water. Store on ice

Add 50 µl of the enzyme solution per well (typically 5–50 ng enzyme/well depending on the specific activity of the kinase)

Add 25 µl 4×inhibitor

Add 25 µl 4×ATP for inhibitor assay

Incubate for 10 minutes at room temperature

Stop reaction by adding 50 µl 0.05N HCl per well

Wash plate

**Final Concentrations for Reaction: 5 µM ATP, 5% DMSO

3. Antibody Binding

Dilute 1 mg/ml aliquot of PY20-HRP (Pierce) antibody(a phosphotyrosine antibody)to 50 ng/ml in 0.1% BSA in PBS by a 2 step dilution (100×, then 200×)

Add 100 μl Ab per well. Incubate 1 hr at room temp. Incubate 1 hr at 4° C.

Wash 4× plate

4. Color Reaction

Prepare TMB substrate and add 100 μl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot.

For Lck, the Reaction Buffer utilized was 100 mM MOPSO, pH 6.5, 4 mM $MnCl_2$, 20 mM $MgCl_2$, 5 mM DTT, 0.2% BSA, 200 mM $NaVO_4$ under the analogous assay conditions.

Representative compounds of the present invention inhibited KDR at $IC_{50}$ values between about 0.002 μM and about 50 μM. Preferred compounds inhibited KDR at $IC_{50}$ values between about 0.002 μM and about 1.5 μM.

Representative compounds of the present invention inhibited Lck at $IC_{50}$ values between about 0.03 μM and about 50 μM.

Compounds of the present invention may have therapeutic utility in the treatment of diseases involving both identified, including those mentioned and unmentioned herein, and as yet unidentified protein tyrosine kinases. Examples of protein kinases include, but are not limited to, KDR, Ckit, CSF-1R, PDGFRβ, PDGFRα, Flt-1, Flt-3, Flt-4, Tie-2, Lck, Src, Fyn, Lyn, Blk, Hck, Fgr, Cot, and Yes.

Cdc2 Source

The human recombinant enzyme and assay buffer may be obtained commercially (New England Biolabs, Beverly, Mass. USA) or purified from known natural or recombinant sources using conventional methods.

Cdc2 Assay

A protocol that can be used is that provided with the purchased reagents with minor modifications. In brief, the reaction is carried out in a buffer consisting of 50 mM Tris pH 7.5, 100 mM NaCl, 1 mM EGTA, 2 mM DTT, 0.01% Brij, 5% DMSO and 10 mM $MgCl_2$ (commercial buffer) supplemented with fresh 300 μM ATP (31 μCi/ml) and 30 μg/ml histone type IIIss final concentrations. A reaction volume of 80 μL, containing units of enzyme, is run for 20 minutes at 25 degrees C. in the presence or absence of inhibitor. The reaction is terminated by the addition of 120 μL of 10% acetic acid. The substrate is separated from unincorporated label by spotting the mixture on phosphocellulose paper, followed by 3 washes of 5 minutes each with 75 mM phosphoric acid. Counts are measured by a betacounter in the presence of liquid scintillant.

PKC Kinase Source

The catalytic subunit of PKC may be obtained commercially (Calbiochem).

PKC Kinase Assay

A radioactive kinase assay is employed following a published procedure (Yasuda, I., Kirshimoto, A., Tanaka, S., Tominaga, M., Sakurai, A., Nishizuka, Y. Biochemical and Biophysical Research Communication 3:166, 1220–1227 (1990)). Briefly, all reactions are performed in a kinase buffer consisting of 50 mM Tris-HCl pH7.5, 10 mM $MgCl_2$, 2 mM DTT, 1 mM EGTA, 100 μM ATP, 8 μM peptide, 5% DMSO and $^{33}P$ ATP (8 Ci/mM). Compound and enzyme are mixed in the reaction vessel and the reaction is initiated by addition of the ATP and substrate mixture. Following termination of the reaction by the addition of 10 μL stop buffer (5 mM ATP in 75 mM phosphoric acid), a portion of the mixture is spotted on phosphocellulose filters. The spotted samples are washed 3 times in 75 mM phosphoric acid at room temperature for 5 to 15 minutes. Incorporation of radiolabel is quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction is carried out in a buffer consisting of 50 mM Tris pH 7.5, 1 mM EGTA, 2 mM DTT, 0.01% Brij, 5% DMSO and 10 mM $MgCl_2$ (commercial buffer) supplemented with fresh 100 μM ATP (31 μCi/ml) and 30 μM myelin basic protein under conditions recommended by the supplier. Reaction volumes and method of assaying incorporated radioactivity are as described for the PKC assay (vide supra).

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) can be purchased from Clonetics (San Diego, Calif.) and cultured according to the manufacturer directions. Only early passages (3–8) are used for this assay. Cells are cultured in 100 mm dishes (Falcon for tissue culture; Becton Dickinson; Plymouth, England) using complete EBM media (Clonetics).

2. For evaluating a compound's inhibitory activity, cells are trypsinized and seeded at $0.5-1.0 \times 10^5$ cells/well in each well of 6-well cluster plates (Costar; Cambridge, Mass.).

3. 3–4 days after seeding, plates are typically 90–100% confluent. Medium is removed from all the wells, cells are rinsed with 5–10 ml of PBS and incubated 18–24 h with 5 ml of EBM base media with no supplements added (i.e., serum starvation).

4. Serial dilutions of inhibitors are added in 1 ml of EBM media (25 μM, 5 μM, or 1 μM final concentration to cells and incubated for one hour at 37° C. Human recombinant $VEGF_{165}$ (R & D Systems) is then added to all the wells in 2 ml of EBM medium at a final concentration of 50 ng/ml and incubated at 37° C. for 10 minutes. Control cells untreated or treated with VEGF only are used to assess background phosphorylation and phosphorylation induction by VEGF.

All wells are then rinsed with 5–10 ml of cold PBS containing 1 mM Sodium Orthovanadate (Sigma) and cells are lysed and scraped in 200 μl of RIPA buffer (50 mM Tris-HCl) pH7, 150 mM NaCl, 1% NP-40, 0.25% sodium deoxycholate, 1 mM EDTA) containing protease inhibitors (PMSF 1 mM, aprotinin 1 μg/ml, pepstatin 1 μg/ml, leupeptin 1 μg/ml, Na vanadate 1 mM, Na fluoride 1 mM) and 1

μg/ml of Dnase (all chemicals from Sigma Chemical Company, St Louis, Mo.). The lysate is spun at 14,000 rpm for 30 min, to eliminate nuclei.

Equal amounts of proteins are then precipitated by addition of cold (−20° C.) Ethanol (2 volumes) for a minimum of 1 hour or a maximum of overnight. Pellets are reconstituted in Laemli sample buffer containing 5% mercaptoethanol (BioRad; Hercules, Calif.) and boiled for 5 min. The proteins are resolved by polyacrylamide gel electrophoresis (6%, 1.5 mm Novex, San Deigo, Calif.) and transferred onto a nitrocellulose membrane using the Novex system. After blocking with bovine serum albumin (3%), the proteins are probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4° C. After washing and incubating for 1 hour with HRP-conjugated F(ab)$_2$ of goat anti-rabbit or goat-anti-mouse IgG the bands are visualized using the emission chemiluminescience (ECL) system (Amersham Life Sciences, Arlington Heights, Ill.).

In Vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (Endocrinology (1993), 133:829–837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones can be purchased from Sigma (St. Louis, Mo.) or Cal Biochem (La Jolla, Calif.) as lyophilized powders and prepared according to supplier instructions. Vehicle components (DMSO, Cremaphor EL) can be purchased from Sigma (St. Louis, Mo.). Mice (Balb/c, 8–12 weeks old) can be purchased from Taconic (Germantown, N.Y.) and housed in a pathogen-free animal facility in accordance with institutional Animal Care and Use Committee Guidelines.

Method:

Day 1: Balb/c mice are given an intraperitoneal (i.p.) injection of 12.5 units of pregnant mare's serum gonadotropin (PMSG).

Day 3: Mice receive 15 units of human chorionic gonadotropin (hCG) i.p.

Day 4: Mice are randomized and divided into groups of 5–10. Test compounds are administered by i.p., i.v. or p.o. routes depending on solubility and vehicle at doses ranging from 1–100 mg/kg. Vehicle control group receive vehicle only and two groups are left untreated.

Thirty minutes later, experimental, vehicle and 1 of the untreated groups are given an i.p. injection of 17-estradiol (500 mg/kg). After 2–3 hours, the animals are sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri are blotted to remove fluid by pressing between two sheets of filter paper with a one liter glass bottle filled with water. Uteri are weighed following blotting (blotted weight). The difference between wet and blotted weights is taken as the fluid content of the uterus. Mean fluid content of treated groups is compared to untreated or vehicle treated groups. Significance is determined by Student's test. Non-stimulated control group is used to monitor estradiol response.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63(5), 694–701; Vasc. Biol. (1995), 15(11), 1857–6). The model preferably runs over 3–4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

The compounds of the present invention may be used in the treatment of protein kinase-mediated conditions, such as benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (e.g., kidney rejection, graft versus host disease), benign and neoplastic proliferative diseases, human cancers such as lung, breast, stomach, bladder, colon, pancreatic, ovarian, prostate and rectal cancer and hematopoietic malignancies (leukemia and lymphoma), glioblastoma, infantile hemangioma, and diseases involving inappropriate vascularization (for example diabetic retinopathy, retinopathy of prematurity, choroidal neovascularization due to age-related macular degeneration, and infantile hemangiomas in human beings). Such inhibitors may be useful in the treatment of disorders involving VEGF mediated edema, ascites, effusions, and exudates, including for example macular edema, cerebral edema, acute lung injury and adult respiratory distress syndrome (ARDS). In addition, the compounds of the invention may be useful in the treatment of pulmonary hypertension, particularly in patients with thromboembolic disease (J. Thorac. Cardiovasc. Surg. 2001, 122 (1), 65–73).

Synthetic Methods

Abbreviations which have been used in the descriptions of the scheme and the examples that follow are: LDA for lithium diisopropylamide; DMF for N,N-dimethylformamide; dppf for diphenylphosphinoferrocene; PPh$_3$ for triphenylphosphine; DMSO for dimethylsulfoxide; TFA for trifluoroacetic acid; HOBT for 1-hydroxybenzotriazole; EDCI for 1-(3-dimethylaminopropyl)-3-ethylcarbodiimide; THF for tetrahydrofuran; DME for 1,2-dimethoxyethane; Et$_3$N for triethylamine; TBTU for O-benzotriazol-1-yl-N,N,N',N'-tetramethyluronium tetrafluoroborate; OAc for acetate; DIBAL-H for diisobutylaluminum hydride; HBTU for O-benzotriazol-1-yl-N,N,N',N'-tetramethyluronium hexafluorophosphate; and BOC for tert-butoxycarbonyl.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1999). Suitable protecting groups include, but are not limited to, tert-butoxycarbonyl (BOC), trimethylsilylethanesulfonamide (SES), benzyloxycarbonyl (CBZ) and benzyl (Bn) protecting groups. The BOC protecting group may be removed by treatment with an acid such as trifluoroacetic acid or concentrated hydrochloric acid and the SES protecting group may be removed with a fluoride salt, such as cesium fluoride or tetrabutylammonium fluoride. The CBZ and Bn protection groups may be removed by catalytic hydrogenation. Additional suitable protecting groups for hydroxy substituents include, but are not limited to, t-butyldimethylsilyl (TBDMS), tetra-hydropyranyl (THP), or isopropyl (i-Pr) protecting groups. The TBDMS and THP protecting groups may be removed by treatment with an acid such as acetic acid or hydrochloric acid while the i-Pr protecting group may be removed by aluminum trichloride.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

The groups $R^1$, $R^2$, $R^3$, $R^4$, and $R^5$ are as defined above unless otherwise noted below.

Scheme 1 shows the synthesis of compounds of formula (6). Compounds of formula (3) can be reacted with ethyl (diethoxyphosphino)acetate in the presence of a base such as sodium hydride, LDA, or lithium hexamethyldisilazide to provide compounds of formula (4). This reaction is typically conducted at about 0 to about 25° C. for about 1 to about 6 hours.

Alternatively, compounds of formula (3) can be treated with malonic acid in the presence of pyridine and piperidine to provide compounds of formula (4). The reaction is typically conducted at about 90 to about 110° C. for about 6 to about 18 hours.

Compounds of formula (4) can be converted to compounds of formula (5) by treatment with thionyl chloride and DMF followed by treatment with sodium azide and subsequent heating. The reaction is conducted at about 30 to about 260° C. for about 5 to about 10 hours.

Conversion of compounds of formula (5) to compounds of formula (6) can be accomplished by treatment with $POCl_3$ at about 108° C. for about 1 to about 4 hours followed by treatment with ammonia under pressure at about 140 to about 160° C.

Scheme 1

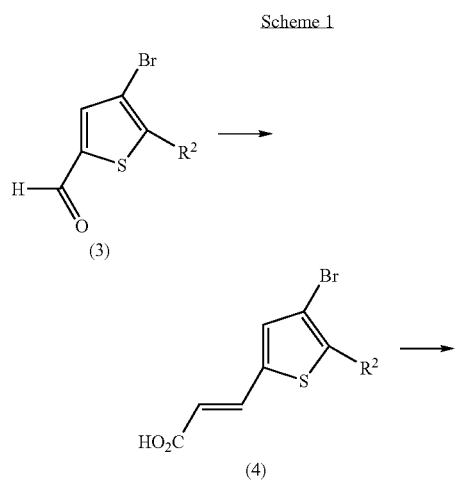

-continued

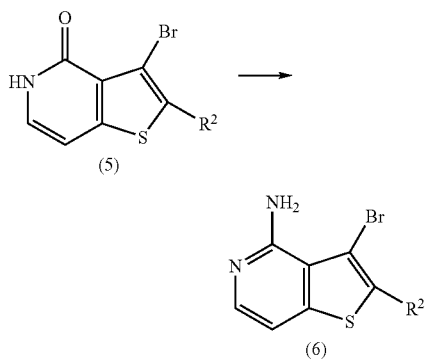

Scheme 2

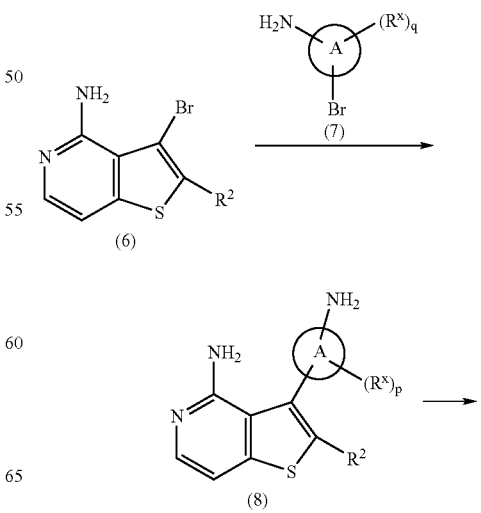

-continued

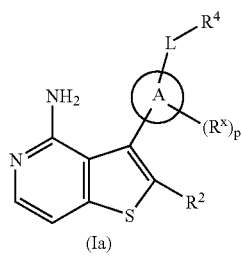

(Ia)

Compounds of formula (Ia) can be synthesized by the methods shown in Scheme 2. Compounds of formula (6) can be converted to compounds of formula (8) by transition metal-mediated cross-coupling with compounds of formula (7) (q is 1 or 2 and each $R^x$ is independently selected from the group consisting of alkoxy, alkyl, aryl, cyano, halo, haloalkoxy, haloalkyl, heteroaryl, heterocyclyl, hydroxy, hydroxyalkyl, and $NR^aR^b$) in the presence of bis(pinacolato) diboron, potassium acetate, and a base. Examples of transition metal catalysts used in these couplings include, but are not limited to, $PdCl_2(dppf)$, $Pd(PPh_3)_4$, and $Pd(PPh_3)_2Cl_2$. Representative bases include sodium carbonate, potassium carbonate, and cesium carbonate. The reaction is typically conducted at about 70 to about 90° C. for about 2 to about 24 hours.

Compounds of formula (8) can be converted to compounds of formula (Ia) (where L is selected from the group consisting of $NR^5C(O)(CH_2)_m$, $NR^5SO_2$, $(CH_2)_mN(R^5)C(O)N(R^6)(CH_2)_n$) by treatment with the appropriate acylating/sulfonylating reagent (i.e., a substituted acid chloride, sulfonyl chloride, or isocyanate) optionally in the presence of a base such as pyridine or triethylamine.

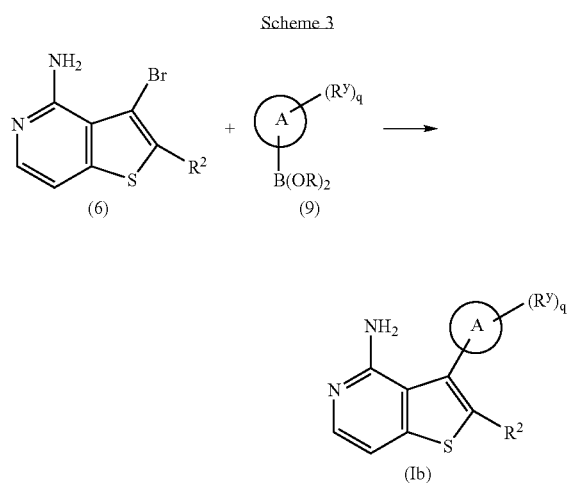

As shown in Scheme 3, compounds of formula (6) can be reacted with compounds of formula (9) (where q is 1, 2, or 3 and each $R^y$ is selected from the group consisting of alkoxy, alkyl, aryl, cyano, halo, haloalkoxy, haloalkyl, heteroaryl, heterocyclyl, hydroxy, hydroxyalkyl, $LR^4$, and $NR^aR^b$; provided that at least two of the three substituents are other than $LR^4$) in the presence of a transition metal catalyst and a base to provide compounds of formula (Ia). Examples of transition metal catalysts used in these couplings include, but are not limited to, $PdCl_2(dppf)$, $Pd(PPh_3)_4$, and $Pd(PPh_3)_2Cl_2$. Representative bases include sodium carbonate, potassium carbonate, and cesium carbonate.

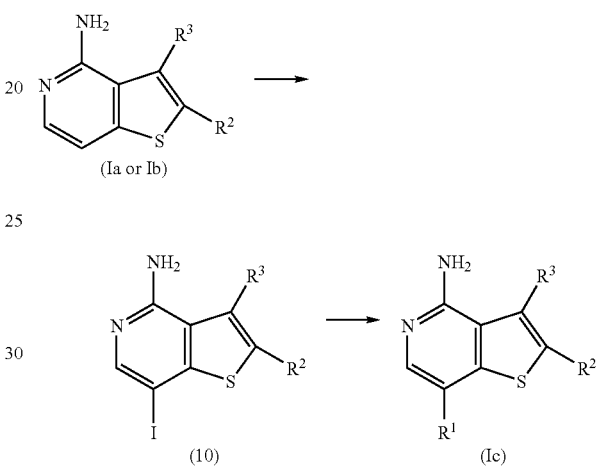

Compounds of formula (Ic) can be synthesized following the procedures shown in Scheme 4. Compounds of formula (Ia) or (Ib) can be reacted with N-iodosuccinimide at about 20 to about 35° C. for about 1 to about 4 hours to provide compounds of formula (10).

Compounds of formula (Ic) can be prepared by coupling compounds of formula (10) with an appropriately substituted organometallic coupling partner (for example, an organoborane or an organostannane) in the presence of a transition metal catalyst. Examples of transition metal catalysts used in these couplings include, but are not limited to, $PdCl_2(dppf)$, $Pd(PPh_3)_4$, and $Pd(PPh_3)_2Cl_2$. When an organoborane is used in the coupling, a base is also required. Representative bases include sodium carbonate, potassium carbonate, and cesium carbonate.

Compounds of formula (Ic) can be further functionalized at $R^1$ using methods known to those of ordinary skill in the art. For example, when $R^1$ contains an aldehyde (formed by coupling an alkenyl acetal with the compound of formula (10) and subsequent deprotection) reductive amination provides an alkenylamine. Similarly, when $R^1$ contains a primary amine, reaction with an aldehyde under reductive amination provides the secondary amine. In another example, when $R^1$ contains a carboxylic acid (prepared by hydrolysis of the corresponding ester) coupling with an amine provides an alkenylamide.

Scheme 5

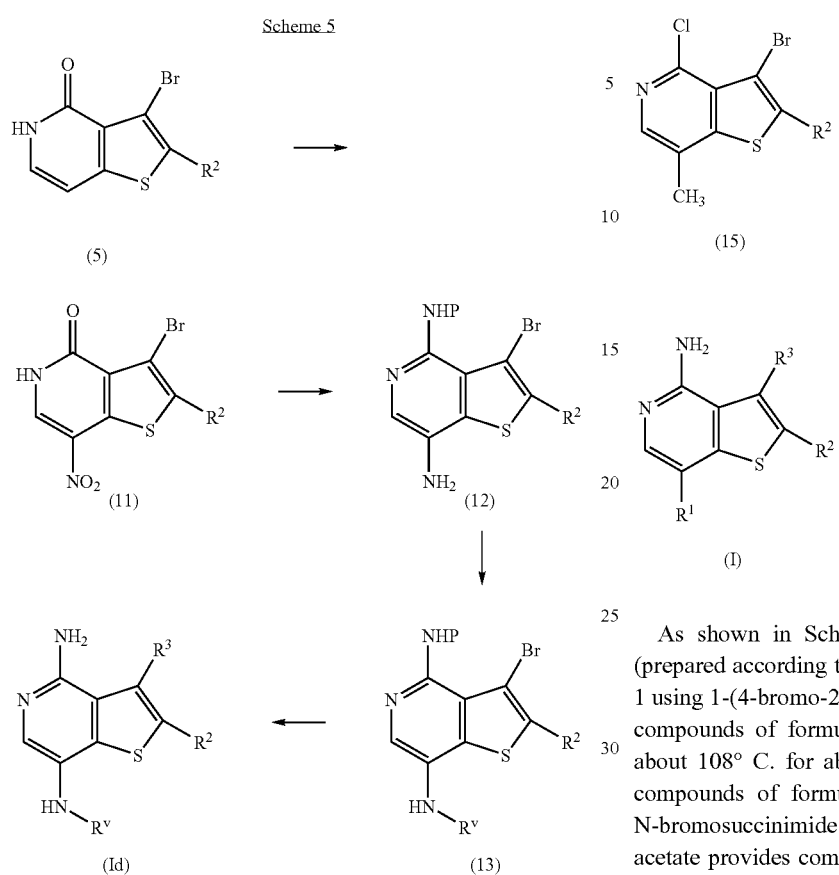

Scheme 6

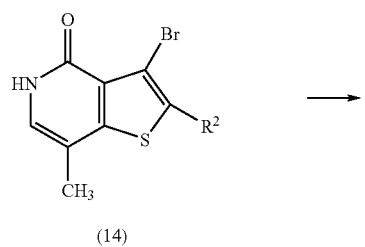

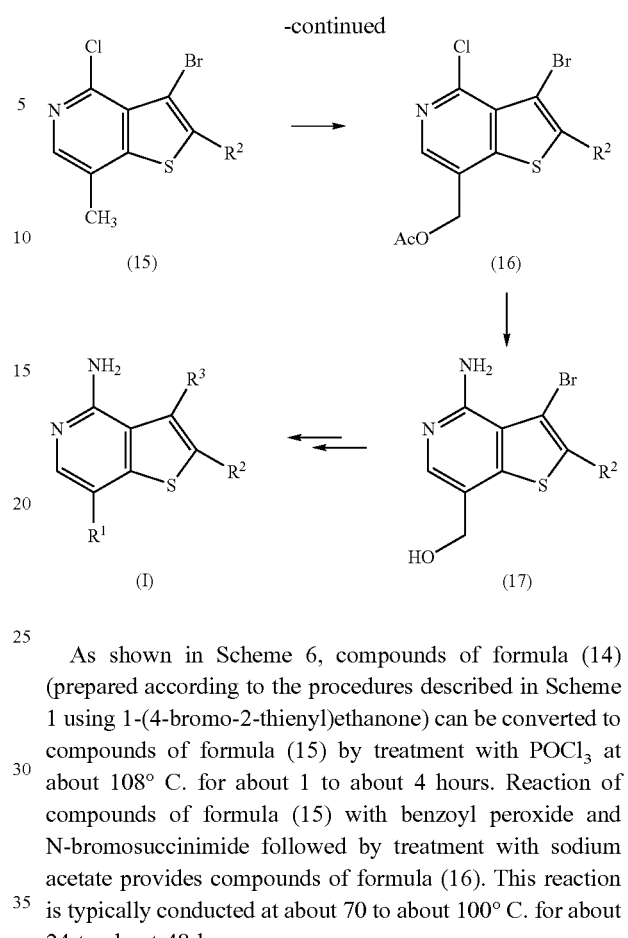

The synthesis of compounds of formula (Id) is shown in Scheme 5. Compounds of formula (5) can be treated with nitric acid and sulfuric acid to provide compounds of formula (11). Conversion of the pyridone to the aminopyridine can be accomplished using the conditions described in Scheme 1. Protection of the amine followed by reduction of the nitro group using conditions known to those of ordinary skill in the art provides compounds of formula (12) where P is a nitrogen protecting group. The unprotected amine can be further functionalized by reacting with an appropriately substituted acyl halide, sulfonyl chloride, or isocyanate to provide compounds of formula (13) where RV is the resulting functionality (i.e., alkylsulfonyl, alkylcarbonyl). Removal of the protecting group followed by coupling of the bromide as described in Scheme 2 or Scheme 3 provides compounds of formula (Id).

As shown in Scheme 6, compounds of formula (14) (prepared according to the procedures described in Scheme 1 using 1-(4-bromo-2-thienyl)ethanone) can be converted to compounds of formula (15) by treatment with POCl₃ at about 108° C. for about 1 to about 4 hours. Reaction of compounds of formula (15) with benzoyl peroxide and N-bromosuccinimide followed by treatment with sodium acetate provides compounds of formula (16). This reaction is typically conducted at about 70 to about 100° C. for about 24 to about 48 hours.

Removal of the acetate group and displacement of the chloride can be accomplished by treating compounds of formula (16) with concentrated ammonium hydroxide at a temperature of about 120 to about 160° C. to provide compounds of formula (17). Coupling of the bromide using the conditions described in Schemes 2 or 3 and further functionalization of the hydroxymethyl group provides compounds of formula (I). An example of further functionalization is oxidation of the hydroxymethyl group to provide the aldehyde followed by reductive amination to provide an aminomethyl group.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada).

EXAMPLE 1

N-[4-(4-aminothieno[3,2-c]pyridin-3-yl)-2-fluorophenyl]-N'-(3-methylphenyl)urea

EXAMPLE 1A 3-bromothieno[3,2-c]pyridin-4(5H)-one

A suspension of (2E)-3-(4-bromo-2-thienyl)acrylic acid (commercially available, 50.2 g, 0.215 mol) in dichloromethane (150 mL) was treated with DMF (2 drops) and $SOCl_2$ (23 mL, 0.315 mol), stirred at room temperature for 48 hours, heated to reflux for 2 hours, and concentrated. The residue was dissolved in dioxane (100 mL) and added to a vigorously stirred solution of $NaN_3$ (25 g, 0.384 mol) in water (100 mL) and dioxane (100 mL) over 10 minutes. The resulting mixture was stirred at room temperature for 2.5 hours and extracted twice with 150 mL of ethyl acetate. The combined organics were washed with water and brine, dried ($Na_2SO_4$), filtered, and concentrated. A solution of the residue in dichloromethane (150 mL) was added dropwise over 5 hours to boiling diphenyl ether (150 mL) in a 3-neck flask fitted with 2 air-cooled condensers. The mixture was stirred at reflux for an additional 1 hour, cooled to room temperature, and concentrated. The residue was suspended in diethyl ether (100 mL) and hexanes (200 mL), cooled, and filtered. The filter cake was washed with additional diethyl ether/hexanes and dried to provide 37.4 g of the desired product. MS (ESI(+)) m/e 231 (M+H)$^+$.

EXAMPLE 1B 3-bromothieno[3,2-c]pyridin-4-amine

A suspension of Example 1A (35.91 g, 0.156 mol) in $POCl_3$ (80 mL) was heated to reflux for 2.5 hours, cooled to room temperature, poured onto 800 g of ice, and extracted repeatedly with dichloromethane. The combined extracts were washed with water and brine, dried ($Na_2SO_4$), filtered, and concentrated. The residue was purified by flash column chromatography on silica gel with 0 to 5% methanol/dichloromethane to provide 29.3 g of 3-bromo-4-chlorothieno[3,2-c]pyridine (mp 158–159° C.), which was diluted with dioxane (500 mL) and concentrated aqueous $NH_3$ (500 mL), heated to 150° C. under pressure (260 psi) for 20 hours, and concentrated. The residue was triturated from MTBE then from methanol to provide 20.29 g of the desired product. m.p. 153–155° C.

EXAMPLE 1C 3-(4-amino-3-fluorophenyl)thieno[3,2-c]pyridin-4-amine

A solution of 4-bromo-2-fluoroaniline (1.83 g, 9.6 mmol), bis(pinacolato)diboron (2.65 g, 10.4 mmol) and potassium acetate (2.56 g, 26.1 mmol) in DMF (50 mL) was purged with nitrogen, treated with $PdCl_2$(dppf) (0.355 g, 0.05 mmol), heated to 80° C. for 2.5 hours, cooled to room temperature, and treated with a solution of $Na_2CO_3$ (4.61 g, 43.5 mmol) in water (20 mL), Example 1B (2.02 g, 8.8 mmol), and additional $PdCl_2$(dppf) (0.355 g, 0.05 mmol). The mixture was heated to 80° C. overnight, cooled to room temperature, poured into water, and extracted with ethyl acetate. The organic extract was dried ($NaSO_4$), filtered, and concentrated. The residue was purified by flash column chromatography on silica gel with 50 to 60% ethyl acetate/hexanes (0.5% triethylamine added) to provide 1.5 g of the desired product. MS (ESI(+)) m/e 260 (M+H)$^+$.

EXAMPLE 1D

N-[4-(4-aminothieno[3,2-c]pyridin-3-yl)-2-fluorophenyl]-N'-(3-methylphenyl)urea

A solution of Example 1C (125 mg, 0.48 mmol) in dichloromethane (1 mL) was treated with 1-isocyanato-3-methylbenzene (0.065 mL, 0.5 mmol), stirred overnight at room temperature, and filtered. The filter cake was purified by preparative HPLC on a Waters Symmetry C8 column (25 mm×100 mm, 7 µm particle size) using a solvent gradient of 10% to 100% acetonitrile/10 mM aqueous ammonium acetate over 8 minutes (10 minute run time) at a flow rate of 40 mL/minute to provide 74 mg of the desired product. $^1$H NMR (300 MHz, DMSO-$d_6$) δ 2.30 (s, 3H), 5.48 (s, 2H), 6.83 (d, J=7.8 Hz, 1H), 7.18 (t, J=7.6 Hz, 1H), 7.22–7.29 (m, 2H), 7.28 (d, J=5.8 Hz, 1H), 7.32 (s, 1H), 7.38 (dd, J=12.0, 1.9 Hz, 1H), 7.50 (s, 1H), 7.84 (d, J=5.8 Hz, 1H), 8.31 (t, J=8.5 Hz, 1H), 8.70 (d, J=2.4 Hz, 1H), 9.06 (s, 1H), MS (ESI(+)) m/e 393.0 (M+H)$^+$.

EXAMPLE 2

N-[4-(4-aminothieno[3,2-c]pyridin-3-yl)-2-fluorophenyl]-N'-(3-chlorophenyl)urea

The desired product was prepared by substituting 1-isocyanato-3-chlorobenzene for 1-isocyanato-3-methylbenzene in Example 1. $^1$H NMR (300 MHz, DMSO-$d_6$) δ 5.44 (s, 2H), 7.06 (ddd, J=7.8, 2.0, 1.4 Hz, 1H), 7.24–7.25 (m, J=1.7 Hz, 1H), 7.27 (d, J=5.4 Hz, 1H), 7.26–7.27 (m, 1H), 7.34 (t, J=8.1 Hz, 1H), 7.39 (dd, J=11.9, 2.0 Hz, 1H), 7.50 (s, 1H), 7.75 (t, J=2.0 Hz, 1H), 7.84 (d, J=5.8 Hz, 1H), 8.27 (t, J=8.5 Hz, 1H), 8.78 (d, J=2.4 Hz, 1H), 9.32 (s, 1H); MS (ESI(+)) m/e 413.0, 415.1 (M+H)$^+$.

EXAMPLE 3

N-[4-(4-aminothieno[3,2-c]pyridin-3-yl)-2-fluorophenyl]-N'-[3-(trifluoromethyl)phenyl]urea The desired product was prepared by substituting 1-isocyanato-3-trifluoromethylbenzene for 1-isocyanato-3-methylbenzene in Example 1. $^1$H NMR (300 MHz, DMSO-$d_6$) d 5.45 (s, 2H), 7.26 (dd, J=8.1, 1.7 Hz, 1H), 7.28 (d, J=5.8 Hz, 1H), 7.34–7.37 (m, 1H), 7.40 (dd, J=12.0, 1.9 Hz, 1H), 7.51 (s, 1H), 7.54–7.57 (m, 2H), 7.84 (d, J=5.4 Hz, 1H), 8.06 (s, 1H), 8.27 (t, J=8.5 Hz, 1H), 8.81 (d, J=2.4 Hz, 1H), 9.47 (s, 1H); MS (ESI(+)) m/e 447.0 (M+H)$^+$.

EXAMPLE 4

N-[4-(4-aminothieno[3,2-c]pyridin-3-yl)-2-fluorophenyl]-N'-[2-fluoro-5-(trifluoromethyl)phenyl]urea The desired product was prepared by substituting 1-fluoro-2-isocyanato-4-(trifluoromethyl)benzene for 1-isocyanato-3-methylbenzene in Example 1. $^1$H NMR (300 MHz, DMSO-$d_6$) δ 5.43 (s, 2H), 7.26 (dd, J=9.0, 2.2 Hz, 1H), 7.28 (d, J=5.4 Hz, 1H), 7.41 (dd, J=12.0, 1.9 Hz, 1H), 7.40–7.45 (m, 1H), 7.51 (s, 1H), 7.53 (dd, J=11.2, 8.5 Hz, 1H), 7.85 (d, J=5.8 Hz, 1H), 8.32 (t, J=8.5 Hz, 1H), 8.66 (dd, J=7.3, 2.2 Hz, 1H), 9.33 (d, J=2.4 Hz, 1H), 9.45 (d, J=2.7 Hz, 1H); MS (ESI(+)) m/e 465.0 (M+H)⁺.

EXAMPLE 5

N-[4-(4-aminothieno[3,2-c]pyridin-3-yl)-2-fluorophenyl]-N'-(3-bromophenyl)urea

The desired product was prepared by substituting 1-bromo-3-isocyanatobenzene for 1-isocyanato-3-methylbenzene in Example 1. $^1$H NMR (300 MHz, DMSO-$d_6$) δ 5.44 (s, 2H), 7.19 (dt, J=7.1, 1.9 Hz, 1H), 7.24–7.33 (m, 4H), 7.39 (dd, J=11.9, 2.0 Hz, 1H), 7.50 (s, 1H), 7.84 (d, J=5.8 Hz, 1H), 7.89–7.91 (m, 1H), 8.27 (t, J=8.5 Hz, 1H), 8.77 (d, J=2.7 Hz, 1H), 9.31 (s, 1H); MS (ESI(+)) m/e 457.0, 458.8 (M+H)⁺.

EXAMPLE 6

N-[4-(4-aminothieno[3,2-c]pyridin-3-yl)-3-fluorophenyl]-N'-(3-methylphenyl)urea

EXAMPLE 6A 3-(4-amino-2-fluorophenyl)thieno[3,2-c]pyridin-4-amine

The desired product was prepared by substituting 4-bromo-3-fluoroaniline for 4-bromo-2-fluoroaniline in Example 1C. MS (ESI(+)) m/e 260.0 (M+H)⁺.

EXAMPLE 6B

N-[4-(4-aminothieno[3,2-c]pyridin-3-yl)-3-fluorophenyl]-N'-(3-methylphenyl)urea

The desired product was prepared by substituting Example 6A for Example 1C in Example 1D. $^1$H NMR (300 MHz, DMSO-$d_6$) δ 2.29 (s, 3H), 5.34 (s, 2H), 6.82 (d, J=7.1 Hz, 1H), 7.18 (t, J=7.6 Hz, 1H), 7.24–7.28 (m, 3H), 7.32 (s, 1H), 7.37 (t, J=8.5 Hz, 1H), 7.53 (s, 1H), 7.65 (dd, J=12.2, 2.0 Hz, 1H), 7.83 (d, J=5.4 Hz, 1H), 8.73 (s, 1H), 9.06 (s, 1H); MS (ESI(+)) m/e 393.0 (M+H)⁺.

EXAMPLE 7

N-[4-(4-aminothieno[3,2-c]pyridin-3-yl)-3-fluorophenyl]-N'-[3-(trifluoromethyl)phenyl]urea The desired product was prepared by substituting Example 6A and 1-isocyanato-3-(trifluoromethyl)benzene for Example 1C and 1-isocyanato-3-methylbenzene, respectively, in Example 1D. $^1$H NMR (300 MHz, DMSO-$d_6$) δ 5.34 (s, 2H), 7.28 (d, J=5.8 Hz, 1H), 7.30–7.42 (m, 3H), 7.51–7.57 (m, 2H), 7.61–7.68 (m, 2H), 7.83 (d, J=5.8 Hz, 1H), 8.02 (s, 1H), 9.21 (s, 1H), 9.22 (s, 1H); MS (ESI(+)) m/e 447.0 (M+H)⁺.

EXAMPLE 8

N-[4-(4-aminothieno[3,2-c]pyridin-3-yl)-3-fluorophenyl]-N'-(3-chlorophenyl)urea

The desired product was prepared by substituting Example 6A and 1-chloro-3-isocyanatobenzene for Example 1C and 1-isocyanato-3-methylbenzene, respectively, in Example 1D. $^1$H NMR (300 MHz, DMSO-$d_6$) δ 5.34 (s, 2H), 7.05 (ddd, J=6.2, 2.4, 2.2 Hz, 1H), 7.27 (d, J=5.4 Hz, 1H), 7.28–7.32 (m, 3H), 7.39 (t, J=8.3 Hz, 1H), 7.54 (s, 1H), 7.64 (dd, J=12.5, 2.0 Hz, 1H), 7.72–7.73 (m, 1H), 7.83 (d, J=5.4 Hz, 1H), 9.04 (s, 1H), 9.17 (s, 1H); MS (ESI(+)) m/e 413.0, 414.9 (M+H)⁺.

EXAMPLE 9

N-[4-(4-aminothieno[3,2-c]pyridin-3-yl)-3-chlorophenyl]-N'-(3-methylphenyl)urea

EXAMPLE 9A 3-(4-amino-2-chlorophenyl)thieno[3,2-c]pyridin-4-amine

The desired product was prepared by substituting 4-bromo-3-chloroaniline for 4-bromo-2-fluoroaniline in Example 1C. MS (ESI(+)) m/e 275.9, 278.1 (M+H)⁺.

EXAMPLE 9B

N-[4-(4-aminothieno[3,2-c]pyridin-3-yl)-3-chlorophenyl]-N'-(3-methylphenyl)urea

The desired product was prepared by substituting Example 9A for Example 1C in Example 1D. $^1$H NMR (300 MHz, DMSO-$d_6$) δ 2.29 (s, 3H), 5.22 (s, 2H), 6.82 (d, J=7.1 Hz, 1H), 7.18 (t, J=7.8 Hz, 1H), 7.24–7.26 (m, 1H), 7.26 (d, J=5.4 Hz, 1H), 7.33 (s, 1H), 7.41 (app. s, 2H), 7.48 (s, 1H), 7.82 (d, J=5.8 Hz, 1H), 7.91 (s, 1H), 8.75 (s, 1H), 9.04 (s, 1H); MS (ESI(+)) m/e 409.0, 411.1 (M+H)⁺.

EXAMPLE 10

3-(4-phenoxyphenyl)-7-(4-pyridinyl)thieno[3,2-c]pyridin-4-amine

EXAMPLE 10A 3-(4-phenoxyphenyl)thieno[3,2-c]pyridin-4-amine

A mixture of Example 1B (1.5 g, 6.5 mmol), 4-phenoxyphenylboronic acid (1.53 g, 7.1 mmol) and Na$_2$CO$_3$ (1.81 g, 17.1 mmol) in toluene (26 mL), ethanol (5 mL), and water (10 mL) was purged with nitrogen for 45 minutes, then treated with Pd(PPh$_3$)$_4$ (0.382 g, 0.33 mmol) and heated to 90° C. overnight. The reaction was cooled to room temperature and partitioned between water and ethyl acetate. The aqueous phase was extracted with ethyl acetate twice and the combined organic extracts were washed with brine, dried (Na$_2$SO$_4$), filtered, and concentrated. The residue was purified by flash column chromatography on silica gel with 40% ethyl acetate/hexanes to provide 1.69 g (82% yield) of the desired product. MS (ESI(+)) m/e 318.9 (M+H)⁺.

EXAMPLE 10B 7-iodo-3-(4-phenoxyphenyl)thieno[3,2-c]pyridin-4-amine

A solution of Example 10A (1.69 g, 5.3 mmol) in DMF (20 mL) was treated with NIS (1.26 g, 5.6 mmol), stirred at room temperature for 3 hours, poured into water, and filtered. The filter cake was purified by flash column chromatography on silica gel with 15% ethyl acetate/hexanes to provide 1.64 g (70% yield) of the desired product. MS (ESI(+)) m/e 444.8 (M+H)⁺.

EXAMPLE 10C 3-(4-phenoxyphenyl)-7-(4-pyridinyl)thieno[3,2-c]pyridin-4-amine

The desired product was prepared by substituting Example 10B, 4-pyridylboronic acid, and PdCl$_2$(dppf) for Example 1B, 4-phenoxyphenylboronic acid, and Pd(PPh$_3$)$_4$ respectively, in Example 10A. $^1$H NMR (300 MHz, DMSO-d$_6$) δ 5.74 (s, 2H), 7.12–7.16 (m, 4H), 7.21 (t, J=7.5 Hz, 1H), 7.45 (dd, J=8.7, 7.3 Hz, 2H), 7.50 (d, J=8.5 Hz, 2H), 7.58 (s, 1H), 7.72 (d, J=6.1 Hz, 2H), 8.09 (s, 1H), 8.68 (d, J=6.1 Hz, 2H); MS (ESI(+)) m/e 339.0 (M+H)$^+$.

EXAMPLE 11

4-{(2E)-3-[4-amino-3-(4-phenoxyphenyl)thieno[3,2-c]pyridin-7-yl]-2-propenoyl}-2-piperazinone

EXAMPLE 11A tert-butyl (2E)-3-[4-amino-3-(4-phenoxyphenyl)thieno[3,2-c]pyridin-7-yl]acrylate A mixture of Example 10B (0.417 g, 0.94 mmol), tert-butyl acrylate (0.26 mL, 1.74 mol) and triethylamine (0.7 mL, 5 mmol) in DMF (3 mL) was degassed with nitrogen for 45 minutes, treated with PdCl$_2$(o-tol$_3$P)$_2$ (0.032 g, 0.046 mmol), and heated to 80° C. overnight. The resulting mixture was cooled to room temperature, then partitioned between water and ethyl acetate. The organic extract was washed with brine, dried (Na$_2$SO$_4$), filtered, and concentrated. The residue was purified by flash column chromatography on silica gel with 30% ethyl acetate/hexanes to provide 0.25 g (61% yield) of the desired product. MS (ESI(+)) m/e 445 (M+H)$^+$.

EXAMPLE 11B (2E)-3-[4-amino-3-(4-phenoxyphenyl)thieno[3,2-c]pyridin-7-yl]acrylic acid A solution of Example 11A (0.25 g, 0.57 mmol) in TFA (5 mL) was stirred at room temperature for 14 hours then concentrated under a stream of nitrogen to provide the desired product. MS (ESI(+)) m/e 388.9 (M+H)$^+$.

EXAMPLE 11C

4-{(2E)-3-[4-amino-3-(4-phenoxyphenyl)thieno[3,2-c]pyridin-7-yl]-2-propenoyl}-2-piperazinone A mixture of Example 11B (0.09 g, 0.23 mmol), 2-piperazinone (0.069 g, 0.69 mmol), HOBT (0.095 g, 0.7 mmol), N-methylmorpholine (0.22 mL, 0.92 mmol), and EDCI (0.136 g, 0.71 mmol) in DMF (1 mL) was stirred at room temperature overnight, treated with water (20 mL), and filtered. The filter cake was dried to provide 110 mg of the desired product. $^1$H NMR (300 MHz, DMSO-d$_6$) δ 3.20–3.36 (br m, 2H), 3.71–3.91 (br m, 2H), 4.03–4.35 (m, 2H), 5.94 (br s, 2H), 6.92–7.15 (br m, 1H), 7.11–7.16 (m, 4H), 7.21 (t, J=7.3 Hz, 1H), 7.42–7.52 (m, 4H), 7.63 (s, 1H), 7.71 (d, J=14.9 Hz, 1H), 8.13 (br s, 1H), 8.33 (s, 1H); MS (ESI(−)) m/e 469.3 (M−H)$^-$.

EXAMPLE 12 tert-butyl (2E)-3-(4-amino-3-phenylthieno[3,2-c]pyridin-7-yl)acrylate

EXAMPLE 12A 7-iodo-3-phenylthieno[3,2-c]pyridin-4-amine

The desired product was prepared by substituting phenylboronic acid for 4-phenoxyphenylboronic acid in Example 10A and 10B.

EXAMPLE 12B tert-butyl (2E)-3-(4-amino-3-phenylthieno[3,2-c]pyridin-7-yl)acrylate The desired product was prepared by substituting Example 12A for Example 10B in Example 11A. $^1$H NMR (300 MHz, DMSO-d$_6$) δ 1.51 (m, 9H), 5.95 (br s, 1H), 6.33 (d, J=15.9 Hz, 1H), 7.53 (m, 5H), 7.64 (s, 1H), 7.72 (d, J=16.3 Hz, 1H), 8.24 (s, 1H); MS (ESI(+)) m/e 353 (M+H)$^+$.

EXAMPLE 13

(2E)-3-(4-amino-3-phenylthieno[3,2-c]pyridin-7-yl)acrylic acid

The desired product was prepared as the trifluoroacetate salt by substituting Example 12B for Example 11A in Example 11B. $^1$H NMR (300 MHz, DMSO-d$_6$) δ 6.52 (d, J=16.3 Hz, 1H), 6.6–6.8 (br s, 2H), 7.55 (m, 5H), 7.76 (d, J=16.3 Hz, 1H), 7.86 (s, 1H), 8.34 (s, 1H); MS (ESI(+)) m/e 297 (M+H)$^+$.

EXAMPLE 14

(2E)-3-(4-amino-3-phenylthieno[3,2-c]pyridin-7-yl)-N-methylacrylamide

A mixture of Example 13 (0.1 g, 0.34 mmol), methylamine hydrochloride (0.115 g, 1.69 mmol), HOBT (0.137 g, 1.01 mmol), N-methylmorpholine (0.25 mL, 2.36 mmol), and EDCI (0.199 g, 1.01 mmol) in DMF (5 mL) was stirred at room temperature for 2 hours, diluted with water (20 mL), and extracted with ethyl acetate (2×20 mL). The combined extracts were washed with brine, dried (MgSO$_4$), filtered, and concentrated to provide 89 mg of the desired product. $^1$H NMR (300 MHz, DMSO-d$_6$) δ 2.73 (d, J=4.8 Hz, 3H), 5.75–5.85 (br s, 2H), 6.58 (d, J=15.9 Hz, 1H), 7.53 (m, 5H), 7.58 (d, J=15.9 Hz, 1H), 7.67 (s, 1H), 8.14 (m, 2H); MS (ESI(+)) m/e 310 (M+H)$^+$.

EXAMPLE 15

3-(4-amino-3-phenylthieno[3,2-c]pyridin-7-yl)-N-methylpropanamide

A mixture of Example 14 (30 mg, 0.1 mmol) and 10% Pd on carbon (30 mg) in 1:1 methanol/DMF (4 mL) was stirred under an atmosphere of hydrogen overnight. The suspension was filtered through diatomaceous earth (Celite®). The pad was washed with methanol and the filtrate was concentrated to half its original volume. The residue was diluted with diethyl ether and filtered. The filter cake was dried to provide 26 mg of the desired product. $^1$H NMR (300 MHz, DMSO-d$_6$) δ 2.47 (m, 2H), 2.58 (d, J=4.6 Hz, 2H), 2.91 (t, J=7.9 Hz, 2H), 5.21 (s, 1H), 7.50 (m, 6H), 7.66 (s, 1H), 7.81 (m, J=4.3 Hz, 1H); MS (ESI(+)) m/e 312 (M+H)$^+$.

EXAMPLE 16

4-[(2E)-3-(4-amino-3-phenylthieno[3,2-c]pyridin-7-yl)-2-propenoyl]-2-piperazinone The desired product was prepared by substituting Example 13 for Example 11B in Example 11C. $^1$H NMR (300 MHz, DMSO-d$_6$) δ 3.82 (br m, 2H), 4.20 (br m, 2H), 5.86 (br s, 2H), 7.03 (br m, 1H), 7.53 (m, 5H), 7.64 (s, 1H), 7.71 (d, J=14.9 Hz, 1H), 8.14 (s, 1H), 8.33 (s, 1H); MS (ESI(+)) m/e 379 (M+H)$^+$.

EXAMPLE 17 tert-butyl (2E)-3-{3-[4-(acetylamino)phenyl]-4-aminothieno[3,2-c]pyridin-7-yl}acrylate

EXAMPLE 17A 3-(4-aminophenyl)thieno[3,2-c]pyridin-4-amine

The desired product was prepared by substituting 4-(4,4,5,5-tetramethyl-1,3,2-dioxaborolan-2-yl)aniline for 4-phenoxyphenylboronic acid in Example 10A. MS (ESI(+)) m/e 242 (M+H)$^+$; $^1$H NMR (300 MHz, DMSO-d$_6$) δ 5.35 (s, 2H), 5.48 (s, 2H), 6.66 (d, J=8.14 Hz, 2H), 7.08 (d, J=8.14 Hz, 2H), 7.20 (d, J=5.42 Hz, 1H), 7.27 (s, 1H), 7.78 (d, J=5.76 Hz, 1H).

EXAMPLE 17B

N-[4-(4-aminothieno[3,2-c]pyridin-3-yl)phenyl]acetamide

A −30° C. solution of Example 17A (0.1 g, 0.41 mmol) and N-methylmorpholine (0.03 mL, 0.41 mmol) in THF (5 mL) was treated dropwise with acetyl chloride (0.03 mL, 0.41 mmol), stirred for 1 hour, warmed to 0° C. over 1 hour, quenched with water, and extracted twice with ethyl acetate. The combined extracts were washed with brine, dried (MgSO$_4$), filtered, and concentrated to provide 111 mg of the desired product. R$_f$=0.24 (5% methanol/dichloromethane).

EXAMPLE 17C

N-[4-(4-amino-7-iodothieno[3,2-c]pyridin-3-yl)phenyl]acetamide

The desired product was prepared by substituting Example 17B for Example 10A in Example 10B.

EXAMPLE 17D tert-butyl (2E)-3-{3-[4-(acetylamino)phenyl]-4-aminothieno[3,2-c]pyridin-7-yl}acrylate The desired product was prepared by substituting Example 17C for Example 10B in Example 11A. $^1$H NMR (300 MHz, DMSO-d$_6$) δ 1.51 (m, 9H), 2.09 (m, 3H), 5.98 (s, 2H), 6.31 (d, J=15.9 Hz, 1H), 7.41 (d, J=8.5 Hz, 2H), 7.59 (s, 1H), 7.72 (m, 3H), 8.23 (s, 1H), 10.14 (s, 1H); MS (ESI(+)) m/e 410 (M+H)$^+$.

EXAMPLE 18

(2E)-3-{3-[4-(acetylamino)phenyl]-4-aminothieno[3,2-c]pyridin-7-yl}acrylic acid

The desired product was prepared as the trifluoroacetate salt by substituting Example 17D for Example 11A in Example 11B. $^1$H NMR (300 MHz, DMSO-d$_6$) δ 2.10 (m, 3H), 6.51 (d, J=16.3 Hz, 1H), 6.74 (br s, 2H), 7.44 (d, J=8.5 Hz, 2H), 7.76 (dd, J=16.6, 7.8 Hz, 4H), 8.33 (s, 1H), 10.18 (s, 1H); MS (ESI(+)) m/e 354 (M+H)$^+$.

EXAMPLE 19

(2E)-3-{3-[4-(acetylamino)phenyl]-4-aminothieno[3,2-c]pyridin-7-yl}-N-methylacrylamide The desired product was prepared by substituting Example 18 for Example 13 in Example 14. $^1$H NMR (300 MHz, DMSO-d$_6$) δ 2.09 (m, 3H), 2.73 (m, 3H), 5.82 (s, 2H), 6.57 (d, J=15.9 Hz, 1H), 7.41 (d, J=8.5 Hz, 2H), 7.59 (m, 2H), 7.73 (d, J=8.5 Hz, 2H), 8.14 (m, 2H), 10.14 (s, 1H); MS (ESI(+)) m/e 367 (M+H)$^+$.

EXAMPLE 20

N-(4-{4-amino-7-[(1E)-3-oxo-3-(3-oxo-1-piperazinyl)-1-propenyl]thieno[3,2-c]pyridin-3-yl}phenyl)acetamide The desired product was prepared by substituting Example 18 for Example 11B in Example 11C. $^1$H NMR (300 MHz, DMSO-d$_6$) δ 2.09 (m, 3H), 3.81 (br m, 2H), 4.19 (br m, 2H), 5.89 (br s, 2H), 7.02 (br m, 1H), 7.41 (d, J=8.5 Hz, 2H), 7.59 (s, 1H), 7.72 (m, 3H), 8.14 (br s, 1H), 8.32 (s, 1H), 10.14 (s, 1H); MS (ESI(+)) m/e 436 (M+H)$^+$.

EXAMPLE 21

(2E)-3-[4-amino-3-(4-chlorophenyl)thieno[3,2-c]pyridin-7-yl]-N-methylacrylamide

EXAMPLE 21A 3-bromo-7-iodothieno[3,2-c]pyridin-4-amine

The desired product was prepared by substituting Example 1B for Example 10A in Example 10B.

EXAMPLE 21B (2E)-3-(4-amino-3-bromothieno[3,2-c]pyridin-7-yl)-N-methylacrylamide The desired product was prepared by substituting Example 21A for Example 10B and methylamine for piperazin-2-one in Examples 11A–C. MS (ESI(+)) m/e 311.6, 313.6 (M+H)$^+$.

EXAMPLE 21C (2E)-3-[4-amino-3-(4-chlorophenyl)thieno[3,2-c]pyridin-7-yl]-N-methylacrylamide A mixture of Example 21B (150 mg, 0.48 mmol), 4-chlorophenylboronic acid (75 mg, 0.48 mmol), PdCl$_2$(PPh$_3$)$_2$ (3 mg) and Cs$_2$CO$_3$ (188 mg) in DME/water/ethanol (70:30:20 mixture, 2 mL) was heated in a sealed vial to 160° C. for 7.5 minutes with stirring in a Smith Synthesizer microwave oven (at 300 W). The reaction was partinioned between water and dichloromethane and the organic layer was concentrated. The residue collected was purified by preparative HPLC on a Waters Symmetry C8 column (25 mm×100 mm, 7 μm particle size) using a gradient of 10% to 100% acetonitrile:5 mM aqueous ammonium acetate over 8 minutes (10 minute run time) at a flow rate of 40 mL/min to provide 59 mg (36% yield) of the desired product. $^1$H NMR (300 MHz, DMSO-$d_6$) δ 2.73 (d, J=4.7 Hz, 3H), 5.81 (s, 2H), 6.58 (d, J=15.9 Hz, 1H), 7.51 (d, J=8.5 Hz, 2H), 7.58 (d, J=15.9 Hz, 1H), 7.60 (d, J=8.5 Hz, 2H), 7.70 (s, 1H), 8.13 (s, 1H), 8.16 (q, J=4.7 Hz, 1H), MS (ESI(−)) m/e 341.8 (M−H)$^-$.

Examples 22–35 were prepared by substituting the appropriate boronic acid (X) for 4-chloro-phenylboronic acid in Example 21C.

EXAMPLE 22

(2E)-3-{4-amino-3-[4-(trifluoromethoxy)phenyl]thieno[3,2-c]pyridin-7-yl}-N-methylacrylamide X=4-trifluoromethoxyphenylboronic acid. $^1$H NMR (300 MHz, DMSO-$d_6$) δ 2.73 (d, J=4.7 Hz, 3H), 5.83 (s, 2H), 6.59 (d, J=15.9 Hz, 1H), 7.52 (dd, J=8.8, 1.0 Hz, 2H), 7.58 (d, J=15.9 Hz, 1H), 7.63 (d, J=8.8 Hz, 2H), 7.75 (s, 1H), 8.14 (s, 1H), 8.16 (q, J=4.7 Hz, 1H); MS (ESI(+)) m/e 393.9 (M+H)$^+$.

EXAMPLE 23

(2E)-3-[4-amino-3-(1,3-benzodioxol-5-yl)thieno[3,2-c]pyridin-7-yl]-N-methylacrylamide X=1,3-benzodioxol-5-ylboronic acid. $^1$H NMR (300 MHz, DMSO-$d_6$) δ 2.73 (d, J=4.7 Hz, 3H), 5.89 (s, 2H), 6.12 (s, 2H), 6.56 (d, J=15.6 Hz, 1H), 6.93 (dd, J=7.8, 1.7 Hz, 1H), 7.05 (d, J=1.7 Hz, 1H), 7.06 (d, J=7.8 Hz, 1H), 7.57 (d, J=15.6 Hz, 1H), 7.61 (s, 1H), 8.11 (s, 1H), 8.14 (q, J=4.7 Hz, 1H); MS (ESI(+)) m/e 353.9 (M+H)$^+$.

EXAMPLE 24

(2E)-3-[4-amino-3-(4-methylphenyl)thieno[3,2-c]pyridin-7-yl]-N-methylacrylamide

X=4-methylphenylboronic acid. $^1$H NMR (400 MHz, DMSO-$d_6$) δ 2.49 (s, 3H), 2.82 (d, J=4.6 Hz, 3H), 5.88 (s, 2H), 6.66 (d, J=16.0 Hz, 1H), 7.44 (m, 4H), 7.66 (d, J=16.0 Hz, 1H), 7.69 (s, 1H), 8.20 (s, 1H), 8.22 (q, J=4.6 Hz, 1H); MS (ESI(+)) m/e 324.0 (M+H)$^+$.

EXAMPLE 25

(2E)-3-[4-amino-3-(4-fluorophenyl)thieno[3,2-c]pyridin-7-yl]-N-methylacrylamide

X=4-fluorophenylboronic acid. $^1$H NMR (400 MHz, DMSO-$d_6$) δ 2.73 (d, J=4.6 Hz, 3H), 5.78 (s, 2H), 6.58 (d, J=16.0 Hz, 1H), 7.37 (t, J=8.8 Hz, 2H), 7.54 (dd, J=8.8, 5.5 Hz, 2H), 7.58 (d, J=16.0 Hz, 1H), 7.67 (s, 1H), 8.13 (s, 1H), 8.14 (q, J=4.7 Hz, 1H); MS (ESI(+)) m/e 327.9 (M+H)$^+$.

EXAMPLE 26

(2E)-3-[4-amino-3-(4-methoxyphenyl)thieno[3,2-c]pyridin-7-yl]-N-methylacrylamide X=4-methoxyphenylboronic acid. $^1$H NMR (400 MHz, DMSO-$d_6$) δ 2.50 (d, J=4.6 Hz, 3H), 3.60 (s, 3H), 5.58 (s, 2H), 6.34 (d, J=16.0 Hz, 1H), 6.86 (d, J=8.8 Hz, 2H), 7.17 (d, J=8.8 Hz, 2H), 7.34 (d, J=16.0 Hz, 1H), 7.35 (s, 1H), 7.87 (s, 1H), 7.90 (q, J=4.6 Hz, 1H); MS (ESI(+)) m/e 339.9 (M+H)$^+$.

EXAMPLE 27

(2E)-3-{4-amino-3-[4-(trifluoromethyl)phenyl]thieno[3,2-c]pyridin-7-yl}-N-methylacrylamide X=4-(trifluoromethyl)phenylboronic acid. $^1$H NMR (400 MHz, DMSO-$d_6$) δ 2.50 (d, J=4.6 Hz, 3H), 5.56 (s, 2H), 6.35 (d, J=16.0 Hz, 1H), 7.35 (d, J=16.0 Hz, 1H), 7.49 (d, J=8.0 Hz, 2H), 7.54 (s, 1H), 7.65 (d, J=8.0 Hz, 2H), 7.91 (q, J=4.6 Hz, 1H), 7.92 (s, 1H); MS (ESI(+)) m/e 377.9 (M+H)$^+$.

EXAMPLE 28

(2E)-3-{4-amino-3-[4-(benzyloxy)phenyl]thieno[3,2-c]pyridin-7-yl}-N-methylacrylamide X=4-(benzyloxy)phenylboronic acid. $^1$H NMR (400 MHz, DMSO-$d_6$) δ 2.50 (d, J=4.6 Hz, 3H), 4.95 (s, 2H), 5.59 (s, 2H), 6.34 (d, J=16.0 Hz, 1H), 6.94 (d, J=8.6 Hz, 2H), 7.12 (t, J=7.2 Hz, 1H), 7.16–7.20 (m, 4H), 7.26 (d, J=7.0 Hz, 2H), 7.34 (d, J=16.0 Hz, 1H), 7.36 (s, 1H), 7.87 (s, 1H), 7.90 (q, J=4.6 Hz, 1H); MS (ESI(+)) m/e 416.0 (M+H)$^+$.

EXAMPLE 29

(2E)-3-[4-amino-3-(1H-indol-5-yl)thieno[3,2-c]pyridin-7-yl]-N-methylacrylamide

X=1H-indol-5-ylboronic acid. $^1$H NMR (400 MHz, DMSO-$d_6$) δ 2.80 (d, J=4.7 Hz, 3H), 5.86 (s, 2H), 6.58 (m, 1H), 6.65 (d, J=15.7 Hz, 1H), 7.21 (dd, J=8.3, 1.8 Hz, 1H), 7.53 (app t, J=2.5 Hz, 1H), 7.61 (d, J=8.3 Hz, 1H), 7.64 (s, 1H), 7.65 (d, J=15.7 Hz, 1H), 7.70 (d, J=1.8 Hz, 1H), 8.16 (s, 1H), 8.20 (q, J=4.7 Hz, 1H), 11.39 (s, 1H); MS (ESI(+)) m/e 348.9 (M+H)$^+$.

EXAMPLE 30

(2E)-3-[4-amino-3-(3-aminophenyl)thieno[3,2-c]pyridin-7-yl]-N-methylacrylamide

X=3-aminophenylboronic acid. $^1$H NMR (300 MHz, DMSO-$d_6$) δ 2.73 (d, J=4.4 Hz, 3H), 5.37 (s, 2H), 5.98 (s, 2H), 6.52–6.56 (m, 1H), 6.56 (d, J=15.9 Hz, 1H), 6.60 (t, J=2.0 Hz, 1H), 6.68 (ddd, J=8.1, 2.0, 0.7 Hz, 1H), 7.16 (t, J=7.6 Hz, 1H), 7.57 (d, J=15.9 Hz, 1H), 7.57 (s, 1H), 8.09 (s, 1H), 8.14 (q, J=4.4 Hz, 1H); MS (ESI(+)) m/e 325.0 (M+H)$^+$.

EXAMPLE 31

(2E)-3-[4-amino-3-(4-bromophenyl)thieno[3,2-c]pyridin-7-yl]-N-methylacrylamide

X=4-bromophenylboronic acid. $^1$H NMR (300 MHz, DMSO-$d_6$) δ 2.73 (d, J=4.7 Hz, 3H), 5.82 (s, 2H), 6.58 (d, J=15.9 Hz, 1H), 7.45 (d, J=8.5 Hz, 2H), 7.58 (d, J=15.9 Hz, 1H), 7.71 (s, 1H), 7.73 (d, J=8.5 Hz, 2H), 8.13 (s, 1H), 8.15 (q, J=4.7 Hz, 1H); MS(ESI(+)) m/e 387.8, 389.8 (M+H)$^+$.

EXAMPLE 32

(2E)-3-[4-amino-3-(1,1'-biphenyl-4-yl)thieno[3,2-c]pyridin-7-yl]-N-methylacrylamide X=1,1'-biphenyl-4-ylboronic acid. $^1$H NMR (300 MHz, DMSO-d$_6$) δ 2.74 (d, J=4.7 Hz, 3H), 5.88 (s, 2H), 6.59 (d, J=15.9 Hz, 1H), 7.41 (t, J=7.3 Hz, 1H), 7.47–7.62 (m, 2H), 7.59 (d, J=15.6 Hz, 1H), 7.59 (d, J=8.5 Hz, 2H), 7.72 (s, 1H), 7.73–7.87 (m, 4H), 8.14 (s, 1H), 8.16 (q, J=4.7 Hz, 1H); MS (ESI(+)) m/e 386.0 (M+H)$^+$.

EXAMPLE 33

(2E)-3-[4-amino-3-(4-cyanophenyl)thieno[3,2-c]pyridin-7-yl]-N-methylacrylamide

X=4-cyanophenylboronic acid. $^1$H NMR (300 MHz, DMSO-d$_6$) δ 2.73 (d, J=4.4 Hz, 3H), 5.86 (s, 2H), 6.58 (d, J=15.9 Hz, 1H), 7.59 (d, J=15.9 Hz, 1H), 7.69 (d, J=8.5 Hz, 2H), 7.80 (s, 1H), 7.99 (d, J=8.5 Hz, 2H), 8.15 (q, J=4.4 Hz, 1H), 8.16 (s, 1H); MS (ESI(+)) m/e 335.0 (M+H)$^+$.

EXAMPLE 34

(2E)-3-[4-amino-3-(3-methylphenyl)thieno[3,2-c]pyridin-7-yl]-N-methylacrylamide

X=3-methylphenylboronic acid. $^1$H NMR (300 MHz, DMSO-d$_6$) δ 2.39 (s, 3H), 2.73 (d, J=4.7 Hz, 3H), 5.80 (s, 2H), 6.58 (d, J=15.9 Hz, 1H), 7.26–7.35 (m, 3H), 7.43 (t, J=7.5 Hz, 1H), 7.58 (d, J=15.9 Hz, 1H), 7.64 (s, 1H), 8.12 (s, 1H), 8.15 (q, J=4.7 Hz, 1H); MS (ESI(+)) m/e 324.0 (M+H)$^+$.

EXAMPLE 35

(2E)-3-[4-amino-3-(4-phenoxyphenyl)thieno[3,2-c]pyridin-7-yl]-N-methylacrylamide X=4-phenoxyphenylboronic acid. $^1$H NMR (400 MHz, DMSO-d$_6$) δ 2.73 (d, J=4.6 Hz, 3H), 5.97 (s, 2H), 6.60 (d, J=15.7 Hz, 1H), 7.12–7.15 (m, 4H), 7.21 (t, J=7.4 Hz, 1H), 7.45 (dd, J=8.3, 7.4 Hz, 2H), 7.50 (d, J=8.6 Hz, 2H), 7.58 (d, J=15.7 Hz, 1H), 7.69 (s, 1H), 8.14 (s, 1H), 8.16 (q, J=4.6 Hz, 1H); MS (ESI(+)) m/e 402.0 (M+H)$^+$.

EXAMPLE 36

(2E)-3-[4-amino-3-(3-phenoxy-1-propynyl)thieno[3,2-c]pyridin-7-yl]-N-methylacrylamide A mixture of Example 21A (150 mg, 0.48 mmol), (2-propynyloxy)benzene (0.13 mL, 0.96 mmol), PdCl$_2$(PPh$_3$)$_2$ (17 mg, 0.024 mmol), PPh$_3$ (15 mg, 0.057 mmol), CuI (3 mg), and Et$_3$N (1 mL, 7.2 mmol) in DME/water/ethanol (70:30:20 mixture, 2 mL) was heated in a sealed vial to 125° C. for 25 minutes with stirring in a Smith Synthesizer microwave oven (at 300 W). The reaction mixture was concentrated and the residue was purified by HPLC using the conditions described in Example 21C to provide 47 mg (27% yield) of the desired product. $^1$H NMR (400 MHz, DMSO-d$_6$) δ 2.71 (d, J=4.6 Hz, 3H), 5.18 (s, 2H), 6.50 (d, J=16.0 Hz, 1H), 6.91 (s, 2H), 7.00 (t, J=7.4 Hz, 1H), 7.08 (dd, J=8.8, 0.9 Hz, 2H), 7.35 (dd, J=8.8, 7.4 Hz, 2H), 7.52 (d, J=16.0 Hz, 1H), 8.10–8.13 (m, 2H), 8.14 (s, 1H); MS (ESI(+)) m/e 364.0 (M+H)$^+$.

Examples 37–65 were prepared by substituting Example 17A and the appropriate isocyanide (X) for Example 1C and 1-isocyanato-3-methylbenzene, respectively, in Example 1D. The crude product was purified either by trituration from dichloromethane by flash column chromatography on silica gel.

EXAMPLE 37

N-[4-(4-aminothieno[3,2-c]pyridin-3-yl)phenyl]-N'-(3-methylphenyl)urea

X=1-isocyanato-3-methylbenzene. $^1$H NMR (300 MHz, DMSO-d$_6$) δ 2.29 (s, 3H), 5.44 (s, 2H), 6.81 (d, J=7.12 Hz, 1H), 7.17 (t, J=7.80 Hz, 1H), 7.26 (d, J=5.76 Hz, 2H), 7.34 (d, J=11.53 Hz, 2H), 7.40 (d, J=11.87 Hz, 2H), 7.60 (d, J=8.48 Hz, 2H), 7.83 (d, J=5.43 Hz, 1H), 8.67 (s, 1H), 8.86 (s, 1H); MS (ESI(+)) m/e 375 (M+H)$^+$.

EXAMPLE 38

1-[4-(4-Amino-thieno[3,2-c]pyridin-3-yl)-phenyl]-3-(3-chloro-phenyl)-urea

X=1-isocyanato-3-chlorobenzene. $^1$H NMR (300 MHz, DMSO-d$_6$) δ 5.42 (s, 2H), 7.03–7.13 (m, 1H), 7.26 (d, J=5.76 Hz, 1H), 7.31–7.33 (m, 2H), 7.38 (d, J=8.48 Hz, 2H), 7.42 (s, 1H), 7.60 (d, J=8.48 Hz, 2H), 7.73 (d, J=1.70 Hz, 1H), 7.83 (d, J=5.76 Hz, 1H), 8.95 (s, 1H), 8.96 (s, 1H); MS (ESI(+)) m/e 395 (M+H)$^+$.

EXAMPLE 39

N-[4-(4-aminothieno[3,2-c]pyridin-3-yl)phenyl]-N'-[2-fluoro-5-(trifluoromethyl)phenyl]urea X=1-isocyanato-2-fluoro-5-(trifluoromethyl)benzene. $^1$H NMR (300 MHz, DMSO-d$_6$) δ 5.42 (s, 2H), 7.26 (d, J=5.76 Hz, 1H), 7.39 (s, 1H), 7.43 (d, J=5.43 Hz, 3H), 7.52–7.56 (m, 1H), 7.62 (d, J=8.48 Hz, 2H), 7.83 (d, J=5.76 Hz, 1H), 8.64 (dd, J=7.29, 1.86 Hz, 1H), 8.97 (d, J=2.37 Hz, 1H), 9.37 (s, 1H); MS (ESI(+)) m/e 447 (M+H)$^+$.

EXAMPLE 40

N-[4-(4-aminothieno[3,2-c]pyridin-3-yl)phenyl]-N'-[3-(trifluoromethyl)phenyl]urea X=1-isocyanato-3-(trifluoromethyl)benzene. $^1$H NMR (300 MHz, DMSO-d$_6$) δ 5.42 (s, 2H), 7.26 (d, J=5.76 Hz, 1H), 7.33 (d, J=7.46 Hz, 1H), 7.39 (d, J=8.48 Hz, 2H), 7.43 (s, 1H), 7.53 (t, J=7.80 Hz, 1H), 7.59–7.63 (m, 3H), 7.83 (d, J=5.76 Hz, 1H), 8.04 (s, 1H), 9.00 (s, 1H), 9.12 (s, 1H); MS (ESI(+)) m/e 429 (M+H)$^+$.

EXAMPLE 41

N-[4-(4-aminothieno[3,2-c]pyridin-3-yl)phenyl]-N'-(3,5-dimethylphenyl)urea

X=1-isocyanato-3,5-dimethylbenzene. $^1$H NMR (300 MHz, DMSO-d$_6$) δ 2.24 (s, 6H), 5.42 (s, 2H), 6.63 (s, 1H), 7.09 (s, 2H), 7.25 (d, J=5.76 Hz, 1H), 7.36 (d, J=8.48 Hz, 2H), 7.42 (s, 1H), 7.59 (d, J=8.81 Hz, 2H), 7.82 (d, J=5.76 Hz, 1H), 8.57 (s, 1H), 8.83 (s, 1H); MS (ESI(+)) m/e 389 (M+H)$^+$.

EXAMPLE 42

N-[4-(4-aminothieno[3,2-c]pyridin-3-yl)phenyl]-N'-[4-fluoro-3-(trifluoromethyl)phenyl]urea X=1-isocyanato-4-fluoro-3-(trifluoromethyl)benzene. $^1$H NMR (300 MHz, DMSO-d$_6$) δ 5.43 (s, 2H), 7.26 (d, J=5.76 Hz, 1H), 7.38 (d, J=8.48 Hz, 2H), 7.43 (s, 1H), 7.47 (d, J=10.17 Hz, 1H), 7.61 (d, J=8.48 Hz, 2H), 7.67–7.70 (m, 1H), 7.83 (d, J=5.76 Hz, 1H), 8.03 (dd, J=6.44, 2.71 Hz, 1H), 9.01 (s, 1H), 9.11 (s, 1H); MS (ESI(+)) m/e 447 (M+H)$^+$.

EXAMPLE 43

N-[4-(4-aminothieno[3,2-c]pyridin-3-yl)phenyl]-N'-1,3-benzodioxol-5-ylurea

X=5-isocyanato-1,3-benzodioxole. $^1$H NMR (300 MHz, DMSO-d$_6$) δ 5.42 (s, 2H), 5.98 (s, 2H), 6.78–6.80 (m, 1H), 6.85–6.87 (m, 1H), 7.22 (d, J=2.03 Hz, 1H), 7.25 (d, J=5.76 Hz, 1H), 7.36 (d, J=8.48 Hz, 2H), 7.41 (s, 1H), 7.58 (d, J=8.48 Hz, 2H), 7.82 (d, J=5.76 Hz, 1H), 8.62 (s, 1H), 8.80 (s, 1H); MS (ESI(+)) m/e 405 (M+H)$^+$.

EXAMPLE 44

N-[4-(4-aminothieno[3,2-c]pyridin-3-yl)phenyl]-N'-(3-nitrophenyl)urea

X=1-isocyanato-3-nitrobenzene. $^1$H NMR (300 MHz, DMSO-d$_6$) δ 5.42 (s, 2H), 7.26 (d, J=5.76 Hz, 1H), 7.40 (d, J=8.48 Hz, 2H), 7.43 (s, 1H), 7.63 (d, J=8.48 Hz, 3H), 7.74–7.76 (m, 1H), 7.83 (d, J=5.42 Hz, 2H), 8.58 (t, J=2.20 Hz, 1H), 9.05 (s, 1H), 9.30 (s, 1H); MS (ESI(+)) m/e 406 (M+H)$^+$.

EXAMPLE 45

N-[4-(4-aminothieno[3,2-c]pyridin-3-yl)phenyl]-N'-(3-chloro-4-methoxyphenyl)urea X=1-isocyanato-3-chloro-4-methoxybenzene. $^1$H NMR (300 MHz, DMSO-d$_6$) δ 3.82 (s, 3H), 5.42 (s, 2H), 7.10 (d, J=9.16 Hz, 1H), 7.25 (d, J=5.43 Hz, 1H), 7.29 (dd, J=8.82, 2.71 Hz, 1H), 7.37 (d, J=8.48 Hz, 2H), 7.42 (s, 1H), 7.59 (d, J=8.82 Hz, 2H), 7.68 (d, J=2.37 Hz, 1H), 7.82 (d, J=5.76 Hz, 1H), 8.71 (s, 1H), 8.87 (s, 1H); MS (ESI(+)) m/e 425 (M+H)$^+$.

EXAMPLE 46

N-[4-(4-aminothieno[3,2-c]pyridin-3-yl)phenyl]-N'-(3,4-dimethylphenyl)urea

X=1-isocyanato-3,4-dimethylbenzene. $^1$H NMR (300 MHz, DMSO-d$_6$) δ 2.24 (s, 6H), 5.42 (s, 2H), 6.63 (m, 1H), 7.09 (s, 2H), 7.25 (d, J=5.43 Hz, 1H), 7.36 (d, J=8.48 Hz, 2H), 7.42 (s, 1H), 7.59 (d, J=8.48 Hz, 2H), 7.82 (d, J=5.43 Hz, 1H), 8.57 (s, 1H), 8.83 (s, 1H); MS (ESI(+)) m/e 389 (M+H)$^+$.

EXAMPLE 47

N-[4-(4-aminothieno[3,2-c]pyridin-3-yl)phenyl]-N'-[2-(trifluoromethyl)phenyl]urea X=1-isocyanato-2-(trifluoromethyl)benzene. $^1$H NMR (300 MHz, DMSO-d$_6$) δ 5.41 (s, 2H), 7.26 (d, J=5.76 Hz, 1H), 7.30 (t, J=7.63 Hz, 1H), 7.39 (d, J=8.81 Hz, 2H), 7.43 (s, 1H), 7.61 (d, J=8.81 Hz, 2H), 7.69 (t, J=7.80 Hz, 2H), 7.83 (d, J=5.42 Hz, 1H), 7.96 (d, J=8.48 Hz, 1H), 8.15 (s, 1H), 9.56 (s, 1H); MS (ESI(+)) m/e 429 (M+H)$^+$.

EXAMPLE 48

N-[4-(4-aminothieno[3,2-c]pyridin-3-yl)phenyl]-N'-(2-fluoro-5-methylphenyl)urea

X=1-isocyanato-2-fluoro-5-methylbenzene. $^1$H NMR (300 MHz, DMSO-d$_6$) δ 2.28 (s, 3H), 5.41 (s, 2H), 6.79–6.84 (m, 1H), 7.12 (dd, J=11.36, 8.31 Hz, 1H), 7.26 (d, J=5.43 Hz, 1H), 7.38 (d, J=8.48 Hz, 2H), 7.43 (s, 1H), 7.60 (d, J=8.48 Hz, 2H), 7.83 (d, J=5.43 Hz, 1H), 8.00 (dd, J=7.97, 2.20 Hz, 1H), 8.54 (d, J=2.71 Hz, 1H), 9.25 (s, 1H); MS (ESI(+)) m/e 393 (M+H)$^+$.

EXAMPLE 49

N-[4-(4-aminothieno[3,2-c]pyridin-3-yl)phenyl]-N'-(3-fluorophenyl)urea

X=1-isocyanato-3-fluorobenzene. $^1$H NMR (300 MHz, DMSO-d$_6$) δ 5.42 (s, 2H), 6.77–6.83 (m, 1H), 7.15 (dd, J=7.46, 2.03 Hz, 1H), 7.26 (d, J=5.76 Hz, 1H), 7.38 (d, J=8.81 Hz, 2H), 7.42 (s, 1H), 7.48–7.54 (m, 2H), 7.60–7.62 (m, 2H), 7.83 (d, J=5.42 Hz, 1H), 8.94 (s, 1H), 8.98 (s, 1H); MS (ESI(+)) m/e 379 (M+H)$^+$.

EXAMPLE 50

N-[4-(4-aminothieno[3,2-c]pyridin-3-yl)phenyl]-N'-(3-phenoxyphenyl)urea

X=1-isocyanato-3-phenoxybenzene. $^1$H NMR (300 MHz, DMSO-d$_6$) δ 5.41 (s, 2H), 6.61–6.65 (m, 1H), 7.03–7.05 (m, 2H), 7.15–7.20 (m, 2H), 7.24–7.30 (m, 3H), 7.34 (s, 1H), 7.38–7.44 (d, J=3.39 Hz, 2H), 7.42 (m, 2H), 7.56 (d, J=8.81 Hz, 2H), 7.82 (d, J=5.42 Hz, 1H), 8.84 (s, 1H), 8.87 (s, 1H); MS (ESI(+)) m/e 453 (M+H)$^+$.

EXAMPLE 51

N-[4-(4-aminothieno[3,2-c]pyridin-3-yl)phenyl]-N'-(3-cyanophenyl)urea

X=1-isocyanato-3-cyanobenzene. $^1$H NMR (300 MHz, DMSO-d$_6$) δ 5.42 (s, 2H), 7.26 (d, J=5.43 Hz, 1H), 7.39 (d, J=8.48 Hz, 2H), 7.43 (s, 1H), 7.50 (d, J=7.80 Hz, 2H), 7.61 (d, J=8.48 Hz, 2H), 7.69–7.72 (m, 1H), 7.83 (d, J=5.43 Hz, 1H), 8.00 (s, 1H), 9.05 (s, 1H), 9.10 (s, 1H); MS (ESI(+)) m/e 386 (M+H)$^+$.

EXAMPLE 52

N-[4-(4-aminothieno[3,2-c]pyridin-3-yl)phenyl]-N'-(2-fluorophenyl)urea

X=1-isocyanato-2-fluorobenzene. $^1$H NMR (300 MHz, DMSO-d$_6$) δ 5.42 (s, 2H), 7.04–7.06 (m, 1H), 7.15 (d, J=7.12 Hz, 1H), 7.26–7.28 (m, 2H), 7.39 (d, J=8.81 Hz, 2H), 7.43 (s, 1H), 7.60–7.62 (m, 2H), 7.83 (d, J=5.42 Hz, 1H), 8.17–8.20 (m, 1H), 8.62 (d, J=2.37 Hz, 1H), 9.27 (s, 1H); MS (ESI(+)) m/e 379 (M+H)$^+$.

EXAMPLE 53

N-[4-(4-aminothieno[3,2-c]pyridin-3-yl)phenyl]-N'-(3-chloro-4-methylphenyl)urea

X=1-isocyanato-3-chloro-4-methylbenzene. $^1$H NMR (300 MHz, DMSO-d$_6$) δ 2.27 (s, 3H), 5.42 (s, 2H), 7.25 (t, J=5.93 Hz, 3H), 7.37 (d, J=8.48 Hz, 2H), 7.42 (s, 1H), 7.59 (d, J=8.81 Hz, 2H), 7.71 (d, J=2.03 Hz, 1H), 7.82 (d, J=5.76 Hz, 1H), 8.84 (s, 1H), 8.91 (s, 1H) MS (ESI(+)) m/e 409 (M+H)$^+$.

EXAMPLE 54

N-[4-(4-aminothieno[3,2-c]pyridin-3-yl)phenyl]-N'-(4-ethylphenyl)urea

X=1-isocyanato-4-ethylbenzene. $^1$H NMR (300 MHz, DMSO-d$_6$) δ 1.19 (t, J=7.46 Hz, 3H), 2.58 (q, J=7.46 Hz, 2H), 5.42 (s, 2H), 6.84 (d, J=7.46 Hz, 1H), 7.19 (t, J=7.63 Hz, 1H), 7.25 (d, J=5.76 Hz, 2H), 7.34 (s, 1H), 7.37 (d, J=8.48 Hz, 2H), 7.42 (s, 1H), 7.60 (d, J=8.48 Hz, 2H), 7.82 (d, J=5.76 Hz, 1H), 8.67 (s, 1H), 8.84 (s, 1H); MS (ESI(+)) m/e 389 (M+H)$^+$.

EXAMPLE 55

N-[4-(4-aminothieno[3,2-c]pyridin-3-yl)phenyl]-N'-(4-fluorophenyl)urea

X=1-isocyanato-4-fluorobenzene. $^1$H NMR (300 MHz, DMSO-d$_6$) δ 5.42 (s, 2H), 7.14 (t, J=8.99 Hz, 2H), 7.26 (d, J=5.76 Hz, 1H), 7.37 (d, J=8.48 Hz, 2H), 7.42 (s, 1H), 7.49 (dd, J=9.16, 4.75 Hz, 2H), 7.59 (d, J=8.48 Hz, 2H), 7.82 (d, J=5.76 Hz, 1H), 8.77 (s, 1H), 8.86 (s, 1H); MS (ESI(+)) m/e 379 (M+H)$^+$.

EXAMPLE 56

N-[4-(4-aminothieno[3,2-c]pyridin-3-yl)phenyl]-N'-phenylurea

X=isocyanatobenzene. $^1$H NMR (300 MHz, DMSO-d$_6$) δ 5.42 (s, 2H), 6.98 (t, J=7.46 Hz, 1H), 7.26 (d, J=5.76 Hz, 1H), 7.31 (d, J=7.80 Hz, 2H), 7.37 (d, J=8.48 Hz, 2H), 7.42 (s, 1H), 7.48 (d, J=7.80 Hz, 2H), 7.60 (d, J=8.48 Hz, 2H), 7.82 (d, J=5.43 Hz, 1H), 8.73 (s, 1H), 8.86 (s, 1H); MS (ESI(+)) m/e 361 (M+H)$^+$.

EXAMPLE 57

N-[4-(4-aminothieno[3,2-c]pyridin-3-yl)phenyl]-N'-(3-bromophenyl)urea

X=1-isocyanato-3-bromobenzene. $^1$H NMR (300 MHz, DMSO-d$_6$) δ 5.42 (s, 2H), 7.18–7.28 (m, 4H), 7.27 (s, 1H), 7.38–7.40 (m, 2H), 7.43 (s, 1H), 7.60 (d, J=8.81 Hz, 2H), 7.82 (d, J=5.76 Hz, 1H), 8.95 (s, 2H); MS (ESI(+)) m/e 440 (M+H)$^+$.

EXAMPLE 58

N-(3-acetylphenyl)-N'-[4-(4-aminothieno[3,2-c]pyridin-3-yl)phenyl]urea

X=1-isocyanato-3-acetylbenzene. $^1$H NMR (300 MHz, DMSO-d$_6$) δ 2.58 (s, 3H), 5.42 (s, 2H), 7.26 (d, J=5.76 Hz, 1H), 7.39 (d, J=8.48 Hz, 2H), 7.43 (s, 1H), 7.47 (d, J=7.80 Hz, 1H), 7.59–7.63 (m, 3H), 7.70 (dd, J=7.12, 2.37 Hz, 1H), 7.83 (d, J=5.76 Hz, 1H), 8.10 (d, J=2.03 Hz, 1H), 8.92 (s, 1H), 8.99 (s, 1H); MS (ESI(+)) m/e 403 (M+H)$^+$.

EXAMPLE 59 methyl 3-[({[4-(4-aminothieno[3,2-c]pyridin-3-yl)phenyl]amino}carbonyl)amino]benzoate X=methyl 3-isocyanatobenzoate. $^1$H NMR (300 MHz, DMSO-d$_6$) δ 3.87 (s, 3H), 5.42 (s, 2H), 7.26 (d, J=5.76 Hz, 1H), 7.39 (d, J=8.82 Hz, 2H), 7.45–7.49 (m, 2H), 7.59 (d, J=8.82 Hz, 2H), 7.65–7.67 (m, 2H), 7.83 (d, J=5.43 Hz, 1H), 8.23 (t, J=1.87 Hz, 1H), 8.91 (s, 1H), 9.02 (s, 1H); MS (ESI(+)) m/e 419 (M+H)$^+$.

EXAMPLE 60

N-[4-(4-aminothieno[3,2-c]pyridin-3-yl)phenyl]-N'-2,3-dihydro-1H-inden-5-ylurea

X=5-isocyanatoindane. $^1$H NMR (300 MHz, DMSO-d$_6$) δ 1.96–2.05 (m, 2H), 2.77–2.86 (m, 4H), 5.42 (s, 2H), 7.13 (s, 1H), 7.15 (d, J=1.70 Hz, 1H), 7.25 (d, J=5.42 Hz, 1H), 7.36 (d, J=8.81 Hz, 2H), 7.39 (s, 1H), 7.41 (s, 1H), 7.59 (d, J=8.82 Hz, 2H), 7.82 (d, J=5.76 Hz, 1H), 8.59 (s, 1H), 8.81 (s, 1H); MS (ESI(+)) m/e 401 (M+H)$^+$.

EXAMPLE 61

N-[4-(4-aminothieno[3,2-c]pyridin-3-yl)phenyl]-N'-[4-(trifluoromethyl)phenyl]urea X=1-isocyanato-4-(trifluoromethyl)benzene. $^1$H NMR (300 MHz, DMSO-d$_6$) δ 5.42 (s, 2H), 7.26 (d, J=5.76 Hz, 1H), 7.39 (d, J=8.48 Hz, 2H), 7.43 (s, 1H), 7.62 (d, J=8.48 Hz, 2H), 7.67 (d, J=4.75 Hz, 4H), 7.83 (d, J=5.43 Hz, 1H), 9.01 (s, 1H), 9.18 (s, 1H); MS (ESI(+)) m/e 429 (M+H)$^+$.

EXAMPLE 62

N-[4-(4-aminothieno[3,2-c]pyridin-3-yl)phenyl]-N'-(3-fluoro-4-methylphenyl)urea

X=1-isocyanato-3-fluoro-4-methylbenzene. $^1$H NMR (300 MHz, DMSO-d$_6$) δ 2.17 (d, J=1.36 Hz, 3H), 5.42 (s, 2H), 7.05 (dd, J=8.31, 2.20 Hz, 1H), 7.18 (t, J=8.48 Hz, 1H), 7.26 (d, J=5.42 Hz, 1H), 7.37 (d, J=8.48 Hz, 2H), 7.42 (s, 1H), 7.47 (d, J=2.03 Hz, 1H), 7.59 (d, J=8.48 Hz, 2H), 7.82 (d, J=5.76 Hz, 1H), 8.85 (s, 1H), 8.89 (s, 1H); MS (ESI(+)) m/e 393 (M+H)$^+$.

EXAMPLE 63

N-[4-(4-aminothieno[3,2-c]pyridin-3-yl)phenyl]-N'-(4-bromo-3-methylphenyl)urea

X=1-isocyanato-4-bromo-3-methylbenzene. $^1$H NMR (300 MHz, DMSO-d$_6$) δ 2.33 (s, 3H), 5.42 (s, 2H), 7.26 (d, J=5.76 Hz, 1H), 7.29 (d, J=2.37 Hz, 1H), 7.37 (d, J=8.82 Hz, 2H), 7.42 (s, 1H), 7.45–7.51 (m, 2H), 7.59 (d, J=8.82 Hz, 2H), 7.82 (d, J=5.76 Hz, 1H), 8.81 (s, 1H), 8.90 (s, 1H); MS (ESI(+)) m/e 454 (M+H)$^+$.

EXAMPLE 64

N-[4-(4-aminothieno[3,2-c]pyridin-3-yl)phenyl]-N'-[4-chloro-3-(trifluoromethyl)phenyl]urea X=1-isocyanato-4-chloro-3-(trifluoromethyl)benzene. $^1$H NMR (300 MHz, DMSO-$d_6$) δ 5.42 (s, 2H), 7.26 (d, J=5.43 Hz, 1H), 7.39 (d, J=8.48 Hz, 2H), 7.43 (s, 1H), 7.60 (s, 1H), 7.64 (d, J=4.07 Hz, 2H), 7.66 (d, J=2.37 Hz, 1H), 7.83 (d, J=5.43 Hz, 1H), 8.13 (d, J=2.03 Hz, 1H), 9.05 (s, 1H), 9.24 (s, 1H); MS (ESI(+)) m/e 463 (M+H)$^+$.

EXAMPLE 65

N-[4-(4-aminothieno[3,2-c]pyridin-3-yl)phenyl]-N'-(3-chloro-4-fluorophenyl)urea

X=1-isocyanato-3-chloro-4-fluorobenzene. $^1$H NMR (300 MHz, DMSO-$d_6$) δ 5.42 (s, 2H), 7.26 (d, J=5.76 Hz, 1H), 7.357.39 (m, 3H), 7.41 (d, J=8.81 Hz, 2H), 7.60 (d, J=8.48 Hz, 2H), 7.82 (d, J=5.42 Hz, 2H), 8.95 (s, 1H), 8.97 (s, 1H); MS (ESI(+)) m/e 413 (M+H)$^+$.

EXAMPLE 66

N-[4-(4-amino-2-methyl-7-nitrothieno[3,2-c]pyridin-3-yl)phenyl]-N'-(3-methylphenyl)urea

EXAMPLE 66A 3-bromo-2-methylthieno[3,2-c]pyridin-4(5H)-one

The desired product was prepared by substituting 3-(4-bromo-5-methyl-2-thienyl)acrylic acid for (2E)-3-(4-bromo-2-thienyl)acrylic acid in Example 1A. MS (ESI(+)) m/e 245 (M+H)$^+$.

EXAMPLE 66B 3-bromo-2-methyl-7-nitrothieno[3,2-c]pyridin-4(5H)-one

A solution of nitric acid (1.68 mL, 70%, 26.8 mmol) in sulfuric acid (5 mL) was added dropwise to a 0° C. solution of Example 66A (3.27 g, 13.4 mmol) in sulfuric acic (15 mL). The resulting mixture was stirred at 0° C. for 1 hour, warmed to room temperature overnight, and poured into ice water. The resulting precipitate was collected by filtration, washed with water, and dried in a vacuum oven to provide 2.47 g (64% yield) of the desired product. MS (ESI(+)) m/e 290 (M+H)$^+$.

EXAMPLE 66C 3-bromo-2-methyl-7-nitrothieno[3,2-c]pyridin-4-amine

The desired product was prepared by substituting Example 66B for Example 1A in Example 1B. MS (ESI(+)) m/e 289 (M+H)$^+$.

EXAMPLE 66D

N-(3-methylphenyl)-N'-[4-(4,4,5,5-tetramethyl-1,3,2-dioxaborolan-2-yl)phenyl]urea A 0° C. mixture of 4-(4,4,5,5-tetramethyl-1,3,2-dioxaborolan-2-yl)aniline (5.03 g, 23 mmol) and 1-isocyanato-3-methylbenzene (2.95 mL, 23 mmol) in THF (90 mL) was stirred at room temperature for 1 hour, concentrated, suspended in acetonitrile, and filtered. The filter cake was dried to provide 8.09 g of the desired product.

EXAMPLE 66E

N-[4-(4-amino-2-methyl-7-nitrothieno[3,2-c]pyridin-3-yl)phenyl]-N'-(3-methylphenyl)urea The desired product was prepared by substituting Example 66C and Example 66D for Example 1B and 4-phenoxyphenylboronic acid, respectively, in Example 10A. $^1$H NMR (300 MHz, DMSO-$d_6$) δ 2.29 (s, 3H), 2.31 (s, 3H), 4.91 (br s, 2H), 6.81 (d, J=7.46 Hz, 1H), 7.17 (t, J=7.63 Hz, 1H), 7.26–7.27 (m, 1H), 7.30–7.33 (m, 3H), 7.66 (d, J=8.48 Hz, 2H), 8.68 (s, 1H), 8.91 (s, 1H), 8.93 (s, 1H); MS (ESI(+)) m/e 434 (M+H)$^+$.

EXAMPLE 67

N-[4-(4-amino-2-methylthieno[3,2-c]pyridin-3-yl)phenyl]-N'-(3-methylphenyl)urea

EXAMPLE 67A 3-bromo-2-methylthieno[3,2-c]pyridin-4-amine

The desired product was prepared by substituting Example 66A for Example 1A in Example 1B. MS (ESI(+)) m/e 244 (M+H)$^+$.

EXAMPLE 67B

N-[4-(4-amino-2-methylthieno[3,2-c]pyridin-3-yl)phenyl]-N'-(3-methylphenyl)urea

The desired product was prepared by substituting Example 67A and Example 66D for Example 1B and 4-phenoxyphenylboronic acid, respectively, in Example 10A. $^1$H NMR (300 MHz, DMSO-$d_6$) δ 2.26 (s, 3H), 2.29 (s, 3H), 5.18 (s, 2H), 6.81 (d, J=7.46 Hz, 1H), 7.17–7.25 (m, 2H), 7.30 (m, 4H), 7.62 (d, J=8.82 Hz, 2H), 7.75 (d, J=5.43 Hz, 1H), 8.66 (s, 1H), 8.86 (s, 1H); MS (ESI(+)) m/e 389 (M+H)$^+$.

EXAMPLE 68

N-[4-(4-amino-2-methylthieno[3,2-c]pyridin-3-yl)phenyl]-N'-(3-chlorophenyl)urea

The desired product was prepared by substituting Example 67A and 4-({[(3-chlorophenyl)amino]carbonyl}amino)phenylboronic acid (prepared by substituting 1-isocyanato-3-chlorobenzene for 1-isocyanato-3-methylbenzene in Example 66D) for Example 1B and 4-phenoxyphenylboronic acid, respectively, in Example 10A. $^1$H NMR (300 MHz, DMSO-$d_6$) δ 2.26 (s, 3H), 5.17 (s, 2H), 7.04–7.11 (m, 1H), 7.16 (d, J=5.43 Hz, 1H), 7.29 (d, J=8.48 Hz, 2H), 7.32 (d, J=3.39 Hz, 2H), 7.63 (d, J=8.82 Hz, 2H), 7.73 (s, 1H), 7.75 (d, J=5.43 Hz, 1H), 8.96 (s, 1H), 8.97 (s, 1H); MS (ESI(+)) m/e 409 (M+H)$^+$.

EXAMPLE 69

N-[4-(4-amino-2-methylthieno[3,2-c]pyridin-3-yl) phenyl]-5,7-dimethyl-1,3-benzoxazol-2-amine

EXAMPLE 69A 5,7-dimethyl-N-[4-(4,4,5,5-tetramethyl-1,3,2-dioxaborolan-2-yl)phenyl]-1,3-benzoxazol-2-amine A mixture of 1-bromo-4-isothiocyanatobenzene (63.92 g, 0.298 mol) and THF (1200 mL) was treated with 2-amino-4,6-dimethylphenol (41.8 g, 0.304 mol), stirred at room temperature for 3 hours, treated with EDCI (68.46 g, 0.358 mol), warmed to 40° C. for 16 hours, cooled to room temperature, and filtered. The filtrate was concentrated at 50° C. to a final volume of about 300 mL, treated with acetonitrile (800 mL), concentrated to a volume of about 200 mL, treated with acetonitrile (800 mL), and again concentrated to a volume of about 200 mL. The mixture was treated with acetonitrile (800 mL), cooled to room temperature, and filtered. The filter cake was washed with acetonitrile (100 mL) and dried to constant weight in a vacuum oven at 45° C. over 24 hours to provide 85.8 g (85%) of 5,7-dimethyl-1,3-benzoxazol-2-amine. A mixture of 5,7-dimethyl-1,3-benzoxazol-2-amine (76.4 g, 0.230 mol), 4,4,4',4',5,5,5',5'-octamethyl-2,2'-bi-1,3,2-dioxaborolane (73.9 g, 0.292 mol), potassium acetate (71.5 g, 0.730 mol), and DMF (760 mL) was cycled three times through vacuum degassing and nitrogen purging, treated with Pd(dppf)Cl$_2$.CH$_2$Cl$_2$ (19.9 g, 0.024 mol), sealed, cycled three times through vacuum degassing and N$_2$ purging, heated to 80° C. for 5 hours, and distilled on high vacuum (0.2 mm Hg) at 40° C. to 80° C. to remove DMF. The residue was treated with CH$_2$Cl$_2$ (1300 mL), stirred for 10 minutes, and filtered. The filter cake was washed with CH$_2$Cl$_2$ (300 mL) and the filtrate was concentrated to a volume of about 800 mL. The solution was treated with SiO$_2$ (509 g), stirred for 10 minutes, poured onto a bed of SiO$_2$ (790 g) in a 4 L coarse glass fritted funnel. The SiO$_2$ was washed with 16 L of 15% ethyl acetate and the solution was concentarated at 50° C. The concentrate was treated with heptane (800 mL), concentrated, treated with heptane (900 mL), stirred at 50° C. for 30 minutes, cooled to room temperature over 2 hours, and filtered. The filter cake was washed with 100 mL heptane and dried to constant weight in a vacuum oven at 45° C. over 24 hours to provide 68.3 g (77%) of the desired product. The final product was determined to be 98.2% potency (vs. analytical standard) by HPLC. R$_t$=6.5 min. HPLC conditions: Zorbax SB-C8 Rapid Resolution (4.6 mm×75 mm, 3.5 um); flow 1.5 mL/min; 5:95 to 95:5 acetonitrile:water (0.1% H$_3$PO$_4$) over 7 minutes.

EXAMPLE 69B

N-[4-(4-amino-2-methylthieno[3,2-c]pyridin-3-yl) phenyl]-5,7-dimethyl-1,3-benzoxazol-2-amine The desired product was prepared by substituting Example 67A and Example 69A for Example 1B and 4-phenoxyphenylboronic acid, respectively, in Example 10A. $^1$H NMR (300 MHz, DMSO-d$_6$) δ 2.27 (s, 3H), 2.34 (s, 3H), 2.41 (s, 3H), 5.19 (s, 2H), 6.80 (s, 1H), 7.11 (s, 1H), 7.17 (d, J=5.42 Hz, 1H), 7.37 (d, J=8.48 Hz, 2H), 7.76 (d, J=5.76 Hz, 1H), 7.92 (d, J=8.48 Hz, 2H), 10.86 (s, 1H); MS (ESI(+)) m/e 401 (M+H)$^+$.

EXAMPLE 70

N-[4-(4-aminothieno[3,2-c]pyridin-3-yl)phenyl]-5,7-dimethyl-1,3-benzoxazol-2-amine The desired product was prepared by substituting Example 69A for 4-phenoxyphenylboronic acid in Example 10A. $^1$H NMR (300 MHz, DMSO-d$_6$) δ 2.34 (s, 3H), 2.40 (s, 3H), 5.41 (s, 2H), 6.79 (s, 1H), 7.11 (s, 1H), 7.26 (d, J=5.76 Hz, 1H), 7.44–7.50 (m, 2H), 7.48 (s, 1H), 7.83 (d, J=5.76 Hz, 1H), 7.89 (d, J=8.48 Hz, 2H), 10.84 (s, 1H); MS (ESI(+)) m/e 387 (M+H)$^+$.

EXAMPLE 71

N-[4-(4,7-diamino-2-methylthieno[3,2-c]pyridin-3-yl)phenyl]-N'-(3-methylphenyl)urea A suspension of Example 66E (0.44 g, 1.01 mmol), NH$_4$Cl (0.054 g, 1.01 mmol), and iron powder (0.45 g, 8.1 mmol) in ethanol (16 mL) and water (4 mL) was heated at 80° C. for 3 hours, cooled to room temperature, and filtered through diatomaceous earth (Celite®). The pad was washed with ethyl acetate and ethanol and the filtrate was extracted three times with ethyl acetate. The combined extracts were washed with brine, dried (Na$_2$SO$_4$), filtered, and concentrated. The residue was purified by flash column chromatography on silica gel with 5% methanol/dichloromethane to provide 0.15 g of the desired product. $^1$H NMR (300 MHz, DMSO-d$_6$) δ 2.27 (s, 3H), 2.29 (s, 3H), 4.48 (s, 2H), 4.59 (s, 2H), 6.80 (d, J=7.46 Hz, 1H), 7.17 (t, J=7.80 Hz, 1H), 7.25–7.29 (m, 3H), 7.30 (s, 1H), 7.31 (s, 1H), 7.60 (d, J=8.81 Hz, 2H), 8.67 (s, 1H), 8.86 (s, 1H); MS (ESI(+)) m/e 404 (M+H)$^+$.

EXAMPLE 72

N-{4-amino-2-methyl-3-[4-({[(3-methylphenyl) amino]carbonyl}amino)phenyl]thieno[3,2-c]pyridin-7-yl}nicotinamide

EXAMPLE 72A tert-butyl 3-bromo-2-methyl-7-nitrothieno[3,2-c] pyridin-4-ylcarbamate A 0° C. mixture of Example 66C (0.506 g, 1.76 mmol) and NaH (111 mg, 95% dispersion, 4.4 mmol) was stirred for 20 minutes, treated with a solution of di-tert-butyl dicarbonate (461 mg, 2.1 mmol) in DMF (15 mL), stirred for an additional 2 hours at 0° C., quenched with saturated aqueous NH$_4$Cl, and extracted three times with ethyl acetate. The combined extracts were washed with water and brine, dried (Na$_2$SO$_4$), filtered, and concentrated to provide 0.605 g of the desired product. MS (ESI(+)) m/e 389 (M+H)$^+$.

EXAMPLE 72B tert-butyl 7-amino-3-bromo-2-methylthieno[3,2-c] pyridin-4-ylcarbamate The desired product was prepared by substituting Example 72A for Example 66E in Example 71. MS (ESI(+)) m/e 359 (M+H)$^+$.

EXAMPLE 72C tert-butyl 3-bromo-2-methyl-7-[(3-pyridinylcarbonyl)amino]thieno[3,2-c]pyridin-4-ylcarbamate The desired product was prepared by substituting Example 72B and nicotinoyl chloride for Example 17A and acetyl chloride, respectively, in Example 17B. MS (ESI(−)) m/e 462 (M−H)⁻.

EXAMPLE 72D

N-{4-amino-2-methyl-3-[4-({[(3-methylphenyl)amino]carbonyl}amino)phenyl]thieno[3,2-c]pyridin-7-yl}nicotinamide The desired product was prepared by substituting Example 72C and Example 66D for Example 1B and 4-phenoxyphenylboronic acid, respectively, in Example 10A. $^1$H NMR (300 MHz, DMSO-d$_6$) δ 2.27 (s, 3H), 2.29 (s, 3H), 5.24 (s, 2H), 6.81 (d, J=7.46 Hz, 1H), 7.17 (t, J=7.80 Hz, 1H), 7.27 (d, J=11.53 Hz, 2H), 7.32 (s, 2H), 7.59 (d, J=5.09 Hz, 1H), 7.64 (d, J=8.48 Hz, 2H), 7.76 (s, 1H), 8.35 (d, J=7.80 Hz, 1H), 8.69 (s, 1H), 8.79 (d, J=5.76 Hz, 1H), 8.90 (s, 1H), 9.17 (s, 1H), 10.47 (s, 1H); MS (ESI(+)) m/e 509 (M+H)⁺.

EXAMPLE 73

N-{4-amino-2-methyl-3-[4-({[(3-methylphenyl)amino]carbonyl}amino)phenyl]thieno[3,2-c]pyridin-7-yl}-2-fluoro-5-(trifluoromethyl)benzamide The desired product was prepared by substituting 2-fluoro-5-trifluromethylbenzoyl chloride for nicotinoyl chloride in Examples 72C–D. $^1$H NMR (300 MHz, DMSO-d$_6$) δ 2.29 (s, 6H), 5.36 (s, 2H), 6.81 (d, J=7.12 Hz, 1H), 7.17 (t, J=7.80 Hz, 1H), 7.27 (d, J=12.88 Hz, 2H), 7.32 (s, 2H), 7.64 (d, J=8.81 Hz, 3H), 7.83 (s, 1H), 8.04 (d, J=5.76 Hz, 1H), 8.09 (s, 1H), 8.69 (s, 1H), 8.91 (s, 1H), 10.46 (s, 1H); MS (ESI(+)) m/e 594 (M+H)⁺.

EXAMPLE 74

N-{4-amino-2-methyl-3-[4-({[(3-methylphenyl)amino]carbonyl}amino)phenyl]thieno[3,2-c]pyridin-7-yl}-3-(dimethylamino)benzamide The desired product was prepared by substituting 3-dimethylaminobenzoyl chloride for nicotinoyl chloride in Examples 72C–D. $^1$H NMR (300 MHz, DMSO-d$_6$) δ 2.26 (s, 3H), 2.29 (s, 3H), 2.98 (s, 6H), 5.20 (s, 2H), 6.81 (d, J=7.46 Hz, 1H), 6.95 (d, J=7.46 Hz, 1H), 7.17 (t, J=7.63 Hz, 1H), 7.27 (d, J=10.85 Hz, 2H), 7.31 (s, 5H), 7.64 (d, J=8.48 Hz, 2H), 7.71 (s, 1H), 8.67 (s, 1H), 8.87 (s, 1H), 10.14 (s, 1H); MS (ESI(+)) m/e 551 (M+H)⁺.

EXAMPLE 75

N-{4-amino-2-methyl-3-[4-({[(3-methylphenyl)amino]carbonyl}amino)phenyl]thieno[3,2-c]pyridin-7-yl}pentanamide The desired product was prepared by substituting pentanoyl chloride for nicotinoyl chloride in Examples 72C–D. $^1$H NMR (300 MHz, DMSO-d$_6$) δ 0.94 (t, J=7.29 Hz, 3H), 1.33–1.45 (m, 2H), 1.57–1.67 (m, 2H), 2.25 (s, 3H), 2.29 (s, 3H), 2.33 (t, J=7.29 Hz, 2H), 5.13 (s, 2H), 6.81 (d, J=7.12 Hz, 1H), 7.17 (t, J=7.63 Hz, 1H), 7.25 (d, J=3.05 Hz, 2H), 7.30 (d, J=8.82 Hz, 2H), 7.62 (d, J=4.07 Hz, 2H), 7.64 (s, 1H), 8.67 (s, 1H), 8.87 (s, 1H), 9.64 (s, 1H); MS (ESI(+)) m/e 488 (M+H)⁺.

EXAMPLE 76

N-[4-(4-amino-7-bromothieno[3,2-c]pyridin-3-yl)phenyl]-N'-(3-methylphenyl)urea

EXAMPLE 76A tert-butyl 4-(4-aminothieno[3,2-c]pyridin-3-yl)phenylcarbamate

The desired product was prepared by substituting Example 17A for Example 66C in Example 72A. MS (ESI(−)) m/e 340 (M−H)⁻.

EXAMPLE 76B tert-butyl 4-(4-amino-7-bromothieno[3,2-c]pyridin-3-yl)phenylcarbamate A solution of bromine (0.4 mL, 4.6 mmol) in dichloromethane (5 mL) was added dropwise to a −5° C. solution of Example 76A (1.57 g, 4.6 mmol) in dichloromethane (30 mL). The mixture was stirred at −5° C. to 0° C. for 15 minutes and quenched with 1:1 saturated NaHCO$_3$ and saturated NaHSO$_3$ (10 mL). The organic phase was separated, washed with water and brine, dried (NaSO$_4$), filtered, and concentrated to provide 1.85 g of the desired product. MS (ESI(+)) m/e 421 (M+H)⁺.

EXAMPLE 76C 3-(4-aminophenyl)-7-bromothieno[3,2-c]pyridin-4-amine

A solution of Example 76B (0.5 g, 1.1 mmol) in TFA (4 mL) and dichloromethane (5 mL) was stirred at 0° C. for 5 minutes, warmed to room temperature for 2 hours, then concentrated. The residue was dissolved in dichloromethane, washed with brine, dried (Na$_2$SO$_4$), filtered, and concentrated to provide 0.332 g of the desired product. MS (ESI(+)) m/e 321 (M+H)⁺.

EXAMPLE 76D

N-[4-(4-amino-7-bromothieno[3,2-c]pyridin-3-yl)phenyl]-N'-(3-methylphenyl)urea

The desired product was prepared by substituting Example 76C for Example 1C in Example 1D. $^1$H NMR (300 MHz, DMSO-d$_6$) δ 2.29 (s, 3H), 5.62 (s, 2H), 6.81 (d, J=7.46 Hz, 1H), 7.17 (t, J=7.63 Hz, 1H), 7.25–7.27 (m, 1H), 7.31 (s, 1H), 7.38 (d, J=8.48 Hz, 2H), 7.56 (s, 1H), 7.60 (d, J=8.48 Hz, 2H), 7.94 (s, 1H), 8.66 (s, 1H), 8.87 (s, 1H); MS (ESI(+)) m/e 454 (M+H)$^+$.

EXAMPLE 77 tert-butyl (2E)-3-{4-amino-3-[4-({[(3-methylphenyl) amino]carbonyl}amino)phenyl]thieno[3,2-c]pyridin-7-yl}acrylate

EXAMPLE 77A tert-butyl 4-(4-amino-7-iodothieno[3,2-c]pyridin-3-yl)phenylcarbamate The desired product was prepared by substituting Example 76A for Example 10A in Example 10B. MS (ESI(+)) m/e 468 (M+H)$^+$.

EXAMPLE 77B 3-(4-aminophenyl)-7-iodothieno[3,2-c]pyridin-4-amine

The desired product was prepared by substituting Example 77A for Example 76B in Example 76C. MS (ESI(+)) m/e 368 (M+H)$^+$.

EXAMPLE 77C tert-butyl (2E)-3-{4-amino-3-[4-({[(3-methylphenyl) amino]carbonyl}amino)phenyl]thieno[3,2-c]pyridin-7-yl}acrylate The desired product was prepared by substituting Example 77B for Example 10B in Example 11A then substituting the product for Example 1C in Example 1D. $^1$H NMR (300 MHz, DMSO-d$_6$) δ 1.51 (s, 9H), 2.29 (s, 3H), 6.03 (s, 2H), 6.32 (d, J=15.94 Hz, 1H), 6.81 (d, J=7.46 Hz, 1H), 7.17 (t, J=7.80 Hz, 1H), 7.26–7.27 (m, 1H), 7.32 (s, 1H), 7.40 (d, J=8.48 Hz, 2H), 7.60 (d, J=3.73 Hz, 2H), 7.63 (s, 1H), 7.72 (d, J=15.94 Hz, 1H), 8.23 (s, 1H), 8.67 (s, 1H), 8.87 (s, 1H); MS (ESI(+)) m/e 501 (M+H)$^+$.

EXAMPLE 78

(2E)-3-{4-amino-3-[4-({[(3-methylphenyl)amino] carbonyl}amino)phenyl]thieno[3,2-c]pyridin-7-yl}acrylic acid The desired product was prepared by substituting Example 77C for Example 11A in Example 11B. $^1$H NMR (300 MHz, DMSO-d$_6$) δ 2.29 (s, 3H), 5.09 (s, 2H), 6.59 (d, J=16.28 Hz, 1H), 6.81 (d, J=7.80 Hz, 1H), 7.10 (s, 1H), 7.17 (t, J=7.63 Hz, 1H), 7.25–7.29 (m, 1H), 7.32 (s, 1H), 7.44 (d, J=8.48 Hz, 2H), 7.66 (d, J=8.82 Hz, 2H), 7.76 (d, J=16.28 Hz, 1H), 7.90 (s, 1H), 8.37 (s, 1H), 8.80 (s, 1H), 9.06 (s, 1H); MS (ESI(+)) m/e 445 (M+H)$^+$.

Examples 79–103 were prepared by substituting the appropriate amine (X), Example 78, and TBTU for 2-piperazinone, Example 11B, and HOBT, respectively, in Example 11C.

EXAMPLE 79

(2E)-3-{4-amino-3-[4-({[(3-methylphenyl)amino] carbonyl}amino)phenyl]thieno[3,2-c]pyridin-7-yl}-N,N-dimethylacrylamide X=dimethylamine hydrochloride. $^1$H NMR (300 MHz, DMSO-d$_6$) δ 2.29 (s, 3H), 2.97 (s, 3H), 3.19 (s, 3H), 5.90 (s, 2H), 6.81 (d, J=7.46 Hz, 1H), 7.02 (d, J=15.60 Hz, 1H), 7.17 (t, J=7.80 Hz, 1H), 7.26–7.28 (m, 1H), 7.32 (s, 1H), 7.39 (d, J=8.48 Hz, 2H), 7.60–7.62 (m, 2H), 7.65–7.68 (m, 1H), 7.95 (s, 1H), 8.25 (s, 1H), 8.66 (s, 1H), 8.87 (s, 1H); MS (ESI(+)) m/e 472 (M+H)$^+$.

EXAMPLE 80

N-(4-{4-amino-7-[(1E)-3-oxo-3-(3-oxo-1-piperazinyl)-1-propenyl]thieno[3,2-c]pyridin-3-yl}phenyl)-N'-(3-methylphenyl)urea X=2-piperazinone. The product was prepared as the trifluoroacetate salt by purifying the crude product as described in Example 82. $^1$H NMR (300 MHz, DMSO-d$_6$) δ 2.29 (s, 3H), 3.81 (d, J=36.96 Hz, 4H), 4.21 (d, J=65.77 Hz, 2H), 6.81 (d, J=7.46 Hz, 1H), 6.88 (s, 2H), 7.17–7.20 (m, 1H), 7.26–7.28 (m, 2H), 7.32 (s, 1H), 7.44 (d, J=8.48 Hz, 2H), 7.64 (s, 2H), 7.68–7.70 (m, 1H), 7.85 (s, 1H), 8.16 (s, 1H), 8.41 (s, 1H), 8.76 (s, 1H), 9.01 (s, 1H); MS (ESI(+)) m/e 527 (M+H)$^+$.

EXAMPLE 81

(2E)-3-{4-amino-3-[4-({[(3-methylphenyl)amino] carbonyl}amino)phenyl]thieno[3,2-c]pyridin-7-yl}-N-(2-pyridinylmethyl)acrylamide X=1-(2-pyridinyl)methanamine. $^1$H NMR (300 MHz, DMSO-d$_6$) δ 2.29 (s, 3H), 4.52 (d, J=6.10 Hz, 2H), 5.91 (s, 2H), 6.73 (d, J=15.94 Hz, 1H), 6.81 (d, J=7.12 Hz, 1H), 7.17 (t, J=7.80 Hz, 1H), 7.24–7.36 (m, 4H), 7.40 (d, J=8.48 Hz, 2H), 7.61 (d, J=3.73 Hz, 2H), 7.65–7.67 (m, 2H), 7.78–7.81 (m, 1H), 8.14 (s, 1H), 8.53 (d, J=4.75 Hz, 1H), 8.66 (s, 1H), 8.83 (t, J=5.93 Hz, 1H), 8.87 (s, 1H); MS (ESI(+)) m/e 535 (M+H)$^+$.

EXAMPLE 82

3-[((2E)-3-{4-amino-3-[4-({[(3-methylphenyl) amino]carbonyl}amino)phenyl]thieno[3,2-c]pyridin-7-yl}-2-propenoyl)amino]-2-thiophenecarboxamide X=3-amino-2-thiophenecarboxamide. The product was prepared as the trifluoroacetate salt by preparative HPLC purification on a Waters Symmetry C8 column (25 mm×100 mm, 7 μm particle size) using a gradient of 10% to 100% acetonitrile/0.1% aqueous TFA over 8 minutes (10 minute run time) at a flow rate of 40 mL/min. $^1$H NMR (300 MHz, DMSO-d$_6$) δ 2.29 (s, 3H), 3.87 (s, 2H), 6.81 (d, J=7.46 Hz, 1H), 6.88–6.96 (m, 2H), 7.17 (t, J=7.80 Hz, 1H), 7.26–7.29 (m, 1H), 7.32 (s, 1H), 7.45 (d, J=8.82 Hz, 2H), 7.66 (d, J=8.48 Hz, 3H), 7.77 (dd, J=10.51, 5.09 Hz, 2H), 7.86 (s, 1H), 8.07 (d, J=5.43 Hz, 1H), 8.42 (s, 1H), 8.77 (s, 1H), 9.02 (s, 1H), 11.49 (s, 1H); MS (ESI(+)) m/e 569 (M+H)$^+$.

EXAMPLE 83

(2E)-3-{4-amino-3-[4-({[(3-methylphenyl)amino] carbonyl}amino)phenyl]thieno[3,2-c]pyridin-7-yl}-N-[2-(4-morpholinyl)ethyl]acrylamide X=2-(4-morpholinyl)ethanamine. $^1$H NMR (300 MHz, DMSO-d$_6$) δ 2.29 (s, 3H), 2.43 (t, J=6.10 Hz, 4H), 3.32–3.37

(m, 5H), 3.59–3.61 (m, 4H), 5.87 (s, 2H), 6.62 (d, J=15.94 Hz, 1H), 6.81 (d, J=7.12 Hz, 1H), 7.17 (t, J=7.80 Hz, 1H), 7.26–7.28 (m, 1H), 7.32 (s, 1H), 7.40 (d, J=8.82 Hz, 2H), 7.55–7.63 (m, 3H), 8.12 (s, 1H), 8.18 (t, J=5.59 Hz, 1H), 8.67 (s, 1H), 8.87 (s, 1H); MS (ESI(+)) m/e 557 (M+H)+.

EXAMPLE 84

(2E)-3-{4-amino-3-[4-({[(3-methylphenyl)amino]carbonyl}amino)phenyl]thieno[3,2-c]pyridin-7-yl}-N-[3-(1-pyrrolidinyl)propyl]acrylamide X=3-(1-pyrrolidinyl)-1-propanamine. $^1$H NMR (300 MHz, DMSO-$d_6$) δ 1.67–1.70 (m, 5H), 2.29 (s, 3H), 3.28–3.37 (m, 9H), 5.86 (s, 2H), 6.59 (d, J=15.94 Hz, 1H), 6.81 (d, J=7.12 Hz, 1H), 7.17 (t, J=7.63 Hz, 1H), 7.26–7.28 (m, 1H), 7.32 (s, 1H), 7.40 (d, J=8.48 Hz, 2H), 7.55–7.63 (m, 4H), 8.11 (s, 1H), 8.23 (t, J=5.43 Hz, 1H), 8.67 (s, 1H), 8.88 (s, 1H); MS (ESI(+)) m/e 555 (M+H)+.

EXAMPLE 85

(2E)-3-{4-amino-3-[4-({[(3-methylphenyl)amino]carbonyl}amino)phenyl]thieno[3,2-c]pyridin-7-yl}-N-[(1-ethyl-2-pyrrolidinyl)methyl]acrylamide X=(1-ethyl-2-pyrrolidinyl)methylamine. $^1$H NMR (300 MHz, DMSO-$d_6$) δ 1.06 (t, J=7.29 Hz, 3H), 1.53–1.87(m, 4H), 2.07–2.27 (m, 2H), 2.29 (s, 3H), 2.84–2.87 (m, 2H), 3.02–3.08 (m, 2H), 3.39–3.47 (m, 1H), 5.87 (s, 2H), 6.66 (d, J=15.94 Hz, 1H), 6.81 (d, J=7.46 Hz, 1H), 7.17 (t, J=7.63 Hz, 1H), 7.26–7.28 (m, 1H), 7.32 (s, 1H), 7.40 (d, J=8.48 Hz, 2H), 7.55–7.63 (m, 4H), 8.10 (d, J=7.46 Hz, 2H), 8.67 (s, 1H), 8.88 (s, 1H); MS (ESI(+)) m/e 555 (M+H)+.

EXAMPLE 86

(2E)-3-{4-amino-3-[4-({[(3-methylphenyl)amino]carbonyl}amino)phenyl]thieno[3,2-c]pyridin-7-yl}-N-[2-(diethylamino)ethyl]acrylamide X=N,N-diethyl-1,2-ethanediamine. $^1$H NMR (300 MHz, DMSO-$d_6$) δ 0.97 (t, J=7.12 Hz, 6H), 2.29 (s, 3H), 2.51–2.55 (m, 4H), 3.27–3.29 (m, 4H), 5.87 (s, 2H), 6.61 (d, J=15.94 Hz, 1H), 6.81 (d, J=7.12 Hz, 1H), 7.17 (t, J=7.63 Hz, 1H), 7.26–7.28 (m, 1H), 7.32 (s, 1H), 7.40 (d, J=8.48 Hz, 2H), 7.55–7.63 (m, 4H), 8.11 (s, 1H), 8.14–8.17 (m, 1H), 8.67 (s, 1H), 8.87 (s, 1H); MS (ESI(+)) m/e 543 (M+H)+.

EXAMPLE 87

(2E)-3-{4-amino-3-[4-({[(3-methylphenyl)amino]carbonyl}amino)phenyl]thieno[3,2-c]pyridin-7-yl}-N-(2-hydroxyethyl)acrylamide X=2-aminoethanol. $^1$H NMR (300 MHz, DMSO-$d_6$) δ 2.29 (s, 3H), 3.29–3.37 (m, 2H), 3.49 (q, J=5.88 Hz, 2H), 4.75 (t, J=5.43 Hz, 1H), 5.87 (s, 2H), 6.64 (d, J=15.94 Hz, 1H), 6.80 (d, J=7.46 Hz, 1H), 7.16 (t, J=7.80 Hz, 1H), 7.28 (d, J=8.14 Hz, 1H), 7.31 (s, 1H), 7.39 (d, J=8.48 Hz, 2H), 7.61–7.64 (m, 4H), 8.11 (s, 1H), 8.28 (t, J=5.76 Hz, 1H), 9.09 (s, 1H), 9.35 (s, 1H); MS (ESI(+)) m/e 488 (M+H)+.

EXAMPLE 88

(2E)-3-{4-amino-3-[4-({[(3-methylphenyl)amino]carbonyl}amino)phenyl]thieno[3,2-c]pyridin-7-yl}-N-(3-pyridinylmethyl)acrylamide X=1-(3-pyridinyl)methanamine. $^1$H NMR (300 MHz, DMSO-$d_6$) δ 2.29 (s, 3H), 4.45 (d, J=5.76 Hz, 2H), 5.90 (s, 2H), 6.65 (d, J=15.94 Hz, 1H), 6.81 (d, J=7.46 Hz, 1H), 7.17 (t, J=7.80 Hz, 1H), 7.26–7.28 (m, 1H), 7.32 (s, 1H), 7.39–7.41 (m, 2H), 7.63–7.67 (m, 5H), 7.73 (d, J=7.80 Hz, 1H), 8.13 (s, 1H), 8.48 (dd, J=4.75, 1.70 Hz, 1H), 8.56 (d, J=2.03 Hz, 1H), 8.66 (s, 1H), 8.78 (t, J=5.76 Hz, 1H), 8.87 (s, 1H); MS (ESI(+)) m/e 535 (M+H)+.

EXAMPLE 89

(2E)-3-{4-amino-3-[4-({[(3-methylphenyl)amino]carbonyl}amino)phenyl]thieno[3,2-c]pyridin-7-yl}-N-(2,3-dihydroxypropyl)acrylamide X=3-amino-1,2-propanediol. $^1$H NMR (300 MHz, DMSO-$d_6$) δ 2.29 (s, 3H), 3.12–3.37 (m, 4H), 3.58–3.60 (m, 1H), 4.59 (t, J=5.76 Hz, 1H), 4.83 (d, J=4.75 Hz, 1H), 5.87 (s, 2H), 6.69 (d, J=15.94 Hz, 1H), 6.81 (d, J=7.12 Hz, 1H), 7.17 (t, J=7.80 Hz, 1H), 7.26–7.28 (m, 1H), 7.32 (s, 1H), 7.40 (d, J=8.48 Hz, 2H), 7.56–7.63 (m, 4H), 8.12 (s, 1H), 8.26 (t, J=5.76 Hz, 1H), 8.67 (s, 1H), 8.87 (s, 1H); MS (ESI(−)) m/e 516 (M−H)−.

EXAMPLE 90

(2E)-3-{4-amino-3-[4-({[(3-methylphenyl)amino]carbonyl}amino)phenyl]thieno[3,2-c]pyridin-7-yl}-N-(4-pyridinylmethyl)acrylamide X=1-(4-pyridinyl)methanamine. $^1$H NMR (300 MHz, DMSO-$d_6$) δ 2.29 (s, 3H), 4.46 (d, J=5.76 Hz, 2H), 5.92 (s, 2H), 6.69 (d, J=15.94 Hz, 1H), 6.81 (d, J=7.46 Hz, 1H), 7.17 (t, J=7.80 Hz, 1H), 7.26–7.28 (m, 1H), 7.31 (d, J=5.76 Hz, 3H), 7.40 (d, J=8.82 Hz, 2H), 7.64–7.68 (m, 4H), 8.15 (s, 1H), 8.52 (d, J=1.70 Hz, 1H), 8.53 (d, J=1.70 Hz, 1H), 8.67 (s, 1H), 8.83 (t, J=6.10 Hz, 1H), 8.87 (s, 1H); MS (ESI(+)) m/e 535 (M+H)+.

EXAMPLE 91

N-(4-{4-amino-7-[(1E)-3-oxo-3-(1-piperazinyl)-1-propenyl]thieno[3,2-c]pyridin-3-yl}phenyl)-N'-(3-methylphenyl)urea X=piperazine. $^1$H NMR (300 MHz, DMSO-$d_6$) δ 2.29 (s, 3H), 3.63–3.90 (m, 8H), 6.66 (s, 2H), 6.81 (d, J=6.78 Hz, 1H), 7.22–7.28 (m, 2H), 7.33 (s, 1H), 7.42 (d, J=7.12 Hz, 2H), 7.65 (d, J=6.10 Hz, 2H), 7.75 (d, J=21.36 Hz, 2H), 8.38 (s, 1H), 8.86 (s, 3H), 9.10 (s, 1H); MS (ESI(+)) m/e 513 (M+H)+.

EXAMPLE 92

(2E)-3-{4-amino-3-[4-({[(3-methylphenyl)amino]carbonyl}amino)phenyl]thieno[3,2-c]pyridin-7-yl}-N-[3-(2-oxo-1-pyrrolidinyl)propyl]acrylamide X=1-(3-aminopropyl)-2-pyrrolidinone. $^1$H NMR (300 MHz, DMSO-$d_6$) δ 1.67–1.72 (m, 2H), 1.93–1.98 (m, 2H), 2.22 (t, J=7.97 Hz, 2H), 2.29 (s, 3H), 3.15–3.38 (m, 6H), 5.87 (s, 2H), 6.59 (d, J=15.94 Hz, 1H), 6.81 (d, J=7.12 Hz, 1H), 7.17 (t, J=7.63 Hz, 1H), 7.26–7.28 (m, 1H), 7.32 (s, 1H), 7.40 (d, J=8.48 Hz, 2H), 7.56–7.63 (m, 4H), 8.12 (s, 1H), 8.21 (t, J=5.60 Hz, 1H), 8.66 (s, 1H), 8.87 (s, 1H); MS (ESI(+)) m/e 569 (M+H)$^+$.

EXAMPLE 93

(2E)-3-{4-amino-3-[4-({[(3-methylphenyl)amino]carbonyl}amino)phenyl]thieno[3,2-c]pyridin-7-yl}-N-phenylacrylamide X=aniline. $^1$H NMR (300 MHz, DMSO-d$_6$) δ 2.29 (s, 3H), 5.97 (s, 2H), 6.79–8.84 (m, 2H), 7.07 (t, J=7.29 Hz, 1H), 7.17 (t, J=7.80 Hz, 1H), 7.25–7.27 (m, 1H), 7.35–7.37 (m, 3H), 7.41 (d, J=8.48 Hz, 2H), 7.63 (d, J=8.48 Hz, 2H), 7.68 (s, 1H), 7.74–7.75 (m, 2H), 7.78 (s, 1H), 8.19 (s, 1H), 8.79 (s, 1H), 9.02 (s, 1H), 10.28 (s, 1H); MS (ESI(−)) m/e 518 (M−H)$^−$.

EXAMPLE 94

(2E)-3-{4-amino-3-[4-({[(3-methylphenyl)amino]carbonyl}amino)phenyl]thieno[3,2-c]pyridin-7-yl}-N-3-pyridinylacrylamide X=3-pyridinamine. $^1$H NMR (300 MHz, DMSO-d$_6$) δ 2.29 (s, 3H), 6.02 (s, 2H), 6.79 (d, J=5.09 Hz, 2H), 6.83 (d, J=3.39 Hz, 1H), 7.17 (t, J=7.80 Hz, 1H), 7.26–7.27 (m, 1H), 7.32 (s, 1H), 7.40–7.43 (m, 2H), 7.62–7.65 (m, 2H), 7.69 (s, 1H), 7.80 (d, J=15.93 Hz, 1H), 8.18–8.20 (m, 1H), 8.21 (s, 1H), 8.28 (dd, J=4.75, 1.36 Hz, 1H), 8.68 (s, 1H), 8.87 (d, J=2.03 Hz, 1H), 8.89 (s, 1H), 10.49 (s, 1H); MS (ESI(−)) m/e 519 (M−H)$^−$.

EXAMPLE 95

N-((2E)-3-{4-amino-3-[4-({[(3-methylphenyl)amino]carbonyl}amino)phenyl]thieno[3,2-c]pyridin-7-yl}-2-propenoyl)glycinamide X=glycinamide. $^1$H NMR (300 MHz, DMSO-d$_6$) δ 2.29 (s, 3H), 3.80 (d, J=5.76 Hz, 2H), 5.89 (s, 2H), 6.70 (d, J=15.94 Hz, 1H), 6.81 (d, J=7.12 Hz, 1H), 7.03 (s, 1H), 7.17 (t, J=7.63 Hz, 1H), 7.26–7.27 (m, 1H), 7.32 (s, 1H), 7.40 (d, J=8.48 Hz, 3H), 7.59 (d, J=8.82 Hz, 2H), 7.63 (s, 2H), 8.13 (s, 1H), 8.43 (t, J=5.76 Hz, 1H), 8.67 (s, 1H), 8.87 (s, 1H); MS (ESI(+)) m/e 501 (M+H)$^+$.

EXAMPLE 96

(2E)-3-{4-amino-3-[4-({[(3-methylphenyl)amino]carbonyl}amino)phenyl]thieno[3,2-c]pyridin-7-yl}-N-[3-(1H-imidazol-1-yl)propyl]acrylamide X=3-(1H-imidazol-1-yl)-1-propanamine. $^1$H NMR (300 MHz, DMSO-d$_6$) δ 1.89–1.99 (m, 2H), 2.29 (s, 3H), 3.18 (dd, J=12.55, 6.78 Hz, 2H), 4.05 (t, J=6.95 Hz, 2H), 5.90 (s, 2H), 6.59 (d, J=15.94 Hz, 1H), 6.81 (d, J=7.46 Hz, 1H), 7.00 (s, 1H), 7.17 (t, J=7.80 Hz, 1H), 7.26 (d, J=8.48 Hz, 2H), 7.31 (d, J=7.46 Hz, 1H), 7.40 (d, J=8.48 Hz, 2H), 7.59 (d, J=8.82 Hz, 2H), 7.63 (s, 1H), 7.84 (s, 1H), 8.13 (s, 1H), 8.30 (t, J=5.59 Hz, 1H), 8.67 (s, 1H), 8.88 (s, 1H); MS (ESI(+)) m/e 552 (M+H)$^+$.

EXAMPLE 97 tert-butyl N-((2E)-3-{4-amino-3-[4-({[(3-methylphenyl)amino]carbonyl}amino)phenyl]thieno[3,2-c]pyridin-7-yl}-2-propenoyl)-β-alaninate X=tert-butyl β-alaninate. $^1$H NMR (300 MHz, DMSO-d$_6$) δ 1.42 (s, 9H), 2.29 (s, 3H), 2.45 (t, J=6.78 Hz, 2H), 3.36–3.42 (m, 2H), 5.89 (s, 2H), 6.59 (d, J=15.94 Hz, 1H), 6.81 (d, J=7.12 Hz, 1H), 7.17 (t, J=7.80 Hz, 1H), 7.26–7.28 (m, 1H), 7.32 (s, 1H), 7.40 (d, J=8.48 Hz, 2H), 7.56–7.63 (m, 4H), 8.12 (s, 1H), 8.30 (t, J=5.59 Hz, 1H), 8.68 (s, 1H), 8.88 (s, 1H); MS (ESI(+)) m/e 572 (M+H)$^+$.

EXAMPLE 98

N-(4-{4-amino-7-[(1E)-3-(4-morpholinyl)-3-oxo-1-propenyl]thieno[3,2-c]pyridin-3-yl}phenyl)-N'-(3-methylphenyl)urea X=morpholine. $^1$H NMR (300 MHz, DMSO-d$_6$) δ 2.29 (s, 3H), 3.64 (s, 8H), 5.93 (s, 2H), 6.81 (d, J=7.46 Hz, 1H), 7.05 (d, J=15.26 Hz, 1H), 7.17 (t, J=7.80 Hz, 1H), 7.23–7.27 (m, 1H), 7.32 (s, 1H), 7.39 (d, J=8.48 Hz, 2H), 7.58 (s, 1H), 7.62 (d, J=8.48 Hz, 2H), 7.70 (d, J=15.60 Hz, 1H), 8.29 (s, 1H), 8.67 (s, 1H), 8.88 (s, 1H); MS (ESI(+)) m/e 514 (M+H)$^+$.

EXAMPLE 99

(2E)-3-{4-amino-3-[4-({[(3-methylphenyl)amino]carbonyl}amino)phenyl]thieno[3,2-c]pyridin-7-yl}-N-methylacrylamide X=methylamine hydrochloride. $^1$H NMR (300 MHz, DMSO-d$_6$) δ 2.29 (s, 3H), 2.73 (s, 3H), 5.87 (s, 2H), 6.58 (d, J=15.94 Hz, 1H), 6.81 (d, J=7.12 Hz, 1H), 7.17 (t, J=7.63 Hz, 1H), 7.26–7.28 (m, 1H), 7.32 (s, 1H), 7.39 (d, J=8.48 Hz, 2H), 7.62–7.65 (m, 4H), 8.11 (s, 1H), 8.16 (d, J=4.75 Hz, 1H), 8.77 (s, 1H), 8.99 (s, 1H); MS (ESI(+)) m/e 458 (M+H)$^+$.

EXAMPLE 100

(2E)-3-{4-amino-3-[4-({[(3-methylphenyl)amino]carbonyl}amino)phenyl]thieno[3,2-c]pyridin-7-yl}acrylamide X=ammonia. $^1$H NMR (300 MHz, DMSO-d$_6$) δ 2.29 (s, 3H), 5.88 (s, 2H), 6.58 (d, J=16.27 Hz, 1H), 6.81 (d, J=7.12 Hz, 1H), 7.05 (s, 1H), 7.17 (t, J=7.46 Hz, 1H), 7.25–7.27 (m, 1H), 7.32 (s, 1H), 7.40 (d, J=8.14 Hz, 2H), 7.60–7.62 (m, 5H), 8.11 (s, 1H), 8.67 (s, 1H), 8.87 (s, 1H); MS (ESI(+)) m/e 444 (M+H)$^+$.

EXAMPLE 101

N-(4-{4-amino-7-[(1E)-3-(5-amino-1H-pyrazol-1-yl)-3-oxo-1-propenyl]thieno[3,2-c]pyridin-3-yl}phenyl)-N'-(3-methylphenyl)urea X=1H-pyrazol-5-amine. $^1$H NMR (300 MHz, DMSO-d$_6$) δ 1.73–1.75 (m, 1H), 2.29 (s, 3H), 3.02–3.07 (m, 1H), 3.58 (s, 2H), 6.02 (d, J=2.71 Hz, 1H), 6.81 (d, J=7.46 Hz, 1H), 7.17 (t, J=7.63 Hz, 1H), 7.27–7.29 (m, 1H), 7.33 (s, 1H), 7.45 (d, J=8.48 Hz, 2H), 7.66 (d, J=8.82 Hz, 2H), 7.80 (d, J=16.28 Hz, 1H), 7.88 (s, 1H), 8.02 (d, J=16.27 Hz, 1H), 8.19 (d, J=3.05 Hz, 1H), 8.42 (s, 1H), 8.76 (s, 1H), 9.01 (s, 1H); MS (ESI(+)) m/e 510 (M+H)$^+$.

EXAMPLE 102 tert-butyl N-((2E)-3-{4-amino-3-[4-({[(3-methylphenyl)amino]carbonyl}amino)phenyl]thieno[3,2-c]pyridin-7-yl}-2-propenoyl)glycinate X=tert-butyl glycinate. $^1$H NMR (300 MHz, DMSO-d$_6$) δ 1.44 (s, 9H), 2.29 (s, 3H), 3.88 (d, J=6.10 Hz, 2H), 5.91 (s, 2H), 6.66 (d, J=16.28 Hz, 1H), 6.81 (d, J=7.12 Hz, 1H), 7.17 (t, J=7.80 Hz, 1H), 7.26–7.28 (m, 1H), 7.32 (s, 1H), 7.40 (d, J=8.48 Hz, 2H), 7.60 (d, J=3.73 Hz, 2H), 7.64–7.66 (m, 2H), 8.14 (s, 1H), 8.59 (t, J=5.93 Hz, 1H), 8.77 (s, 1H), 8.99 (s, 1H); MS (ESI(+)) m/e 558 (M+H)$^+$.

EXAMPLE 103

N-((2E)-3-{4-amino-3-[4-({[(3-methylphenyl)amino]carbonyl}amino)phenyl]thieno[3,2-c]pyridin-7-yl}-2-propenoyl)-β-alanine The desired product was prepared by substituting Example 97 for Example 11A in Example 11B. $^1$H NMR (300 MHz, DMSO-d$_6$) δ 2.29 (s, 3H), 2.48 (d, J=10.85 Hz, 2H), 3.41 (q, J=6.44 Hz, 2H), 6.75 (s, 1H), 6.82–6.87 (m, 4H), 7.17 (t, J=7.80 Hz, 1H), 7.26–7.29 (m, 1H), 7.33 (s, 1H), 7.44 (d, J=8.81 Hz, 2H), 7.58–7.64 (m, 2H), 7.67 (s, 1H), 7.90 (s, 1H), 8.23 (s, 1H), 8.46 (t, J=5.59 Hz, 1H), 8.81 (s, 1H), 9.06 (s, 1H); MS (ESI(+)) m/e 516 (M+H)$^+$.

EXAMPLE 104

N-((2E)-3-{4-amino-3-[4-({[(3-methylphenyl)amino]carbonyl}amino)phenyl]thieno[3,2-c]pyridin-7-yl}-2-propenoyl)glycine The desired product was prepared as the trifluoroacetate salt by substituting Example 102 for Example 11A in Example 11B. $^1$H NMR (300 MHz, DMSO-d$_6$) δ 2.29 (s, 3H), 3.94 (d, J=5.76 Hz, 2H), 4.95 (s, 2H), 6.81 (d, J=7.46 Hz, 1H), 6.90 (d, J=16 Hz, 1H), 7.16 (dd, J=16.28, 8.48 Hz, 2H), 7.27–7.29 (m, 1H), 7.33 (s, 1H), 7.45 (d, J=8.48 Hz, 2H), 7.62–7.69 (m, 3H), 7.96 (d, J=5.43 Hz, 1H), 8.29 (s, 1H), 8.75 (t, J=5.76 Hz, 1H), 8.92 (s, 1H), 9.18 (s, 1H); MS (ESI(+)) m/e 502 (M+H)$^+$.

EXAMPLE 105 tert-butyl 3-{4-amino-3-[4-({[(3-methylphenyl)amino]carbonyl}amino)phenyl]thieno[3,2-c]pyridin-7-yl}propanoate The desired product was prepared by substituting Example 77 for Example 14 in Example 15. $^1$H NMR (300 MHz, DMSO-d$_6$) δ 1.38 (s, 9H), 2.29 (s, 3H), 2.63 (t, J=7.29 Hz, 2H), 2.93 (t, J=7.46 Hz, 2H), 5.31 (s, 2H), 6.80 (d, J=7.46 Hz, 1H), 7.17 (t, J=7.80 Hz, 1H), 7.25–7.27 (m, 1H), 7.31 (s, 1H), 7.34–7.37 (m, 2H), 7.44 (s, 1H), 7.59 (d, J=8.81 Hz, 2H), 7.68 (s, 1H), 8.67 (s, 1H), 8.87 (s, 1H); MS (ESI(+)) m/e 503 (M+H)$^+$.

EXAMPLE 106

3-{4-amino-3-[4-({[(3-methylphenyl)amino]carbonyl}amino)phenyl]thieno[3,2-c]pyridin-7-yl}propanoic acid The desired product was prepared as the trifluoroacetate salt by substituting Example 105 for 11A in Example 11B. $^1$H NMR (300 MHz, DMSO-d$_6$) δ 2.29 (s, 3H), 2.74 (t, J=7.29 Hz, 2H), 3.02 (t, J=7.46 Hz, 2H), 3.85 (s, 1H), 6.81 (d, J=7.46 Hz, 1H), 6.96 (s, 2H), 7.17 (t, J=7.63 Hz, 1H), 7.26–7.27 (m, 1H), 7.32 (s, 1H), 7.44 (d, J=8.48 Hz, 2H), 7.66 (d, J=8.48 Hz, 2H), 7.76 (s, 1H), 7.89 (s, 1H), 8.82 (s, 1H), 9.08 (s, 1H); MS (ESI(+)) m/e 447 (M+H)$^+$.

EXAMPLE 107

3-{4-amino-3-[4-({[(3-methylphenyl)amino]carbonyl}amino)phenyl]thieno[3,2-c]pyridin-7-yl}-N-[2-(4-morpholinyl)ethyl]propanamide The desired product was prepared by substituting 2-(4-morpholinyl)ethanamine, Example 106, and TBTU for 2-piperazinone, Example 11B, and HOBT, respectively, in Example 11C. $^1$H NMR (300 MHz, DMSO-d$_6$) δ 2.31–2.36 (m, 9H), 2.92 (m, 2H), 3.16 (q, J=6.67 Hz, 2H), 3.26–3.37 (m, 2H), 3.54–3.56 (m, 4H), 5.27 (s, 2H), 6.80 (d, J=7.46 Hz, 1H), 7.17 (t, J=7.63 Hz, 1H), 7.25–7.27 (m, 1H), 7.31 (s, 1H), 7.35 (d, J=8.48 Hz, 2H), 7.44 (s, 1H), 7.59 (d, J=8.48 Hz, 2H), 7.66 (s, 1H), 7.80 (t, J=5.59 Hz, 1H), 8.65 (s, 1H), 8.84 (s, 1H); MS (ESI(+)) m/e 559 (M+H)$^+$.

EXAMPLE 108

3-{4-amino-3-[4-({[(3-methylphenyl)amino]carbonyl}amino)phenyl]thieno[3,2-c]pyridin-7-yl}-N-methylpropanamide The desired product was prepared by substituting methylamine, Example 106, and TBTU for 2-piperazinone, Example 11B, and HOBT, respectively, in Example 11C. $^1$H NMR (300 MHz, DMSO-d$_6$) δ 2.29 (s, 3H), 2.57 (d, J=4.41 Hz, 3H), 2.89–2.94 (m, 4H), 5.28 (s, 2H), 6.80 (d, J=7.46 Hz, 1H), 7.17 (t, J=7.63 Hz, 1H), 7.25–7.27 (m, 1H), 7.31 (s, 1H), 7.36 (d, J=8.48 Hz, 2H), 7.44 (s, 1H), 7.59 (d, J=8.48 Hz, 2H), 7.65 (s, 1H), 7.80 (d, J=4.41 Hz, 1H), 8.65 (s, 1H), 8.84 (s, 1H); MS (ESI(+)) m/e 460 (M+H)$^+$.

EXAMPLE 109

3-{4-amino-3-[4-({[(3-methylphenyl)amino]carbonyl}amino)phenyl]thieno[3,2-c]pyridin-7-yl}propanamide The desired product was prepared by substituting Example 100 for Example 14 in Example 15. $^1$H NMR (500 MHz, DMSO-d$_6$) δ 2.29 (s, 3H), 2.50 (s, 2H), 2.92 (s, 2H), 5.26 (s, 2H), 6.79 (s, 2H), 7.21 (d, J=44.61 Hz, 2H), 7.34 (d, J=17.78 Hz, 4H), 7.43 (s, 1H), 7.60 (s, 2H), 7.68 (s, 1H), 8.76 (s, 1H), 8.96 (s, 1H); MS (ESI(+)) m/e 446 (M+H)$^+$.

EXAMPLE 110 ethyl (2E)-3-{4-amino-3-[4-({[(3-methylphenyl)amino]carbonyl}amino)phenyl]thieno[3,2-c]pyridin-7-yl}acrylate The desired product was prepared by substituting Example 76B and ethyl acrylate for Example 10B and tert-butyl acrylate, respectively, in Example 11A, then substituting the product for Example 76B in Examples 76C–D. $^1$H NMR (300 MHz, DMSO-d$_6$) δ 1.29 (t, J=7.12 Hz, 3H), 2.29 (s, 3H), 4.22 (q, J=7.23 Hz, 2H), 6.05 (s, 2H), 6.39 (d, J=16.27 Hz, 1H), 6.81 (d, J=7.12 Hz, 1H), 7.17 (t, J=7.63 Hz, 1H), 7.23–7.27 (m, 1H), 7.32 (s, 1H), 7.39 (d, J=8.82 Hz, 2H), 7.61 (s, 2H), 7.63 (s, 1H), 7.81 (d, J=15.60 Hz, 1H), 8.27 (s, 1H), 8.67 (s, 1H), 8.88 (s, 1H); MS (ESI(+)) m/e 473 (M+H)$^+$.

EXAMPLE 111 ethyl 3-{4-amino-3-[4-({[(3-methylphenyl)amino]
carbonyl}amino)phenyl]thieno[3,2-c]pyridin-7-
yl}propanoate The desired product was prepared by substituting Example 110 for Example 14 in Example 15. $^1$H NMR (300 MHz, DMSO-$d_6$) δ 1.17 (t, J=7.12 Hz, 3H), 2.29 (s, 3H), 2.72 (t, J=7.46 Hz, 2H), 2.97 (t, J=7.29 Hz, 2H), 4.07 (q, J=7.12 Hz, 2H), 5.31 (s, 2H), 6.80 (d, J=7.12 Hz, 1H), 7.16 (t, J=7.63 Hz, 1H), 7.25 (d, J=8.14 Hz, 1H), 7.31 (s, 1H), 7.36 (d, J=8.48 Hz, 2H), 7.44 (s, 1H), 7.59 (d, J=8.48 Hz, 2H), 7.69 (s, 1H), 8.69 (s, 1H), 8.88 (s, 1H); MS (ESI(+)) m/e 475 (M+H)$^+$.

EXAMPLE 112

(2E)-3-[4-amino-3-(4-aminophenyl)thieno[3,2-c]
pyridin-7-yl]-N-methylacrylamide

EXAMPLE 112A (2E)-3-[4-amino-3-(4-aminophenyl)thieno[3,2-c]
pyridin-7-yl]acrylic acid The desired product was prepared by substituting Example 77A for Example 10B in Examples 11A–B. $^1$H NMR (300 MHz, DMSO-$d_6$) δ 5.44–5.48 (br s, 2H), 6.55 (d, J=16.27 Hz, 1H), 6.78 (d, J=8.48 Hz, 2H), 7.03 (s, 3H), 7.20 (d, J=8.48 Hz, 2H), 7.72–7.77 (m, 2H), 8.33 (s, 1H); MS (ESI(+)) m/e 312 (M+H)$^+$.

EXAMPLE 112B (2E)-3-[4-amino-3-(4-aminophenyl)thieno[3,2-c]
pyridin-7-yl]-N-methylacrylamide The desired product was prepared by substituting methylamine, Example 112A, and TBTU for 2-piperazinone, Example 11B, and HOBT, respectively, in Example 11C. $^1$H NMR (300 MHz, DMSO-$d_6$) δ 2.72 (s, 3H), 5.39 (s, 2H), 5.92 (s, 2H), 6.55 (d, J=15.94 Hz, 1H), 6.68 (d, J=8.48 Hz, 2H), 7.10 (d, J=8.48 Hz, 2H), 7.47 (s, 1H), 7.56 (d, J=15.94 Hz, 1H), 8.08 (s, 1H), 8.14 (q, J=4.18 Hz); MS (ESI(+)) m/e 325 (M+H)$^+$.

EXAMPLE 113

N-(4-{4-amino-7-[(1E)-3-(methylamino)-3-oxo-1-
propenyl]thieno[3,2-c]pyridin-3-yl}phenyl)-3-methylbenzamide The desired product was prepared by substituting 3-methylbenzoyl chloride and Example 112 for acetyl chloride and Example 17A, respectively, in Example 17B. $^1$H NMR (300 MHz, DMSO-$d_6$) δ 2.42 (s, 3H), 2.74 (d, J=4.41 Hz, 3H), 5.86 (s, 2H), 6.58 (d, J=15.60 Hz, 1H), 7.44 (d, J=5.43 Hz, 2H), 7.48 (d, J=8.48 Hz, 2H), 7.59 (d, J=15.94 Hz, 1H), 7.66 (s, 1H), 7.80 (s, 2H), 7.95 (d, J=8.14 Hz, 2H), 8.13 (s, 1H), 8.16 (d, J=4.75 Hz, 1H), 10.41 (s, 1H); MS (ESI(+)) m/e 443 (M+H)$^+$.

EXAMPLE 114

(2E)-3-[4-amino-3-(4-{[(3-methylphenyl)sulfonyl]
amino}phenyl)thieno[3,2-c]pyridin-7-yl]-N-methylacrylamide A solution of 3-methylbenzenesulfonyl chloride (70 mg, 0.37 mmol) in DMF (1 mL) was added dropwise to a −30° C. solution of Example 112 (0.117 g, 0.36 mmol) and N-methylmorpholine (0.057 mL, 0.54 mmol) in DMF (3 mL). The resulting mixture was stirred at −30° C. for 30 minutes, warmed to room temperature over 1.5 hours, and partitioned between water and ethyl acetate. The aqueous phase was extracted with ethyl acetate two times. The combined organics were dried (Na$_2$SO$_4$), filtered, concentrated and the residue was purified by flash column chromatography on silica gel with 5% methanol/dichloromethane to provide 55 mg (32% yield) of the desired product. $^1$H NMR (300 MHz, DMSO-$d_6$) δ 2.37 (s, 3H), 2.72 (d, J=4.75 Hz, 3H), 5.73 (s, 2H), 6.56 (d, J=15.94 Hz, 1H), 7.22 (d, J=8.82 Hz, 2H), 7.36 (d, J=8.48 Hz, 2H), 7.46 (d, J=5.43 Hz, 2H), 7.58 (s, 2H), 7.64 (s, 2H), 8.10 (s, 1H), 8.14 (d, J=5.09 Hz, 1H), 10.50 (s, 1H); MS (ESI(+)) m/e 479 (M+H)$^+$.

EXAMPLE 115

N-(4-{4-amino-7-[(1E)-3-(methylamino)-3-oxo-1-
propenyl]thieno[3,2-c]pyridin-3-yl}phenyl)benzamide The desired product was prepared by substituting benzoyl chloride and Example 112 for acetyl chloride and Example 17A, respectively, in Example 17B. $^1$H NMR (300 MHz, DMSO-$d_6$) δ 2.74 (d, J=4.75 Hz, 3H), 5.87 (s, 2H), 6.58 (d, J=15.93 Hz, 1H), 7.48–7.50 (m, 2H), 7.56 (s, 1H), 7.60–7.62 (m, 3H), 7.66 (s, 1H), 7.95 (s, 1H), 7.99–8.0 (m, 3H), 8.13 (s, 1H), 8.16 (d, J=4.75 Hz, 1H), 10.46 (s, 1H); MS (ESI(+)) m/e 429 (M+H)$^+$.

EXAMPLE 116

(2E)-3-(4-amino-3-phenylthieno[3,2-c]pyridin-7-yl)-
N,N-dimethylacrylamide

The desired product was prepared by substituting dimethylamine for methylamine hydrochloride in Example 14. $^1$H NMR (300 MHz, DMSO-$d_6$) δ 2.97 (s, 3H), 3.19 (s, 3H), 5.83 (s, 2H), 7.03 (d, J=15.60 Hz, 1H), 7.52–7.57 (m, 5H), 7.64–7.68 (m, 2H), 8.26 (s, 1H); MS (ESI(+)) m/e 324 (M+H)$^+$.

EXAMPLE 117

(2E)-3-[4-amino-3-(4-aminophenyl)thieno[3,2-c]
pyridin-7-yl]-N-[4-(dimethylamino)butyl]acrylamide The desired product was prepared by substituting N,N-dimethyl-1,4-butanediamine, Example 112A, and TBTU for 2-piperazinone, Example 11B, and HOBT, respectively, in Example 11C. $^1$H NMR (300 MHz, DMSO-$d_6$) δ 1.10 (s, 6H), 2.83 (s, 4H), 3.40 (s, 4H), 5.40 (s, 2H), 5.94 (s, 2H), 6.57 (d, J=15.94 Hz, 1H), 6.68 (d, J=8.48 Hz, 2H), 7.10 (d, J=8.48 Hz, 2H), 7.48 (s, 1H), 7.59 (d, J=15.94 Hz, 1H), 8.09 (s, 1H), 8.34 (s, 1H); MS (ESI(+)) m/e 410 (M+H)$^+$.

EXAMPLE 118

(2E)-3-[4-amino-3-(4-aminophenyl)thieno[3,2-c]pyridin-7-yl]-N-(3-pyridinylmethyl)acrylamide The desired product was prepared by substituting 1-(3-pyridinyl)methanamine, Example 112A, and TBTU for 2-piperazinone, Example 11B, and HOBT, respectively, in Example 11C. $^1$H NMR (300 MHz, DMSO-$d_6$) δ 3.33 (s, 2H), 4.46 (d, J=5.76 Hz, 2H), 6.30 (s, 2H), 6.68 (d, J=5.42 Hz, 1H), 6.72 (d, J=2.03 Hz, 2H), 7.13 (d, J=8.48 Hz, 2H), 7.41 (dd, J=7.46, 4.41 Hz, 1H), 7.59 (s, 1H), 7.63 (d, J=15.93 Hz, 1H), 7.77–7.80 (m, 1H), 8.14 (s, 1H), 8.50 (dd, J=4.75, 1.70 Hz, 1H), 8.57 (d, J=1.36 Hz, 1H), 8.84 (t, J=5.76 Hz, 1H); MS (ESI(+)) m/e 402 (M+H)$^+$.

EXAMPLE 119

3-(4-aminophenyl)-7-[(1E)-3-oxo-3-(1-piperazinyl)-1-propenyl]thieno[3,2-c]pyridin-4-amine The desired product was prepared as the bis-trifluoroacetate salt by substituting tert-butyl 1-piperazinecarboxylate and Example 112A for piperazin-2-one and Example 11B, respectively, in Example 11C, then by removing the protecting group following the procedure of Example 11B. $^1$H NMR (300 MHz, DMSO-$d_6$) δ 3.85 (s, 8H), 4.24 (s, 2H), 6.76 (d, J=8.48 Hz, 2H), 6.98 (s, 1H), 7.18 (d, J=8.48 Hz, 2H), 7.26 (d, J=15.60 Hz, 1H), 7.66 (d, J=15.60 Hz, 1H), 7.74 (s, 1H), 8.38 (s, 1H), 8.92 (s, 2H); MS (ESI(+)) m/e 380 (M+H)$^+$.

EXAMPLE 120

3-[4-amino-3-(4-aminophenyl)thieno[3,2-c]pyridin-7-yl]propanoic acid

The desired product was prepared by substituting Example 112A for Example 14 in Example 15. $^1$H NMR (300 MHz, DMSO-$d_6$) δ 2.72 (d, J=6.78 Hz, 4H), 2.89–2.99 (m, 2H), 6.71 (d, J=7.80 Hz, 2H), 6.97 (s, 2H), 7.15 (d, J=7.80 Hz, 2H), 7.73 (d, J=6.10 Hz, 2H), 12.36 (s, 1H); MS (ESI(+)) m/e 314 (M+H)$^+$.

EXAMPLE 121

3-(4-aminophenyl)-7-(4-pyridinyl)thieno[3,2-c]pyridin-4-amine

EXAMPLE 121A tert-butyl 4-[4-amino-7-(4-pyridinyl)thieno[3,2-c]pyridin-3-yl]phenylcarbamate A mixture of Example 77A (1.559 g, 3.34 mmol), 4-pyridylboronic acid (0.431 g, 3.51 mmol) and Na$_2$CO$_3$ (0.37 g, 3.51 mmol) in THF/methanol/water (12 mL:2.4 mL:4 mL) was degassed by bubbling nitrogen through the solution for 15 minutes, then treated with Pd(dppf)Cl$_2$ (136 mg, 0.17 mmol). The reaction vessel was sealed and heated to 90° C. for 17 hours. The reaction was cooled to room temperature and partitioned between water and ethyl acetate. The aqueous phase was extracted twice with ethyl acetate. The combined extracts were dried (Na$_2$SO$_4$), filtered, concentrated, and the residue was purified by flash column chromatography on silica gel with 3% methanol/dichloromethane to provide 0.65 g (46%) of the desired product. MS (ESI(+)) m/e 419 (M+H)$^+$.

EXAMPLE 121B 3-(4-aminophenyl)-7-(4-pyridinyl)thieno[3,2-c]pyridin-4-amine

A solution of Example 121A (0.11 g, 0.263 mmol) in TFA (3 mL) and dichloromethane (1 mL) was stirred at room temperature for 30 minutes and concentrated under a stream of nitrogen. The residue was triturated from ethyl acetate/hexanes to provide 108 mg of the desired product. $^1$H NMR (300 MHz, DMSO-$d_6$) δ 5.66 (s, 2H), 6.78 (d, J=8.14 Hz, 2H), 6.97 (s, 2H), 7.20 (d, J=8.48 Hz, 2H), 7.75 (s, 1H), 7.91 (d, J=6.44 Hz, 2H), 8.19 (s, 1H), 8.83 (d, J=6.44 Hz, 2H); MS (ESI(+)) m/e 319 (M+H)$^+$.

EXAMPLE 122

N-{4-[4-amino-7-(4-pyridinyl)thieno[3,2-c]pyridin-3-yl]phenyl}-N'-[2-fluoro-5-(trifluoromethyl)phenyl]urea A −20° C. solution of Example 121B (0.18 g, 0.57 mmol) in DMF (3 mL) and THF (3 mL) was treated dropwise with 1-fluoro-2-isocyanato-4-(trifluoromethyl)benzene (0.085 mL, 0.57 mmol) and warmed to room temperature over 1.5 hours. The resulting mixture was diluted with water and extracted twice with ethyl acetate. The combined extracts were dried (Na$_2$SO$_4$), filtered, concentrated and the residue was purified by flash column chromatography on silica gel with 3–5% methanol/dichloromethane to provide 138 mg of the desired product. $^1$H NMR (300 MHz, DMSO-$d_6$) δ 5.74 (s, 2H), 7.44 (d, J=8.48 Hz, 3H), 7.51 (d, J=10.85 Hz, 1H), 7.55 (s, 1H), 7.64 (d, J=8.82 Hz, 2H), 7.71–7.72 (m, 1H), 7.74 (d, J=1.70 Hz, 1H), 8.10 (s, 1H), 8.64 (dd, J=7.29, 2.20 Hz, 1H), 8.67–8.69 (m, 1H), 8.70 (d, J=1.70 Hz, 1H), 8.98 (d, J=2.71 Hz, 1H), 9.40 (s, 1H); MS (ESI(+)) m/e 524 (M+H)$^+$.

EXAMPLE 123

N-{4-[4-amino-7-(4-pyridinyl)thieno[3,2-c]pyridin-3-yl]phenyl}-N'-(2-fluoro-5-methylphenyl)urea The desired product was prepared by substituting 1-fluoro-2-isocyanato-4-methylbenzene for 1-fluoro-2-isocyanato-4-(trifluoromethyl)benzene in Example 122. $^1$H NMR (300 MHz, DMSO-$d_6$) δ 2.29 (s, 3H), 5.74 (s, 2H), 6.80–6.85 (m, 1H), 7.12 (dd, J=11.36, 8.31 Hz, 1H), 7.42 (d, J=8.82 Hz, 2H), 7.54 (s, 1H), 7.62 (d, J=8.48 Hz, 2H), 7.73–7.75 (m, 2H), 8.00 (dd, J=7.80, 2.03 Hz, 1H), 8.09 (s, 1H), 8.56 (d, J=2.71 Hz, 1H), 8.65–8.68 (m, 1H), 8.69 (d, J=1.70 Hz, 1H), 9.28 (s, 1H); MS (ESI(+)) m/e 470 (M+H)$^+$.

EXAMPLE 124

3-(4-aminophenyl)-7-(3-pyridinyl)thieno[3,2-c]pyridin-4-amine

The desired product was prepared by substituting 3-pyridylboronic acid for 4-pyridylboronic acid in Examples 121A–B. $^1$H NMR (300 MHz, DMSO-$d_6$) δ 5.39 (s, 2H), 5.69 (s, 2H), 6.69 (d, J=8.48 Hz, 2H), 7.11 (d, J=8.14 Hz, 2H), 7.36 (s, 1H), 7.54 (dd, J=7.80, 4.75 Hz, 1H), 7.92 (s, 1H), 8.08 (d, J=7.80 Hz, 1H), 8.61 (d, J=4.07 Hz, 1H), 8.86 (s, 1H); MS (ESI(+)) m/e 319 (M+H)+.

EXAMPLE 125

N-{4-[4-amino-7-(3-pyridinyl)thieno[3,2-c]pyridin-3-yl]phenyl}-N'-(3-methylphenyl)urea The desired product was prepared by substituting 1-isocyanato-3-methylbenzene and Example 124 for 1-fluoro-2-isocyanato-4-(trifluoromethyl)benzene and Example 121B, respectively, in Example 122. $^1$H NMR (300 MHz, DMSO-d$_6$) δ 2.29 (s, 3H), 5.64 (s, 2H), 6.81 (d, J=7.46 Hz, 1H), 7.17 (t, J=7.80 Hz, 1H), 7.26–7.27 (m, 1H), 7.32 (s, 1H), 7.41 (d, J=8.82 Hz, 2H), 7.51 (s, 1H), 7.56 (dd, J=8.14, 4.75 Hz, 1H), 7.62 (d, J=8.82 Hz, 2H), 7.96 (s, 1H), 8.10–8.13 (m, 1H), 8.62 (dd, J=4.75, 1.70 Hz, 1H), 8.67 (s, 1H), 8.87 (s, 1H), 8.88 (s, 1H); MS (ESI(+)) m/e 452 (M+H)+.

EXAMPLE 126

3-(4-aminophenyl)-7-(3-thienyl)thieno[3,2-c]pyridin-4-amine

The desired product was prepared by substituting Example 77B and 3-thienylboronic acid for Example 77A and 4-pyridylboronic acid, respectively, in Example 121A. $^1$H NMR (300 MHz, DMSO-d$_6$) δ 5.37 (s, 2H), 5.59 (s, 2H), 6.68 (d, J=8.48 Hz, 2H), 7.11 (d, J=8.48 Hz, 2H), 7.36 (s, 1H), 7.55 (dd, J=5.09, 1.36 Hz, 1H), 7.72–7.73 (m, 1H), 7.78–7.79 (m, 1H), 8.05 (s, 1H); MS (ESI(+)) m/e 324 (M+H)+.

EXAMPLE 127

N-{4-[4-amino-7-(3-thienyl)thieno[3,2-c]pyridin-3-yl]phenyl}-N'-(3-methylphenyl)urea The desired product was prepared by substituting for 1-isocyanato-3-methylbenzene and Example 126 for 1-fluoro-2-isocyanato-4-(trifluoromethyl)benzene and Example 121B, respectively, in Example 122. $^1$H NMR (300 MHz, DMSO-d$_6$) δ 2.29 (s, 3H), 5.53 (s, 2H), 6.81 (d, J=7.46 Hz, 1H), 7.17 (t, J=7.80 Hz, 1H), 7.26–7.28 (m, 1H), 7.32 (s, 1H), 7.40 (d, J=8.81 Hz, 2H), 7.51 (s, 1H), 7.57 (dd, J=5.09, 1.36 Hz, 1H), 7.61 (d, J=8.81 Hz, 2H), 7.73 (dd, J=4.92, 2.88 Hz, 1H), 7.80–7.83 (m, 1H), 8.09 (s, 1H), 8.66 (s, 1H), 8.86 (s, 1H); MS (ESI(−)) m/e 455 (M−H)−.

EXAMPLE 128

N-{4-[4-amino-7-(6-methoxy-3-pyridinyl)thieno[3,2-c]pyridin-3-yl]phenyl}-N'-[2-fluoro-5-(trifluoromethyl)phenyl]urea

EXAMPLE 128A 3-(4-aminophenyl)-7-(6-methoxy-3-pyridinyl)thieno[3,2-c]pyridin-4-amine The desired product was prepared by substituting Example 77B and 6-methoxy-3-pyridinylboronic acid for Example 77A and 4-pyridylboronic acid, respectively, in Example 121A. MS (ESI(+)) m/e 349 (M+H)+.

EXAMPLE 128B

N-{4-[4-amino-7-(6-methoxy-3-pyridinyl)thieno[3,2-c]pyridin-3-yl]phenyl}-N'-[2-fluoro-5-(trifluoromethyl)phenyl]urea The desired product was prepared by substituting Example 128A for Example 121B in Example 122. $^1$H NMR (300 MHz, DMSO-d$_6$) δ 3.93 (s, 3H), 5.55 (s, 2H), 6.99 (d, J=8.48 Hz, 1H), 7.39–7.45 (m, 3H), 7.49–7.55 (m, 2H), 7.64 (d, J=8.48 Hz, 2H), 7.89 (s, 1H), 8.00 (dd, J=8.65, 2.54 Hz, 1H), 8.45 (d, J=2.37 Hz, 1H), 8.64 (dd, J=7.46, 2.03 Hz, 1H), 8.98 (d, J=2.71 Hz, 1H), 9.39 (s, 1H); MS (ESI(+)) m/e 554 (M+H)+.

EXAMPLE 129

N-{4-[4-amino-7-(6-methoxy-3-pyridinyl)thieno[3,2-c]pyridin-3-yl]phenyl}-N'-(2-fluoro-5-methylphenyl)urea The desired product was prepared by substituting for 1-fluoro-2-isocyanato-4-methylbenzene and Example 128A for 1-fluoro-2-isocyanato-4-(trifluoromethyl)benzene and Example 121B, respectively, in Example 122. $^1$H NMR (300 MHz, DMSO-d$_6$) δ 2.29 (s, 3H), 3.93 (s, 3H), 5.55 (s, 2H), 6.82–6.84 (m, 1H), 6.97–7.00 (m, 1H), 7.12 (dd, J=11.53, 8.48 Hz, 1H), 7.41 (d, J=8.48 Hz, 2H), 7.50 (s, 1H), 7.62 (d, J=8.48 Hz, 2H), 7.88 (s, 1H), 8.00–8.03 (m, 2H), 8.44 (d, J=2.37 Hz, 1H), 8.56 (d, J=2.37 Hz, 1H), 9.27 (s, 1H); MS (ESI(+)) m/e 500 (M+H)+.

EXAMPLE 130

N-{4-[4-amino-7-(6-methoxy-3-pyridinyl)thieno[3,2-c]pyridin-3-yl]phenyl}-N'-[3-(trifluoromethyl)phenyl]urea The desired product was prepared by substituting for 1-isocyanato-3-(trifluoromethyl)benzene and Example 128A for 1-fluoro-2-isocyanato-4-(trifluoromethyl)benzene and Example 121B, respectively, in Example 122. $^1$H NMR (300 MHz, DMSO-d$_6$) δ 3.93 (s, 3H), 5.56 (s, 2H), 6.99 (d, J=8.48 Hz, 1H), 7.33 (d, J=7.46 Hz, 1H), 7.42 (d, J=8.48 Hz, 2H), 7.50 (s, 1H), 7.55 (d, J=7.46 Hz, 1H), 7.60 (s, 1H), 7.64 (d, J=8.48 Hz, 2H), 7.89 (s, 1H), 8.00 (dd, J=8.48, 2.71 Hz, 1H), 8.04 (s, 1H), 8.44 (d, J=2.37 Hz, 1H), 9.02 (s, 1H), 9.13 (s, 1H); MS (ESI(+)) m/e 534 (M+H)+.

EXAMPLE 131

N-{4-[4-amino-7-(4-cyanophenyl)thieno[3,2-c]pyridin-3-yl]phenyl}-N'-[2-fluoro-5-(trifluoromethyl)phenyl]urea

EXAMPLE 131A

4-[4-Amino-3-(4-amino-phenyl)-thieno[3,2-c]pyridin-7-yl]-benzonitrile

The desired product was prepared by substituting Example 77B and 4-cyanophenylboronic acid for Example 77A and 4-pyridylboronic acid, respectively, in Example 121A. MS (ESI(+)) m/e 343 (M+H)+.

EXAMPLE 131B

N-{4-[4-amino-7-(4-cyanophenyl)thieno[3,2-c]pyridin-3-yl]phenyl}-N'-[2-fluoro-5-(trifluoromethyl)phenyl]urea The desired product was prepared by substituting Example 131A for Example 121B in Example 122. $^1$H NMR (300 MHz, DMSO-$d_6$) δ 5.71 (s, 2H), 7.40–7.45 (m, 3H), 7.51 (d, J=10.85 Hz, 1H), 7.54 (s, 1H), 7.64 (d, J=8.81 Hz, 2H), 7.90 (d, J=8.81 Hz, 2H), 7.96–8.00 (m, 2H), 8.02 (s, 1H), 8.64 (dd, J=7.46, 2.37 Hz, 1H), 8.98 (d, J=3.05 Hz, 1H), 9.39 (s, 1H); MS (ESI(+)) m/e 548 (M+H)$^+$.

EXAMPLE 132

N-{4-[4-amino-7-(4-cyanophenyl)thieno[3,2-c]pyridin-3-yl]phenyl}-N'-(2-fluoro-5-methylphenyl)urea The desired product was prepared by substituting for 1-fluoro-2-isocyanato-4-methylbenzene and Example 131A for 1-fluoro-2-isocyanato-4-(trifluoromethyl)benzene and Example 121B, respectively, in Example 122. $^1$H NMR (300 MHz, DMSO-$d_6$) δ 3.31 (s, 3H), 5.71 (s, 2H), 6.79–6.84 (m, 1H), 7.12 (dd, J=11.36, 8.31 Hz, 1H), 7.42 (d, J=8.48 Hz, 2H), 7.53 (s, 1H), 7.62 (d, J=8.48 Hz, 2H), 7.90 (d, J=8.48 Hz, 2H), 7.97–8.03 (m, 4H), 8.56 (d, J=2.37 Hz, 1H), 9.28 (s, 1H); MS (ESI(+)) m/e 494 (M+H)$^+$.

EXAMPLE 133

N-{4-[4-amino-7-(2-methoxy-5-pyrimidinyl)thieno[3,2-c]pyridin-3-yl]phenyl}-N'-[2-fluoro-5-(trifluoromethyl)phenyl]urea

EXAMPLE 133A 3-(4-aminophenyl)-7-(2-methoxy-5-pyrimidinyl)thieno[3,2-c]pyridin-4-amine The desired product was prepared by substituting 2-methoxy-5-pyrimidinylboronic acid for 4-pyridylboronic acid in Examples 121A–B. MS (ESI(+)) m/e 350 (M+H)$^+$.

EXAMPLE 133B

N-{4-[4-amino-7-(2-methoxy-5-pyrimidinyl)thieno[3,2-c]pyridin-3-yl]phenyl}-N'-[2-fluoro-5-(trifluoromethyl)phenyl]urea The desired product was prepared by substituting Example 131A for Example 121B in Example 122. $^1$H NMR (300 MHz, DMSO-$d_6$) δ 4.00 (s, 3H), 5.64 (s, 2H), 7.43 (d, J=8.48 Hz, 3H), 7.49–7.55 (m, 2H), 7.64 (d, J=8.48 Hz, 2H), 7.95 (s, 1H), 8.63–8.66 (m, 1H), 8.90 (s, 2H), 8.98 (d, J=2.37 Hz, 1H), 9.39 (s, 1H); MS (ESI(+)) m/e 555 (M+H)$^+$.

EXAMPLE 134

N-{4-[4-amino-7-(2-methoxy-5-pyrimidinyl)thieno[3,2-c]pyridin-3-yl]phenyl}-N'-[3-(trifluoromethyl)phenyl]urea The desired product was prepared by substituting 1-isocyanato-3-(trifluoromethyl)benzene and Example 131A for 1-fluoro-2-isocyanato-4-(trifluoromethyl)benzene and Example 121B, respectively, in Example 122. $^1$H NMR (300 MHz, DMSO-$d_6$) δ 4.00 (s, 3H), 5.65 (s, 2H), 7.33 (d, J=7.80 Hz, 1H), 7.42 (d, J=8.48 Hz, 2H), 7.51–7.56 (m, 2H), 7.61 (d, J=8.48 Hz, 2H), 7.65 (s, 1H), 7.94 (s, 1H), 8.04 (s, 1H), 8.90 (s, 2H), 9.03 (s, 1H), 9.13 (s, 1H); MS (ESI(+)) m/e 537 (M+H)$^+$.

EXAMPLE 135

N-{4-[4-amino-7-(2,6-dimethyl-3-pyridinyl)thieno[3,2-c]pyridin-3-yl]phenyl}-N'-[2-fluoro-5-(trifluoromethyl)phenyl]urea

EXAMPLE 135A 3-(4-aminophenyl)-7-(2,6-dimethyl-3-pyridinyl)thieno[3,2-c]pyridin-4-amine The desired product was prepared by substituting 2,6-dimethyl-3-pyridinylboronic acid for 4-pyridylboronic acid in Examples 121A–B. MS (ESI(+)) m/e 347 (M+H)$^+$.

EXAMPLE 135B

N-{4-[4-amino-7-(2,6-dimethyl-3-pyridinyl)thieno[3,2-c]pyridin-3-yl]phenyl}-N'-[2-fluoro-5-(trifluoromethyl)phenyl]urea The desired product was prepared by substituting Example 135A for Example 121B in Example 122. $^1$H NMR (300 MHz, DMSO-$d_6$) δ 2.31 (s, 3H), 2.32 (s, 3H), 5.54 (s, 2H), 6.68 (d, J=8.48 Hz, 1H), 7.12 (d, J=8.48 Hz, 1H), 7.17–7.21 (m, 2H), 7.40–7.49 (m, 3H), 7.57–7.67 (m, 2H), 7.72 (s, 1H), 8.64 (dd, J=7.46, 2.03 Hz, 1H), 8.98 (d, J=2.71 Hz, 1H), 9.38 (s, 1H); MS (ESI(+)) m/e 552 (M+H)$^+$.

EXAMPLE 136

N-{4-[4-amino-7-(5-pyrimidinyl)thieno[3,2-c]pyridin-3-yl]phenyl}-N'-(3-methylphenyl)urea

EXAMPLE 136A 3-(4-aminophenyl)-7-(5-pyrimidinyl)thieno[3,2-c]pyridin-4-amine The desired product was prepared by substituting 5-pyrimidinylboronic acid for 4-pyridylboronic acid in Examples 121A–B. MS (ESI(+)) m/e 320 (M+H)$^+$.

EXAMPLE 136B

N-{4-[4-amino-7-(5-pyrimidinyl)thieno[3,2-c]pyridin-3-yl]phenyl}-N'-(3-methylphenyl)urea The desired product was prepared by substituting 1-isocyanato-3-methylbenzene and Example 136A for 1-fluoro-2-isocyanato-4-(trifluoromethyl)benzene and Example 121B, respectively, in Example 122. $^1$H NMR (300 MHz, DMSO-$d_6$) δ 2.29 (s, 3H), 5.75 (d, J=2.71 Hz, 2H), 6.81 (d, J=7.46 Hz, 1H), 7.17 (t, J=7.80 Hz, 1H), 7.26–7.28 (m, 1H), 7.32 (s, 1H), 7.40 (d, J=8.48 Hz, 2H), 7.54 (s, 1H), 7.62 (d, J=8.48 Hz, 2H), 8.04 (s, 1H), 8.67 (s, 1H), 8.88 (s, 1H), 9.14 (s, 2H), 9.23 (s, 1H); MS (ESI(+)) m/e 453 (M+H)$^+$.

EXAMPLE 137

N-{4-[4-amino-7-(5-pyrimidinyl)thieno[3,2-c]pyridin-3-yl]phenyl}-N'-[2-fluoro-5-(trifluoromethyl)phenyl]urea The desired product was prepared by substituting Example 136A for Example 121B in Example 122. $^1$H NMR (300 MHz, DMSO-$d_6$) δ 5.74 (s, 2H), 7.44 (d, J=8.48 Hz, 3H), 7.49–7.56 (m, 2H), 7.65 (d, J=8.48 Hz, 2H), 8.05 (s, 1H), 8.65 (d, J=7.12 Hz, 1H), 8.98 (d, J=2.37 Hz, 1H), 9.14 (s, 2H), 9.24 (s, 1H), 9.40 (s, 1H); MS (ESI(+)) m/e 525 (M+H)$^+$.

EXAMPLE 138

3-(4-aminophenyl)-7-[4-(benzyloxy)phenyl]thieno[3,2-c]pyridin-4-amine

The desired product was prepared by substituting Example 77B and 4-benzyloxyphenylboronic acid for Example 77A and 4-pyridylboronic acid, respectively, in Example 121A. $^1$H NMR (300 MHz, DMSO-$d_6$) δ 5.18 (s, 2H), 5.37 (s, 2H), 5.53 (s, 2H), 6.68 (d, J=8.14 Hz, 2H), 7.10 (d, J=8.14 Hz, 2H), 7.15 (d, J=8.82 Hz, 2H), 7.32 (s, 1H), 7.48–7.51 (m, 3H), 7.53–7.55 (m, 2H), 7.57 (d, J=8.82 Hz, 2H), 7.81 (s, 1H); MS (ESI(+)) m/e 424 (M+H)$^+$.

EXAMPLE 139

4-[4-amino-3-(4-aminophenyl)thieno[3,2-c]pyridin-7-yl]phenol

A suspension of Example 138 (132 mg) in 48% HBr (2 mL) and acetic acid (4 mL) was heated to 80° C. for 3 hours. The resulting homogeneous solution was concentrated and the residue was triturated from ethanol/diethyl ether to provide 130 mg of the desired product the dihydrobromide salt. $^1$H NMR (300 MHz, DMSO-$d_6$) δ 3.67 (s, 2H), 6.95–6.98 (m, 6H), 7.34 (d, J=8.48 Hz, 2H), 7.51 (d, J=8.82 Hz, 2H), 7.85 (d, J=8.82 Hz, 2H), 9.83 (s, 1H); MS (ESI(+)) m/e 334 (M+H)$^+$.

EXAMPLE 140

N-{4-[4-amino-7-(4-hydroxyphenyl)thieno[3,2-c]pyridin-3-yl]phenyl}-N'-(3-methylphenyl)urea The desired product was prepared as the hydrobromide salt by substituting Example 138 for Example 1C in Example 1D, then substituting the product for Example 138 in Example 139. $^1$H NMR (300 MHz, DMSO-$d_6$) δ 2.29 (s, 3H), 6.82 (d, J=7.12 Hz, 1H), 6.90 (s, 2H), 6.96–6.99 (m, 2H), 7.18 (t, J=7.80 Hz, 1H), 7.27 (d, J=8.48 Hz, 1H), 7.32 (s, 1H), 7.46 (d, J=8.48 Hz, 2H), 7.52–7.55 (m, 2H), 7.67 (d, J=8.48 Hz, 2H), 7.89 (d, J=4.07 Hz, 2H), 8.75 (s, 1H), 9.02 (s, 1H), 9.88 (s, 1H); MS (ESI(+)) m/e 467 (M+H)$^+$.

EXAMPLE 141

3-{4-amino-3-[4-({[(3-methylphenyl)amino]carbonyl}amino)phenyl]thieno[3,2-c]pyridin-7-yl}-N-methylbenzamide The desired product was prepared as the trifluoroacetate salt by substituting 3-[(methylamino)carbonyl]phenylboronic acid for 4-pyridylboronic acid in Examples 121A–B, then substituting the product and 1-isocyanato-3-methylbenzene for Example 121B and 1-fluoro-2-isocyanato-4-(trifluoromethyl)benzene, respectively, in Example 122. The product was purified by HPLC as described in Example 82. $^1$H NMR (300 MHz, DMSO-$d_6$) δ 2.09 (s, 3H), 2.29 (s, 3H), 6.82 (d, J=7.46 Hz, 1H), 6.96 (s, 2H), 7.18 (t, J=7.80 Hz, 1H), 7.27–7.29 (m, 1H), 7.34–7.36 (m, 2H), 7.47 (d, J=8.82 Hz, 2H), 7.53–7.55 (m, 1H), 7.61–7.63 (m, 1H), 7.67 (d, J=8.48 Hz, 2H), 7.88 (s, 1H), 7.95 (s, 1H), 8.12 (s, 1H), 8.83 (s, 1H), 9.09 (s, 1H), 10.19 (s, 1H); MS (ESI(+)) m/e 508 (M+H)$^+$.

EXAMPLE 142

N-[4-(4-amino-7-phenylthieno[3,2-c]pyridin-3-yl)phenyl]-N'-(3-methylphenyl)urea

The desired product was prepared by substituting phenylboronic acid for 4-pyridylboronic acid in Examples 121A–B, then substituting the product and 1-isocyanato-3-methylbenzene for Example 121B and 1-fluoro-2-isocyanato-4-(trifluoromethyl)benzene, respectively, in Example 122. $^1$H NMR (300 MHz, DMSO-$d_6$) δ 2.29 (s, 3H), 5.54 (s, 2H), 6.81 (d, J=7.46 Hz, 1H), 7.17 (t, J=7.63 Hz, 1H), 7.26–7.28 (m, 1H), 7.32 (s, 1H), 7.40 (d, J=8.14 Hz, 2H), 7.48–7.55 (m, 4H), 7.61 (d, J=8.48 Hz, 2H), 7.67 (d, J=7.12 Hz, 2H), 7.91 (s, 1H), 8.67 (s, 1H), 8.86 (s, 1H); MS (ESI(+)) m/e 451 (M+H)$^+$.

EXAMPLE 143

N-{4-[4-amino-7-(4-pyridinyl)thieno[3,2-c]pyridin-3-yl]phenyl}-N'-(3-methylphenyl)urea The desired product was prepared by substituting 1-isocyanato-3-methylbenzene for 1-fluoro-2-isocyanato-4-(trifluoromethyl)benzene in Example 122. $^1$H NMR (300 MHz, DMSO-$d_6$) δ 2.29 (s, 3H), 5.74 (s, 2H), 6.81 (d, J=7.46 Hz, 1H), 7.17 (t, J=7.80 Hz, 1H), 7.26–7.27 (m, 1H), 7.32 (s, 1H), 7.40 (d, J=8.81 Hz, 2H), 7.53 (s, 1H), 7.62 (d, J=8.48 Hz, 2H), 7.72–7.73 (m, 1H), 7.73 (d, J=1.70 Hz, 1H), 8.09 (s, 1H), 8.67 (t, J=2.20 Hz, 2H), 8.69 (d, J=1.36 Hz, 1H), 8.87 (s, 1H); MS (ESI(+)) m/e 452 (M+H)$^+$.

EXAMPLE 144

N-{4-[4-amino-7-(4-hydroxy-1-butynyl)thieno[3,2-c]pyridin-3-yl]phenyl}-N'-(3-methylphenyl)urea

EXAMPLE 144A

N-[4-(4-amino-7-iodothieno[3,2-c]pyridin-3-yl)phenyl]-N'-(3-methylphenyl)urea

The desired product was prepared by substituting Example 77B for Example 1C in Example 1D. MS (ESI(+)) m/e 501 (M+H)$^+$.

EXAMPLE 144B

N-{4-[4-amino-7-(4-hydroxy-1-butynyl)thieno[3,2-c]pyridin-3-yl]phenyl}-N'-(3-methylphenyl)urea A suspension of Example 144A (0.227 g, 0.45 mmol) in piperidine (3 mL) was degassed by bubbling nitrogen through the suspension for 5 minutes, treated with 3-butyn-1-ol (0.069 mL, 0.91 mmol), Pd(PPh$_3$)$_4$ (26 mg, 0.023 mmol), and CuI (5 mg, 0.023 mmol), then heated to 80° C. in a sealed tube for 30 minutes. The resulting homogeneous solution was cooled to room temperature and concentrated under a stream of nitrogen. The residue was purified by flash column chromatography on silica gel with 5% methanol/ dichloromethane to provide 164 mg (81%) of the desired product. $^1$H NMR (300 MHz, DMSO-d$_6$) δ 2.29 (s, 3H), 2.65 (t, J=6.78 Hz, 2H), 3.63 (q, J=6.73 Hz, 2H), 4.92 (t, J=5.59 Hz, 1H), 5.70 (s, 2H), 6.81 (d, J=7.46 Hz, 1H), 7.17 (t, J=7.80 Hz, 1H), 7.25–7.28 (m, 1H), 7.32 (s, 1H), 7.37 (d, J=8.48 Hz, 2H), 7.49 (s, 1H), 7.60 (d, J=8.48 Hz, 2H), 7.93 (s, 1H), 8.65 (s, 1H), 8.85 (s, 1H); MS (ESI(+)) m/e 443 (M+H)$^+$.

Examples 145–156 were prepared by substituting the appropriate alkyne (X) for 3-butyn-1-ol in Example 144B.

EXAMPLE 145

N-{4-[4-amino-7-(3-phenoxy-1-propynyl)thieno[3,2-c]pyridin-3-yl]phenyl}-N'-(3-methylphenyl)urea X=(2-propynyloxy)benzene. $^1$H NMR (300 MHz, DMSO-d$_6$) δ 2.29 (s, 3H), 5.14 (s, 2H), 5.85 (s, 2H), 6.80 (d, J=7.46 Hz, 1H), 6.99 (t, J=7.29 Hz, 1H), 7.09 (d, J=7.46 Hz, 2H), 7.16 (t, J=7.80 Hz, 1H), 7.25–7.27 (m, 1H), 7.31–7.38 (m, 5H), 7.51 (s, 1H), 7.60 (d, J=8.48 Hz, 2H), 8.00 (s, 1H), 8.65 (s, 1H), 8.85 (s, 1H); MS (ESI(+)) m/e 505 (M+H)$^+$.

EXAMPLE 146

N-{4-[4-amino-7-(4-pyridinylethynyl)thieno[3,2-c]pyridin-3-yl]phenyl}-N'-(3-methylphenyl)urea X=4-ethynylpyridine. $^1$H NMR (300 MHz, DMSO-d$_6$) δ 2.29 (s, 3H), 6.00 (s, 2H), 6.81 (d, J=6.78 Hz, 1H), 7.17 (t, J=7.80 Hz, 1H), 7.24–7.27 (m, 1H), 7.32 (s,1H), 7.40 (d, J=8.48 Hz, 2H), 7.53 (d, J=5.09 Hz, 2H), 7.59 (d, J=6.10 Hz, 2H), 7.63 (s, 1H), 8.18 (s, 1H), 8.66 (s, 3H), 8.87 (s, 1H); MS (ESI(+)) m/e 476 (M+H)$^+$.

EXAMPLE 147

N-[4-(4-amino-7-{3-[benzyl(methyl)amino]-1-propynyl}thieno[3,2-c]pyridin-3-yl)phenyl]-N'-(3-methylphenyl)urea X=N-benzyl-N-methyl-N-2-propynylamine. $^1$H NMR (300 MHz, DMSO-d$_6$) δ 2.29 (s, 3H), 2.34 (s, 3H), 3.61 (s, 2H), 3.66 (s, 2H), 5.78 (s, 2H), 6.81 (d, J=7.46 Hz, 1H), 7.17 (t, J=7.63 Hz, 1H), 7.32–7.40 (m, 9H), 7.53 (s, 1H), 7.61 (d, J=8.81 Hz, 2H), 8.01 (s, 1H), 8.66 (s, 1H), 8.86 (s, 1H); MS (ESI(+)) m/e 532 (M+H)$^+$.

EXAMPLE 148

N-{4-[4-amino-7-(3-hydroxy-1-propynyl)thieno[3,2-c]pyridin-3-yl]phenyl}-N'-(3-methylphenyl)urea X=2-propyn-1-ol. The product was prepared as the trifluoroacetate salt by HPLC purification using the conditions described in Example 82. $^1$H NMR (300 MHz, DMSO-d$_6$) δ 2.29 (s, 3H), 4.41 (s, 2H), 6.54 (s, 2H), 6.81 (d, J=7.12 Hz, 1H), 7.17 (t, J=7.80 Hz, 1H), 7.26 (t, J=4.41 Hz, 2H), 7.32 (s, 1H), 7.41 (d, J=8.48 Hz, 2H), 7.63 (d, J-8.81 Hz, 2H), 7.71 (s, 1H), 8.06 (s, 1H), 8.78 (s, 1H), 9.01 (s, 1H); MS (ESI(+)) m/e 429 (M+H)$^+$.

EXAMPLE 149

N-{4-[4-amino-7-(3-pyridinylethynyl)thieno[3,2-c]pyridin-3-yl]phenyl}-N'-(3-methylphenyl)urea X=3-ethynylpyridine. The product was prepared as the bis(trifluoroacetate) salt HPLC purification using the conditions described in Example 82. $^1$H NMR (300 MHz, DMSO-d$_6$) δ 2.29 (s, 3H), 6.61 (s, 2H), 6.81 (d, J=7.46 Hz, 1H), 7.17 (t, J=7.63 Hz, 1H), 7.26–7.28 (m, 1H), 7.32 (s, 1H), 7.43 (d, J=8.81 Hz, 2H), 7.50–7.55 (m, 1H), 7.62–7.66 (m, 2H), 7.75 (s, 1H), 8.04 (ddd, J=8.31, 1.86, 1.70 Hz, 1H), 8.24 (s, 1H), 8.64 (d, J=4.07 Hz, 1H), 8.76 (s, 1H), 8.82 (s, 1H), 8.99 (s, 1H); MS (ESI(+)) m/e 476 (M+H)$^+$.

EXAMPLE 150

N-(4-{4-amino-7-[3-(phenylsulfanyl)-1-propynyl]thieno[3,2-c]pyridin-3-yl}phenyl)-N'-(3-methylphenyl)urea X=(2-propynylsulfanyl)benzene. The product was prepared as the trifluoroacetate salt by HPLC purification using the conditions described in Example 82. $^1$H NMR (400 MHz, DMSO-d$_6$) δ 2.29 (s, 3H), 4.24 (s, 2H), 6.80 (d, J=7.36 Hz, 2H), 7.17 (t, J=7.67 Hz, 1H), 7.27 (d, J=4.60 Hz, 2H), 7.34 (s, 1H), 7.38–7.41 (m, 5H), 7.53 (d, J=7.36 Hz, 2H), 7.65 (d, J=8.59 Hz, 2H), 7.73 (s, 1H), 8.01 (s, 1H), 8.94 (s, 1H), 9.18 (s, 1H); MS (ESI(+)) m/e 521 (M+H)$^+$.

EXAMPLE 151

N-{4-[4-amino-7-(4-cyano-1-butynyl)thieno[3,2-c]pyridin-3-yl]phenyl}-N'-(3-methylphenyl)urea X=4-pentynenitrile. The product was prepared as the trifluoroacetate salt by HPLC purification using the conditions described in Example 82. $^1$H NMR (300 MHz, DMSO-d$_6$) δ 2.29 (s, 3H), 2.85–2.95 (m, 4H), 6.66 (s, 2H), 6.81 (d, J=7.46 Hz, 1H), 7.17 (t, J=7.63 Hz, 1H), 7.26–7.27 (m, 1H), 7.32 (s, 1H), 7.41 (d, J=8.48 Hz, 2H), 7.64 (d, J=8.48 Hz, 2H), 7.76 (s, 1H), 8.06 (s, 1H), 8.76 (s, 1H), 8.99 (s, 1H); MS (ESI(+)) m/e 452 (M+H)$^+$.

EXAMPLE 152

N-{4-[4-amino-7-(1-pentynyl)thieno[3,2-c]pyridin-3-yl]phenyl}-N'-(3-methylphenyl)urea X=1-pentyne. The product was prepared as the trifluoroacetate salt by HPLC purification using the conditions described in Example 82. $^1$H NMR (300 MHz, DMSO-d$_6$) δ 1.07 (t, J=7.29 Hz, 3H), 1.63 (m, 2H), 2.29 (s, 3H), 2.52–2.56 (m, 2H), 6.75 (s, 2H), 6.81 (d, J=7.46 Hz, 1H), 7.17 (t, J=7.63 Hz, 1H), 7.26–7.28 (m, 1H), 7.32 (s, 1H), 7.42 (d, J=8.48 Hz, 2H), 7.64 (d, J=8.48 Hz, 2H), 7.77 (s, 1H), 8.04 (s, 1H), 8.78 (s, 1H), 9.02 (s, 1H); MS (ESI(+)) m/e 441 (M+H)$^+$.

EXAMPLE 153

N-(4-{4-amino-7-[3-(diethylamino)-1-propynyl]thieno[3,2-c]pyridin-3-yl}phenyl)-N'-(3-methylphenyl)urea X=N,N-diethyl-N-2-propynylamine. $^1$H NMR (300 MHz, DMSO-d$_6$) δ 1.06 (t, J=7.12 Hz, 6H), 2.29 (s, 3H), 2.59 (q, J=7.12 Hz, 4H), 3.70 (s, 2H), 5.75 (s, 2H), 6.80 (d, J=7.46 Hz, 1H), 7.17 (t, J=7.63 Hz, 1H), 7.25–7.28 (m, 1H), 7.32 (s, 1H), 7.37 (d, J=8.48 Hz, 2H), 7.50 (s, 1H), 7.60 (d, J=8.48 Hz, 2H), 7.96 (s, 1H), 8.66 (s, 1H), 8.87 (s, 1H); MS (ESI(+)) m/e 484 (M+H)$^+$.

EXAMPLE 154

N-{4-[4-amino-7-(4-phenyl-1-butynyl)thieno[3,2-c]pyridin-3-yl]phenyl}-N'-(3-methylphenyl)urea X=3-butynylbenzene. The product was prepared as the trifluoroacetate salt by HPLC purification using the conditions described in Example 82. $^1$H NMR (300 MHz, DMSO-d$_6$) δ 2.29 (s, 3H), 2.83–2.96 (m, 4H), 6.67 (s, 2H), 6.81 (d, J=7.46 Hz, 1H), 7.17 (t, J=7.80 Hz, 1H), 7.25–7.28 (m, 2H), 7.34–7.38 (m, 5H), 7.40 (d, J=8.81 Hz, 2H), 7.64 (d, J=8.81 Hz, 2H), 7.75 (s, 1H), 7.98 (s, 1H), 8.78 (s, 1H), 9.02 (s, 1H); MS (ESI(–)) m/e 501 (M–H)$^-$.

EXAMPLE 155

N-(4-{4-amino-7-[3-(methylamino)-1-propynyl]thieno[3,2-c]pyridin-3-yl}phenyl)-N'-(3-methylphenyl)urea X=N-methyl-N-2-propynylamine. $^1$H NMR (300 MHz, DMSO-d$_6$) δ 2.29 (s, 3H), 2.41 (s, 3H), 3.39 (s, 1H), 3.60 (s, 2H), 5.74 (s, 2H), 6.81 (d, J=7.46 Hz, 1H), 7.17 (t, J=7.80 Hz, 1H), 7.24–7.27 (m, 1H), 7.32 (s, 1H), 7.38 (d, J=8.82 Hz, 2H), 7.50 (s, 1H), 7.60 (d, J=8.82 Hz, 2H), 7.95 (s, 1H), 8.69 (s, 1H), 8.89 (s, 1H); MS (ESI(+)) m/e 442 (M+H)$^+$.

EXAMPLE 156

N-[4-(4-amino-7-{3-[(aminocarbonyl)amino]-1-propynyl}thieno[3,2-c]pyridin-3-yl)phenyl]-N'-(3-methylphenyl)urea X=N-2-propynylurea. The product was prepared as the bis(trifluoroacetate) salt by HPLC purification using the conditions described in Example 82. $^1$H NMR (300 MHz, DMSO-d$_6$) δ 2.29 (s, 3H), 4.14 (d, J=4.75 Hz, 2H), 5.67 (s, 2H), 6.45 (t, J=5.59 Hz, 1H), 6.71 (s, 2H), 6.81 (d, J=7.12 Hz, 1H), 7.17 (t, J=7.80 Hz, 1H), 7.24–7.27 (m, 1H), 7.32 (s, 1H), 7.42 (d, J=8.48 Hz, 2H), 7.64 (d, J=8.48 Hz, 2H), 7.77 (s, 1H), 8.06 (s, 1H), 8.78 (s, 1H), 9.02 (s, 1H); MS (ESI(+)) m/e 471 (M+H)$^+$.

EXAMPLE 157

N-{4-[4-amino-7-(4-hydroxybutyl)thieno[3,2-c]pyridin-3-yl]phenyl}-N'-(3-methylphenyl)urea The desired product was prepared by substituting Example 144B for Example 14 in Example 15. $^1$H NMR (300 MHz, DMSO-d$_6$) δ 1.48–1.57 (m, 2H), 1.69–1.74 (m, 2H), 2.29 (s, 3H), 2.71 (t, J=7.29 Hz, 2H), 3.43–3.46 (m, 2H), 4.39 (t, J=5.09 Hz, 1H), 5.39 (s, 2H), 6.81 (d, J=7.12 Hz, 1H), 7.17 (t, J=7.63 Hz, 1H), 7.25–7.28 (m, 1H), 7.31 (s, 1H), 7.37 (d, J=8.48 Hz, 2H), 7.46 (s, 1H), 7.59 (d, J=8.48 Hz, 2H), 7.68 (s, 1H), 8.66 (s, 1H), 8.85 (s, 1H); MS (ESI(+)) m/e 447 (M+H)$^+$.

EXAMPLE 158

3-(4-aminophenyl)-7-(4-isoquinolinyl)thieno[3,2-c]pyridin-4-amine

The desired product was prepared by substituting 4-isoquinolinylboronic acid for 4-pyridylboronic acid in Examples 121A–B. $^1$H NMR (300 MHz, DMSO-d$_6$) δ 5.40 (s, 2H), 5.75 (s, 2H), 6.70 (d, J=8.48 Hz, 2H), 7.14 (d, J=8.48 Hz, 2H), 7.39 (s, 1H), 7.65–7.70 (m, 1H), 7.81 (ddd, J=8.39, 6.87, 1.70 Hz, 1H), 8.09–8.11 (m, 3H), 8.63 (d, J=2.37 Hz, 1H), 9.21 (d, J=2.03 Hz, 1H). MS (ESI(+)) m/e 369 (M+H)$^+$.

EXAMPLE 159

3-(4-aminophenyl)-7-(2,6-difluoro-3-pyridinyl)thieno[3,2-c]pyridin-4-amine

The desired product was prepared by substituting 2,6-difluoro-3-pyridinylboronic acid for 4-pyridylboronic acid in Examples 121A–B. $^1$H NMR (300 MHz, DMSO-d$_6$) δ 5.39 (s, 2H), 5.75 (s, 2H), 6.67–6.70 (m, 2H), 7.11 (d, J=8.48 Hz, 2H), 7.33–7.37 (m, 2H), 7.85 (s, 1H), 8.34–8.42 (m, 1H). MS (ESI(+)) m/e 355 (M+H)$^+$.

EXAMPLE 160

3-(1H-indol-6-yl)thieno[3,2-c]pyridin-4-amine

The desired product was prepared by substituting 1H-indol-6-ylboronic acid for 4-phenoxyphenylboronic acid in Example 10A. $^1$H NMR (300 MHz, DMSO-d$_6$) δ 5.41 (s, 2H), 6.52 (s, 1H), 7.05 (dd, J=8.14, 1.70 Hz, 1H), 7.26 (d, J=5.76 Hz, 1H), 7.45 (m, 3H), 7.67 (d, J=8.14 Hz, 1H), 7.82 (d, J=5.43 Hz, 1H), 11.29 (s, 1H); MS (ESI(+)) m/e 266 (M+H)$^+$.

EXAMPLE 161

N-{4-[4-amino-7-(2,6-difluoro-3-pyridinyl)thieno[3,2-c]pyridin-3-yl]phenyl}-N'-(2-fluoro-5-methylphenyl)urea The desired product was prepared by substituting Example 159 and 1-fluoro-2-isocyanato-4-methylbenzene for Example 121 and 1-fluoro-2-isocyanato-4-(trifluoromethyl)benzene, respectively, in Example 122. $^1$H NMR (300 MHz, DMSO-d$_6$) δ 2.28 (s, 3H), 5.71 (s, 2H), 6.83 (dd, J=4.58, 2.20 Hz, 1H), 7.09–7.16 (m, 1H), 7.36 (dd, J=8.14, 2.37 Hz, 1H), 7.42 (d, J=8.48 Hz, 2H), 7.51 (s, 1H), 7.62 (d, J=8.48 Hz, 2H), 7.90 (s, 1H), 8.00 (dd, J=7.97, 1.87 Hz, 1H), 8.36–8.44 (m, 1H), 8.56 (d, J=2.37 Hz, 1H), 9.27 (s, 1H). MS (ESI(+)) m/e 506 (M+H)$^+$.

EXAMPLE 162

N-{4-[4-amino-7-(2,6-difluoro-3-pyridinyl)thieno[3,2-c]pyridin-3-yl]phenyl}-N'-(3-methylphenyl)urea The desired product was prepared by substituting Example 159 and 1-isocyanato-3-methylbenzene for Example 121 and 1-fluoro-2-isocyanato-4-(trfluoromethy)benzene, respectively, in Example 122. $^1$H NMR (300 MHz, DMSO-d$_6$) δ 2.29 (s, 3H), 5.71 (s, 2H), 6.81 (d, J=7.46 Hz, 1H), 7.17 (t, J=7.63 Hz, 1H), 7.26–7.28 (m, 1H), 7.32 (s, 1H), 7.36–7.39 (m, 1H), 7.41 (d, J=8.81 Hz, 2H), 7.50 (s, 1H), 7.62 (d, J=8.48 Hz, 2H), 7.89 (s, 1H), 8.39–8.44 (m, 1H), 8.67 (s, 1H), 8.87 (s, 1H). MS (ESI(−)) m/e 486 (M−H)⁻.

EXAMPLE 163

N-{4-[4-amino-7-(4-isoquinolinyl)thieno[3,2-c]pyridin-3-yl]phenyl}-N'-[2-fluoro-5-(trifluoromethyl)phenyl]urea The desired product was prepared by substituting Example 158 for Example 121 in Example 122. $^1$H NMR (300 MHz, DMSO-$d_6$) δ 5.69 (s, 2H), 7.39–7.74 (m, 1H), 7.46 (d, J=8.48 Hz, 2H), 7.51 (d, J=11.19 Hz, 1H), 7.56 (s, 1H), 7.64 (s, 1H), 7.67 (d, J=2.37 Hz, 1H), 7.70 (d, J=7.80 Hz, 1H), 7.79–7.84 (m, 1H), 8.08 (s, 1H), 8.11 (d, J=2.03 Hz, 1H), 8.12 (s, 1H), 8.64 (d, J=2.03 Hz, 1H), 8.65 (d, J=2.03 Hz, 1H), 8.98 (d, J=2.71 Hz, 1H), 9.22 (d, J=2.37 Hz, 1H), 9.40 (s, 1H). MS (ESI(−)) m/e 572 (M−H)⁻.

EXAMPLE 164

N-{4-[4-amino-7-(4-isoquinolinyl)thieno[3,2-c]pyridin-3-yl]phenyl}-N'-(3-methylphenyl)urea The desired product was prepared by substituting Example 158 and 1-isocyanato-3-methylbenzene for Example 121 and 1-fluoro-2-isocyanato-4-(trfluoromethy)benzene, respectively, in Example 122. $^1$H NMR (300 MHz, DMSO-$d_6$) δ 2.30 (s, 3H), 5.70 (s, 2H), 6.81 (d, J=7.46 Hz, 1H), 7.18–7.21 (m, 1H), 7.27–7.29 (m, 1H), 7.33 (s, 1H), 7.43 (d, J=8.82 Hz, 2H), 7.54 (s, 1H), 7.63 (d, J=8.48 Hz, 2H), 7.70 (d, J=7.80 Hz, 1H), 7.79–7.85 (m, 1H), 8.08 (s, 1H), 8.12 (s, 2H), 8.65 (d, J=2.37 Hz, 1H), 8.68 (s, 1H), 8.89 (s, 1H), 9.22 (d, J=2.37 Hz, 1H). MS (ESI(+)) m/e 502 (M+H)⁺.

EXAMPLE 165

N-{4-[4-amino-7-(3-pyridinyl)thieno[3,2-c]pyridin-3-yl]phenyl}-N'-[2-fluoro-5-(trifluoromethyl)phenyl]urea The desired product was prepared by substituting Example 124 for Example 121 in Example 122. $^1$H NMR (300 MHz, DMSO-$d_6$) δ 5.63 (s, 2H), 7.39–7.47 (m, 3H), 7.53–7.58 (m, 3H), 7.64 (d, J=8.81 Hz, 2H), 7.97 (s, 1H), 8.10 (m, J=8.48, 2.03, 1.70 Hz, 1H), 8.63–8.66 (m, 2H), 8.88 (d, J=1.70 Hz, 1H), 8.98 (d, J=3.05 Hz, 1H), 9.39 (s, 1H). MS (ESI(+)) m/e 524 (M+H)⁺.

EXAMPLE 166

N-{4-[4-amino-7-(3-pyridinyl)thieno[3,2-c]pyridin-3-yl]phenyl}-N'-(2-fluoro-5-methylphenyl)urea The desired product was prepared by substituting Example 124 and 1-fluoro-2-isocyanato-4-methylbenzene for Example 121 and 1-fluoro-2-isocyanato-4-(trfluoromethy)benzene, respectively, in Example 122. $^1$H NMR (300 MHz, DMSO-$d_6$) δ 2.29 (s, 3H), 5.63 (s, 2H), 6.82–6.85 (m, 1H), 7.12 (dd, J=11.53, 8.48 Hz, 1H), 7.42 (d, J=8.48 Hz, 2H), 7.52 (s, 1H), 7.55 (dd, J=8.14, 5.09 Hz, 1H), 7.62 (d, J=8.48 Hz, 2H), 7.96 (s, 1H), 8.00 (dd, J=7.97, 1.86 Hz, 1H), 8.10 (ddd, J=8.14, 2.03, 1.70 Hz, 1H), 8.56 (d, J=2.71 Hz, 1H), 8.62 (dd, J=4.75, 1.36 Hz, 1H), 8.88 (d, J=1.70 Hz, 1H), 9.27 (s, 1H). MS (ESI(+)) m/e 470 (M+H)⁺.

Examples 167–170 were prepared substituting the appropriate boronic acid (X) for 4-chlorophenylboronic acid in Example 21C.

EXAMPLE 167

(2E)-3-{4-amino-3-[4-(hydroxymethyl)phenyl]thieno[3,2-c]pyridin-7-yl}-N-methylacrylamide X=4-(hydroxymethyl)phenylboronic acid. $^1$H NMR (300 MHz, DMSO-$d_6$) δ 2.73 (d, J=4.4 Hz, 3H), 4.60 (d, J=5.7 Hz, 2H), 5.31 (t, J=5.7 Hz, 1H), 5.81 (s, 2H), 6.58 (d, J=15.9 Hz, 1H), 7.43–7.50 (m, 4H), 7.58 (d, J=15.9 Hz, 1H), 7.64 (s, 1H), 8.12 (s, 1H), 8.15 (q, J=4.4 Hz, 1H), MS (ESI(+)) m/e 340.1 (M+H)⁺.

EXAMPLE 168

(2E)-3-[4-amino-3-(3,4-dimethoxyphenyl)thieno[3,2-c]pyridin-7-yl]-N-methylacrylamide X=3,4-dimethoxyphenylboronic acid. $^1$H NMR (300 MHz, DMSO-$d_6$) δ 2.73 (d, J=4.7 Hz, 3H), 3.79 (s, 3H), 3.83 (s, 3H), 5.88 (s, 2H), 6.57 (d, J=15.9 Hz, 1H), 7.00 (dd, J=8.1, 2.0 Hz, 1H), 7.05 (d, J=2.0 Hz, 1H), 7.11 (d, J=8.5 Hz, 1H), 7.57 (d, J=15.9 Hz, 1H), 7.62 (s, 1H), 8.11 (s, 1H), 8.15 (q, J=4.7 Hz, 1H), MS (ESI(+)) m/e 370.1 (M+H)⁺.

EXAMPLE 169

(2E)-3-[4-amino-3-(3-chlorophenyl)thieno[3,2-c]pyridin-7-yl]-N-methylacrylamide

X=3-chlorophenylboronic acid. $^1$H NMR (300 MHz, DMSO-$d_6$) δ 2.73 (d, J=4.4 Hz, 3H), 5.83 (s, 2H), 6.58 (d, J=15.9 Hz, 1H), 7.44–7.48 (m, 1H), 7.53–7.61 (m, 4H), 7.776 (s, 1H), 8.14 (s, 1H), 8.15 (q, J=4.4 Hz, 1H), MS (ESI(+)) m/e 344.0, 346.2 (M+H)⁺.

EXAMPLE 170

(2E)-3-[4-amino-3-(3-chloro-4-fluorophenyl)thieno[3,2-c]pyridin-7-yl]-N-methylacrylamide X=3-chloro-4-fluorophenylboronic acid. $^1$H NMR (300 MHz, DMSO-$d_6$) δ 2.73 (d, J=4.7 Hz, 3H), 5.88 (s, 2H), 6.57 (d, J=15.9 Hz, 1H), 7.49 (ddd, J=8.5, 4.9, 2.2 Hz, 1H), 7.56 (t, J=8.8 Hz, 1H), 7.58 (d, J=15.9 Hz, 1H), 7.74 (dd, J=7.1, 2.0 Hz, 1H), 7.75 (s, 1H), 8.14 (s, 1H), 8.14 (q, J=4.7 Hz, 1H), MS (ESI(+)) m/e 362.0, 364.2 (M+H)⁺.

EXAMPLE 171

(2E)-3-[4-amino-3-(4-bromophenyl)thieno[3,2-c]pyridin-7-yl]-N-(4-pyridinylmethyl)acrylamide

EXAMPLE 171A (2E)-3-[4-amino-3-(4-bromophenyl)thieno[3,2-c]pyridin-7-yl]acrylic acid The desired compound was prepared by substituting Example 1B for Example 10A in Example 10B, then substituting the product and methylamine for Example 11A and piperazin-2-one, respectively, in Examples 11A–B.

EXAMPLE 171B (2E)-3-[4-amino-3-(4-bromophenyl)thieno[3,2-c]pyridin-7-yl]-N-(4-pyridinylmethyl)acrylamide The desired product was prepared as the bis(trifluoroacetate) salt substituting 1-(4-pyridinyl)methanamine and Example 171A for methylamine and Example 13, respectively, in Example 14, then purifying the product by HPLC using the conditions described in Example 82. $^1$H NMR (300 MHz, DMSO-d$_6$) δ 4.59 (d, J=5.8 Hz, 2H), 6.57 (s, 2H), 6.81 (d, J=15.9 Hz, 1H), 7.48 (d, J=8.5 Hz, 2H), 7.61 (d, J=5.4 Hz, 2H), 7.68 (d, J=15.9 Hz, 1H), 7.75 (d, J=8.5 Hz, 2H), 7.90 (s, 1H), 8.25 (s, 1H), 8.69 (d, J=6.1 Hz, 2H), 9.02 (t, J=5.8 Hz, 1H). MS (ESI(+)) m/e 465.0, 467.0 (M+H)$^+$.

Examples 172–174 were prepared as the bis(trifluoroacetate) salts by substituting the appropriate amine (X) for 1-(4-pyridinyl)methanamine in Example 171B.

EXAMPLE 172

3-(4-bromophenyl)-7-[(1E)-3-(4-morpholinyl)-3-oxo-1-propenyl]thieno[3,2-c]pyridin-4-amine X=morpholine. $^1$H NMR (300 MHz, DMSO-d$_6$) δ 3.59–3.67 (m, 8H), 5.87 (s, 2H), 7.06 (d, J=15.3 Hz, 1H), 7.45 (d, J=8.5 Hz, 2H), 7.67–7.74 (m, 4H), 8.32 (s, 1H).

EXAMPLE 173

(2E)-3-[4-amino-3-(4-bromophenyl)thieno[3,2-c]pyridin-7-yl]-N-[3-(1H-imidazol-1-yl)propyl]acrylamide X=3-(1H-imidazol-1-yl)-1-propanamine. $^1$H NMR (300 MHz, DMSO-d$_6$) δ 2.05 (p, J=7.1, Hz, 2H), 3.23 (q, J=6.2 Hz, 2H), 4.25 (t, J=7.1 Hz, 2H), 6.41 (s, 2H), 6.66 (d, J=15.9 Hz, 1H), 7.47 (d, J=8.5 Hz, 2H), 7.61 (d, J=15.9 Hz, 1H), 7.71 (t, J=1.7 Hz, 1H), 7.75 (d, J=8.5 Hz, 2H), 7.84 (t, J=1.7 Hz, 1H), 7.86 (s, 1H), 8.20 (s, 1H), 8.41 (t, J=5.8 Hz, 1H), 9.14 (s, 1H). MS (ESI(+)) m/e 482.0, 483.8 (M+H)$^+$.

EXAMPLE 174

(2E)-3-[4-amino-3-(4-bromophenyl)thieno[3,2-c]pyridin-7-yl]-N-[2-(diethylamino)ethyl]acrylamide X=N,N-diethyl-1,2-ethanediamine. $^1$H NMR (300 MHz, DMSO-d$_6$) δ 1.22 (t, J=7.3 Hz, 6H), 3.17–3.26 (m, 4H), 3.55 (q, J=5.8 Hz, 4H), 6.37 (s, 2H), 6.65 (d, J=15.9 Hz, 1H), 7.46 (d, J=8.5 Hz, 2H), 7.66 (d, J=15.9 Hz, 1H), 7.75 (d, J=8.5 Hz, 2H), 7.84 (s, 1H), 8.22 (s, 1H), 8.58 (t, J=5.6 Hz, 1H), 9.17 (s, 1H, TFA salt-H). MS (ESI(+)) m/e 473.0, 474.9 (M+H)$^+$.

EXAMPLE 175

N-[2-methoxy-4-(4,4,5,5-tetramethyl-1,3,2-dioxaborolan-2-yl)phenyl]-1-methyl-1H-indole-3-carboxamide

EXAMPLE 175A 4-bromo-2-methoxyaniline

A mixture of o-anisidine (27.1 g, 219 mmol) and dichloromethane (500 mL) was stirred under an atmosphere of nitrogen and treated with 2,4,4,6-tetrabromo-2,5-cyclohexadienone (90.0 g, 219 mmol) in four roughly equal portions over the course of 20 minutes. The temperature of the reaction was maintained between 10 and 15° C. by cooling with a cold water bath during the addition of the 2,4,4,6-tetrabromo-2,5-cyclohexadienone. The mixture was warmed to ambient temperature and stirred for an additional 1.5 hours at which time HPLC [Hypersil HS C18, 5 µm, 100 Å, 250×4.6 mm; 25–100% acetonitrile/0.1M ammonium acetate over 10 minutes, 1 mL/min) o-anisidine t$_r$=7.63 min, 4-bromo-2-methoxyaniline R$_t$=9.77 min] indicated very little o-anisidine remaining. The mixture was washed with 0.67N NaOH (300 mL) and 1N aqueous sodium hydroxide (300 mL). The combined aqueous washes were extracted with dichloromethane (150 mL) and the combined organic solutions were then washed with water (2×200 mL) and brine (200 mL), dried (MgSO$_4$), filtered, and concentrated to provide about 48 g of the desired product.

EXAMPLE 175B tert-butyl 4-bromo-2-methoxyphenylcarbamate

A mixture of Example 175A (36.4 g, 180 mmol), and di-tert-butyl dicarbonate (47.2 g, 216 mmol) in THF (500 mL) was heated to reflux for 20 hours and cooled to ambient temperature. HPLC (using the conditions from Example 175A, product R$_t$=13.55 min and TLC (8:2 heptane/ethyl acetate, R$_f$ of product=0.53, R$_f$ of 4-bromo-2-methoxyaniline=0.27) indicated approximately 10% starting material was remaining. Additional di-tert-butyl dicarbonate (3.9 g, 18 mmol) was added and heating was continued for another 5 hours. The mixture was cooled and evaporated under reduced pressure. The residue was applied to a 400 gram silica gel column and eluted with 8:2 heptane/ethyl acetate. The fractions showing the desired product were combined and washed with saturated NaHCO$_3$ and then brine. The organic solution was dried (MgSO$_4$), filtered, and concentrated to provide 61.3 g of a mixture of the desired product and di-tert-butyl dicarbonate which was used directly in the next step.

EXAMPLE 175C tert-butyl 2-methoxy-4-(4,4,5,5-tetramethyl-1,3,2-dioxaborolan-2-yl)phenylcarbamate A mixture of Example 175B (61.3 g, 203 mmol), 4,4,4',4',5,5,5',5'-octamethyl-2,2'-bi-1,3,2-dioxaborolane (51.6 g, 203 mmol), [1.1'-bis(diphenylphosphino)ferrocene]dichloropalladium (II) complex with dichloromethane (1:1) (3.2 g, 3.9 mmol), and potassium acetate (59.7 g, 609 mmol) in DMF (1.0 L) was heated to 80° C. under an atmosphere of nitrogen for 16 hours, cooled to ambient temperature, and concentrated. Dichloromethane (500 mL) was added to the residue and the resulting solid was removed by filtration through a pad of diatomaceous earth (Celite®). The pad was washed with dichloromethane (4×50 mL) and the combined filtrates were concentrated, applied to a 550 gram silica gel column, and quickly eluted with heptane/ethyl acetate (85:15) The fractions showing product [R$_t$ with conditions described in Example 175A=14.33 minutes, R$_f$ of product=0.33 TLC (85:15 heptane/ethyl acetate), R$_f$ of tert-butyl N-(4-bromo-2-methoxyphenyl)carbamate=0.48]. This material was treated with heptane (300 mL ) and stirred at ambient temperature for 30 minutes. The mixture was cooled to about 5° C. for 3 hours and the resulting precipitate was collected by filtration to provide 24.4 g of the desired product. The filtrate was evaporated and the residue was purified by flash chromatography on a 400 gram silica gel column with 9:1 heptane/ethyl acetate to give an additional 8.8 g of the desired product.

EXAMPLE 175D tert-butyl 2-methoxy-4-(4,4,5,5-tetramethyl-1,3,2-dioxaborolan-2-yl)phenylcarbamate A mixture of Example 175C (45.0 g, 0.129 mole) in dichloromethane (270 mL) was cooled to <5° C. in an ice bath and treated with a 1:1 solution of TFA/dichloromethane (500 mL) while maintaining the reaction temperature below 5° C. The reaction was warmed to ambient temperature and stirred for 2 hours. The solvents were removed by evaporation at a pressure of 30 Torr and a bath temperature of <30° C. The residue was dissolved in dichloromethane (250 mL) and carefully washed with 2.5N sodium hydroxide (300 mL). The organic layer was extracted with brine (100 mL), dried ($MgSO_4$), filtered, and concentrated to provide the desired product (21.7 g, 68%). $^1$H NMR (DMSO-$d_6$, 400 MHz) δ 7.05 (d, 1H), 6.98 (d, 1H), 6.59 (d, 1H), 5.13 (s, 2H), 3.75 (s, 3H), 1.25 (s, 12H); reverse phase HPLC (Hypersil HS, 5 μm, 100 A, 4.6×250 mm; 25%-100% acetonitrile/0.05M ammonium acetate over 10 minutes, 1 mL/min) $R_t$ 11.03 min.

EXAMPLE 175E

N-[2-methoxy-4-(4,4,5,5-tetramethyl-1,3,2-dioxaborolan-2-yl)phenyl]-1-methyl-1H-indole-3-carboxamide A mixture of Example 175D (19.75 g, 79.3 mmol) in dichloromethane (150 mL) was treated with N,N-diisopropylethylamine (12.3 g, 95.2 mmol), cooled to <5° C. with an ice bath, and treated slowly with a solution of 1-methyl-1H-indole-2-carbonyl chloride (87.3 mmol) in dichloromethane (300 mL) while maintaining the reaction temperature below 5° C. The mixture was warmed to ambient temperature, stirred for 12 hours, extracted twice with water (150 mL, 100 mL), once with brine (100 mL), dried ($MgSO_4$), filtered, and concentrated. The material was purified by flash chromatography using 400 g of silica gel and 3:1 heptane/ethyl acetate to provide the desired product (30.3 g, 94%). $^1$H NMR (DMSO-$d_6$, 400 MHz) δ 9.35 (s, 1H), 8.03 (d, 1H), 7.69 (d, 1H), 7.57 (d, 1H), 7.1–7.3 (m, 4H), 7.12 (t, 1H), 4.02 (s, 3H), 3.91 (s, 3H), 1.31 (s, 12H); RP-HPLC (Hypersil HS, 5 μm, 100 Å, 4.6×250 mm; 25%-100% acetonitrile/0.05M ammonium acetate over 10 min, 1 mL/min) $R_t$ 14.65 min.

EXAMPLE 176

N-(4-{4-amino-7-[(1E)-3-oxo-1-propenyl]thieno[3,2-c]pyridin-3-yl}-2-methoxyphenyl)-1-methyl-1H-indole-2-carboxamide

EXAMPLE 176A 3-bromo-7-[(1E)-3,3-diethoxy-1-propenyl]thieno[3,2-c]pyridin-4-amine A mixture Example 21A (200 mg, 0.56 mmol), 2-[(1E)-3,3-diethoxy-1-propenyl]-4,4,5,5-tetramethyl-1,3,2-dioxaborolane (175 mg, 0.67 mmol), Pd(PPh$_3$)$_4$ (40 mg, 0.03 mmol) and Na$_2$CO$_3$ (120 mg, 1.13 mmol) in 1,2-dimethoxyethane (10 mL) and water (5 mL) was heated in an 85° C. oil bath for 15 hours. The mixture was cooled to room temperature and concentrated under reduced pressure. The mixture was extracted with dichloromethane and the extract was dried ($MgSO_4$), filtered, and concentrated. The residue was purified by flash column chromatography on silica gel to provide the desired product (150 mg, 75%). $^1$H NMR (DMSO-$d_6$, 400 MHz) δ 8.02 (s, 1H), 7.88 (s, 1H), 6.74 (d, 1H), 6.09 (dd, 1H), 5.09 (d,1H), 3.62 (m, 2H), 3.48 (m, 2H), 1.15 (t, 6H); MS m/e 357.1, 359.1 (M+H)$^+$.

EXAMPLE 176B

N-(4-{4-amino-7-[(1E)-3,3-diethoxy-1-propenyl]thieno[3,2-c]pyridin-3-yl}-2-methoxyphenyl)-1-methyl-1H-indole-2-carboxamide A mixture of Example 176A (150 mg, 0.42 mmol), Example 175E, 255 mg, 0.63 mmol), Pd(PPh$_3$)$_4$ (35 mg, 0.03 mmol) and Na$_2$CO$_3$ (90 mg, 0.84 mmol) in 1,2-dimethoxyethane (6 mL) and water (3 mL) was heated at reflux for 18 hours. The mixture was cooled to room temperature and concentrated under reduced pressure. The mixture was extracted with dichloromethane then the extract was dried ($MgSO_4$), filtered, and concentrated. The residue was purified by flash chromatography on silica gel to provide the desired product (178 mg, 76%). $^1$H NMR (DMSO-$d_6$, 400 MHz) δ 9.5 (s, 1H), 8.03 (m, 2H), 7.7 (d, 1H), 7.59 (m, 2H), 7.33 (m, 2H), 7.21 (s, 1H), 7.14 (t, 1H), 7.09 (d, 1H), 6.82 (d, 1H), 6.17 (dd, 1H), 5.14 (d, 1H), 4.03 (s, 3H), 3.91 (s, 3H), 3.65 (m, 2H), 3.53 (m, 2H), 1.17 (t, 6H); MS m/e 557.3 (M+H)$^+$.

EXAMPLE 176C

N-(4-{4-amino-7-[(1E)-3-oxo-1-propenyl]thieno[3,2-c]pyridin-3-yl}-2-methoxyphenyl)-1-methyl-1H-indole-2-carboxamide A mixture of Example 176B (90 mg, 0.16 mmol) in acetone (9 mL) and water (1 mL) was treated with p-toluenesulfonic acid (5 mg, 0.016 mmol) then stirred for 30 minutes. The solvent was evaporated under reduced pressure then the residue was partitioned between dichloromethane and water. The organic layer was concentrated and the residue was purified by flash chromatography on silica gel to provide the desired product (77 mg). $^1$H NMR (DMSO-$d_6$, 400 MHz) δ 9.67 (d, 1H), 9.52 (s, 1H), 8.34 (s, 1H), 8.03 (d, 1H), 7.91 (d, 1H), 7.75 (s, 1H), 7.70 (d, 1H), 7.32 (m, 2H), 7.25 (s, 1H), 7.10 (m, 3H), 6.69 (m, 1H), 4.04 (s, 3H), 3.92 (s, 3H); MS m/e 483.3.

General Procedure for Reductive Aminations

Example 176C (40 mg, 0.083 mmol), sodium triacetoxyborohydride (35 mg, 0.166 mmol) and the appropriate amine (0.166 mmol) in 1,2-dichloromethane (2 mL) were stirred for 2 to 72 hours at ambient temperature. The mixture was concentrated and the product was purified by normal or reverse phase chromatography.

EXAMPLE 177

N-(4-{4-amino-7-[(1E)-3-(diethylamino)-1-propenyl]thieno[3,2-c]pyridin-3-yl}-2-methoxyphenyl)-1-methyl-1H-indole-2-carboxamide amine: diethylamine. Reverse phase HPLC (5% to 95% acetonitrile over 25 minutes, 1 mL/min, 254 nm, Hypersil HS 100 Å, C18, 5 μm, 250×4.6 column) $R_f$=19.32 min. $^1$H NMR (DMSO-$d_6$, 400 MHz) δ 9.50 (s, 1H), 8.00 (m, 1H), 7.94 (m, 1H), 7.69 (d, 1H), 7.60 (m, 2H), 7.32 (m, 2H), 7.18 (s, 1H), 7.13 (t, 1H), 7.06 (d, 1H), 6.67 (d, 1H), 6.22 (m, 1H), 5.6 (br s, 2H), 4.02 (s, 3H), 3.89 (s, 3H), 3.32 (d, 2H), 2.52 (q, 4H), 1.01 (t, 6H); MS m/e 540.3 (M+H)$^+$, 538.3 (M−H)$^-$.

EXAMPLE 178

N-(4-{4-amino-7-[(1E)-3-(ethylamino)-1-propenyl]thieno[3,2-c]pyridin-3-yl}-2-methoxyphenyl)-1-methyl-1H-indole-2-carboxamide amine: ethylamine. Reverse phase HPLC (5% to 95% acetonitrile over 25 minutes, 1 mL/min, 254 nm, Hypersil HS 100 Å, C18, 5 μm, 250×4.6 column) $R_f$=18.46 min. $^1$H NMR (DMSO-$d_6$, 400 MHz) δ 9.50 (s, 1H), 8.01 (m, 1H), 7.94 (s, 1H), 7.70 (d, 1H), 7.61 (s, 1H), 7.58 (d, 1H), 7.35 (s, 1H), 7.33 (m, 1H), 7.20 (s, 1H), 7.15 (t, 1H), 7.07 (d, 1H), 6.65 (d, 1H), 6.28 (m, 1H), 5.60 (br s, 2H), 4.03 (s, 3H), 3.91 (s, 3H), 3.37 (d, 2H), 2.59 (q, 2H), 1.05 (t, 3H); MS m/e 512.4 (M+H)$^+$, 510.5 (M−H)$^-$.

EXAMPLE 179

N-[4-(4-amino-7-{(1E)-3-[[2-(dimethylamino)ethyl](methyl)amino]-1-propenyl}thieno[3,2-c]pyridin-3-yl)-2-methoxyphenyl]-1-methyl-1H-indole-2-carboxamide amine: N,N,N'-trimethyl-1,2-ethanediamine. $^1$H NMR (DMSO-$d_6$, 400 MHz) δ 9.50 (s, 1H), 7.99 (d, 1H), 7.96 (s, 1H), 7.72 (d, 1H), 7.6 (m, 2H), 7.35 (m, 2H), 7.33 (m, 2H), 7.21 (s, 1H), 7.14 (t, 1H), 7.07 (d, 1H), 6.24 (m, 1H), 5.64 (br s, 2H), 4.04 (s, 1H), 3.91 (s, 3H), 3.22 (d, 2H), 2.48 (m, 2H), 2.37 (m, 2H), 2.23 (s, 3H), 2.14 (s, 6H); MS m/e 569.4 (M+H)$^+$, 568.5 (M−H)$^-$.

EXAMPLE 180

N-{4-[4-amino-7-((1E)-3-{[3-(5-methyl-1H-pyrazol-4-yl)propyl]amino}-1-propenyl)thieno[3,2-c]pyridin-3-yl]-2-methoxyphenyl}-1-methyl-1H-indole-2-carboxamide amine: 3-(5-methyl-1H-pyrazol-4-yl)-1-propanamine. $^1$H NMR (DMSO-$d_6$, 400 MHz) δ 9.50 (s, 1H), 8.00 (t, 1H), 7.93 (s, 1H), 7.71 (d, 1H), 7.61 (s, 1H), 7.58 (d, 1H), 7.33 (m, 3H), 7.2 (s, 1H), 7.15 (t, 1H), 7.08 (d, 1H), 6.65 (d, 1H), 6.28 (m, 1H), 5.59 (br s, 2H), 4.05 (s, 3H), 3.91 (s, 3H), 3.36 (d, 2H), 2.56 (t, 2H), 2.37 (t, 2H), 2.11 (s, 3H), 1.64 (m, 2H); MS m/e 606.3 (M+H)$^+$, 604.3 (M−H)$^-$.

EXAMPLE 181

N-{4-[4-amino-7-((1E)-3-{[(5-methyl-2-pyrazinyl)methyl]amino}-1-propenyl)thieno[3,2-c]pyridin-3-yl]-2-methoxyphenyl}-1-methyl-1H-indole-2-carboxamide amine: (5-methyl-2-pyrazinyl)methylamine. $^1$H NMR (DMSO-$d_6$, 400 MHz) δ 9.49 (s, 1H), 8.59 (s, 1H), 8.46 (s, 1H), 8.00 (t, 1H), 7.94 (s, 1H), 7.69 (d, 1H), 7.61 (s, 1H), 7.57 (d, 1H), 7.35 (s, 1H), 7.32 (d, 1H), 7.20 (d, 1H), 7.15 (t, 1H), 7.08 (dd, 1H), 6.67 (d, 1H), 6.28 (m, 1H), 5.61 (br s, 2H), 4.04 (s, 3H), 3.91 (s, 3H), 3.88 (s, 2H), 3.43 (d, 2H), 2.47 (s, 3H); MS m/e 590.3 (M+H)$^+$, 588.4 (M−H)$^-$.

EXAMPLE 182

N-(4-{4-amino-7-[(1E)-3-(4-phenyl-1-piperazinyl)-1-propenyl]thieno[3,2-c]pyridin-3-yl}-2-methoxyphenyl)-1-methyl-1H-indole-2-carboxamide amine: 1-phenylpiperazine. $^1$H NMR (DMSO-$d_6$, 400 MHz) δ 9.50 (s, 1H), 7.99 (m, 2H), 7.69 (d, 1H), 7.62 (s, 1H), 7.58 (d, 1H), 7.33 (m, 2H), 7.20 (m, 3H), 7.15 (t, 1H), 7.08 (d, 1H), 6.93 (d, 2H), 6.72 (m, 2H), 6.27 (m, 1H), 5.65 (br s, 2H), 4.04 (s, 3H), 3.91 (s, 3H), 3.24 (d, 2H), 3.17 (m, 4H), 2.60 (m, 4H); MS m/e 629.4 (M+H)$^+$, 627.4 (M−H)$^-$.

EXAMPLE 183

N-[4-(4-amino-7-{(1E)-3-[(3-pyridinylmethyl)amino]-1-propenyl}thieno[3,2-c]pyridin-3-yl)-2-methoxyphenyl]-1-methyl-1H-indole-2-carboxamide amine: 1-(3-pyridinyl)methanamine. $^1$H NMR (DMSO-$d_6$, 400 MHz) δ 9.49 (s, 1H), 8.56 (s, 1H), 8.45 (d, 1H), 8.00 (m, 1H), 7.95 (s, 1H), 7.78 (d, 1H), 7.71 (d, 1H), 7.61 (s, 1H), 7.57 (d, 1H), 7.34 (m, 3H), 7.20 (d, 1H), 7.14 (t, 1H), 7.07 (dd, 1H), 6.66 (d, 1H), 6.30 (m, 1H), 5.61 (br s, 2H), 4.03 (s, 3H), 3.91 (s, 3H), 3.77 (s, 2H), 3.38 (d, 2H); MS m/e 575.3 (M+H)$^+$, 573.5 (M−H)$^-$.

EXAMPLE 184

N-[4-(4-amino-7-{(1E)-3-[(2-pyridinylmethyl)amino]-1-propenyl}thieno[3,2-c]pyridin-3-yl)-2-methoxyphenyl]-1-methyl-1H-indole-2-carboxamide amine: 1-(2-pyridinyl)methanamine. $^1$H NMR (DMSO-$d_6$, 400 MHz) δ 9.50 (s, 1H), 8.51 (s, 1H), 8.0 (m, 1H), 7.96 (s, 1H), 7.77 (m, 1H), 7.71 (m, 1H), 7.60 (m, 2H), 7.49 (m, 1H), 7.3 (m, 4H), 7.14 (m, 1H), 7.09 (m, 1H), 6.67 (d, 1H), 6.34 (m, 1H), 5.6 (br s, 2H), 4.04 (s, 3H), 3.91 (s, 3H), 3.87 (s, 2H), 3.42 (d, 2H); MS m/e 575.4 (M+H)$^+$, 573.4 (M−H)$^-$.

EXAMPLE 185

N-{4-[4-amino-7-((1E)-3-{[2-(2-pyridinyl)ethyl]amino}-1-propenyl)thieno[3,2-c]pyridin-3-yl]-2-methoxyphenyl}-1-methyl-1H-indole-2-carboxamide amine: 2-(2-pyridinyl)ethanamine. $^1$H NMR (DMSO-$d_6$, 400 MHz) δ 9.50 (s, 1H), 8.47 (m, 1H), 8.00 (m, 1H), 7.93 (s, 1H), 7.69 (m, 2H), 7.59 (m, 2H), 7.35 (s, 1H), 7.31 (m, 2H), 7.2 (m, 3H), 7.07 (m, 1H), 6.65 (d, 1H), 6.28 (m, 1H), 5.60 (br s, 2H), 4.03 (s, 3H), 3.91 (s, 3H), 3.45 (m, 2H), 3.42 (d, 2H), 2.85 (m, 2H); MS m/e 587.3 (M+H)$^+$, 588.8 (M−H)$^-$.

EXAMPLE 186

N-{4-[4-amino-7-((1E)-3-{[2-(1H-indol-3-yl)ethyl]amino}-1-propenyl)thieno[3,2-c]pyridin-3-yl]-2-methoxyphenyl}-1-methyl-1H-indole-2-carboxamide amine: 2-(1H-indol-3-yl)ethanamine. $^1$H NMR (DMSO-d$_6$, 400 MHz) δ 10.82 (s, 1H), 9.51 (s, 1H), 8.01 (m, 1H), 7.93 (m, 1H), 7.72 (m, 1H), 7.58 (m, 3H), 7.36 (m, 3H), 7.20 (m, 3H), 7.08 (m, 2H), 6.98 (m, 1H), 6.67 (d, 1H), 6.32 (m, 1H), 5.6 (br s, 2H), 4.04 (s, 3H), 3.91 (s, 3H), 3–3.6 (m, 6H); MS m/e 627.4 (M+H)$^+$, 625.6 (M–H)$^-$.

EXAMPLE 187

N-(4-{4-amino-7-[(1E)-3-(4-morpholinyl)-1-propenyl]thieno[3,2-c]pyridin-3-yl}-2-methoxyphenyl)-1-methyl-1H-indole-2-carboxamide amine: morpholine. Reverse phase HPLC (5% to 95% acetonitrile over 10 minutes, 1 mL/min, 254 nm, hypersil HS 100 Å, C18, 5 µm, 250×4.6 column) R$_t$=13 min. $^1$H NMR (DMSO-d$_6$, 400 MHz) δ 9.51 (s, 1H), 8.00 (d, 1H), 7.95 (s, 1H), 7.71 (d, 1H), 7.58–7.62 (m, 2H), 7.05–7.21 (m, 3H), 6.65 (d, 1H), 6.25 (dt, 1H), 5.62 (br s, 2H), 4.04 (s, 3H), 3.91 (s, 3H), 3.61 (t, 4H), 3.19 (d, 2H), 2.44 (m, 4H); MS m/e 554.3 (M+H)$^+$.

EXAMPLE 188

N-(4-{4-amino-7-[(1E)-3-(4-hydroxy-1-piperidinyl)-1-propenyl]thieno[3,2-c]pyridin-3-yl}-2-methoxyphenyl)-1-methyl-1H-indole-2-carboxamide amine: 4-piperidinol. Purification by reverse phase HPLC using ammonium acetate buffer followed by lyophilization provided the desired product as the diacetate salt. Reverse phase HPLC (5% to 95% acetonitrile over 10 minutes, 1 mL/min, 254 nm, hypersil HS 100 Å, C18, 5 µm, 250×4.6 column) R$_t$=10.2 min. $^1$H NMR (DMSO-d$_6$, 400 MHz) δ 9.47 (s, 1H), 7.98 (d, 1H), 7.94 (s, 1H), 7.68 (d, 1H), 7.55–7.62 (m, 2H), 7.30–7.32 (m, 2H), 7.04–7.17 (m, 3H), 6.63 (d, 1H), 6.23 (dt, 1H), 5.61 (br s, 2H), 4.01 (s, 3H), 3.89 (s, 3H), 3.12 (d, 2H), 2.73 (m, 2H), 2.06 (t, 2H), 1.85 (s, 6H), 1.70 (m, 2H), 1.38 (q, 2H); MS m/e 568.9 (M+H)$^+$.

EXAMPLE 189

N-[4-(4-amino-7-{(1E)-3-[ethyl(2-hydroxyethyl)amino]-1-propenyl}thieno[3,2-c]pyridin-3-yl)-2-methoxyphenyl]-1-methyl-1H-indole-2-carboxamide amine: 2-(ethylamino)ethanol. Purification by reverse phase HPLC using ammonium acetate buffer followed by lyophilization provided the desired product as the acetate salt. Reverse phase HPLC (5% to 95% acetonitrile over 10 minutes, 1 mL/min, 254 nm, hypersil HS 100 Å, C18, 5 µm, 250×4.6 column) R$_t$=10.4 min. $^1$H NMR (DMSO-d$_6$, 400 MHz) δ 9.51 (s, 1H), 8.00 (d, 1H), 7.96 (s, 1H), 7.71 (d, 1H), 7.58–7.62 (m, 3H), 7.33–7.35 (m, 2H), 7.07–7.21 (m, 2H), 6.68 (d, 1H), 6.26 (dt, 1H), 5.62 (br s, 2H), 4.04 (s, 3H), 3.91 (s, 3H), 3.50 (t, 2H), 3.32 (d, 2H), 2.56–2.59 (m, 3H), 1.88 (s, 3H), 1.02 (t, 3H); MS m/e 556.4 (M+H)$^+$.

EXAMPLE 190

N-[4-(4-amino-7-{(1E)-3-[4-(2-hydroxyethyl)-1-piperidinyl]-1-propenyl}thieno[3,2-c]pyridin-3-yl)-2-methoxyphenyl]-1-methyl-1H-indole-2-carboxamide amine: 2-(4-piperidinyl)ethanol. Purification by reverse phase HPLC using ammonium acetate buffer followed by lyophilization provided the desired product as the diacetate salt. Reverse phase HPLC (5% to 95% acetonitrile over 10 minutes, 1 mL/min, 254 nm, hypersil HS 100 Å, C18, 5 µm, 250×4.6 column) R$_t$=10.3 min. $^1$H NMR (DMSO-d$_6$, 400 MHz) δ 9.51 (s, 1H), 8.00 (d, 1H), 7.96 (s, 1H), 7.71 (d, 1H), 7.58–7.62 (m, 2H), 7.33–7.35 (m, 2H), 7.05–7.21 (m, 3H), 6.65 (d, 1H), 6.25 (dt, 1H), 5.62 (br s, 2H), 4.04 (s, 3H), 3.91 (s, 3H), 3.43 (t, 2H), 3.15 (d, 2H), 2.90 (d, 2H), 1.93 (t, 2H), 1.88 (s, 6H), 1.62 (d, 2H), 1.36 (t, 2H), 1.18 (m, 1H); MS m/e 596.8 (M+H)$^+$.

EXAMPLE 191

N-(4-{7-[(1E)-3-(4-acetyl-1-piperazinyl)-1-propenyl]-4-aminothieno[3,2-c]pyridin-3-yl}-2-methoxyphenyl)-1-methyl-1H-indole-2-carboxamide amine: 1-acetylpiperazine. Purification by reverse phase HPLC using ammonium acetate buffer followed by lyophilization provided the desired product as the acetate salt. Reverse phase HPLC (5% to 95% acetonitrile over 10 minutes, 1 mL/min, 254 nm, hypersil HS 100 Å, C18, 5 µm, 250×4.6 column) R$_t$=11.3 min. $^1$H NMR (DMSO-d$_6$, 400 MHz) δ 9.52 (s, 1H), 8.01 (d, 1H), 7.98 (s, 1H), 7.71 (d, 1H), 7.58–7.62 (m, 2H), 7.33–7.35 (m, 2H), 7.05–7.21 (m, 3H), 6.65 (d, 1H), 6.25 (dt, 1H), 5.62 (br s, 2H), 4.04 (s, 3H), 3.92 (s, 3H), 3.46 (t, 4H), 3.22 (d, 2H), 2.42 (dt, 4H), 2.00 (s, 3H), 1.91 (s, 3H); MS m/e 595.4 (M+H)$^+$.

EXAMPLE 192

N-(4-{4-amino-7-[(1E)-3-(4-methyl-1-piperazinyl)-1-propenyl]thieno[3,2-c]pyridin-3-yl}-2-methoxyphenyl)-1-methyl-1H-indole-2-carboxamide amine: 1-methylpiperazine. Reverse phase HPLC (5% to 95% acetonitrile over 10 minutes, 1 mL/min, 254 nm, hypersil HS 100 Å, C18, 5 µm, 250×4.6 column) R$_t$=10.6 min. 1H NMR (DMSO-d$_6$, 400 MHz) δ 9.51 (s, 1H), 8.01 (d, 1H), 7.97 (s, 1H), 7.71 (d, 1H), 7.58–7.62 (m, 2H), 7.32–7.35 (m, 2H), 7.05–7.21 (m, 3H), 6.68 (d, 1H), 6.23 (dt, 1H), 5.64 (br s, 2H), 4.04 (s, 3H), 3.92 (s, 3H), 3.17 (d, 2H), 2.36–2.46 (m, 4H), 2.17 (s, 3H); MS m/e 567.4 (M+H)$^+$.

EXAMPLE 193

N-{4-[4-amino-7-((1E)-3-{[2-(1-pyrrolidinyl)ethyl]amino}-1-propenyl)thieno[3,2-c]pyridin-3-yl]-2-methoxyphenyl}-1-methyl-1H-indole-2-carboxamide amine: 2-(1-pyrrolidinyl)ethanamine. Purification by reverse phase HPLC using ammonium acetate buffer followed by lyophilization provided the desired product as the diacetate salt. Reverse phase HPLC (5% to 95% acetonitrile over 10 minutes, 1 mL/min, 254 nm, hypersil HS 100 Å, C18, 5 µm, 250×4.6 column) R$_t$=11 min. $^1$H NMR (DMSO-d$_6$, 400 MHz) δ 9.51 (s, 1H), 8.00 (d, 1H), 7.95 (s, 1H), 7.71 (d, 1H), 7.62 (s, 1H), 7.59 (d, 1H), 7.33–7.35 (m, 2H), 7.10–7.21 (m, 3H), 6.65 (d, 1H), 6.28 (dt, 1H), 5.64 (br s, 2H), 4.04 (s, 3H), 3.91 (s, 3H), 3.41 (d, 2H), 2.67 (t, 2H), 2.51–2.54 (m, 3H), 2.44 (t, 4H), 1.88 (s, 3H), 1.67 (s, 4H); MS m/e 581.0 (M+H)$^+$.

EXAMPLE 194

N-{4-[4-amino-7-((1E)-3-{[2-(2-oxo-1-imidazolidinyl)ethyl]amino}-1-propenyl)thieno[3,2-c]pyridin-3-yl]-2-methoxyphenyl}-1-methyl-1H-indole-2-carboxamide amine: 1-(2-aminoethyl)-2-imidazolidinone. $^1$H NMR (DMSO-d$_6$, 400 MHz) δ 9.51 (s, 1H), 8.00–8.02 (m, 2H), 7.71 (d, 1H), 7.58–7.62 (m, 2H), 7.05–7.21 (m, 3H), 6.75 (d, 1H), 6.34 (dt, 1H), 5.64 (br s, 2H), 4.04 (s, 3H), 3.91 (s, 3H), 3.37–3.46 (m, 3H), 3.21–3.31 (m, 3H), 3.17 (m, 2H), 2.70 (t, 1H); R$_f$=0.3 (dichloromethane/methanol/ammonium hydroxide=9:1:0.003).

EXAMPLE 195

N-{4-[4-amino-7-((1E)-3-{[2-(1-methyl-2-pyrrolidinyl)ethyl]amino}-1-propenyl)thieno[3,2-c]pyridin-3-yl]-2-methoxyphenyl}-1-methyl-1H-indole-2-carboxamide amine: 2-(1-methyl-2-pyrrolidinyl)ethanamine. Purification by reverse phase HPLC using ammonium acetate buffer followed by lyophilization provided the desired product as the diacetate salt. Reverse phase HPLC (5% to 95% acetonitrile over 10 minutes, 1 mL/min, 254 nm, hypersil HS 100 Å, C18, 5 μm, 250×4.6 column) R$_t$=11 min. $^1$H NMR (DMSO-d$_6$, 400 MHz) δ 9.51 (s, 1H), 8.00 (d, 1H), 7.95 (s, 1H), 7.71 (d, 1H), 7.62 (s, 1H), 7.59 (d, 1H), 7.33–7.35 (m, 2H), 7.07–7.21 (m, 3H), 6.65 (d, 1H), 6.28 (dt, 1H), 5.62 (br s, 2H), 4.04 (s, 3H), 3.91 (s, 3H), 3.40 (d, 2H), 2.90 (m, 1H), 2.55–2.70 (m, 2H), 2.21 (s, 3H), 2.02 (m, 2H), 1.88 (s, 6H), 1.75–1.85 (m, 2H), 1.58–1.68 (m, 2H), 1.35–1.45 (m, 2H); MS m/e 581.0 (M+H)$^+$.

EXAMPLE 196

N-[4-(4-amino-7-{(1E)-3-[(4-pyridinylmethyl)amino]-1-propenyl}thieno[3,2-c]pyridin-3-yl)-2-methoxyphenyl]-1-methyl-1H-indole-2-carboxamide amine: 1-(4-pyridinyl)methanamine. Purification by reverse phase HPLC using ammonium acetate buffer followed by lyophilization provided the desired product as the diacetate salt. Reverse phase HPLC (5% to 95% acetonitrile over 10 minutes, 1 mL/min, 254 nm, hypersil HS 100 Å, C18, 5 μm, 250×4.6 column) R$_t$=10.6 min. $^1$H NMR (DMSO-d$_6$, 400 MHz) δ 9.51 (s, 1H), 8.48–8.52 (m, 4H), 8.00 (d, 1H), 7.95 (s, 1H), 7.58–7.72 (m, 3H), 7.07–7.40 (m, 6H), 6.70 (d, 1H), 6.30 (d, 1H), 5.62 (br s, 2H), 4.27 (d, 2H), 4.04 (s, 3H), 3.92 (s, 3H), 3.39 (d, 2H), 1.90 (s, 3H); MS m/e 575.4 (M+H)$^+$.

EXAMPLE 197

N-(4-{4-amino-7-[(1E)-3-amino-1-propenyl]thieno[3,2-c]pyridin-3-yl}-2-methoxyphenyl)-1-methyl-1H-indole-2-carboxamide

EXAMPLE 197A tert-butyl (2E)-3-(4-amino-3-bromothieno[3,2-c]pyridin-7-yl)-2-propenylcarbamate A mixture of Example 21A (1.0 g, 2.8 mmol), tert-butyl (2E)-3-(tributylstannyl)-2-propenylcarbamate (prepared according to the procedure described in Synthesis, 1991, (12), 1201, 1.5 g, 3.36 mmol), and potassium flouride (195 mg, 3.36 mmol) in toluene (10 mL) was degassed, treated with Pd(PPh$_3$)$_4$ (194 mg, 0.17 mmol), degassed, and heated to 110° C. for 14 hours under a nitrogen atmosphere. The mixture was concentrated and purified by flash chromatography on silica gel with dichloromethane/ethyl acetate (6:4) to provide the desired product (1.3 g, 3.36 mmol). $^1$H NMR (DMSO-d$_6$, 400 MHz) δ 7.93 (s, 1H), 7.35 (s, 1H), 6.55 (d, 1H), 6.21 (dt, 1H), 5.81 (br s, 2H), 4.73 (br s, 1H), 3.98 (s, 2H), 1.48 (s, 9H); reverse phase HPLC (5% to 95% acetonitrile over 25 minutes, 1 mL/min, 254 nm, hypersil HS 100 Å, C18, 5 μm, 250×4.6 column) R$_t$=15.5 minutes; MS m/e 385.1.

EXAMPLE 197B tert-butyl (2E)-3-[4-amino-3-(3-methoxy-4-{[(1-methyl-1H-indol-2-yl)carbonyl]amino}phenyl)thieno[3,2-c]pyridin-7-yl]-2-propenylcarbamate A mixture of Example 197A (275 mg, 0.716 mmol), Example 175E (436 mg, 1.074 mmol), Na$_2$CO$_3$ (151 mg, 1.43 mmol), and Pd(PPh$_3$)$_4$ (50 mg, 0.043 mmol) in 1,2-dimethoxyethane/water (12:6 mL) was heated to 95° C. for 20 hours and partitioned between water (30 mL) and dichloromethane (40 mL). The organic layer was separated and the aqueous layer was further extracted with dichloromethane (2×40 mL). The organic layer was filtered to provide some desired product (117 mg). The filtrate was dried (MgSO$_4$), filtered, concentrated, dissolved in dichloromethane (10 mL), and filtered to provide additional desired product (107 mg). The remaining filtrate was purified by flash chromatography on silica gel with dichloromethane/methanol (97:3). Product-containing fractions were filtered to provide another 25 mg of the desired product to provide a total of 249 mg (0.430 mmol). $^1$H NMR (DMSO-d$_6$, 400 MHz) δ 9.51 (s, 1H), 8.01 (t, 1H), 7.95 (s, 1H), 7.70–7.72 (d, 1H), 7.58–7.62 (m, 2H), 7.30–7.35 (m, 2H), 7.07–7.21 (m, 3H), 6.59 (d, 1H), 6.21 (dt, 1H), 5.62 (br s, 2H), 4.04 (s, 3H), 3.91 (s, 3H), 3.78 (t, 2H), 1.42 (s, 9H); reverse phase HPLC (5% to 95% acetonitrile over 10 minutes, 1 mL/min, 254 nm, hypersil HS 100 Å, C18, 5 μm, 250×4.6 column) R$_t$=19.2 min. MS m/e 584.3 (M+H)$^+$.

EXAMPLE 197C

N-(4-{4-amino-7-[(1E)-3-amino-1-propenyl]thieno[3,2-c]pyridin-3-yl}-2-methoxyphenyl)-1-methyl-1H-indole-2-carboxamide A mixture of Example 197B (250 mg, 0.43 mmol), 6N HCl (2.5 mL), and acetone (5 mL) was stirred for 3 hours at ambient temperature and heated to 40° C. for 4 hours. The mixture was partitioned between 2N NaOH (10 mL) and dichloromethane (20 mL). The organic layer was separated and the aqueous layer was further extracted with dichloromethane (2×20 mL). The organic layer was dried (MgSO$_4$), filtered, and concentrated to provide the desired product (146 mg): $^1$H NMR (CDCl$_3$, 400 MHz) δ 8.66 (s, 1H), 8.58–8.60 (d, 1H), 7.95 (m, 1H), 7.70–7.72 (d, 1H), 7.00–7.52 (m, 6H), 6.69 (d, 1H), 6.46 (m, 1H), 4.89 (br s, 2H), 4.14 (s, 3H), 3.98 (s, 3H), 3.60–3.61 (d, 2H); reverse phase HPLC (5% to 95% acetonitrile over 10 minutes, 1 mL/min, 254 nm, hypersil HS 100 Å, C18, 5 μm, 250×4.6 column) R$_t$=10.1 min. MS m/e 482.4 (M–H)$^-$.

General Procedure for the Preparation of Amides, Sulfonamides, Carbamates and Ureas from

EXAMPLE 197C

A mixture of Example 197C (30 mg, 0.062 mmol) in dichloromethane (2 mL) and pyridine (0.1 mL) was treated with the appropriate acid chloride, sulfonyl chloride, or alkylchloroformate (1.2 eq) at ambient temperature. Ureas were prepared in the same manner from Example 197C and the appropriate isocyanate, but pyridine was omitted from the reaction mixture. The mixtures were stirred for 2 hours at ambient temperature and concentrated. The products were purified by normal or reverse phase chromatography.

EXAMPLE 198

N-(4-{7-[(1E)-3-(acetylamino)-1-propenyl]-4-aminothieno[3,2-c]pyridin-3-yl}-2-methoxyphenyl)-1-methyl-1H-indole-2-carboxamide starting reagent: acetyl chloride. Reverse phase HPLC (5% to 95% acetonitrile over 10 minutes, 1 mL/min, 254 nm, hypersil HS 100 Å, C18, 5 μm, 250×4.6 column) R$_t$=11.5 min. $^1$H NMR (DMSO-d$_6$, 400 MHz) δ 9.51 (s, 1H), 8.17 (t, 1H), 8.00 (s, 1H), 7.96 (s, 1H), 7.71 (d, 1H), 7.62 (s, 1H), 7.58 (d, 1H), 7.30–7.35 (m, 2H), 7.21 (s, 1H), 7.07–7.15 (m, 2H), 6.63 (d, 1H), 6.20 (dt, 1H), 5.64 (br s, 2H), 4.04 (s, 3H), 3.93 (br s, 5H), 1.88 (s, 3H); MS m/e 524.2 (M–H)$^-$.

EXAMPLE 199

N-[4-(4-amino-7-{(1E)-3-[(methylsulfonyl)amino]-1-propenyl}thieno[3,2-c]pyridin-3-yl)-2-methoxyphenyl]-1-methyl-1H-indole-2-carboxamide starting reagent: methylsulfonyl chloride. Reverse phase HPLC (5% to 95% acetonitrile over 10 minutes, 1 mL/min, 254 nm, hypersil HS 100 Å, C18, 5 μm, 250×4.6 column) R$_t$=12.3 min. $^1$H NMR (DMSO-d$_6$, 400 MHz) δ 9.51 (s, 1H), 8.02 (t, 1H), 8.00 (s, 1H), 7.71 (d, 1H), 7.64 (s, 1H), 7.59 (d, 1H), 7.30–7.35 (m, 2H), 7.21 (s, 1H), 7.07–7.15 (m, 2H), 6.75 (d, 1H), 6.20 (dt, 1H), 5.65 (br s, 2H), 4.04 (s, 3H), 3.91 (s, 3H), 3.84 (t, 2H), 2.96 (s, 3H); MS m/e 562.3 (M+H)$^+$.

EXAMPLE 200 methyl (2E)-3-[4-amino-3-(3-methoxy-4-{[(1-methyl-1H-indol-2-yl)carbonyl]amino}phenyl)thieno[3,2-c]pyridin-7-yl]-2-propenylcarbamate starting reagent: methyl chloroformate. Reverse phase HPLC (5% to 95% acetonitrile over 10 minutes, 1 mL/min, 254 nm, hypersil HS 100 Å, C18, 5 μm, 250×4.6 column) R$_t$=12.8 min. $^1$H NMR (DMSO-d$_6$, 400 MHz) δ 9.51 (s, 1H), 8.02 (t, 1H), 7.96 (s, 1H), 7.71 (d, 1H), 7.58–7.62 (m, 2H), 7.50 (t, 1H), 7.30–7.35 (m, 2H), 7.08–7.21 (m, 3H), 6.63 (d, 2H), 6.22 (dt, 1H), 5.65 (br s, 2H), 4.04 (s, 3H), 3.92 (s, 3H), 3.88 (t, 2H), 3.57 (s, 3H); MS m/e 542.3.

EXAMPLE 201

N-{4-[4-amino-7-((1E)-3-{[(ethylamino)carbonyl]amino}-1-propenyl)thieno[3,2-c]pyridin-3-yl]-2-methoxyphenyl}-1-methyl-1H-indole-2-carboxamide starting reagent: isocyanatoethane. Reverse phase HPLC (5% to 95% acetonitrile over 10 minutes, 1 mL/min, 254 nm, hypersil HS 100 Å, C18, 5 μm, 250×4.6 column) R$_t$=9.9 min. $^1$H NMR (DMSO-d$_6$, 400 MHz) δ 9.51 (s, 1H), 8.0 (d, 1H), 7.95 (s, 1H), 7.71 (d, 1H), 7.62 (s, 1H), 7.58 (d, 1H), 7.30–7.35 (m, 2H), 7.07–7.21 (m, 3H), 6.60 (d, 1H), 6.23 (dt, 1H), 6.11 (t, 1H), 5.89 (t, 1H), 5.62 (br s, 2H), 4.04 (s, 3H), 3.93 (s, 3H), 3.87 (t, 2H), 3.05, (p, 2H), 1.02 (t, 3H); MS m/e 555.4 (M+H)$^+$.

EXAMPLE 202

N-[4-(4-amino-7-{(1E)-3-[(3-pyridinylcarbonyl)amino]-1-propenyl}thieno[3,2-c]pyridin-3-yl)-2-methoxyphenyl]-1-methyl-1H-indole-2-carboxamide starting reagent: nicotinyl chloride. Reverse phase HPLC (5% to 95% acetonitrile over 10 minutes, 1 mL/min, 254 nm, hypersil HS 100 Å, C18, 5 μm, 250×4.6 column) R$_t$=11.7 min. $^1$H NMR (DMSO-d$_6$, 400 MHz) δ 9.49 (s, 1H), 9.10–9.18 (m, 2H), 8.75, (d, 1H), 8.25 (d, 1H), 8.14 (t, 1H), 8.10 (s, 1H), 7.97 (s, 1H), 7.71 (d, 1H), 7.55–7.62 (m, 2H), 7.58 (d, 1H), 7.29–7.35 (m, 3H), 7.16 (t, 2H), 7.00 (br s, 1H), 6.75 (d, 1H), 6.58 (dt, 1H), 4.21 (t, 2H), 4.04 (s, 3H), 3.93 (s, 3H); MS m/e 587.1 (M–H)$^-$.

EXAMPLE 203

N-(4-{4-amino-7-[(1E)-3-(isonicotinoylamino)-1-propenyl]thieno[3,2-c]pyridin-3-yl}-2-methoxyphenyl)-1-methyl-1H-indole-2-carboxamide starting reagent: isonicotinyl chloride. Reverse phase HPLC (5% to 95% acetonitrile over 10 minutes, 1 mL/min, 254 nm, hypersil HS 100 Å, C18, 5 μm, 250×4.6 column) R$_t$=11.8 min. $^1$H NMR (DMSO-d$_6$, 400 MHz) δ 9.50 (s, 1H), 9.16 (t, 1H), 8.75 (m, 2H), 8.00 (d, 2H), 7.83 (m, 2H), 7.71 (d, 1H), 7.58–7.62 (m, 2H), 7.31–7.35 (m, 2H), 7.21 (s, 1H), 7.07–7.16 (m, 3H), 6.73 (d, 1H), 6.33 (dt, 1H), 4.19 (t, 2H), 4.04 (s, 3H), 3.92 (s, 3H); MS m/e 587.7 (M–H)$^-$.

EXAMPLE 204

N-{4-[4-amino-7-((1E)-3-{[3-(dimethylamino)benzoyl]amino}-1-propenyl)thieno[3,2-c]pyridin-3-yl]-2-methoxyphenyl}-1-methyl-1H-indole-2-carboxamide starting reagent: 3-(dimethylamino)benzoyl chloride. Reverse phase HPLC (5% to 95% acetonitrile over 10 minutes, 1 mL/min, 254 nm, hypersil HS 100 Å, C18, 5 μm, 250×4.6 column) R$_t$=13.8 min. $^1$H NMR (DMSO-d$_6$, 400 MHz) δ 9.47 (s, 1H), 8.74 (t, 1H), 8.00 (m, 2H), 7.68 (d, 1H), 7.55–7.59 (m, 2H), 7.05–7.32 (m, 7H), 6.84–6.86 (m, 1H), 6.67 (d, 1H), 6.30 (dt, 1H), 5.62 (br s, 2H), 4.12 (t, 2H), 4.06 (s, 3H), 3.83 (s, 3H), 2.92 (s, 6H); MS m/e 629.4 (M−H)−.

EXAMPLE 205

N-[4-(4-amino-7-{(1E)-3-[(anilinocarbonyl)amino]-1-propenyl}thieno[3,2-c]pyridin-3-yl)-2-methoxyphenyl]-1-methyl-1H-indole-2-carboxamide starting reagent: isocyanatobenzene. $^1$H NMR (DMSO-$d_6$, 400 MHz) δ 9.49 (s, 1H), 8.56 (s, 1H), 8.00 (d, 1H), 7.96 (d, 1H), 7.69 (d, 1H), 7.61 (s, 1H), 7.57 (d, 1H), 7.41 (d, 1H), 7.33 (s, 1H), 7.32 (m, 1H), 7.22 (m, 3H), 7.14 (t, 1H), 7.07 (m, 1H), 6.89 (t, 1H), 6.67 (d, 1H), 6.43 (t, 1H), 6.28 (m, 1H), 4.02 (s, 3H), 3.96 (m, 2H), 3.90 (s, 3H); MS m/e 603.4 (M+H)+.

EXAMPLE 206

N-(4-{4-amino-7-[(1E)-3-(benzoylamino)-1-propenyl]thieno[3,2-c]pyridin-3-yl}-2-methoxyphenyl)-1-methyl-1H-indole-2-carboxamide starting reagent: benzoyl chloride. $^1$H NMR (DMSO-$d_6$, 400 MHz) δ 9.43 (s, 1H), 8.79 (t, 1H), 7.94 (m, 2H), 7.76 (m, 2H), 7.64 (s, 1H), 7.55 (s, 1H), 7.40–7.53 (m, 4H), 7.26 (m, 2H), 7.13 (s, 1H), 7.08 (t, 1H), 7.01 (m, 1H), 6.64 (d, 1H), 6.27 (m, 1H), 5.57 (br s, 2H), 4.09 (t, 2H), 3.97 (s, 3H), 3.85 (s, 3H); MS m/e 588.4 (M+H)+.

EXAMPLE 207

N-[4-(4-amino-7-{(1E)-3-[(phenylsulfonyl)amino]-1-propenyl}thieno[3,2-c]pyridin-3-yl)-2-methoxyphenyl]-1-methyl-1H-indole-2-carboxamide starting reagent: benzenesulfonyl chloride. $^1$H NMR (DMSO-$d_6$, 400 MHz) 9.49 (s, 1H), 8.0 (t, 1H), 7.85 (m, 3H), 7.69 (d, 1H), 7.60 (m, 5H), 7.34 (s, 1H), 7.32 (d, 1H), 7.19 (d, 1H), 7.14 (t, 1H), 7.06 (d, 1H), 6.60 (d, 1H), 6.02 (m, 1H), 5.65 (br s, 2H), 4.03 (s, 3H), 3.90 (s, 3H), 3.68 (d, 2H); MS m/e 624.3 (M+H)+.

EXAMPLE 208 benzyl (2E)-3-[4-amino-3-(3-methoxy-4-{[(1-methyl-1H-indol-2-yl)carbonyl]amino}phenyl)thieno[3,2-c]pyridin-7-yl]-2-propenylcarbamate starting reagent: benzyl chloroformate. $^1$H NMR (DMSO-$d_6$, 400 MHz) δ 9.49 (s, 1H), 8.01 (t, 1H), 7.94 (s, 1H), 7.71 (d, 1H), 7.62 (m, 2H), 7.58 (d, 1H), 7.31–7.39 (m, 5H), 7.21 (s, 1H), 7.15 (t, 1H), 7.08 (d, 1H), 6.63 (d, 1H), 6.23 (m, 1H), 5.64 (br s, 2H), 5.07 (s, 2H), 4.04 (s, 3H), 3.91 (s, 3H), 3.89 (t, 1H); MS m/e 618.4 (M+H)+.

EXAMPLE 209

N-[4-(4-amino-7-{(1E)-3-[(5-isoxazolylcarbonyl)amino]-1-propenyl}thieno[3,2-c]pyridin-3-yl)-2-methoxyphenyl]-1-methyl-1H-indole-2-carboxamide starting reagent: 5-isoxazolecarbonyl chloride. $^1$H NMR (DMSO-$d_6$, 400 MHz) δ 9.49 (s, 1H), 9.32 (t, 1H), 8.76 (d, 1H), 7.98 (m, 2H), 7.71 (d, 1H), 7.69 (d, 1H), 7.58 (d, 1H), 7.34 (s, 1H), 7.32 (m, 1H), 7.20 (d, 1H), 7.14 (d, 1H), 7.12 (d, 1H), 7.08 (dd, 1H), 6.70 (d, 1H), 6.30 (m, 1H), 5.66 (br s, 2H), 4.15 (t, 1H), 4.03 (s, 3H), 3.91 (s, 3H); MS m/e 579.3 (M+H)+.

General Procedure for Suzuki Coupling in Southern Domain

A mixture of Example 21A (0.250 g, 0.74 mmol) in 1,2-dimethoxyethane (10 mL) and water (5 mL) was treated with the appropriate boronic acid (0.85 mmol), Na$_2$CO$_3$ (0.179 g, 1.69 mmol) and Pd(PPh$_3$)$_4$ (0.081 g, 0.07 mmol) at 80° C. for 18 hours. The organic solvent was removed in vacuo and the solid was isolated by filtration and purified by flash column chromatography on silica gel with 2% methanol/dichloromethane to provide the desired product in 40–88% yield.

EXAMPLE 210

3-bromo-7-(3-furyl)thieno[3,2-c]pyridin-4-amine boronic acid: 3-furylboronic acid. $^1$H NMR (DMSO-$d_6$, 400 MHz) δ 8.09 (d, 2H), 8.08 (t, 1H), 7.89 (s, 1H), 7.82 (t, 1H), 6.99 (dd, 1H), 6.62 (br s, 2H); reverse phase HPLC (Delta Pak C18, 5 μm, 300 Å, 15 cm; 5%-95% acetonitrile/0.1M ammonium acetate over 10 minutes, then isocratic 3 minutes, 1 mL/min) R$_t$=1.50 min.; MS m/e 295, 297.

EXAMPLE 211

3-bromo-7-(4-pyridinyl)thieno[3,2-c]pyridin-4-amine boronic acid: 4-pyridinylboronic acid. $^1$H NMR (DMSO-$d_6$, 400 MHz) δ 8.65 (d, 2H), 8.07 (s, 1H), 7.88 (s, 1H), 7.65 (d, 2H), 6.86 (br s, 2H); reverse phase HPLC (Delta Pak C18, 5 μm, 300 Å, 15 cm; 5%-95% acetonitrile/0.1M ammonium acetate over 10 minutes, 1 mL/min) R$_t$=9.77 minutes; MS m/e 306, 308 (M+H)+.

EXAMPLE 212

3-bromo-7-(3-pyridinyl)thieno[3,2-c]pyridin-4-amine boronic acid: 3-pyridinylboronic acid. $^1$H NMR (DMSO-$d_6$, 400 MHz) δ 8.81 (dd, 1H), 8.60 (dd, 1H), 8.01–8.05 (m, 1H), 7.96 (s, 1H), 7.86 (s, 1H), 7.51–7.55 (m, 1H), 6.75 (br s, 2H); reverse phase HPLC (Delta Pak C18, 5 μm, 300 Å, 15 cm; 5%-95% acetonitrile/0.1 M ammonium acetate over 10 minutes, 1 mL/min) R$_t$=9.84 minutes; MS m/e 306, 308 (M+H)+.

EXAMPLE 213

3-bromo-7-(3-thienyl)thieno[3,2-c]pyridin-4-amine boronic acid: 3-thienylboronic acid. Reverse phase HPLC (Delta Pak C18, 5 μm, 300 Å, 15 cm; 5%-95% acetonitrile/0.1M ammonium acetate over 10 minutes, then isocratic 3 minutes, 1 mL/min) R$_t$=12.09 min. $^1$H NMR (DMSO-$d_6$, 400 MHz) δ 8.07 (s, 1H), 7.87 (s, 1H), 7.65–7.78 (m, 1H), 7.69–7.73 (m, 1H), 7.50 (dd, 1H), 6.64 (br s, 2H); MS m/e 311,313 (M+H)+.

EXAMPLE 214

3-bromo-7-(2-thienyl)thieno[3,2-c]pyridin-4-amine boronic acid: 2-thienylboronic acid. Reverse phase HPLC (Delta Pak C18, 5 μm, 300 Å, 15 cm; 5%-95% acetonitrile/0.1M ammonium acetate over 10 minutes, then isocratic 3 minutes, 1 mL/min) $R_t$=12.09 min. $^1$H NMR (DMSO-$d_6$, 400 MHz) δ 8.07 (s, 1H), 7.87 (s, 1H), 7.65–7.78 (m, 1H), 7.69–7.73 (m, 1H), 7.50 (dd, 1H), 6.64 (br s, 2H); MS m/e 311,313 (M+H)$^+$.

EXAMPLE 215

3-bromo-7-(6-methoxy-3-pyridinyl)thieno[3,2-c]pyridin-4-amine boronic acid: 6-methoxy-3-pyridinylboronic acid. Reverse phase HPLC (Delta Pak C18, 5 μm, 300 Å, 15 cm; 50%-100% acetonitrile/0.1M ammonium acetate over 10 min, 1 mL/min) $R_t$=6.60 min. $^1$H NMR (DMSO-$d_6$, 400 MHz) δ 8.37 (dd, 1H), 7.93 (dd, 1H), 7.88 (s, 1H), 7.85 (s, 1H), 6.96 (dd, 1H), 6.66 (br s, 2H), 3.91 (s, 1H); MS m/e 336, 338 (M+H)$^+$.

General Procedure for Suzuki Coupling in Northern Domain

A mixture of the 3-bromothienyl compound (Examples 210–212) (1.0 eq) in 1,2-dimethoxyethane (10 mL) and water (5 mL) was reacted with Example 175E (1.2 eq), Na$_2$CO$_3$ (2.4 eq), and Pd(PPh$_3$)$_4$ (0.06 eq) at 95° C. for 18 hours. The organic solvent was removed in vacuo and the the mixture was extracted with dichloromethane. The extract was dried (MgSO$_4$), filtered, and concentrated. The residue was purified by preparative reverse phase HPLC (Rainin C18, 8 mm, 300 Å, 25 cm; 40% acetonitrile/0.1M ammonium acetate isocratic for 5 minutes, then 40–100% acetonitrile/0.1M ammonium acetate over 30 minutes, 21 mL/min). The acetonitrile was removed in vacuo and the aqueous mixture was lyophilized to provide the desired product.

EXAMPLE 216

N-{4-[4-amino-7-(4-pyridinyl)thieno[3,2-c]pyridin-3-yl]-2-methoxyphenyl}-1-methyl-1H-indole-2-carboxamide bromide: Example 211. $^1$H NMR (DMSO-$d_6$, 400 MHz) δ 9.52 (s, 1H), 8.69 (d, 2H), 8.12 (s, 1H), 8.03 (t, 1H), 7.68–7.76 (m, 3H), 7.65 (s, 1H), 7.59 (d, 1H), 7.29–7.37 (m, 2H), 7.24 (s, 1H), 7.08–7.18 (m, 2H), 5.75–5.90 (br s, 2H), 4.04 (s, 3H), 3.92 (s, 3H); LCMS (Thermoquest AQA single-quad MS, Genesis C18 column, 3 mm particle size, 33×4.6 mm; 30–95% acetonitrile/0.050M ammonium acetate over 3 minutes, then isocratic 95% acetonitrile/0.050M ammonium acetate over 1.5 minutes, 0.8 mL/min): MS m/e 506 (M+H)$^+$, RT=3.95 min.

EXAMPLE 217

N-{4-[4-amino-7-(3-furyl)thieno[3,2-c]pyridin-3-yl]-2-methoxyphenyl}-1-methyl-1H-indole-2-carboxamide bromide: Example 210. $^1$H NMR (DMSO-$d_6$, 400 MHz) δ 9.52 (s, 1H), 8.69 (d, 2H), 8.12 (s, 1H), 8.03 (t, 1H), 7.68–7.76 (m, 3H), 7.65 (s, 1H), 7.59 (d, 1H), 7.29–7.37 (m, 2H), 7.24 (s, 1H), 7.08–7.18 (m, 2H), 5.75–5.90 (br s, 2H), 4.04 (s, 3H), 3.92 (s, 3H); reverse phase HPLC (Delta Pak C18, 5 μm, 300 Å, 15 cm; 5%-95% acetonitrile/0.1M ammonium acetate over 10 min, 1 mL/min) $R_t$=8.75 minutes; MS m/e 495 (M+H)$^+$.

EXAMPLE 218

N-{4-[4-amino-7-(3-pyridinyl)thieno[3,2-c]pyridin-3-yl]-2-methoxyphenyl}-1-methyl-1H-indole-2-carboxamide bromide: Example 212. $^1$H NMR (DMSO-$d_6$, 400 MHz) δ 9.52 (s, 1H), 8.88 (d, 1H), 8.63 (dd, 1H), 8.08–8.13 (m, 1H), 8.02 (t, 1H), 7.99 (s, 1H), 7.71 (d, 1H), 7.54–7.63 (m, 3H), 7.30–7.37 (m, 2H), 7.24 (d, 1H), 7.09–7.18 (m, 2H), 5.67–5.76 (br s, 2H), 4.04 (s, 3H), 3.92 (s, 3H); reverse phase HPLC (Delta Pak C18, 5 μm, 300 Å, 15 cm; 50%-100% acetonitrile/0.1M ammonium acetate over 10 minutes, 1 mL/min) $R_t$=8.50 minutes; MS m/e 506 (M+H)$^+$.

EXAMPLE 219

3-(4-phenoxyphenyl)thieno[3,2-c]pyridin-4-amine

EXAMPLE 219A 3-bromothieno[3,2-c]pyridin-4-amine

A mixture of 3-bromo-4-chlorothieno[3,2-c]pyridine (prepared according to the procedure described in Bull. Soc. Chim. Belges 1970, 79, 407–414, 3 g, 12 mmol), concentrated aqueous NH$_4$OH (100 mL), and p-dioxane (100 mL) was sealed in a stainless steel, high-pressure reactor and stirred for 18 hours at 150° C. The mixture was concentrated to half its original volume, diluted with water, and extracted with ethyl acetate. The combined organic extracts were washed with brine, dried (MgSO$_4$), filtered, and concentrated to provide 2.6 g (94%) of the desired product. $^1$H NMR (DMSO-$d_6$, 400 MHz) δ 7.83 (d, 1H), 7.77 (s, 1H), 7.26 (d, 1H), 6.48 (br s, 2H); MS m/e 229 (M+H)$^+$.

EXAMPLE 219B 3-(4-phenoxyphenyl)thieno[3,2-c]pyridin-4-amine

A mixture of Example 219A (5.43 g, 23.7 mmol), 4-phenoxyphenylboronic acid (6 g, 28.03 mmol), Na$_2$CO$_3$ (3.7 g, 34.9 mmol), Pd(PPh$_3$)$_4$ (5.4 g, 4.7 mmol), DMF (96 mL), and water (24 mL) was stirred for 18 hours at 80° C. under nitrogen, poured into 10% aqueous NaCl (400 mL), and extracted with ethyl acetate (3×70 mL). The combined organic extracts were washed with brine, dried (MgSO$_4$), filtered, and concentrated under reduced pressure. The residue was dissolved in 300 mL of dichloromethane. Silica gel (90 g) was added to the solution and the mixture was concentrated under vacuum. The residual silica gel with the absorbed crude product was transferred to a silica gel column (600 g) and chromatographed (eluent 40% ethyl acetate/heptane) to provide 5.61 g (75%) of the desired product. $^1$H NMR (DMSO-$d_6$, 400 MHz) δ 7.85 (d, 1H), 7.49–7.44 (m, 5H), 7.29 (d, 1H), 7.22 (t, 1H), 7.16–7.12 (m, 4H), 5.44 (br s, 2H); $^{13}$C NMR (DMSO-d$_6$, 100 MHz) δ 156.9, 156.1, 154.5, 148.3, 141.8, 136.1, 130.9, 130.1, 123.9, 123.0, 119.2, 118.4, 118.1, 107.8.

EXAMPLE 220

N-[4-(4-aminothieno[3,2-c]pyridin-3-yl)-2-methoxyphenyl]-1-methyl-1H-indole-2-carboxamide The desired product was prepared by substituting Example 175E for 4-phenoxyphenylboronic acid in Example 219B. LCMS m/e 429.3 (M+H)$^+$; R$_t$: 4.05 min.

EXAMPLE 221 tert-butyl (2E)-3-[4-amino-3-(4-phenoxyphenyl)thieno[3,2-c]pyridin-7-yl]acrylate

EXAMPLE 221A 7-iodo-3-(4-phenoxyphenyl)thieno[3,2-c]pyridin-4-amine

A solution of Example 219B (5 g, 15.7 mmol) in DMF (100 mL) was treated with N-iodosuccinimide (4.23 g, 18.8 mmol), stirred at ambient temperature for 2 hours, concentrated to half the original volume, and poured into 5% sodium thiosulfate (400 mL). The mixture was filtered and the filter cake was washed with water and dried. The solids were dissolved in dichloromethane (300 mL), treated with silica gel (80 g), and concentrated. The residue was transferred to a silica gel column (600 g) and chromatographed with ethyl acetate/heptane (1:6) to provide 5.2 g (75%) of the desired product. $^1$H NMR (CD$_2$Cl$_2$, 400 MHz) δ 7.95 (s, 1H), 7.33–7.29 (m, 4H), 7.12 (s, 1H), 7.10 (t, 1H), 7.02–6.99 (m, 4H), 4.76 (br s, 1H); $^{13}$C NMR (CD$_2$Cl$_2$, 400 MHz) δ 158.4, 156.8, 154.7, 154.4, 148.6, 138.4, 131.3, 131.2, 130.4, 124.4, 122.9, 120.0, 119,9, 118.8, 72.0.

EXAMPLE 221B tert-butyl (2E)-3-[4-amino-3-(4-phenoxyphenyl)thieno[3,2-c]pyridin-7-yl]acrylate A mixture of Example 221A (2 g, 4.5 mmol), tert-butyl acrylate (1.3 mL, 8.8 mmol), Pd(OAc)$_2$ (100 mg, 0.44 mmol), PPh$_3$ (236 mg, 0.89 mmol), Na$_2$CO$_3$ (0.95 g, 8.9 mmol), and DMF (40 mL) was stirred for 18 hours at 80° C. under a nitrogen atmosphere. The mixture was concentrated to half its original volume and poured into 10% NaCl (300 mL). The product was extracted with ethyl acetate (3×70 mL). The combined organic extracts were washed with brine, dried (MgSO$_4$), filtered, and concentrated. The residue was dissolved in dichloromethane (300 mL), treated with silica gel (25 g), and concentrated. The preabsorbed silica gel was subsequently transferred to a silica gel (200 g) column and chromatographed with ethyl acetate/heptane (1:6) to provide 1.52 g (76%) of the desired product. $^1$H NMR (CD$_2$Cl$_2$, 400 MHz) δ 8.13 (s, 1H), 7.78 (d, 1H), 7.49–7.43 (m, 4H), 7.32 (s, 1H), 7.22 (t, 1H), 7.15 (d, 4H), 6.46 (d, 1H), 5.18 (br s, 2H), 1.59 (s, 9H); $^{13}$C NMR (CD$_2$Cl$_2$, 100 MHz) δ 166.8, 158.5, 156.8, 155.5, 147.1, 146.9, 139.8, 137.5, 131.3, 130.7, 130.4, 124.4, 123.8, 119.9, 119.7, 118.8, 118.7, 117.2, 80.6, 28.4.

EXAMPLE 222 butyl (2E)-3-[4-amino-3-(4-phenoxyphenyl)thieno[3,2-c]pyridin-7-yl]acrylate

The desired product was prepared by substituting butyl acrylate for tert-butyl acrylate in Example 221. LCMS m/e 445.5 (M+H)$^+$; retention time: 5.00 min.

EXAMPLE 223 ethyl (2E)-3-[4-amino-3-(4-phenoxyphenyl)thieno[3,2-c]pyridin-7-yl]acrylate

The desired product was prepared by substituting ethyl acrylate for tert-butyl acrylate in Example 221.

EXAMPLE 224

(2E)-3-[4-amino-3-(4-phenoxyphenyl)thieno[3,2-c]pyridin-7-yl]-2-propen-1-ol

A solution of Example 223 (0.45 g, 10.8 mmol) in THF at −78° C. was treated with 5.4 mL DIBAL-H solution (1.0M in toluene, 5.4 mmol) and methanol (1 mL), warmed to room temperature, and concentrated. The residue was dissolved in methanol (100 mL), treated with silica gel (5 g), and concentrated. The preabsorbed silica gel was subsequently transferred to a silica gel column and chromatographed (ethyl acetate/heptane 3:1) to provide 200 mg (49%) of the product.

EXAMPLE 225

(2E)-3-[4-amino-3-(4-phenoxyphenyl)thieno[3,2-c]pyridin-7-yl]acrylic acid

A solution of Example 221B (1.5 g, 3.4 mmol) in dichloromethane and trifluoroacetic acid (10 mL) was stirred for 2 hours at ambient temperature, treated with toluene (200 mL), and concentrated to provide 1.7 g (100%) of the desired product as the trifluoroacetate salt. $^1$H NMR (DMSO-d$_6$, 400 MHz) δ 8.42 (s, 1H), 7.95 (s, 1H), 7.76 (d, 1H), 7.54 (dd, 2H), 7.46 (dt, 2H), 7.21 (t, 1H), 7.16 (dd, 4H), 6.61 (d, 1H); $^{13}$C NMR (DMSO-d$_6$, 100 MHz) δ 167.0, 159.0, 158.6, 157.6, 156.0, 148.8, 137.7, 137.5, 131.0, 130.1, 128.2, 127.6, 124.0, 120.3, 119.4, 119.2, 118.7, 115.7.

EXAMPLE 226

(2E)-3-[4-amino-3-(4-phenoxyphenyl)thieno[3,2-c]pyridin-7-yl]acrylic acid

A solution of Example 225 (1.2 g, 2.3 mmol) and p-dioxane (50 mL) was treated with 2.5M HCl. The mixture was stirred for 20 minutes at ambient temperature and concentrated. The process was repeated once more after which the residue was azeotropically dried with toluene (2×100 mL) to provide the desired product as the hydrochloride salt.

General Procedure for Amide Formation

A mixture of Example 226 (50 mg, 0.12 mmol), N,N-diisopropylethyl amine (90 µL, 5.1 mmol), the amine (0.24 mmol), and DMF (2.5 mL) was treated sequentially with 0.5M HBTU in DMF and 0.5M HOBT in DMF. The reaction was stirred for 18 hours at ambient temperature, diluted with water, and extracted with ethyl acetate. The combined organic extracts were dried (Na$_2$SO$_4$), filtered, and concentrated. The residue was purified using normal or reverse phase chromatography.

EXAMPLE 227 tert-butyl 3-[({(2E)-3-[4-amino-3-(4-phenoxyphenyl)thieno[3,2-c]pyridin-7-yl]-2-propenoyl}amino)methyl]-1-pyrrolidinecarboxylate amine: tert-butyl 3-(aminomethyl)-1-pyrrolidinecarboxylate.

EXAMPLE 228

(2E)-3-[4-amino-3-(4-phenoxyphenyl)thieno[3,2-c]pyridin-7-yl]-N-(3-pyrrolidinylmethyl)acrylamide The desired product was prepared by dissolving Example 227 in dichloromethane (8 mL) and adding TFA (2 mL). The mixture was stirred for 4 hours at room temperature and concentrated to provide the desired product.

EXAMPLE 229

(2E)-3-[4-amino-3-(4-phenoxyphenyl)thieno[3,2-c]pyridin-7-yl]-N-[(3S)-3-pyrrolidinylmethyl]acrylamide

EXAMPLE 229A tert-butyl (3R)-3-[({(2E)-3-[4-amino-3-(4-phenoxyphenyl)thieno[3,2-c]pyridin-7-yl]-2-propenoyl}amino)methyl]-1-pyrrolidinecarboxylate amine: tert-butyl (3R)-3-(aminomethyl)-1-pyrrolidinecarboxylate.

EXAMPLE 229B (2E)-3-[4-amino-3-(4-phenoxyphenyl)thieno[3,2-c]pyridin-7-yl]-N-[(3S)-3-pyrrolidinylmethyl]acrylamide Example 229A was dissolved in dichloromethane (8 mL), treated with TFA (2 mL), stirred for 4 hours at room temperature, and concentrated to provide the desired product.

EXAMPLE 230

(2E)-3-[4-amino-3-(4-phenoxyphenyl)thieno[3,2-c]pyridin-7-yl]-N-[(3R)-3-pyrrolidinylmethyl]acrylamide

EXAMPLE 230A tert-butyl (3S)-3-[({(2E)-3-[4-amino-3-(4-phenoxyphenyl)thieno[3,2-c]pyridin-7-yl]-2-propenoyl}amino)methyl]-1-pyrrolidinecarboxylate amine: tert-butyl (3S)-3-(aminomethyl)-1-pyrrolidinecarboxylate. $^1$H NMR (CD$_2$Cl$_2$, 400 MHz) δ 8.07 (s, 1H), 7.73 (d, 1H), 7.43–7.37 (m, 4H), 7.25 (s, 1H), 7.16 (t, 1H), 7.09 (d, 4H), 6.47 (d, 1H), 5.94 (br d, 1H), 5.07 (s, 2H), 3.49 (dd, 1H), 3.30–3.26 (m, 1H), 3.04 (m, 1H), 2.45 (m, 1H), 1.99 (m, 1H), 1.70–1.65 (m, 4H), 1.42 (s, 9H).

EXAMPLE 230B (2E)-3-[4-amino-3-(4-phenoxyphenyl)thieno[3,2-c]pyridin-7-yl]-N-[(3R)-3-pyrrolidinylmethyl]acrylamide Example 230A was dissolved in dichloromethane (8 mL), treated with TFA (2 mL), stirred for 4 hours at room temperature, and concentrated to provide the desired product. $^1$H NMR (DMSO-d$_6$, 400 MHz) δ 8.31 (m, 1H), 8.12 (s, 1H), 7.67 (s, 1H), 7.64 (d, 1H), 7.57–7.43 (m, 4H), 7.21 (t, 1H), 7.15–7.12 (m, 4H), 6.63 (d, 1H), 5.87 (br s, 2H), 4.15–4.12 (m, 1H), 3.24–3.13 (m, 2H), 2.97–2.87 (m, 1H), 2.82–2.60 (m, 2H), 2.35–2.14 (m, 2H), 1.90–1.80 (m, 1H), 1.80–1.70 (m, 1H); MS m/e 471.

EXAMPLE 231

(2E)-3-[4-amino-3-(4-phenoxyphenyl)thieno[3,2-c]pyridin-7-yl]-N-methylacrylamide amine: methylamine. $^1$H NMR (DMSO-d$_6$, 400 MHz) δ 8.16 (q, 1H), 8.13 (s, 1H), 7.66 (s, 1H), 7.58 (d, 1H), 7.51–7.43 (m, 4H), 7.21 (t, 1H), 7.15–7.12 (m, 4H), 6.58 (d, 1H), 5.87 (br s, 2H), 2.73 (d, 3H); MS m/e 402.

EXAMPLE 232 tert-butyl 3-[({(2E)-3-[4-amino-3-(4-phenoxyphenyl)thieno[3,2-c]pyridin-7-yl]-2-propenoyl}amino)methyl]-1-pyrrolidinecarboxylate amine: tert-butyl 3-(aminomethyl)-1-pyrrolidinecarboxylate.

EXAMPLE 233

(2E)-3-[4-amino-3-(4-phenoxyphenyl)thieno[3,2-c]pyridin-7-yl]-N-(3-pyrrolidinylmethyl)acrylamide The desired product was prepared by substituting Example 232 for Example 229A in Example 229B.

EXAMPLE 234 tert-butyl 4-({(2E)-3-[4-amino-3-(4-phenoxyphenyl)thieno[3,2-c]pyridin-7-yl]-2-propenoyl}amino)-1-piperidinecarboxylate amine: tert-butyl 4-amino-1-piperidinecarboxylate.

EXAMPLE 235

(2E)-3-[4-amino-3-(4-phenoxyphenyl)thieno[3,2-c]pyridin-7-yl]-N-4-piperidinylacrylamide The desired product was prepared by substituting Example 234 for Example 229A in Example 229B. MS m/e 471.3 (M+H)$^+$.

EXAMPLE 236 tert-butyl 2-[2-({(2E)-3-[4-amino-3-(4-phenoxyphenyl)thieno[3,2-c]pyridin-7-yl]-2-propenoyl}amino)ethyl]-1-piperidinecarboxylate amine: tert-butyl 2-(2-aminoethyl)-1-piperidinecarboxylate.

EXAMPLE 237

(2E)-3-[4-amino-3-(4-phenoxyphenyl)thieno[3,2-c]pyridin-7-yl]-N-[2-(2-piperidinyl)ethyl]acrylamide The desired product was prepared by substituting Example 236 for Example 229A in Example 229B. MS m/e 499.4 (M+H)+.

EXAMPLE 238 tert-butyl 3-[({1(2E)-3-[4-amino-3-(4-phenoxyphenyl)thieno[3,2-c]pyridin-7-yl]-2-propenoyl}amino)methyl]-1-piperidinecarboxylate amine: tert-butyl 3-(aminomethyl)-1-piperidinecarboxylate.

EXAMPLE 239

(2E)-3-[4-amino-3-(4-phenoxyphenyl)thieno[3,2-c]pyridin-7-yl]-N-(3-piperidinylmethyl)acrylamide The desired product was prepared by substituting Example 238 for Example 229A in Example 229B. MS m/e 485.3 (M+H)+.

EXAMPLE 240 tert-butyl 3-({(2E)-3-[4-amino-3-(4-phenoxyphenyl)thieno[3,2-c]pyridin-7-yl]-2-propenoyl}amino)-1-pyrrolidinecarboxylate amine: tert-butyl 3-amino-1-pyrrolidinecarboxylate.

EXAMPLE 241

(2E)-3-[4-amino-3-(4-phenoxyphenyl)thieno[3,2-c]pyridin-7-yl]-N-3-pyrrolidinylacrylamide The desired product was prepared by substituting Example 241 for Example 229A in Example 229B. MS m/e 457.3 (M+H)+.

EXAMPLE 242

(2E)-3-[4-amino-3-(4-phenoxyphenyl)thieno[3,2-c]pyridin-7-yl]-N-[(3S)-3-pyrrolidinyl]acrylamide The desired product was prepared by substituting tert-butyl (3S)-3-amino-1-pyrrolidinecarboxylate into the general procedure for amide formation, then substituting the resulting amide for Example 229A in Example 229B. MS m/e 457.2 (M+H)+.

EXAMPLE 243

(2E)-3-[4-amino-3-(4-phenoxyphenyl)thieno[3,2-c]pyridin-7-yl]-N-[(3R)-3-pyrrolidinyl]acrylamide The desired product was prepared by substituting tert-butyl (3S)-3-amino-1-pyrrolidinecarboxylate into the general procedure for amide formation, then substituting the resulting amide for Example 229A in Example 229B. MS m/e 457.1 (M+H)+.

EXAMPLE 244

(2E)-3-[4-amino-3-(4-phenoxyphenyl)thieno[3,2-c]pyridin-7-yl]-N-[3-(4-morpholinyl)propyl]acrylamide amine: 3-(4-morpholinyl)-1-propanamine.

EXAMPLE 245

(2E)-3-[4-amino-3-(4-phenoxyphenyl)thieno[3,2-c]pyridin-7-yl]-N-[2-(2-pyridinyl)ethyl]acrylamide amine: 2-(2-pyridinyl)ethanamine.

EXAMPLE 246

(2E)-3-[4-amino-3-(4-phenoxyphenyl)thieno[3,2-c]pyridin-7-yl]-N-[2-(1-methyl-2-pyrrolidinyl)ethyl]acrylamide amine: 2-(1-methyl-2-pyrrolidinyl)ethanamine.

EXAMPLE 247

(2E)-3-[4-amino-3-(4-phenoxyphenyl)thieno[3,2-c]pyridin-7-yl]-N-[3-(dimethylamino)propyl]acrylamide amine: N,N-dimethyl-1,3-propanediamine.

EXAMPLE 248

(2E)-3-[4-amino-3-(4-phenoxyphenyl)thieno[3,2-c]pyridin-7-yl]-N-[3-(1H-imidazol-1-yl)propyl]acrylamide amine: 3-(1H-imidazol-1-yl)-1-propanamine.

EXAMPLE 249

(2E)-3-[4-amino-3-(4-phenoxyphenyl)thieno[3,2-c]pyridin-7-yl]-N-[3-(1-piperidinyl)propyl]acrylamide amine: 3-(1-piperidinyl)-1-propanamine.

EXAMPLE 250

(2E)-3-[4-amino-3-(4-phenoxyphenyl)thieno[3,2-c]pyridin-7-yl]-N-(3-pyridinylmethyl)acrylamide amine: 1-(3-pyridinyl)methanamine.

EXAMPLE 251

(2E)-3-[4-amino-3-(4-phenoxyphenyl)thieno[3,2-c]pyridin-7-yl]-N-[2-(4-morpholinyl)ethyl]acrylamide amine: 2-(4-morpholinyl)ethanamine.

EXAMPLE 252

(2E)-3-[4-amino-3-(4-phenoxyphenyl)thieno[3,2-c]pyridin-7-yl]-N-[2-(1-pyrrolidinyl)ethyl]acrylamide amine: 2-(1-pyrrolidinyl)ethanamine.

EXAMPLE 253

(2E)-3-[4-amino-3-(4-phenoxyphenyl)thieno[3,2-c]pyridin-7-yl]-N-[(1-ethyl-2-pyrrolidinyl)methyl]acrylamide amine: (1-ethyl-2-pyrrolidinyl)methylamine.

EXAMPLE 254

(2E)-3-[4-amino-3-(4-phenoxyphenyl)thieno[3,2-c]pyridin-7-yl]-N-[2-(dimethylamino)ethyl]acrylamide amine: N,N-dimethyl-1,2-ethanediamine.

EXAMPLE 255

(2E)-3-[4-amino-3-(4-phenoxyphenyl)thieno[3,2-c]pyridin-7-yl]-N-[2-(1-piperidinyl)ethyl]acrylamide amine: 2-(1-piperidinyl)ethanamine.

EXAMPLE 256

(2E)-3-[4-amino-3-(4-phenoxyphenyl)thieno[3,2-c]pyridin-7-yl]-N-(2-pyridinylmethyl)acrylamide amine: 1-(2-pyridinyl)methanamine.

EXAMPLE 257

(2E)-3-[4-amino-3-(4-phenoxyphenyl)thieno[3,2-c]pyridin-7-yl]-N-(4-pyridinylmethyl)acrylamide amine: 1-(4-pyridinyl)methanamine.

EXAMPLE 258

(2E)-3-[4-amino-3-(4-phenoxyphenyl)thieno[3,2-c]pyridin-7-yl]-N-3-piperidinylacrylamide The desired product was prepared by substituting tert-butyl 3-amino-1-piperidinecarboxylate into the general procedure for amide formation, then substituting the resulting amide for Example 229A in Example 229B.

EXAMPLE 259

(2E)-3-[4-amino-3-(4-phenoxyphenyl)thieno[3,2-c]pyridin-7-yl]-N-[(3R)-3-piperidinyl]acrylamide The desired product was prepared by substituting tert-butyl (3R)-3-(methylamino)-1-piperidinecarboxylate into the general procedure for amide formation, then substituting the resulting amide for Example 229A in Example 229B.

EXAMPLE 260

(2E)-3-[4-amino-3-(4-phenoxyphenyl)thieno[3,2-c]pyridin-7-yl]-N-(4-piperidinylmethyl)acrylamide The desired product was prepared by substituting tert-butyl 4-(aminomethyl)-1-piperidinecarboxylate into the general procedure for amide formation, then substituting the resulting amide for Example 229A in Example 229B.

General Procedure for Suzuki Coupling

A mixture of Example 10B (50 mg, 0.11 mmol), a substituted boronic acid (1.5 equiv.), palladium(II) acetate (2.5 mg, 0.011 mmol), PPh$_3$ (12 mg, 0.045 mmol), sodium acetate (35 mg, 0.033 mmol), and DMF (2.5 mL) was stirred at 100° C. for 18 hours under a nitrogen atmosphere. The mixture was poured to 50 mL of 10% NaCl in water and the product was extracted with ethyl acetate (3×25 mL). The combined organic extracts were washed with brine, dried (MgSO$_4$), filtered, and concentrated. The residue was dissolved in dichloromethane (100 mL), treated with 2.5 g of silica gel, and concentrated. The residue was transferred onto a silica gel column (10 g of silica) and eluted with ethyl acetate/heptane mixtures, typically 1:3, depending on the substrate.

EXAMPLE 261

7-(2-furyl)-3-(4-phenoxyphenyl)thieno[3,2-c]pyridin-4-amine boronic acid: 2-furylboronic acid. MS m/e 385.3 (M+H)$^+$.

EXAMPLE 262

7-(3-furyl)-3-(4-phenoxyphenyl)thieno[3,2-c]pyridin-4-amine boronic acid: 3-furylboronic acid. MS m/e 385.3 (M+H)$^+$.

EXAMPLE 263

7-(1-benzofuran-2-yl)-3-(4-phenoxyphenyl)thieno[3,2-c]pyridin-4-amine boronic acid: 1-benzofuran-2-ylboronic acid. MS m/e 435.2 (M+H)$^+$.

EXAMPLE 264

5-[4-amino-3-(4-phenoxyphenyl)thieno[3,2-c]pyridin-7-yl]-2-furaldehyde boronic acid: 5-formyl-2-furylboronic acid. MS m/e 413.3 (M+H)$^+$.

EXAMPLE 265

3-(4-phenoxyphenyl)-7-(1H-pyrrol-3-yl)thieno[3,2-c]pyridin-4-amine

The desired product was prepared by substituting 1-(tert-butoxycarbonyl)-1H-pyrrol-3-ylboronic acid into the general procedure for Suzuki couplings, then substituting the resulting product for Example 229A in Example 229B. MS m/e 384.2 (M+H)+.

EXAMPLE 266

3-(4-phenoxyphenyl)-7-(1H-pyrrol-2-yl)thieno[3,2-c]pyridin-4-amine

The desired product was prepared by substituting 1-(tert-butoxycarbonyl)-1H-pyrrol-2-ylboronic acid into the general procedure for Suzuki couplings, then substituting the resulting product for Example 229A in Example 229B. MS m/e 384.2 (M+H)+.

EXAMPLE 267

7-(1H-indol-2-yl)-3-(4-phenoxyphenyl)thieno[3,2-c]pyridin-4-amine

The desired product was prepared by substituting 1-(tert-butoxycarbonyl)-1H-indol-2-ylboronic acid into the general procedure for Suzuki couplings, then substituting the resulting product for Example 229A in Example 229B. MS m/e 534.3 (M+H)+(BOC protected compound).

EXAMPLE 268 tert-butyl (2E)-3-(4-amino-3-bromothieno[3,2-c]pyridin-7-yl)acrylate

A solution of Example 21A (2.50 g, 7.04 mmol), PPh$_3$ (0.370 g, 1.41 mmol), and Na$_2$CO$_3$ (1.49 g, 14.1 mmol) in DMF (35 mL) was treated with tert-butyl acrylate (2.00 mL, 14.1 mmol) and palladium(II)acetate (0.158 g, 0.704 mmol). The reaction was heated to 80° C. under an atmosphere of nitrogen for 16 hours. The reaction was cooled to ambient temperature and partitioned between ethyl acetate (100 mL) and brine. The organic phase was washed with brine (2×100 mL), dried (Na$_2$SO$_4$), filtered, and concentrated. The compound was purified by flash chromatography on silica gel using heptane/ethyl acetate (6:1) to (3:1) to provide the desired product (1.70 g, 3.01 mmol). $^1$HNMR (DMSO-d$_6$, 400 MHz) δ 8.24 (s, 1H), 7.94 (s, 1H), 7.62 (d, 1H), 7.17 (br s, 2H), 6.22 (d, 1H), 1.48 (s, 9H); MS m/e 355/357 (M+H)+.

EXAMPLE 269 tert-butyl (2E)-3-[4-amino-3-(3-methoxy-4-{[(1-methyl-1H-indol-2-yl)carbonyl]amino}phenyl)thieno[3,2-c]pyridin-7-yl]acrylate A mixture of Example 268 (1.70 g, 4.79 mmol), Example 175E (2.91 g, 7.18 mmol), Na$_2$CO$_3$ (1.01 g, 9.57 mmol), and Pd(PPh$_3$)$_4$ (0.332 g, 0.287 mmol) was heated in a mixture of DME (60 mL) and water (30 mL) at 95° C. for 15 hours under an atmosphere of nitrogen. The reaction was cooled to ambient temperature, treated with additional Example 175E (0.97 g, 2.39 mmol) and Pd(PPh$_3$)$_4$ (0.332 g, 0.287 mmol), heated to 95° C. for another 5 hours, and cooled to ambient temperature. The resulting precipitate was collected by filteration and washed with diethyl ether (40 mL). The precipitate was dissolved in dichloromethane (200 mL), dried (Na$_2$SO$_4$), filtered, and concentrated to provide the desired product (1.98 g, 3.57 mmol). $^1$HNMR (DMSO-d$_6$, 400 MHz) δ 9.49 (s, 1H), 8.24 (s, 1H), 8.01 (d, 1H), 7.72 (d, 1H), 7.69 (s, 2H), 7.57 (d, 1H), 7.31 (m, 2H), 7.22 (d, 1H), 7.10 (m, 2H), 6.32 (d, 1H), 6.10 (br s, 2H), 4.03 (s, 3H), 3.91 (s, 3H), 1.51 (s, 9H); MS m/e 555 (M+H)+.

EXAMPLE 270

(2E)-3-[4-amino-3-(3-methoxy-4-{[(1-methyl-1H-indol-2-yl)carbonyl]amino}phenyl)thieno[3,2-c]pyridin-7-yl]acrylic acid The desired product was prepared as the trifluoroacetate salt by substituting Example 269 for Example 221B in Example 225. LCMS m/e 499.2; retention time: 2.08 min.

EXAMPLE 271

(2E)-3-[4-amino-3-(3-methoxy-4-{[(1-methyl-1H-indol-2-yl)carbonyl]amino}phenyl)thieno[3,2-c]pyridin-7-yl]acrylic acid The desired product was prepared as the hydrochloride salt by substituting Example 270 for Example 225 in Example 226.

EXAMPLE 272

N-{4-[4-amino-7-((1E)-3-oxo-3-{[2-(1-piperidinyl)ethyl]amino}-1-propenyl)thieno[3,2-c]pyridin-3-yl]-2-methoxyphenyl}-1-methyl-1H-indole-2-carboxamide A mixture of Example 271 (30.6 mg, 0.044 mmol), N,N-diisopropylethylamine (35 µL, 0.20 mmol), 2-piperidin-1-ylethylamine (14.3 µL, 0.10 mmol), and DMF (1 mL) was treated sequentially with 0.5M (0.09 mL) of HBTU in DMF and 0.5M (0.09 mL) of HOBT in DMF. The reaction was stirred for 24 hours at ambient temperature and partitioned between 1N NaOH and ethyl acetate. The combined extracts were dried (Na$_2$SO$_4$), filtered, and concentrated to provide the desired product (20.4 mg, 0.034 mmol). LCMS m/e 609.2; retention time: 2.93 min.

EXAMPLE 273

N-(4-{4-amino-7-[(1Z)-3-oxo-3-(4-piperidinylamino)-1-propenyl]thieno[3,2-c]pyridin-3-yl}-2-methoxyphenyl)-1-methyl-1H-indole-2-carboxamide A mixture of Example 272 (50 mg, 0.12 mmol), N,N-diisopropylethylamine (90 µL, 5.1 mmol), 4-piperidinamine (0.24 mmol), and DMF (2.5 mL) was treated sequentially with 0.5M HBTU in DMF and 0.5M HOBt in DMF. The reaction was stirred for 18 hours at ambient temperature, diluted with water, and extracted with ethyl acetate. The combined organic extracts were dried (Na$_2$SO$_4$), filtered, and concentrated. The residue was purified using normal or reverse phase chromatography. LCMS m/e 581.3; R$_t$=2.67 min.

EXAMPLE 274

N-[4-(4-amino-7-{(1Z)-3-oxo-3-[(3-piperidinylmethyl)amino]-1-propenyl}thieno[3,2-c]pyridin-3-yl)-2-methoxyphenyl]-1-methyl-1H-indole-2-carboxamide A mixture of Example 270 (11 mg, 0.020 mmol), tert-butyl 3-(aminomethyl)-1-piperidinecarboxylate (5 mg, 0.024 mmol), and Na$_2$CO$_3$ (0.060 mmol, 6 mg) in dichloromethane (1 mL) and water (0.5 mL) was treated with a solution of tetramethylfluoroformadinium hexafluorophosphate (TFFH, 8 mg, 0.030 mmol) in dichloromethane (0.5 mL), stirred for 3 days at ambient temperature, treated with additional amine (12 mg, 0.056 mmol), stirred another day, treated with additional TFFH (30 mg, 0.11 mmol), and partitioned between dichloromethane and saturated NaHCO$_3$. The combine organic phases were dried (Na$_2$SO$_4$), filtered, and concentrated. The residue was purified by reversed phase HPLC. The acetonitrile was removed under vacuum and the residue was lyophilized to provide the BOC-protected amine which was dissolved in dichloromethane (1 mL), triethylsilane (0.2 mL), and trifluoroacetic acid (0.5 mL). The mixture was stirred at room temperature for 1 hour and concentrated. The residue was purified by reverse phase HPLC. The acetonitrile was removed under vacuum and the desired product was isolated by lyophilization (1.9 mg). LCMS m/e 595.2; $R_f$=2.67 min.

EXAMPLE 275

(2E)-3-[4-amino-3-(4-bromophenyl)thieno[3,2-c]pyridin-7-yl]-N-3-pyridinylacrylamide The desired product was prepared as the tris(trifluoroacetate) salt by substituting 3-pyridinamine for 1-(4-pyridinyl)methanamine in Example 171B. $^1$H NMR (300 MHz, DMSO-d$_6$) δ 6.75 (s, 2H), 6.93 (d, J=15.9 Hz, 1H), 7.50 (d, J=8.1 Hz, 2H), 7.56 (dd, J=8.5, 4.7 Hz, 1H), 7.76 (d, J=8.1 Hz, 2H), 7.84 (d, J=15.9 Hz, 1H), 7.97 (s, 1H), 8.25–8.28 (m, 1H), 8.33 (s, 1H), 8.39 (dd, J=5.1, 1.0 Hz, 1H), 9.00 (d, J=2.0 Hz, 1H), 10.76 (s, 1H). MS (ESI(+)) m/e 450.9, 452.8 (M+H)$^+$.

EXAMPLE 276

3-(1H-indol-5-yl)thieno[3,2-c]pyridin-4-amine

The desired product was prepared by substituting 1H-indol-5-ylboronic acid and Example 1B for 4-chlorophenylboronic acid and Example 21B, respectively, in Example 21C. $^1$H NMR (300 MHz, DMSO-d$_6$) δ 5.37 (s, 2H), 6.50 (ddd, J=3.0, 2.0, 1.0 Hz, 1H), 7.13 (dd, J=8.5, 1.7 Hz, 1H), 7.24 (d, J=5.4 Hz, 1H), 7.38 (s, 1H), 7.45–7.46 (m, 1H), 7.52 (dt, J=8.5, 1.0 Hz, 1H), 7.60–7.61 (m, 1H), 7.81 (d, J=6.1 Hz, 1H), 11.31 (s, 1H), MS (ESI(+)) m/e 265.9 (M+H)$^+$.

EXAMPLE 277

N-{4-[4-amino-7-(hydroxymethyl)thieno[3,2-c]pyridin-3-yl]phenyl}-N'-(3-methylphenyl)urea

EXAMPLE 277A 3-(4-bromo-2-thienyl)-2-butenoic acid

A solution of ethyl (diethoxyphosphino)acetate (34 mL, 171 mmol) in THF (35 mL) was added dropwise via addition funnel, over 20 minutes, to a 0° C. suspension of NaH (6.9 g, 60% oil dispersion, 172 mmol) in THF (200 mL). The resulting mixture was stirred at 0° C. for 30 minutes, then treated with a solution of 1-(4-bromo-2-thienyl)ethanone (23.6 g, 115 mmol) in THF (75 mL). The reaction was warmed to room temperature, stirred for 4 hours, quenched with water, neutralized with 2N HCl, and extracted three times with ethyl acetate. The combined extracts were washed with brine, dried (Na$_2$SO$_4$), filtered, and concentrated. The concentrate was dissolved in ethanol (350 mL) and THF (190 mL), treated with 2N LiOH (115 mL), stirred overnight at room temperature, and concentrated. The remaining aqueous solution was washed with diethyl ether, acidified with 2N HCl, and filtered. The filter cake was washed with water and dried to provide 22.38 g (79% yield) of the desired product as a mixture of E and Z isomers. MS (ESI(+)) m/e 244.7, 246.7 (M+H)$^+$.

EXAMPLE 277B 3-bromo-7-methylthieno[3,2-c]pyridin-4(5H)-one

The desired product was prepared by substituting Example 277A for (2E)-3-(4-bromo-2-thienyl)acrylic acid in Example 1A. MS (ESI(+)) m/e 244, 246 (M+H)$^+$.

EXAMPLE 277C 3-bromo-4-chloro-7-methylthieno[3,2-c]pyridine

A solution of Example 277B (10.25 g, 42.1 mmol) in POCl$_3$ (50 mL) was stirred at reflux for 2 hours, cooled to room temperature, diluted with ice water, and stirred vigorously resulting in a precipitate which was collected by filtration. The filter cake was further purified by silica gel chromatography on silica gel with dichloromethane to provide 7.14 g (64% yield) of the desired product. MS (ESI(+)) m/e 261.9, 263.9 (M+H)$^+$.

EXAMPLE 277D (3-bromo-4-chlorothieno[3,2-c]pyridin-7-yl)methyl acetate

A solution of Example 277C (1 g, 3.81 mmol) in CCl$_4$ (30 mL) was treated with NBS (0.755 g, 4.24 mmol) and benzoyl peroxide (0.093 g, 0.38 mmol), heated to reflux for 24 hours, cooled to room temperature, and filtered. The filtrate was concentrated to provide 3-bromo-7-(bromomethyl)-4-chlorothieno[3,2-c]pyridine, which was used directly. MS (ESI(+)) m/e 339.5, 341.6, 343.4 (M+H)$^+$. The crude product was dissolved in DMF (7.5 mL), treated with sodium acetate (1.6 g, 19.5 mmol), heated to 100° C. overnight, and partitioned between water and ethyl acetate. The organic extract was washed with brine, dried (NaSO$_4$), filtered, and concentrated. The residue was purified by silica gel chromatography with 10% ethyl acetate/hexanes to provide 0.65 g (53% yield) of the desired product. MS (ESI(+)) m/e 319.7, 321.7, 323.7 (M+H)$^+$.

EXAMPLE 277E (4-amino-3-bromothieno[3,2-c]pyridin-7-yl)methanol

A mixture of Example 277D (3.1 g, 9.7 mmol), concentrated NH$_4$OH (62 mL), and dioxane (62 mL) was heated to 150° C. in a sealed tube for 36 hours, filtered, and concentrated to provide a soid which was triturated with water (20 mL), collected and dried to give 2.1 g (84% yield) of the desired product. MS (ESI(+)) m/e 258.9, 260.8 (M+H)$^+$.

EXAMPLE 277F

N-{4-[4-amino-7-(hydroxymethyl)thieno[3,2-c]pyridin-3-yl]phenyl}-N'-(3-methylphenyl)urea The desired product was prepared by substituting Example 277E and Example 66D for Example 1B and 4-phenoxyphenylboronic acid respectively, in Example 10A. $^1$H NMR (300 MHz, DMSO-$d_6$) δ 2.29 (s, 3H), 4.61 (d, J=5.4 Hz, 2H), 5.15 (t, J=5.3 Hz, 1H), 5.37 (s, 2H), 6.80 (d, J=7.5 Hz, 1H), 7.17 (t, J=7.6 Hz, 1H), 7.25 (d, J=8.8 Hz, 1H), 7.32 (s, 1H), 7.36 (d, J=8.5 Hz, 2H), 7.44 (s, 1H), 7.60 (d, J=8.5 Hz, 2H), 7.75 (s, 1H), 8.67 (s, 1H), 8.87 (s, 1H). MS (ESI(+)) m/e 405.1 (M+H)$^+$.

EXAMPLE 278

N-{4-[4-amino-7-(4-morpholinylmethyl)thieno[3,2-c]pyridin-3-yl]phenyl}-N'-(3-methylphenyl)urea

EXAMPLE 278A 4-amino-3-bromothieno[3,2-c]pyridine-7-carbaldehyde

A solution of Example 277E (1 g, 3.86 mmol) in THF (100 mL) was treated with $MnO_2$ (2.66 g, 42.1 mmol), stirred overnight at room temperature, and filtered through diatomaceous earth (Celite®). The pad was washed with THF and dichloromethane and the combined filtrates were concentrated to provide 0.88 g (89% yield) of the desired product. MS (ESI(+)) m/e 256.8, 258.8 (M+H)$^+$.

EXAMPLE 278B 3-bromo-7-(4-morpholinylmethyl)thieno[3,2-c]pyridin-4-amine

A solution of Example 278A (0.048 g, 0.187 mmol) in THF (15 mL) and dichloromethane (15 mL) was treated with acetic acid (0.012 mL, 0.21 mmol), morpholine (0.02 mL, 0.23 mmol), and sodium triacetoxyborohydride (0.063 g, 0.3 mmol), stirred at room temperature overnight, treated with additional morpholine (0.08 mL), acetic acid (0.05 mL) and sodium triacetoxyborohydride (0.23 g), and stirred an additional 8 hours. The reaction was quenched with 1N NaOH and extracted three times with ethyl acetate. The combined organic extracts were dried ($NaSO_4$), filtered, and concentrated and the residue was purified by preparative HPLC on a Waters Symmetry C8 column (25 mm×100 mm, 7 μm particle size) using a gradient of 10% to 90% acetonitrile: 0.1% aqueous TFA over 30 minutes to provide 0.045 g (55% yield) of the desired product. MS (ESI(+)) m/e 327.9, 329.8 (M+H)$^+$.

EXAMPLE 278C

N-{4-[4-amino-7-(4-morpholinylmethyl)thieno[3,2-c]pyridin-3-yl]phenyl}-N'-(3-methylphenyl)urea The desired product was prepared by substituting Example 278B and Example 66D for Example 1B and 4-phenoxyphenylboronic acid respectively, in Example 10A. $^1$H NMR (300 MHz, DMSO-$d_6$) δ 2.29 (s, 3H), 2.37–2.40 (m, 4H), 3.56–3.63 (m, 6H), 5.36 (s, 2H), 6.80 (d, J=7.8 Hz, 1H), 7.14–7.19 (m, 1H), 7.24–7.27 (m, 1H), 7.31 (s, 1H), 7.36 (d, J=8.5 Hz, 2H), 7.40 (s, 1H), 7.58 (d, J=8.8 Hz, 2H), 7.70 (s, 1H), 8.66 (s, 1H), 8.84 (s, 1H); MS (ESI(+)) m/e 474.1 (M+H)$^+$.

EXAMPLE 279

N-(4-{4-amino-7-[(3-oxo-1-piperazinyl)methyl]thieno[3,2-c]pyridin-3-yl}phenyl)-N'-(3-methylphenyl)urea The desired product was prepared substituting piperazin-2-one for morpholine in Examples 278B–C. $^1$H NMR (300 MHz, DMSO-$d_6$) δ 2.29 (s, 3H), 2.58 (t, J=5.1 Hz, 2H), 2.95 (s, 2H), 3.13–3.20 (m, 2H), 3.67 (s, 2H), 5.40 (s, 2H), 6.80 (d, J=7.5 Hz, 1H), 7.17 (t, J=7.8 Hz, 1H), 7.25 (d, J=8.1 Hz, 1H), 7.31 (s, 1H), 7.37 (d, J=8.5 Hz, 2H), 7.40 (s, 1H), 7.59 (d, J=8.5 Hz, 2H), 7.72 (s, 1H), 7.77 (s, 1H), 8.68 (s, 1H), 8.86 (s, 1H); MS (ESI(+)) m/e 487.1 (M+H)$^+$.

EXAMPLE 280

N-[4-(4-amino-7-{[(2-methoxyethyl)amino]methyl}thieno[3,2-c]pyridin-3-yl)phenyl]-N'-(3-methylphenyl)urea The desired product was prepared substituting 2-methoxyethylamine for morpholine in Examples 278B–C. $^1$H NMR (300 MHz, DMSO-$d_6$) δ 2.29 (s, 3H), 2.65 (t, J=5.6 Hz, 2H), 3.25 (s, 3H), 3.42 (t, J=5.6 Hz, 2H), 3.86 (s, 2H), 5.31 (s, 2H), 6.80 (d, J=7.6 Hz, 1H), 7.17 (t, J=7.6 Hz, 1H), 7.25 (d, J=8.5 Hz, 1H), 7.31 (s, 1H), 7.36 (d, J=8.5 Hz, 2H), 7.40 (s, 1H), 7.59 (d, J=8.8 Hz, 2H), 7.73 (s, 1H), 8.65 (s, 1H), 8.84 (s, 1H); MS (ESI(+)) m/e 462.1 (M+H)$^+$.

EXAMPLE 281

N-{4-[4-amino-7-(6-methoxy-3-pyridinyl)thieno[3,2-c]pyridin-3-yl]-2-methoxyphenyl}-1-methyl-1H-indole-2-carboxamide A mixture of Example 215 (1.0 eq) in 1,2-dimethoxyethane (10 mL) and water (5 mL) was reacted with N-[2-methoxy-4-(4,4,5,5-tetramethyl-1,3,2-dioxaborolan-2-yl)phenyl]-1-methyl-1H-indole-2-carboxamide (1.2 eq), $Na_2CO_3$ (2.4 eq), and Pd(PPh$_3$)$_4$ (0.06 eq) at 95° C. for 18 hours. The organic solvent was removed in vacuo and the the mixture was extracted with dichloromethane. The extract was dried (MgSO$_4$), filtered, and concentrated. The residue was purified by preparative reverse phase HPLC (Rainin C18, 8 mm, 300 Å, 25 cm; 40% acetonitrile/0.1M ammonium acetate isocratic for 5 minutes, then 40–100% acetonitrile/0.1M ammonium acetate over 30 minutes, 21 mL/min). The acetonitrile was removed in vacuo and the aqueous mixture was lyophilized to provide the desired product. $^1$H NMR (DMSO-$d_6$, 400 MHz) δ 9.52 (s, 1H), 8.45 (s, 1H), 8.02 (t, 1H), 7.91 (s, 1H), 7.71 (d, 1H), 7.55–7.63 (m, 2H), 7.28–7.38 (m, 2H), 7.23 (s, 1H), 7.08–7.18 (m, 2H), 7.03 (d, 1H), 5.57–5.69 (br s, 2H), 4.04 (s, 3H), 3.93 (s, 3H), 3.92 (s, 3H); reverse phase HPLC (Delta Pak C18, 5 μm, 300 Å, 15 cm; 50%-100% acetonitrile/0.1M ammonium acetate over 10 min, 1 mL/min) $R_t$=9.30 min.; MS m/e 536 (M+H)$^+$.

EXAMPLE 282

N-{4-[4-amino-7-(3-thienyl)thieno[3,2-c]pyridin-3-yl]-2-methoxyphenyl}-1-methyl-1H-indole-2-carboxamide A mixture of Example 213 (1.0 eq) in 1,2-dimethoxyethane (10 mL) and water (5 mL) was reacted with Example 175E (1.2 eq), $Na_2CO_3$ (2.4 eq), and $Pd(PPh_3)_4$ (0.06 eq) at 95° C. for 18 hours. The organic solvent was removed in vacuo and the the mixture was extracted with dichloromethane. The extract was dried ($MgSO_4$), filtered, and concentrated. The residue was purified by preparative reverse phase HPLC (Rainin C18, 8 mm, 300 Å, 25 cm; 40% acetonitrile/0.1M ammonium acetate isocratic for 5 minutes, then 40–100% acetonitrile/0.1M ammonium acetate over 30 minutes, 21 mL/min). The acetonitrile was removed in vacuo and the aqueous mixture was lyophilized to provide the desired product. $^1$H NMR (DMSO-$d_6$, 400 MHz) δ 9.52 (s, 1H), 8.11 (s, 1H), 8.01 (t, 1H), 7.80–7.85 (m, 1H), 7.72–7.77 (m, 1H), 7.70 (d, 1H), 7.62 (s, 1H), 7.55–7.61 (m, 2H), 7.29–7.36 (m, 2H), 7.22 (d, 1H), 7.07–7.17 (m, 2H), 5.56–5.67 (br s, 2H), 4.04 (s, 3H), 3.92 (s, 3H); RP-HPLC (Delta Pak C18, 5 μm, 300 Å, 15 cm; 50%-100%, acetonitrile/0.1M ammonium acetate over 10 min, 1 mL/min) $R_t$=1.82 min.; MS m/e 511 (M+H)$^+$.

EXAMPLE 283

N-{4-[4-amino-7-(2-thienyl)thieno[3,2-c]pyridin-3-yl]-2-methoxyphenyl}-1-methyl-indole-2-carboxamide A mixture of Example 214 (1.0 eq) in 1,2-dimethoxyethane (10 mL) and water (5 mL) was reacted with Example 175E (1.2 eq), $Na_2CO_3$ (2.4 eq), and $Pd(PPh_3)_4$ (0.06 eq) at 95° C. for 18 hours. The organic solvent was removed in vacuo and the the mixture was extracted with dichloromethane. The extract was dried ($MgSO_4$), filtered, and concentrated. The residue was purified by preparative reverse phase HPLC (Rainin C18, 8 mm, 300 Å, 25 cm; 40% acetonitrile/0.1M ammonium acetate isocratic for 5 minutes, then 40–100% acetonitrile/0.1M ammonium acetate over 30 minutes, 21 mL/min). The acetonitrile was removed in vacuo and the aqueous mixture was lyophilized to provide the desired product. $^1$H NMR (DMSO-$d_6$, 400 MHz) δ 9.51 (s, 1H), 8.12 (s, 1H), 8.02 (t, 1H), 7.70 (d, 1H), 7.65 (s, 1H), 7.61 (dd, 1H), 7.59 (d, 1H), 7.49 (dd, 1H), 7.30–7.37 (m, 2H), 7.21–7.26 (m, 2H), 7.15 (t, 1H), 7.11 (dd, 1H), 5.68–5.77 (br s, 2H), 4.04 (s, 3H), 3.92 (s, 3H); reverse phase HPLC (Delta Pak C18, 5 μm, 300 Å, 15 cm; 50%-100% acetonitrile/0.1M ammonium acetate over 10 min, 1 mL/min) $R_t$=9.61 min.; MS m/e 511 (M+H)$^+$.

EXAMPLE 284

N-{4-[4-amino-7-(1H-indol-5-yl)thieno[3,2-c]pyridin-3-yl]phenyl}-N'-[2-fluoro-5-(trifluoromethyl)phenyl]urea

EXAMPLE 284A 3-(4-aminophenyl)-7-(1H-indol-5-yl)thieno[3,2-c]pyridin-4-amine The desired product was prepared by substituting Example 77B and 1H-indol-5-ylboronic acid for Example 77A and 4-pyridylboronic acid, respectively, in Example 121A. MS (ESI(+)) m/e 357 (M+H)$^+$.

EXAMPLE 284B

N-{4-[4-amino-7-(1H-indol-5-yl)thieno[3,2-c]pyridin-3-yl]phenyl}-N'-[2-fluoro-5-(trifluoromethyl)phenyl]urea The desired product was prepared by substituting Example 284A for Example 121B in Example 122. $^1$H NMR (300 MHz, DMSO-$d_6$) δ 5.43 (s, 2H), 6.51 (s, 1H), 7.37–7.39 (m, 1H), 7.42–7.44 (m, 3H), 7.47–7.50 (m, 2H), 7.53–7.55 (m, 2H), 7.64 (d, J=8.48 Hz, 2H), 7.80 (d, J=1.70 Hz, 1H), 7.89 (s, 1H), 8.65 (dd, J=7.29, 2.20 Hz, 1H), 8.98 (d, J=3.05 Hz, 1H), 9.39 (s, 1H), 11.22 (s, 1H); MS (ESI(+)) m/e 562 (M+H)$^+$.

EXAMPLE 285

N-{4-[4-amino-7-(1H-indol-5-yl)thieno[3,2-c]pyridin-3-yl]phenyl}-N'-(3-methylphenyl)urea The desired product was prepared by substituting Example 284A and 1-isocyanato-3-methylbenzene for Example 121B and 1-fluoro-2-isocyanato-4-(trifluoromethyl)benzene, respectively in Example 122. $^1$H NMR (300 MHz, DMSO-$d_6$) δ 2.29 (s, 3H), 5.42 (s, 2H), 6.51 (s, 1H), 6.81 (d, J=7.12 Hz, 1H), 7.17 (t, J=7.63 Hz, 1H), 7.26–7.28 (m, 1H), 7.32 (s, 1H), 7.36 (dd, J=8.31, 1.87 Hz, 1H), 7.41–7.43 (m, 3H), 7.45 (s, 1H), 7.53 (d, J=8.14 Hz, 1H), 7.62 (d, J=8.82 Hz, 2H), 7.79 (d, J=1.36 Hz, 1H), 7.88 (s, 1H), 8.66 (s, 1H), 8.86 (s, 1H), 11.21 (s, 1H); MS (ESI(+)) m/e 490 (M+H)$^+$.

Examples 286–288 were prepared by substituting the appropriate boronic acid (X) for 4-chloro-phenylboronic acid in Example 21C.

EXAMPLE 286

(2E)-3-[4-amino-3-(1H-indol-6-yl)thieno[3,2-c]pyridin-7-yl]-N-methylacrylamide

X=1H-indol-6-ylboronic acid. $^1$H NMR (300 MHz, DMSO-$d_6$) δ 2.74 (d, J=4.4 Hz, 3H), 5.84 (s, 2H), 6.53–6.55 (m, 1H), 6.59 (d, J=15.9 Hz, 1H), 7.07 (dd, J=8.1, 1.4 Hz, 1H), 7.45–7.48 (m, 2H), 7.59 (d, J=15.9 Hz, 1H), 7.62 (s, 1H), 7.69 (d, J=8.1 Hz, 1H), 8.11 (s, 1H), 8.16 (q, J=4.4 Hz, 1H), 11.32 (s, 1H); MS (ESI(+)) m/e 349.0 (M+H)$^+$.

EXAMPLE 287

(2E)-3-[4-amino-3-(1-methyl-1H-indol-6-yl)thieno[3,2-c]pyridin-7-yl]-N-methylacrylamide X=1-methyl-1H-indol-6-ylboronic acid. $^1$H NMR (300 MHz, DMSO-$d_6$) δ 2.74 (d, J=4.4 Hz, 3H), 3.87 (s, 3H), 5.81 (s, 2H), 6.51 (dd, J=3.4, 0.7 Hz, 1H), 6.58 (d, J=15.9 Hz, 1H), 7.22 (dd, J=8.1, 1.7 Hz, 1H), 7.46 (d, J=3.4 Hz, 1H), 7.56–7.64 (m, 4H), 8.10 (s, 1H), 8.15 (q, J=4.4 Hz, 1H); MS (ESI(+)) m/e 363.0 (M+H)$^+$.

EXAMPLE 288

(2E)-3-[4-amino-3-(2-methyl-1H-indol-5-yl)thieno[3,2-c]pyridin-7-yl]-N-methylacrylamide X=2-methyl-1H-indol-5-ylboronic acid. $^1$H NMR (300 MHz, DMSO-$d_6$) δ 2.42 (s, 3H), 2.73 (d, J=4.4 Hz, 3H), 5.82 (s, 2H), 6.20 (s, 1H), 6.58 (d, J=15.9 Hz, 1H), 7.05 (dd, J=8.5, 1.7 Hz, 1H), 7.41 (d, J=8.5 Hz, 1H), 7.47 (d, J=1.4 Hz, 1H), 7.56 (s, 1H), 7.58 (d, J=15.9 Hz, 1H), 8.09 (s, 1H), 8.15 (q, J=4.4 Hz, 1H), 11.17 (s, 1H); MS (ESI(+)) m/e 463.0 (M+H)$^+$.

EXAMPLE 289

4-{[4-amino-3-(1H-indol-5-yl)thieno[3,2-c]pyridin-7-yl]methyl}-2-piperazinone

The desired product was prepared by substituting piperazin-2-one for morpholine in Example 278B, then substituting the product for Example 21B in Example 29. $^1$H NMR (300 MHz, DMSO-$d_6$) δ 2.63 (t, J=5.3 Hz, 2H), 2.98 (s, 2H), 3.17–3.22 (m, 2H), 3.71 (s, 2H), 5.82 (s, 2H), 6.51 (m, 1H), 7.15 (dd, J=8.5, 1.7 Hz, 1H), 7.46–7.47 (m, 1H), 7.51 (s, 1H), 7.53 (d, J=8.5 Hz, 1H), 7.63 (s, 1H), 7.74–7.79 (m, 2H), 11.33 (s, 1H); MS (ESI(+)) m/e 378.1 (M+H)$^+$.

EXAMPLE 290

N-(4-{4-amino-7-[(3-oxo-1-piperazinyl)methyl]thieno[3,2-c]pyridin-3-yl}phenyl)-N'-[3-(trifluoromethyl)phenyl]urea The desired product was prepared substituting piperazin-2-one for morpholine in Example 278B, then substituting the product and N-[4-(4,4,5,5-tetramethyl-1,3,2-dioxaborolan-2-yl)phenyl]-N'-[3-(trifluoromethyl)phenyl]urea for Example 1B and 4-phenoxyphenylboronic acid, respectively, in Example 10A. $^1$H NMR (300 MHz, DMSO-$d_6$) δ 2.57–2.60 (m, 2H), 2.95 (s, 2H), 3.15–3.19 (m, 2H), 3.67 (s, 2H), 5.40 (s, 2H), 7.32 (d, J=7.8 Hz, 1H), 7.39 (d, J=8.5 Hz, 2H), 7.41 (s, 1H), 7.53 (t, J=8.0 Hz, 1H), 7.58–7.63 (m, 3H), 7.72 (s, 1H), 7.77 (s, 1H), 8.03 (s, 1H), 9.00 (s, 1H), 9.13 (s, 1H); MS (ESI(+)) m/e 541.1 (M+H)$^+$.

EXAMPLE 291

(2E)-3-[4-amino-3-(1H-indol-5-yl)thieno[3,2-c]pyridin-7-yl]-N-(4-pyridinylmethyl)acrylamide

EXAMPLE 291A (2E)-3-(4-amino-3-bromothieno[3,2-c]pyridin-7-yl)acrylic acid

The desired product was prepared substituting Example 1B for Example 10A in Example 10B, then substituting the product for Example 10B in Examples 11A–B. MS (ESI(+)) m/e 298.8, 300.8 (M+H)$^+$.

EXAMPLE 291B (2E)-3-[4-amino-3-(1H-indol-5-yl)thieno[3,2-c]pyridin-7-yl]-N-(4-pyridinylmethyl)acrylamide The desired product was prepared substituting Example 291A for Example 78 in Example 90, then substituting the product for Example 21B in Example 29. $^1$H NMR (300 MHz, DMSO-$d_6$) δ 4.46 (d, J=6.0 Hz, 2H), 5.87 (s, 2H), 6.51–6.53 (m, 1H), 6.70 (d, J=15.9 Hz, 1H), 7.16 (dd, J=8.1, 1.7 Hz, 1H), 7.32 (d, J=5.8 Hz, 2H), 7.47–7.49 (m, 1H), 7.55 (d, J=8.5 Hz, 1H), 7.60 (s, 1H), 7.65 (m, 2H), 8.13 (s, 1H), 8.52 (d, J=5.8 Hz, 2H), 8.83 (t, J=6.0 Hz, 1H), 11.35 (s, 1H).

EXAMPLE 292

(2E)-3-[4-amino-3-(1H-indol-5-yl)thieno[3,2-c]pyridin-7-yl]-N-[3-(1H-imidazol-1-yl)propyl]acrylamide The desired product was prepared substituting Example 291A for Example 78 in Example 96, then substituting the product for Example 21B in Example 29. $^1$H NMR (300 MHz, DMSO-$d_6$) δ 1.88–1.97 (m, 2H), 3.15–3.21 (m, 2H), 4.03 (t, J=7.0 Hz, 2H), 5.83 (s, 2H), 6.52 (m, 1H), 6.60 (d, J=15.9 Hz, 1H), 6.90 (t, J=1.0 Hz, 1H), 7.16 (dd, J=8.5, 1.7 Hz, 1H), 7.22 (t, J=1.2 Hz, 1H), 7.46–7.48 (m, 1H), 7.55 (d, J=8.5 Hz, 1H), 7.59 (s, 1H), 7.61 (d, J=15.9 Hz, 1H), 7.63–7.64 (m, 1H), 7.67 (s, 1H), 8.11 (s, 1H), 8.29 (t, J=5.6 Hz, 1H), 11.34 (s, 1H); MS (ESI(+)) m/e 443.1 (M+H)$^+$.

EXAMPLE 293

(2E)-3-[4-amino-3-(1H-indol-5-yl)thieno[3,2-c]pyridin-7-yl]-N-[2-(diethylamino)ethyl]acrylamide The desired product was prepared by substituting Example 291A for Example 78 in Example 86, then substituting the product for Example 21B in Example 29. $^1$H NMR (300 MHz, DMSO-$d_6$) δ 0.98 (t, J=7.0 Hz, 6H), 2.48–2.55 (m, 6H), 3.23–3.29 (m, 2H), 5.81 (s, 2H), 6.51–6.52 (m, 1H), 6.61 (d, J=15.6 Hz, 1H), 7.15 (dd, J=8.1, 1.7 Hz, 1H), 7.46–7.48 (m, 1H), 7.54 (d, J=8.1 Hz, 1H), 7.58 (d, J=15.6 Hz, 1H), 7.58 (s, 1H), 7.63–7.64 (m, 1H), 8.10 (s, 1H), 8.13 (t, J=5.4 Hz, 1H), 11.34 (s, 1H); MS (ESI(+)) m/e 434.1 (M+H)$^+$.

EXAMPLE 294

N-[4-(4-amino-7-iodothieno[3,2-c]pyridin-3-yl)-2-methoxyphenyl]-1-methyl-1H-indole-2-carboxamide

EXAMPLE 294A tert-butyl 4-(4-aminothieno[3,2-c]pyridin-3-yl)-2-methoxyphenylcarbamate A solution of Example 1B (1.0 g, 4.365 mmol) in ethyleneglycol dimethyl ether (20 mL) was treated with tert-butyl 2-methoxy-4-(4,4,5,5-tetramethyl-1,3,2-dioxaborolan-2-yl)phenylcarbamate (1.83 g, 5.238 mmol), Pd(PPh$_3$)$_4$ (0.303 g, 0.262 mmol), and a solution of sodium carbonate (1.1 g, 10.473 mmol) in water (10 mL), stirred at 85° C. for 16 hours under nitrogen, concentrated, and treated with dichloromethane. The organic layer was dried (MgSO$_4$), filtered, and concentrated. The concentrate was purified by flash column chromatography on silica gel with 100% ethyl acetate to provide 1.62 g (100%) of the desired product. $^1$H NMR (DMSO-$d_6$, 400 MHz) δ 8.1 (s, 1H), 7.8 (m, 2H), 7.41 (s, 1H), 7.2 (m, 1H), 7.1 (s, 1H), 7–6.95 (m, 1H), 3.8 (s, 3H), 1.458 (s, 9H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) R$_f$=3.73 min (95%), MS m/e 372.2 (M+H)$^+$.

EXAMPLE 294B tert-butyl 4-(4-amino-7-iodothieno[3,2-c]pyridin-3-yl)-2-methoxyphenylcarbamate A solution of Example 294A (1.49 g, 4.01 mmol) in dimethylformamide (20 mL) was treated portionwise with N-iodosuccinimide (1.083 g, 4.813 mmol), stirred at room temperature for 2 hours, treated with saturated sodium thiosulfate, stirred for 30 minutes, and filtered. The filter cake was washed with water and dried in a vacuum oven to provide 1.884 g (94%) of the desired product. $^1$H NMR (DMSO-$d_6$, 400 MHz) δ 8.111 (s, 1H), 8.018 (s, 1H), 7.8 (m, 1H), 7.566 (s, 1H), 7.086–7.082 (m, 1H), 7.0 (m, 1H), 5.6 (s, 2H), 3.841 (s, 3H), 1.478 (s, 9H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) $R_t$=4.42 min (95%), MS m/e 498.2 (M+H)$^+$.

EXAMPLE 294C 3-(4-amino-3-methoxyphenyl)-7-iodothieno[3,2-c]pyridin-4-amine

A solution of Example 294B (8.641 g, 17.374 mmol) in dichloromethane (100 mL) at 0° C. was treated dropwise with trifluoroacetic acid (30 mL) in dichloromethane (20 mL), stirred at 0° C. for 1 hour and at room temperature for 3 hours, concentrated, and dried under high vacuum. The residue was treated with dichloromethane and 6N HCl. The layers were partitioned and the organic layer was extracted with 6N HCl. The combined aqueous layers were cooled to 0° C. The aqueous layer was basified to pH 11 and the resulting precipitate was collected by filtration to provide 4.787 g of the desired product. The filtrate was extracted three times with ethyl acetate and the combined extracts were dried (MgSO$_4$), filtered, and concentrated to provide 2.41 g of additional product. $^1$H NMR (DMSO-$d_6$, 400 MHz) δ 8.1 (s, 1H), 7.67 (s, 1H), 6.93 (s, 1H), 6.8 (s, 2H), 6.5 (s, 2H), 3.8 (s, 3H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) $R_t$=3.25 min (95%), MS m/e 398.0 (M+H)$^+$.

EXAMPLE 294D 1-methyl-1H-indole-2-carbonyl chloride

A suspension of 1-methyl-1H-2-indolecarboxylic acid (0.485 g, 2.769 mmol) in dichloromethane (10 mL) at 0° C. was treated with oxalyl chloride (0.369 g, 2.91 mmol) and one drop of dimethyl formamide. The reaction mixture was stirred at 0° C. for 1 hour and at room temperature for 2 hours. The solvent was removed under reduced pressure and dried on the high vacuum for 1 hour. The residue was used directly in the subsequent reaction without further purification or analysis.

EXAMPLE 294E

N-[4-(4-amino-7-iodothieno[3,2-c]pyridin-3-yl)-2-methoxyphenyl]-1-methyl-1H-indole-2-carboxamide A solution of Example 294C (1.0 g, 2.517 mmol) in pyridine (10 mL) at 0° C. was treated dropwise with a solution of Example 294D (0.536 g, 2.769 mmol) in dichloromethane (5 mL), stirred at 0° C. for 1 hour and at room temperature for 2 hours, treated with 1N NaOH, stirred for 15 minutes, and concentrated. Dichloromethane was added and the layers were partitioned. The aqueous layer was extracted with dichloromethane. The combined organic layers were washed with water, dried (MgSO$_4$), filtered, and concentrated. The solid was dried on the high vacuum to remove residual pyridine to provide 0.906 g (65%) of the desired product. $^1$H NMR (DMSO-$d_6$, 400 MHz) δ 9.5 (s, 1H), 8.042–7.993 (m, 2H), 7.72–7.70 (m, 1H), 7.641–7.637 (m, 1H), 7.602–7.581 (m, 1H), 7.337–7.317 (m, 2H), 7.212 (m, 1H), 7.174–7.136 (m, 1H), 7.095–7.075 (m, 1H), 5.673 (s, 2H), 4.043 (s, 3H), 3.916 (s, 3H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) $R_t$=4.33 min (95%), MS m/e 553.11 (M−H)$^-$.

General Procedure for Sonogashira Couplings

A Milestone® microwave tube was charged with Example 294E (0.050 g to 0.065 g, ~0.09 mmol), the appropriately functionalized alkyne (0.27 mmol), Pd(PPh$_3$)$_4$ (0.005 g, 0.0045 mmol), cuprous iodide (0.001 g, 0.0045 mmol), and piperidine (3 mL). The reaction mixture was stirred at 85° C. under Milestone® microwave conditions for 5 minutes and concentrated. The concentrate was purified by flash chromatography on silica gel or by preparative HPLC. LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min).

The following compounds were prepared following this procedure using the indicated alkyne.

| Example | Final Product | Starting Alkyne | Amt. (mg) (Yield %) | MS m/z |
|---|---|---|---|---|
| 295 | N-{4-[4-amino-7-(phenylethynyl)thieno[3,2-c]pyridin-3-yl]-2-methoxyphenyl}-1-methyl-1H-indole-2-carboxamide | ethynylbenzene | 11 (23%) | 529.4 |
| 296 | N-{4-[4-amino-7-(3-amino-3-methyl-1-butynyl)thieno[3,2-c]pyridin-3-yl]-2-methoxyphenyl}-1-methyl-1H-indole-2-carboxamide | 1,1-dimethyl-2-propynylamine | 18 (30%) | 510.4 |
| 297 | N-(4-{4-amino-7-[3-(dimethylamino)-1-propynyl]thieno[3,2-c]pyridin-3-yl}-2- | N,N-dimethyl-N-2-propynylamine | 17 (28%) | 510.4 |

| Example | Final Product | Starting Alkyne | Amt. (mg) (Yield %) | MS m/z |
|---|---|---|---|---|
| | methoxyphenyl)-1-methyl-1H-indole-2-carboxamide | | | |
| 298 | N-{4-[4-amino-7-(3-hydroxy-3-methyl-1-butynyl)thieno[3,2-c]pyridin-3-yl]-2-methoxyphenyl}-1-methyl-1H-indole-2-carboxamide | 2-methyl-3-butyn-2-ol | 27 (45%) | 511.4 |
| 299 | N-{4-[4-amino-7-(2-pyridinylethynyl)thieno[3,2-c]pyridin-3-yl]-2-methoxyphenyl}-1-methyl-1H-indole-2-carboxamide | 2-ethynylpyridine | 16 (27%) | 530.4 |
| 300 | N-{4-[4-amino-7-(3-methoxy-1-propynyl)thieno[3,2-c]pyridin-3-yl]-2-methoxyphenyl}-1-methyl-1H-indole-2-carboxamide | 3-methoxy-1-propyne | 21 (36%) | 497.4 |
| 301 | N-{4-[4-amino-7-(5-hydroxy-1-pentynyl)thieno[3,2-c]pyridin-3-yl]-2-methoxyphenyl}-1-methyl-1H-indole-2-carboxamide | 4-pentyn-1-ol | 22 (37%) | 511.4 |
| 302 | N-(4-{4-amino-7-[(1-aminocyclohexyl)ethynyl]thieno[3,2-c]pyridin-3-yl}-2-methoxyphenyl)-1-methyl-1H-indole-2-carboxamide | 1-ethynylcyclohexanamine | 36 (56%) | 533.5 |
| 303 | 5-[4-amino-3-(3-methoxy-4-{[(1-methyl-1H-indol-2-yl)carbonyl]amino}phenyl)thieno[3,2-c]pyridin-7-yl]-4-pentynoic acid | 4-pentynoic acid | 12 (20%) | 525.3 |
| 304 | N-{4-[4-amino-7-(4-hydroxy-1-butynyl)thieno[3,2-c]pyridin-3-yl]-2-methoxyphenyl}-1-methyl-1H-indole-2-carboxamide | 3-butyn-1-ol | 10 (17%) | 497.4 |
| 305 | N-(4-{4-amino-7-[3-(methylamino)-1-propynyl]thieno[3,2-c]pyridin-3-yl}-2-methoxyphenyl)-1-methyl-1H-indole-2-carboxamide | N-methyl-N-2-propynylamine | 3 (<1%) | 496.5 |
| 306 | N-(4-{4-amino-7-[3-(diethylamino)-1-propynyl]thieno[3,2-c]pyridin-3-yl}-2-methoxyphenyl)-1-methyl-1H-indole-2-carboxamide | N,N-diethyl-N-2-propynylamine | 34 (54%) | 538.6 |
| 307 | N-{4-[4-amino-7-(3-hydroxy-1-propynyl)thieno[3,2-c]pyridin-3-yl]-2-methoxyphenyl}-1-methyl-1H-indole-2-carboxamide (acetate salt) | 2-propyn-1-ol | 15 (27%) | 483.4 |
| 308 | tert-butyl 3-[4-amino-3-(3-methoxy-4-{[(1-methyl-1H-indol-2-yl)carbonyl]amino}phenyl)thieno[3,2-c]pyridin-7-yl]-2-propynylcarbamate | tert-butyl 2-propynylcarbamate | 100 (95%) | 582.5 |
| 309 | tert-butyl 5-{[4-amino-3-(3-methoxy-4-{[(1-methyl-1H-indol-2-yl)carbonyl]amino}phenyl)thieno[3,2-c]pyridin-7-yl]ethynyl}-2-pyridinylcarbamate | tert-butyl 5-ethynyl-2-pyridinylcarbamate | 93 (91%) | 645.6 |

EXAMPLE 310

N-{4-[4-amino-7-(3-amino-1-propynyl)thieno[3,2-c]pyridin-3-yl]-2-methoxyphenyl}-1H-methyl-1H-indole-2-carboxamide A solution of Example 308 (0.095 g, 0.163 mmol) in dichloromethane (10 mL) at 0° C. was treated with a solution of trifluoroacetic acid (4 mL) in dichloromethane (5 mL). The reaction mixture was stirred at 0° C. for 35 minutes and at room temperature for 15 hours. The solvent was removed under reduced pressure and the residue was dried under high vacuum. Ethyl acetate and 5N NaOH were added. The layers were partitioned and the organic layer was washed with NaOH, dried (MgSO$_4$), filtered and concentrated to provide 0.039 g (49%) of the desired product. $^1$H NMR (DMSO-d$_6$, 400 MHz) δ 9.518 (s, 1H), 8.015–7.995 (m, 2H), 7.719–7.699 (m, 1H), 7.632–7.581 (m, 2H), 7.352–7.314 (m, 2H), 7.213 (m, 1H), 7.172–7.15 (m, 1H), 7.134–7.076 (m, 1H), 5.85 (br s, 2H), 4.038 (s, 3H), 3.915 (s, 3H), 3.681 (s, 2H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) R$_t$=3.12 min (100%), MS m/e 482.5 (M+H)$^+$.

EXAMPLE 311

N-(4-{4-amino-7-[(6-amino-3-pyridinyl)ethynyl]thieno[3,2-c]pyridin-3-yl}-2-methoxyphenyl)-1-methyl-1H-indole-2-carboxamide A solution of Example 309 (0.080 g, 0.12 mmol) in dichloromethane (5 mL) at 0° C. was treated with a solution of trifluoroacetic acid (2 mL) in dichloromethane (5 mL). The reaction mixture was stirred at 0° C. for 35 minutes and at room temperature for 15 hours. The solvent was removed under reduced pressure and the residue was dried under high vacuum. Ethyl acetate and 5N NaOH were added. The layers were partitioned and the organic layer was washed with NaOH, dried (MgSO$_4$), filtered, and evaporated under reduced pressure. The crude material was purified by preparative HPLC to provide 0.003 g (1%) of the desired product. $^1$H NMR (DMSO-d$_6$, 400 MHz) δ 9.517 (s, 1H), 8.15–8.146 (m, 1H), 8.06–8.005 (m, 2H), 7.72–7.701 (m, 1H), 7.647 (s, 1H), 7.604–7.583 (m, 1H), 7.554–7.527 (m, 2H), 7.356–7.315 (m, 2H), 7.233 (m, 1H), 7.173–7.091 (m, 2H), 6.494–6.459 (m, 2H), 5.8 (br s, 2H), 4.041 (s, 3H), 3.923 (s, 3H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) R$_t$=3.65 min (100%), MS m/e 545.5 (M+H)$^+$.

EXAMPLE 312

N-(4-{4-amino-7-[6-(1,3-dioxo-1,3-dihydro-2H-isoindol-2-yl)-1-hexynyl]thieno[3,2-c]pyridin-3-yl}-2-methoxyphenyl)-1-methyl-1H-indole-2-carboxamide A microwave tube charged with Example 294E (0.001 g, 0.18 mmol), 2-(5-hexynyl)-1H-isoindole-1,3(2H)-dione (0.123 g, 0.541 mmol), PdCl$_2$(PPh$_3$)$_2$ (0.006 g, 0.009 mmol), cuprous chloride (0.002 g, 0.009 mmol), triethylamine (0.054 g, 0.541 mmol), and DMF (4 mL) was stirred at 85° C. for 5 minutes under microwave conditions and concentrated. The residue was purified by flash chromatography on silica gel using 1:1 ethyl acetate/heptane then 100% ethyl acetate to provide 0.078 g (66%) of the desired product $^1$H NMR (DMSO-d$_6$, 400 MHz) δ 9.479 (s, 1H), 7.988–7.957 (m, 1H), 7.878–7.763 (m, 5H), 7.686–7.666 (m, 1H), 7.57–7.549 (m, 2H), 7.319–7.28 (m, 2H), 7.175–7.171 (m, 1H), 7.139–7.101 (m, 1H), 7.059–7.034 (m, 1H), 5.673 (br s, 2H), 4.006 (s, 3H), 3.882 (s, 3H), 3.654–3.62 (m, 2H), 2.572 (m, 2H), 1.839–1.776 (m, 2H), 1.619–1.546 (m, 2H); LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min) R$_t$=4.6 min (95%), MS m/e 654.6 (M+H)$^+$.

EXAMPLE 313

N-{4-[4-amino-7-(3-formyl-2-furyl)-1-benzothien-3-yl]-2-methoxyphenyl}-1-methyl-1H-indole-2-carboxamide A mixture of Example 294E (0.120 g, 0.217 mmol), 3-formyl-2-furylboronic acid (0.033 g, 0.236 mmol), Pd(PPh$_3$)$_4$ (0.012 g, 0.010 mmol), and sodium carbonate (0.057 g, 0.538 mmol) in DMF (2 mL) and water (1 mL) was heated at 80° C. for 16 hours, cooled to ambient temperature, and concentrated. The residue was partitioned between water (20 mL) and methanol/dichloromethane (1:9, 20 mL). The layers were separated and the aqueous layer was extracted further with methanol/dichloromethane (1:9, 2×20 mL). The organic layers were combined, dried (MgSO$_4$), filtered, and concentrated. The residue was purified by flash column chromatography on silica gel deactivated with triethylamine, using methanol/dichloromethane (1:24) as the mobile phase to provide the desired product (0.017 g, 0.032 mmol). $^1$H NMR (DMSO-d$_6$, 400 MHz) δ 9.48 (s, 1H), 7.96 (d, 1H), 7.82 (d, 1H), 7.68 (d, 1H), 7.57 (m, 2H), 7.51 (s, 1H), 7.33 (s, 1H), 7.29 (m, 1H), 7.26 (d, 1H), 7.17 (m, 1H), 7.13 (t, 1H), 7.05 (m, 1H), 4.04 (s, 3H), 3.91 (s, 3H); MS m/e 521 (M–H)$^-$.

EXAMPLE 314 tert-butyl (2E)-3-[4-amino-3-(3-methoxy-4-{[(1-methyl-1H-indol-2-yl)carbonyl]amino}phenyl)thieno[3,2-c]pyridin-7-yl]-2-propenylcarbamate

EXAMPLE 314A tert-butyl allylcarbamate

A solution of copper cyanide (1.15 g, 12.9 mmol) in THF (30 mL) at –78° C. was treated slowly with n-butyllithium (16.9 mL, 27.1 mmol), stirred for 15 minutes at –78° C., treated with tributyltin hydride (7.88 g, 7.30 mL, 27.1 mmol) over a period of 5 minutes, stirred for 15 minutes, treated with tert-butyl 2-propynylcarbamate (2.00 g, 12.9 mmol) in tetrahydrofuran (7 mL), stirred at –78° C. for 1 hour, and treated with a 9:1 aqueous solution of ammonium chloride:ammonium hydroxide (250 mL) and dichloromethane (200 mL). The suspension was filtered through a short pad of diatomaceous earth (Celite®). The organic phase of the filtrate was washed with brine and concentrated. The residue was purified on silica gel using 1–2% ethyl acetate/heptane to provide the desired product (3.66 g, 63%). $^1$H NMR (400 MHz, CDCl$_3$) δ 6.08 (dt, B part of an AB system, J=19.3 Hz, 1.3 Hz, 1H); 5.93 (dt, A part of an AB system, J=19.3 Hz, 4.8 Hz, 1H), 4.59 (br s, 1H), 3.78 (br s, 2H), 1.45 (s, 9H), 1.32–1.26, (m, 12H), 0.90–0.85 (m, 15H).

EXAMPLE 314B tert-butyl (2E)-3-[4-amino-3-(3-methoxy-4-{[(1-methyl-1H-indol-2-yl)carbonyl]amino}phenyl)thieno[3,2-c]pyridin-7-yl]-2-propenylcarbamate A degassed suspension of Example 294E (2.50 g, 4.51 mmol), Example 314A (2.62 g, 5.87 mmol), and potassium fluoride (0.340 g, 5.87 mmol) in toluene (45 mL) was treated with Pd(PPh$_3$)$_4$ (0.360 g, 0.316 mmol), degassed twice more, and then heated to 115° C. for 14 hours. The suspension was cooled to room temperature and the solvent was removed under reduced pressure. The resulting solid was triturated with ethanol/dichloromethane (10:1) (100 mL) and collected by vacuum filtration provide the desired product (2.3 g, 90%). LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min); MS m/e 584.6 (M+H)$^+$, R$_t$=4.1 minutes; $^1$H NMR (DMSO-d$_6$, 400 MHz) δ 9.51 (s,1H), 7.99 (d, J=8.0 Hz,1H), 7.95 (s, 1H), 7.70 (d, J=8.0 Hz, 1H), 7.63 (s, 1H), 7.58 (d, J=8.4 Hz, 1H), 7.35 (s, 1H), 7.32 (d, J=8.4 Hz, 1H), 7.21 (d, J=1.5 Hz, 1H), 7.15 (dd, J=7.8 Hz, 7.0 Hz, 1H), 7.08 (dd, J=8.0 Hz, 1.9 Hz, 1H), 6.58 (d, J=16.2 Hz, 1H), 6.21 (td, J=16.2 Hz, J=5.5 Hz, 1H), 5.65 (br s, 1H), 4.04 (s, 3H), 3.91 (s, 3H), 3.80 (br m, 2H), 1.42 (s, 9H).

EXAMPLE 315

N-(4-{4-amino-7-[(1E)-3-amino-1H-propenyl]thieno[3,2-c]pyridin-3-yl}-2-methoxyphenyl)-1-methyl-1H-indole-2-carboxamide A suspension of Example 314B (0.625 g, 1.07 mmol) in dichloromethane (9 mL) at 0° C. was treated with a solution of trifluoroacetic acid (2.4 g, 21.4 mmol) in dichloromethane (2 mL). The solution was slowly warmed to room temperature, stirred for 4 hours, and concentrated. The resulting trifluoroacetate salt was treated with 50% NaOH and extracted with 10:1 dichloromethane/methanol (4×200 mL). The solvents were removed under reduced pressure to provide the crude product which was purified by silica gel chromatography using 10% methanol/dichloromethane to 25% methanol (with 2.5% ammonium hydroxide)/dichloromethane to provide the desired product (0.330 g, 58%): LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min); MS m/e 484.6 (M+H)$^+$; $R_t$=3.0 minutes; $^1$H NMR (DMSO-d$_6$, 400 MHz) δ 9.50 (s, 1H), 7.98 (d, J=8.0 Hz, 1H), 7.94 (s, 1H), 7.69 (d, J=7.8 Hz, 1H), 7.62 (s, 1H), 7.58 (d, J=8.6 Hz, 1H), 7.34 (s, 1H), 7.31 (d, J=7.2 Hz, 1H), 7.20 (d, J=1.9 Hz, 1H), 7.14 (dd, J=7.8 Hz, 8.0 Hz, 1H), 7.08 (dd, J=8.2 Hz, 1.9 Hz, 1H), 6.67 (d, J=16.2 Hz, 1H), 6.33 (td, J=16.2 Hz, 5.5 Hz, 1H), 5.60 (br s, 1H), 4.03 (s, 3H), 3.91 (s, 3H), 3.44 (dd, J=5.6 Hz, 1.3 Hz, 2H).

General Procedure for Reductive Amination with Example 315

A suspension of Example 315 (0.050 g, 0.104 mmol) and the appropriate ketone/aldehyde (0.087 mmol) in dichloroethane (1.5 mL) was treated with sodium triacetoxyborohydride (0.036 g, 0.173 mmol), stirred at room temperature for 2–12 hours, treated with 10% NaOH (3 mL) and dichloromethane (3 mL), stirred for 15 minutes, filtered through an Empore® cartridge, and concentrated. The crude product was purified in one of three ways: Method A: Triturated in ethanol and collected by filtration. Method B: Purified by preparative reverse phase HPLC (Rainin C18, 8 mm, 300 Å, 25 cm; 40% acetonitrile—0.1M ammonium acetate isocratic for 5 minutes, then 40–100% acetonitrile/0.1M ammonium acetate over 30 min, 21 mL/min) followed by lyophilization. Method C: Purified by reverse phase HPLC (Rainin C18, 8 mm, 300 Å, 25 cm; 40% acetonitrile—0.1M ammonium acetate isocratic for 5 minutes, then 5–100% acetonitrile/0.1M ammonium acetate over 30 min, 21 mL/min) then lyophilized. LCMS conditions: LCMS (Thermoquest AQA single-quad MS, Genesis C18 column, 3 μm particle size, 33×4.6 mm; 70% 50 mM ammonium acetate in water to 95% acetonitrile over 6 min, 0.8 to 0.5 mL/min).

The following examples were prepared by this procedure using the indicated ketone or aldehyde.

| Example | Final Product | Starting Ketone/Aldehyde | Yield % | MS m/e |
|---|---|---|---|---|
| 316 | N-[4-(7-{(1E)-3-[(1-acetyl-4-piperidinyl)amino]-1-propenyl}-4-aminothieno[3,2-c]pyridin-3-yl)-2-methoxyphenyl]-1-methyl-1H-indole-2-carboxamide | 1-acetyl-4-piperidinone | 25 | 609.5 |
| 317 | N-(4-{4-amino-7-[(1E)-3-(tetrahydro-2H-pyran-4-ylamino)-1-propenyl]thieno[3,2-c]pyridin-3-yl}-2-methoxyphenyl)-1-methyl-1H-indole-2-carboxamide (acetate salt) | tetrahydro-4H-pyran-4-one | 31 | 568.1 |
| 318 | N-(4-{4-amino-7-[(1E)-3-(1,4-dioxaspiro[4.5]dec-8-ylamino)-1-propenyl]thieno[3,2-c]pyridin-3-yl}-2-methoxyphenyl)-1-methyl-1H-indole-2-carboxamide | 1,4-dioxaspiro[4.5]decan-8-one | 48 | 624.3 |
| 319 | N-[4-(4-amino-7-{(1E)-3-[(3,3-dimethyl-1,5-dioxaspiro[5.5]undec-9-yl)amino]-1-propenyl}thieno[3,2-c]pyridin-3-yl)-2-methoxyphenyl]-1-methyl-1H-indole-2-carboxamide (acetate salt) | 3,3-dimethyl-1,5-dioxaspiro[5.5]undecan-9-one | 50 | 666.3 |
| 320 | N-{4-[4-amino-7-((1E)-3-{[(6-methyl-2-pyridinyl)methyl]amino}-1-propenyl)thieno[3,2-c]pyridin-3-yl]-2-methoxyphenyl}-1-methyl-1H-indole-2-carboxamide (acetate salt) | 6-methyl-2-pyridinecarbaldehyde | 10 | 589.5 |
| 321 | N-{4-[4-amino-7-((1E)-3-{[2,3-dihydroxypropyl]amino}-1-propenyl)thieno[3,2-c]pyridin-3-yl]-2-methoxyphenyl}-1-methyl-1H-indole-2-carboxamide | 2,3-dihydroxypropanal | 2 | 558.1 |

| Example | Final Product | Starting Ketone/Aldehyde | Yield % | MS m/e |
|---|---|---|---|---|
| 322 | N-[4-(4-amino-7-{(1E)-3-[(1-isopropyl-4-piperidinyl)amino]-1-propenyl}thieno[3,2-c]pyridin-3-yl)-2-methoxyphenyl]-1-methyl-1H-indole-2-carboxamide | 1-isopropyl-4-piperidinone | 25 | 609.7 |

Purification Methods and Spectral Data

EXAMPLE 316

Purification Method: A; $^1$H NMR (400 MHz, DMSO-d$_6$) δ 9.51 (s, 1H), 8.01–7.99 (m, 2H), 7.70 (d, J=7.4 Hz, 1H), 7.66 (s, 1H), 7.58 (d, J=8.2 Hz, 1H), 7.35 (s, 1H), 7.32 (d, J=7.4 Hz, 1H), 7.20 (d, J=1.9 Hz, 1H), 7.15 (dd, J=7.6 Hz, 8.0 Hz, 1H), 7.08 (dd, J=6.5 Hz, 1.9 Hz, 1H), 6.89 (d (br), 1H), 6.27 (td, J=16.0 Hz, 6.2 Hz, 1H), 5.76 (br s, 1H), 4.04 (s, 3H), 3.91 (s, 3H), 3.70 (m, 2H), 3.07 (m, 2H), 2.62 (m, 2H), 2.01 (s, m, 4H), missing signals for 4 aliphatic protons that are under residual solvent and water signals.

EXAMPLE 317

Purification Method: B; $^1$H NMR (400 MHz, DMSO-d$_6$) δ 9.51 (s, 1H), 8.00 (t, J=8.0 Hz, 1H), 7.70 (d, J=7.70 Hz, 1H), 7.62 (s, 1H), 7.58 (d, J=8.6 Hz, 1H), 7.34 (s, 1H), 7.31 (d, J=7.2 Hz, 1H), 7.19 (d, J=1.9 Hz, 1H), 7.14 (t, J=7.2 Hz, 1H), 7.08 (dd, J=8.0 Hz, 1.8 Hz, 1H), 6.68 (d, J=16.4 Hz, 1H), 6.28 (td, J=16.2 Hz, 6.2 Hz, 1H), 5.62 (br s, 1H), 4.04 (s, 3H), 3.91 (s, 3H), 3.84 (m, 2H), 3.45 (m, 2H), 3.27 (m, 2H), 2.32 (m, 1H), 1.86 (m, 2H), 1.30 (m, 2H), 1.91 (s, 3H, acetate).

EXAMPLE 318

Purification Method: B; $^1$H NMR (400 MHz, DMSO-d$_6$) δ 9.51 (s, 1H), 7.99 (d, J=8.0 Hz, 1H), 7.93 (s, 1H), 7.69 (d, J=7.8 Hz, 1H), 7.61 (s, 1H), 7.58 (d, J=7.6 Hz, 1H), 7.34 (s, 1H), 7.31 (d, J=8.4 Hz, 1H), 7.20 (d, J=1.8 Hz, 1H), 7.14 (dd, J=8.0 Hz, 7.2 Hz, 1H), 7.07 (dd, J=7.6 Hz, 1.9 Hz, 1H), 6.65 (d, J=16.0 Hz, 1H), 6.28 (td, J=16.2 Hz, 6.0 Hz, 1H), 5.60 (br s, 1H), 4.04 (s, 3H), 3.91 (s, 3H), 3.84 (m, 4H), 3.39 (m, 2H), 2.54 (m, 1H), 1.79 (m, 2H), 1.68 (m, 2H), 1.48–1.34 (m, 4H).

EXAMPLE 319

Purification Method: C; $^1$H NMR (400 MHz, DMSO-d$_6$) δ 9.51 (s, 1H), 7.99 (dd, (J=8.0 Hz, 8.2 Hz, 1H), 7.93 (s, 1H), 7.69 (d, J=8.2 Hz, 1H), 7.61 (s, 1H), 7.57 (d, J=8.4 Hz, 1H), 7.34 (s, 1H), 7.31 (d, J=7.2 Hz, 1H), 7.20 (d, J=1.8 Hz, 1H), 7.14 (dd, J=8.0 Hz, 7.8 Hz, 1H), 7.07 (dd, J=8.0 Hz, 1.8 Hz, 1H), 6.65 (d, J=16.1 Hz, 1H), 6.27 (td, J=16.2 Hz, 6.0 Hz, 1H), 5.59 (br s, 1H), 4.03 (s, 3H), 3.91 (s, 3H), 3.42–3.39 (m, 6H), 2.32 (m, 1H), 2.08 (m, 2H), 1.71 (m, 2H), 1.38–1.22 (m, 4H), 0.886 (s, 6H), 1.89 (s, 3H, acetate).

EXAMPLE 320

Purification Method: C; $^1$H NMR (400 MHz, DMSO-d$_6$) δ 9.50 (s, 1H), 7.99 (dd, J=8.2 Hz, 7.8 Hz, 1H), 7.96 (s, 1H), 7.70–7.67 (m, 2H), 7.63 (s, 1H), 7.58 (d, J=8.4 Hz, 1H), 7.34 (s, 1H), 7.31 (d, J=8.2 Hz, 1H), 7.27 (d, J=7.4 Hz, 1H), 7.19 (d, J=1.9 Hz, 1H), 7.15–7.12 (m, 2H), 7.07 (dd, J=7.8 Hz, 1.8 Hz, 1H), 6.73 (d (br), J=16.0 Hz, 1H), 6.30 (td, J=16.0 Hz, 6.0 Hz, 1H), 4.03 (s, 3H), 3.91 (s, 3H), 3.54 (br s, 2H), 2.47 (s, 3H), 2.33 (m, 2H), 1.90 (s, 3H, acetate).

EXAMPLE 321

Purification Method: C; $^1$H NMR too dilute for definitive analysis. Analytical HPLC (Rainin C18, 8 mm, 300 Å, 25 cm; 5–100% acetonitrile over 15 minutes then isocratic 5 minutes-1.0 mL/min): R$_f$=11.9 minutes.

EXAMPLE 322

Purification Method: A; $^1$H NMR (400 MHz, DMSO-d$_6$) δ 9.51 (s, 1H), 8.00 (dd, J=8.2 Hz, 8.0 Hz, 1H), 7.94 (s, 1H), 7.70 (d, J=8.0 Hz, 1H), 7.61 (s, 1H), 7.59 (d, J=8.0 Hz, 1H), 7.35 (s, 1H), 7.32 (d, J=7.4 Hz, 1H), 7.20 (d, J=1.8 Hz, 1H), 7.15 (t, J=7.6 Hz, 1H), 7.08 (dd, J=8.2 Hz, 1.8 Hz, 1H), 6.65 (d, J=16.2 Hz, 1H), 6.28 (td, J=16.2 Hz, 6.0 Hz, 1H), 5.59 (br s, 1H), 4.04 (s, 3H), 3.91 (s, 3H), 3.39 (m, 2H), 2.74 (m, 2H), 2.65 (m, 1H), 2.40 (m, 1H), 2.08 (m, 2H), 1.84 (m, 2H), 1.27–1.17 (m, 2H), 0.940 (d, 6H).

General Procedure for Reductive Aminations with Example 176C

A mixture of Example 176C (40 mg, 0.083 mmol), sodium triacetoxyborohydride (35 mg, 0.166 mmol) and the appropriate amine (0166 mmol) in 1,2-dichloromethane (2 mL) was stirred for 2 to 72 hours at ambient temperature. The mixture was concentrated and the residue was purified by normal or reverse phase chromatography. Where necessary a Boc-protected diamine was used for the reductive amination then the protecting group was removed by stirring the reaction mixture in a 2:1 mixture of acetone and 6N hydrochloric acid for 2 hours followed by concentration and purification of the residue.

The following examples were prepared by this general method using the indicated amines:

EXAMPLE 323

N-{4-[4-amino-7-((1E)-3-{4-[2-(dimethylamino)ethyl]-1-piperazinyl}-1-propenyl)thieno[3,2-c]pyridin-3-yl]-2-methoxyphenyl}-1-methyl-1H-indole-2-carboxamide Prepared as the diacetate salt from N,N-dimethyl-N-[2-(1-piperazinyl)ethyl]amine. $^1$H NMR (DMSO-d$_6$, 400 MHz) δ 9.50 (s, 1H), 8.00 (d, 1H), 7.96 (s, 1H), 7.69 (d, 1H), 7.61 (s, 1H), 7.59 (d, 1H), 7.34 (s, 1H), 7.33 (d, 1H), 7.19 (s, 1H), 7.15 (t, 1H), 7.07 (d, 1H), 6.66 (d, 1H), 6.21 (m, 1H), 5.63 (br s, 2H), 4.04 (s, 3H), 3.91 (s, 3H), 3.16 (d, 2H), 2.2–2.5 (m, 12H), 2.13 (s, 6H), 1.87 (s, 6H); MS m/e 624.5 (M+H)$^+$, 622.6 (M−H)$^-$.

EXAMPLE 324

N-[4-(4-amino-7-{(1E)-3-[4-(2-methoxyethyl)-1-piperazinyl]-1-propenyl}thieno[3,2-c]pyridin-3-yl)-2-methoxyphenyl]-1-methyl-1H-indole-2-carboxamide Prepared from 1-(2-methoxyethyl)piperazine. $^1$H NMR (DMSO-d$_6$, 400 MHz) δ 9.49 (s, 1H), 7.99 (d, 1H), 7.95 (s, 1H), 7.69 (d, 1H), 7.60 (s, 1H), 7.57 (d, 1H), 7.34 (s, 1H), 7.31 (d, 1H), 7.19 (s, 1H), 7.14 (t, 1H), 7.06 (d, 1H), 6.66 (d, 1H), 6.20 (m, 1H), 5.62 (br s, 2H), 4.03 (s, 3H), 3.90 (s, 1H), 3.41 (t, 2H), 3.22 (s, 3H), 3.16 (d, 2H), 2.3–2.5 (m, 10H); MS m/e 611.5 (M+H)$^+$.

EXAMPLE 325

N-{4-[4-amino-7-((1E)-3-{4-[3-(dimethylamino)propyl]-1-piperazinyl}-1-propenyl)thieno[3,2-c]pyridin-3-yl]-2-methoxyphenyl}-1-methyl-1H-indole-2-carboxamide Prepared as the triacetate salt from N,N-dimethyl-N-[3-(1-piperazinyl)propyl]amine. $^1$H NMR (DMSO-d$_6$, 400 MHz) δ 9.50 (s, 1H), 7.99 (d, 1H), 7.96 (s, 1H), 7.69 (d, 1H), 7.60 (s, 1H), 7.58 (d, 1H), 7.35 (s, 1H), 7.32 (t, 1H), 7.20 (s, 1H), 7.14 (t, 1H), 7.06 (d, 1H), 6.65 (d, 1H), 6.21 (m, 1H), 5.62 (br s, 1H), 4.03 (s, 3H), 3.90 (s, 3H), 3.16 (d, 2H), 2.39 (m, 8H), 2.26 (t, 2H), 2.19 (m, 2H), 2.09 (s, 6H), 1.85 (s, 9H), 1.53 (m, 2H); MS m/e 638.8 (M+H)$^+$, 636.7 (M−H)$^-$.

EXAMPLE 326

N-{4-[4-amino-7-((1E)-3-{4-[(2-pyrimidinylamino)methyl]-1-piperidinyl}-1-propenyl)thieno[3,2-c]pyridin-3-yl]-2-methoxyphenyl}-1-methyl-1H-indole-2-carboxamide Prepared as the acetate salt from N-(4-piperidinylmethyl)-2-pyrimidinamine. $^1$H NMR (DMSO-d$_6$, 400 MHz) δ 9.50 (s, 1H), 8.00 (d, 1H), 7.96 (s, 1H), 7.71 (d, 1H), 7.61 (s, 1H), 7.32 (t, 1H), 7.19 (s, 2H), 7.15 (t, 1H), 7.07 (d, 1H), 6.65 (d, 1H), 6.51 (t, 1H), 6.22 (m, 1H), 5.63 (br s, 2H), 4.03 (s, 3H), 3.91 (s, 3H), 3.15 (d, 2H), 2.91 (d, 2H), 2.63 (m, 2H), 1.6–2.0 (m, 12H); MS m/e 659.5 (M+H)$^+$, 657.5 (M−H)$^-$.

EXAMPLE 327

N-[4-(4-amino-7-{(1E)-3-[4-(aminocarbonyl)-1-piperidinyl]-1-propenyl}thieno[3,2-c]pyridin-3-yl)-2-methoxyphenyl]-1-methyl-1H-indole-2-carboxamide Prepared as the diacetate salt from 4-piperidinecarboxamide. $^1$H NMR (DMSO-d$_6$, 400 MHz) δ 9.50 (s, 1H), 8.00 (d, 1H), 7.97 (s, 1H), 7.70 (d, 1H), 7.62 (s, 1H), 7.58 (d, 1H), 7.35 (s, 1H), 7.33 (t, 1H), 7.21 (m, 2H), 7.15 (t, 1H), 7.07 (d, 1H), 6.74 (s, 1H), 6.66 (d, 1H), 6.24 (m, 1H), 5.63 (br s, 2H), 4.04 (s, 3H), 3.92 (s, 3H), 3.16 (d, 2H), 2.95 (m, 1H), 1.85–2.09 (m, 4H), 1.89 (s, 6H), 1.53–1.74 (m, 4H); MS m/e 595.5 (M+H)$^+$, 593.2 (M−H)$^-$.

EXAMPLE 328

N-[4-(4-amino-7-{(1E)-3-[[3-(dimethylamino)propyl](methyl)amino]-1-propenyl}thieno[3,2-c]pyridin-3-yl)-2-methoxyphenyl]-1-methyl-1H-indole-2-carboxamide Prepared as the diacetate salt from N,N,N'-trimethyl-1,3-propanediamine. $^1$H NMR (DMSO-d$_6$, 400 MHz) δ 9.50 (s, 1H), 8.00 (d, 1H), 7.96 (s, 1H), 7.71 (d, 1H), 7.61 (s, 1H), 7.59 (d, 1H), 7.35 (s, 1H), 7.32 (t, 1H), 7.19 (s, 1H), 7.14 (t, 1H), 7.07 (d, 1H), 6.67 (d, 1H), 6.23 (m, 1H), 5.63 (br s, 2H), 4.03 (s, 3H), 3.91 (s, 3H), 3.19 (d, 2H), 2.38 (t, 2H), 2.23 (t, 2H), 2.20 (s, 3H), 2.11 (s, 6H), 1.86 (s, 6H), 1.58 (m, 2H); MS m/e 583.0 (M+H)$^+$, 581.3 (M−H)$^-$.

EXAMPLE 329

N-(4-{4-amino-7-[(1E)-3-(4-piperidinylamino)-1-propenyl]thieno[3,2-c]pyridin-3-yl}-2-methoxyphenyl)-1-methyl-1H-indole-2-carboxamide Prepared as the triacetate salt from tert-butyl 4-amino-1-piperidinecarboxylate and deprotected. $^1$H NMR (DMSO-d$_6$, 400 MHz) δ 9.50 (s, 1H), 7.98 (d, 1H), 7.94 (s, 1H), 7.69 (d, 1H), 7.60 (s, 1H), 7.57 (d, 1H), 7.34 (s, 1H), 7.32 (t, 1H), 7.19 (s, 1H), 7.14 (t, 1H), 7.08 (d, 1H), 6.67 (d, 1H), 6.28 (m, 1H), 5.61 (br s, 2H), 4.04 (s, 3H), 3.91 (s, 3H), 3.41 (d, 2H), 3.02 (m, 1H), 2.59 (m, 4H), 1.89 (s, 9H), 1.85 (m, 2H), 1.32 (m, 2H); MS m/e 567 (M+H)$^+$, 565.3 (M−H)$^-$.

EXAMPLE 330

N-[4-(4-amino-7-{(1E)-3-[4-(aminomethyl)-1-piperidinyl]-1-propenyl}thieno[3,2-c]pyridin-3-yl)-2-methoxyphenyl]-1-methyl-1H-indole-2-carboxamide Prepared as the tetraacetate salt from tert-butyl 4-piperidinylmethylcarbamate and deprotected. $^1$H NMR (DMSO-d$_6$, 400 MHz) δ 9.51 (s, 1H), 7.99 (d, 1H), 7.96 (s, 1H), 7.69 (d, 1H), 7.61 (s, 1H), 7.58 (d, 1H), 7.35 (s, 1H), 7.33 (t, 1H), 7.19 (d, 1H), 7.14 (t, 1H), 7.06 (dd, 1H), 6.66 (d, 1H), 6.22 (m, 1H), 5.65 (br s, 2H), 4.03 (s, 3H), 3.91 (s, 3H), 3.16 (d, 2H), 2.94 (m, 2H), 2.64 (d, 2H), 1.94 (m, 2H), 1.87 (s, 12H), 1.72 (m, 2H), 1.50 (m, 1H), 1.20 (m, 2H); MS m/e 581.5 (M+H)$^+$, 579.5 (M−H)$^-$.

EXAMPLE 331

1-{(2E)-3-[4-amino-3-(3-methoxy-4-{[(1-methyl-1H-indol-2-yl)carbonyl]amino}phenyl)thieno[3,2-c]pyridin-7-yl]-2-propenyl}-4-piperidinecarboxylic acid Prepared as the diacetate salt from 4-piperidinecarboxylic acid. $^1$H NMR (DMSO-d$_6$, 400 MHz) δ 9.52 (s, 1H), 8.00 (d, 1H), 7.97 (s, 1H), 7.72 (d, 1H), 7.61 (s, 1H), 7.59 (d, 1H), 7.35 (s, 1H), 7.33 (m, 1H), 7.20 (s, 1H), 7.15 (t, 1H), 7.07 (d, 1H), 6.67 (d, 1H), 6.24 (m, 1H), 5.65 (br s, 2H), 4.04 (s, 3H), 3.91 (s, 3H), 3.16 (d, 2H), 2.86 (m, 2H), 2.15 (m, 1H), 2.02 (m, 2H), 1.88 (s, 6H), 1.80 (m, 2H), 1.57 (m, 2H); MS m/e 596.5 (M+H)$^+$, 594.5 (M−H)$^-$.

EXAMPLE 332

N-[4-(4-amino-7-{(1E)-3-[(4-aminocyclohexyl)amino]-1-propenyl}thieno[3,2-c]pyridin-3-yl)-2-methoxyphenyl]-1-methyl-1H-indole-2-carboxamide Prepared as the triacetate salt from tert-butyl 4-aminocyclohexylcarbamate and deprotected. $^1$H NMR (DMSO-d$_6$, 400 MHz) δ 9.52 (s, 1H), 7.98 (d, 1H), 7.94 (s, 1H), 7.70 (d, 1H), 7.62 (s, 1H), 7.59 (m, 1H), 7.35 (s, 1H), 7.33 (m, 1H), 7.20 (s, 1H), 7.15 (t, 1H), 7.09 (d, 1H), 6.66 (d, 1H), 6.29 (m, 1H), 5.62 (br s, 2H), 4.04 (s, 3H), 3.91 (s, 3H), 3.42 (d, 2H), 2.76 (m, 1H), 2.40 (m, 1H), 1.89 (m, 4H), 1.83 (s, 9H), 1.03–1.28 (m, 4H); MS m/e 681.6 (M+H)$^+$, 679.6 (M−H)$^−$.

EXAMPLE 333

N-[4-(4-amino-7-{(1E)-3-[methyl(1-methyl-4-piperidinyl)amino]-1-propenyl}thieno[3,2-c]pyridin-3-yl)-2-methoxyphenyl]-1-methyl-1H-indole-2-carboxamide Prepared as the tetraacetate salt from N,1-dimethyl-4-piperidinamine. $^1$H NMR (DMSO-d$_6$, 400 MHz) δ 9.52 (s, 1H), 7.99 (d, 1H), 7.95 (s, 1H), 7.70 (d, 1H), 7.61 (s, 1H), 7.59 (d, 1H), 7.35 (s, 1H), 7.33 (t, 1H), 7.20 (s, 1H), 7.15 (t, 1H), 7.08 (d. 1H), 6.67 (d, 1H), 6.22 (m, 1H), 5.63 (br s, 2H), 4.04 (s, 3H), 3.91 (s, 3H), 3.29 (d, 2H), 2.82 (m, 2H), 2.36 (m, 1H), 2.21 (s, 3H), 2.13 (s, 3H), 1.84 (s, 12H), 1.82 (m, 2H), 1.73 (m, 2H), 1.49 (m, 2H); MS m/e 595.5 (M+H)$^+$, 593.6 (M−H)$^−$.

EXAMPLE 334

N-[4-(4-amino-7-{(1E)-3-[4-(6-oxo-1,6-dihydro-2-pyridinyl)-1-piperazinyl]-1-propenyl}thieno[3,2-c]pyridin-3-yl)-2-methoxyphenyl]-1-methyl-1H-indole-2-carboxamide Prepared as the acetate salt from 6-(1-piperazinyl)-2(1H)-pyridinone. $^1$H NMR (DMSO-d$_6$, 400 MHz) δ 9.53 (s, 1H), 7.99 (m, 2H), 7.71 (d, 1H), 7.62 (s, 1H), 7.58 (d, 1H), 7.33 (m, 3H), 7.20 (m, 1H), 7.15 (t, 1H), 7.08 (m, 1H), 6.72 (d, 1H), 6.27 (m, 1H), 6.05 (d, 1H), 5.85 (d, 1H), 5.67 (br s, 2H), 4.04 (s, 3H), 3.91 (s, 3H), 3.39 (m, 4H), 3.23 (d, 2H), 2.53 (m, 4H), 1.89 (s, 3H); MS m/e 646.6.6 (M+H)$^+$, 644.7(M−H)$^−$.

EXAMPLE 335

N-(4-{4-amino-7-[(1E)-3-(4-methyl-1,4-diazepan-1-yl)-1-propenyl]thieno[3,2-c]pyridin-3-yl}-2-methoxyphenyl)-1-methyl-1H-indole-2-carboxamide Prepared as the acetate salt from 1-methyl-1,4-diazepane. $^1$H NMR (DMSO-d$_6$, 400 MHz) δ 9.52 (s, 1H), 8.00 (d, 1H), 7.96 (s, 1H), 7.72 (d, 1H), 7.61 (s, 1H), 7.58 (d, 1H), 7.35 (s, 1H), 7.33 (t, 1H), 7.19 (s, 1H), 7.15 (t, 1H), 7.07 (d, 1H), 6.67 (d, 1H), 6.24 (m, 1H), 5.64 (br s, 2H), 4.04 (s, 3H), 3.91 (s, 3H), 3.29 (d, 2H), 2.68 (m, 4H), 2.56 (m, 4H), 2.25 (s, 3H), 1.86 (s, 3H), 1.73 (m, 2H); MS m/e 581.5 (M+H)$^+$, 579.4 (M−H)$^−$.

EXAMPLE 336

N-[4-(4-amino-7-{(1E)-3-[4-(2-pyrazinyl)-1-piperazinyl]-1-propenyl}thieno[3,2-c]pyridin-3-yl)-2-methoxyphenyl]-1-methyl-1H-indole-2-carboxamide Prepared from 2-(1-piperazinyl)pyrazine. $^1$H NMR (DMSO-d$_6$, 400 MHz) δ 9.52 (s, 1H), 8.33 (d, 1H), 8.08 (m, 1H), 8.01 (d, 1H), 7.99 (s, 1H), 7.84 (d, 1H), 7.72 (d, 1H), 7.62 (s, 1H), 7.59 (d, 1H), 7.33 (m, 2H), 7.20 (m, 1H), 7.15 (t, 1H), 7.08 (dd, 1H), 6.73 (d, 1H), 6.28 (m, 1H), 5.67 (br s, 2H), 4.04 (s, 3H), 3.91 (s, 3H), 3.59 (m, 4H), 3.25 (d, 2H), 2.56 (m, 4H); MS m/e 631.6 (M+H)$^+$.

EXAMPLE 337

N-{4-[4-amino-7-((1E)-3-{[2-(2-hydroxyethoxy)ethyl]amino}-1-propenyl)thieno[3,2-c]pyridin-3-yl]-2-methoxyphenyl}-1-methyl-1H-indole-2-carboxamide Prepared as the diacetate salt from 2-(2-aminoethoxy)ethanol. $^1$H NMR (DMSO-d$_6$, 400 MHz) δ 9.51 (s, 1H), 8.00 (d, 1H), 7.95 (s, 1H), 7.70 (d, 1H), 7.58–7.62 (m, 2H), 7.07–7.35 (m, 5H), 6.70 (d, 1H), 6.30 (dt, 1H), 5.62 (br s, 2H), 4.04 (s, 3H), 3.91 (s, 3H), 3.40–3.53 (m, 8H), 2.73 (t, 2H), 1.87 (s, 6H); reverse phase HPLC (5% to 95% acetonitrile over 10 minutes, 1 mL/min, 254 nm, hypersil HS 100 Å, C18, 5 μm, 250×4.6 column) R$_t$=10.2 min; MS m/e 570.5 (M+H)$^+$.

EXAMPLE 338

N-(4-{4-amino-7-[(1E)-3-({2-[bis(2-hydroxyethyl)amino]ethyl}amino)-1-propenyl]thieno[3,2-c]pyridin-3-yl}-2-methoxyphenyl)-1-methyl-1H-indole-2-carboxamide Prepared as the diacetate salt from 2-[(2-aminoethyl)(2-hydroxyethyl)amino]ethanol. $^1$H NMR (DMSO-d$_6$, 400 MHz) δ 9.51 (s, 1H), 8.00 (d, 1H), 7.95 (s, 1H), 7.70 (d, 1H), 7.58–7.62 (m, 2H), 7.07–7.35 (m, 5H), 6.70 (d, 1H), 6.30 (dt, 1H), 5.62 (br s, 2H), 4.04 (s, 3H), 3.91 (s, 3H), 3.39–3.44 (m, 6H), 2.53–2.61 (m, 8H), 1.87 (s, 6H); reverse phase HPLC (5% to 95% acetonitrile over 10 minutes, 1 mL/min, 254 nm, hypersil HS 100 Å, C18, 5 μm, 250×4.6 column) R$_t$=10.0 min; MS m/e 613.5 (M+H)$^+$.

EXAMPLE 339

N-{4-[4-amino-7-((1E)-3-{[2-(4-piperidinyl)ethyl]amino}-1-propenyl)thieno[3,2-c]pyridin-3-yl]-2-methoxyphenyl}-1-methyl-1H-indole-2-carboxamide Prepared as the trihydrochloride salt from tert-butyl-4-(2-aminoethyl)-1-piperidinecarboxylate and deprotected. $^1$H NMR (DMSO-d$_6$, 400 MHz) δ 9.49 (s, 1H), 8.15 (m, 2H), 8.01 (s, 1H), 7.71 (d, 1H), 7.60 (d, 1H), 6.98–7.35 (m, 6H), 6.55 (m, 1H), 4.04 (s, 3H), 3.93 (s, 3H), 3.84 (m, 2H), 2.27 (d, 2H), 2.89 (m, 4H), 2.07 (m, 1H), 1.28–1.46 (m, 4H); reverse phase HPLC (5% to 95% acetonitrile over 10 minutes, 1 mL/min, 254 nm, hypersil HS 100 Å, C18, 5 μm, 250×4.6 column) R$_t$=12.6 min; MS m/e 679.6 (M−H)$^−$.

EXAMPLE 340

N-{4-[4-amino-7-((1E)-3-{[2-(4-pyridinyl)ethyl]amino}-1-propenyl)thieno[3,2-c]pyridin-3-yl]-2-methoxyphenyl}-1-methyl-1H-indole-2-carboxamide Prepared as the acetate salt from 2-(4-pyridinyl)ethanamine. $^1$H NMR (DMSO-$d_6$, 400 MHz) δ 9.51 (s, 1H), 8.46 (s, 2H), 8.00 (d, 1H), 7.94 (s, 1H), 7.71 (d, 1H), 7.58–7.62 (m, 3H), 7.08–7.35 (m, 6H), 6.65 (d, 1H), 6.27 (dt, 1H), 5.62 (br s, 2H), 4.04 (s, 3H), 3.91 (s, 3H), 2.81 (dt, 4H), 1.87 (s, 3H); reverse phase HPLC (5% to 95% acetonitrile over 10 minutes, 1 mL/min, 254 nm, hypersil HS 100 Å, C18, 5 μm, 250×4.6 column) $R_t$=10.4 min; MS m/e 587.5 (M−H)$^-$.

EXAMPLE 341

N-[4-(4-amino-7-{(1E)-3-[4-(2-cyanoethyl)-1-piperazinyl]-1-propenyl}thieno[3,2-c]pyridin-3-yl)-2-methoxyphenyl]-1-methyl-1H-indole-2-carboxamide Prepared as the acetate salt from 3-(1-piperazinyl)propanenitrile. $^1$H NMR (DMSO-$d_6$, 400 MHz) δ 9.51 (s, 1H), 8.00 (d, 1H), 7.97 (s, 1H), 7.70 (d, 1H), 7.58–7.62 (m, 2H), 7.07–7.35 (m, 5H), 6.70 (d, 1H), 6.25 (dt, 1H), 5.65 (br s, 2H), 4.04 (s, 3H), 3.91 (s, 3H), 3.34 (t, 2H), 3.19 (br s, 2H), 2.68 (t, 2H), 2.57 (t, 2H), 1.91 (s, 3H); reverse phase HPLC (25% to 100% acetonitrile over 10 minutes, 1 mL/min, 254 nm, hypersil HS 100 Å, C18, 5 μm, 250×4.6 column) $R_t$=9.9 min; MS m/e 604.5 (M−H)$^-$.

EXAMPLE 342

N-(4-{4-amino-7-[(1E)-3-(4-amino-1-piperidinyl)-1-propenyl]thieno[3,2-c]pyridin-3-yl}-2-methoxyphenyl)-1-methyl-1H-indole-2-carboxamide Prepared as the diacetate salt from tert-butyl 4-piperidinylcarbamate and deprotected. $^1$H NMR (DMSO-$d_6$, 400 MHz) δ 9.51 (s, 1H), 8.00 (d, 1H), 7.98 (s, 1H), 7.70 (d, 1H), 7.58–7.62 (m, 2H), 7.07–7.35 (m, 5H), 6.70 (d, 1H), 6.25 (dt, 1H), 5.65 (br s, 2H), 4.04 (s, 3H), 3.92 (s, 3H), 3.20 (d, 2H), 2.82–2.95 (m, 3H), 2.03 (t, 2H), 1.91 (s, 3H), 1.85 (d, 2H), 1.50 (q, 2H); reverse phase HPLC (5% to 95% acetonitrile over 10 minutes, 1 mL/min, 254 nm, hypersil HS 100 Å, C18, 5 μm, 250×4.6 column) $R_t$=11.3 min; MS m/e 565.5 (M−H)$^-$.

EXAMPLE 343

N-[4-(4-amino-7-{(1E)-3-[4-(3-amino-3-oxopropyl)-1-piperazinyl]-1-propenyl}thieno[3,2-c]pyridin-3-yl)-2-methoxyphenyl]-1-methyl-1H-indole-2-carboxamide Prepared as the diacetate salt from 3-(1-piperazinyl)propanamide. $^1$H NMR (DMSO-$d_6$, 400 MHz) δ 9.52 (s, 1H), 8.00 (d, 1H), 7.97 (s, 1H), 7.71 (d, 1H), 7.58–7.62 (m, 2H), 7.07–7.38 (m, 6H), 6.80 (d, 1H), 6.23 (dt, 1H), 5.65 (br s, 2H), 4.04 (s, 3H), 3.91 (s, 3H), 3.17 (d, 2H), 2.49 (br s, 2H), 2.21 (t, 2H), 1.88 (s, 6H); reverse phase HPLC (5% to 95% acetonitrile over 10 minutes, 1 mL/min, 254 nm, hypersil HS 100 Å, C18, 5 μm, 250×4.6 column) $R_t$=9.7 min; MS m/e 622.7 (M−H)$^-$.

EXAMPLE 344

N-(4-{4-amino-7-[(1E)-3-(3-oxo-1-piperazinyl)-1-propenyl]thieno[3,2-c]pyridin-3-yl}-2-methoxyphenyl)-1-methyl-1H-indole-2-carboxamide Prepared as the acetate salt from 2-piperazinone. $^1$H NMR (DMSO-$d_6$, 400 MHz) δ 9.52 (s, 1H), 7.99–8.01 (m, 2H), 7.97 (s, 1H), 7.71 (d, 1H), 7.58–7.63 (m, 2H), 7.07–7.38 (m, 5H), 6.71 (d, 1H), 6.23 (dt, 1H), 5.65 (br s, 2H), 4.04 (s, 3H), 3.91 (s, 3H), 3.13–3.26 (m, 4H), 2.63 (m, 2H), 1.87 (s, 3H); reverse phase HPLC (5% to 95% acetonitrile over 25 minutes, 1 mL/min, 254 nm, hypersil HS 100 Å, C18, 5 μm, 250×4.6 column) $R_t$=18.9 min; MS m/e 567.5 (M+H)$^+$.

EXAMPLE 345

N-[4-(4-amino-7-{(1E)-3-[(2-furylmethyl)(methyl)amino]-1-propenyl}thieno[3,2-c]pyridin-3-yl)-2-methoxyphenyl]-1-methyl-1H-indole-2-carboxamide Prepared as the acetate salt from N-(2-furylmethyl)-N-methylamine. $^1$H NMR (DMSO-$d_6$, 400 MHz) δ 9.52 (s, 1H), 7.99–8.01 (m, 2H), 7.72 (d, 1H), 7.58–7.63 (m, 2H), 7.07–7.38 (m, 5H), 6.71 (d, 1H), 6.23–6.45 (m, 3H), 5.65 (br s, 2H), 4.04 (s, 3H), 3.91 (s, 3H), 3.6 (s, 2H), 3.22 (d, 2H), 2.21 (s, 3H), 1.91 (s, 3H); reverse phase HPLC (5% to 95% acetonitrile over 10 minutes, 1 mL/min, 254 nm, hypersil HS 100 Å, C18, 5 μm, 250×4.6 column) $R_t$=13.5 min; MS m/e 578.3 (M+H)$^+$.

EXAMPLE 346

N-[4-(4-amino-7-{(1E)-3-[4-(2-furoyl)-1-piperazinyl]-1-propenyl}thieno[3,2-c]pyridin-3-yl)-2-methoxyphenyl]-1-methyl-1H-indole-2-carboxamide Prepared from 1-(2-furoyl)piperazine. $^1$H NMR (DMSO-$d_6$, 400 MHz) δ 9.52 (s, 1H), 7.99–8.01 (m, 2H), 7.84 (s, 1H), 7.70 (d, 1H), 7.58–7.63 (m, 2H), 6.99–7.38 (m, 6H), 6.62–6.73 (m, 2H), 6.23 (dt, 1H), 5.65 (br s, 2H), 4.04 (s, 3H), 3.91 (s, 3H), 3.70 (br s, 4H), 3.24 (d, 2H); reverse phase HPLC (5% to 95% acetonitrile over 10 minutes, 1 mL/min, 254 nm, hypersil HS 100 Å, C18, 5 μm, 250×4.6 column) $R_t$=12.7 min; MS m/e 645.4 (M−H)$^-$.

EXAMPLE 347

N-{4-[4-amino-7-((1E)-3-{4-[2-(4-morpholinyl)ethyl]-1-piperazinyl}-1-propenyl)thieno[3,2-c]pyridin-3-yl]-2-methoxyphenyl}-1-methyl-1H-indole-2-carboxamide Prepared as the acetate salt from 4-[2-(1-piperazinyl)ethyl]morpholine. $^1$H NMR (DMSO-$d_6$, 400 MHz) δ 9.52 (s, 1H), 8.00 (d, 1H), 7.99 (s, 1H), 7.71 (d, 1H), 7.58–7.62 (m, 2H), 7.07–7.36 (m, 5H), 6.67 (d, 1H), 6.22 (dt, 1H), 5.65 (br s, 2H), 4.04 (s, 3H), 3.91 (s, 3H), 3.54 (t, 4H), 3.16 (d, 2H), 2.37–2.50 (m, 16H), 1.86 (s, 6H); reverse phase HPLC (5% to 95% acetonitrile over 10 minutes, 1 mL/min, 254 nm, hypersil HS 100 Å, C18, 5 μm, 250×4.6 column) $R_t$=17.1 min; MS m/e 664.7 (M−H)$^-$.

EXAMPLE 348

N-{4-[4-amino-7-((1E)-3-{4-[3-(diethylamino)propyl]-1-piperazinyl}-1-propenyl)thieno[3,2-c]pyridin-3-yl]-2-methoxyphenyl}-1-methyl-1H-indole-2-carboxamide Prepared as the triacetate salt from N,N-diethyl-N-[3-(1-piperazinyl)propyl]amine. $^1$H NMR (DMSO-$d_6$, 400 MHz) δ 9.52 (s, 1H), 8.01 (d, 1H), 7.96 (s, 1H), 7.71 (d, 1H), 7.58–7.62 (m, 2H), 7.07–7.36 (m, 5H), 6.67 (d, 1H), 6.23 (dt, 1H), 5.64 (br s, 2H), 4.04 (s, 3H), 3.91 (s, 3H), 3.16 (d, 2H), 2.35–2.45 (m, 10H), 2.27 (t, 2H), 1.86 (s, 9H), 1.74 (m, 2H), 0.94 (t, 6H); reverse phase HPLC (5% to 95% acetonitrile over 10 minutes, 1 mL/min, 254 nm, hypersil HS 100 Å, C18, 5 μm, 250×4.6 column) $R_t$=9.9 min; MS m/e 664.6 (M–H)$^-$.

EXAMPLE 349

N-[4-(4-amino-7-{(1E)-3-[4-(1-methyl-4-piperidinyl)-1-piperazinyl]-1-propenyl}thieno[3,2-c]pyridin-3-yl)-2-methoxyphenyl]-1-methyl-1H-indole-2-carboxamide Prepared as the tetraacetate from 1-(1-methyl-4-piperidinyl)piperazine. $^1$H NMR (DMSO-$d_6$, 400 MHz) δ 9.52 (s, 1H), 8.01 (d, 1H), 7.96 (s, 1H), 7.71 (d, 1H), 7.58–7.62 (m, 2H), 7.07–7.36 (m, 5H), 6.67 (d, 1H), 6.22 (dt, 1H), 5.64 (br s, 2H), 4.04 (s, 3H), 3.91 (s, 3H), 3.16 (d, 2H), 2.79 (d, 2H), 2.12 (s, 3H), 2.08 (m, 1H), 1.85 (s, 12H), 1.68–1.72 (m, 2H), 1.37–1.40 (m, 2H); reverse phase HPLC (5% to 95% acetonitrile over 10 minutes, 1 mL/min, 254 nm, hypersil HS 100 Å, C18, 5 μm, 250×4.6 column) $R_t$=9.4 min; MS m/e 648.7 (M–H)$^-$.

EXAMPLE 350

N-{4-[4-amino-7-((1E)-3-{4-[2-(1-piperidinyl)ethyl]-1-piperazinyl}-1-propenyl)thieno[3,2-c]pyridin-3-yl]-2-methoxyphenyl}-1-methyl-1H-indole-2-carboxamide Prepared as the triacetate from 1-[2-(1-piperidinyl)ethyl]piperazine. $^1$H NMR (DMSO-$d_6$, 400 MHz) δ 9.52 (s, 1H), 8.01 (d, 1H), 7.97 (s, 1H), 7.71 (d, 1H), 7.58–7.62 (m, 2H), 7.07–7.35 (m, 5H), 6.68 (d, 1H), 6.22 (dt, 1H), 5.64 (br s, 2H), 4.04 (s, 3H), 3.91 (s, 3H), 3.16 (d, 2H), 2.32–2.41 (m, 14H), 1.85 (s, 9H), 1.48 (m, 4H), 1.35 (m, 2H); reverse phase HPLC (5% to 95% acetonitrile over 10 minutes, 1 mL/min, 254 nm, hypersil HS 100 Å, C18, 5 μm, 250×4.6 column) $R_t$=9.9 min; MS m/e 664.7 (M–H)$^-$.

EXAMPLE 351

N-{4-[4-amino-7-((1E)-3-{4-[2-(2-thienyl)ethyl]-1-piperazinyl}-1-propenyl)thieno[3,2-c]pyridin-3-yl]-2-methoxyphenyl}-1-methyl-1H-indole-2-carboxamide Prepared from 1-[2-(2-thienyl)ethyl]piperazine. $^1$H NMR (DMSO-$d_6$, 400 MHz) δ 9.52 (s, 1H), 8.00 (d, 1H), 7.98 (s, 1H), 7.58–7.72 (m, 4H), 7.29–7.35 (m, 3H), 7.07–7.20 (m, 3H), 6.40–6.90 (m, 2H), 6.70 (d, 1H), 6.24 (dt, 1H), 5.64 (br s, 2H), 4.04 (s, 3H), 3.91 (s, 3H), 3.20 (d, 2H), 2.96 (t, 2H), 2.50–2.57 (m, 10H), 2.65–2.76 (m, 3H), 2.28–2.50 (m, 2H), 2.10 (s, 6H), 1.85 (s, 12H), 1.59–1.65 (m, 1H); reverse phase HPLC (5% to 95% acetonitrile over 10 minutes, 1 mL/min, 254 nm, hypersil HS 100 Å, C18, 5 μm, 250×4.6 column) $R_t$=13.0 min; MS m/e 661.6 (M–H)$^-$.

EXAMPLE 352

N-{4-[4-amino-7-((1E)-3-{4-[(2R)-tetrahydro-2-furanylmethyl]-1-piperazinyl}-1-propenyl)thieno[3,2-c]pyridin-3-yl]-2-methoxyphenyl}-1-methyl-1H-indole-2-carboxamide Prepared as the diacetate salt from 1-[(2R)-tetrahydro-2-furanylmethyl]piperazine. $^1$H NMR (DMSO-$d_6$, 400 MHz) δ 9.52 (s, 1H), 8.00 (d, 1H), 7.97 (s, 1H), 7.71 (d, 1H), 7.58–7.62 (m, 2H), 7.07–7.36 (m, 5H), 6.68 (d, 1H), 6.23 (dt, 1H), 5.64 (br s, 2H), 4.04 (s, 3H), 3.91 (m, 4H), 3.56–3.73 (dq, 2H), 3.16 (d, 2H), 2.35–2.50 (m, 7H), 1.89 (m, 8H), 1.72–1.80 (m, 2H), 1.41–1.49 (m, 1H); reverse phase HPLC (5% to 95% acetonitrile over 10 minutes, 1 mL/min, 254 nm, hypersil HS 100 Å, C18, 5 μm, 250×4.6 column) $R_t$=20.0 min; MS m/e 635.5 (M–H)$^-$.

EXAMPLE 353

N-{4-[4-amino-7-((1E)-3-{[3-(4-methyl-1-piperazinyl)propyl]amino}-1-propenyl)thieno[3,2-c]pyridin-3-yl]-2-methoxyphenyl}-1-methyl-1H-indole-2-carboxamide Prepared as the tetraacetate salt from 3-(4-methyl-1-piperazinyl)-1-propanamine. $^1$H NMR (DMSO-$d_6$, 400 MHz) δ 9.52 (s, 1H), 8.00 (d, 1H), 7.96 (s, 1H), 7.71 (d, 1H), 7.58–7.62 (m, 2H), 7.07–7.36 (m, 5H), 6.70 (d, 1H), 6.28 (dt, 1H), 5.64 (br s, 2H), 4.04 (s, 3H), 3.91 (s, 3H), 3.42 (d, 2H), 2.62 (t, 2H), 2.32–2.34 (m, 8H), 2.30 (s, 3H), 1.83 (s, 12H), 1.60 (m, 2H); reverse phase HPLC (5% to 95% acetonitrile over 10 minutes, 1 mL/min, 254 nm, hypersil HS 100 Å, C18, 5 μm, 250×4.6 column) $R_t$=9.0 min; MS m/e 666.2 (M+H+CH$_3$CN)$^+$.

EXAMPLE 354

N-{4-[4-amino-7-((1E)-3-{4-[3-(4-morpholinyl)propyl]-1-piperazinyl}-1-propenyl)thieno[3,2-c]pyridin-3-yl]-2-methoxyphenyl}-1-methyl-1H-indole-2-carboxamide Prepared from 4-[3-(1-piperazinyl)propyl]morpholine as the tetraacetate salt. $^1$H NMR (DMSO-$d_6$, 400 MHz) δ 9.52 (s, 1H), 8.01 (d, 1H), 7.96 (s, 1H), 7.71 (d, 1H), 7.58–7.62 (m, 2H), 7.07–7.36 (m, 5H), 6.66 (d, 1H), 6.25 (dt, 1H), 5.64 (br s, 2H), 4.04 (s, 3H), 3.91 (s, 3H), 3.55 (t, 4H), 3.15 (d, 2H), 2.24–2.32 (m, 14H), 1.88 (t, 12H), 1.56 (p, 2H); reverse phase HPLC (5% to 95% acetonitrile over 25 minutes, 1 mL/min, 254 nm, hypersil HS 100 Å, C18, 5 μm, 250×4.6 column) $R_t$=17.1 min; MS m/e 678.7 (M–H)$^-$.

EXAMPLE 355

N-{4-[4-amino-7-((1E)-3-{4-[3-(1-pyrrolidinyl)propyl]-1-piperazinyl}-1-propenyl)thieno[3,2-c]pyridin-3-yl]-2-methoxyphenyl}-1-methyl-1H-indole-2-carboxamide Prepared as the diacetate salt from 1-[3-(1-pyrrolidinyl)propyl]piperazine. $^1$H NMR (DMSO-$d_6$, 400 MHz) δ 9.52 (s, 1H), 8.01 (d, 1H), 7.96 (s, 1H), 7.71 (d, 1H), 7.58–7.62

(m, 2H), 7.07–7.36 (m, 5H), 6.66 (d, 1H), 6.23 (dt, 1H), 5.64 (br s, 2H), 4.04 (s, 3H), 3.91 (s, 3H), 3.15 (d, 2H), 2.26–2.39 (m, 16H), 1.88 (s, 6H), 1.59–1.66 (m, 6H); reverse phase HPLC (5% to 95% acetonitrile over 10 minutes, 1 mL/min, 254 nm, hypersil HS 100 Å, C18, 5 μm, 250×4.6 column) $R_t$=9.4 min; MS m/e 662.5 (M–H)$^-$.

EXAMPLE 356

N-[2-({(2E)-3-[4-amino-3-(3-methoxy-4-{[(1-methyl-1H-indol-2-yl)carbonyl]amino}phenyl)thieno[3,2-c]pyridin-7-yl]-2-propenyl}amino)ethyl]glycine Prepared as the acetate salt from N-(2-aminoethyl)glycine. $^1$H NMR (DMSO-d$_6$, 400 MHz) δ 9.52 (s, 1H), 8.01 (d, 1H), 8.00 (s, 1H), 7.79 (s, 1H), 7.71 (d, 1H), 7.58–7.62 (m, 2H), 7.07–7.36 (m, 5H), 6.73 (d, 1H), 6.25 (dt, 1H), 5.67 (br s, 2H), 4.04 (s, 3H), 3.91 (s, 3H), 3.20–3.28 (m, 6H), 3.00 (s, 2H), 2.64 (t, 2H), 1.88 (s, 3H); reverse phase HPLC (5% to 95% acetonitrile over 10 minutes, 1 mL/min, 254 nm, hypersil HS 100 Å, C18, 5 μm, 250×4.6 column) $R_t$=11.0 min; MS m/e 565.7 (M–H$_2$O)$^+$.

EXAMPLE 357

N-[4-(4-amino-7-{(1E)-3-[(3S)-3-(dimethylamino)-1-pyrrolidinyl]-1-propenyl}thieno[3,2-c]pyridin-3-yl)-2-methoxyphenyl]-1-methyl-1H-indole-2-carboxamide Prepared as the tetraacetate salt from (3S)-N,N-dimethyl-3-pyrrolidinamine. $^1$H NMR (DMSO-d$_6$, 400 MHz) δ 9.51 (s, 1H), 8.00 (d, 1H), 7.96 (s, 1H), 7.70 (d, 1H), 7.58–7.61 (m, 2H), 7.07–7.36 (m, 5H), 6.68 (d, 1H), 6.23 (dt, 1H), 5.64 (br s, 2H), 4.04 (s, 3H), 3.91 (s, 3H), 3.18–3.34 (m, 4H), 2.65–2.76 (m, 3H), 2.28–2.50 (m, 2H), 2.10 (s, 6H), 1.85 (s, 12H), 1.59–1.65 (m, 1H); reverse phase HPLC (5% to 95% acetonitrile over 25 minutes, 1 mL/min, 254 nm, hypersil HS 100 Å, C18, 5 μm, 250×4.6 column) $R_t$=20.0 min; MS m/e 579.5 (M–H)$^-$.

EXAMPLE 358

N-{4-[4-amino-7-((1E)-3-{[4-(dimethylamino)phenyl]amino}-1-propenyl)thieno[3,2-c]pyridin-3-yl]-2-methoxyphenyl}-1-methyl-1H-indole-2-carboxamide Prepared from N,N-dimethyl-1,4-benzenediamine. $^1$H NMR (DMSO-d$_6$, 400 MHz) δ 9.50 (s, 1H), 7.99 (d, 1H), 7.94 (s, 1H), 7.70 (d, 1H), 7.60 (s, 1H), 7.58 (d, 1H), 7.35 (s, 1H), 7.33 (m, 1H), 7.19 (m, 1H), 7.15 (t, 1H), 7.07 (dd, 1H), 6.74 (d, 1H), 6.62 (m, 4H), 6.33 (m, 1H), 5.62 (br s, 2H), 5.3 (br s, 1H), 4.03 (s, 3H), 3.90 (s, 3H), 3.86 (d, 2H), 2.71 (s, 6H); MS m/e 603.7 (M+H)$^+$ 601.8 (M–H)$^-$.

EXAMPLE 359

N-[4-(4-amino-7-{(1E)-3-[(4-hydroxycyclohexyl)amino]-1-propenyl}thieno[3,2-c]pyridin-3-yl)-2-methoxyphenyl]-1-methyl-1H-indole-2-carboxamide Prepared as the diacetate salt from 4-aminocyclohexanol. $^1$H NMR (DMSO-d$_6$, 400 MHz) δ 9.51 (s, 1H), 8.00 (d, 1H), 7.94 (s, 1H), 7.69 (d, 1H), 7.62 (s, 1H), 7.58 (d, 1H), 7.35 (s, 1H), 7.33 (m, 1H), 7.21 (s, 1H), 7.15 (t, 1H), 7.08 (d, 1H), 6.65 (d, 1H), 6.27 (m, 1H), 5.61 (br s, 2H), 4.04 (s, 3H), 3.91 (s, 3H), 3.41 (d, 2H), 3.36 (m, 1H), 2.4 (m, 1H), 1.7–1.9 (m, 4H), 1.89 (s, 3H), 1.11 (m, 4H); MS m/e 582.7 (M+H)$^+$ 580.8 (M–H)$^-$.

EXAMPLE 360

7-[(1E)-3-(diethylamino)-1-propenyl]-3-(4-phenoxyphenyl)thieno[3,2-c]pyridin-4-amine

EXAMPLE 360A

7-[(1E)-3,3-diethoxy-1-propenyl]-3-(4-phenoxyphenyl)thieno[3,2-c]pyridin-4-amine A mixture of Example 176A (250 mg, 0.70 mmol), 4-phenoxyphenylboronic acid (180 mg, 0.84 mmol), Pd(PPh$_3$)$_4$ (50 mg, 0.04 mmol), and sodium carbonate (150 mg, 1.4 mmol) in 1,2-dimethoxyethane (8 mL) and water (4 mL) was heated to reflux for 15 hours. The mixture was cooled to room temperature and concentrated under reduced pressure. The mixture was extracted with dichloromethane and the extract was dried (MgSO$_4$), filtered, and concentrated. The residue was purified by flash column chromatography on silica gel to provide the desired product (170 mg, 55%). $^1$H NMR (DMSO-d$_6$, 400 MHz) δ 8.00 (s, 1H), 7.56 (s, 1H), 7.47 (m, 4H), 7.20 (t, 1H), 7.13 (m, 4H), 6.81 (d, 1H), 6.17 (dd, 1H), 5.67 (br s, 2H), 5.13 (d, 1H), 3.57 (m, 4H), 1.18 (t, 6H); MS m/e 447.3 (M+H)$^+$.

EXAMPLE 360B (2E)-3-[4-amino-3-(4-phenoxyphenyl)thieno[3,2-c]pyridin-7-yl]acrylaldehyde A mixture of Example 360A (170 mg, 0.38 mmol), p-toluenesulfonic acid (10 mg), acetone (9 mL), and water (1 mL) was stirred for 1.25 hours and concentrated. The residue partioned between saturated aqueous sodium bicarbonate and dichloromethane. The organic layer was dried (MgSO$_4$), filtered, and concentrated to provide the desired product (150 mg). $^1$H NMR (DMSO-d$_6$, 400 MHz) δ 9.66 (d, 1H), 8.32 (s, 1H), 7.89 (d, 1H), 7.68 (s, 1H), 7.47 (m, 4H), 7.20 (t, 1H), 7.14 (m, 4H), 6.65 (dd, 1H); MS m/e 373.3 (M+H)$^+$, 371.1 (M–H)$^-$.

EXAMPLE 360C

7-[(1E)-3-(diethylamino)-1-propenyl]-3-(4-phenoxyphenyl)thieno[3,2-c]pyridin-4-amine A mixture of Example 360B (30 mg, 0.080 mmol), sodium triacetoxyborohydride (35 mg, 0.16 mmol), 1 drop of acetic acid, and diethylamine (12 mg, 0166 mmol) in 1,2-dichloroethane (2 mL) was stirred for 2 hours at ambient temperature. The mixture was concentrated and the residue was purified by reverse phase chromatography followed by lyophilization to provide the desired product as the acetate salt. $^1$H NMR (DMSO-d$_6$, 400 MHz) δ 7.94 (s, 1H), 7.55 (s, 1H), 7.44 (m, 4H), 7.20 (t, 1H), 7.11 (m, 4H), 6.67 (d, 1H), 6.22 (m, 1H), 5.55 (br s, 2H), 3.28 (d, 2H), 2.52 (q, 4H), 1.87 (s, 3H), 1.00 (t, 6H); MS m/e 430.4 (M+H)$^+$.

EXAMPLE 361

7-[(1E)-3-({2-[(2R)-1-methyl-2-pyrrolidinyl]
ethyl}amino)-1-propenyl]-3-(4-phenoxyphenyl)
thieno[3,2-c]pyridin-4-amine The desired product was prepared as the acetate salt by substituting 2-[(2R)-1-methyl-2-pyrrolidinyl]ethanamine for diethylamine in Example 360. $^1$H NMR (DMSO-$d_6$, 400 MHz) δ 7.96 (s, 1H), 7.58 (s, 1H), 7.45 (m, 4H), 7.21 (t, 1H), 7.13 (m, 4H), 6.76 (d, 1H), 6.25 (m, 1H), 5.61 (br s, 2H), 3.54 (d, 2H), 2.95 (m, 1H), 2.71 (m, 2H), 2.24 (s, 3H), 2.16 (m, 2H), 1.89 (s, 3H), 1.85 (m, 2H), 1.35–1.67 (m, 4H); MS m/e 483.4 (M+H)$^+$.

EXAMPLE 362

2-(1-{(2E)-3-[4-amino-3-(4-phenoxyphenyl)thieno
[3,2-c]pyridin-7-yl]-2-propenyl}-4-piperidinyl)
ethanol The desired product was prepared as the acetate salt by substituting 2-(4-piperidinyl)ethanol for diethylamine in Example 360. $^1$H NMR (DMSO-$d_6$, 400 MHz) δ 7.94 (s, 1H), 7.55 (s, 1H), 7.46 (m, 4H), 7.20 (t, 1H), 7.12 (m, 4H), 6.64 (d, 1H), 6.21 (m, 1H), 5.56 (br s, 2H), 4.35 (br s, 1H), 3.42 (t, 2H), 3.14 (d, 2H), 2.89 (m, 2H), 1.92 (m, 2H), 1.87 (s, 3H), 1.62 (m, 2H), 1.34 (m, 3H), 1.14 (m, 2H); MS m/e 485.4 (M+H)$^+$.

EXAMPLE 363

2-[{(2E)-3-[4-amino-3-(4-phenoxyphenyl)thieno[3,
2-c]pyridin-7-yl]-2-propenyl}(ethyl)amino]ethanol The desired product was prepared as the diacetate salt by substituting 2-(ethylamino)ethanol for diethylamine in Example 360. $^1$H NMR (DMSO-$d_6$, 400 MHz) δ 7.94 (s, 1H), 7.55 (s, 1H), 7.46 (m, 4H), 7.20 (t, 1H), 7.13 (m, 4H), 6.67 (d, 1H), 6.23 (m, 1H), 5.78 (br s, 2H), 3.50 (t, 2H), 3.33 (d, 2H), 2.56 (m, 4H), 1.85 (s, 6H), 1.01 (t, 3H); MS m/e 446.3 (M+H)$^+$.

EXAMPLE 364

N-(4-{4-amino-7-[(1E)-3-hydroxy-1-propenyl]
thieno[3,2-c]pyridin-3-yl}-2-methoxyphenyl)-1-
methyl-1H-indole-2-carboxamide A mixture of Example 176C (30 mg, 0.062 mmol) and sodium borohydride (10 mg, 0.186 mmol) in methanol was stirred at ambient temperature for one hour then concentrated under reduced pressure. The residue was purified by preparative reverse phase HPLC then lyophilized to provide the desired product as the acetate salt. $^1$H NMR (DMSO-$d_6$, 400 MHz) δ 9.51 (s, 1H), 7.99 (d, 1H), 7.97 (s, 1H), 7.69 (d, 1H), 7.62 (s, 1H), 7.58 (m, 1H), 7.35 (s, 1H), 7.33 (t, 1H), 7.21 (t, 1H), 7.15 (t, 1H), 7.08 (d, 1H), 6.70 (d, 1H), 6.36 (m, 1H), 5.62 (br s, 2H), 4.20 (d, 2H), 4.04 (s, 3H), 3.91 (s, 3H), 1.87 (s, 3H); MS m/e 485.4 (M+H)$^+$.

EXAMPLE 365 tert-butyl 4-{4-amino-7-[(1E)-3-(diethylamino)-1-
propenyl]thieno[3,2-c]pyridin-3-yl}-2-methoxyphe-
nylcarbamate

EXAMPLE 365A tert-butyl 4-{4-amino-7-[(1E)-3-oxo-1-propenyl]
thieno[3,2-c]pyridin-3-yl}-2-methoxyphenyl
carbamate A mixture of Example 294B (1.0 g, 2.0 mmol), 2-(3,3-diethoxy-1-propenyl)-4,4,5,5-tetramethyl-1,3,2-dioxaborolane (620 mg, 2.4 mmol), Pd(PPh$_3$)$_4$ (140 mg, 0.12 mmol) and sodium carbonate (640 mg, 6.04 mmol) in 1,2-dimethoxyethane (20 mL) and water (10 mL) was heated to reflux for 15 hours. The mixture was cooled to room temperature and concentrated under reduced pressure. The mixture was extracted with dichloromethane and the extract was dried (MgSO$_4$), filtered, and concentrated. The residue was purified by flash column chromatography on silica gel to provide tert-butyl 4-{4-amino-7-[(1E)-3,3-diethoxy-1-propenyl]thieno[3,2-c]pyridin-3-yl}-2-methoxyphenylcarbamate (790 mg) which was then stirred for 12 hours in a mixture of acetone (18 mL) and water (2 mL) containing p-toluene sulfonic acid (35 mg). The solvents were removed under reduced pressure and the residue was partitioned between saturated aqueous sodium bicarbonate and dichloromethane. The organic phase was dried (MgSO$_4$), filtered, and concentrated to provide the desired product (610 mg).

EXAMPLE 365B tert-butyl 4-{4-amino-7-[(1E)-3-(diethylamino)-1-
propenyl]thieno[3,2-c]pyridin-3-yl}-2-methoxyphe-
nylcarbamate The desired product was prepared by substituting Example 365A for Example 360B in Example 360C. $^1$H NMR (DMSO-$d_6$, 400 MHz) δ 8.11 (s, 1H), 7.92 (s, 1H), 7.82 (m, 1H), 7.53 (s, 1H), 7.06 (s, 1H), 6.96 (dd, 1H), 6.65 (d,1H), 6.22 (m, 1H), 5.57 (br s, 2H), 3.84 (s, 3H), 3.28 (d, 2H), 2.54 (q, 4H), 1.48 (s, 9H), 1.00 (t, 6H); MS m/e 483.5 (M+H)$^+$.

EXAMPLE 366

3-(4-amino-3-methoxyphenyl)-7-[(1E)-3-(diethy-
lamino)-1-propenyl]thieno[3,2-c]pyridin-4-amine A mixture of Example 365B (425 mg, 0.88 mmol) in acetone (10 mL) and 6N aqueous hydrochloric acid (2 mL) was stirred for 18 hours at ambient temperature then concentrated under reduced pressure. The residue was then purified by preparative reverse phase HPLC to provide the desired product as the diacetate salt. $^1$H NMR (DMSO-$d_6$, 400 MHz) δ 7.89 (s, 1H), 7.39 (s, 1H), 6.82 (s, 1H), 6.73 (s, 2H), 6.20 (m, 1H), 5.65 (br s, 2H), 3.78 (s, 3H), 3.30 (d, 2H), 2.56 (q, 4H), 1.88 (s, 6H), 1.01 (t, 6H); MS m/e 383.4 (M+H)$^+$.

General Procedure for Acylation Reactions

A mixture of Example 366 (50 mg, 0.13 mmol) and pyridine (0.2 mL) in dichloromethane was treated with the appropriate acid chloride (1.2 eq), stirred for 2 hours at ambient temperature, and concentrated. The products were purified by reverse phase chromatography.

The following examples were prepared by this general procedure using the indicated acid chloride.

EXAMPLE 367

N-(4-{4-amino-7-[(1E)-3-(diethylamino)-1-propenyl]thieno[3,2-c]pyridin-3-yl}-2-methoxyphenyl)-5-bromo-1-methyl-1H-indole-2-carboxamide Prepared as the diacetate salt from 5-bromo-1-methyl-1H-indole-2-carbonyl chloride. $^1$H NMR (DMSO-$d_6$, 400 MHz) δ 9.64 (s, 1H), 7.95 (m, 3H), 7.61 (s, 1H), 7.59 (d, 1H), 7.42 (dd, 1H), 7.31 (s, 1H), 7.19 (d, 1H), 7.06 (dd, 1H), 6.72 (d, 1H), 6.25 (m, 1H), 5.65 (br s, 2H), 4.02 (s, 3H), 3.90 (s, 3H), 3.35 (d, 2H), 2.61 (q, 4H), 1.90 (s, 6H), 1.04 (t, 6H); MS m/e 618, 620 (M+H)$^+$, 616.4, 618.4 (M–H)$^-$.

EXAMPLE 368

N-(4-{4-amino-7-[(1E)-3-(diethylamino)-1-propenyl]thieno[3,2-c]pyridin-3-yl}-2-methoxyphenyl)-1H-indole-2-carboxamide Prepared as the diacetate salt from 1H-indole-2-carbonyl chloride. $^1$H NMR (DMSO-$d_6$, 400 MHz) δ 11.84 (br s, 1H), 9.52 (s, 1H), 8.00 (d, 1H), 7.95 (s, 1H), 7.66 (d, 1H), 7.61 (s, 1H), 7.47 (d, 1H), 7.39 (s, 1H), 7.23 (t, 1H), 7.19 (d, 1H), 7.08 (m, 2H), 6.68 (d, 1H), 6.25 (m, 1H), 5.63 (br s, 2H), 3.92 (s, 3H), 3.28 (d, 2H), 2.54 (q, 4H), 1.89 (s, 6H), 1.01 (t, 6H); MS m/e 526.5 (M+H)$^+$, 524.5 (M–H)$^-$.

EXAMPLE 369

N-(4-{4-amino-7-[(1E)-3-(diethylamino)-1-propenyl]thieno[3,2-c]pyridin-3-yl}-2-methoxyphenyl)-1-benzofuran-2-carboxamide Prepared as the diacetate salt from 1-benzofuran-2-carbonyl chloride. $^1$H NMR (DMSO-$d_6$, 400 MHz) δ 8.12 (d, 1H), 7.95 (s, 1H), 7.84 (d, 1H), 7.80 (s, 1H), 7.76 (d, 1H), 7.61 (s, 1H), 7.53 (m, 1H), 7.38 (t, 1H), 7.23 (d, 1H), 7.09 (dd, 1H), 6.86 (d, 1H), 6.24 (m, 1H), 5.62 (br s, 2H), 3.95 (s, 3H), 3.28 (d, 2H), 2.53 (q, 4H), 1.87 (s, 6H), 1.01 (t, 6H); MS m/e 527.6 (M+H)$^+$, 526.8 (M–H)$^-$.

EXAMPLE 370

N-(4-{4-amino-7-[(1E)-3-(diethylamino)-1-propenyl]thieno[3,2-c]pyridin-3-yl}-2-methoxyphenyl)-1-benzothiophene-2-carboxamide Prepared as the acetate salt from 1-benzothiophene-2-carbonyl chloride. $^1$H NMR (DMSO-$d_6$, 400 MHz) δ 9.92 (br s, 1H), 8.39 (s, 1H), 8.08 (d, 1H), 8.00 (d, 1H), 7.96 (s, 1H), 7.87 (d, 1H), 7.63 (s, 1H), 7.49 (m, 2H), 7.22 (s, 1H), 7.08 (dd, 1H), 6.69 (d, 1H), 6.25 (m, 1H), 5.63 (br s, 2H), 3.92 (s, 3H), 3.28 (d, 2H), 2.53 (q, 4H), 1.89 (s, 3H), 1.01 (t, 6H); MS m/e 543.6 (M+H)$^+$, 541.6 (M–H)$^-$.

EXAMPLE 371

N-(4-{4-amino-7-[(1E)-3-(diethylamino)-1-propenyl]thieno[3,2-c]pyridin-3-yl}-2-methoxyphenyl)-5-methyl-1H-indole-2-carboxamide Prepared as the acetate salt from 5-methyl-1H-indole-2-carbonyl chloride. $^1$H NMR (DMSO-$d_6$, 400 MHz) δ 11.71 (s, 1H), 9.47 (s, 1H), 8.01 (d, 1H), 7.96 (s, 1H), 7.61 (s, 1H), 7.44 (s, 1H), 7.36 (d, 1H), 7.29 (s, 1H), 7.19 (s, 1H), 7.07 (m, 2H), 6.69 (d, 1H), 6.25 (m, 1H), 5.64 (br s, 2H), 3.92 (s, 3H), 3.29 (d, 2H), 2.54 (q, 4H), 2.39 (s, 3H), 1.90 (s, 3H), 1.01 (t, 6H); MS m/e 540.6 (M+H)$^+$, 538.6 (M–H)$^-$.

EXAMPLE 372

N-(4-{4-amino-7-[(1E)-3-(diethylamino)-1-propenyl]thieno[3,2-c]pyridin-3-yl}-2-methoxyphenyl)-5-ethyl-1H-indole-2-carboxamide Prepared as the diacetate salt from 5-ethyl-1H-indole-2-carbonyl chloride. $^1$H NMR (DMSO-$d_6$, 400 MHz) δ 11.72 (br s, 1H), 9.47 (s, 1H), 8.00 (d, 1H), 7.95 (s, 1H), 7.61 (s, 1H), 7.45 (s, 1H), 7.38 (d, 1H), 7.31 (d, 1H), 7.20 (s, 1H), 7.09 (m, 2H), 6.69 (d, 1H), 6.24 (m, 1H), 5.63 (br s, 2H), 3.92 (s, 3H), 3.29 (d, 2H), 2.69 (q, 2H), 2.53 (q, 4H), 1.88 (s, 6H), 1.23 (t, 3H), 1.01 (t, 6H); MS m/e 554.6 (M+H)$^+$, 552.6 (M–H)$^-$.

EXAMPLE 373

7-[(1E)-3-(diethylamino)-1-propenyl]-3-(3-methoxyphenyl)thieno[3,2-c]pyridin-4-amine

EXAMPLE 373A (2E)-3-(4-amino-3-bromothieno[3,2-c]pyridin-7-yl)acrylaldehyde

A mixture of Example 176A (200 mg, 0.56 mmol), p-toluenesulfonic acid (10 mg), acetone (10 mL), and water (1 mL) at ambient temperature was stirred for 16 hours. The mixture was concentrated and washed with sodium bicarbonate (12 mL). The aqueous layer was extracted with dichloromethane/methanol (9:1). The combined organic extracts were concentrated to provide the desired product (160 mg, 0.92 mmol). Reverse phase HPLC (5% to 95% acetonitrile over 25 minutes, 1 mL/min, 254 nm, hypersil HS 100 Å, C18, 5 µm, 250×4.6 column) $R_t$=15.5 min.

EXAMPLE 373B 3-bromo-7-[(E)-3-(diethylamino)-1-propenyl]thieno[3,2-c]pyridin-4-amine A mixture of Example 373A (260 mg, 0.92 mmol), diethylamine (134 mg, 1.84 mmol), and sodium triacetoxyborohydride (400 mg, 1.84 mmol) was stirred at ambient temperature in dichloroethane (15 mL) for 3 hours, treated with additional diethylamine (400 mg) and sodium triacetoxyborohydride (500 mg), and stirred for 14 hours. The mixture was concentrated, redissolved in dichloromethane (15 mL), and washed with sodium bicarbonate (10 mL). The aqueous layer was extracted with dichloromethane (4×15 mL). The combined organic extracts were concentrated and purified by flash column chromatography with dichloromethane/methanol (85:15) to provide the desired product (143 mg, 0.39 mmol): $^1$H NMR (DMSO-$d_6$, 400 MHz) δ 7.94 (s, 1H), 7.87 (s, 1H), 6.66 (br s, 2H), 6.60 (d, 1H), 6.15

(dt, 1H), 3.25 (d, 2H), 2.48–2.50 (m, 4H), 0.99 (t, 6H); reverse phase HPLC (5% to 100% acetonitrile over 10 minutes, 1 mL/min, 254 nm, hypersil HS 100 Å, C18, 5 μm, 250×4.6 column) $R_t$=8.0 min; MS m/e 341.4 $(M+H)^+$.

EXAMPLE 373C

7-[(1E)-3-(diethylamino)-1-propenyl]-3-(3-methoxyphenyl)thieno[3,2-c]pyridin-4-amine A mixture of Example 373B (45 mg, 0.14 mmol), 3-methoxyphenylboronic acid (23 mg, 0.15 mmol), sodium carbonate (28 mg, 0.26 mmol), and $Pd(PPh_3)_4$ (9 mg, 0.008 mmol) was heated to 95° C. for 16 hours in dimethoxy ethylene glycol (2 mL) and water (1 mL). Additional boronic acid (17 mg), $Pd(PPh_3)_4$ (9 mg), and sodium carbonate (20 mg) were added, and the mixture was stirred for another 3 hours. The mixture was concentrated and extracted with dichloromethane (4×2 mL). The organic layers were combined, concentrated, and purified by flash column chromatography with dichloromethane/methanol (8:2) to provide the desired product (15 mg, 0.04 mmol). $^1$H NMR (DMSO-$d_6$, 400 MHz) δ 7.94 (s, 1H), 7.54 (s, 1H), 7.45 (t, 1H), 7.01–7.12 (m, 3H), 6.68 (d, 1H), 6.23 (dt, 1H), 5.65 (br s, 2H), 3.81 (s, 3H), 3.29 (d, 2H), 1.01 (t, 6H); reverse phase HPLC (5% to 100% acetonitrile over 25 minutes, 1 mL/min, 254 nm, hypersil HS 100 Å, C 18, 5 μm, 250×4.6 column) $R_t$=14.2 min; MS m/e 366.4 $(M-H)^-$.

General Procedure for Suzuki Coupling of Northern Domain Followed by Reductive Amination A mixture of Example 176A (100 mg, 0.28 mmol), sodium carbonate (60 mg, 0.56 mmol), $Pd(PPh_3)_4$ (19 mg, 0.017 mmol), and the appropriate boronate (0.34 mmol) was heated to 95° C. for 16 hours in dimethoxyethylene glycol (4 mL) and water (2 mL), treated with additional boronate (10 mmol), palladium (10 mg), and sodium carbonate (30 mg), stirred for 3 hours, concentrated, and extracted with dichloromethane (4×2 mL). The organic extracts werere combined, concentrated, and purified by flash column chromatography with dichloromethane/ethyl acetate (6:4) to provide the coupled product.

A mixture of the coupled product (100 mg), p-toluenesulfonic acid (10 mg), acetone (10 mL), and water (1 mL) was stirred at room temperature for 16 hours, concentrated, and washed with sodium bicarbonate (12 mL). The aqueous layer was extracted with dichloromethane/methanol (9:1) and the combined organic extracts were concentrated to provide the desired aldehydes which were used in the next reaction without further purification.

A mixture of diethylamine (12 mg, 0.166 mmol), sodium triacetoxyborohydride (35 mg, 0.166 mmol) and the aldehyde (0.083 mmol) in 1,2-dichloromethane (2 mL) was stirred for 2 to 72 hours at ambient temperature. The mixture was concentrated and the product purified by normal and/or reverse phase chromatography to provide the desired product.

The following examples were prepared according to this procedure using the boronate indicated:

EXAMPLE 374

N-(4-[4-amino-7-[(1E)-3-(diethylamino)-1-propenyl] thieno[3,2-c]pyridin-3-yl]phenyl)-1-methyl-1H-indole-2-carboxamide

EXAMPLE 374A 1-methyl-N-[4-(4,4,5,5-tetramethyl-1,3,2-dioxaborolan-2-yl)phenyl]-1H-indole-2-carboxamide A mixture of oxalyl chloride (0.35 mL) and dimethylformamide (1 drop) was added to a solution of 1-methyl-1H-2-indolecarboxylic acid (440 mg, 2.51 mmol) in dichloromethane (10 mL). After one hour the mixture was evaporated, dissolved in dichloromethane (10 mL), and added to a mixture of 4-(4,4,5,5-tetramethyl-1,3,2-dioxaborolan-2-yl)aniline (500 mg, 2.28 mmol) and diisopropylethylamine (0.35 mL) in dichloromethane (10 mL). After 16 hours the mixture was washed with water (10 mL), dried ($MgSO_4$), filtered, concentrated, and purified by flash column chromatography to provide the desired product (600 mg, 1.60 mmol) after lyophilization: MS m/e 377.4 $(M+H)^+$.

EXAMPLE 374B

N-(4-{4-amino-7-[(1E)-3-(diethylamino)-1-propenyl]thieno[3,2-c]pyridin-3-yl}phenyl)-1-methyl-1H-indole-2-carboxamide boronate: Example 374A. $^1$H NMR (DMSO-$d_6$, 400 MHz) δ 10.56 (s, 1H), 7.93–7.98 (m, 3H), 7.10–7.75 (m, 9H), 6.67 (d, 1H), 6.21 (dt, 1H), 5.58 (br s, 2H), 4.02 (s, 3H), 3.22 (d, 2H), 2.48 (q, 4H), 1.00 (t, 6H); reverse phase HPLC (5% to 95% acetonitrile over 10 minutes, 1 mL/min, 254 nm, hypersil HS 100 Å, C18, 5 μm, 250×4.6 column) $R_t$=10.4 min.; MS m/e 508.6 $(M-H)^-$.

EXAMPLE 375

N-(4-{4-amino-7-[(1E)-3-(diethylamino)-1-propenyl]thieno[3,2-c]pyridin-3-yl}-2-methoxyphenyl)-1-methyl-1H-benzimidazole-2-carboxamide

EXAMPLE 375A 1-methyl-1H-benzimidazole-2-carboxylic acid

A suspension of 1-methyl-1H-benzimidazole (5.0 g, 37.83 mmol) in diethyl ether at −78° C. was treated slowly with 1.6M n-butyllithium in hexanes (26 mL, 41.61 mmol) while maintaining the temperature at below −60° C., and stirred at −78° C. for 30 minutes. Carbon dioxide was bubbled through the reaction solution for 40 minutes. The dry ice bath was then removed to bring the temperature to −5° C. Concentrated hydrochloric acid (7 mL) was added slowly. The reaction mixture was stirred at −5° C. for 30 minutes, and then water (10 mL) was added. The solid was collected by filtration and dried to remove the excess water to provide 4.8 g (72%) of the desired product which was directly used in the next reaction without further purification or analysis.

EXAMPLE 375B 1-methyl-1H-benzimidazole-2-carbonyl chloride

A suspension of 1Example 375A (0.298 g, 1.69 mmol) in dichloromethane (5 mL) at 0° C. was treated with oxalyl chloride (0.255 g, 1.77 mmol) and 1 drop of DMF. The reaction mixture was stirred for 15 minutes at 0° C. and at room temperature for 4 hours. The solvent was removed under reduced pressure and the residue was dried on the high vacuum. The reaction mix was directly used in the subsequent reaction without further purification or analysis.

EXAMPLE 375C

N-[2-methoxy-4-(4,4,5,5-tetramethyl-1,3,2-dioxaborolan-2-yl)phenyl]-1-methyl-1H-benzimidazole-2-carboxamide A solution of 2-methoxy-4-(4,4,5,5-tetramethyl-1,3,2-dioxaborolan-2-yl)aniline (0.384 g, 1.54 mmol) in tetrahydrofuran (10 mL) was treated with Example 375B(0.330 g, 1.696 mmol) and diisopropylethyl amine (0.239 g, 1.85 mmol). The reaction mixture was stirred for 18 hours at room temperature under a nitrogen atmosphere, treated with 1N NaOH (5 mL), concentrated, and treated with dichloromethane. The layers were partitioned and the aqueous layer was extracted with dichloromethane. The combined organic layers were dried ($MgSO_4$), filtered, and concentrated. Diethyl ether was added and the solid was collected by filtration to provide 0.220 g (35%) of the desired product. $^1H$ NMR (DMSO-$d_6$, 400 MHz) δ 10.184 (s, 1H), 8.4396–8.4197 (d, 1H, J=7.96 Hz), 7.8453–7.8253 (d, 1H, J=8 Hz), 7.7614–7.7410 (d, 1H, J=8.16 Hz), 7.471–7.435 (t, 1H), 7.399–7.367 (m, 2H), 7.306 (s, 1H), 4.226 (s, 3H), 3.995 (s, 3H), 1.315 (s, 12H); TLC (30% ethyl acetate in heptane) $R_f$=0.5.

EXAMPLE 375D

N-(4-{4-amino-7-[(1E)-3-(diethylamino)-1-propenyl]thieno[3,2-c]pyridin-3-yl}-2-methoxyphenyl)-1-methyl-1H-benzimidazole-2-carboxamide boronate: N-[2-methoxy-4-(4,4,5,5-tetramethyl-1,3,2-dioxaborolan-2-yl)phenyl]-1-methyl-1H-benzimidazole-2-carboxamide. $^1H$ NMR (DMSO-$d_6$, 400 MHz) δ 10.2 (s, 1H), 8.52 (d, 1H), 8.10 (s, 1H), 7.86 (d, 1H), 7.74–7.79 (m, 3H), 7.38–7.49 (m, 2H), 7.05–7.15 (m, 2H), 6.25 (m, 1H), 4.25 (s, 3H), 3.90–4.02 (m, 5H), 3.18 (q, 4H), 1.28 (t, 6H); reverse phase HPLC (5% to 95% acetonitrile over 10 minutes, 1 mL/min, 254 nm, hypersil HS 100 Å, C18, 5 µm, 250×4.6 column) $R_t$=11.0 min.; MS m/e 539.4 (M−H)$^−$.

General Procedure for Preparation of Amides from Oxalyl Chloride (Synthetic Method 1)

A suspension of the sodium salt of Example 270 (0.050 g, 0.096 mmol, prepared by treating Example 270 with 1N NaOH) in dichloromethane (2.0 mL) was treated with oxalyl chloride (0.020 mL, 0.219 mmol) and N,N-dimethylformamide (0.010 mL, 0.129 mmol), stirred at room temperature under nitrogen for 20 minutes, treated dropwise with a 2.0M solution of the appropriate amine in THF (1.0 mL, 2.00 mmol), stirred at ambient temperature for 20 minutes, and concentrated to a dry powder under reduced pressure. The crude material was purified by preparative HPLC using method B described below.

General Procedure for the Preparation of Amides using O-Benzotriazol-1-yl-N,N,N',N'-tetramethyluronium hexafluorophosphate (Synthetic Method 2)

A mixture of the sodium salt of Example 270 (0.040 g, 0.071 mmol, prepared by treating Example 270 with 1N NaOH) in N,N-dimethylformamide (1.00 mL) was treated with diisopropylethylamine (0.060 mL, 0.344 mmol), the appropriate amine (0.230 mmol), O-benzotriazol-1-yl-N,N,N',N'-tetramethyluronium hexafluorophosphate (0.031 g, 0.081 mmol), and hydroxybenzotriazole (0.013 g, 0.081 mmol). The reaction was stirred at ambient temperature under an atmosphere of nitrogen for 18 hours. The products not containing protecting groups were purified by preparative HPLC using method A or B. The products containing a t-butoxycarbonyl protected amines were concentrated to dry powders under reduced pressure and deprotected using the conditions described below.

General Procedure for the Deprotection of N-tert-Butoxycarbonyl Protected Amines from Synthetic Method 2

A mixture of the protected coupling product, trifluoracetic acid (0.30 mL), and dichloromethane (0.90 mL) was stirred at ambient temperature for 2 hours and concentrated. The crude material was purified by preparative HPLC using method A or B.

General Procedure for the Saponification of Ester-Containing Amines

A mixture of the ester (0.016 mmol) in tetrahydrofuran (0.30 mL) and methanol (0.30 mL) was treated with 2N NaOH (0.03 mL, 0.60 mmol). The reaction was stirred at room temperature for 18 hours before the solvents were removed under reduced pressure. The compound was extracted with 1:1 tetrahydrofuran/ethyl acetate (3×1 mL). The combined extracts were dried ($Na_2SO_4$, 20 mg), filtered, and concentrated.

Preparative HPLC Conditions (Purification Method A)

Micromass, Hypersil BDS C18, 5 µm, 100×21.2 mm; 25%-75% acetonitrile—50 mM ammonium acetate over 7 min, 100% acetonitrile for 2 min, 100%-25% acetonitrile—50 mM ammonium acetate over 1.5 min, 25 mL/min.

Preparative HPLC conditions (Purification Method B)

Hyperprep HS C18, 8 µm, 250×21.2 mm; 20% acetonitrile—50 mM ammonium acetate over 1 min, 20–100% acetonitrile—50 mM ammonium acetate for 24 min, 100% acetonitrile for 5 min, 20 mL/min.

LCMS (Analytical Method 1)

Agilent HP 1100, Genesis C18, 33×4.6 mm, 4 µm. Flow rate: 2.0 mL/min. Mobile phase: acetonitrile/5 mM ammonium acetate. Gradient: 5%-95% acetonitrile—5 mM ammonium acetate over 3.5 min, 95–100% acetonitrile—5 mM ammonium acetate over 1.0 min., 5% acetonitrile—5 mM ammonium acetate over 0.5 min. Total run time 5 min.

LCMS (Analytical Method 2)

Finnigan Advantage LCQ-MS, Genesis C18, 30×4.6 mm, 3 μm. Flow rate: 0.8 mL/min. Mobile phase: acetonitrile/10 mM ammonium acetate. Gradient: 30%–95% acetonitrile—10 mM ammonium acetate over 3.0 min, hoursold 1.5 min 95% acetonitrile—10 mM ammonium acetate,: 95%–30% acetonitrile—10 mM ammonium acetate over 0.5 min, 30% acetonitrile—10 mM ammonium acetate over 1 min. Total run time 6 min.

The following examples were prepared using the above methods:

| Example | Final Product | Starting Amine | Yield (%) | R$_t$ (min) | m/z (M + H)$^+$ | Methods Used (Synthetic, Purification, Analytical) |
|---|---|---|---|---|---|---|
| 376 | N-(4-{4-amino-7-[(1E)-3-({2-[bis(2-hydroxyethyl)amino]-ethyl}amino)-3-oxo-1-propenyl]thieno[3,2-c]pyridin-3-yl}-2-methoxyphenyl)-1-methyl-1H-indole-2-carboxamide | 2-[(2-aminoethyl)(2-hydroxyethyl)-amino]ethanol | 55.0 | 2.37 | 629.0 | 2, 1, A |
| 377 | N-{4-[4-amino-7-((1E)-3-oxo-3-{[3-(2-oxo-1-pyrrolidinyl)-propyl]amino}-1-propenyl)thieno[3,2-c]pyridin-3-yl]-2-methoxyphenyl}-1-methyl-1H-indole-2-carboxamide | 1-(3-aminopropyl)-2-pyrrolidinone | 45.7 | 2.76 | 623.0 | 2, 1, A |
| 378 | N-(4-{4-amino-7-[(1E)-3-({3-[(2R)-2-methyl-1-piperidinyl]propyl}amino)-3-oxo-1-propenyl]thieno[3,2-c]pyridin-3-yl}-2-methoxyphenyl)-1-methyl-1H-indole-2-carboxamide | 3-[(2R)-2-methyl-1-piperidinyl]-1-propanamine | 54.9 | 2.72 | 637.2 | 2, 1, A |
| 379 | N-{4-[4-amino-7-((1E)-3-{[2-(diisopropylamino)ethyl]amino}-3-oxo-1-propenyl)thieno[3,2-c]pyridin-3-yl]-2-methoxyphenyl}-1-methyl-1H-indole-2-carboxamide | N,N-diisopropyl-1,2-ethanediamine | 46.0 | 2.68 | 625.2 | 2, 1, A |
| 380 | N-(4-{4-amino-7-[(1E)-3-({2-[ethyl(3-methylphenyl)amino]-ethyl}amino)-3-oxo-1-propenyl]thieno[3,2-c]pyridin-3-yl}-2-methoxyphenyl)-1-methyl-1H-indole-2-carboxamide | N-(2-aminoethyl)-N-ethyl-N-(3-methylphenyl)-amine | 28.0 | 3.76 | 659.0 | 2, 1, A |
| 381 | N-{4-[4-amino-7-((1E)-3-{[3-(dimethylamino)-2,2-dimethylpropyl]amino}-3-oxo-1-propenyl)thieno[3,2-c]pyridin-3-yl]-2-methoxyphenyl}-1-methyl-1H-indole-2-carboxamide | N,N,2,2-tetramethyl-1,3-propanediamine | 47.5 | 2.67 | 611.2 | 2, 1, A |
| 382 | N-{4-[4-amino-7-((1E)-3-{[3-(4-methyl-1-piperidinyl)propyl]amino}-3-oxo-1-propenyl)thieno[3,2-c]pyridin-3-yl]-2-methoxyphenyl}-1-methyl-1H-indole-2-carboxamide | 3-(4-methyl-1-piperidinyl)-1-propanamine | 44.3 | 2.70 | 637.2 | 2, 1, A |
| 383 | N-{4-[4-amino-7-((1E)-3-{[3-(dimethylamino)propyl]amino}-3-oxo-1-propenyl)thieno[3,2-c]pyridin-3-yl]-2-methoxyphenyl}-1-methyl-1H-indole-2-carboxamide | N,N-dimethyl-1,3-propanediamine | 48.2 | 2.46 | 583.2 | 2, 1, A |
| 384 | N-[4-(4-amino-7-{(1E)-3-[(2-hydroxyethyl)amino]-3-oxo-1-propenyl}thieno[3,2-c]pyridin-3-yl)-2-methoxyphenyl]-1-methyl-1H-indole-2-carboxamide | 2-aminoethanol | 39.8 | 2.63 | 542.0 | 2, 1, A |
| 385 | N-{4-[4-amino-7-((1E)-3-{[2-(dimethylamino)ethyl]amino}-3-oxo-1-propenyl)thieno[3,2-c]pyridin-3-yl]-2-methoxyphenyl}-1-methyl-1H-indole-2-carboxamide | N,N-dimethyl-1,2-ethanediamine | 50.5 | 2.43 | 569.2 | 2, 1, A |
| 386 | N-[4-(4-amino-7-{(1E)-3-[(3-hydroxypropyl)amino]-3-oxo-1-propenyl}thieno[3,2-c]pyridin-3-yl]-2-methoxyphenyl]-1-methyl-1H-indole-2-carboxamide | 3-amino-1-propanol | 40.5 | 2.68 | 556.2 | 2, 1, A |

-continued

| Example | Final Product | Starting Amine | Yield (%) | R_t (min) | m/z (M + H)+ | Methods Used (Synthetic, Purification, Analytical) |
|---|---|---|---|---|---|---|
| 387 | N-{4-[4-amino-7-((1E)-3-{[3-(1H-imidazol-1-yl)propyl]amino}-3-oxo-1-propenyl)thieno[3,2-c]pyridin-3-yl]-2-methoxyphenyl}-1-methyl-1H-indole-2-carboxamide | 3-(1H-imidazol-1-yl)-1-propanamine | 42.1 | 2.49 | 606.0 | 2, 1, A |
| 388 | N-{4-[4-amino-7-((1E)-3-{[(2S)-2-(dimethylamino)propyl]amino}-3-oxo-1-propenyl)thieno[3,2-c]pyridin-3-yl]-2-methoxyphenyl}-1-methyl-1H-indole-2-carboxamide | N-[(1S)-2-amino-1-methylethyl]-N,N-dimethylamine | 50.2 | 2.40 | 583.2 | 2, 1, A |
| 389 | N-{4-[4-amino-7-((1E)-3-oxo-3-{[3-(1-pyrrolidinyl)propyl]amino}-1-propenyl)thieno[3,2-c]pyridin-3-yl]-2-methoxyphenyl}-1-methyl-1H-indole-2-carboxamide | 3-(1-pyrrolidinyl)-1-propanamine | 44.2 | 2.48 | 609.2 | 2, 1, A |
| 390 | N-{4-[4-amino-7-((1E)-3-{[3-(4-morpholinyl)propyl]amino}-3-oxo-1-propenyl)thieno[3,2-c]pyridin-3-yl]-2-methoxyphenyl}-1-methyl-1H-indole-2-carboxamide | 3-(4-morpholinyl)-1-propanamine | 32.5 | 2.24 | 625.0 | 2, 1, A |
| 391 | N-{4-[4-amino-7-((1E)-3-{[1-(2,6-dimethoxybenzyl)-4-piperidinyl]amino}-3-oxo-1-propenyl)thieno[3,2-c]pyridin-3-yl]-2-methoxyphenyl}-1-methyl-1H-indole-2-carboxamide | 1-(2,6-dimethoxy-benzyl)-4-piperidinamine | 27.0 | 2.80 | 731.0 | 2, 1, A |
| 392 | N-(4-{4-amino-7-[(1E)-3-({[(2R)-1-ethyl-2-pyrrolidinyl]methyl}amino)-3-oxo-1-propenyl]thieno[3,2-c]pyridin-3-yl}-2-methoxyphenyl)-1-methyl-1H-indole-2-carboxamide | [(2R)-1-ethyl-2-pyrrolidinyl]-methylamine | 40.6 | 2.54 | 609.2 | 2, 1, A |
| 393 | N-[4-(4-amino-7-{(1E)-3-[(1-benzyl-4-piperidinyl)amino]-3-oxo-1-propenyl}thieno[3,2-c]pyridin-3-yl)-2-methoxyphenyl]-1-methyl-1H-indole-2-carboxamide | 1-benzyl-4-piperidinamine | 38.0 | 2.71 | 671.0 | 2, 1, A |
| 394 | N-(4-{4-amino-7-[(1E)-3-({[1-(2-methoxyphenyl)-4-piperidinyl]methyl}amino)-3-oxo-1-propenyl]thieno[3,2-c]pyridin-3-yl}-2-methoxyphenyl)-1-methyl-1H-indole-2-carboxamide | [1-(2-methoxyphenyl)-4-piperidinyl]-methylamine | 21.9 | 3.51 | 701.0 | 2, 1, A |
| 395 | N-{4-[4-amino-7-((1E)-3-{[2,3-dihydroxypropyl]amino}-3-oxo-1-propenyl)thieno[3,2-c]pyridin-3-yl]-2-methoxyphenyl}-1-methyl-1H-indole-2-carboxamide | 3-amino-1,2-propanediol | 37.5 | 2.51 | 572.0 | 2, 1, A |
| 396 | N-{4-[4-amino-7-((1E)-3-{[3-(diethylamino)propyl]amino}-3-oxo-1-propenyl)thieno[3,2-c]pyridin-3-yl]-2-methoxyphenyl}-1-methyl-1H-indole-2-carboxamide | N,N-diethyl-1,3-propanediamine | 31.3 | 2.56 | 611.2 | 2, 1, A |
| 397 | N-{4-[4-amino-7-((1E)-3-{[2-(diethylamino)ethyl]amino}-3-oxo-1-propenyl)thieno[3,2-c]pyridin-3-yl]-2-methoxyphenyl}-1-methyl-1H-indole-2-carboxamide | N,N-diethyl-1,2-ethanediamine | 46.0 | 2.60 | 597.2 | 2, 1, A |
| 398 | N-(4-{4-amino-7-[(1E)-3-({[(2S)-1-ethyl-2-pyrrolidinyl]methyl}amino)-3-oxo-1-propenyl]thieno[3,2-c]pyridin-3-yl}-2- | [(2S)-1-ethyl-2-pyrrolidinyl]-methylamine | 44.2 | 2.64 | 609.2 | 2, 1, A |

| Example | Final Product | Starting Amine | Yield (%) | R$_t$ (min) | m/z (M + H)$^+$ | Methods Used (Synthetic, Purification, Analytical) |
|---|---|---|---|---|---|---|
| | methoxyphenyl)-1-methyl-1H-indole-2-carboxamide | | | | | |
| 399 | N-{4-[4-amino-7-((1E)-3-{[2-(dimethylamino)-1-methylethyl]amino}-3-oxo-1-propenyl)thieno[3,2-c]pyridin-3-yl]-2-methoxyphenyl}-1-methyl-1H-indole-2-carboxamide | N-[2-aminopropyl]-N,N-dimethylamine | 46.0 | 2.49 | 583.2 | 2, 1, A |
| 400 | N-{4-[4-amino-7-((1E)-3-oxo-3-{[2-(1-pyrrolidinyl)ethyl]amino}-1-propenyl)thieno[3,2-c]pyridin-3-yl]-2-methoxyphenyl}-1-methyl-1H-indole-2-carboxamide | 2-(1-pyrrolidinyl)-ethanamine | 43.1 | 2.53 | 595.2 | 2, 1, A |
| 401 | N-{4-[4-amino-7-((1E)-3-oxo-3-{[2-(2-oxo-1-imidazolidinyl)ethyl]amino}-1-propenyl)thieno[3,2-c]pyridin-3-yl]-2-methoxyphenyl}-1-methyl-1H-indole-2-carboxamide | 1-(2-aminoethyl)-2-imidazol-idinone | 27.9 | 2.60 | 610.0 | 2, 1, A |
| 402 | N-{4-[4-amino-7-((1E)-3-{[3-(4-methyl-1-piperazinyl)propyl]amino}-3-oxo-1-propenyl)thieno[3,2-c]pyridin-3-yl]-2-methoxyphenyl}-1-methyl-1H-indole-2-carboxamide | 3-(4-methyl-1-piperazinyl)-1-propanamine | 50.1 | 2.39 | 638.2 | 2, 1, A |
| 403 | N-[4-(4-amino-7-{(1E)-3-[1-azabicyclo[2.2.2]oct-3-ylamino]-3-oxo-1-propenyl}thieno[3,2-c]pyridin-3-yl)-2-methoxyphenyl]-1-methyl-1H-indole-2-carboxamide | quinuclidin-3-amine | 8.1 | 2.52 | 607.0 | 2, 1, A |
| 404 | N-(4-{4-amino-7-[(1E)-3-({2-[1-methyl-2-pyrrolidinyl]ethyl}amino)-3-oxo-1-propenyl]thieno[3,2-c]pyridin-3-yl}-2-methoxyphenyl)-1-methyl-1H-indole-2-carboxamide | 2-[1-methyl-2-pyrrolidinyl]-ethanamine | 48.9 | 2.5 | 609.0 | 2, 1, A |
| 405 | N-{4-[4-amino-7-((1E)-3-{[2-(2,4-dioxo-1,3-thiazolidin-3-yl)ethyl]amino}-3-oxo-1-propenyl)thieno[3,2-c]pyridin-3-yl]-2-methoxyphenyl}-1-methyl-1H-indole-2-carboxamide | 3-(2-aminoethyl)-1,3-thiazolidine-2,4-dione | 30.0 | 2.97 | 641.0 | 2, 1, A |
| 406 | N-{4-[4-amino-7-((1E)-3-{[2-(1-methyl-1H-pyrrol-2-yl)ethyl]amino}-3-oxo-1-propenyl)thieno[3,2-c]pyridin-3-yl]-2-methoxyphenyl}-1-methyl-1H-indole-2-carboxamide | 2-(1-methyl-1H-pyrrol-2-yl)ethanamine | 30.5 | 3.27 | 605.0 | 2, 1, A |
| 407 | N-(4-{4-amino-7-[(1E)-3-({2-[methyl(phenyl)amino]-ethyl}amino)-3-oxo-1-propenyl]thieno[3,2-c]pyridin-3-yl}-2-methoxyphenyl)-1-methyl-1H-indole-2-carboxamide | N-(2-aminoethyl)-N-methyl-N-phenylamine | 33.6 | 3.52 | 631.0 | 2, 1, A |
| 408 | N-{4-[4-amino-7-((1E)-3-{[3-(methylamino)propyl]amino}-3-oxo-1-propenyl)thieno[3,2-c]pyridin-3-yl]-2-methoxyphenyl}-1-methyl-1H-indole-2-carboxamide | tert-butyl 3-aminopropyl-(methyl)-carbamate | 64.7 | 2.42 | 569.0 | 2, 1, A |
| 409 | N-(4-{4-amino-7-[(1E)-3-oxo-3-({2-[2-piperidinyl]ethyl}amino)-1-propenyl]thieno[3,2-c]pyridin-3-yl}-2-methoxyphenyl)-1-methyl-1H-indole-2-carboxamide | tert-butyl 2-(2-aminoethyl)-1-piperidine-carboxylate | 43.1 | 2.6 | 609.0 | 2, 1, A |
| 410 | N-{4-[4-amino-7-((1E)-3-{[2-(methylamino)ethyl]amino}-3-oxo-1-propenyl)thieno[3,2- | tert-butyl 2-aminoethyl-carbamate | 55.1 | 2.41 | 555.0 | 2, 1, A |

| Example | Final Product | Starting Amine | Yield (%) | R$_t$ (min) | m/z (M + H)$^+$ | Methods Used (Synthetic, Purification, Analytical) |
|---|---|---|---|---|---|---|
|  | c]pyridin-3-yl]-2-methoxyphenyl}-1-methyl-1H-indole-2-carboxamide |  |  |  |  |  |
| 411 | N-{4-[4-amino-7-((1E)-3-oxo-3-{[(3R)-3-pyrrolidinylmethyl]amino}-1-propenyl)thieno[3,2-c]pyridin-3-yl]-2-methoxyphenyl}-1-methyl-1H-indole-2-carboxamide | tert-butyl (3S)-3-(aminomethyl)-1-pyrrolidine-carboxylate | 66.5 | 2.42 | 581.0 | 2, 1, A |
| 412 | N-{(2E)-3-[4-amino-3-(3-methoxy-4-{[(1-methyl-1H-indol-2-yl)carbonyl]amino}phenyl)-thieno[3,2-c]pyridin-7-yl]-2-propenoyl}glycinamide(acetate salt) | glycinamide | 41.0 | 2.47 | 555.1 | 2, 2, B |
| 413 | N-(4-{4-amino-7-[(1E)-3-amino-3-oxo-1-propenyl]thieno[3,2-c]pyridin-3-yl}-2-methoxyphenyl)-1-methyl-1H-indole-2-carboxamide(acetate salt) | ammonium hydroxide | 21.0 | 2.92 | 498.4 | 1, 2, B |
| 414 | N-(4-{4-amino-7-[(1E)-3-(methylamino)-3-oxo-1-propenyl]thieno[3,2-c]pyridin-3-yl}-2-methoxyphenyl)-1-methyl-1H-indole-2-carboxamide (acetate salt) | methylamine | 22.0 | 3.1 | 512.3 | 1, 2, B |
| 415 | N-(4-{4-amino-7-[(1E)-3-(dimethylamino)-3-oxo-1-propenyl]thieno[3,2-c]pyridin-3-yl}-2-methoxyphenyl)-1-methyl-1H-indole-2-carboxamide | N,N-dmethylamine | 21.0 | 3.5 | 526.4 | 1, 2, B |
| 416 | ethyl N-{(2E)-3-[4-amino-3-(3-methoxy-4-{[(1-methyl-1H-indol-2-yl)carbonyl]amino}phenyl)-thieno[3,2-c]pyridin-7-yl]-2-propenoyl}-β-alaninate | ethyl β-alaninate | 44.0 | 3.22 | 598.3 | 2, 2, B |
| 417 | ethyl 4-({(2E)-3-[4-amino-3-(3-methoxy-4-{[(1-methyl-1H-indol-2-yl)carbonyl]amino}phenyl)-thieno[3,2-c]pyridin-7-yl]-2-propenoyl}amino)butanoate | ethyl 4-aminobutanoate | 37.0 | 3.5 | 612.5 | 2, 2, B |
| 418 | N-{(2E)-3-[4-amino-3-(3-methoxy-4-{[(1-methyl-1H-indol-2-yl)carbonyl]amino}phenyl)-thieno[3,2-c]pyridin-7-yl]-2-propenoyl}-β-alanine(sodium salt) | ethyl β-alaninate | 10.0 | 2.1 | 570.4 | 2, 2, B |
| 419 | 4-({(2E)-3-[4-amino-3-(3-methoxy-4-{[(1-methyl-1H-indol-2-yl)carbonyl]amino}phenyl)-thieno[3,2-c]pyridin-7-yl]-2-propenoyl}amino)butanoic acid (sodium salt) | ethyl 4-aminobutanoate | 81.0 | 2.12 | 584.5 | 2, 2, B |

EXAMPLE 420

N-[4-(4-amino-7-{(1E)-3-[4-(2-hydroxyethyl)-1-piperazinyl]-1-propenyl}thieno[3,2-c]pyridin-3-yl)-2-methoxyphenyl]-1-methyl-1H-indole-2-carboxamide A mixture of Example 176C (40 mg, 0.083 mmol), sodium triacetoxyborohydride (35 mg, 0.166 mmol) and 2-(1-piperazinyl)ethanol (0166 mmol) in 1,2-dichloromethane (2 mL) was stirred for 2 to 72 hours at ambient temperature. The mixture was concentrated and the residue was purified by chromatography to provide the desired product as the diacetate salt. $^1$H NMR (DMSO, 400 MHz) δ 9.50 (s, 1H), 8.00 (d, 1H), 7.97 (s, 1H), 7.71 (d, 1H), 7.61 (m, 2H), 7.36 (m, 2H), 7.20 (s, 1H), 7.15 (t, 1H), 7.05 (d, 1H), 6.70 (d, 1H), 6.25 (m, 1H), 5.6 (bs, 2H), 4.04 (s, 3H), 3.91 (s, 3H), 3.47 (t, 2H), 3.4 (m, 4H), 3.15 (d, 2H), 2.5 (m, 4H), 2.45 (t, 2H), 1.88 (s, 6H); MS m/e 597.5 (M+H)+, 595.5 (M−H)−.

EXAMPLE 421

N-(4-{4-amino-7-[(3-oxopiperazin-1-yl)methyl]thieno[3,2-c]pyridin-3-yl}phenyl)-N'-[2-fluoro-5-(trifluoromethyl)phenyl]urea

EXAMPLE 421A

4-[(4-amino-3-bromothieno[3,2-c]pyridin-7-yl)methyl]piperazin-2-one

The desired product was prepared by substituting piperazin-2-one for morpholine in Example 278B.

EXAMPLE 421B

N-(4-{4-amino-7-[(3-oxopiperazin-1-yl)methyl]thieno[3,2-c]pyridin-3-yl}phenyl)-N'-[2-fluoro-5-(trifluoromethyl)phenyl]urea The desired product was prepared by substituting Example 421A and N-[4-(4,4,5,5-tetramethyl-1,3,2-dioxaborolan-2-yl)phenyl]-N'-[2-fluoro-5-(trifluoromethyl)phenyl]urea for Example 1B and 4-phenoxyphenylboronic acid, respectively, in Example 10A. $^1$H NMR (300 MHz, DMSO-D$_6$) δ ppm 2.58 (m, 2H) 2.95 (s, 2H) 3.17 (m, 2H) 3.67 (s, 2H) 5.39 (s, 2H) 7.38–7.42 (m, 4H) 7.48–7.54 (m, 1H) 7.61 (d, J=8.5 Hz, 2H) 7.72 (s, 1H) (s, 1H) 7.76 (s, 1H) 8.63 (dd, J=7.5, 2.0 Hz, 1H) 8.98 (s, 1H) 9.37 (s, 1H) MS (ESI(+)) m/e 559.1 (M+H)+.

EXAMPLE 422

N-[4-(4-amino-7-methylthieno[3,2-c]pyridin-3-yl)phenyl]-N'-(3-methylphenyl)urea

EXAMPLE 422A 3-bromo-7-methylthieno[3,2-c]pyridin-4-amine

The desired product was prepared by substituting Example 277C for Example 277D in Example 277E. MS (ESI(+)) m/e 242.9, 244.9 (M+H)+.

EXAMPLE 422B

N-[4-(4-amino-7-methylthieno[3,2-c]pyridin-3-yl)phenyl]-N'-(3-methylphenyl)urea

The desired product was prepared by substituting Example 422A and Example 66D for Example 1B and 4-phenoxyphenylboronic acid, respectively, in Example 10A. $^1$H NMR (300 MHz, DMSO-D$_6$) δ ppm 2.29 (s, 3H) 2.33 (s, 3H) 5.25 (s, 2H) 6.80 (br d, J=6.4 Hz, 1H) 7.17 (t, J=7.8 Hz, 1H) 7.25 (br d, J=8.5 Hz, 1H) 7.31 (s, 1H) 7.36 (d, J=8.8 Hz, 2H) 7.43 (d, J=8.1 Hz, 1H) 7.59 (d, J=8.8 Hz, 2H) 7.67 (s, 1H) 8.65 (s, 1H) 8.84 (s, 1H) MS (ESI(+)) m/e 389.0 (M+H)+.

EXAMPLE 423

N-(4-{4-amino-7-[(diethylamino)methyl]thieno[3,2-c]pyridin-3-yl}phenyl)-N'-[2-fluoro-5-(trifluoromethyl)phenyl]urea

EXAMPLE 423A 3-bromo-7-[(diethylamino)methyl]thieno[3,2-c]pyridin-4-amine

The desired product was prepared substituting diethylamine for morpholine in Example 278B.

EXAMPLE 423B

N-(4-{4-amino-7-[(diethylamino)methyl]thieno[3,2-c]pyridin-3-yl}phenyl)-N'-[2-fluoro-5-(trifluoromethyl)phenyl]urea The desired product was prepared substituting Example 423A and N-[4-(4,4,5,5-tetramethyl-1,3,2-dioxaborolan-2-yl)phenyl]-N'-[2-fluoro-5-(trifluoromethyl)phenyl]urea for Example 1B and 4-phenoxyphenylboronic acid, respectively, in Example 10A. $^1$H NMR (300 MHz, DMSO-D$_6$) δ ppm 1.03 (t, J=7.1 Hz, 6H), 2.49–2.51 (m, 4H), 3.65 (s, 2H) 5.31 (s, 2H) 7.38–7.41 (m, 4H) 7.48–7.55 (m, 1H) 7.60 (d, J=8.5 Hz, 2H) 7.69 (s, 1H) 8.64 (dd, J=7.5, 2.4 Hz, 1H) 8.97 (s, 1H) 9.36 (s, 1H) MS (ESI(+)) m/e 532.1 (M+H)+.

EXAMPLE 424

N-{4-[4-amino-7-(1,4-dioxa-8-azaspiro[4.5]dec-8-ylmethyl)thieno[3,2-c]pyridin-3-yl]phenyl}-N'-[2-fluoro-5-(trifluoromethyl)phenyl]urea

EXAMPLE 424A 3-bromo-7-(1,4-dioxa-8-azaspiror[4.5]dec-8-ylmethyl)thieno[3,2-c]pyridin-4-amine The desired product was prepared substituting 1,4-dioxa-8-azaspiro[4.5]decane for morpholine in Example 278B.

EXAMPLE 424B

N-{4-[4-amino-7-(1,4-dioxa-8-azaspiro[4.5]dec-8-ylmethyl)thieno[3,2-c]pyridin-3-yl]phenyl}-N'-[2-fluoro-5-(trifluoromethyl)phenyl]urea The desired product was prepared substituting Example 424A and N-[4-(4,4,5,5-tetramethyl-1,3,2-dioxaborolan-2-yl)phenyl]-N'-[2-fluoro-5-(trifluoromethyl)phenyl]urea for Example 1B and 4-phenoxyphenylboronic acid, respectively, in Example 10A. $^1$H NMR (300 MHz, DMSO-D$_6$) δ ppm 1.64 (t, J=5.3 Hz, 4H) 2.45–2.50 (m, 4H) 3.61 (s, 2H) 3.87 (s, 4H) 5.33 (s, 2H) 7.39–7.43 (m, 4H) 7.51 (m, 1H) 7.60 (d, J=8.5 Hz, 2H) 7.68 (s, 1H) 8.64 (dd, J=7.3, 2.2 Hz, 1H) 8.97 (d, J=2.7 Hz, 1H) 9.35 (s, 1H) MS (ESI(−)) m/e 600.3 (M−H)−.

EXAMPLE 425

N-{4-[4-amino-7-(1H-indol-5-yl)thieno[3,2-c]pyridin-3-yl]phenyl}-N'-(3-methylphenyl)urea

EXAMPLE 425A 3-(4-aminophenyl)-7-(1H-indol-5-yl)thieno[3,2-c]pyridin-4-amine The desired product was prepared substituting Example 77B, indole-5-boronic acid and PdCl$_2$(dppf) for Example 21A, 2-[(1E)-3,3-diethoxy-1-propenyl]-4,4,5,5-tetramethyl-1,3,2-dioxaborolane and Pd(PPh$_3$)$_4$, respectively, in Example 176A. MS (ESI(+)) m/e 357.0 (M+H)$^+$.

EXAMPLE 425B

N-{4-[4-amino-7-(1H-indol-5-yl)thieno[3,2-c]pyridin-3-yl]phenyl}-N'-(3-methylphenyl)urea The desired product was prepared by substituting Example 425A and 1-isocyanato-3-methylbenzene for Example 121B and 1-fluoro-2-isocyanato-4-(trifluoromethyl)benzene, respectively, in Example 122. $^1$H NMR (300 MHz, DMSO-D$_6$) δ ppm 2.29 (s, 3H) 5.42 (s, 2H) 6.50–6.51 (m, 1H) 6.81 (d, J=7.1 Hz, 1H) 7.17 (t, J=7.6 Hz, 1H) 7.24–7.27 (m, 1H) 7.32 (s, 1H) 7.35–7.45 (m, 5H) 7.53 (d, J=8.1 Hz, 1H) 7.62 (d, J=8.8 Hz, 2H) 7.79 (d, J=1.4 Hz, 1H) 7.88 (s, 1H) 8.66 (s, 1H) 8.86 (s, 1H) 11.21 (s, 1H) MS (ESI(+)) m/e 490.1 (M+H)$^+$.

EXAMPLE 426

3-(4-aminophenyl)-7-[3-(diethylamino)prop-1-ynyl]thieno[3,2-c]pyridin-4-amine

The desired product was prepared substituting Example 77B and diethyl-prop-2-ynylamine for Example 144A and 3-butyn-1-ol, respectively, in Example 144B. $^1$H NMR (300 MHz, DMSO-D$_6$) δ ppm 1.06 (t, J=7.1 Hz, 6H) 2.59 (q, J=7.1 Hz, 4H) 3.70 (s, 2H) 5.37 (s, 2H) 5.79 (s, 2H) 6.67 (d, J=8.5 Hz, 2H) 7.08 (d, J=8.5 Hz, 2H) 7.36 (s, 1H) 7.92 (s, 1H) MS (ESI(+)) m/e 351.0 (M+H)$^+$.

EXAMPLE 427

3-(4-aminophenyl)-7-[3-(dipropylamino)prop-1-ynyl]thieno[3,2-c]pyridin-4-amine

The desired product was prepared substituting Example 77B and dipropyl-prop-2-ynylamine for Example 144A and 3-butyn-1-ol, respectively, in Example 144B. $^1$H NMR (300 MHz, DMSO-D$_6$) δ ppm 0.89 (t, J=7.3 Hz, 6H) 1.41–1.54 (m, 4H) 2.46–2.51 (m, 4H) 3.66 (s, 2H) 5.37 (s, 2H) 5.78 (s, 2H) 6.67 (d, J=8.5 Hz, 2H) 7.08 (d, J=8.5 Hz, 2H) 7.36 (s, 1H) 7.91 (s, 1H) MS (ESI(+)) m/e 379.1 (M+H)$^+$.

EXAMPLE 428

3-(4-aminophenyl)-7-[3-(dimethylamino)prop-1-ynyl]thieno[3,2-c]pyridin-4-amine

The desired product was prepared substituting Example 77B and dimethyl-prop-2-ynylamine for Example 144A and 3-butyn-1-ol, respectively, in Example 144B. $^1$H NMR (300 MHz, DMSO-D$_6$) δ ppm 2.33 (s, 6H) 3.61 (s, 2H) 5.38 (s, 2H) 5.81 (s, 2H) 6.67 (d, J=8.1 Hz, 2H) 7.09 (d, J=8.1 Hz, 2H) 7.37 (s, 1H) 7.95 (s, 1H) MS (ESI(+)) m/e 323.0 (M+H)$^+$.

EXAMPLE 429

N-(4-{4-amino-7-[3-(diethylamino)prop-1-ynyl]thieno[3,2-c]pyridin-3-yl}phenyl)-N'-[2-fluoro-5-(trifluoromethyl)phenyl]urea The desired product was prepared by substituting Example 426 for Example 121B in Example 122. $^1$H NMR (300 MHz, DMSO-D$_6$) δ ppm 1.06 (t, J=7.1 Hz, 6H) 2.59 (q, J=7.1 Hz, 4H) 3.70 (s, 2H) 5.74 (s, 2H) 7.38–7.43 (m, 3H) 7.48–7.55 (m, 2H) 7.62 (d, J=8.8 Hz, 2H) 7.96 (s, 1H) 8.63 (dd, J=7.3, 2.2 Hz, 1H) 8.97 (d, J=2.7 Hz, 1H) 9.38 (s, 1H) MS (ESI(+)) m/e 556.1 (M+H)$^+$.

EXAMPLE 430

N-(4-{4-amino-7-[3-(diethylamino)prop-1-ynyl]thieno[3,2-c]pyridin-3-yl}phenyl)-N'-(2-fluoro-5-methylphenyl)urea The desired product was prepared by substituting Example 426 and 1-fluoro-2-isocyanato-4-methylbenzene for Example 121B and 1-fluoro-2-isocyanato-4-(trifluoromethyl)benzene, respectively, in Example 122. $^1$H NMR (300 MHz, DMSO-D$_6$) δ ppm 1.06 (t, J=7.1 Hz, 6H) 2.28 (s, 3H) 2.59 (q, J=7.1 Hz, 4H) 3.70 (s, 2H) 5.75 (s, 2H) 6.82 (ddd, J=7.8, 5.3, 2.0 Hz, 1H) 7.12 (dd, J=11.2, 8.5 Hz, 1H) 7.39 (d, J=8.5 Hz, 2H) 7.51 (s, 1H) 7.61 (d, J=8.5 Hz, 2H) 7.96 (s, 1H) 8.00 (dd, J=8.1, 2.0 Hz, 1H) 8.55 (d, J=2.4 Hz, 1H) 9.27 (s, 1H) MS (ESI(+)) m/e 502.1 (M+H)$^+$.

EXAMPLE 431

N-(4-{4-amino-7-[3-(diethylamino)prop-1-ynyl]thieno[3,2-c]pyridin-3-yl}phenyl)-N'-(3-chlorophenyl)urea The desired product was prepared by substituting Example 426 and 1-chloro-3-isocyanatobenzene for Example 121B and 1-fluoro-2-isocyanato-4-(trifluoromethyl)benzene, respectively, in Example 122. $^1$H NMR (300 MHz, DMSO-D$_6$) δ ppm 1.06 (t, J=7.1 Hz, 6H) 2.59 (q, J=7.1 Hz, 4H) 3.70 (s, 2H) 5.75 (s, 2H) 7.03 (td, J=4.4, 2.0 Hz, 1H) 7.29–7.32 (m, 2H) 7.38 (d, J=8.5 Hz, 2H) 7.51 (s, 1H) 7.61 (d, J=8.5 Hz, 2H) 7.72–7.73 (m, 1H) 7.96 (s, 1H) 8.96 (s, 1H) 8.97 (s, 1H) MS (ESI(+)) m/e 504.1 (M+H)$^+$.

EXAMPLE 432

N-(4-{4-amino-7-[3-(dipropylamino)prop-1-ynyl]thieno[3,2-c]pyridin-3-yl}phenyl)-N'-(3-methylphenyl)urea The desired product was prepared by substituting Example 427 and 1-isocyanato-3-methylbenzene for Example 121B and 1-fluoro-2-isocyanato-4-(trifluoromethyl)benzene, respectively, in Example 122. $^1$H NMR (300 MHz, DMSO-D$_6$) δ ppm 0.90 (t, J=7.5 Hz, 6H) 1.42–1.54 (m, 4H) 2.29 (s, 3H) 2.47–2.52 (m, 4H) 3.67 (s, 2H) 5.75 (s, 2H) 6.81 (d, J=7.8 Hz, 1H) 7.17 (t, J=7.8 Hz, 1H) 7.25 (d, J=8.5 Hz, 1H) 7.32 (s, 1H) 7.37 (d, J=8.5 Hz, 2H) 7.51 (s, 1H) 7.60 (d, J=8.5 Hz, 2H) 7.96 (s, 1H) 8.66 (s, 1H) 8.86 (s, 1H) MS (ESI(+)) m/e 512.2 (M+H)$^+$.

EXAMPLE 433

N-(4-{4-amino-7-[3-(dipropylamino)prop-1-ynyl]thieno[3,2-c]pyridin-3-yl}phenyl)-N'-[2-fluoro-5-(trifluoromethyl)phenyl]urea The desired product was prepared by substituting Example 427 for Example 121B in Example 122. $^1$H NMR (300 MHz, DMSO-D$_6$) δ ppm 0.90 (t, J=7.3 Hz, 6H) 1.42–1.54 (m, 4H) 2.47–2.52 (m, 4H) 3.67 (s, 2H) 5.74 (s, 2H) 7.38–7.43 (m, 3H) 7.52 (dd, J=11.2, 8.5 Hz, 1H) 7.53 (s, 1H) 7.62 (d, J=8.8 Hz, 2H) 7.96 (s, 1H) 8.63 (dd, J=7.5, 2.0 Hz, 1H) 8.98 (s, 1H) 9.39 (s, 1H) MS (ESI(+)) m/e 584.1 (M+H)$^+$.

EXAMPLE 434

N-(4-{4-amino-7-[3-(dipropylamino)prop-1-ynyl]thieno[3,2-c]pyridin-3-yl}phenyl)-N'-(2-fluoro-5-methylphenyl)urea The desired product was prepared by substituting Example 427 and 1-fluoro-2-isocyanato-4-methylbenzene for Example 121B and 1-fluoro-2-isocyanato-4-(trifluoromethyl)benzene, respectively, in Example 122. $^1$H NMR (300 MHz, DMSO-D$_6$) δ ppm 0.90 (t, J=7.3 Hz, 6H) 1.42–1.54 (m, 4H) 2.28 (s, 3H) 2.47–2.52 (m, 4H) 3.67 (s, 2H) 5.74 (s, 2H) 6.79–6.84 (m, 1H) 7.11 (dd, J=11.4, 8.3 Hz, 1H) 7.38 (d, J=8.5 Hz, 2H) 7.52 (s, 1H) 7.60 (d, J=8.5 Hz, 2H) 7.95 (s, 1H) 8.00 (dd, J=7.8, 2.0 Hz, 1H) 8.54 (d, J=2.7 Hz, 1H) 9.26 (s, 1H) MS (ESI(+)) m/e 530.2 (M+H)$^+$.

EXAMPLE 435

N-(4-{4-amino-7-[3-(dipropylamino)prop-1-ynyl]thieno[3,2-c]pyridin-3-yl}phenyl)-N'-(3-chlorophenyl)urea The desired product was prepared by substituting Example 427 and 1-chloro-3-isocyanatobenzene for Example 121B and 1-fluoro-2-isocyanato-4-(trifluoromethyl)benzene, respectively, in Example 122. $^1$H NMR (300 MHz, DMSO-D$_6$) δ ppm 0.90 (t, J=7.5 Hz, 6H) 1.42–1.54 (m, 4H) 2.47–2.52 (m, 4H) 3.67 (s, 2H) 5.74 (s, 2H) 7.03 (td, J=4.4, 2.0 Hz, 1H) 7.29–7.32 (m, 2H) 7.38 (d, J=8.5 Hz, 2H) 7.52 (s, 1H) 7.61 (d, J=8.5 Hz, 2H) 7.72–7.73 (m, 1H) 7.96 (s, 1H) 8.96 (s, 1H) 8.97 (s, 1H) MS (ESI(+)) m/e 532.1 (M+H)$^+$.

EXAMPLE 436

N-(4-{4-amino-7-[3-(dipropylamino)prop-1-ynyl]thieno[3,2-c]pyridin-3-yl}phenyl)-N'-[3-(trifluoromethyl)phenyl]urea The desired product was prepared by substituting Example 427 and 1-isocyanato-3-(trifluoromethyl)benzene for Example 121B and 1-fluoro-2-isocyanato-4-(trifluoromethyl)benzene, respectively, in Example 122. $^1$H NMR (300 MHz, DMSO-D$_6$) δ ppm 0.90 (t, J=7.3 Hz, 6H) 1.42–1.54 (m, 4H) 2.47–2.52 (m, 4H) 3.67 (s, 2H) 5.75 (s, 2H) 7.33 (d, J=7.5 Hz, 1H) 7.39 (d, J=8.5 Hz, 2H) 7.50–7.55 (m, 2H) 7.59–7.64 (m, 3H) 7.96 (s, 1H) 8.03 (s, 1H) 9.02 (s, 1H) 9.13 (s, 1H); MS (ESI(+)) m/e 566.2 (M+H)$^+$.

EXAMPLE 437

3-(4-aminophenyl)-7-pyrimidin-5-ylthieno[3,2-c]pyridin-4-amine

The desired product was prepared substituting Example 77B, pyrimidine-5-boronic acid and PdCl$_2$(dppf) for Example 21A, 2-[(1E)-3,3-diethoxy-1-propenyl]-4,4,5,5-tetramethyl-1,3,2-dioxaborolane and Pd(PPh$_3$)$_4$, respectively, in Example 176A. $^1$H NMR (300 MHz, DMSO-D$_6$) δ ppm 5.40 (s, 2H) 5.80 (s, 2H) 6.69 (d, J=8.5 Hz, 2H) 7.11 (d, J=8.5 Hz, 2H) 7.39 (s, 1H) 8.01 (s, 1H) 9.13 (s, 2H) 9.22 (s, 1H) MS (ESI(+)) m/e 320.0 (M+H)$^+$.

EXAMPLE 438

N-[4-(4-amino-7-pyrimidin-5-ylthieno[3,2-c]pyridin-3-yl)phenyl]-N'-(3-chlorophenyl)urea The desired product was prepared by substituting Example 437 and 1-chloro-3-isocyanatobenzene for Example 121B and 1-fluoro-2-isocyanato-4-(trifluoromethyl)benzene, respectively, in Example 122. $^1$H NMR (300 MHz, DMSO-D$_6$) δ ppm 5.74 (s, 2H) 7.04 (dt, J=6.1, 2.4 Hz, 1H) 7.30–7.33 (m, 2H) 7.42 (d, J=8.5 Hz, 2H) 7.55 (s, 1H) 7.63 (d, J=8.5 Hz, 2H) 7.73 (s, 1H) 8.04 (s, 1H) 8.98 (s, 1H) 9.00 (s, 1H) 9.14 (s, 2H) 9.23 (s, 1H) MS (ESI(+)) m/e 473.0 (M+H)$^+$.

EXAMPLE 439

N-[4-(4-amino-7-pyrimidin-5-ylthieno[3,2-c]pyridin-3-yl)phenyl]-N'-[3-(trifluoromethyl)phenyl]urea The desired product was prepared by substituting Example 437 and 1-isocyanato-3-(trifluoromethyl)benzene for Example 121B and 1-fluoro-2-isocyanato-4-(trifluoromethyl)benzene, respectively, in Example 122. $^1$H NMR (300 MHz, DMSO-D$_6$) δ ppm 5.74 (s, 2H) 7.33 (d, J=7.5 Hz, 1H) 7.42 (d, J=8.8 Hz, 2H) 7.53 (t, J=8.0 Hz, 1H) 7.55 (s, 1H) 7.59–7.66 (m, 3H) 8.03–8.04 (m, 2H) 9.03 (s, 1H) 9.14 (app. s., 3H) 9.23 (s, 1H) MS (ESI(+)) m/e 507.0 (M+H)$^+$.

EXAMPLE 440

3-(4-aminophenyl)-7-(2-methoxypyrimidin-5-yl)thieno[3,2-c]pyridin-4-amine

The desired product was prepared substituting Example 77B, 2-methoxypyrimidine-5-boronic acid and PdCl$_2$(dppf) for Example 21A, 2-[(1E)-3,3-diethoxy-1-propenyl]-4,4,5,5-tetramethyl-1,3,2-dioxaborolane and Pd(PPh$_3$)$_4$, respectively, in Example 176A. $^1$H NMR (300 MHz, DMSO-D$_6$) δ ppm 4.00 (s, 3H) 5.39 (s, 2H) 5.70 (br. s., 2H) 6.69 (d, J=8.5 Hz, 2H) 7.10 (d, J=8.5 Hz, 2H) 7.37 (s, 1H) 7.90 (s, 1H) 8.88 (s, 2H) MS (ESI(+)) m/e 350.0 (M+H)$^+$.

EXAMPLE 441

N-(4-{4-amino-7-[3-(dimethylamino)prop-1-ynyl]thieno[3,2-c]pyridin-3-yl}phenyl)-N'-(3-methylphenyl)urea The desired product was prepared by substituting Example 428 and 1-isocyanato-3-methylbenzene for Example 121B and 1-fluoro-2-isocyanato-4-(trifluoromethyl)benzene, respectively, in Example 122. $^1$H NMR (300 MHz, DMSO-D$_6$) δ ppm 2.29 (s, 3H) 2.30 (s, 6H) 3.56 (s, 2H) 5.75 (s, 2H) 6.80 (d, J=7.1 Hz, 1H) 7.17 (t, J=7.8 Hz, 1H) 7.25 (d, J=8.5 Hz, 1H) 7.31 (s, 1H) 7.38 (d, J=8.5 Hz, 2H) 7.51 (s, 1H) 7.60 (d, J=8.5H) 7.98 (s, 1H) 8.67 (s, 1H) 8.87 (s, 1H) MS (ESI(+)) m/e 456.1 (M+H)$^+$.

EXAMPLE 442

N-(4-{4-amino-7-[3-(dimethylamino)prop-1-ynyl]thieno[3,2-c]pyridin-3-yl}phenyl)-N'-[3-(trifluoromethyl)phenyl]urea The desired product was prepared by substituting Example 428 and 1-isocyanato-3-(trifluoromethyl)benzene for Example 121B and 1-fluoro-2-isocyanato-4-(trifluoromethyl)benzene, respectively, in Example 122. $^1$H NMR (300 MHz, DMSO-D$_6$) δ ppm 2.30 (s, 6H) 3.56 (s, 2H) 5.75 (s, 2H) 7.33 (d, J=7.5 Hz, 1H) 7.40 (d, J=8.5 Hz, 2H) 7.51 (s, 1H) 7.53 (t, J=7.8 Hz, 1H) 7.58–7.64 (m, 3H) 7.98 (s, 1H) 8.03 (s, 1H) 9.02 (s, 1H) 9.13 (s, 1H) MS (ESI(+)) m/e 510.1 (M+H)$^+$.

EXAMPLE 443

N-(4-{4-amino-7-[3-(dimethylamino)prop-1-ynyl]thieno[3,2-c]pyridin-3-yl}phenyl)-N'-[2-fluoro-5-(trifluoromethyl)phenyl]urea The desired product was prepared by substituting Example 428 for Example 121B in Example 122. $^1$H NMR (300 MHz, DMSO-D$_6$) δ ppm 2.30 (s, 6H) 3.56 (s, 2H) 5.75 (s, 2H) 7.38–7.44 (m, 3H) 7.48–7.55 (m, 2H) 7.62 (d, J=8.8 Hz, 2H) 7.98 (s, 1H) 8.63 (dd, J=7.3, 2.2 Hz, 1H) 8.97 (d, J=2.4 Hz, 1H) 9.38 (s, 1H) MS (ESI(+)) m/e 528.0 (M+H)$^+$.

EXAMPLE 444

N-(4-{4-amino-7-[3-(diethylamino)propyl]thieno[3,2-c]pyridin-3-yl}phenyl)-N'-(3-methylphenyl)urea A mixture of Example 153 (185 mg, 0.53 mmol) and 10% Pd/C (37 mg) in MeOH (10 mL) was stirred under hydrogen (60 psi) for 16 h. The catalyst was removed by filtration through Celite, and the filtrate was concentrated to dryness. The residue was purified by flash chromatography on silica gel to give the desired product (107 mg, 72%). $^1$H NMR (300 MHz, DMSO-D$_6$) δ ppm 0.95 (t, J=7.1 Hz, 6H) 1.73–1.82 (m, 2H) 2.29 (s, 3H) 2.41–2.50 (m, 6H) 2.68–2.73 (m, 2H) 5.25 (s, 2H) 6.80 (d, J=7.5 Hz, 1H) 7.17 (t, J=7.8 Hz, 1H) 7.25 (d, J=8.5 Hz, 1H) 7.31 (s, 1H) 7.36 (d, J=8.5 Hz, 2H) 7.43 (s, 1H) 7.59 (d, J=8.5 Hz, 2H) 7.68 (s, 1H) 8.66 (s, 1H) 8.85 (s, 1H) MS (ESI(+)) m/e 488.1 (M+H)$^+$.

EXAMPLE 445

N-[4-(4-amino-7-pyridin-2-ylthieno[3,2-c]pyridin-3-yl)phenyl]-N'-(3-methylphenyl)urea

EXAMPLE 445A tert-butyl 4-(4-amino-7-pyridin-2-ylthieno[3,2-c]pyridin-3-yl)phenylcarbamate A suspension of Example 77A (734 mg, 1.6 mmol) and pyridyl-2-trimethylstannane (418 mg, 1.72 mmol) in DME (12 mL) was degassed with nitrogen, and PdCl$_2$(o-tol$_3$P)$_2$ (62 mg, 0.078 mmol) and CuI (15 mg, 0.078 mmol) were added. The reaction vessel was sealed and the reaction was heated to 90° C. for 16 h. After cooling, the mixture was partitioned between EtOAc and H2O. The extracts were dried (Na2SO4) and concentrated, and the residue was purified by flash chromatography on silica gel, eluting with 40–75% EtOAc/hexanes to give the desired product (222 mg). MS (ESI(+)) m/e 419.0 (M+H)$^+$.

EXAMPLE 445B 3-(4-aminophenyl)-7-pyridin-2-ylthieno[3,2-c]pyridin-4-amine

The desired product was prepared by substituting Example 445A for Example 76B in Example 76C. MS (ESI(+)) m/e 319.0 (M+H)$^+$.

EXAMPLE 445C

N-[4-(4-amino-7-pyridin-2-ylthieno[3,2-c]pyridin-3-yl)phenyl]-N'-(3-methylphenyl)urea The desired product was prepared by substituting Example 445B for Example 1C in Example 1D. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give the desired product as the trifluoroacetic acid salt. $^1$H NMR (300 MHz, DMSO-D$_6$) δ ppm 2.29 (s, 3H) 6.81 (d, J=7.5 Hz, 1H) 6.89 (br. s., 2H) 7.17 (t, J=7.6 Hz, 1H) 7.27 (d, J=8.5 Hz, 1H) 7.33 (s, 1H) 7.44–7.48 (m, 3H) 7.66 (d, J=8.5 Hz, 2H) 7.85 (s, 1H) 8.00 (td, J=7.8, 1.7 Hz, 1H) 8.21 (d, J=8.1 Hz, 1H) 8.70 (s, 1H) 8.78–8.82 (m, 2H) 9.05 (s, 1H) MS (ESI(+)) m/e 452.1 (M+H)$^+$.

EXAMPLE 446

N-[4-(4-amino-7-pyridin-2-ylthieno[3,2-c]pyridin-3-yl)phenyl]-N'-[2-fluoro-5-(trifluoromethyl)phenyl]urea The desired product was prepared by substituting Example 445B and 1-fluoro-2-isocyanato-4-(trifluoromethyl)benzene for Example 1C and 1-isocyanato-3-methylbenzene, respectively, in Example 1D. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give the desired product as the trifluoroacetic acid salt. $^1$H NMR (300 MHz, DMSO-D$_6$) δ ppm 7.03 (br. s., 2H) 7.39–7.45 (m, 1H) 7.46–7.56 (m, 4H) 7.68 (d, J=8.5 Hz, 2H) 7.90 (s, 1H) 8.02 (td, J=7.8, 1.7 Hz, 1H) 8.22 (d, J=8.1 Hz, 1H) 8.63 (dd, J=7.3, 2.2 Hz, 1H) 8.71 (s, 1H) 8.80 (ddd, J=4.8, 1.8, 0.9 Hz, 1H) 9.02 (d, J=3.1 Hz, 1H) 9.48 (s, 1H) MS (ESI(+)) m/e 524.0 (M+H)$^+$.

EXAMPLE 447

N-[4-(4-amino-7-pyridin-2-ylthieno[3,2-c]pyridin-3-yl)phenyl]-N'-[3-(trifluoromethyl)phenyl]urea The desired product was prepared by substituting Example 445B and 1-isocyanato-3-(trifluoromethyl)benzene for Example 1C and 1-isocyanato-3-methylbenzene, respectively, in Example 1D. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give the desired product as the trifluoroacetic acid salt. $^1$H NMR (300 MHz, DMSO-D$_6$) δ ppm 6.99 (br. s., 2H) 7.33 (d, J=7.8 Hz, 1H) 7.45–7.50 (m, 3H) 7.54 (t, J=7.8 Hz, 1H) 7.62 (d, J=8.1 Hz, 1H) 7.69 (d, J=8.5 Hz, 2H) 7.90 (s, 1H) 8.02 (td, J=7.8, 2.0 Hz, 1H) 8.06 (s, 1H) 8.22 (d, J=8.1 Hz, 1H) 8.71 (s, 1H) 8.80 (ddd, J=4.8, 1.7, 1.0 Hz, 1H) 9.26 (s, 1H) 9.33 (s, 1H) MS (ESI(+)) m/e 506.0 (M+H)$^+$.

EXAMPLE 448

3-[4-amino-3-(1H-indol-6-yl)thieno[3,2-c]pyridin-7-yl]-N-methylpropanamide

The desired product was prepared by substituting Example 286 for Example 14 in Example 15. $^1$H NMR (300 MHz, DMSO-D$_6$) δ ppm 2.49 (m, 2H), 2.58 (d, J=4.8 Hz, 3H), 2.93 (t, J=7.6 Hz, 2H), 5.25 (br s, 2H), 6.52 (m, 1H), 7.04 (dd, J=8.14, 1.4 Hz, 1H), 7.44 (m, 3H), 7.66 (m, 2H), 7.81 (q, J=4.8 Hz, 1H), 11.28 (s, 1H); MS ESI(+) m/e 351 (M+H)$^+$.

EXAMPLE 449

3-[4-amino-3-(1H-indol-5-yl)thieno[3,2-c]pyridin-7-yl]-N-methylpropanamide

The desired product was prepared by substituting Example 29 for Example 14 in Example 15. $^1$H NMR (300 MHz, DMSO-D$_6$) δ ppm 2.49 (m, 2H), 2.57 (d, J=4.8 Hz, 2H), 2.92 (t, J=7.6 Hz, 1H), 5.23 (br s, 2H), 6.48 (m, 1H), 7.12 (dd, J=8.1, 1.7 Hz, 1H), 7.40 (s, 1H), 7.45 (m, 1H), 7.52 (d, J=8.1 Hz, 1H), 7.59 (s, 1H), 7.63 (s, 1H), 7.81 (q, J=3.7 Hz, 1H), 11.31 (br s, 1H); MS ESI(+) m/e 351 (M+H)$^+$.

EXAMPLE 450

3-[4-amino-3-(4-aminophenyl)thieno[3,2-c]pyridin-7-yl]-N-methylpropanamide

The desired product was prepared by substituting Example 112B for Example 14 in Example 15. $^1$H NMR (300 MHz, DMSO-D$_6$) δ ppm 2.45 (m, 2H), 2.56 (d, J=4.4 Hz, 3H), 2.90 (t, J=7.6 Hz, 2H), 5.34 (s, 4H), 6.66 (d, J=8.5 Hz, 2H), 7.07 (d, J=8.5 Hz, 2H), 7.29 (s, 1H), 7.61 (s, 1H), 7.79 (q, J=4.41 Hz, 1H); MS ESI(+) m/e 327 (M+H)$^+$.

EXAMPLE 451

7-(3-aminophenyl)-3-(4-aminophenyl)thieno[3,2-c]pyridin-4-amine

The desired product was prepared by substituting Example 77B and 3-aminophenylboronic acid for Example 1B and 4-phenoxyphenylboronic acid, respectively, in Example 10A. $^1$H NMR (300 MHz, DMSO-D$_6$) δ ppm 5.22 (br s, 2H), 5.35 (br s, 2H), 5.52 (br s, 2H), 6.57 (m, 1H), 6.68 (d, J=8.5 Hz, 2H), 6.77 (d, J=8.1 Hz, 1H), 6.83 (m, 1H), 7.12 (m, 3H), 7.31 (s, 1H), 7.78 (s, 1H); MS ESI(+) m/e 333 (M+H)$^+$.

EXAMPLE 452

3,7-bis(4-aminophenyl)thieno[3,2-c]pyridin-4-amine

The desired product was prepared by substituting Example 77B and 4-aminophenylboronic acid for Example 1B and 4-phenoxyphenylboronic acid, respectively, in Example 10A. $^1$H NMR (300 MHz, DMSO-D$_6$) δ ppm 5.23 (br s, 2H), 5.35 (br s, 2H), 5.42 (br s, 2H), 6.68 (d, J=7.8 Hz, 4H), 7.10 (d, J=8.5 Hz, 2H), 7.29 (m, 3H), 7.73 (s, 1H); MS ESI(+) m/e 333 (M+H)$^+$.

EXAMPLE 453

N-{3-[4-amino-3-(4-aminophenyl)thieno[3,2-c]pyridin-7-yl]phenyl}acetamide

The desired product was prepared by substituting Example 77B and 3-acetamidophenylboronic acid for Example 1B and 4-phenoxyphenylboronic acid, respectively, in Example 10A. $^1$H NMR (300 MHz, DMSO-D$_6$) δ ppm 2.07 (s, 3H), 5.38 (br s, 2H), 5.60 (br s, 2H), 6.68 (d, J=8.5 Hz, 2H), 7.11 (d, J=8.5 Hz, 2H), 7.30 (d, J=8.1 Hz, 1H), 7.34 (s, 1H), 7.42 (t, J=8.0 Hz, 1H), 7.58 (d, J=8.8 Hz, 1H), 7.84 (s, 1H), 7.95 (m, 1H), 10.06 (s, 1H); MS ESI(+)) m/e 375 (M+H)$^+$.

EXAMPLE 454

N-{4-[4-amino-3-(4-aminophenyl)thieno[3,2-c]pyridin-7-yl]phenyl}acetamide

The desired product was prepared by substituting Example 77B and 4-acetamidophenylboronic acid for Example 1B and 4-phenoxyphenylboronic acid, respectively, in Example 10A. $^1$H NMR (300 MHz, DMSO-D$_6$) δ ppm 2.08 (s, 3H), 5.36 (br s, 2H), 5.55 (br s, 2H), 6.68 (d, J=8.5 Hz, 2H), 7.10 (d, J=8.5 Hz, 2H), 7.32 (s, 1H), 7.57 (m, 2H), 7.70 (m, 2H), 7.83 (s, 1H), 10.05 (s, 1H); MS ESI(+) m/e 375 (M+H)$^+$.

EXAMPLE 455

3-(4-aminophenyl)-7-phenylthieno[3,2-c]pyridin-4-amine

The desired product was prepared by substituting Example 77B and phenylboronic acid for Example 1B and 4-phenoxyphenylboronic acid, respectively, in Example 10A. $^1$H NMR (400 MHz, DMSO-D$_6$) δ ppm 5.36 (br s, 2H), 5.58 (br s, 2H), 6.69 (d, J=8.3 Hz, 2H), 7.12 (d, J=8.3 Hz, 2H), 7.32 (s, 1H), 7.40 (t, J=7.4 Hz, 1H), 7.51 (t, J=7.7 Hz, 2H), 7.66 (d, J=7.4 Hz, 2H), 7.87 (s, 1H); MS ESI(+) m/e 318 (M+H)$^+$.

EXAMPLE 456

4-[4-amino-3-(4-aminophenyl)thieno[3,2-c]pyridin-7-yl]benzonitrile

The desired product was prepared by substituting Example 77B and 4-cyanophenylboronic acid for Example 1B and 4-phenoxyphenylboronic acid, respectively, in Example 10A. $^1$H NMR (300 MHz, DMSO-D$_6$) δ ppm 5.39 (s, 2H), 5.76 (br s, 2H), 6.69 (d, J=8.5 Hz, 2H), 7.11 (d, J=8.5 Hz, 2H), 7.38 (s, 1H), 7.89 (d, J=8.1 Hz, 2H), 7.97 (d, J=7.5 Hz, 3H); MS ESI(+) m/e 343 (M+H)$^+$.

EXAMPLE 457

N-{3-[4-amino-3-(4-aminophenyl)thieno[3,2-c]pyridin-7-yl]phenyl}methanesulfonamide The desired product was prepared by substituting Example 77B and 3-(methylsulfonylamino)phenylboronic acid for Example 1B and 4-phenoxyphenylboronic acid, respectively, in Example 10A. $^1$H NMR (300 MHz, DMSO-D$_6$) δ ppm 3.07 (s, 3H), 5.37 (s, 2H), 5.62 (br s, 2H), 6.68 (m, 2H), 7.11 (d, J=8.5 Hz, 2H), 7.22 (m, 1H), 7.37 (m, 2H), 7.47 (t, J=9.0 Hz, 1H), 7.53 (t, J=1.9 Hz, 1H), 7.86 (s, 1H), 9.91 (s, 1H); MS ESI(+)) m/e 411 (M+H)$^+$.

EXAMPLE 458

N-{4-[4-amino-3-(4-aminophenyl)thieno[3,2-c]pyridin-7-yl]phenyl}methanesulfonamide The desired product was prepared by substituting Example 77B and 4-(methylsulfonylamino)phenylboronic acid for Example 1B and 4-phenoxyphenylboronic acid, respectively, in Example 10A. $^1$H NMR (300 MHz, DMSO-D$_6$) δ ppm 3.06 (s, 3H), 5.37 (s, 2H), 5.57 (br s, 2H), 6.68 (d, J=8.5 Hz, 2H), 7.10 (d, J=8.5 Hz, 2H), 7.33 (t, J=4.2 Hz, 3H), 7.63 (d, J=8.8 Hz, 2H), 7.84 (s, 1H), 9.88 (s, 1H); MS ESI(+)) m/e 411 (M+H)$^+$.

EXAMPLE 459

3-(4-aminophenyl)-7-[2-phenylvinyl]thieno[3,2-c]pyridin-4-amine

The desired product was prepared by substituting Example 77B and phenylethyleneboronic acid for Example 1B and 4-phenoxyphenylboronic acid, respectively, in Example 10A. $^1$H NMR (300 MHz, DMSO-D$_6$) δ ppm 5.38 (s, 2H), 5.71 (br s, 2H), 6.69 (d, J=8.5 Hz, 2H), 7.13 (m, 3H), 7.26 (t, J=7.3 Hz, 1H), 7.39 (m, 4H), 7.62 (d, J=7.5 Hz, 2H), 8.11 (s, 1H); MS ESI(+)) m/e 344 (M+H)$^+$.

EXAMPLE 460

N-{4-[4-amino-7-(4-aminophenyl)thieno[3,2-c]pyridin-3-yl]phenyl}-N'-(3-methylphenyl)urea

EXAMPLE 460A

N-[4-(4-amino-7-iodothieno[3,2-c]pyridin-3-yl)phenyl]-N'-(3-methylphenyl)urea

The desired product was prepared by substituting Example 77B for Example 1C in Example 1D. $^1$H NMR (300 MHz, DMSO-D$_6$) δ ppm 2.29 (s, 3H), 5.59 (s, 2H), 6.81 (d, J=7.1 Hz, 1H), 7.17 (t, J=7.6 Hz, 1H), 7.25 (m, 1H), 7.31 (s, 1H), 7.37 (d, J=8.5 Hz, 2H), 7.53 (s, 1H), 7.60 (d, J=8.8 Hz, 2H), 8.01 (s, 1H), 8.65 (s, 1H), 8.86 (s, 1H); MS ESI(+)) m/e 501 (M+H)$^+$.

EXAMPLE 460B

N-{4-[4-amino-7-(4-aminophenyl)thieno[3,2-c]pyridin-3-yl]phenyl}-N'-(3-methylphenyl)urea The desired product was prepared by substituting Example 460A and 4-aminophenylboronic acid for Example 1B and 4-phenoxyphenylboronic acid, respectively, in Example 10A. $^1$H NMR (300 MHz, DMSO-D$_6$) δ ppm 2.29 (s, 3H), 5.41 (m, 4H), 6.69 (d, J=8.5 Hz, 2H), 6.81 (d, J=7.5 Hz, 1H), 7.17 (t, J=7.8 Hz, 1H), 7.29 (m, 4H), 7.39 (d, J=8.5 Hz, 2H), 7.45 (s, 1H), 7.61 (d, J=8.5 Hz, 2H), 7.77 (s, 1H), 8.67 (s, 1H), 8.87 (s, 1H); MS ESI(+)) m/e 466 (M+H)$^+$.

EXAMPLE 461

N-{4-[4-amino-7-(3-aminophenyl)thieno[3,2-c]pyridin-3-yl]phenyl}-N'-(3-methylphenyl)urea The desired product was prepared by substituting Example 460A and 3-aminophenylboronic acid for Example 1B and 4-phenoxyphenylboronic acid, respectively, in Example 10A. $^1$H NMR (300 MHz, DMSO-D$_6$) δ ppm 2.29 (s, 3H), 5.23 (s, 2H), 5.47 (s, 2H), 6.59 (dd, J=8.1, 1.4 Hz, 1H), 6.79 (t, J=7.8 Hz, 2H), 6.84 (m, J=2.0 Hz, 1H), 7.16 (m, 2H), 7.26 (m, 1H), 7.31 (m, 1H), 7.40 (d, J=8.8 Hz, 2H), 7.45 (s, 1H), 7.61 (d, J=8.5 Hz, 2H), 7.82 (s, 1H), 8.66 (s, 1H), 8.86 (s, 1H); MS ESI(+)) m/e 466 (M+H)$^+$.

EXAMPLE 462

N-(4-{4-amino-7-[4-(dimethylamino)phenyl]thieno[3,2-c]pyridin-3-yl}phenyl)-N'-(3-methylphenyl)urea The desired product was prepared by substituting Example 460A and 4-(N,N-dimethylamino)phenylboronic acid for Example 1B and 4-phenoxyphenylboronic acid, respectively, in Example 10A. $^1$H NMR (300 MHz, DMSO-D$_6$) δ ppm 2.29 (s, 3H), 2.96 (s, 6H), 5.40 (br s, 2H), 6.81 (d, J=7.5 Hz, 1H), 6.86 (d, J=8.8 Hz, 2H), 7.17 (t, J=7.6 Hz, 1H), 7.26 (m, 1H), 7.32 (s, 1H), 7.39 (d, J=8.8 Hz, 2H), 7.44 (m, 1H), 7.48 (d, J=8.8 Hz, 2H), 7.61 (d, J=8.8 Hz, 2H), 7.81 (s, 1H), 8.66 (s, 1H), 8.85 (s, 1H); MS ESI(+)) m/e 494 (M+H)$^+$.

EXAMPLE 463

N-{4-[4-amino-7-(4-formylphenyl)thieno[3,2-c]pyridin-3-yl]phenyl}-N'-(3-methylphenyl)urea The desired product was prepared by substituting Example 460A and 4-formylphenylboronic acid for Example 1B and 4-phenoxyphenylboronic acid, respectively, in Example 10A. $^1$H NMR (300 MHz, DMSO-D$_6$) δ ppm 2.29 (s, 3H), 5.71 (br s, 2H), 6.81 (d, J=7.1 Hz, 1H), 7.17 (t, J=7.6 Hz, 1H), 7.26 (m, 1H), 7.32 (s, 1H), 7.41 (d, J=8.5 Hz, 2H), 7.52 (s, 1H), 7.62 (d, J=8.5 Hz, 2H), 7.94 (d, J=8.5 Hz, 2H), 8.06 (m, 3H), 8.68 (s, 1H), 8.88 (s, 1H), 10.07 (s, 1H); MS ESI(+)) m/e 479 (M+H)$^+$.

EXAMPLE 464

N-(4-{4-amino-7-[3-oxoprop-1-enyl]thieno[3,2-c]pyridin-3-yl}phenyl)-N'-(3-methylphenyl)urea

EXAMPLE 464A

N-(4-{4-amino-7-[3,3-diethoxyprop-1-enyl]thieno[3,2-c]pyridin-3-yl}phenyl)-N'-(3-methylphenyl)urea The desired product was prepared by substituting Example 460A for Example 21A in Example 176A. $^1$H NMR (300 MHz, DMSO-D$_6$) δ ppm 1.19 (m, 6H), 2.29 (s, 3H), 3.54 (m, 2H), 3.65 (m, 2H), 5.13 (d, J=5.1 Hz, 1H), 5.65 (br s, 2H), 6.18 (t, J=4.6 Hz, 1H), 6.83 (m, 2H), 7.17 (t, J=7.8 Hz, 1H), 7.25 (m, 1H), 7.32 (s, 1H), 7.38 (d, J=8.8 Hz, 2H), 7.52 (s, 1H), 7.60 (d, J=8.8 Hz, 2H), 7.99 (s, 1H), 8.65 (s, 1H), 8.86 (s, 1H); MS ESI(+) m/e 503 (M+H)$^+$.

EXAMPLE 464B

N-(4-{4-amino-7-[3-oxoprop-1-enyl]thieno[3,2-c]pyridin-3-yl}phenyl)-N'-(3-methylphenyl)urea The desired product was prepared by substituting Example 464A for Example 176B in Example 176C. $^1$H NMR (300 MHz, DMSO-D$_6$) δ ppm 2.29 (s, 3H), 6.66 (dd, J=16.0, 7.46 Hz, 1H), 6.81 (d, J=7.5 Hz, 1H), 7.17 (t, J=7.8 Hz, 1H), 7.26 (m, 1H), 7.32 (s, 1H), 7.40 (d, J=8.5 Hz, 2H), 7.63 (apparent d, J=8.8 Hz, 3H), 7.89 (d, J=16.0 Hz, 1H), 8.31 (s, 1H), 8.67 (s, 1H), 8.88 (s, 1H), 9.66 (d, J=7.5 Hz, 1H); MS ESI(+)) m/e 429 (M+H)$^+$.

EXAMPLE 465

N-(4-{4-amino-7-[3-(diethylamino)prop-1-enyl]thieno[3,2-c]pyridin-3-yl}phenyl)-N'-(3-methylphenyl)urea The desired product was prepared by substituting Example 464B for Example 176C in Example 177. $^1$H NMR (300 MHz, DMSO-D$_6$) δ ppm 1.03 (t, J=7.1 Hz, 6H), 2.29 (s, 3H) 2.57 (br m, 4H) 5.56 (br s, 2H), 6.24 (dt, J=18.0,6.0 Hz, 1H) 6.77 (d, J=18.0 Hz, 1H) 6.80 (d, J=7.1 Hz, 1H), 7.17 (t, J=7.6 Hz, 1H), 7.32 (s, 1H), 7.26 (d, J=9.0 Hz, 1H) 7.37 (d, J=8.5 Hz, 2H), 7.50 (s, 1H), 7.60 (d, J=8.8 Hz, 2H), 7.93 (s, 1H), 8.69 (s, 1H), 8.90 (s, 1H); MS ESI(+)) m/e 486 (M+H)$^+$.

EXAMPLE 466

3-[4-amino-3-(2-methyl-1H-indol-5-yl)thieno[3,2-c]pyridin-7-yl]-N-[2-(diethylamino)ethyl]acrylamide

EXAMPLE 466A tert-butyl 3-(4-amino-3-bromothieno[3,2-c]pyridin-7-yl)acrylate

The desired product was prepared by substituting Example 21A for Example 10B in Example 11A.

EXAMPLE 466B 3-(4-amino-3-bromothieno[3,2-c]pyridin-7-yl)acrylic acid

The desired product was prepared by substituting Example 466A for Example 11A in Example 11B.

EXAMPLE 466C 3-(4-amino-3-bromothieno[3,2-c]pyridin-7-yl)-N-[2-(diethylamino)ethyl]acrylamide The desired product was prepared by substituting Example 466B and N,N-diethylethane-1,2-diamine for Example 11B and piperazin-2-one, respectively, in Examples 11C. MS ESI(+) m/e 397.0, 398.6 (M+H)$^+$.

EXAMPLE 466D

3-[4-amino-3-(2-methyl-1H-indol-5-yl)thieno[3,2-c]pyridin-7-yl]-N-[2-(diethylamino)ethyl]acrylamide The desired product was prepared by substituting Example 466C and 2-methyl-1H-indol-5-ylboronic acid for Example 21B and 4-chlorophenylboronic acid in Example 21C. $^1$H NMR (300 MHz, DMSO-D$_6$) δ ppm 1.23 (t, J=7.3 Hz, 6H), 2.43 (s, 3H), 3.18–3.27 (m, 6H), 3.57 (q, J=5.8 Hz, 2H), 6.22 (s, 1H), 6.71 (d, J=15.9 Hz, 1H), 7.08 (dd, J=8.3, 1.5 Hz, 1H), 7.44 (d, J=8.1 Hz, 1H), 7.51 (s, 1H), 7.67 (d, J=15.9 Hz, 1H), 7.79 (s, 1H), 8.22 (s, 1H), 8.62 (t, J=5.4 Hz, 1H), 9.11–9.19 (m, 1H), 11.24 (s, 1H); MS (ESI(+)) m/e 448.2 (M+H)$^+$.

EXAMPLE 467

N-{4-[4-amino-7-(2-methyl-1H-indol-5-yl)thieno[3,2-c]pyridin-3-yl]phenyl}-N'-(3-methylphenyl)urea

EXAMPLE 467A 2-methyl-5-(4,4,5,5-tetramethyl-1,3,2-dioxaborolan-2-yl)-1H-indole

A solution of 5-bromo-2-methyl-1H-indole (5.04 g, 24 mmol) in THF (25 mL) was added dropwise to a suspension of potassium hydride (3.2 g, 24 mmol) in THF at 0° C. After fifteen minutes at 0° C., the solution was cooled to −78° C. and a t-butyl lithium solution (1.7 M in pentane, 28.2 mL, 48 mmol) was added dropwise via syringe while maintaining the temperature below −55° C. After an additional 15 minutes, the solution was cooled to −78° C. and treated with a 2-isopropoxy-4,4,5,5-tetramethyl-[1,3,2]dioxaborolane (9.8 mL, 48 mmol) dropwise via syringe. The solution was stirred at −78° C. for 1.5 hours, allowed to warm to room temperature and quenched with saturated aqueous ammonium chloride. The solution was diluted with ethyl acetate and filtered to remove inorganic material. The filtrate was extracted with ethyl acetate. The combined organics were washed with brine, dried (MgSO$_4$) and concentrated. The concentrate was purified by flash chromatography on silica gel using 10% ethyl acetate/hexanes to give 3.9 g (63% yield) of the desired product. MS (ESI(+)) m/e 258 (M+H)$^+$.

EXAMPLE 467B 3-(4-aminophenyl)-7-(2-methyl-1H-indol-5-yl)thieno[3,2-c]pyridin-4-amine The desired product was prepared by substituting Example 77B, Example 467A, and PdCl$_2$(dppf) for Example 21A, 2-[(1E)-3,3-diethoxy-1-propenyl]-4,4,5,5,-tetramethyl-1,3,2-dioxaborolane and Pd(PPh$_3$)$_4$, respectively, in Example 176A. MS ESI(+)) m/e 371.1 (M+H)$^+$.

EXAMPLE 467C

N-{4-[4-amino-7-(2-methyl-1H-indol-5-yl)thieno[3,2-c]pyridin-3-yl]phenyl}-N'-(3-methylphenyl)urea The desired product was prepared by substituting Example 467B and 1-isocyanato-3-methylbenzene for Example 121B and 1-fluoro-2-isocyanato-4-(tricluoromethyl)benzene, respectively in Example 122. $^1$H NMR (300 MHz, DMSO-D$_6$) δ ppm 2.29 (s, 3H), 2.42 (s, 3H), 5.40 (s, 2H), 6.19 (s, 1H), 6.81 (d, J=7.5 Hz, 1H), 7.17 (t, J=7.8 Hz, 1H), 7.25–7.28 (m, 2H), 7.32 (s, 1H), 7.39 (d, J=8.1 Hz, 1H), 7.40 (d, J=8.5 Hz, 2H), 7.44 (s, 1H), 7.61 (d, J=8.5 Hz, 2H), 7.64 (d, J=1.4 Hz, 1H), 7.86 (s, 1H), 8.67 (s, 1H), 8.87 (s, 1H), 11.03 (s, 1H); MS (ESI(+)) m/e 504.2 (M+H)$^+$.

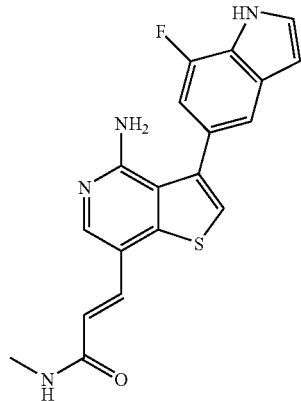

EXAMPLE 468

3-[4-amino-3-(7-fluoro-1H-indol-5-yl)thieno[3,2-c]pyridin-7-yl]-N-methylacrylamide

EXAMPLE 468A 3-fluoro-4-nitrophenyl trifluoromethanesulfonate

A solution of 3-fluoro-4-nitro-phenol (2.0 g, 12.7 mmol) in dichloromethane (100 mL) at 0° C. was treated with trifluoroaceticmethanesulfonic anhydride (5.0 g, 17.7 mmol), followed by the slow addition of triethylamine (7.1 mL. 50.9 mmol). The solution was stirred at room temperature for three hours, poured into water, extracted with dichloromethane. The combined organic layers were dried (Na$_2$SO$_4$), filtered and concentrated. The residue was purified by flash chromatography on silica gel using 10% ethyl acetate/hexanes to provide 3.5 g (95% yield) of the desired product. MS (ESI(+)) m/e 288 (M+H)$^+$.

EXAMPLE 468B 7-fluoro-1H-indol-5-yl trifluoromethanesulfonate

A solution of 468A (1.5 g, 5.2 mmol) in THF (65 mL) at −40° C. was treated dropwise with a solution of vinylmagnesium bromide (1.0 M solution in THF, 15.6 mL, 15.6 mmol). The solution was stirred at −40° C. for two hours, quenched with saturated ammonium chloride, warmed to room temperature, partitioned between water and ethyl acetate. The aqueous layer was extracted with ethyl acetate. The combined organic layers were washed with brine, dried (Na$_2$SO$_4$), filtered and concentrated. The residue was purified by flash chromatography on silica gel using 5–15% ethyl acetate/hexanes to provide 270 mg (18% yield) of the desired product. MS (ESI(−)) m/e 282 (M−H)$^-$.

EXAMPLE 468C 7-fluoro-5-(4,4,5,5-tetramethyl-1,3,2-dioxaborolan-2-yl)-1H-indole A solution of Example 468B (270 mg, 0.95 mmol), bis(pinacolato)diboron (292 mg, 1.15 mmol) and potassium acetate (262 mg, 2.66 mmol) in DMF was purged with nitrogen, treated with PdCl$_2$(dppf), heated to 90° C. overnight, cooled to room temperature, filtered through celite, washing with ethyl acetate and concentrated. The residue was purified by flash chromatography on silica gel using 3–5% ethyl acetate/hexanes to give 160 mg (65% yield) of the desired product. MS (ESI(−)) m/e 260 (M−H)$^-$.

EXAMPLE 468D

3-[4-amino-3-(7-fluoro-1H-indol-5-yl)thieno[3,2-c]pyridin-7-yl]-N-methylacrylamide The desired product was prepared by substituting Example 468C for 4-chlorophenylboronic acid in Example 21C. $^1$H NMR (300 MHz, DMSO-D$_6$) δ ppm 2.73 (d, J=4.8 Hz, 3H), 5.78–5.87 (br. s, 2H), 6.56–6.63 (m, 2H), 7.04 (dd, J=11.9, 1.4 Hz, 1H), 7.48 (d, J=1.4 Hz, 1H), 7.54 (d, J=3.4 Hz, 1H), 7.58 (d, J=15.6 Hz, 1H), 7.64 (s, 1H), 8.11 (s, 1H), 8.13–8.17 (m, 1H), 11.85 (s, 1H); MS (ESI(+)) m/e 367.2 (M+H)$^+$.

EXAMPLE 469

N-{4-[4-amino-7-(2-methyl-1H-indol-5-yl)thieno[3,2-c]pyridin-3-yl]phenyl}-N'-[3-(trifluoromethyl)phenyl]urea The desired product was prepared by substituting Example 467B and 1-isocyanato-3-(trifluoromethyl)benzne for Example 121B and 1-fluoro-2-isocyanato-4-(trifluoromethyl)benzene, repectively, in Example 122. $^1$H NMR (300 MHz, DMSO-D$_6$) δ ppm 2.42 (s, 3H), 5.40 (s, 2H), 6.19 (s, 1H), 7.26 (dd, J=8.1, 1.7 Hz, 1H), 7.33 (d, J=7.8 Hz, 1H), 7.39 (d, J=8.1 Hz, 1H), 7.42 (d, J=8.5 Hz, 2H), 7.45 (s, 1H), 7.53 (t, J=8.0 Hz, 1H), 7.60–7.64 (m, 4H), 7.86 (s, 1H), 8.04 (s, 1H), 9.04 (s, 1H), 9.16 (s, 1H), 11.04 (s, 1H); MS (ESI(+)) m/e 558.2 (M+H)$^+$.

EXAMPLE 470

N-{4-[4-amino-7-(2-methyl-1H-indol-5-yl)thieno[3,2-c]pyridin-3-yl]phenyl}-N'-[2-fluoro-5-(trifluoromethyl)phenyl]urea The desired product was prepared by substituting Example 467B and 1-fluoro-2-isocyanto-4-(trifluoromethyl)benzene for Example 1C and 1-isocyanato-3-methylbenzene, respectively, in Example 1D. $^1$H NMR (300 MHz, DMSO-D$_6$) δ ppm 2.42 (s, 3H), 5.39 (s, 2H), 6.19 (s, 1H), 7.26 (dd, J=8.48, 1.70 Hz, 1H), 7.42 (m, 5H), 7.54 (m, 1H), 7.63 (m, 3H), 7.86 (s, 1H), 8.64 (dd, J=7.12, 2.03 Hz, 1H), 8.98 (d, J=2.71 Hz, 1H), 9.38 (s, 1H), 11.03 (s, 1H); MS (ESI(+)) m/e 576.1 (M+H)$^+$.

EXAMPLE 471

N-{4-[4-amino-7-(2-methyl-1H-indol-5-yl)thieno[3,2-c]pyridin-3-yl]phenyl}-N'-(2-fluoro-5-methylphenyl)urea The desired product was prepared by substituting Example 467B for Example 121B in Example 122. $^1$H NMR (300 MHz, DMSO-D$_6$) δ ppm 2.29 (s, 3H), 2.42 (s, 3H), 5.39 (s, 2H), 6.19 (s, 1H), 6.79–6.84 (m, 1H), 7.12 (dd, J=11.2, 8.5 Hz, 1H), 7.26 (dd, J=8.5, 1.9 Hz, 1H), 7.37–7.44 (m, 1H), 7.42 (d, J=8.8 Hz, 2H), 7.44 (s, 1H), 7.61 (d, J=8.8 Hz, 2H), 7.64 (d, J=1.7 Hz, 1H), 7.86 (s, 1H), 8.01 (dd, J=7.8, 2.0 Hz, 1H), 8.56 (d, J=2.7 Hz, 1H), 9.27 (s, 1H), 11.03 (s, 1H); MS (ESI(+)) m/e 522.2 (M+H)$^+$.

EXAMPLE 472

3-[4-amino-3-(7-fluoro-2-methyl-1H-indol-5-yl)thieno[3,2-c]pyridin-7-yl]-N-methylacrylamide

EXAMPLE 472A 7-fluoro-2-methyl-1H-indol-5-yl trifluoromethanesulfonate

The desired product was prepared by substituting isopropenylmagnesium bromide for vinylmagnesium bromide in Example 468B. MS (ESI(−)) m/e 296 (M−H)$^−$.

EXAMPLE 472B 7-fluoro-2-methyl-5-(4,4,5,5-tetramethyl-1,3,2-dioxaborolan-2-yl)-1H-indole The desired product was prepared by substituting Example 472A for Example 468B in Example 468C. MS ESI(+)) m/e 276.1 (M+H)$^+$.

EXAMPLE 472C

3-[4-amino-3-(7-fluoro-2-methyl-1H-indol-5-yl)thieno[3,2-c]pyridin-7-yl]-N-methylacrylamide The desired product was prepared by substituting Example 472B for 4-chlorophenylboronic acid in Example 21C. $^1$H NMR (300 MHz, DMSO-D$_6$) δ ppm 2.43 (s, 3H), 2.73 (d, J=4.8 Hz, 3H), 5.82 (s, 2H), 6.30 (br. s., 1H), 6.58 (d, J=15.9 Hz, 1H), 6.94 (dd, J=11.9, 1.4 Hz, 1H), 7.32 (s, 1H), 7.58 (d, J=15.9 Hz, 1H), 7.62 (s, 1H), 8.10 (s, 1H), 8.15 (q, J=4.8 Hz, 1H), 11.64 (s, 1H); MS (ESI(+)) m/e 381.3 (M+H)$^+$.

EXAMPLE 473

3-[4-amino-3-(2-methyl-1H-indol-5-yl)thieno[3,2-c]pyridin-7-yl]-N-[3-(1H-imidazol-1-yl)propyl]acrylamide

EXAMPLE 473A 3-(4-amino-3-bromothieno[3,2-c]pyridin-7-yl)-N-[3-(1H-imidazol-1-yl)propyl]acrylamide The desired product was prepared by substituting Example 291A for Example 78 in Example 96.

EXAMPLE 473B 3-(4-amino-3-bromothieno[3,2-c]pyridin-7-yl)-N-[3-(1H-imidazol-1-yl)propyl]acrylamide The desired product was prepared by substituting Example 473A and Example 467A for Example 21 and 4-chlorophenylboronic acid in Example 21C. $^1$H NMR (300 MHz, DMSO-D$_6$) δ ppm 2.01–2.10 (m, 2H), 2.43 (s, 3H), 3.24 (q, J=6.0 Hz, 2H), 4.26 (t, J=7.1 Hz, 2H), 6.23 (s, 1H), 6.73 (d, J=15.9 Hz, 1H), 7.08 (dd, J=8.5, 1.7 Hz, 1H), 7.44 (d, J=7.1 Hz, 1H), 7.52–7.53 (m, 1H), 7.63 (d, J=15.9 Hz, 1H), 7.72 (t, J=1.7 Hz, 1H), 7.84–7.85 (m, 2H), 8.21 (s, 1H), 8.46 (t, J=5.4 Hz, 1H), 9.14 (s, 1H), 11.24 (s, 1H); MS (ESI(+)) m/e 457.2 (M+H)$^+$.

EXAMPLE 474

N-{4-[4-amino-7-(1H-indol-6-yl)thieno[3,2-c]pyridin-3-yl]phenyl}-N'-(3-methylphenyl)urea

EXAMPLE 474A 1H-indol-6-ylboronic acid

A solution of 6-Bromo-1H-indole (1.5 g, 7.65 mmol) in THF (10 mL) was added dropwise to a suspension of potassium hydride (0.31 g, 7.65 mmol) in THF at 0° C. After fifteen minutes at 0° C., the solution was cooled to −78° C. and a t-butyl lithium solution (1.7 M in pentane, 9.0 mL, 15.3 mmol) was added dropwise via syringe while maintaining a temperature below −55° C. After 15 minutes, the solution was cooled to −78° C. and treated with a tributyl borate (4.14 mL, 15.3 mmol). The solution was stirred at −78° C. for 2 hours and then allowed to warm to −10° C. The solution was the added 75 mL of 1 M HCl, warmed to room temperature and separated. The aqueous phase was extracted with diethyl ether (3×75 mL) and the combined organics were extracted with 1 M NaOH (4×40 mL). The aqueous layers were combined, adjusted to pH ~2 with 6 M HCl and extracted with diethyl ether (4×50 mL). The combined organic layers were washed with brine (20 mL), dried (MgSO$_4$), filtered and concentrated. The concentrate was purified by flash chromatography on silica gel using 3.5–5% methanol/dichloromethane to give 838 mg (68% yield) of the desired product. MS (ESI(+)) m/e 161 (M+H)$^+$.

EXAMPLE 474B 3-(4-aminophenyl)-7-(1H-indol-6-yl)thieno[3,2-c]pyridin-4-amine The desired product was prepared by substituting Example 77B, Example 474A, and PdCl$_2$(dppf) for Example 21A, 2-[(1E)-3,3-diethoxy-1-propenyl]-4,4,5,5,-tetramethyl-1,3,2-dioxaborolane and Pd(PPh$_3$)$_4$, respectively, in Example 176A. $^1$H NMR (300 MHz, DMSO-D$_6$) δ ppm 5.36 (s, 2H), 5.50 (s, 2H), 6.48 (ddd, J=3.0, 1.9, 0.9 Hz, 1H), 6.69 (d, J=8.5 Hz, 2H), 7.12 (d, J=8.5 Hz, 2H), 7.27 (dd, J=8.3, 1.5 Hz, 1H), 7.32 (s, 1H), 7.39–7.41 (m, 1H), 7.64–7.66 (m, 2H), 7.87 (s, 1H), 11.20 (s, 1H); MS (ESI(+)) m/e 357.2 (M+H)$^+$.

EXAMPLE 474C

N-{4-[4-amino-7-(1H-indol-6-yl)thieno[3,2-c]pyridin-3-yl]phenyl}-N'-(3-methylphenyl)urea The desired product was prepared by substituting Example 474B and 1-isocyanato-3-methylbenzene for Example 121B and 1-fluoro-2-isocyanato-4-(trifluoromethyl)benzene, respectively, in Example 122. $^1$H NMR (300 MHz, DMSO-D$_6$) δ ppm 2.29 (s, 3H), 5.45 (s, 2H), 6.49 (ddd, J=3.0, 2.1, 0.7 Hz, 1H), 6.81 (d, J=7.1 Hz, 1H), 7.17 (t, J=7.6 Hz, 1H), 7.25 (s, 1H), 7.29 (dd, J=8.3, 1.5 Hz, 1H), 7.32–7.33 (m, 1H), 7.40–7.43 (m, 3H), 7.46 (s, 1H), 7.62 (d, J=8.8 Hz, 2H), 7.66–7.67 (m, 1H), 7.66 (d, J=8.1 Hz, 1H), 7.91 (s, 1H), 8.68 (s, 1H), 8.88 (s, 1H), 11.21 (s, 1H); MS (ESI(+)) m/e 490.2 (M+H)$^+$.

EXAMPLE 475

N-{4-[4-amino-7-(1H-indol-6-yl)thieno[3,2-c]pyridin-3-yl]phenyl}-N'-[3-(trifluoromethyl)phenyl]urea The desired product was prepared by substituting Example 474B and 1-isocyanato-3-(trifluoromethyl)benzene for Example 121B and 1-fluoro-2-isocyanato-4-(trifluoromethyl)benzene, respectively, in Example 122. $^1$H NMR (300 MHz, DMSO-D$_6$) δ ppm 5.45 (s, 2H), 6.48–6.50 (m, 1H), 7.29 (dd, J=8.3, 1.5 Hz, 1H), 7.33 (d, J=7.8 Hz, 1H), 7.40–7.45 (m, 3H), 7.47 (s, 1H), 7.53 (t, J=8.0 Hz, 1H), 7.60–7.68 (m, 5H), 7.91 (s, 1H), 8.04 (s, 1H), 9.02 (s, 1H), 9.14 (s, 1H), 11.22 (s, 1H); MS (ESI(+)) m/e 544.2 (M+H)$^+$.

EXAMPLE 476

N-{4-[4-amino-7-(1H-indol-6-yl)thieno[3,2-c]pyridin-3-yl]phenyl}-N'-[2-fluoro-5-(trifluoromethyl)phenyl]urea The desired product was prepared by substituting Example 474B for Example 121B in Example 122. $^1$H NMR (300 MHz, DMSO-D$_6$) δ ppm 5.44 (s, 2H), 6.49 (d, J=2.7 Hz, 1H), 7.29 (dd, J=8.3, 1.5 Hz, 1H), 7.39–7.42 (m, 2H), 7.45 (d, J=8.5 Hz, 2H), 7.48 (s, 1H), 7.49–7.55 (m, 1H), 7.64 (d, J=8.5 Hz, 2H), 7.66–7.68 (m, 2H), 7.91 (s, 1H), 8.65 (dd, J=7.3, 2.5 Hz, 1H), 8.99 (s, 1H), 9.39 (s, 1H), 11.22 (s, 1H); MS (ESI(+)) m/e 562.1 (M+H)$^+$.

EXAMPLE 477

3-[4-amino-3-(1-benzothien-5-yl)thieno[3,2-c]pyridin-7-yl]-N-methylacrylamide

EXAMPLE 477A 2-(1-benzothien-5-yl)-4,4,5,5-tetramethyl-1,3,2-dioxaborolane

The desired product was prepared by substituting 5-bromo-benzo[b]thiophene (commercially available) for Example 468B in Example 468C. MS ESI(+)) m/e 277.1 (M+NH$_4$)$^+$.

EXAMPLE 477B

3-[4-amino-3-(1-benzothien-5-yl)thieno[3,2-c]pyridin-7-yl]-N-methylacrylamide

The desired product was prepared by substituting Example 477A for 4-chlorophenylboronic acid in Example 21C. $^1$H NMR (300 MHz, DMSO-D$_6$) δ ppm 2.75 (d, J=4.8 Hz, 3H), 6.45 (s, 2H), 6.71 (d, J=15.9 Hz, 1H), 7.48 (dd, J=8.3, 1.5 Hz, 1H), 7.56 (d, J=5.4 Hz, 1H), 7.61 (d, J=15.9 Hz, 1H), 7.90 (s, 1H), 7.92 (d, J=5.4 Hz, 1H), 8.04 (d, J=1.4 Hz, 1H), 8.19–8.22 (m, 2H), 8.26 (q, J=4.8 Hz, 1H); MS (ESI(+)) m/e 366.0 (M+H)$^+$.

EXAMPLE 478

3-{4-amino-3-[2-(trifluoromethyl)-1H-indol-5-yl]thieno[3,2-c]pyridin-7-yl}-N-methylacrylamide

EXAMPLE 478A

N-(4-bromo-2-methylphenyl)-2,2,2-trifluoroacetamide

A solution of 4-bromo-2-methyl-phenylamine (commercially available, 2.5 g, 13.4 mmol) in dichloromethane (27 mL) was treated with trifluoroacetic anhydride (2.3 mL, 16.3 mmol), stirred at room temperature for one hour and concentrated to dryness to give 3.7 g (98% yield) of the desired product. MS (ESI(−)) m/e 279.8, 281.9 (M−H)$^-$.

EXAMPLE 478B

N-[4-bromo-2-(bromomethyl)phenyl]-2,2,2-trifluoroacetamide

A solution of Example 478A (2.5 g, 8.9 mmol) and N-bromosuccinimide (1.58 g, 8.9 mmol) in carbon tetrachloride (25 mL) was irradiated with a 100-watt incandescent bulb overnight. The solution was filtered and the filtrate was concentrated. The concentrate was purified by flash chromatography on silica gel using 3–4% ethyl acetate/hexanes to give 2.17 g (68% yield) of the desired product. MS (ESI(−)) m/e 360, 362 (M−H)$^-$.

EXAMPLE 478C

{5-bromo-2-[(trifluoroacetyl)amino]benzyl}(triphenyl)phosphonium bromide

A solution of 478B (2.17 g, 6.01 mmol) in toluene (20 mL) was treated with triphenylphosphine (1.89 g, 7.2 mmol), heated at 60° C. overnight, cooled to room temperature and filtered. The filter cake was washed with diethyl ether to give 3.15 g (84% yield) of the desired product. $^1$H NMR (300 MHz, DMSO-D$_6$) δ ppm 5.14 (d, J=15.26 Hz, 2H), 7.08 (t, J=2.20 Hz, 1H), 7.16 (m, 1H), 7.41 (d, J=8.14 Hz, 1H), 7.59 (m, 6H), 7.74 (m, 6H), 7.91 (m, 3H), 10.91 (s, 1H).

EXAMPLE 478D 5-bromo-2-(trifluoromethyl)-1H-indole

A microwave tube charged with Example 478C (1.33 g, 4.25 mmol) and DMF (4 mL) was stirred at 200° C. for 15 minutes under microwave conditions and partitioned

EXAMPLE 478E 5-(4,4,5,5-tetramethyl-1,3,2-dioxaborolan-2-yl)-2-(trifluoromethyl)-1H-indole The desired product was prepared by substituting Example 478D for 468B in Example 468C. MS ESI(−)) m/e 310.0 (M−H)⁻.

EXAMPLE 478F

3-[4-amino-3-(1-benzothien-5-yl)thieno[3,2-c]pyridin-7-yl]-N-methylacrylamide

The desired product was prepared by substituting Example 478E for 4-chlorophenylboronic acid in Example 21C. $^1$H NMR (300 MHz, DMSO-D$_6$) δ ppm 2.74 (d, J=4.8 Hz, 3H), 5.77 (s, 2H), 6.59 (d, J=15.9 Hz, 1H), 7.11 (s, 1H), 7.37 (dd, J=8.8, 1.4 Hz, 1H), 7.59 (d, J=15.9 Hz, 1H), 7.62–7.65 (m, 2H), 7.79 (s, 1H), 8.12 (s, 1H), 8.16 (q, J=4.5 Hz, 1H), 12.53 (s, 1H); MS (ESI(+)) m/e 417.0 (M+H)⁺.

EXAMPLE 479

3-[4-amino-3-(2-methyl-1H-indol-5-yl)thieno[3,2-c]pyridin-7-yl]-N-(pyridin-4-ylmethyl)acrylamide

EXAMPLE 479A 3-(4-amino-3-bromothieno[3,2-c]pyridin-7-yl)-N-(pyridin-4-ylmethyl)acrylamide The desired product was prepared substituting Example 291A for Example 78 in Example 90.

EXAMPLE 479B

3-[4-amino-3-(2-methyl-1H-indol-5-yl)thieno[3,2-c]pyridin-7-yl]-N-(pyridin-4-ylmethyl)acrylamide The desired product was prepared substituting Example 479A and Example 467A for Example 21B and 4-chlorophenylboronic acid in Example 21C. $^1$H NMR (300 MHz, DMSO-D$_6$) δ ppm 2.42 (s, 3H), 4.49 (d, J=5.8 Hz, 2H), 6.11 (s, 2H), 6.21 (s, 1H), 6.74 (d, J=15.9 Hz, 1H), 7.07 (dd, J=8.1, 1.7 Hz, 1H), 7.39 (d, J=5.8 Hz, 2H), 7.42 (d, J=8.1 Hz, 1H), 7.49 (s, 1H), 7.66 (s, 1H), 7.67 (d, J=15.9 Hz, 1H), 8.16 (s, 1H), 8.57 (d, J=5.4 Hz, 2H), 8.89 (t, J=5.8 Hz, 1H), 11.20 (s, 1H); MS (ESI(+)) m/e 440.0 (M+H)⁺.

EXAMPLE 480

N-{4-[4-amino-7-(1-methyl-1H-indol-5-yl)thieno[3,2-c]pyridin-3-yl]phenyl}-N'-(3-methylphenyl)urea

EXAMPLE 480A 1-methyl-5-(4,4,5,5-tetramethyl-1,3,2-dioxaborolan-2-yl)-1H-indole The desired product was prepared by substituting 5-bromo-1-methyl-1H-indole for 5-bromo-2-methyl-1H-indole in Example 467A. MS (ESI(+)) m/e 258 (M+H)⁺.

EXAMPLE 480B 3-(4-aminophenyl)-7-(1-methyl-1H-indol-5-yl)thieno[3,2-c]pyridin-4-amine The desired product was prepared by substituting Example 77B, Example 480A, and PdCl$_2$(dppf) for Example 21A, 2-[(1E)-3,3-diethoxy-1-propenyl]-4,4,5,5,-tetramethyl-1,3,2-dioxaborolane and Pd(PPh$_3$)$_4$, respectively, in Example 176A. MS ESI(+)) m/e 371.0 (M+H)⁺.

EXAMPLE 480C

N-{4-[4-amino-7-(1-methyl-1H-indol-5-yl)thieno[3,2-c]pyridin-3-yl]phenyl}-N'-(3-methylphenyl)urea The desired product was prepared by substituting Example 480B for Example 1C in Example 1D. $^1$H NMR (300 MHz, DMSO-D$_6$) δ ppm 2.29 (s, 3H), 3.85 (s, 3H), 5.43 (s, 2H), 6.50 (d, J=2.7 Hz, 1H), 6.81 (d, J=7.1 Hz, 1H), 7.17 (t, J=7.8 Hz, 1H), 7.26 (d, 8.5 Hz, 1H), 7.32 (s, 1H), 7.40–7.45 (m, 5H), 7.57 (d, J=8.5 Hz, 1H), 7.61 (d, J=8.8 Hz, 2H), 7.79 (d, J=1.7 Hz, 1H), 7.88 (s, 1H), 8.66 (s, 1H), 8.86 (s, 1H); MS (ESI(+)) m/e 504.1 (M+H)⁺.

EXAMPLE 481

N-{4-[4-amino-7-(1-methyl-1H-indol-5-yl)thieno[3,2-c]pyridin-3-yl]phenyl}-N'-(3-chlorophenyl)urea The desired product was prepared by substituting Example 480B and 1-isocyanato-3-chlorobenzene for Example 121B and 1-fluoro-2-isocyanato-4-(trifluoromethyl)benzene, respectively, in Example 122. $^1$H NMR (300 MHz, DMSO-D$_6$) δ ppm 3.85 (s, 3H), 5.43 (s, 2H), 6.50 (dd, J=3.1, 0.7 Hz, 1H), 7.02–7.06 (m, 1H), 7.30–7.33 (m, 2H), 7.40–7.44 (m, 4H), 7.45 (s, 1H), 7.57 (d, J=8.5 Hz, 1H), 7.62 (d, J=8.8 Hz, 2H), 7.73 (dd, J=2.5, 1.5 Hz, 1H), 7.79 (dd, J=1.7, 0.7 Hz, 1H), 7.89 (s, 1H), 8.97 (app. s, 2H); MS (ESI(+)) m/e 524.1 (M+H)⁺.

EXAMPLE 482

3-[4-amino-3-(2-methyl-1,3-benzothiazol-5-yl)thieno[3,2-c]pyridin-7-yl]-N-methylacrylamide

EXAMPLE 482A 2-methyl-5-(4,4,5,5-tetramethyl-1,3,2-dioxaborolan-2-yl)-1,3-benzothiazole The desired product was prepared by substituting 5-bromo-2-methyl-benzothiazole for 468B in Example 468C. MS ESI(+)) m/e 276.0 (M+H)⁺.

EXAMPLE 482B

3-[4-amino-3-(2-methyl-1,3-benzothiazol-5-yl)thieno[3,2-c]pyridin-7-yl]-N-methylacrylamide The desired product was prepared by substituting Example 482A for 4-chlorophenylboronic acid in Example 21C. $^1$H NMR (300 MHz, DMSO-D$_6$) δ ppm 2.74 (d, J=4.8 Hz, 3H), 2.85 (s, 3H), 5.80 (s, 2H), 6.60 (d, J=15.9 Hz, 1H), 7.50 (dd, J=8.1, 1.7 Hz, 1H), 7.60 (d, J=15.9 Hz, 1H), 7.74 (s, 1H), 8.00 (d, J=1.4 Hz, 1H), 8.14 (s, 1H), 8.14–8.19 (m, 1H), 8.19 (d, J=8.1 Hz, 1H); MS (ESI(+)) m/e 381.0 (M+H)⁺.

EXAMPLE 483

3-[4-amino-3-(2-oxo-2,3-dihydro-1H-indol-5-yl)thieno[3,2-c]pyridin-7-yl]-N-methylacrylamide

EXAMPLE 483A 5-bromo-1,3-dihydro-2H-indol-2-one

A suspension of 1,3-dihydro-indol-2-one (1.3 g, 9.76 mmol) in acetonitrile (20 mL) at −5° C. was treated with N-bromosuccinimide, warmed to room temperature, stirred overnight and filtered to give 1.8 g (87% yield) of the desired product. MS (ESI(+)) m/e 209.9, 211.9 (M−H)−.

EXAMPLE 483B 5-(4,4,5,5-tetramethyl-1,3,2-dioxaborolan-2-yl)-1,3-dihydro-2H-indol-2-one The desired product was prepared by substituting Example 483A for 468B in Example 468C. MS ESI(+)) m/e 260 (M+H)+.

EXAMPLE 483C

3-[4-amino-3-(2-oxo-2,3-dihydro-1H-indol-5-yl)thieno[3,2-c]pyridin-7-yl]-N-methylacrylamide The desired product was prepared by substituting Example 483B for 4-chlorophenylboronic acid in Example 21C. $^1$H NMR (300 MHz, DMSO-D$_6$) δ ppm 2.73 (d, J=4.8 Hz, 3H), 3.56 (s, 2H), 5.86 (s, 2H), 6.57 (d, J=15.9 Hz, 1H), 6.95 (d, J=7.8 Hz, 1H), 7.26 (dd, J=7.8, 1.4 Hz, 1H), 7.31 (s, 1H), 7.55–7.60 (m, 2H), 8.11 (s, 1H), 8.14 (q, J=4.8 Hz, 1H), 10.56 (s, 1H); MS (ESI(+)) m/e 365.0 (M+H)+.

EXAMPLE 484

3-[4-amino-3-(2-naphthyl)thieno[3,2-c]pyridin-7-yl]-N-methylacrylamide

The desired product was prepared by substituting 2-naphthaleneboronic acid for 4-chlorophenylboronic acid in Example 21C. $^1$H NMR (300 MHz, DMSO-D$_6$) δ ppm 2.75 (d, J=4.8 Hz, 3H), 6.30 (s, 2H), 6.69 (d, J=15.9 Hz, 1H), 7.59–7.65 (m, 4H), 7.91 (s, 1H), 8.01–8.06 (m, 2H), 8.10 (dd, J=1.7, 0.7 Hz, 1H), 8.10 (d, J=8.5 Hz, 1H), 8.21 (s, 1H), 8.24 (q, J=4.8 Hz, 1H); MS (ESI(+)) m/e 360.0 (M+H)+.

EXAMPLE 485

3-[4-amino-3-(1-benzofuran-2-yl)thieno[3,2-c]pyridin-7-yl]-N-methylacrylamide

The desired product was prepared by substituting benzofuran-2-ylboronic acid for 4-chlorophenylboronic acid in Example 21C. $^1$H NMR (300 MHz, DMSO-D$_6$) δ ppm 2.74 (d, J=4.8 Hz, 3H), 6.47 (s, 2H), 6.60 (d, J=15.9 Hz, 1H), 7.28 (d, J=0.7 Hz, 1H), 7.34 (td, J=7.5, 1.4 Hz, 1H), 7.41 (td, J=7.5, 1.7 Hz, 1H), 7.59 (d, J=15.9 Hz, 1H), 7.70 (d, J=7.5 Hz, 1H), 7.74–7.77 (m, 1H), 8.17 (q, J=4.8 Hz, 1H), 8.19 (s, 1H), 8.21 (s, 1H); MS (ESI(+) m/e 350.0 (M+H)+.

EXAMPLE 486

3-[4-amino-3-(1-benzofuran-5-yl)thieno[3,2-c]pyridin-7-yl]-N-methylacrylamide

EXAMPLE 486A 5-(4,4,5,5-tetramethyl-1,3,2-dioxaborolan-2-yl)-1-benzofuran

The desired product was prepared by substituting 5-bromo-benzofuran (commercially available) for Example 468B in Example 468C. MS ESI(+)) m/e 245.1 (M+H)+.

EXAMPLE 486B

3-[4-amino-3-(1-benzofuran-5-yl)thieno[3,2-c]pyridin-7-yl]-N-methylacrylamide

The desired product was prepared by substituting Example 486A for 4-chlorophenylboronic acid in Example 21C. $^1$H NMR (300 MHz, DMSO-D$_6$) δ ppm 2.75 (d, J=4.8 Hz, 3H), 6.48–6.67 (br. s, 2H), 6.73 (d, J=15.9 Hz, 1H), 7.07 (dd, J=2.2, 0.9 Hz, 1H), 7.44 (dd, J=8.5, 2.0 Hz, 1H), 7.61 (d, J=15.9 Hz, 1H), 7.79 (d, J=8.5 Hz, 1H), 7.82 (d, J=1.7 Hz, 1H), 7.91 (s, 1H), 8.14 (d, J=2.0 Hz, 1H), 8.22 (s, 1H), 8.29 (q, J=4.8 Hz, 1H); MS (ESI(+)) m/e 350.0 (M+H)+.

EXAMPLE 487

3-(4-amino-3-quinolin-6-ylthieno[3,2-c]pyridin-7-yl)-N-methylacrylamide

EXAMPLE 487A 6-(4,4,5,5-tetramethyl-1,3,2-dioxaborolan-2-yl)quinoline

The desired product was prepared by substituting 6-bromoquinoline (commercially available) for Example 468B in Example 468C. MS ESI(+)) m/e 256.0 (M+H)+.

EXAMPLE 487B 3-(4-amino-3-quinolin-6-ylthieno[3,2-c]pyridin-7-yl)-N-methylacrylamide The desired product was prepared by substituting Example 487A for 4-chlorophenylboronic acid in Example 21C. $^1$H NMR (300 MHz, DMSO-D$_6$) δ ppm 2.74 (d, J=4.8 Hz, 3H), 5.83 (s, 2H), 6.61 (d, J=15.9 Hz, 1H), 7.61 (d, J=15.9 Hz, 1H), 7.63 (dd, J=8.1, 4.4 Hz, 1H), 7.82 (s, 1H), 7.86 (dd, J=8.8, 1.7 Hz, 1H), 8.14–8.18 (m, 4H), 8.47 (dd, J=8.5, 1.7 Hz, 1H), 8.99 (dd, J=4.2, 1.9 Hz, 1H); MS (ESI(+)) m/e 361.0 (M+H)+.

EXAMPLE 488

3-[4-amino-3-(1,2-benzisoxazol-5-yl)thieno[3,2-c]pyridin-7-yl]-N-methylacrylamide

EXAMPLE 488A 5-bromo-1,2-benzisoxazole

A solution of 5-bromo-2-hydroxy-benzaldehyde (2.0 g, 10 mmol) in ethanol (10 mL) at room temperature was treated with hydroxylamine-O-sulfonic acid (1.69 g, 15 mmol), stirred for 20 minutes, diluted with dichloromethane (50 mL), cooled to 0° C. and treated with a solution of sodium bicarbonate (3 g) in water (25 mL). The solution was stirred at 0° C. for 30 minutes. The organic layer was removed and the aqueous layer was extracted with dichloromethane. The aqueous layer was treated with additional dichloromethane (50 mL) and stirring was continued for one hour. The layers were separated and the aqueous layer was extracted with dicloromethane. The combined organic layers were washed with brine, dried ($MgSO_4$) and concentrated. The concentrate was recrystallized from ethanol to give 970 mg (49%) yield of the desired product. MS (ESI(−)) m/e 195.9, 197.9 (M−H)⁻

EXAMPLE 488B 5-(4,4,5,5-tetramethyl-1,3,2-dioxaborolan-2-yl)-1,2-benzisoxazole The desired product was prepared by substituting Example 488A for Example 468B in Example 468C. MS (ESI(−)) m/e 244.0486 (M−H)⁻.

EXAMPLE 488C

3-[4-amino-3-(1,2-benzisoxazol-5-yl)thieno[3,2-c]pyridin-7-yl]-N-methylacrylamide The desired product was prepared by substituting Example 488B for 4-chlorophenylboronic acid in Example 21C. ¹H NMR (300 MHz, DMSO-$D_6$) δ ppm 2.73 (d, J=4.8 Hz, 3H), 5.86 (s, 2H), 6.57 (d, J=15.9 Hz, 1H), 7.11 (d, J=8.8 Hz, 1H), 7.54–7.58 (m, 1H), 7.57 (d, J=15.9 Hz, 1H), 7.66 (s, 1H), 7.72 (d, J=2.0 Hz, 1H), 8.12 (s, 1H), 8.14 (q, J=4.8 Hz, 1H), 11.45 (s, 1H); MS (ESI(+)) m/e 351.0 (M+H)⁺.

EXAMPLE 489

3-[4-amino-3-(2,3-dihydro-1H-indol-5-yl)thieno[3,2-c]pyridin-7-yl]-N-methylacrylamide

EXAMPLE 489A tert-butyl 5-bromoindoline-1-carboxylate

A suspension of 5-bromo-2,3-dihydro-1H-indole (1.0 g, 5.05 mmol) in diethyl ether (50 mL) was treated with di-tert-butyl-dicarbonate (1.32 g, 6.05 mmol), stirred overnight at room temperature and filtered. The filtrate was diluted with hexanes and concentrated in vacuo until crystal formed. The crystals were collected via filtration to give 1.05 g (70% yield) of the desired product. ¹H NMR (300 MHz, DMSO-$D_6$) δ ppm 1.50 (s, 9H), 3.06 (t, J=8.82 Hz, 2H), 3.90 (m, 2H), 7.30 (dd, J=8.48, 2.03 Hz, 1H), 7.37 (m, 1H), 7.56 (s, 1H),

EXAMPLE 489B tert-butyl 5-(4,4,5,5-tetramethyl-1,3,2-dioxaborolan-2-yl)indoline-1-carboxylate The desired product was prepared by substituting Example 489A for Example 468B in Example 468C. MS (ESI(+)) m/e 246 (M+H-Boc)⁺.

EXAMPLE 489C tert-butyl 5-{4-amino-7-[3-(methylamino)-3-oxo-prop-1-enyl]thieno[3,2-c]pyridin-3-yl}indoline-1-carboxylate The desired product was prepared by substituting Example 489B for 4-chlorophenylboronic acid in Example 21C. MS ESI(+)) m/e 451.1 (M+H)⁺.

EXAMPLE 489D

3-[4-amino-3-(2,3-dihydro-1H-indol-5-yl)thieno[3,2-c]pyridin-7-yl]-N-methylacrylamide The desired product was prepared by substituting Example 489C for Example 76B in Example 76C. ¹H NMR (300 MHz, DMSO-$D_6$) δ ppm 2.73 (d, J=4.8 Hz, 3H), 2.98 (t, J=8.5 Hz, 2H), 3.50 (td, J=8.5, 1.4 Hz, 2H), 5.80 (s, 1H), 5.96 (s, 2H), 6.55 (d, J=15.9 Hz, 1H), 6.60 (d, J=8.5 Hz, 1H), 6.98 (dd, J=8.0, 1.9 Hz, 1H), 7.10 (s, 1H), 7.48 (s, 1H), 7.56 (d, J=15.9 Hz, 1H), 8.08 (s, 1H), 8.14 (q, J=4.3 Hz, 1H); MS (ESI(+)) m/e 351.0 (M+H)⁺.

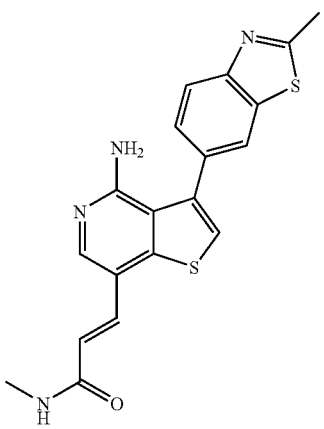

EXAMPLE 490

3-[4-amino-3-(2-methyl-1,3-benzothiazol-6-yl)thieno[3,2-c]pyridin-7-yl]-N-methylacrylamide

EXAMPLE 490A 6-bromo-2-methyl-1,3-benzothiazole

A solution of 4-bromo-2-iodo-phenylamine (1.5 g, 5.0 mmol), thiacetamide (381 mg, 5.0), cupric oxide (280 mg, 3.5 mmol), dppf (56 mg, 0.10 mmol), $Pd_2(dba)_3$ (48 mg, 0.052 mmol) in DMF was heated at 60° C. for 1 hour, cooled to room temperature, partitioned between water and ethyl acetate. The organic phase was dried ($Na_2SO_4$) and concentrated. The concentrate was purified by flash chromatography on silica gel using 20% hexanes/methylene chloride to give 550 mg (40% yield) of the desired product. MS (ESI(+)) m/e 227.8, 229.8 (M+H)⁺.

EXAMPLE 490B 2-methyl-6-(4,4,5,5-tetramethyl-1,3,2-dioxaborolan-2-yl)-1,3-benzothiazole The desired product was prepared by substituting Example 490A for Example 468B in Example 468C. MS ESI(+)) m/e 276 (M+H)⁺.

EXAMPLE 490C

3-[4-amino-3-(2-methyl-1,3-benzothiazol-6-yl)thieno[3,2-c]pyridin-7-yl]-N-methylacrylamide The desired product was prepared by substituting Example 490B for 4-chlorophenylboronic acid in Example 21C. $^1$H NMR (300 MHz, DMSO-D$_6$) δ ppm 2.75 (d, J=4.8 Hz, 3H), 2.86 (s, 3H), 6.57 (s, 2H), 6.72 (d, J=16.3 Hz, 1H), 7.59 (dd, J=8.5, 1.7 Hz, 1H), 7.61 (d, J=16.3 Hz, 1H), 7.94 (s, 1H), 8.06 (d, J=8.5 Hz, 1H), 8.22 (app. s, 2H), 8.27 (q, J=4.8 Hz, 1H); MS (ESI(+)) m/e 380.9 (M+H)$^+$.

EXAMPLE 491

3-(2-methyl-1H-indol-5-yl)-7-pyridin-4-ylthieno[3,2-c]pyridin-4-amine

The desired product was prepared by substituting Example 467A for Example 175E in Example 216. $^1$H NMR (300 MHz, DMSO-D$_6$) δ ppm 2.42 (s, 3H), 5.70 (s, 2H), 6.21 (s, 1H), 7.06 (dd, J=8.14, 1.70 Hz, 1H), 7.41 (d, J=8.14 Hz, 1H), 7.48 (m, 2H), 7.73 (d, J=6.10 Hz, 2H), 8.07 (s, 1H), 8.68 (d, J=6.10 Hz, 2H), 11.17 (s, 1H); MS (ESI(+)) m/e 357.0 (M+H)$^+$.

EXAMPLE 492

7-(4-aminophenyl)-3-(2-methyl-1H-indol-5-yl)thieno[3,2-c]pyridin-4-amine

EXAMPLE 492A 7-(4-aminophenyl)-3-bromothieno[3,2-c]pyridin-4-amine

The desired product was prepared by substituting Example 21A, 4-(4,4,5,5-tetramethyl-1,3,2-dioxaborolan-2-yl)aniline and PdCl$_2$(dppf) for Example 1B, 4-phenoxyphenylboronic acid, and Pd(PPh$_3$)$_4$, respectively, in Example 10A. MS (ESI(+)) m/e 319.9, 321.9 (M+H)$^+$.

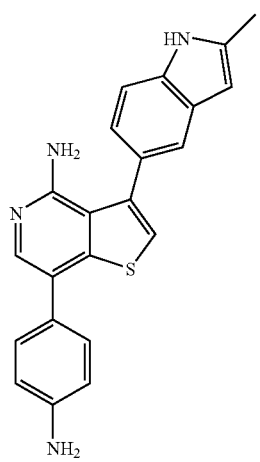

EXAMPLE 492B 7-(4-aminophenyl)-3-(2-methyl-1H-indol-5-yl)thieno[3,2-c]pyridin-4-amine The desired product was prepared by substituting Example 492A and 467A for Example 21B and 4-chlorophenylboronic acid, respectively, in Example 21C. $^1$H NMR (300 MHz, DMSO-D$_6$) δ ppm 2.42 (s, 3H), 5.23 (s, 2H), 5.31 (s, 2H), 6.20 (s, 1H), 6.69 (d, J=8.5 Hz, 2H), 7.05 (dd, J=8.1, 1.7 Hz, 1H), 7.32 (d, J=8.5 Hz, 2H), 7.37 (s, 1H), 7.39 (d, J=8.1 Hz, 1H), 7.46 (d, J=0.7 Hz, 1H), 7.75 (s, 1H), 11.14 (s, 1H); MS (ESI(+)) m/e 371.0 (M+H)$^+$.

EXAMPLE 493

N-{3-[4-amino-3-(2-methyl-1H-indol-5-yl)thieno[3,2-c]pyridin-7-yl]phenyl}acetamide

EXAMPLE 493A

N-[3-(4-amino-3-bromothieno[3,2-c]pyridin-7-yl)phenyl]acetamide

The desired product was prepared by substituting Example 21A and 3-acetamidophenylboronic acid for Example 1B and 4-phenoxyphenylboronic acid, respectively, in Example 10A. MS ESI(+)) m/e 361.9, 363.7 (M+H)$^+$.

EXAMPLE 493B

N-{3-[4-amino-3-(2-methyl-1H-indol-5-yl)thieno[3,2-c]pyridin-7-yl]phenyl}acetamide The desired product was prepared by substituting Example 493A and 467A for Example 21B and 4-chlorophenylboronic acid, respectively, in Example 21C. $^1$H NMR (300 MHz, DMSO-D$_6$) δ ppm 2.09 (s, 3H), 2.43 (s, 3H), 6.24 (dd, J=1.9, 1.2 Hz, 1H), 6.64–6.81 (br. s, 2H), 7.12 (dd, J=8.1, 1.7 Hz, 1H), 7.35 (ddd, J=3.0, 2.0, 1.4 Hz, 1H), 7.46 (d, J=8.1 Hz, 1H), 7.52 (d, J=7.8 Hz, 1H), 7.55–7.56 (m, 1H), 7.58–7.61 (m, 1H), 7.82 (s, 1H), 7.93 (s, 1H), 8.13 (dd, J=2.6, 1.2 Hz, 1H), 10.17 (s, 1H), 11.25 (s, 1H); MS (ESI(+)) m/e 413.0 (M+H)$^+$.

EXAMPLE 494

N-{4-[4-amino-7-(4-fluorophenyl)thieno[3,2-c]pyridin-3-yl]phenyl}-N'-(3-methylphenyl)urea The desired product was prepared by substituting Example 460A and 4-fluorophenylboronic acid for Example 1B and 4-phenoxyphenylboronic acid, respectively, in Example 10A. $^1$H NMR (300 MHz, DMSO-D$_6$) δ ppm 2.29 (s, 3H), 6.78 (s, 2H), 6.81 (d, J=7.1 Hz, 1H), 7.17 (t, J=7.6 Hz, 1H), 7.25–7.28 (m, 1H), 7.32 (s, 1H), 7.41–7.47 (m, 4H), 7.66 (d, J=8.8 Hz, 2H), 7.75 (dd, J=8.8, 5.4 Hz, 2H), 7.84 (s, 1H), 7.96 (s, 1H), 8.77 (s, 1H), 9.02 (s, 1H); MS (ESI(+)) m/e 469.0 (M+H)$^+$.

EXAMPLE 495

N-{4-[4-amino-7-(4-cyanophenyl)thieno[3,2-c]pyridin-3-yl]phenyl}-N'-(3-methylphenyl)urea The desired product was prepared by substituting Example 460A and 4-cyanophenylboronic acid for Example 1B and 4-phenoxyphenylboronic acid, respectively, in Example 10A. $^1$H NMR (300 MHz, DMSO-D$_6$) δ ppm 2.29 (s, 3H), 6.66 (s, 2H), 6.81 (d, J=7.5 Hz, 1H), 7.17 (t, J=7.8 Hz, 1H), 7.26 (d, J=8.5 Hz, 1H), 7.32 (s, 1H), 7.44 (d, J=8.5 Hz, 2H), 7.66 (d, J=8.5 Hz, 2H), 7.80 (s, 1H), 7.93 (d, J=8.5 Hz, 2H), 8.06 (d, J=8.5 Hz, 2H), 8.06 (s, 1H), 8.72 (s, 1H), 8.97 (s, 1H); MS (ESI(+)) m/e 476.0 (M+H)$^+$.

EXAMPLE 496

N-{4-[4-amino-7-(4-methoxyphenyl)thieno[3,2-c]pyridin-3-yl]phenyl}-N'-(3-methylphenyl)urea The desired product was prepared by substituting Example 460A and 4-methoxyphenylboronic acid for Example 1B and 4-phenoxyphenylboronic acid, respectively, in Example 10A. $^1$H NMR (300 MHz, DMSO-D$_6$) δ ppm 2.29 (s, 3H), 3.83 (s, 3H), 5.47 (s, 2H), 6.81 (d, J=7.5 Hz, 1H), 7.09 (d, J=8.8 Hz, 2H), 7.17 (t, J=7.6 Hz, 1H), 7.26 (d, J=8.5 Hz, 1H), 7.32 (s, 1H), 7.40 (d, J=8.5 Hz, 2H), 7.46 (s, 1H), 7.57–7.63 (m, 4H), 7.84 (s, 1H), 8.67 (s, 1H), 8.87 (s, 1H); MS (ESI(+)) m/e 481.1 (M+H)$^+$.

EXAMPLE 497

N-{4-[4-amino-7-(3-chlorophenyl)thieno[3,2-c]pyridin-3-yl]phenyl}-N'-(3-methylphenyl)urea The desired product was prepared by substituting Example 460A and 3-chlorophenylboronic acid for Example 1B and 4-phenoxyphenylboronic acid, respectively, in Example 10A. $^1$H NMR (300 MHz, DMSO-D$_6$) δ ppm 2.29 (s, 3H), 6.72 (s, 2H), 6.81 (d, J=7.5 Hz, 1H), 7.15–7.20 (m, 1H), 7.27 (d, J=8.5 Hz, 1H), 7.32 (s, 1H), 7.45 (d, J=8.5 Hz, 2H), 7.60–7.68 (m, 4H), 7.71 (dt, J=7.0, 1.7 Hz, 1H), 7.77 (t, J=1.5 Hz, 1H), 7.81 (s, 1H), 8.03 (s, 1H), 8.75 (s, 1H), 9.00 (s, 1H); MS (ESI(+)) m/e 485.0 (M+H)$^+$.

EXAMPLE 498

N-{4-[4-amino-7-(1,3-benzodioxol-5-yl)thieno[3,2-c]pyridin-3-yl]phenyl}-N'-(3-methylphenyl)urea The desired product was prepared by substituting Example 460A and 3,4-methylenedioxyphenylboronic acid for Example 1B and 4-phenoxyphenylboronic acid, respectively, in Example 10A. $^1$H NMR (300 MHz, DMSO-D$_6$) δ ppm 2.29 (s, 3H), 6.14 (s, 2H), 6.67 (s, 2H), 6.81 (d, J=7.1 Hz, 1H), 7.12 (d, J=7.8 Hz, 1H), 7.15–7.19 (m, 1H), 7.19 (d, J=7.8 Hz, 1H), 7.25–7.28 (m, 2H), 7.32 (s, 1H), 7.44 (d, J=8.8 Hz, 2H), 7.65 (d, J=8.8 Hz, 2H), 7.81 (s, 1H), 7.90 (s, 1H), 8.72 (s, 1H), 8.97 (s, 1H); MS (ESI(+)) m/e 495.1 (M+H)$^+$.

EXAMPLE 499

N-(3-{4-amino-3-[4-({[(3-methylphenyl)amino]carbonyl}amino)phenyl]thieno[3,2-c]pyridin-7-yl}phenyl)acetamide The desired product was prepared by substituting Example 460A and 3-acetamidophenylboronic acid for Example 1B and 4-phenoxyphenylboronic acid, respectively, in Example 10A. $^1$H NMR (300 MHz, DMSO-D$_6$) δ ppm 2.09 (s, 3H), 2.29 (s, 3H), 6.81 (d, J=7.1 Hz, 1H), 6.74–6.89 (br. s, 2H), 7.17 (t, J=7.5 Hz, 1H), 7.25–7.28 (m, 1H), 7.31–7.36 (m, 2H), 7.45–7.43 (m, 3H), 7.60 (ddd, J=7.8, 1.7, 1.0 Hz, 1H), 7.66 (d, J=8.5 Hz, 2H), 7.85 (s, 1H), 7.95 (s, 1H), 8.11 (s, 1H), 8.75 (s, 1H), 9.01 (s, 1H), 10.17 (s, 1H); MS (ESI(+)) m/e 508.1 (M+H)$^+$.

EXAMPLE 500

N-(4-{4-amino-7-[4-(trifluoromethoxy)phenyl]thieno[3,2-c]pyridin-3-yl}phenyl)-N'-(3-methylphenyl)urea The desired product was prepared by substituting Example 460A and 4-(trifluoromethoxy)phenylboronic acid for Example 1B and 4-phenoxyphenylboronic acid, respectively, in Example 10A. $^1$H NMR (300 MHz, DMSO-D$_6$) δ ppm 2.29 (s, 3H), 5.60 (s, 2H), 6.81 (d, J=7.1 Hz, 1H), 7.17 (t, J=7.8 Hz, 1H), 7.26 (d, J=8.5 Hz, 1H), 7.32 (s, 1H), 7.40 (d, J=8.5 Hz, 2H), 7.50–7.53 (m, 3H), 7.62 (d, J=8.5 Hz, 2H), 7.80 (d, J=8.8 Hz, 2H), 7.93 (s, 1H), 8.68 (s, 1H), 8.88 (s, 1H); MS (ESI(+)) m/e 535.1 (M+H)$^+$.

EXAMPLE 501

N-(3-{4-amino-3-[4-({[(3-methylphenyl)amino]carbonyl}amino)phenyl]thieno[3,2-c]pyridin-7-yl}phenyl)methanesulfonamide The desired product was prepared by substituting Example 460A and 4-(methylsulfonylamino)phenylboronic acid for Example 1B and 4-phenoxyphenylboronic acid, respectively, in Example 10A. $^1$H NMR (300 MHz, DMSO-D$_6$) δ ppm 2.29 (s, 3H), 3.10 (s, 3H), 6.77 (s, 2H), 6.81 (d, J=7.5 Hz, 1H), 7.17 (t, J=7.8 Hz, 1H), 7.27 (d, J=8.8 Hz, 1H), 7.29–7.33 (m, 2H), 7.40 (ddd, J=7.8, 1.7, 1.0 Hz, 1H), 7.45 (d, J=8.8 Hz, 2H), 7.52–7.58 (m, 2H), 7.66 (d, J=8.8 Hz, 2H), 7.83 (s, 1H), 7.97 (s, 1H), 8.75 (s, 1H), 9.00 (s, 1H), 10.05 (s, 1H); MS (ESI(+)) m/e 544.0 (M+H)$^+$.

EXAMPLE 502

N-(4-{4-amino-3-[4-({[(3-methylphenyl)amino]carbonyl}amino)phenyl]thieno[3,2-c]pyridin-7-yl}phenyl)acetamide The desired product was prepared by substituting Example 460A and 4-acetamidophenylboronic acid for Example 1B and 4-phenoxyphenylboronic acid, respectively, in Example 10A. $^1$H NMR (300 MHz, DMSO-D$_6$) δ ppm 2.10 (s, 3H), 2.29 (s, 3H), 6.76 (s, 2H), 6.81 (d, J=7.5 Hz, 1H), 7.17 (t, J=7.8 Hz, 1H), 7.27 (d, J=8.5 Hz, 1H), 7.32 (s, 1H), 7.46 (d, J=8.5 Hz, 2H), 7.62–7.68 (m, 4H), 7.78 (d, J=8.8 Hz, 2H), 7.85 (s, 1H), 7.93 (s, 1H), 8.76 (s, 1H), 9.01 (s, 1H), 10.17 (s, 1H); MS (ESI(+)) m/e 508.1 (M+H)$^+$.

EXAMPLE 503

N-(4-{4-amino-7-[3-morpholin-4-ylprop-1-enyl]thieno[3,2-c]pyridin-3-yl}phenyl)-N'-methylphenyl)urea The desired product was prepared by substituting Example 464B and morpholine for Example 176C and diethylamine, respectively, in Example 177. $^1$H NMR (300 MHz, DMSO-D$_6$) δ ppm 2.29 (s, 3H), 2.42–2.45 (m, 4H), 3.18 (d, J=6.4 Hz, 2H), 3.59–3.62 (m, 4H), 5.57 (s, 2H), 6.21 (dt, J=16.3, 6.4 Hz, 1H), 6.68 (d, J=16.3 Hz, 1H), 6.80 (d, J=7.5 Hz, 1H), 7.17 (t, J=7.8 Hz, 1H), 7.25 (d, J=8.5 Hz, 1H), 7.32 (s, 1H), 7.37 (d, J=8.5 Hz, 2H), 7.50 (s, 1H), 7.60 (d, J=8.5 Hz, 2H), 7.94 (s, 1H), 8.67 (s, 1H), 8.88 (s, 1H); MS (ESI(+)) m/e 500.2 (M+H)$^+$.

EXAMPLE 504

3,7-di-1H-indol-6-ylthieno[3,2-c]pyridin-4-amine

The desired product was prepared by substituting Example 21A, Example 474A (2.1 equivalents) and PdCl$_2$ (dppf) for Example 21B, 4-chlorophenylboronic acid and PdCl$_2$(PPh$_3$)$_4$, respectively in Example 21C. $^1$H NMR (300 MHz, DMSO-D$_6$) δ ppm 6.53–6.57 (m, 4H), 7.14 (dd, J=8.1, 1.4 Hz, 1H), 7.32 (dd, J=8.1, 1.7 Hz, 1H), 7.48–7.52 (m, 2H), 7.55 (s, 1H), 7.71–7.73 (m, 2H), 7.75 (d, J=2.4 Hz, 1H), 7.80 (s, 1H), 7.95 (s, 1H), 11.34 (s, 1H), 11.38 (s, 1H); MS (ESI(+)) m/e 381.0 (M+H)$^+$.

EXAMPLE 505

N-(3-{4-amino-3-[4-({[(3-methylphenyl)amino]carbonyl}amino)phenyl]thieno[3,2-c]pyridin-7-yl}prop-2-ynyl)-2-(piperidin-1-ylcarbonyl)benzamide

EXAMPLE 505A

N-{3-[4-amino-3-(4-aminophenyl)thieno[3,2-c]pyridin-7-yl]prop-2-ynyl}-2-(piperidin-1-ylcarbonyl)benzamide The desired product was prepared by substituting Example 77B and N-propargylphthalimide for Example 144A and 3-butyn-1-ol in Example 144B. MS (ESI(+)) m/e 510 (M+H)$^+$.

EXAMPLE 505B

N-(3-{4-amino-3-[4-({[(3-methylphenyl)amino]carbonyl}amino)phenyl]thieno[3,2-c]pyridin-7-yl}prop-2-ynyl)-2-(piperidin-1-ylcarbonyl)benzamide The desired product was prepared by substituting Example 505A for Example 1C in Example 1D. $^1$H NMR (300 MHz, DMSO-d6) δ ppm 1.51 (s, 6H), 2.29 (s, 3H), 3.07–3.09 (m, 2H), 3.54 (s, 2H), 4.36 (s, 2H), 5.78 (s, 2H), 6.81 (d, J=7.12 Hz, 1H), 7.17 (t, J=7.80 Hz, 1H), 7.23–7.31 (m, 2H), 7.31 (s, 1H), 7.37 (d, J=8.82 Hz, 2H), 7.45–7.56 (m, 3H), 7.60 (d, J=8.48 Hz, 2H), 7.69 (d, J=7.46 Hz, 1H), 7.98 (s, 1H), 8.66 (s, 1H), 8.86 (s, 1H), 8.96 (t, J=5.43 Hz, 1H); MS (ESI(+)) m/e 643 (M+H)$^+$.

EXAMPLE 506

N-{4-[4-amino-7-(3-pyrrolidin-1-ylprop-1-ynyl)thieno[3,2-c]pyridin-3-yl]phenyl}-N'-(3-methylphenyl)urea

EXAMPLE 506A

1-prop-2-ynylpyrrolidine

A suspension of pyrrolidine (3.71 mL, 44.92 mmol) and cesium carbonate (14.64 g, 44.92 mmol) in acetone was treated with propargyl bromide (5.0 mL, 44.92 mmol) and stirred at room temperature for 2 days. The solution was filtered, washing with acetone. The filtrate was concentrated, taken up in ethyl acetate, washed with aqueous sodium bicarbonate, dried (Na$_2$SO$_4$), filtered and concentrated to give 1.67 g of the desired product. MS (ESI(+)) m/e 110 (M+H)$^+$.

EXAMPLE 506B

3-(4-aminophenyl)-7-(3-pyrrolidin-1-ylprop-1-ynyl)thieno[3,2-c]pyridin-4-amine The desired product was prepared by substituting Example 77B and Example 506A for Example 144A and 3-butyn-1-ol in Example 144B. MS (ESI(+)) m/e 349 (M+H)$^+$.

EXAMPLE 506C

N-{4-[4-amino-7-(3-pyrrolidin-1-ylprop-1-ynyl)thieno[3,2-c]pyridin-3-yl]phenyl}-N'-(3-methylphenyl)urea The desired product was prepared by substituting Example 506B for Example 1C in Example 1D. $^1$H NMR (300 MHz, DMSO-D$_6$) δ ppm 1.73–1.77 (m, 4H), 2.29 (s, 3H), 2.63–2.67 (m, 4H), 3.71 (s, 2H), 5.75 (s, 2H), 6.80 (d, J=7.46 Hz, 1H), 7.17 (t, J=7.80 Hz, 1H), 7.24–7.26 (m, 1H), 7.31 (s, 1H), 7.37 (d, J=8.81 Hz, 2H), 7.50 (s, 1H), 7.60 (d, J=8.48 Hz, 2H), 7.96 (s, 1H), 8.66 (s, 1H), 8.86 (s, 1H); MS (ESI(+)) m/e 482 (M+H)$^+$.

EXAMPLE 507

N-{4-[4-amino-7-(3-pyrrolidin-1-ylprop-1-ynyl)thieno[3,2-c]pyridin-3-yl]phenyl}-N'-[3-(trifluoromethyl)phenyl]urea The desired product was prepared by substituting Example 506B and 1-isocyanato-3-(trifluoromethyl)benzene for Example 1C and 1-isocyanato-3-methylbenzene, respectively, in Example 1D. $^1$H NMR (300 MHz, DMSO-D$_6$) δ ppm 1.73–1.78 (m, 4H), 2.65 (t, J=5.26 Hz, 4H), 3.71 (s, 2H), 5.75 (s, 2H), 7.33 (d, J=7.46 Hz, 1H), 7.39 (d, J=8.48 Hz, 2H), 7.51 (s, 1H), 7.54 (d, J=7.80 Hz, 1H), 7.59 (s, 1H), 7.62 (d, J=8.48 Hz, 2H), 7.97 (s, 1H), 8.04 (s, 1H), 9.02 (s, 1H), 9.13 (s, 1H); MS (ESI(+)) m/e 536 (M+H)$^+$.

EXAMPLE 508

N-{4-[4-amino-7-(3-pyrrolidin-1-ylprop-1-ynyl)thieno[3,2-c]pyridin-3-yl]phenyl}-N'-[2-fluoro-5-(trifluoromethyl)phenyl]urea The desired product was prepared by substituting Example 506B and 1-fluoro-2-isocyanato-4-(trifluoromethyl)benzene for Example 1C and 1-isocyanato-3-methylbenzene, respectively, in Example 1D. $^1$H NMR (300 MHz, DMSO-D$_6$) δ ppm 1.98 (m, 2H), 2.09 (m, 2H), 3.24 (m, 2H), 3.64 (m, 2H), 4.54 (s, 2H), 6.32 (s, 2H), 7.41 (m, 3H), 7.52 (m, 1H), 7.65 (m, 3H), 8.15 (s, 1H), 8.62 (dd, J=7.29, 2.20 Hz, 1H), 9.03 (d, J=2.71 Hz, 1H), 9.47 (s, 1H); MS (ESI(+)) m/e 554 (M+H)$^+$.

EXAMPLE 509

N-{4-[4-amino-7-(3-pyrrolidin-1-ylprop-1-ynyl)thieno[3,2-c]pyridin-3-yl]phenyl}-N'-(2-fluoro-5-methylphenyl)urea The desired product was prepared by substituting Example 506B and 1-fluoro-2-isocyanato-4-methylbenzene for Example 1C and 1-isocyanato-3-methylbenzene, respectively, in Example 1D. $^1$H NMR (300 MHz, DMSO-D$_6$) δ ppm 1.99 (m, 4H), 2.28 (s, 3H), 3.25 (m, 2H), 3.63 (m, 2H), 4.54 (s, 2H), 6.44 (s, 2H), 6.82 (m, 1H), 7.12 (dd, J=11.36, 8.31 Hz, 1H), 7.41 (d, J=8.48 Hz, 2H), 7.63 (d, J=8.48 Hz, 2H), 7.69 (s, 1H), 7.98 (dd, J=7.80, 1.70 Hz, 1H), 8.16 (s, 1H), 8.61 (d, J=2.03 Hz, 1H), 9.36 (s, 1H); MS (ESI(+)) m/e 500 (M+H)$^+$.

EXAMPLE 510

N-{4-[4-amino-7-(3-pyrrolidin-1-ylprop-1-ynyl)thieno[3,2-c]pyridin-3-yl]phenyl}-N'-(3-chlorophenyl)urea The desired product was prepared by substituting Example 506B and 1-chloro-3-isocyanatobenzene for Example 1C and 1-isocyanato-3-methylbenzene, respectively, in Example 1D. $^1$H NMR (300 MHz, DMSO-D$_6$) δ ppm 2.03 (m, 4H), 3.24 (m, 2H), 3.58 (m, 2H), 4.54 (s, 2H), 6.43 (s, 2H), 7.03 (m, 1H), 7.31 (m, 2H), 7.41 (d, J=8.5 Hz, 2H), 7.65 (d, J=8.5 Hz, 2H), 7.68 (s, 1H), 7.75 (s, 1H), 8.16 (s, 1H), 9.29 (s, 1H), 9.31 (s, 1H); MS (ESI(+)) m/e 502 (M+H)$^+$.

EXAMPLE 511

2-{3-[4-amino-3-(4-aminophenyl)thieno[3,2-c]pyridin-7-yl]prop-2-ynyl}-1H-isoindole-1,3(2H)-dione A suspension of Example 77B (0.6 g, 1.63 mmol) in DMF (3 mL) and triethylamine (2 mL) was degassed by bubbling nitrogen through the suspension for 5 minutes, treated with N-propargylphthalimide (0.45 g, 2.45 mmol), PdCl$_2$(PPh$_3$)$_4$ (57 mg, 0.08 mmol), and CuI (15 mg, 0.08 mmol), then heated to 80° C. for 1 hour. The cooled solution was poured into water, extracted with ethyl acetate and the combined organic layers were washed with brine, dried (Na$_2$SO$_4$), filtered and concentrated. The residue was purified by flash chromatography on silica gel using 3% methanol/dichloromethane to provide 300 mg (43% yield) of the desired product. $^1$H NMR (300 MHz, DMSO-D$_6$) δ ppm 4.72 (s, 2H), 5.37 (s, 2H), 5.86 (s, 2H), 6.66 (d, J=8.14 Hz, 2H), 7.07 (d, J=8.14 Hz, 2H), 7.35 (s, 1H), 7.87–7.89 (m, 1H), 7.90 (s, 1H), 7.93 (d, J=4.07 Hz, 2H), 7.96 (d, J=5.76 Hz, 1H); MS (ESI(+)) m/e 425 (M+H)+

EXAMPLE 512

N-(4-{4-amino-7-[3-(diethylamino)prop-1-ynyl]thieno[3,2-c]pyridin-3-yl}phenyl)-N'-[3-(trifluoromethyl)phenyl]urea

EXAMPLE 512A 3-(4-aminophenyl)-7-[3-(diethylamino)prop-1-ynyl]thieno[3,2-c]pyridin-4-amine The desired product was prepared by substituting Example 77B and 3-diethylamino-1-propyne or Example 144A and 3-butyn-1-ol in Example 144B. MS (ESI(+)) m/e 351 (M+H)$^+$.

EXAMPLE 512B

N-(4-{4-amino-7-[3-(diethylamino)prop-1-ynyl]thieno[3,2-c]pyridin-3-yl}phenyl)-N'-[3-(trifluoromethyl)phenyl]urea The desired product was prepared by substituting Example 512A and 1-isocyanato-3-(trifluoromethyl)benzene for Example 1C and 1-isocyanato-3-methylbenzene, respectively, in Example 1D. $^1$H NMR (300 MHz, DMSO-D$_6$) δ ppm 1.06 (t, J=7.12 Hz, 6H), 2.60 (q, J=6.89 Hz, 4H), 3.71 (s, 2H), 5.75 (s, 2H), 7.33 (d, J=7.46 Hz, 1H), 7.39 (d, J=8.48 Hz, 2H), 7.53 (m, 2H), 7.61 (m, 3H), 7.96 (s, 1H), 8.04 (s, 1H), 9.01 (s, 1H), 9.12 (s, 1H); MS (ESI(+)) m/e 538 (M+H)$^+$.

EXAMPLE 513

N-{4-[4-amino-7-(1H-indol-5-yl)thieno[3,2-c]pyridin-3-yl]phenyl}-N'-(3-chlorophenyl)urea The desired product was formed by substituting Example 284A and 3-chloro-1-isocyanatobenzene for Example 1C and 1-isocyanato-3-methylbenzene, respectively, in Example 1D. $^1$H NMR (300 MHz, DMSO-D$_6$) δ ppm 6.56 (m, 1H), 6.84 (s, 2H), 7.04 (m, 1H), 7.32 (d, J=5.43 Hz, 2H), 7.39 (dd, J=8.31, 1.87 Hz, 1H), 7.49 (m, 3H), 7.60 (d, J=8.14 Hz, 1H), 7.69 (d, J=8.48 Hz, 2H), 7.75 (m, 1H), 7.86 (m, 2H), 7.94 (s, 1H), 9.22 (s, 1H), 9.28 (s, 1H), 11.37 (s, 1H); MS (ESI(+)) m/e 510 (M+H)$^+$.

EXAMPLE 514

N-{4-[4-amino-7-(1H-indol-5-yl)thieno[3,2-c]pyridin-3-yl]phenyl}-N'-[3-(trifluoromethyl)phenyl]urea The desired product was prepared by substituting Example 284A and 1-isocyanato-3-(trifluoromethyl)benzene for Example 1C and 1-isocyanato-3-methylbenzene, respectively, in Example 1D. $^1$H NMR (300 MHz, DMSO-D$_6$) δ ppm 6.56 (m, 1H), 6.83 (s, 2H), 7.33 (d, J=7.46 Hz, 1H), 7.39 (dd, J=8.14, 1.70 Hz, 1H), 7.49 (m, 3H), 7.55 (m, 1H), 7.61 (m, 2H), 7.70 (m, 2H), 7.86 (m, 2H), 7.94 (s, 1H), 8.06 (m, 1H), 9.31 (s, 1H), 9.37 (s, 1H), 11.36 (s, 1H); MS (ESI(+)) m/e 544 (M+H)$^+$.

EXAMPLE 515

N-{4-[4-amino-7-(1H-indol-5-yl)thieno[3,2-c]pyridin-3-yl]phenyl}-N'-(2-fluoro-5-methylphenyl)urea The desired product was prepared by substituting Example 284A and 1-fluoro-2-isocyanato-4-methylbenzene for Example 1C and 1-isocyanato-3-methylbenzene, respectively, in Example 1D. $^1$H NMR (300 MHz, DMSO-D$_6$) δ ppm 2.29 (s, 3H), 6.56 (s, 1H), 6.84 (m, J=5.09, 2.37 Hz, 3H), 7.13 (dd, J=11.36, 8.31 Hz, 1H), 7.39 (dd, J=8.48, 1.70 Hz, 1H), 7.49 (m, 3H), 7.60 (d, J=8.14 Hz, 1H), 7.67 (d, J=8.81 Hz, 2H), 7.86 (m, 2H), 7.94 (s, 1H), 7.99 (dd, J=7.97, 1.86 Hz, 1H), 8.60 (d, J=2.37 Hz, 1H), 9.36 (s, 1H), 11.36 (s, 1H); MS (ESI(+)) m/e 508 (M+H)$^+$.

EXAMPLE 516 tert-butyl 3-{4-amino-3-[4-({[(3-methylphenyl)amino]carbonyl}amino)phenyl]thieno[3,2-c]pyridin-7-yl}prop-2-ynyl(ethyl)carbamate

EXAMPLE 516A tert-butyl prop-2-ynylcarbamate

A solution of propargyl amine (2.32 g, 42.1 mmol) in THF (75 mL) and water (200 mL) was treated with a saturated sodium bicarbonate solution (5 mL), followed by the dropwise addition of a solution of di-tert-butyl-dicarbonate (9.19 g, 42.1 mmol) in THF (20 mL). The solution was stirred overnight at room temperature, concentrated in vacuo to remove THF, extracted with ethyl acetate. The combined organics were washed with brine, dried (MgSO$_4$) and concentrated to provide 4.37 g (67% yield) of the desired product. $^1$H NMR (300 MHz, CHLOROFORM-D) δ ppm 1.46 (s, 9H), 2.22 (t, J=2.54 Hz, 1H), 3.92 (dd, J=5.26, 2.20 Hz, 2H), 4.68 (s, 1H).

EXAMPLE 516B tert-butyl ethyl(prop-2-ynyl)carbamate

A suspension of sodium hydride (354 mg, 14.2 mmol) in DMF (33 mL) at room temperature was treated with a solution of Example 516A (2.0 g, 12.9 mmol) in DMF (10 mL) and stirred for one hour at room temperature. The solution was cooled to 0° C., treated with ethyl iodide (1.24 mL, 15.5 mmol), stirred for one hour at 0° and overnight at room temperature. The solution was diluted with water (25 mL),extracted with diethyl ether (2×50 mL) and the combined organic layers were washed with brine (30 mL0, dried (MgSO$_4$), filtered and concentrated. The residue was purified by flash chromatography on silica gel using 5–10% ethyl acetate/hexanes to give the 1.1 g (47% yield) of the desired product. MS (ESI(+)) m/e 184 (M+H)$^+$.

tert-butyl 3-[4-amino-3-(4-aminophenyl)thieno[3,2-c]pyridin-7-yl]prop-2-ynyl(ethyl)carbamate The desired product was prepared by substituting Example 77B and Example 516B for Example 144A and 3-butyn-1-ol, respectively, in Example 144B. $^1$H NMR (300 MHz, DMSO-D$_6$) δ ppm 1.17 (t, J=6.95 Hz, 3H), 1.44 (s, 9H), 3.36 (q, J=7.12 Hz, 2H), 4.32 (s, 2H), 5.38 (s, 2H), 5.83 (s, 2H), 6.67 (d, J=8.48 Hz, 2H), 7.08 (d, J=8.48 Hz, 2H), 7.37 (s, 1H), 7.93 (s, 1H), MS (ESI(+)) m/e 422 (M+H)$^+$.

EXAMPLE 516D tert-butyl 3-{4-amino-3-[4-({[(3-methylphenyl)amino]carbonyl}amino)phenyl]thieno[3,2-c]pyridin-7-yl}prop-2-ynyl(ethyl)carbamate The desired product was prepared by substituting Example 516C for Example 1C in Example 1D. $^1$H NMR (300 MHz, DMSO-D$_6$) δ ppm 1.18 (t, J=6.44 Hz, 3H), 1.45 (s, 9H), 2.29 (s, 3H), 3.37 (q, J=7.12 Hz, 2H), 4.33 (s, 2H), 5.79 (s, 2H), 6.80 (d, J=7.46 Hz, 1H), 7.17 (t, J=7.80 Hz, 1H), 7.25 (m, 1H), 7.31 (m, 1H), 7.37 (d, J=8.48 Hz, 2H), 7.52 (s, 1H), 7.60 (d, J=8.48 Hz, 2H), 7.97 (s, 1H), 8.66 (s, 1H), 8.86 (s, 1H); MS (ESI(+)) m/e 556 (M+H)$^+$.

EXAMPLE 517

N-(4-{4-amino-7-[3-(ethylamino)prop-1-ynyl]thieno[3,2-c]pyridin-3-yl}phenyl)-N'-(3-methylphenyl)urea The desired product was prepared by substituting Example 516D for Example 76B in Example 76C. $^1$H NMR (300 MHz, DMSO-D$_6$) δ ppm 1.07 (t, J=7.12 Hz, 3H), 2.29 (s, 3H), 2.72 (q, J=7.12 Hz, 2H), 3.65 (s, 2H), 5.74 (s, 2H), 6.81 (d, J=7.46 Hz, 1H), 7.17 (t, J=7.80 Hz, 1H), 7.25 (m, 1H), 7.32 (s, 1H), 7.38 (d, J=8.48 Hz, 2H), 7.51 (s, 1H), 7.60 (m, J=8.48 Hz, 3H), 7.95 (s, 1H), 8.66 (s, 1H), 8.86 (s, 1H); MS (ESI(+)) m/e 456 (M+H)$^+$.

EXAMPLE 518 tert-butyl 3-{4-amino-3-[4-({[(2-fluoro-5-methylphenyl)amino]carbonyl}amino)phenyl]thieno[3,2-c]pyridin-7-yl}prop-2-ynyl(ethyl)carbamate The desired product was prepared by substituting Example 516C and 1-fluoro-2-isocyanato-4-methylbenzene for Example 1C and 1-isocyanato-3-methylbenzene, respectively, in Example 1D. $^1$H NMR (300 MHz, DMSO-D$_6$) δ ppm 1.18 (t, J=7.12 Hz, 3H), 1.45 (s, 9H), 2.28 (s, 3H), 3.37 (q, J=7.12 Hz, 2H), 4.33 (s, 2H), 5.77 (m, 2H), 6.83 (m, 1H), 7.12 (dd, J=11.36, 8.31 Hz, 1H), 7.39 (d, J=8.82 Hz, 2H), 7.53 (s, 1H), 7.60 (d, J=8.82 Hz, 2H), 7.97 (s, 1H), 8.00 (dd, J=7.80, 2.03 Hz, 1H), 8.55 (d, J=2.37 Hz, 1H), 9.26 (s, 1H); MS (ESI(+)) m/e 574 (M+H)$^+$.

EXAMPLE 519

N-(4-{4-amino-7-[3-(ethylamino)prop-1-ynyl]thieno[3,2-c]pyridin-3-yl}phenyl)-N'-(2-fluoro-5-methylphenyl)urea The desired product was prepared by substituting Example 518 for Example 76B in Example 76C. $^1$H NMR (300 MHz, DMSO-D$_6$) δ ppm 1.07 (t, J=7.29 Hz, 3H), 2.30 (m, 3H), 2.73 (q, J=7.12 Hz, 2H), 3.66 (s, 2H), 5.73 (s, 2H), 6.82 (m, 1H), 7.11 (m, 1H), 7.38 (m, 3H), 7.51 (s, 1H), 7.60 (m, 2H), 7.95 (s, 1H), 7.99 (m, 1H), 8.55 (d, J=2.37 Hz, 1H), 9.26 (s, 1H); MS (ESI(+)) m/e 474 (M+H)$^+$.

EXAMPLE 520

N-(4-{4-amino-7-[3-(ethylamino)prop-1-ynyl]thieno[3,2-c]pyridin-3-yl}phenyl)-N'-[3-(trifluoromethyl)phenyl]urea

EXAMPLE 520A tert-butyl 3-(4-amino-3-{4-[({[3-(trifluoromethyl)phenyl]amino}carbonyl)amino]phenyl}thieno[3,2-c]pyridin-7-yl)prop-2-ynyl(ethyl)carbamate The desired product was prepared by substituting Example 516C and 1-isocyanato-3-(trifluoromethyl)benzene for Example 1C and 1-isocyanato-3-methylbenzene, respectively, in Example 1D.

EXAMPLE 520B

N-(4-{4-amino-7-[3-(ethylamino)prop-1-ynyl]thieno[3,2-c]pyridin-3-yl}phenyl)-N'-[3-(trifluoromethyl)phenyl]urea The desired product was prepared by substituting Example 520A for Example 76B in Example 76C. $^1$H NMR (300 MHz, DMSO-D$_6$) δ ppm 1.12 (m, 3H), 2.83 (q, J=6.89 Hz, 2H), 3.82 (s, 2H), 5.79 (s, 2H), 7.32 (m, 2H), 7.39 (d, J=8.48 Hz, 2H), 7.53 (m, 2H), 7.62 (t, J=7.80 Hz, 3H), 7.98 (s, 1H), 8.04 (s, 1H), 9.09 (s, 1H), 9.20 (s, 1H); MS (ESI(+)) m/e 510 (M+H)$^+$.

EXAMPLE 521 tert-butyl 3-{4-amino-3-[4-({[(3-chlorophenyl)amino]carbonyl}amino)phenyl]thieno[3,2-c]pyridin-7-yl}prop-2-ynyl(ethyl)carbamate The desired product was prepared by substituting Example 516C and 3-chloro-1-isocyanatobenzene for Example 1C and 1-isocyanato-3-methylbenzene, respectively, in Example 1D. $^1$H NMR (300 MHz, DMSO-D$_6$) δ ppm 1.18 (t, J=6.95 Hz, 3H), 1.45 (s, 9H), 3.37 (q, J=7.12 Hz, 2H), 4.33 (s, 2H), 5.75 (s, 2H), 7.03 (m, 1H), 7.31 (m, 2H), 7.39 (d, J=8.82 Hz, 2H), 7.52 (s, 1H), 7.61 (d, J=8.48 Hz, 2H), 7.73 (m, 1H), 7.97 (s, 1H), 8.97 (m, 2H); MS (ESI(+)) m/e 576 (M+H)$^+$.

EXAMPLE 522

N-(4-{4-amino-7-[3-(ethylamino)prop-1-ynyl]thieno[3,2-c]pyridin-3-yl}phenyl)-N'-(3-chlorophenyl)urea The desired product was prepared by substituting Example 521 for Example 76B in Example 76C. $^1$H NMR (300 MHz, DMSO-D$_6$) δ ppm 1.25 (t, J=7.12 Hz, 3H), 3.13 (m, 2H), 4.32 (m, 2H), 6.76 (s, 2H), 7.03 (m, 1H), 7.32 (m, 2H), 7.42 (d, J=8.48 Hz, 2H), 7.67 (d, J=8.48 Hz, 2H), 7.76 (m, 2H), 8.16 (s, 1H), 9.18 (s, 1H), 9.41 (s, 1H), 9.43 (s, 1H); MS (ESI(+)) m/e 476 (M+H)$^+$.

EXAMPLE 523 tert-butyl 3-(4-amino-3-{4-[({[2-fluoro-5-(trifluoromethyl)phenyl]amino}carbonyl)amino]phenyl}thieno[3,2-c]pyridin-7-yl)prop-2-ynyl(ethyl)carbamate The desired product was prepared by substituting Example 516C and 1-fluoro-2-isocyanato-4-(trifluoromethyl)benzene for Example 1C and 1-isocyanato-3-methylbenzene, respectively, in Example 1D. $^1$H NMR (300 MHz, DMSO-D$_6$) δ ppm 1.18 (t, J=7.12 Hz, 2H), 1.45 (s, 9H), 3.37 (q, J=7.12 Hz, 3H), 4.34 (s, 2H), 5.78 (s, 2H), 7.41 (m, 3H), 7.52 (m, 2H), 7.62 (d, J=8.81 Hz, 2H), 7.97 (s, 1H), 8.64 (dd, J=7.29, 2.20 Hz, 1H), 8.97 (d, J=3.05 Hz, 1H), 9.38 (s, 1H); MS (ESI(+)) m/e 628 (M+H)$^+$.

EXAMPLE 524

N-(4-{4-amino-7-[3-(ethylamino)prop-1-ynyl]thieno[3,2-c]pyridin-3-yl}phenyl)-N'-[2-fluoro-5-(trifluoromethyl)phenyl]urea The desired product was prepared by substituting Example 523 for Example 76B in Example 76C. $^1$H NMR (300 MHz, DMSO-D$_6$) δ ppm 1.25 (m, 3H), 3.13 (s, 2H), 4.32 (s, 2H), 6.48 (s, 2H), 7.42 (m, 3H), 7.52 (m, 1H), 7.65 (d, J=8.81 Hz, 2H), 7.71 (s, 1H), 8.13 (s, 1H), 8.62 (dd, J=7.29, 2.20 Hz, 1H), 9.04 (d, J=2.71 Hz, 1H), 9.14 (s, 1H), 9.48 (s, 1H), MS (ESI(+)) m/e 528 (M+H)$^+$.

EXAMPLE 525 tert-butyl 3-{4-amino-3-[4-({[(3-methylphenyl)amino]carbonyl}amino)phenyl]thieno[3,2-c]pyridin-7-yl}prop-2-ynylcarbamate

EXAMPLE 525A tert-butyl 3-[4-amino-3-(4-aminophenyl)thieno[3,2-c]pyridin-7-yl]prop-2-ynylcarbamate The desired product was prepared by substituting Example 77B and Example 516A for Example 144A and 3-butyn-1-ol, respectively, in Example 144B. MS (ESI(+)) m/e 395 (M+H)$^+$.

EXAMPLE 525B tert-butyl 3-{4-amino-3-[4-({[(3-methylphenyl)amino]carbonyl}amino)phenyl]thieno[3,2-c]pyridin-7-yl}prop-2-ynylcarbamate The desired product was prepared by substituting Example 525A for Example 1C in Example 1D. $^1$H NMR (300 MHz, DMSO-D$_6$) δ ppm 1.42 (s, 9H), 2.29 (s, 3H), 4.06 (d, J=5.09 Hz, 2H), 5.77 (s, 2H), 6.81 (d, J=7.12 Hz, 1H), 7.17 (t, J=7.80 Hz, 1H), 7.25 (m, 1H), 7.32 (s, 1H), 7.38 (m, 3H), 7.52 (s, 1H), 7.60 (d, J=8.48 Hz, 2H), 7.95 (s, 1H), 8.66 (s, 1H), 8.86 (s, 1H); MS (ESI(+)) m/e 528 (M+H)$^+$.

EXAMPLE 526

N-{4-[4-amino-7-(3-aminoprop-1-ynyl)thieno[3,2-c]pyridin-3-yl]phenyl}N'-(3-methylphenyl)urea The desired product was prepared by substituting Example 525B for Example 76B in Example 76C. $^1$H NMR (300 MHz, DMSO-D$_6$) δ ppm 2.29 (s, 3H), 4.14 (d, J=4.75 Hz, 2H), 6.44 (s, 2H), 6.80 (d, J=7.46 Hz, 2H), 7.17 (t, J=7.80 Hz, 1H), 7.26 (m, 1H), 7.33 (s, 1H), 7.39 (d, J=8.48 Hz, 2H), 7.64 (d, J=8.81 Hz, 2H), 7.69 (s, 1H), 8.08 (s, 1H), 8.37 (s, 1H), 8.86 (s, 1H), 9.09 (s, 1H); MS (ESI(+)) m/e 428 (M+H)$^+$.

EXAMPLE 527

N-{4-[4-amino-7-(3-aminoprop-1-ynyl)thieno[3,2-c]pyridin-3-yl]phenyl}-N'-(3-chlorophenyl)urea

EXAMPLE 527A tert-butyl 3-{4-amino-3-[4-({[(3-chlorophenyl)amino]carbonyl}amino)phenyl]thieno[3,2-c]pyridin-7-yl}prop-2-ynylcarbamate The desired product was prepared by substituting Example 525A and 3-chloro-1-isocyanatobenzene for Example 1C and 1-isocyanato-3-methyl benzene, respectively, in Example 1D.

EXAMPLE 527B

N-{4-[4-amino-7-(3-aminoprop-1-ynyl)thieno[3,2-c]pyridin-3-yl]phenyl}-N'-(3-chlorophenyl)urea The desired product was prepared by substituting Example 527A for Example 76B in Example 76C. $^1$H NMR (300 MHz, DMSO-D$_6$) δ ppm 4.14 (m, 2H), 6.38 (s, 2H), 7.03 (m, 2H), 7.31 (m, 2H), 7.41 (d, J=8.82 Hz, 2H), 7.65 (m, 2H), 7.68 (s, 1H), 7.74 (s, 1H), 8.07 (s, 1H), 8.37 (s, 1H), 9.23 (s, 1H), 9.25 (s, 1H); (ESI(+)) m/e 448 (M+H)$^+$.

EXAMPLE 528

N-{4-[4-amino-7-(3-aminoprop-1-ynyl)thieno[3,2-c]pyridin-3-yl]phenyl}-N'-(2-fluoro-5-methylphenyl)urea

EXAMPLE 528A tert-butyl 3-{4-amino-3-[4-({[(2-fluoro-5-methylphenyl)amino]carbonyl}amino)phenyl]thieno[3,2-c]pyridin-7-yl}prop-2-ynylcarbamate The desired product was prepared by substituting Example 525A and 1-fluoro-2-isocyanato-4-methylbenzene for Example 1C and 1-isocyanato-3-methyl benzene, respectively, in Example 1D.

EXAMPLE 528B

N-{4-[4-amino-7-(3-aminoprop-1-ynyl)thieno[3,2-c]pyridin-3-yl]phenyl}-N'-(2-fluoro-5-methylphenyl)urea The desired product was prepared by substituting Example 528A for Example 76B in Example 76C. $^1$H NMR (300 MHz, DMSO-D$_6$) δ ppm 2.28 (s, 3H), 4.14 (d, J=4.75 Hz, 2H), 6.38 (s, 2H), 6.83 (m, 2H), 7.12 (dd, J=11.36, 8.31 Hz, 1H), 7.41 (d, J=8.48 Hz, 2H), 7.63 (d, J=8.81 Hz, 2H), 7.68 (s, 1H), 7.98 (dd, J=7.80, 2.03 Hz, 1H), 8.07 (s, 1H), 8.35 (m, 1H), 8.59 (d, J=2.37 Hz, 1H), 9.33 (s, 1H); ESI(+)) m/e 446 (M+H)$^+$.

EXAMPLE 529 tert-butyl 3-(4-amino-3-{4-[({[2-fluoro-5-(trifluoromethyl)phenyl]amino}carbonyl)amino]phenyl}thieno[3,2-c]pyridin-7-yl)prop-2-ynylcarbamate The desired product was prepared by substituting Example 525A and 1-fluoro-2-isocyanato-4-(trifluoromethyl)benzene for Example 1C and 1-isocyanato-3-methyl benzene, respectively, in Example 1D. $^1$H NMR (500 MHz, DMSO-D$_6$) δ ppm 1.41 (s, 9H), 4.05 (d, J=3.74 Hz, 2H), 5.73 (s, 3H), 7.38 (m, 3H), 7.48 (d, J=10.61 Hz, 1H), 7.51 (s, 1H), 7.61 (d, J=8.42 Hz, 2H), 7.94 (s, 1H), 8.62 (dd, J=7.18, 2.18 Hz, 1H), 8.94 (s, 1H), 9.35 (s, 1H); ESI(+)) m/e 600 (M+H)$^+$.

EXAMPLE 530

N-{4-[4-amino-7-(3-aminoprop-1-ynyl)thieno[3,2-c]pyridin-3-yl]phenyl}-N'-[2-fluoro-5-(trifluoromethyl)phenyl]urea The desired product was prepared by substituting Example 529 for Example 76B in Example 76C. $^1$H NMR (300 MHz, DMSO-D$_6$) δ ppm 4.14 (d, J=5.09 Hz, 2H), 6.38 (s, 2H), 7.43 (m, 4H), 7.52 (m, 1H), 7.65 (d, J=8.82 Hz, 2H), 7.69 (s, 1H), 8.08 (s, 1H), 8.38 (s, 1H), 8.62 (dd, J=7.12, 2.03 Hz, 1H), 9.04 (d, J=2.71 Hz, 1H), 9.47 (s, 1H); ESI(+)) m/e 500 (M+H)$^+$.

EXAMPLE 531 tert-butyl 3-(4-amino-3-{4-[({[3-(trifluoromethyl)phenyl]amino}carbonyl)amino]phenyl}thieno[3,2-c]pyridin-7-yl)prop-2-ynylcarbamate The desired product was prepared by substituting Example 525A and 1-isocyanato-3-(trifluoromethyl)benzene for Example 1C and 1-isocyanato-3-methyl benzene, respectively, in Example 1D. $^1$H NMR (500 MHz, DMSO-D$_6$) δ ppm 1.41 (s, 9H), 4.05 (d, J=3.43 Hz, 2H), 5.73 (s, 3H), 7.35 (m, 3H), 7.52 (m, 2H), 7.60 (m, 3H), 7.94 (s, 1H), 8.02 (s, 1H), 8.98 (s, 1H), 9.09 (s, 1H); ESI(+)) m/e 582 (M+H)$^+$.

EXAMPLE 532

N-{4-[4-amino-7-(3-aminoprop-1-ynyl)thieno[3,2-c]pyridin-3-yl]phenyl}-N'-[3-(trifluoromethyl)phenyl]urea The desired product was prepared by substituting Example 531 for Example 76B in Example 76C. $^1$H NMR (300 MHz, DMSO-D$_6$) δ ppm 4.14 (d, J=5.09 Hz, 2H), 6.46 (s, 2H), 7.33 (d, J=7.80 Hz, 1H), 7.42 (d, J=8.48 Hz, 2H), 7.53 (t, J=7.80 Hz, 1H), 7.66 (m, 4H), 8.08 (m, 2H), 8.38 (m, 2H), 9.37 (s, 1H), 9.46 (s, 1H); ESI(+)) m/e 482 (M+H)$^+$.

EXAMPLE 533

N-{4-[4-amino-7-(3-amino-3-ethylpent-1-ynyl)thieno[3,2-c]pyridin-3-yl]phenyl}-N'-(3-methylphenyl)urea

EXAMPLE 533A tert-butyl 1,1-diethylprop-2-ynylcarbamate

The desired product was prepared by substituting 1,1-diethylpropargylamine for propargylamine in Example 516. $^1$H NMR (500 MHz, DMSO-D$_6$) δ ppm 0.85 (t, J=7.49 Hz, 6H), 1.38 (s, 9H), 1.73 (m, 4H), 3.05 (s, 1H), 6.61 (s, 1H).

EXAMPLE 533B tert-butyl 3-[4-amino-3-(4-aminophenyl)thieno[3,2-c]pyridin-7-yl]-1,1-diethylprop-2-ynylcarbamate The desired product was prepared by substituting Example 77B and Example 533A for Example 144A and 3-butyn-1-ol, respectively, in Example 144B. MS (ESI(+)) m/e 451 (M+H)$^+$.

EXAMPLE 533C tert-butyl 3-{4-amino-3-[4-({[(3-methylphenyl)amino]carbonyl}amino)phenyl]thieno[3,2-c]pyridin-7-yl}-1,1-diethylprop-2-ynylcarbamate The desired product was prepared by substituting Example 533B for Example 1C in Example 1D.

EXAMPLE 533D

N-{4-[4-amino-7-(3-amino-3-ethylpent-1-ynyl) thieno[3,2-c]pyridin-3-yl]phenyl}-N'-(3-methylphenyl)urea The desired product was prepared by substituting Example 533C for Example 76B in Example 76C. $^1$H NMR (300 MHz, DMSO-D$_6$) δ ppm 1.14 (t, J=7.29 Hz, 6H), 1.91 (m, 4H), 2.29 (s, 3H), 6.39 (s, 2H), 6.80 (d, J=7.46 Hz, 1H), 7.17 (t, J=7.63 Hz, 1H), 7.26 (d, J=8.14 Hz, 1H), 7.33 (s, 1H), 7.39 (d, J=8.14 Hz, 1H), 7.65 (m, 3H), 8.10 (s, 1H), 8.56 (s, 3H), 8.86 (s, 1H), 9.09 (s, 1H); MS (ESI(+)) m/e 484 (M+H)$^+$.

EXAMPLE 534

N-{4-[4-amino-7-(3-amino-3-ethylpent-1-ynyl) thieno[3,2-c]pyridin-3-yl]phenyl}-N'-(2-fluoro-5-methylphenyl)urea

EXAMPLE 534A tert-butyl 3-{4-amino-3-[4-({[(2-fluoro-5-methylphenyl)amino]carbonyl}amino)phenyl]thieno[3,2-c]pyridin-7-yl}-1,1-diethylprop-2-ynylcarbamate The desired product was prepared by substituting Example 533B and 1-fluoro-2-isocyanato-4-methylbenzene for Example 1C and 1-isocyanato-3-methylbenzene, respectively, in Example 1D.

EXAMPLE 534B

N-{4-[4-amino-7-(3-amino-3-ethylpent-1-ynyl) thieno[3,2-c]pyridin-3-yl]phenyl}-N'-(2-fluoro-5-methylphenyl)urea The desired product was prepared by substituting Example 534A for Example 76B in Example 76C. $^1$H NMR (300 MHz, DMSO-D$_6$) δ ppm 1.14 (t, J=7.46 Hz, 6H), 1.92 (m, 4H), 2.28 (s, 3H), 6.45 (s, 2H), 6.83 (m, 1H), 7.12 (dd, J=11.36, 8.31 Hz, 1H), 7.41 (d, J=8.48 Hz, 2H), 7.63 (d, J=8.48 Hz, 2H), 7.69 (s, 1H), 7.99 (d, J=2.03 Hz, 1H), 8.11 (s, 1H), 8.58 (m, 3H), 9.33 (s, 1H); MS (ESI(+)) m/e 502 (M+H)$^+$.

EXAMPLE 535

N-{4-[4-amino-7-(3-amino-3-ethylpent-1-ynyl) thieno[3,2-c]pyridin-3-yl]phenyl}-N'-(3-chlorophenyl)urea

EXAMPLE 535A tert-butyl 3-{4-amino-3-[4-({[(3-chlorophenyl)amino]carbonyl}amino)phenyl]thieno[3,2-c]pyridin-7-yl}-1,1-diethylprop-2-ynylcarbamate The desired product was prepared by substituting Example 533B and 3-chloro-1-isocyanatobenzene for Example 1C and 1-isocyanato-3-methylbenzene, respectively, in Example 1D.

EXAMPLE 535B

N-{4-[4-amino-7-(3-amino-3-ethylpent-1-ynyl) thieno[3,2-c]pyridin-3-yl]phenyl}-N'-chlorophenyl)urea The desired product was prepared by substituting Example 535A for Example 76B in Example 76C. $^1$H NMR (300 MHz, DMSO-D$_6$) δ ppm 1.14 (t, J=7.46 Hz, 6H), 1.91 (m, 4H), 6.36 (s, 2H), 7.03 (m, 1H), 7.32 (d, J=5.43 Hz, 2H), 7.40 (d, J=8.48 Hz, 2H), 7.65 (d, J=8.8 Hz, 2H), 7.67 (s, 1H), 7.75 (s, 1H), 8.10 (s, 1H), 8.56 (m, 2H), 9.25 (s, 1H), 9.28 (s, 1H); MS (ESI(+)) m/e 504 (M+H)$^+$.

EXAMPLE 536

N-{4-[4-amino-7-(3-amino-3-ethylpent-1-ynyl) thieno[3,2-c]pyridin-3-yl]phenyl}-N'-[3-(trifluoromethyl)phenyl]urea

EXAMPLE 536A tert-butyl 3-(4-amino-3-{4-[({[3-(trifluoromethyl) phenyl]amino}carbonyl)amino]phenyl}thieno[3,2-c]pyridin-7-yl)-1,1-diethylprop-2-ynylcarbamate The desired product was prepared by substituting Example 533B and 1-isocyanato-3-(trifluoromethyl)benzene for Example 1C and 1-isocyanato-3-methylbenzene, respectively, in Example 1D.

EXAMPLE 536B

N-{4-[4-amino-7-(3-amino-3-ethylpent-1-ynyl) thieno[3,2-c]pyridin-3-yl]phenyl}-N'-[3-(trifluoromethyl)phenyl]urea The desired product was prepared by substituting Example 536A for Example 76B in Example 76C. $^1$H NMR (300 MHz, DMSO-D$_6$) δ ppm 1.14 (t, J=7.46 Hz, 6H), 1.91 (m, 4H), 6.35 (s, 2H), 7.33 (d, J=7.46 Hz, 1H), 7.41 (d, J=8.48 Hz, 2H), 7.53 (t, J=7.80 Hz, 1H), 7.62 (m, 1H), 7.67 (m, 3H), 8.06 (s, 1H), 8.10 (s, 1H), 8.55 (m, 2H), 9.32 (s, 1H), 9.42 (s, 1H); MS (ESI(+)) m/e 538 (M+H)$^+$.

EXAMPLE 537

N-{4-[4-amino-7-(3-amino-3-ethylpent-1-ynyl) thieno[3,2-c]pyridin-3-yl]phenyl}-N'-[2-fluoro-5-(trifluoromethyl)phenyl]urea

EXAMPLE 537A tert-butyl 3-(4-amino-3-{4-[({[2-fluoro-5-(trifluoromethyl)phenyl]amino}carbonyl)amino] phenyl}thieno[3,2-c]pyridin-7-yl)-1,1-diethylprop-2-ynylcarbamate The desired product was prepared by substituting Example 533B and 1-fluoro-2-isocyanato-4-(trifluoromethyl)benzene for Example 1C and 1-isocyanato-3-methylbenzene, respectively, in Example 1D.

EXAMPLE 537B

N-{4-[4-amino-7-(3-amino-3-ethylpent-1-ynyl) thieno[3,2-c]pyridin-3-yl]phenyl}-N'-[2-fluoro-5-(trifluoromethyl)phenyl]urea The desired product was prepared by substituting Example 537A for Example 76B in Example 76C. $^1$H NMR (300 MHz, DMSO-D$_6$) δ ppm 1.14 (t, J=7.46 Hz, 6H), 1.91 (m, 4H), 6.38 (s, 2H), 7.43 (m, 3H), 7.52 (m, 1H), 7.65 (d, J=8.82 Hz, 2H), 7.68 (s, 1H), 8.10 (s, 1H), 8.61 (m, 3H), 9.05 (d, J=2.71 Hz, 1H), 9.49 (s, 1H); MS (ESI(+)) m/e 556 (M+H)$^+$.

EXAMPLE 538

N-(4-{4-amino-7-[(2S)-pyrrolidin-2-ylethynyl] thieno[3,2-c]pyridin-3-yl}phenyl)-N'-(3-methylphenyl)urea

EXAMPLE 538A tert-butyl (2S)-2-(2,2-dibromovinyl)pyrrolidine-1-carboxylate

A solution of triphenylphosphine (21.1 g, 80.3 mmol) and carbon tetrabromide (13.32 g, 40.16 mmol) in dichloromethane (300 mL) at 0° C. was treated with a solution of 2-formyl-pyrrolidine-1-carboxylic acid tert-butyl ester (4.0 g, 20.08 mmol) in dichloromethane (10 mL) dropwise via syringe. The solution was stirred for 1 hour at room temperature, poured into a saturated sodium bicarbonate solution and separated. The organic phase was dried (MgSO$_4$), filtered and concentrated. The concentrate was purified by flash chromatography on silica gel using 0–1% methanol/dichloromethane to give 6.13 g (86% yield) of the desired product. $^1$H NMR (300 MHz, CHLOROFORM-D) δ ppm 1.47 (s, 9H), 1.81 (m, 3H), 2.16 (m, 1H), 3.39 (m, 2H), 4.37 (s, 1H), 6.38 (s, 1H).

EXAMPLE 538B tert-butyl (2S)-2-ethynylpyrrolidine-1-carboxylate

A solution of Example 538A (6.11 g, 17.21 mmol) in THF (150 mL) at −78° C. was treated with sec-butyl lithium (24.6 mL, 34.41 mmol) dropwise via syringe and stirred for 30 minutes at −78° C. The solution was then treated with a saturated ammonium chloride solution (100 mL), allowed to warm to room temperature, diluted with ether and extracted. The combined organic layers were washed with brine, dried (MgSO$_4$) and concentrated to provide the desired product in quantitative yield. MS (ESI(+)) m/e 196 (M+H)$^+$.

EXAMPLE 538C tert-butyl (2S)-2-{[4-amino-3-(4-aminophenyl) thieno[3,2-c]pyridin-7-yl]ethynyl}pyrrolidine-1-carboxylate The desired product was prepared by substituting Example 77B and Example 538B for Example 144A and 3-butyn-1-ol, respectively, in Example 144B. MS (ESI(+)) m/e 435 (M+H)$^+$.

EXAMPLE 538D tert-butyl (2S)-2-({4-amino-3-[4-({[(3-methylphenyl)amino]carbonyl}amino)phenyl]thieno[3,2-c] pyridin-7-yl}ethynyl)pyrrolidine-1-carboxylate The desired product was prepared by substituting Example 538C for Example 1C in Example 1D.

EXAMPLE 538E

N-(4-{4-amino-7-[(2S)-pyrrolidin-2-ylethynyl] thieno[3,2-c]pyridin-3-yl}phenyl)-N'-(3-methylphenyl)urea The desired product was prepared by substituting Example 538D for Example 76B in Example 76C. $^1$H NMR (300 MHz, DMSO-D$_6$) δ ppm 2.06 (m, 3H), 2.29 (s, 3H), 2.40 (m, 1H), 3.37 (m, 2H), 4.76 (m, 1H), 6.66 (m, 1H), 6.80 (d, J=7.46 Hz, 1H), 7.17 (t, J=7.80 Hz, 1H), 7.27 (m, 1H), 7.33 (s, 1H), 7.40 (d, J=8.48 Hz, 2H), 7.65 (d, J=8.48 Hz, 2H), 7.73 (s, 1H), 8.14 (s, 1H), 8.92 (s, 1H), 9.16 (s, 1H), 9.50 (s, 2H); MS (ESI(+)) m/e 468 (M+H)$^+$.

EXAMPLE 539

N-(4-{4-amino-7-[(2S)-pyrrolidin-2-ylethynyl] thieno[3,2-c]pyridin-3-yl}phenyl)-N'-(2-fluoro-5-methylphenyl)urea

EXAMPLE 539 tert-butyl (2S)-2-({4-amino-3-[4-({[(2-fluoro-5-methylphenyl)amino]carbonyl}amino)phenyl]thieno [3,2-c]pyridin-7-yl}ethynyl)pyrrolidine-1-carboxylate The desired product was prepared by substituting Example 538C and 1-fluoro-2-isocyanato-4-methylbenzene for Example 1C and 1-isocyanato-3-methylbenzene, respectively, in Example 1D.

EXAMPLE 539B

N-(4-{4-amino-7-[(2S)-pyrrolidin-2-ylethynyl] thieno[3,2-c]pyridin-3-yl}phenyl)-N'-(2-fluoro-5-methylphenyl)urea The desired product was prepared by substituting Example 539A for Example 76B in Example 76C. $^1$H NMR (300 MHz, DMSO-D$_6$) δ ppm 2.08 (m, 3H); 2.28 (s, 3H); 2.39 (m, 1H), 3.36 (m, 2H), 4.75 (s, 1H), 6.41 (s, 1H), 6.83 (m, 1H); 7.12 (dd, J=11.19, 8.48 Hz, 1H), 7.41 (d, J=8.48 Hz, 2H), 7.63 (d, J=8.48 Hz, 2H), 7.68 (s, 1H), 7.98 (dd, J=7.80, 1.36 Hz, 1H), 8.11 (m, 1H), 8.60 (d, J=1.70 Hz, 1H), 9.34 (s, 1H), 9.46 (s, 2H); MS (ESI(+)) m/e 486 (M+H)$^+$.

EXAMPLE 540

N-(4-{4-amino-7-[(2S)-pyrrolidin-2-ylethynyl]
thieno[3,2-c]pyridin-3-yl}phenyl)-N'-(3-chlorophenyl)urea

EXAMPLE 540A tert-butyl (2S)-2-({4-amino-3-[4-({[(3-chlorophenyl)amino]carbonyl}amino)phenyl]thieno[3,2-c]pyridin-7-yl}ethynyl)pyrrolidine-1-carboxylate The desired product was prepared by substituting Example 538C and 3-chloro-1-isocyanatobenzene for Example 1C and 1-isocyanato-3-methylbenzene, respectively, in Example 1D.

EXAMPLE 540B

N-(4-{4-amino-7-[(2S)-pyrrolidin-2-ylethynyl]
thieno[3,2-c]pyridin-3-yl}phenyl)-N'-(3-chlorophenyl)urea The desired product was prepared by substituting Example 540A for Example 76B in Example 76C. $^1$H NMR (300 MHz, DMSO-D$_6$) δ ppm 2.08 (m, 3H), 2.42 (m, 1H), 3.36 (m, 2H), 4.76 (m, 1H), 6.62 (s, 1H), 7.03 (m, 1H), 7.32 (d, J=5.09 Hz, 2H), 7.41 (d, J=8.82 Hz, 2H), 7.65 (d, J=8.81 Hz, 2H), 7.72 (s, 1H), 7.75 (m, 1H), 8.13 (s, 1H), 9.30 (d, J=8.48 Hz, 2H), 9.47 (s, 2H); MS (ESI(+)) m/e 488 (M+H)$^+$.

EXAMPLE 541

N-(4-{4-amino-7-[(2S)-pyrrolidin-2-ylethynyl]
thieno[3,2-c]pyridin-3-yl}phenyl)-N'-[3-(trifluoromethyl)phenyl]urea

EXAMPLE 541A tert-butyl (2S)-2-[(4-amino-3-{4-[({[3-(trifluoromethyl)phenyl]amino}carbonyl)amino]phenyl}thieno[3,2-c]pyridin-7-yl)ethynyl]pyrrolidine-1-carboxylate The desired product was prepared by substituting Example 538C and 1-isocyanato-3-(trifluoromethyl)benzene for Example 1C and 1-isocyanato-3-methylbenzene, respectively, in Example 1D.

EXAMPLE 541B

N-(4-{4-amino-7-[(2S)-pyrrolidin-2-ylethynyl]
thieno[3,2-c]pyridin-3-yl}phenyl)-N'-[3-(trifluoromethyl)phenyl]urea The desired product was prepared by substituting Example 541A for Example 76B in Example 76C. $^1$H NMR (300 MHz, DMSO-D$_6$) δ ppm 2.07 (m, 3H), 2.41 (m, 1H), 3.36 (m, 2H), 4.75 (m, 1H), 6.43 (s, 1H), 7.32 (d, J=7.80 Hz, 1H), 7.41 (d, J=8.48 Hz, 2H), 7.53 (t, J=7.97 Hz, 1H), 7.60 (s, 1H), 7.67 (d, J=8.81 Hz, 2H), 8.06 (s, 1H), 8.11 (s, 1H), 9.38 (s, 1H), 9.48 (m, 3H); MS (ESI(+)) m/e 522 (M+H)$^+$.

EXAMPLE 542

N-(4-{4-amino-7-[(2S)-pyrrolidin-2-ylethynyl]
thieno[3,2-c]pyridin-3-yl}phenyl)-N'-[2-fluoro-5-(trifluoromethyl)phenyl]urea

EXAMPLE 542A tert-butyl (2S)-2-[(4-amino-3-{4-[({[2-fluoro-5-(trifluoromethyl)phenyl]amino}carbonyl)amino]phenyl}thieno[3,2-c]pyridin-7-yl)ethynyl]pyrrolidine-1-carboxylate The desired product was prepared by substituting Example 538C and 1-fluoro-2-isocyanato-4-(trifluoromethyl)benzene for Example 1C and 1-isocyanato-3-methylbenzene, respectively, in Example 1D.

EXAMPLE 542B

N-(4-{4-amino-7-[(2S)-pyrrolidin-2-ylethynyl]
thieno[3,2-c]pyridin-3-yl}phenyl)-N'-[2-fluoro-5-(trifluoromethyl)phenyl]urea The desired product was prepared by substituting Example 542A for Example 76B in Example 76C. $^1$H NMR (300 MHz, DMSO-D$_6$) δ ppm 2.07 (m, 3H), 2.41 (m, 1H), 3.38 (q, J=7.12 Hz, 2H), 4.76 (m, 1H), 6.61 (s, 1H), 7.42 (m, 3H), 7.52 (m, 1H), 7.66 (d, J=8.48 Hz, 2H), 7.73 (s, 1H), 8.14 (s, 1H), 8.62 (dd, J=7.29, 2.20 Hz, 1H), 9.05 (d, J=2.71 Hz, 1H), 9.52 (m, 3H), MS (ESI(+)) m/e 540 (M+H)$^+$.

EXAMPLE 543

N-[4-(4-aminofuro[3,2-c]pyridin-3-yl)phenyl]-N'-(3-methylphenyl)urea

EXAMPLE 543A 3-bromo-4-chlorofuro[3,2-c]pyridine

A solution of 4-chlorofuro[3,2-c]pyridine (commercially available, 10.60 g, 69 mmol) in carbon tetrachloride (135 mL) was cooled to −15° C. and bromine (12.13 g, 80 mmol) was added drop-wise over a fifteen minute time period. The mixture was stirred at ambient temperature for eighteen hours. The solvent was removed in vacuo, and the residue was dissolved in methanol (250 mL). A solution of 20% aqueous sodium hydroxide (35 mL) was added and the mixture was stirred 1 hour at ambient temperature. The methanol was removed in vacuo, and the residue was partitioned between water (100 mL) and dichloromethane (50 mL). The combined organic layers were dried over anhydrous, agnesium sulfate and the solvent was removed in vacuo to give 3-bromo-4-chloro[3,2-c]pyridine 15.45 g, 96%) as a solid. MS (ESI(+)) m/e 232, 234 (M+H)$^+$.

EXAMPLE 543B 3-bromofuro[3,2-c]pyridin-4-amine

The desired product was prepared by substituting Example 543A for 3-bromo-4-chlorothieno[3,2-c]pyridine in Example 1B. MS (ESI(+)) m/e 213, 215 (M+H)$^+$.

EXAMPLE 543C 3-(4-aminophenyl)furo[3,2-c]pyridin-4-amine

The desired product was prepared by substituting Example 543B and 4-bromoaniline for Example 1B and 4-bromo-2-fluroaniline, respectively, in Example 1C. $^1$H NMR (300 MHz, DMSO-D$_6$) δ ppm 5.32 (br s, 2H), 5.50 (br s, 2H), 6.69 (d, J=8.5 Hz, 2H), 6.88 (d, J=6.1 Hz, 1H), 7.15 (d, J=8.8 Hz, 2H), 7.76 (s, 1H), 7.82 (d, J=5.76 Hz, 1H); MS ESI(+) m/e 226 (M+H)$^+$.

EXAMPLE 543D

N-[4-(4-aminofuro[3,2-c]pyridin-3-yl)phenyl]-N'-(3-methylphenyl)urea

The desired product was prepared by substituting Example 543C for 1C in Example 1D. $^1$H NMR (300 MHz, DMSO-D$_6$) δ ppm 2.29 (s, 3H), 5.52 (s, 2H), 6.80 (d, J=7.1 Hz, 1H), 6.93 (d, J=5.8 Hz, 1H), 7.16 (t, J=7.8 Hz, 1H), 7.25 (m, 1H), 7.31 (s, 1H), 7.43 (m, 2H), 7.60 (d, J=8.8 Hz, 2H), 7.88 (m, 2H), 8.64 (s, 1H), 8.82 (s, 1H); MS ESI(+)) m/e 359 (M+H)$^+$.

EXAMPLE 544

N-[4-(4-aminofuro[3,2-c]pyridin-3-yl)phenyl]-N'-(3-chlorophenyl)urea

The desired product was prepared by substituting Example 543C and 3-chloro-1-isocyanatobenzene for Example 1C and 1-isocyanato-3-methylbenzene, respectively, in Example 1D. $^1$H NMR (300 MHz, DMSO-D$_6$) δ ppm 5.52 (s, 2H), 6.93 (d, J=6.1 Hz, 1H), 7.03 (m, 1H), 7.31 (m, 2H), 7.45 (d, J=8.5 Hz, 2H), 7.61 (d, J=8.5 Hz, 2H), 7.73 (s, 1H), 7.86 (d, J=5.8 Hz, 1H), 7.92 (s, 1H), 8.94 (s, 1H), 8.95 (s, 1H); MS ESI(+)) m/e 379 (M+H)$^+$.

EXAMPLE 545

N-[4-(4-aminofuro[3,2-c]pyridin-3-yl)phenyl]-N'-[2-fluoro-5-(trifluoromethyl)phenyl]urea The desired product was prepared by substituting Example 543C and 1-fluoro-2-isocyanato-4-(trifluoromethyl)benzene for Example 1C and 1-isocyanato-3-methylbenzene, respectively, in Example 1D. $^1$H NMR (300 MHz, DMSO-D$_6$) δ ppm 5.52 (br s, 2H), 6.94 (d, J=5.8 Hz, 1H), 7.44 (m, 4H), 7.63 (d, J=8.8 Hz, 2H), 7.87 (d, J=5.8 Hz, 1H), 7.93 (s, 1H), 8.64 (dd, J=7.3, 2.2 Hz, 1H), 8.95 (d, J=2.7 Hz, 1H), 9.34 (s, 1H); MS ESI(+) m/e 431 (M+H)$^+$.

EXAMPLE 546

N-[4-(4-aminofuro[3,2-c]pyridin-3-yl)phenyl]-N'-[3-(trifluoromethyl)phenyl]urea

The desired product was prepared by substituting Example 543C and 1-isocyanato-3-(trifluoromethyl)benzene for Example 1C and 1-isocyanato-3-methylbenzene, respectively, in Example 1D. $^1$H NMR (300 MHz, DMSO-D$_6$) δ ppm 5.52 (s, 2H), 6.93 (d, J=5.8 Hz, 1H), 7.32 (d, J=7.5 Hz, 1H), 7.45 (d, J=8.5 Hz, 2H), 7.53 (t, J=7.8 Hz, 1H), 7.61 (t, J=8.3 Hz, 3H), 7.87 (d, J=5.8 Hz, 1H), 7.92 (s, 1H), 8.03 (s, 1H), 8.97 (s, 1H), 9.10 (s, 1H); MS ESI(+) m/e 413 (M+H)$^+$.

EXAMPLE 547

N-[4-(4-amino-7-pyridin-3-ylfuro[3,2-c]pyridin-3-yl)phenyl]-N'-(3-methylphenyl)urea

EXAMPLE 547A tert-butyl 4-(4-aminofuro[3,2-c]pyridin-3-yl)phenylcarbamate

The desired product was prepared by substituting Example 543C for Example 66C in Example 72A. MS ESI(+) m/e 326 (M+H)$^+$.

EXAMPLE 547B tert-butyl 4-(4-amino-7-iodofuro[3,2-c]pyridin-3-yl)phenylcarbamate The desired product was prepared by substituting Example 547A for Example 10A in Example 10B.

EXAMPLE 547C 3-(4-aminophenyl)-7-iodofuro[3,2-c]pyridin-4-amine

The desired product was prepared by substituting Example 547B for Example 294B in Example 294C. MS ESI(+) m/e 352 (M+H)$^+$.

EXAMPLE 547D

N-[4-(4-amino-7-iodofuro[3,2-c]pyridin-3-yl)phenyl]-N'-(3-methylphenyl)urea

The desired product was prepared by substituting Example 547C for Example 1C in Example 1D. $^1$H NMR (300 MHz, DMSO-D$_6$) δ ppm 2.29 (s, 3H), 5.69 (br s, 2H), 6.80 (d, J=7.1 Hz, 1H), 7.17 (t, J=7.8 Hz, 1H), 7.25 (m, 1H), 7.31 (s, 1H), 7.43 (d, J=8.5 Hz, 2H), 7.61 (d, J=8.5 Hz, 2H), 8.03 (s, 1H), 8.05 (s, 1H), 8.64 (s, 1H), 8.84 (s, 1H); MS ESI(+) m/e 485 (M+H)$^+$.

EXAMPLE 547E

N-[4-(4-amino-7-pyridin-3-ylfuro[3,2-c]pyridin-3-yl)phenyl]-N'-(3-methylphenyl)urea The desired product was prepared by substituting Example 547D and 3-pyridylboronic acid for Example 10B and 4-pyridylboronic acid, respectively, in Example 10C. $^1$H NMR (300 MHz, DMSO-D$_6$) δ ppm 2.29 (s, 3H), 5.77 (s, 2H), 6.81 (d, J=7.1 Hz, 1H), 7.17 (t, J=7.8 Hz, 1H), 7.25 (m, 1H), 7.32 (s, 1H), 7.50 (m, 3H), 7.63 (d, J=8.5 Hz, 2H), 8.04 (s, 1H), 8.19 (m, 2H), 8.56 (dd, J=4.8, 1.7 Hz, 1H), 8.66 (s, 1H), 8.85 (s, 1H), 9.02 (d, J=1.4 Hz, 1H); MS ESI(+)) m/e 436 (M+H)$^+$.

EXAMPLE 548

N-{4-[4-amino-7-(1H-indol-5-yl)furo[3,2-c]pyridin-3-yl]phenyl}-N'-(3-methylphenyl)urea The desired product was prepared by substituting Example 547D and 5-indolylboronic acid for Example 10B and 4-pyridylboronic acid, respectively, in Example 10C. $^1$H NMR (300 MHz, DMSO-D$_6$) δ ppm 2.29 (s, 3H), 5.51 (s, 2H), 6.50 (m, 1H), 6.81 (d, J=7.1 Hz, 1H), 7.17 (t, J=7.8 Hz, 1H), 7.25 (d, J=9.0 Hz, 1H) 7.32 (s, 1H), 7.39 (m, 1H), 7.48 (m, J=8.8 Hz, 4H), 7.63 (d, J=8.8 Hz, 2H), 7.94 (s, 1H), 8.01 (s, 1H), 8.08 (s, 1H), 8.65 (s, 1H), 8.84 (s, 1H), 11.15 (s, 1H); MS ESI(+)) m/e 474 (M+H)$^+$.

EXAMPLE 549

N-[4-(4-amino-7-pyrimidin-5-ylfuro[3,2-c]pyridin-3-yl)phenyl]-N'-(3-methylphenyl)urea The desired product was prepared by substituting Example 547D and pyrimidin-5-ylboronic acid for Example 10B and 4-pyridylboronic acid, respectively, in Example 10C. $^1$H NMR (300 MHz, DMSO-D$_6$) δ ppm 2.29 (s, 3H), 5.89 (br s, 2H), 6.81 (d, J=7.5 Hz, 1H), 7.17 (t, J=7.8 Hz, 1H), 7.26 (m, 1H), 7.32 (s, 1H), 7.47 (d, J=8.5 Hz, 2H), 7.63 (d, J=8.8 Hz, 2H), 8.07 (s, 1H), 8.32 (s, 1H), 8.65 (s, 1H), 8.85 (s, 1H), 9.16 (s, 1H), 9.26 (s, 2H); MS ESI(+)) m/e 437 (M+H)$^+$.

EXAMPLE 550

N-(4-{4-amino-7-[3-(diethylamino)prop-1-ynyl]furo[3,2-c]pyridin-3-yl}phenyl)-N'-(3-methylphenyl)urea The desired product was prepared by substituting Example 547D and N,N-diethyl-N-prop-2-ynylamine for Example 144A and 3-butyn-1-ol, respectively, in Example 144B. $^1$H NMR (300 MHz, DMSO-D$_6$) δ ppm 1.04 (t, J=7.1 Hz, 6H), 2.29 (s, 3H), 2.57 (m, 4H), 3.67 (s, 2H), 5.85 (s, 2H), 6.80 (d, J=7.5 Hz, 1H), 7.16 (t, J=7.6 Hz, 1H), 7.25 (m, 1H), 7.31 (s, 1H), 7.42 (d, J=8.5 Hz, 2H), 7.61 (d, J=8.5 Hz, 2H), 7.97 (s, 1H), 8.00 (s, 1H), 8.65 (s, 1H), 8.84 (s, 1H); MS ESI(+)) m/e 468 (M+H)$^+$.

EXAMPLE 551

N-{4-[4-amino-7-(3-pyrrolidin-1-ylprop-1-ynyl)furo[3,2-c]pyridin-3-yl]phenyl}-N'-3-methylphenyl)urea The desired product was prepared by substituting Example 547D and Example 506A for Example 144A and 3-butyn-1-ol, respectively, in Example 144B. $^1$H NMR (300 MHz, DMSO-D$_6$) δ ppm 1.74 (m, 4H), 2.29 (s, 3H), 2.64 (m, 4H), 3.69 (s, 2H), 5.86 (s, 2H), 6.80 (d, J=7.8 Hz, 1H), 7.16 (t, J=7.6 Hz, 1H), 7.25 (d, J=6.0 Hz, 1H), 7.31 (s, 1H), 7.42 (d, J=8.5 Hz, 2H), 7.61 (d, J=8.5 Hz, 2H), 7.98 (s, 1H), 8.00 (s, 1H), 8.65 (s, 1H), 8.85 (s, 1H); MS ESI(+)) m/e 466 (M+H)$^+$.

EXAMPLE 552

N-{4-[4-amino-7-(3-amino-3-methylbut-1-ynyl)thieno[3,2-c]pyridin-3-yl]phenyl}-N'-3-methylphenyl)urea

EXAMPLE 552A tert-butyl 1,1-dimethylprop-2-ynylcarbamate

The desired product was prepared by substituting 1,1-dimethyl-prop-2-ynylamine for propargylamine in Example 516A. $^1$H NMR (300 MHz, DMSO-D$_6$) δ ppm 1.39 (s, 9H), 1.42 (s, 6H), 3.02 (s, 1H), 6.94 (s, 1H).

EXAMPLE 552B tert-butyl 3-[4-amino-3-(4-aminophenyl)thieno[3,2-c]pyridin-7-yl]-1,1-dimethylprop-2-ynylcarbamate The desired product was prepared by substituting Example 77B and Example 552A for Example 144A and 3-butyn-1-ol, respectively, in Example 144B. MS ESI(+)) m/e 423 (M+H)$^+$.

EXAMPLE 552C tert-butyl 3-{4-amino-3-[4-({[(3-methylphenyl)amino]carbonyl}amino)phenyl]thieno[3,2-c]pyridin-7-yl}-1,1-dimethylprop-2-ynylcarbamate The desired product was prepared by substituting Example 552B for Example 1C in Example 1D.

EXAMPLE 552D

N-{4-[4-amino-7-(3-amino-3-methylbut-1-ynyl)thieno[3,2-c]pyridin-3-yl]phenyl}-N'-(3-methylphenyl)urea The desired product was prepared by substituting Example 552C for Example 76B in Example 76C. $^1$H NMR (300 MHz, DMSO-D$_6$) δ ppm 1.70 (s, 6H), 2.29 (s, 3H), 5.06 (m, J=81.04 Hz, 2H), 6.47 (s, 2H), 6.80 (d, J=7.46 Hz, 1H), 7.17 (t, J=7.63 Hz, 1H), 7.26 (m, 1H), 7.33 (s, 1H), 7.39 (d, J=8.48 Hz, 2H), 7.64 (d, J=8.82 Hz, 2H), 7.70 (s, 2H), 8.85 (s, 1H), 9.08 (s, 1H); MS ESI(+)) m/e 456 (M+H)$^+$.

EXAMPLE 553

N-{4-[4-amino-7-(3-amino-3-methylbut-1-ynyl)thieno[3,2-c]pyridin-3-yl]phenyl}-N'-(2-fluoro-5-methylphenyl)urea

EXAMPLE 553A tert-butyl 3-{4-amino-3-[4-({[(2-fluoro-5-methylphenyl)amino]carbonyl}amino)phenyl]thieno[3,2-c]pyridin-7-yl}-1,1-dimethylprop-2-ynylcarbamate The desired product was prepared by substituting Example 552B and 1-fluoro-2-isocyanato-4-methylbenzene for Example 1C and 1-isocyanato-3-methylbenzene, respectively, in Example 1D.

EXAMPLE 553B

N-{4-[4-amino-7-(3-amino-3-methylbut-1-ynyl)thieno[3,2-c]pyridin-3-yl]phenyl-}-N'-(2-fluoro-5-methylphenyl)urea The desired product was prepared by substituting Example 553A for Example 76B in Example 76C. $^1$H NMR (300 MHz, DMSO-D$_6$) δ ppm 1.70 (s, 6H), 2.28 (s, 3H), 6.47 (s, 2H), 6.81 (m, 2H), 7.13 (m, 2H), 7.40 (m, 2H), 7.64 (m, 3H), 7.98 (dd, J=7.63, 1.86 Hz, 1H), 8.06 (m, 1H), 8.60 (d, J=2.37 Hz, 1H), 9.34 (s, 1H); MS ESI(+)) m/e 474 (M+H)$^+$.

EXAMPLE 554

N-{4-[4-amino-7-(3-amino-3-methylbut-1-ynyl)thieno[3,2-c]pyridin-3-yl]phenyl}-N'-(3-chlorophenyl)urea

EXAMPLE 554A tert-butyl 3-{4-amino-3-[4-({[(3-chlorophenyl)amino]carbonyl}amino)phenyl]thieno[3,2-c]pyridin-7-yl}-1,1-dimethylprop-2-ynylcarbamate The desired product was prepared by substituting Example 552B and 3-chloro-isocyanato-4-methylbenzene for Example 1C and 1-isocyanato-3-methylbenzene, respectively, in Example 1D.

EXAMPLE 554B tert-butyl 3-{4-amino-3-[4-({[(3-chlorophenyl)amino]carbonyl}amino)phenyl]thieno[3,2-c]pyridin-7-yl}-1,1-dimethylprop-2-ynylcarbamate The desired product was prepared by substituting Example 554A for Example 76B in Example 76C. $^1$H NMR (300 MHz, DMSO-D$_6$) δ ppm 1.70 (s, 6H), 6.45 (s, 2H), 7.04 (m, 1H), 7.31 (d, J=5.09 Hz, 2H), 7.40 (d, J=8.81 Hz, 2H), 7.65 (m, 2H), 7.69 (s, 1H), 7.75 (m, 1H), 8.07 (s, 1H), 8.64 (s, 2H), 9.26 (s, 1H), 9.28 (s, 1H); MS ESI(+)) m/e 476 (M+H)$^+$.

EXAMPLE 555

N-{4-[4-amino-7-(3-amino-3-methylbut-1-ynyl)thieno[3,2-c]pyridin-3-yl]phenyl}-N'-[2-fluoro-5-(trifluoromethyl)phenyl]urea

EXAMPLE 555A tert-butyl 3-(4-amino-3-{4-[({[2-fluoro-5-(trifluoromethyl)phenyl]amino}carbonyl)amino]phenyl}thieno[3,2-c]pyridin-7-yl)-1,1-dimethylprop-2-ynylcarbamate The desired product was prepared by substituting Example 552B and 1-fluoro-2-isocyanato-4-(trifluoromethyl)benzene for Example 1C and 1-isocyanato-3-methylbenzene, respectively, in Example 1D.

EXAMPLE 555B

N-{4-[4-amino-7-(3-amino-3-methylbut-1-ynyl)thieno[3,2-c]pyridin-3-yl]phenyl}-N'-[2-fluoro-5-(trifluoromethyl)phenyl]urea The desired product was prepared by substituting Example 555A for Example 76B in Example 76C. $^1$H NMR (300 MHz, DMSO-D$_6$) δ ppm 1.70 (s, 6H), 6.39 (s, 2H), 7.43 (d, J=8.48 Hz, 2H), 7.52 (m, 1H), 7.65 (d, J=8.82 Hz, 2H), 7.69 (s, 1H), 8.07 (s, 1H), 8.62 (m, 4H), 9.02 (d, J=2.71 Hz, 1H), 9.46 (s, 1H); MS ESI(+)) m/e 528 (M+H)$^+$.

EXAMPLE 556

N-{4-[4-amino-7-(3-amino-3-methylbut-1-ynyl)thieno[3,2-c]pyridin-3-yl]phenyl}-N'-[3-(trifluoromethyl)phenyl]urea

EXAMPLE 556A tert-butyl 3-(4-amino-3-{4-[({[3-(trifluoromethyl)phenyl]amino}carbonyl)amino]phenyl}thieno[3,2-c]pyridin-7-yl)-1,1-dimethylprop-2-ynylcarbamate The desired product was prepared by substituting Example 552B and 1-isocyanato-3-(trifluoromethyl)benzene for Example 1C and 1-isocyanato-3-methylbenzene, respectively, in Example 1D.

EXAMPLE 556B

N-{4-[4-amino-7-(3-amino-3-methylbut-1-ynyl)thieno[3,2-c]pyridin-3-yl]phenyl}-N'-[3-(trifluoromethyl)phenyl]urea The desired product was prepared by substituting Example 556A for Example 76B in Example 76C. $^1$H NMR (300 MHz, DMSO-D$_6$) δ ppm 1.70 (s, 6H), 6.44 (s, 2H), 7.33 (d, J=7.80 Hz, 1H), 7.41 (d, J=8.48 Hz, 2H), 7.53 (t, J=7.97 Hz, 1H), 7.65 (m, 4H), 8.07 (m, J=3.05 Hz, 2H), 8.64 (s, 2H), 9.34 (s, 1H), 9.43 (s, 1H); MS ESI(+)) m/e 510 (M+H)$^+$.

EXAMPLE 557

N-(4-{4-amino-7-[3-(4-methylpiperazin-1-yl)prop-1-ynyl]thieno[3,2-c]pyridin-3-yl}phenyl)-N'-(3-methylphenyl)urea

EXAMPLE 557A 1-methyl-4-prop-2-ynylpiperazine

The desired product was prepared by substituting N-methyl-piperazine for pyrrolidine in Example 506A. $^1$H NMR (300 MHz, DMSO-D$_6$) δ ppm 2.14 (s, 3H), 2.30 (m, 4H), 2.43 (m, 4H), 3.12 (t, J=2.54 Hz, 1H), 3.23 (d, J=2.37 Hz, 2H).

EXAMPLE 557B 3-(4-aminophenyl)-7-[3-(4-methylpiperazin-1-yl)prop-1-ynyl]thieno[3,2-c]pyridin-4-amine The desired product was prepared by substituting Example 77B and Example 557A for Example 144A and 3-butyn-1-ol, respectively, in Example 144B. MS (ESI(+)) m/e 378 (M+H)$^+$.

EXAMPLE 557C

N-(4-{4-amino-7-[3-(4-methylpiperazin-1-yl)prop-1-ynyl]thieno[3,2-c]pyridin-3-yl}phenyl-N'-(3-methylphenyl)urea The desired product was prepared by substituting Example 557B for Example 1C in Example 1D. $^1$H NMR (300 MHz, DMSO-D$_6$) δ ppm 2.17 (s, 3H), 2.29 (s, 3H), 2.38 (m, 4H), 2.60 (m, 4H), 3.61 (s, 2H), 5.76 (s, 2H), 6.80

(d, J=7.12 Hz, 1H), 7.17 (t, J=7.63 Hz, 1H), 7.25 (m, 1H), 7.31 (s, 1H), 7.37 (d, J=8.48 Hz, 2H), 7.51 (s, 1H), 7.60 (d, J=8.48 Hz, 2H), 7.97 (s, 1H), 8.66 (s, 1H), 8.86 (s, 1H); MS ESI(+)) m/e 511 (M+H)$^+$.

EXAMPLE 558

N-(4-{4-amino-7-[3-(4-methylpiperazin-1-yl)prop-1-ynyl]thieno[3,2-c]pyridin-3-yl}phenyl)-N'-(3-chlorophenyl)urea The desired product was prepared by substituting Example 557B and 3-chloro-1-isocyanatobenzene for Example 1C and 1-isocyanato-3-methylbenzne, respectively, in Example 1D. $^1$H NMR (300 MHz, DMSO-D$_6$) δ ppm 2.17 (s, 3H), 2.37 (m, J=2.03 Hz, 4H), 2.59 (m, 4H), 3.61 (s, 2H), 5.76 (s, 2H), 7.03 (m, 1H), 7.32 (m, 2H), 7.39 (d, J=8.48 Hz, 2H), 7.52 (s, 1H), 7.61 (d, J=8.48 Hz, 2H), 7.73 (s, 1H), 7.97 (s, 1H), 8.97 (m, 2H); MS ESI(+)) m/e 531 (M+H)$^+$.

EXAMPLE 559

3-(4-aminophenyl)-7-[4-(ethylsulfonyl)phenyl]thieno[3,2-c]pyridin-4-amine

The desired product was prepared by substituting Example 77B and 4-ethanesulfonyl-phenylboronic acid for Example 1B and 4-phenoxyphenylboronic acid in Example 10A. (300 MHz, DMSO-D$_6$) δ ppm 1.17 (t, J=7.3 Hz, 3H) 3.36 (q, J=7.5 Hz, 2H) 5.39 (s, 2H), 5.75 (br s, 2H) 6.69 (d, J=8.5 Hz, 2H) 7.12 (d, J=8.1 Hz, 2H) 7.38 (s, 1H) 7.99 (m, 5H); MS ESI(+) m/e 410 (M+H)$^+$.

EXAMPLE 560

3-(4-aminophenyl)-7-[3-(methylsulfonyl)phenyl]thieno[3,2-c]pyridin-4-amine

The desired product was prepared by substituting Example 77B and 3-methanesulfonyl-phenylboronic acid for Example 1B and 4-phenoxyphenylboronic acid in Example 10A. $^1$H NMR (300 MHz, DMSO-D$_6$) δ ppm 3.30 (s, 3H) 5.38 (m, 2H) 5.73 (br m, 2H) 6.69 (d, J=8.5 Hz, 2H) 7.12 (d, J=8.5 Hz, 2H) 7.38 (s, 1H) 7.80 (t, J=7.8 Hz, 1H) 7.93 (m, 1H) 7.96 (m, 1H) 8.00 (s, 1H) 8.03 (m, 1H) 8.05 (m, J=2.0 Hz, 1H) 8.19 (t, J=1.7 Hz, 1H); MS ESI(+) m/e 396 (M+H)$^+$.

EXAMPLE 561

3-(4-aminophenyl)-7-[3-(ethylsulfonyl)phenyl]thieno[3,2-c]pyridin-4-amine

The desired product was prepared by substituting Example 77B and 3-ethanesulfonyl-phenylboronic acid for Example 1B and 4-phenoxyphenylboronic acid in Example 10A. $^1$H NMR (300 MHz, DMSO-D$_6$) δ ppm 1.16 (t, J=7.3 Hz, 3H) 3.39 (q, J=7.4 Hz, 2H) 5.39 (s, 2H) 5.74 (br m, 2H) 6.69 (d, J=8.48 Hz, 2H) 7.11 (d, J=8.5 Hz, 2H) 7.38 (s, 1H) 7.81 (t, J=7.8 Hz, 1H) 7.90 (m, 1H) 7.99 (m, 1H) 8.04 (m, 1H) 8.14 (m, 1H); MS ESI(+) m/e 410 (M+H)$^+$.

EXAMPLE 562

3-(4-aminophenyl)-7-[4-(methylsulfonyl)phenyl]thieno[3,2-c]pyridin-4-amine

The desired product was prepared by substituting Example 77B and 4-methanesulfonyl-phenylboronic acid for Example 1B and 4-phenoxyphenylboronic acid in Example 10A. $^1$H NMR (300 MHz, DMSO-D$_6$) δ ppm 3.31 (s, 3H) 5.39 (s, 2H) 5.75 (br s, 2H) 6.69 (d, J=8.5 Hz, 2H) 7.12 (d, J=8.5 Hz, 2H) 7.38 (s, 1H) 7.95 (d, J=8.5 Hz, 2H) 7.99 (s, 1H) 8.05 (d, J=8.5 Hz, 2H); MS ESI(+) m/e 396 (M+H)$^+$.

EXAMPLE 563

3-[4-amino-3-(4-aminophenyl)thieno[3,2-c]pyridin-7-yl]phenol

The desired product was prepared by substituting Example 77B and 3-hydroxyphenylboronic acid for Example 1B and 4-phenoxyphenylboronic acid in Example 10A. $^1$H NMR (300 MHz, DMSO-D$_6$) δ ppm 5.36 (s, 2H) 5.56 (br s, 2H) 6.68 (d, J=8.5 Hz, 2H) 6.78 (m, 1H) 7.07 (m, 4H) 7.29 (m, 2H) 7.82 (s, 1H) 9.58 (s, 1H); MS ESI(+) m/e 334 (M+H)$^+$.

EXAMPLE 564

3-[4-(methylamino)phenyl]thieno[3,2-c]pyridin-4-amine

The desired product was prepared by substituting methyl-[4-(4,4,5,5-tetramethyl-[1,3,2]dioxaborolan-2-yl)-phenyl]-amine for 4-phenoxyphenylboronic acid in example 10A. $^1$H NMR (300 MHz, DMSO-D$_6$) δ ppm 2.73 (d, J=4.8 Hz, 3H) 5.47 (br s, 2H) 5.83–6.09 (m, 1H) 6.65 (d, J=8.5 Hz, 2H) 7.16 (d, J=8.5 Hz, 2H) 7.21 (d, J=5.4 Hz, 1H) 7.28 (s, 1H) 7.79 (d, J=5.8 Hz, 1H); MS ESI(+) m/e 256 (M+H)$^+$.

EXAMPLE 565

N-(4-{4-amino-7-[3-piperidin-1-ylprop-1-enyl]thieno[3,2-c]pyridin-3-yl}phenyl)-N'-(3-methylphenyl)urea The desired product was prepared using the general reductive amination procedure described in example 177, reacting example 464 with piperidine. $^1$H NMR (300 MHz, DMSO-D$_6$) δ ppm 1.49 (br m, 6H) 2.29 (s, 3H) 2.44 (br m, 4H) 3.17 (br m, 2H) 5.56 (br s, 2H) 6.22 (m, 1H) 6.66 (d, J=15.6 Hz, 1H) 6.81 (d, J=7.1 Hz, 1H) 7.17 (t, J=7.8 Hz, 1H) 7.25 (m, 1H) 7.32 (s, 1H) 7.37 (d, J=8.8 Hz, 2H) 7.50 (s, 1H) 7.60 (d, J=8.8 Hz, 2H) 7.94 (s, 1H) 8.67 (s, 1H) 8.87 (s, 1H); MS ESI(+) m/e 498 (M+H)$^+$.

EXAMPLE 566

N-(4-{4-amino-7-[3-(dimethylamino)prop-1-enyl]thieno[3,2-c]pyridin-3-yl}phenyl)-N'-(3-methylphenyl)urea The desired product was prepared using the general reductive amination described in example 177, reacting example 464 with dimethylamine. $^1$H NMR (300 MHz, DMSO-D$_6$) δ ppm 2.29 (s, 9H) 3.22 (d, J=6.4 Hz, 2H) 5.58 (br s, 2H) 6.22 (dt, J=16.1, 6.8 Hz, 1H) 6.70 (d, J=16.3 Hz, 1H) 6.80 (d, J=7.5 Hz, 1H) 7.17 (t, J=7.6 Hz, 1H) 7.26 (d, J=8.1 Hz, 1H) 7.31 (s, 1H) 7.37 (d, J=8.8 Hz, 2H) 7.52 (s, 1H) 7.60 (d, J=8.5 Hz, 2H) 7.95 (s, 1H) 8.71 (s, 1H) 8.92 (s, 1H); MS ESI(+) m/e 458 (M+H)$^+$.

EXAMPLE 567

N-(4-{4-amino-7-[3-(4-methylpiperazin-1-yl)prop-1-enyl]thieno[3,2-c]pyridin-3-yl}phenyl)-N'-(3-methylphenyl)urea The desired product was prepared using the general reductive amination described in example 177, reacting example 464 with 1-methyl-piperazine. $^1$H NMR (300 MHz, DMSO-D$_6$) δ ppm 2.17 (s, 3H) 2.29 (s, 3H) 2.31–2.48 (br m, 8H) 3.17 (d, J=5.8 Hz, 2H) 5.56 (br s, 2H) 6.21 (dt, J=16.3, 6.4 Hz, 1H) 6.66 (d, J=15.9 Hz, 1H) 6.81 (d, J=7.1 Hz, 1H) 7.17 (t, J=7.6 Hz, 1H) 7.25 (d, J=8.8 Hz, 1H) 7.32 (s, 1H) 7.37 (d, J=8.5 Hz, 2H) 7.50 (s, 1H) 7.60 (d, J=8.5 Hz, 2H) 7.94 (s, 1H) 8.67 (s, 1H) 8.87 (s, 1H); MS ESI(+) m/e 513 (M+H)$^+$.

EXAMPLE 568

N-(4-{4-amino-7-[3-(3-oxopiperazin-1-yl)prop-1-enyl]thieno[3,2-c]pyridin-3-yl}phenyl)-N'-(3-methylphenyl)urea The desired product was prepared using the general reductive amination described in example 177, reacting example 464 with piperazin-2-one. $^1$H NMR (300 MHz, DMSO-D$_6$) δ ppm 2.29 (s, 3H) 2.64 (t, J=5.3 Hz, 2H) 3.00 (s, 2H) 3.14–3.23 (m, 2H) 3.26 (d, J=6.8 Hz, 2H) 5.58 (s, 2H) 6.21 (dt, J=16.0, 6.6 Hz, 1H) 6.71 (d, J=15.9 Hz, 1H) 6.81 (d, J=7.5 Hz, 1H) 7.17 (t, J=7.8 Hz, 1H) 7.25 (d, J=8.1 Hz, 1H) 7.32 (s, 1H) 7.37 (d, J=8.5 Hz, 2H) 7.51 (s, 1H) 7.60 (d, J=8.5 Hz, 2H) 7.74 (s, 1H) 7.96 (s, 1H) 8.66 (s, 1H) 8.87 (s, 1H); MS ESI(+) m/e 513 (M+H)$^+$.

EXAMPLE 569

N-(4-{4-amino-7-[4-(methylsulfonyl)phenyl]thieno[3,2-c]pyridin-3-yl}phenyl)-N'-(3-methylphenyl)urea The desired product was prepared by substituting Example 144A and 4-methanesulfonyl-phenylboronic acid for Example 1B and 4-phenoxyphenylboronic acid in Example 10A. $^1$H NMR (400 MHz, DMSO-D$_6$) δ ppm 2.29 (s, 3H) 3.29 (s, 3H) 5.69 (s, 2H) 6.81 (d, J=7.4 Hz, 1H) 7.17 (t, J=7.8 Hz, 1H) 7.26 (d, J=8.6 Hz, 1H) 7.32 (s, 1H) 7.41 (d, J=8.6 Hz, 2H) 7.52 (s, 1H) 7.62 (d, J=8.6 Hz, 2H) 7.97 (d, J=8.6 Hz, 2H) 8.02 (s, 1H) 8.06 (d, J=8.6 Hz, 2H) 8.66 (s, 1H) 8.87 (s, 1H); MS ESI(-) m/e 527 (M-H)-

EXAMPLE 570

N-(4-{4-amino-7-[4-(ethylsulfonyl)phenyl]thieno[3,2-c]pyridin-3-yl}phenyl)-N'-(3-methylphenyl)urea The desired product was prepared by substituting Example 144A and 4-ethanesulfonyl-phenylboronic acid for Example 1B and 4-phenoxyphenylboronic acid in Example 10A. $^1$H NMR (300 MHz, DMSO-D$_6$) δ ppm 1.17 (t, J=7.3 Hz, 3H) 2.29 (s, 3H) 3.37 (q, J=7.4 Hz, 2H) 5.71 (br s, 2H) 6.81 (d, J=7.1 Hz, 1H) 7.17 (t, J=7.8 Hz, 1H) 7.26 (d, J=8.1 Hz, 1H) 7.32 (s, 1H) 7.41 (d, J=8.5 Hz, 2H) 7.53 (s, 1H) 7.62 (d, J=8.5 Hz, 2H) 7.99 (m, 5H) 8.67 (s, 1H) 8.88 (s, 1H); MS ESI(-) m/e 541 (M-H)-.

EXAMPLE 571

N-{4-[4-amino-7-(3-methylphenyl)thieno[3,2-c]pyridin-3-yl]phenyl}-N'-(3-methylphenyl)urea The desired product was prepared by substituting Example 144A and 3-methylphenylboronic acid for Example 1B and 4-phenoxyphenylboronic acid in Example 10 A. $^1$H NMR (300 MHz, DMSO-D$_6$) δ ppm 2.29 (s, 3H) 2.40 (s, 3H) 5.52 (br s, 2H) 6.81 (d, J=7.5 Hz, 1H) 7.21 (m, 4H) 7.32 (s, 1H) 7.43 (m, 5H) 7.61 (d, J=8.8 Hz, 2H) 7.89 (s, 1H) 8.66 (s, 1H) 8.86 (s, 1H); MS ESI(+) m/e 465 (M+H)$^+$.

EXAMPLE 572

N-{4-[4-amino-7-(4-methylphenyl)thieno[3,2-c]pyridin-3-yl]phenyl}-N'-(3-methylphenyl)urea The desired product was prepared by substituting Example 144A and 4-methylphenylboronic acid for Example 1B and 4-phenoxyphenylboronic acid in Example 10A. $^1$H NMR (300 MHz, DMSO-D$_6$) δ ppm 2.29 (s, 3H) 2.38 (s, 3H) 5.50 (br s, 2H) 6.81 (d, J=7.5 Hz, 1H) 7.17 (m, 1H) 7.26 (d, J=8.5 Hz, 1H) 7.33 (m, 3H) 7.40 (d, J=8.5 Hz, 2H) 7.47 (s, 1H) 7.55 (d, J=8.1 Hz, 2H) 7.61 (d, J=8.5 Hz, 2H) 7.87 (s, 1H) 8.66 (s, 1H) 8.86 (s, 1H); MS ESI(+) m/e 465 (M+H)$^+$.

EXAMPLE 573

N-(4-{4-amino-7-[(E)-2-phenylvinyl]thieno[3,2-c]pyridin-3-yl}phenyl)-N'-(3-methylphenyl)urea The desired product was prepared by substituting Example 144A and (E)-2-phenylvinylboronic acid for Example 1B and 4-phenoxyphenylboronic acid in Example 10A. $^1$H NMR (300 MHz, DMSO-D$_6$) δ ppm 2.29 (s, 3H) 5.68 (br s, 2H) 6.81 (d, J=7.5 Hz, 1H) 7.30 (m, 9H) 7.57 (s, 1H) 7.63 (m, 5H) 8.15 (s, 1H) 8.67 (s, 1H) 8.87 (s, 1H); MS ESI(+) m/e 477 (M+H)$^+$.

EXAMPLE 574

N-(4-{4-amino-7-[4-(methylthio)phenyl]thieno[3,2-c]pyridin-3-yl}phenyl)-N'-(3-methylphenyl)urea The desired product was prepared by substituting Example 144A and 4-(methylthio)phenylboronic acid for Example 1B and 4-phenoxyphenylboronic acid in Example 10A. $^1$H NMR (300 MHz, DMSO-D$_6$) δ ppm 2.29 (s, 3H) 2.54 (s, 3H) 5.53 (br s, 2H) 6.81 (d, J=7.5 Hz, 1H) 7.17 (t, J=7.5 Hz, 1H) 7.26 (d, J=8.1 Hz, 1H) 7.32 (s, 1H) 7.40 (m, 4H) 7.48 (s, 1H) 7.61 (m, 4H) 7.89 (s, 1H) 8.66 (s, 1H) 8.86 (s, 1H); MS ESI(+) m/e 497 (M+H)$^+$.

EXAMPLE 575

N-{4-[4-amino-7-(3-hydroxyphenyl)thieno[3,2-c]pyridin-3-yl]phenyl}-N'-(3-methylphenyl)urea The desired product was prepared by substituting Example 144A and 3-hydroxyphenylboronic acid for Example 1B and 4-phenoxyphenylboronic acid in Example 10A. ¹H NMR (300 MHz, DMSO-D$_6$) δ ppm 2.29 (s, 3H) 5.51 (br s, 2H) 6.81 (d, J=7.5 Hz, 2H) 7.07 (m, 2H) 7.17 (t, J=7.8 Hz, 1H) 7.29 (m, 3H) 7.40 (d, J=8.5 Hz, 2H) 7.47 (s, 1H) 7.61 (d, J=8.5 Hz, 2H) 7.86 (s, 1H) 8.67 (s, 1H) 8.86 (s, 1H) 9.60 (s, 1H); MS ESI(+) m/e 467 (M+H)⁺.

EXAMPLE 576

N-(4-{4-amino-7-[3-(methylsulfonyl)phenyl]thieno[3,2-c]pyridin-3-yl}phenyl)-N'-(3-methylphenyl)urea The desired product was prepared by substituting Example 144A and 3-methanesulfonylphenylboronic acid for Example 1B and 4-phenoxyphenylboronic acid in Example 10A. ¹H NMR (300 MHz, DMSO-D$_6$) δ ppm 2.29 (s, 3H) 3.32 (s, 3H) 5.68 (br s, 2H) 6.81 (d, J=7.1 Hz, 1H) 7.17 (t, J=7.6 Hz, 1H) 7.26 (d, J=8.5 Hz, 1H) 7.32 (s, 1H) 7.41 (d, J=8.5 Hz, 2H) 7.52 (s, 1H) 7.62 (d, J=8.5 Hz, 2H) 7.82 (m, 1H) 7.95 (d, J=8.1 Hz, 1H) 8.05 (m, 2H) 8.21 (s, 1H) 8.67 (s, 1H) 8.88 (s, 1H); MS ESI(+) m/e 529 (M+H)⁺.

EXAMPLE 577

N-(4-{4-amino-7-[3-(ethylsulfonyl)phenyl]thieno[3,2-c]pyridin-3-yl}phenyl)-N'-(3-methylphenyl)urea The desired product was prepared by substituting Example 144A and 3-ethanesulfonylphenylboronic acid for Example 1B and 4-phenoxyphenylboronic acid in Example 10A. ¹H NMR (300 MHz, DMSO-D$_6$) δ ppm 1.17 (t, J=7.5 Hz, 3H) 2.29 (s, 3H) 3.40 (q, J=7.5 Hz, 2H) 5.68 (br s, 2H) 6.81 (d, J=7.5 Hz, 1H) 7.17 (t, J=7.8 Hz, 1H) 7.26 (d, J=8.5 Hz, 1H) 7.32 (s, 1H) 7.41 (d, J=8.5 Hz, 2H) 7.52 (s, 1H) 7.62 (d, J=8.5 Hz, 2H) 7.82 (t, J=7.8 Hz, 1H) 7.91 (m, 1H) 8.05 (m, 2H) 8.16 (m, 1H) 8.67 (s, 1H) 8.88 (s, 1H); MS ESI(+) m/e 543 (M+H)⁺.

EXAMPLE 578

N-{4-[4-amino-7-(3,4-dimethoxyphenyl)thieno[3,2-c]pyridin-3-yl]phenyl}-N'-(3-methylphenyl)urea The desired product was prepared by substituting Example 144A and 3,4-dimethoxyphenylboronic acid for Example 1B and 4-phenoxyphenylboronic acid in Example 10A. ¹H NMR (300 MHz, DMSO-D$_6$) δ ppm 2.29 (s, 3H) 3.82 (s, 3H) 3.83 (s, 3H) 5.48 (br s, 2H) 6.81 (d, J=7.1 Hz, 1H) 7.11 (m, 1H) 7.20 (m, 4H) 7.32 (s, 1H) 7.39 (d, J=8.5 Hz, 2H) 7.47 (s, 1H) 7.61 (d, J=8.8 Hz, 2H) 7.90 (s, 1H) 8.66 (s, 1H) 8.86 (s, 1H); MS ESI(+) m/e 511 (M+H)⁺.

EXAMPLE 579

4-{4-amino-3-[4-({[(3-methylphenyl)amino]carbonyl}amino)phenyl]thieno[3,2-c]pyridin-7-yl}-N-methylbenzamide The desired product was prepared by substituting Example 144A and 4-[(methylamino)carbonyl]phenylboronic acid for Example 1B and 4-phenoxyphenylboronic acid in Example 10A. ¹H NMR (300 MHz, DMSO-D$_6$) δ ppm 2.29 (s, 3H) 2.82 (d, J=4.4 Hz, 3H) 5.61 (br s, 2H) 6.81 (d, J=7.1 Hz, 1H) 7.17 (t, J=7.6 Hz, 1H) 7.26 (d, J=8.5 Hz, 1H) 7.32 (s, 1H) 7.40 (d, J=8.8 Hz, 2H) 7.50 (s, 1H) 7.62 (d, J=8.8 Hz, 2H) 7.76 (d, J=8.5 Hz, 2H) 7.96 (m, J=6.4 Hz, 3H) 8.50 (q, J=4.5 Hz, 1H) 8.67 (s, 1H) 8.87 (s, 1H); MS ESI(+) m/e 508 (M+H)⁺.

EXAMPLE 580

N-{4-[4-amino-7-(1-benzothien-2-yl)thieno[3,2-c]pyridin-3-yl]phenyl}-N'-(3-methylphenyl)urea The desired product was prepared by substituting Example 144A and 2-benzothiopheneboronic acid for Example 1B and 4-phenoxyphenylboronic acid in Example 10A. ¹H NMR (300 MHz, DMSO-D$_6$) δ ppm 2.29 (s, 3H) 5.77 (br s, 2H) 6.81 (d, J=7.5 Hz, 1H) 7.17 (t, J=7.8 Hz, 1H) 7.26 (d, J=8.5 Hz, 1H) 7.32 (s, 1H) 7.40 (m, 4H) 7.60 (s, 1H) 7.63 (d, J=8.5 Hz, 2H) 7.80 (s, 1H) 7.92 (m, 1H) 8.02 (d, J=7.5 Hz, 1H) 8.22 (s, 1H) 8.67 (s, 1H) 8.88 (s, 1H); MS ESI(+) m/e 507 (M+H)⁺.

EXAMPLE 581

N-{4-[7-(4-acetylphenyl)-4-aminothieno[3,2-c]pyridin-3-yl]phenyl}-N'-(3-methylphenyl)urea The desired product was prepared by substituting Example 144A and 4-acetylphenylboronic acid for Example 1B and 4-phenoxyphenylboronic acid in Example 10A. ¹H NMR (300 MHz, DMSO-D$_6$) δ ppm 2.29 (s, 3H) 2.64 (s, 3H) 5.67 (br s, 2H) 6.81 (d, J=7.1 Hz, 1H) 7.17 (t, J=7.6 Hz, 1H) 7.26 (d, J=8.1 Hz, 1H) 7.32 (s, 1H) 7.41 (d, J=8.5 Hz, 2H) 7.52 (s, 1H) 7.62 (d, J=8.5 Hz, 2H) 7.85 (d, J=8.1 Hz, 2H) 8.01 (s, 1H) 8.10 (d, J=8.1 Hz, 2H) 8.67 (s, 1H) 8.87 (s, 1H); MS ESI(+) m/e 493 (M+H)⁺.

EXAMPLE 582

N-{4-[7-(3-acetylphenyl)-4-aminothieno[3,2-c]pyridin-3-yl]phenyl}-N'-(3-methylphenyl)urea The desired product was prepared by substituting Example 144A and 3-acetylphenylboronic acid for Example 1B and 4-phenoxyphenylboronic acid in Example 10A. ¹H NMR (300 MHz, DMSO-D$_6$) δ ppm 2.29 (s, 3H) 2.66 (s, 3H) 5.62 (br s, 2H) 6.81 (d, J=7.5 Hz, 1H) 7.17 (t, J=7.6 Hz, 1H) 7.26 (d, J=8.5 Hz, 1H) 7.32 (s, 1H) 7.41 (d, J=8.5 Hz, 2H) 7.50 (s, 1H) 7.62 (d, J=8.5 Hz, 2H) 7.69 (t, J=7.8 Hz, 1H) 7.97 (m, 3H) 8.24 (m, 1H) 8.67 (s, 1H) 8.87 (s, 1H); MS ESI(+) m/e 493 (M+H)⁺.

EXAMPLE 583

N-{4-[4-amino-7-(3-cyanophenyl)thieno[3,2-c]pyridin-3-yl]phenyl}-N'-(3-methylphenyl)urea The desired product was prepared by substituting Example 144A and 3-cyanophenylboronic acid for Example 1B and 4-phenoxyphenylboronic acid in Example 10A. ¹H NMR (300 MHz, DMSO-D$_6$) δ ppm 2.29 (s, 3H) 5.67 (br s, 2H) 6.81 (d, J=7.5 Hz, 1H) 7.17 (t, J=7.8 Hz, 1H) 7.26 (d, J=8.5 Hz, 1H) 7.32 (s, 1H) 7.40 (d, J=8.5 Hz, 2H) 7.51 (s, 1H) 7.62 (d, J=8.5 Hz, 2H) 7.74 (t, J=7.8 Hz, 1H) 7.88 (m, 1H) 7.99 (s, 1H) 8.05 (m, 1H) 8.12 (m, 1H) 8.67 (s, 1H) 8.87 (s, 1H); MS ESI(+) m/e 476 (M+H)⁺.

EXAMPLE 584

4-{4-amino-3-[4-({[(3-methylphenyl)amino]carbonyl}amino)phenyl]thieno[3,2-c]pyridin-7-yl}benzamide The desired product was prepared by substituting Example 144A and 4-aminocarbonylphenylboronic acid for Example 1B and 4-phenoxyphenylboronic acid in Example 10A. $^1$H NMR (300 MHz, DMSO-D$_6$) δ ppm 2.29 (s, 3H) 5.62 (br s, 2H) 6.81 (d, J=7.5 Hz, 1H) 7.17 (t, J=7.8 Hz, 1H) 7.26 (d, J=8.8 Hz, 1H) 7.32 (s, 1H) 7.40 (d, J=8.5 Hz, 2H) 7.50 (s, 1H) 7.62 (d, J=8.5 Hz, 2H) 7.76 (d, J=8.5 Hz, 2H) 8.00 (m, 5H) 8.67 (s, 1H) 8.88 (s, 1H); MS ESI(+) m/e 494 (M+H)$^+$.

EXAMPLE 585

3-{4-amino-3-[4-({[(3-methylphenyl)amino]carbonyl}amino)phenyl]thieno[3,2-c]pyridin-7-yl}benzamide The desired product was prepared by substituting Example 144A and 3-aminocarbonylphenylboronic acid for Example 1B and 4-phenoxyphenylboronic acid in Example 10A. $^1$H NMR (300 MHz, DMSO-D$_6$) δ ppm 2.29 (s, 3H) 5.59 (br s, 2H) 6.81 (d, J=7.5 Hz, 1H) 7.17 (t, J=7.6 Hz, 1H) 7.26 (d, J=8.5 Hz, 1H) 7.32 (s, 1H) 7.41 (d, J=8.5 Hz, 2H) 7.49 (s, 1H) 7.60 (m, 3H) 7.88 (m, 2H) 7.97 (s, 1H) 8.07 (br s, 2H) 8.17 (m, 1H) 8.68 (s, 1H) 8.88 (s, 1H); MS ESI(+) m/e 494 (M+H)$^+$.

EXAMPLE 586

N-{4-[4-amino-7-(3-furyl)thieno[3,2-c]pyridin-3-yl]phenyl}-N'-(3-methylphenyl)urea The desired product was prepared by substituting Example 144A and 3-furylboronic acid for Example 1B and 4-phenoxyphenylboronic acid in Example 10A. $^1$H NMR (300 MHz, DMSO-D$_6$) δ ppm 2.29 (s, 3H) 5.53 (br s, 2H) 6.81 (d, J=7.5 Hz, 1H) 7.05 (m, 1H) 7.17 (t, J=7.6 Hz, 1H) 7.26 (d, J=8.8 Hz, 1H) 7.32 (s, 1H) 7.39 (d, J=8.5 Hz, 2H) 7.53 (s, 1H) 7.61 (d, J=8.5 Hz, 2H) 7.84 (t, J=1.70 Hz, 1H) 8.10 (s, 1H) 8.12 (m, 1H) 8.66 (s, 1H) 8.87 (s, 1H); MS ESI(+) m/e 441 (M+H)$^+$.

EXAMPLE 587

N-{4-[4-amino-7-(3,4,5-trimethoxyphenyl)thieno[3,2-c]pyridin-3-yl]phenyl}-N'-(3-methylphenyl)urea The desired product was prepared by substituting Example 144A and 3,4,5-trimethoxy-phenylboronic acid for Example 1B and 4-phenoxyphenylboronic acid in Example 10A. $^1$H NMR (300 MHz, DMSO-D$_6$) δ ppm 2.29 (s, 3H) 3.73 (s, 3H) 3.86 (s, 6H) 5.53 (br s, 2H) 6.81 (d, J=7.8 Hz, 1H) 6.96 (s, 2H) 7.17 (t, J=7.6 Hz, 1H) 7.26 (d, J=8.5 Hz, 1H) 7.32 (s, 1H) 7.39 (d, J=8.5 Hz, 2H) 7.49 (s, 1H) 7.62 (d, J=8.5 Hz, 2H) 7.98 (s, 1H) 8.66 (s, 1H) 8.87 (s, 1H); MS ESI(+) m/e 541 (M+H)$^+$.

EXAMPLE 588 tert-butyl 3-{4-amino-3-[4-({[(3-methylphenyl)amino]carbonyl}amino)phenyl]thieno[3,2-c]pyridin-7-yl}benzoate The desired product was prepared by substituting Example 144A and 3-tert-butoxycarbonylphenylboronic acid for Example 1B and 4-phenoxyphenylboronic acid in Example 10A. $^1$H NMR (300 MHz, DMSO-D$_6$) δ ppm 1.58 (s, 9H) 2.29 (s, 3H) 5.61 (br s, 2H) 6.81 (d, J=7.1 Hz, 1H) 7.17 (t, J=7.8 Hz, 1H) 7.26 (m, 1H) 7.32 (s, 1H) 7.41 (d, J=8.5 Hz, 2H) 7.50 (s, 1H) 7.62 (d, J=8.5 Hz, 2H) 7.67 (d, 1H) 7.85–8.02 (m, 3H) 8.21 (s, 1H) 8.66 (s, 1H) 8.87 (s, 1H); MS ESI(+) m/e 551 (M+H)$^+$.

EXAMPLE 589 methyl 4-{4-amino-3-[4-({[(3-methylphenyl)amino]carbonyl}amino)phenyl]thieno[3,2-c]pyridin-7-yl}benzoate The desired product was prepared by substituting Example 144A and 4-methoxycarbonylphenylboronic acid for Example 1B and 4-phenoxyphenylboronic acid in Example 10A. $^1$H NMR (300 MHz, DMSO-D$_6$) δ ppm 2.29 (s, 3H) 3.90 (s, 3H) 5.67 (br s, 2H) 6.81 (d, J=7.5 Hz, 1H) 7.17 (t, J=7.6 Hz, 1H) 7.26 (d, J=8.5 Hz, 1H) 7.32 (s, 1H) 7.40 (d, J=8.8 Hz, 2H) 7.51 (s, 1H) 7.62 (d, J=8.5 Hz, 2H) 7.85 (d, J=8.5 Hz, 2H) 8.01 (s, 1H) 8.10 (d, J=8.5 Hz, 2H) 8.66 (s, 1H) 8.87 (s, 1H); MS ESI(+) m/e 509 (M+H)$^+$.

EXAMPLE 590

4-{4-amino-3-[4-({[(3-methylphenyl)amino]carbonyl}amino)phenyl]thieno[3,2-c]pyridin-7-yl}benzoic acid The desired product was prepared by substituting example 589 for example 601 in example 602. $^1$H NMR (300 MHz, DMSO-D$_6$) δ ppm 2.29 (s, 3H) 6.80 (br s, 2H) 6.81 (d, J=7.5 Hz, 1H) 7.17 (t, J=7.8 Hz, 1H) 7.27 (d, J=8.1 Hz, 1H) 7.33 (s, 1H) 7.46 (d, J=8.8 Hz, 2H) 7.67 (d, J=8.5 Hz, 2H) 7.79–7.92 (m, 3H) 8.06 (s, 1H) 8.13 (d, J=8.5 Hz, 2H) 8.79 (s, 1H) 9.04 (s, 1H) 13.20 (br s, 1H); MS ESI(+) m/e 495 (M+H)$^+$.

EXAMPLE 591

3-{4-amino-3-[4-({[(3-methylphenyl)amino]carbonyl}amino)phenyl]thieno[3,2-c]pyridin-7-yl}benzoic acid The desired product was prepared as the trifluoroaceate salt by substituting example 588 for 11A in example 11B. $^1$H NMR (300 MHz, DMSO-D$_6$) δ ppm 2.29 (s, 3H) 6.81 (d, J=7.1 Hz, 1H) 7.03 (br s, 2H) 7.18 (t, J=7.6 Hz, 1H) 7.27 (m, 1H) 7.33 (s, 1H) 7.47 (d, J=8.5 Hz, 2H) 7.68 (d, J=8.5 Hz, 2H) 7.75 (t, J=7.8 Hz, 1H) 7.89 (s, 1H) 7.98 (d, J=7.8 Hz, 1H) 8.04–8.15 (m, 2H) 8.26 (s, 1H) 8.82 (s, 1H) 9.08 (s, 1H); MS ESI(+) m/e 495 (M+H)$^+$.

EXAMPLE 592

N-(4-{4-amino-7-[4-(methylsulfonyl)phenyl]thieno[3,2-c]pyridin-3-yl}phenyl)-N'-(3-chlorophenyl)urea The desired product was prepared by substituting example 562 and 3-chloro-1-isocyanatobenzene for 121B and 1-fluoro-2-isocyanato-4-(trifluoromethyl)benzene in example 122. $^1$H NMR (300 MHz, DMSO-D$_6$) δ ppm 3.30 (s, 3H) 5.70 (br s, 2H) 6.93–7.10 (m, 1H) 7.28–7.34 (m, 2H) 7.42 (d, J=8.5 Hz, 2H) 7.53 (s, 1H) 7.63 (d, J=8.5 Hz, 2H) 7.73 (m, 1H) 7.97 (d, J=8.8 Hz, 2H) 8.02 (s, 1H) 8.06 (d, J=8.5 Hz, 2H) 8.98 (d, J=2.4 Hz, 2H; MS ESI(+) m/e 549 (M+H)$^+$.

EXAMPLE 593

N-(4-{4-amino-7-[4-(methylsulfonyl)phenyl]thieno[3,2-c]pyridin-3-yl}phenyl)-N'-(2-fluoro-5-methylphenyl)urea The desired product was prepared by substituting example 562 and 1-fluoro-2-isocyanato-4-methylbenzene for 121B and 1-fluoro-2-isocyanato-4-(trifluoromethyl)benzene in example 122. $^1$H NMR (300 MHz, DMSO-D$_6$) δ ppm 2.29 (s, 3H) 3.30 (s, 3H) 5.70 (br s, 2H) 6.72–6.94 (m, J=2.4 Hz, 1H) 7.12 (dd, J=11.2, 8.5 Hz, 1H) 7.42 (d, J=8.5 Hz, 2H) 7.54 (s, 1H) 7.62 (d, J=8.8 Hz, 2H) 7.97 (d, J=8.8 Hz, 2H) 8.00–8.04 (m, 2H) 8.06 (d, J=8.8 Hz, 2H) 8.56 (d, J=2.0 Hz, 1H) 9.27 (s, 1H); MS ESI(+) m/e 549 (M+H)$^+$.

EXAMPLE 594

N-(4-{4-amino-3-[4-({[(3-chlorophenyl)amino]carbonyl}amino)phenyl]thieno[3,2-c]pyridin-7-yl}phenyl)acetamide The desired product was prepared by substituting example 454 and 3-chloro-1-isocyanatobenzene for 121B and 1-fluoro-2-isocyanato-4-(trifluoromethyl)benzene in example 122. $^1$H NMR (300 MHz, DMSO-D$_6$) δ ppm 2.08 (s, 3H) 5.50 (br s, 2H) 6.99–7.08 (m, 1H) 7.26–7.33 (m, 2H) 7.41 (d, J=8.5 Hz, 2H) 7.48 (s, 1H) 7.54–7.67 (m, 4H) 7.68–7.76 (m, 3H) 7.87 (s, 1H) 8.97 (s, 2H) 10.07 (s, 1H); MS ESI(+) m/e 528 (M+H)$^+$.

EXAMPLE 595

N-(4-{4-amino-3-[4-({[(2-fluoro-5-methylphenyl)amino]carbonyl}amino)phenyl]thieno[3,2-c]pyridin-7-yl}phenyl)acetamide The desired product was prepared by substituting example 454 and 1-fluoro-2-isocyanato-4-methylbenzene for 121B and 1-fluoro-2-isocyanato-4-(trifluoromethyl)benzene in example 122. $^1$H NMR (300 MHz, DMSO-D$_6$) δ ppm 2.08 (s, 3H) 2.28 (s, 3H) 5.49 (br s, 2H) 6.73–6.92 (m, 1H) 7.12 (dd, J=11.4, 8.3 Hz, 1H) 7.41 (d, J=8.5 Hz, 2H) 7.48 (s, 1H) 7.54–7.65 (m, J=8.0, 7.9 Hz, 4H) 7.72 (d, J=8.8 Hz, 2H) 7.87 (s, 1H) 8.00 (dd, J=8.1, 1.7 Hz, 1H) 8.55 (d, J=2.4 Hz, 1H) 9.26 (s, 1H) 10.06 (s, 1H); MS ESI(+) m/e 526 (M+H)$^+$.

EXAMPLE 596

N-[4-(4-amino-3-{4-[({[3-(trifluoromethyl)phenyl]amino}carbonyl)amino]phenyl}thieno[3,2-c]pyridin-7-yl)phenyl]acetamide The desired product was prepared by substituting example 454 and 1-isocyanato-3-trifluoromethylbenzene for 121B and 1-fluoro-2-isocyanato-4-(trifluoromethyl)benzene in example 122. $^1$H NMR (300 MHz, DMSO-D$_6$) δ ppm 2.08 (s, 3H) 5.49 (br s, 2H) 7.33 (d, J=7.5 Hz, 1H) 7.41 (d, J=8.8 Hz, 2H) 7.48 (s, 1H) 7.53 (t, J=8.0 Hz, 1H) 7.57–7.67 (m, 5H) 7.72 (d, J=8.8 Hz, 2H) 7.87 (s, 1H) 8.04 (s, 1H) 9.01 (s, 1H) 9.13 (s, 1H) 10.06 (s, 1H); MS ESI(+) m/e 562 (M+H)$^+$.

EXAMPLE 597

3-(4-aminophenyl)-7-(1,3-benzodioxol-5-yl)thieno[3,2-c]pyridin-4-amine

The desired product was prepared by Example 77B and benzo[1,3]dioxol-5-yl boronic acid for Example 1B and 4-phenoxyphenylboronic acid, in Example 10A. $^1$H NMR (300 MHz, DMSO-D$_6$) δ ppm 5.37 (br s, 2H) 5.54 (br s, 2H) 6.09 (s, 2H) 6.68 (d, J=8.5 Hz, 2H) 7.00–7.15 (m, 4H) 7.18 (d, J=1.7 Hz, 1H) 7.32 (s, 1H) 7.80 (s, 1H); MS ESI(+)) m/e 362 (M+H)$^+$.

EXAMPLE 598

N-{4-[4-amino-7-(1,3-benzodioxol-5-yl)thieno[3,2-c]pyridin-3-yl]phenyl}-N'-(2-fluoro-5-methylphenyl)urea The desired product was prepared by substituting example 597 and 1-fluoro-2-isocyanato-4-methylbenzene for 121B and 1-fluoro-2-isocyanato-4-(trifluoromethyl)benzene in example 122. $^1$H NMR (300 MHz, DMSO-D$_6$) δ ppm 2.28 (s, 3H) 5.49 (br s, 2H) 6.10 (s, 2H) 6.69–6.92 (m, 1H) 7.03–7.16 (m, 3H) 7.19 (d, J=1.7 Hz, 1H) 7.41 (d, J=8.5 Hz, 2H) 7.47 (s, 1H) 7.61 (d, J=8.5 Hz, 2H) 7.85 (s, 1H) 8.00 (dd, J=7.8, 2.0 Hz, 1H) 8.55 (d, J=2.7 Hz, 1H) 9.27 (s, 1H); MS ESI(+) m/e 513 (M+H)$^+$.

EXAMPLE 599

N-{4-[4-amino-7-(1,3-benzodioxol-5-yl)thieno[3,2-c]pyridin-3-yl]phenyl}-N'-[3-(trifluoromethyl)phenyl]urea The desired product was prepared by substituting example 597 and 1-isocyanato-3-trifluoromethylbenzene for 121B and 1-fluoro-2-isocyanato-4-(trifluoromethyl)benzene in example 122. $^1$H NMR (300 MHz, DMSO-D$_6$) δ ppm 5.49 (s, 2H) 6.10 (s, 2H) 7.06 (d, J=8.1 Hz, 1H) 7.09–7.16 (m, 1H) 7.19 (d, J=1.7 Hz, 1H) 7.33 (d, J=7.8 Hz, 1H) 7.41 (d, J=8.8 Hz, 2H) 7.47 (s, 1H) 7.53 (t, J=8.0 Hz, 1H) 7.58–7.67 (m, 3H) 7.85 (s, 1H) 8.04 (s, 1H) 9.01 (s, 1H) 9.13 (s, 1H); MS ESI(+) m/e 549 (M+H)$^+$.

EXAMPLE 600

N-{4-[4-amino-7-(1,3-benzodioxol-5-yl)thieno[3,2-c]pyridin-3-yl]phenyl}-N'-(3-chlorophenyl)urea The desired product was prepared by substituting example 597 and 3-chloro-1-isocyanatobenzene for 121B and 1-fluoro-2-isocyanato-4-(trifluoromethyl)benzene in example 122. $^1$H NMR (300 MHz, DMSO-D$_6$) δ ppm 5.48 (br s, 2H) 6.10 (s, 2H) 7.00–7.09 (m, 2H) 7.10–7.16 (m, 1H) 7.19 (d, J=1.7 Hz, 1H) 7.27–7.34 (m, 2H) 7.40 (d, J=8.5 Hz, 2H) 7.47 (s, 1H) 7.61 (d, J=8.8 Hz, 2H) 7.69–7.77 (m, 1H) 7.84 (s, 1H) 8.96 (s, 2H); MS ESI(+) m/e 515 (M+H)$^+$.

EXAMPLE 601 methyl 4-amino-3-[4-({[(3-methylphenyl)amino]carbonyl}amino)phenyl]thieno[3,2-c]pyridine-7-carboxylate

EXAMPLE 601A methyl 4-amino-3-(4-aminophenyl)thieno[3,2-c]pyridine-7-carboxylate A solution of example 77B (3 g, 8.17 mmol) in MeOH (90 mL) and Et$_3$N (3.4 mL) was treated with 10 mol % PdCl$_2$(dppf).CH$_2$Cl$_2$) (668 mg, 0.82 mmol) then heated at 120° C. under 300 psi CO fro 16 hours. The reaction mixture was cooled, concentrated, and the residue purified via silica gel chromatography eluting with 5 to 7% MeOH in CH$_2$Cl$_2$. The product isolated was further purified by suspending in 5% MeOH in CH$_2$Cl$_2$, filtering, and washing the solids with CH$_2$Cl$_2$ to give 1.32 g of the title compound. MS (ESI (+) m/e 300 (M+H)$^+$.

EXAMPLE 601B methyl 4-amino-3-[4-({[(3-methylphenyl)amino]carbonyl}amino)phenyl]thieno[3,2-c]pyridine-7-carboxylate The desired product was prepared by substituting example 597 and 1-isocyanato-3-methylbenzene for 121B and 1-fluoro-2-isocyanato-4-(trifluoromethyl)benzene in example 122. $^1$H NMR (300 MHz, DMSO-D$_6$) δ ppm 2.29 (s, 3H) 3.89 (s, 3H) 6.81 (d, J=7.5 Hz, 1H) 7.17 (t, J=7.6 Hz, 1H) 7.25 (d, J=8.1 Hz, 1H) 7.32 (s, 1H) 7.38 (d, J=8.5 Hz, 2H) 7.54 (s, 1H) 7.61 (d, J=8.8 Hz, 2H) 8.54 (s, 1H) 8.66 (s, 1H) 8.86 (s, 1H); MS ESI(+) m/e 433 (M+H)$^+$.

EXAMPLE 602

4-amino-3-[4-({[(3-methylphenyl)amino]carbonyl}amino)phenyl]thieno[3,2-c]pyridine-7-carboxylic acid A suspension of example 601 (2.35 g, 5.44 mmol) in THF (20 mL) and MeOH (10 mL) was treated with 2M aqueous LiOH (13.6 mL, 27.2 mmol) and heated at 70° C. for 1 hour. The mixture was filtered and the solids were washed with water, diethyl ether, and dried to give 1.4 g of the title compound. $^1$H NMR (300 MHz, DMSO-D$_6$) δ ppm 2.29 (s, 3H) 6.22 (br s, 2H) 6.80 (d, J=7.5 Hz, 1H) 7.17 (t, J=7.8 Hz, 1H) 7.26 (d, J=8.5 Hz, 1H) 7.32 (br s, 1H) 7.38 (d, J=8.5 Hz, 2H) 7.54 (s, 1H) 7.61 (d, J=8.5 Hz, 2H) 8.51 (s, 1H) 8.69 (s, 1H) 8.90 (s, 1H) 12.90 (br s, 1H); MS ESI(+) m/e 419 (M+H)$^+$.

EXAMPLE 603

4-amino-N-methyl-3-[4-({[(3-methylphenyl)amino]carbonyl}amino)phenyl]thieno[3,2-c]pyridine-7-carboxamide The desired product was prepared by substituting example 602 and methylamine hydrochloride for example 11B and 2-piperazinone in example 11C. $^1$H NMR (300 MHz, DMSO-D$_6$) δ ppm 2.29 (s, 3H) 2.82 (d, J=4.4 Hz, 3H) 5.89 (br s, 2H) 6.80 (d, J=7.5 Hz, 1H) 7.17 (t, J=7.8 Hz, 1H) 7.25 (d, J=8.5 Hz, 1H) 7.32 (s, 1H) 7.36 (d, J=8.5 Hz, 2H) 7.47 (s, 1H) 7.59 (d, J=8.8 Hz, 2H) 8.42 (m, 1H) 8.48 (s, 1H) 8.66 (s, 1H) 8.85 (s, 1H); MS ESI(+) m/e 432 (M+H)$^+$.

EXAMPLE 604

4-amino-N,N-dimethyl-3-[4-({[(3-methylphenyl)amino]carbonyl}amino)phenyl]thieno[3,2-c]pyridine-7-carboxamide The desired product was prepared by substituting example 602 and dimethylamine hydrochloride for example 11B and 2-piperazinone in example 11C. $^1$H NMR (300 MHz, DMSO-D$_6$) δ ppm 2.29 (s, 3H) 3.07 (s, 6H) 5.80 (br s, 2H) 6.81 (d, J=7.5 Hz, 1H) 7.17 (t, J=7.6 Hz, 1H) 7.26 (d, J=7.8 Hz, 1H) 7.32 (s, 1H) 7.38 (d, J=8.5 Hz, 2H) 7.49 (s, 1H) 7.60 (d, J=8.5 Hz, 2H) 8.03 (s, 1H) 8.66 (s, 1H) 8.86 (s, 1H); MS ESI(+) m/e 446 (M+H)$^+$.

EXAMPLE 605

N-(4-{4-amino-7-[(4-methylpiperazin-1-yl)carbonyl]thieno[3,2-c]pyridin-3-yl}phenyl)-N'-(3-methylphenyl)urea The desired product was prepared by substituting example 602 and 1-methylpiperazine for example 11B and 2-piperazinone in example 11C. $^1$H NMR (300 MHz, DMSO-D$_6$) δ ppm 2.21 (s, 3H) 2.29 (s, 3H) 2.36 (m, 4H) 3.58 (m, 4H) 5.82 (br s, 2H) 6.81 (d, J=7.1 Hz, 1H) 7.17 (t, J=7.6 Hz, 1H) 7.25 (d, J=8.5 Hz, 1H) 7.31 (s, 1H) 7.37 (d, J=8.5 Hz, 2H) 7.49 (s, 1H) 7.60 (d, J=8.5 Hz, 2H) 7.95 (s, 1H) 8.66 (s, 1H) 8.86 (s, 1H); MS ESI(+) m/e 501 (M+H)$^+$.

EXAMPLE 606

4-amino-3-[4-({[(3-methylphenyl)amino]carbonyl}amino)phenyl]-N-(pyridin-3-ylmethyl)thieno[3,2-c]pyridine-7-carboxamide The desired product was prepared by substituting example 602 and pyridin-3-ylmethylamine for example 11B and 2-piperazinone in example 11C. $^1$H NMR (500 MHz, DMSO-D$_6$) δ ppm 2.29 (s, 3H) 4.54 (d, J=5.8 Hz, 2H) 5.97 (br s, 2H) 6.81 (d, J=7.6 Hz, 1H) 7.17 (t, J=7.8 Hz, 1H) 7.26 (d, J=8.2 Hz, 1H) 7.32 (s, 1H) 7.34–7.41 (m, 3H) 7.48 (s, 1H) 7.60 (d, J=8.5 Hz, 2H) 7.76 (d, J=7.9 Hz, 1H) 8.38–8.54 (m, 1H) 8.59 (s, 2H) 8.67 (s, 1H) 8.87 (s, 1H) 9.08 (t, J=5.8 Hz, 1H); MS ESI(+) m/e 509 (M+H)$^+$.

EXAMPLE 607

4-amino-3-[4-({[(3-methylphenyl)amino]carbonyl}amino)phenyl]thieno[3,2-c]pyridine-7-carboxamide The desired product was prepared by substituting example 602 and ammonium hydroxide for example 11B and 2-piperazinone in example 11C. $^1$H NMR (300 MHz, DMSO-$D_6$) δ ppm 2.29 (s, 3H) 5.91 (br s, 2H) 6.80 (d, J=7.1 Hz, 1H) 7.17 (t, J=7.6 Hz, 1H) 7.24 (m, 1H) 7.31 (s, 1H) 7.36 (d, J=8.5 Hz, 2H) 7.45 (s, 1H) 7.59 (d, J=8.5 Hz, 2H) 7.93 (br s, 2H) 8.53 (s, 1H) 8.65 (s, 1H) 8.85 (s, 1H); MS ESI(+) m/e 418 (M+H)$^+$.

EXAMPLE 608

N-[3-(4-aminothieno[3,2-c]pyridin-3-yl)phenyl]-N'-phenylurea

EXAMPLE 608A 3-(3-aminophenyl)thieno[3,2-c]pyridin-4-amine

The desired product was prepared by substituting 3-(4,4,5,5-tetramethyl-1,3,2-dioxaborolan-2-yl)aniline for 4-phenoxyphenylboronic acid in Example 10A. MS ESI(+) m/e 241 (M+H)$^+$.

EXAMPLE 608B

N-[3-(4-aminothieno[3,2-c]pyridin-3-yl)phenyl]-N'-phenylurea

The desired product was prepared by substituting example 608A and 1-isocyanatobenzene for example 121B and 1-fluoro-2-isocyanato-4-(trifluoromethyl)benzene in example 122. $^1$H NMR (300 MHz, DMSO-$D_6$) δ ppm 5.47 (br s, 2H) 6.97 (t, J=7.3 Hz, 1H) 7.05 (d, J=7.1 Hz, 1H) 7.21–7.32 (m, 4H) 7.38–7.55 (m, 4H) 7.59–7.65 (m, 1H) 7.84 (d, J=5.8 Hz, 1H) 8.72 (s, 1H) 8.86 (s, 1H); MS ESI(+) m/e 361 (M+H)$^+$.

EXAMPLE 609

N-[3-(4-aminothieno[3,2-c]pyridin-3-yl)phenyl]-N'-(3-methylphenyl)urea

The desired product was prepared by substituting example 608A and 1-isocyanato-3-methylbenzene for 121B and 1-fluoro-2-isocyanato-4-(trifluoromethyl)benzene in example 122. $^1$H NMR (300 MHz, DMSO-$D_6$) δ ppm 2.27 (s, 3H) 5.47 (s, 2H) 6.79 (d, J=7.1 Hz, 1H) 7.05 (d, J=7.5 Hz, 1H) 7.11–7.18 (m, 1H) 7.21 (d, J=7.8 Hz, 1H) 7.27 (d, J=5.8 Hz, 1H) 7.31 (s, 2H) 7.42 (t, J=7.8 Hz, 1H) 7.48 (s, 1H) 7.63 (s, 1H) 7.84 (d, J=5.8 Hz, 1H) 8.64 (s, 1H) 8.84 (s, 1H); MS ESI(+) m/e 375 (M+H)$^+$.

EXAMPLE 610

N-[4-(4-aminothieno[3,2-c]pyridin-3-yl)phenyl]-N'-(4-methylphenyl)urea

The desired product was prepared by substituting example 17A and 1-isocyanato-4-methylbenzene for 121B and 1-fluoro-2-isocyanato-4-(trifluoromethyl)benzene in example 122. $^1$H NMR (300 MHz, DMSO-$D_6$) δ ppm 2.25 (s, 3H) 5.42 (br s, 2H) 7.10 (d, J=8.1 Hz, 2H) 7.25 (d, J=5.8 Hz, 1H) 7.36 (dd, J=8.5, 2.4 Hz, 4H) 7.41 (s, 1H) 7.59 (d, J=8.5 Hz, 2H) 7.82 (d, J=5.4 Hz, 1H) 8.62 (s, 1H) 8.82 (s, 1H); MS ESI(+) m/e 375 (M+H)$^+$.

EXAMPLE 611

N-[4-(4-aminothieno[3,2-c]pyridin-3-yl)phenyl]-N'-(2-methylphenyl)urea

The desired product was prepared by substituting example 17A and 1-isocyanato-2-methylbenzene for 121B and 1-fluoro-2-isocyanato-4-(trifluoromethyl)benzene in example 122. $^1$H NMR (300 MHz, DMSO-$D_6$) δ ppm 2.26 (s, 3H) 5.42 (br s, 2H) 6.96 (t, J=7.5 Hz, 1H) 7.12–7.22 (m, 2H) 7.25 (d, J=5.4 Hz, 1H) 7.37 (d, J=8.5 Hz, 2H) 7.42 (s, 1H) 7.61 (d, J=8.5 Hz, 2H) 7.80–7.87 (m, 2H) 7.99 (s, 1H) 9.21 (s, 1H); MS ESI(+) m/e 375 (M+H)$^+$.

EXAMPLE 612

N-[4-(4-aminothieno[3,2-c]pyridin-3-yl)phenyl]-N-methyl-N'-(3-methylphenyl)urea

EXAMPLE 612A

3-[4-(methylamino)phenyl]thieno[3,2-c]pyridin-4-amine

The desired product was prepared by substituting substituting methyl-[4-(4,4,5,5-tetramethyl-[1,3,2]dioxaborolan-2-yl)-phenyl]-amine for 4-phenoxyphenylboronic acid in Example 10A. MS ESI(+) m/e 256 (M+H)$^+$.

EXAMPLE 612B

N-[4-(4-aminothieno[3,2-c]pyridin-3-yl)phenyl]-N-methyl-N'-(3-methylphenyl)urea

The desired product was prepared by substituting example 612A and 1-isocyanato-3-methylbenzene for 121B and 1-fluoro-2-isocyanato-4-(trifluoromethyl)benzene in example 122. $^1$H NMR (300 MHz, DMSO-$D_6$) δ ppm 2.25 (s, 3H) 3.32 (s, 3H) 5.61 (br s, 2H) 6.78 (d, J=7.5 Hz, 1H) 7.12 (t, J=7.8 Hz, 1H) 7.20–7.34 (m, 3H) 7.35–7.59 (m, 5H) 7.84 (d, J=5.8 Hz, 1H) 8.28 (s, 1H); MS ESI(+) m/e 389 (M+H)$^+$.

EXAMPLE 613

N-[4-(4-aminothieno[3,2-c]pyridin-3-yl)phenyl]benzamide

The desired product was prepared by substituting benzoyl chloride for acetyl chloride in example 17B. $^1$H NMR (300 MHz, DMSO-$D_6$) δ ppm 5.42 (br s, 2H) 7.27 (d, J=5.8 Hz, 1H) 7.41–7.49 (m, 3H) 7.51–7.66 (m, 3H) 7.83 (d, J=5.8 Hz, 1H) 7.90–8.02 (m, 4H) 10.43 (s, 1H); MS ESI(+) m/e 346 (M+H)$^+$.

Examples 614–634 were prepared coupling the appropriate aryl boronic acid with example 77B using the procedure of example 10A. The products were purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give the desired product as the trifluoroacetic acid salt.

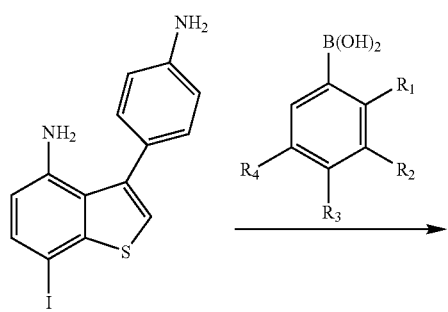

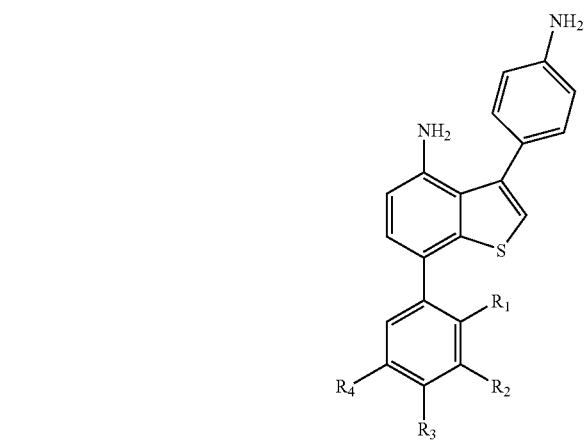

| Example | $R_1$ | $R_2$ | $R_3$ | $R_4$ | MS (ESI) $(M + H^+)^+$ |
|---|---|---|---|---|---|
| 614 | H | OMe | H | H | 348 |
| 615 | H | H | OMe | H | 348 |
| 616 | F | H | H | H | 336 |
| 617 | H | F | H | H | 336 |
| 618 | Cl | H | H | H | 352 |
| 619 | H | Cl | H | H | 352 |
| 620 | H | H | Cl | H | 352 |
| 621 | H | CN | H | H | 343 |
| 622 | H | COMe | H | H | 360 |
| 623 | H | $CF_3$ | H | H | 386 |
| 624 | H | H | $CF_3$ | H | 386 |
| 625 | H | $OCF_3$ | H | H | 402 |
| 626 | H | H | PhO | H | 410 |
| 627 | H | H | $OCF_3$ | H | 402 |
| 628 | H | Me | H | Me | 346 |
| 629 | H | EtO | H | H | 362 |
| 630 | MeO | H | H | MeO | 378 |
| 631 | H | MeO | MeO | H | 378 |
| 632 | H | MeO | MeO | MeO | 408 |
| 633 | H | Cl | Cl | H | 386 |
| 634 | H | Cl | H | Cl | 386 |

EXAMPLE 635

N-{3-[4-amino-3-(4-aminophenyl)thieno[3,2-c]pyridin-7-yl]prop-2-ynyl}isonicotinamide The desired product was prepared by substituting example 77B and N-prop-2-ynyl-isonicotinamide for example 144A and 3-butyn-1-ol in example 144B. $^1$H NMR (300 MHz, DMSO-$D_6$) δ ppm 4.44 (d, J=5.76 Hz, 2H) 5.37 (s, 2H) 5.82 (s, 2H) 6.66 (d, J=8.48 Hz, 2H) 7.08 (d, J=8.48 Hz, 2H) 7.36 (s, 1H) 7.81 (d, J=6.10 Hz, 2H) 7.94 (s, 1H) 8.75 (d, J=6.10 Hz, 2H) 9.40 (t, J=5.59 Hz, 1H); MS (ESI(+)) m/e 400 (M+H)$^+$.

EXAMPLE 636

N-(3-{4-amino-3-[4-({[(3-methylphenyl)amino]carbonyl}amino)phenyl]thieno[3,2-c]pyridin-7-yl}prop-2-ynyl)isonicotinamide The desired product was prepared by substituting example 635 and 1-isocyanato-3-methylbenzene for example 121B and 1-fluoro-2-isocyanato-4-(trifluoromethyl)benzene in example 122. $^1$H NMR (300 MHz, DMSO-$D_6$) δ ppm 2.29 (s, 3H) 4.45 (d, J=5.42 Hz, 2H) 5.79 (s, 2H) 6.80 (d, J=7.46 Hz, 1H) 7.16 (t, J=7.80 Hz, 1H) 7.22–7.27 (m, 1H) 7.31 (s, 1H) 7.37 (d, J=8.81 Hz, 2H) 7.51 (s, 1H) 7.60 (d, J=8.81 Hz, 2H) 7.81 (d, J=6.10 Hz, 2H) 7.98 (s, 1H) 8.66 (s, 1H) 8.75 (d, J=6.10 Hz, 2H) 8.86 (s, 1H) 9.41 (t, J=5.59 Hz, 1H); MS ESI(+)) m/e 533 (M+H)$^+$.

EXAMPLE 637

N-(3-{4-amino-3-[4-({[(3-chlorophenyl)amino]carbonyl}amino)phenyl]thieno[3,2-c]pyridin-7-yl}prop-2-ynyl)isonicotinamide The desired product was prepared by substituting example 635 and 1-chloro-3-isocyanatobenzene for example 121B and 1-fluoro-2-isocyanato-4-(trifluoromethyl)benzene in example 122. $^1$H NMR (300 MHz, DMSO-$D_6$) δ ppm 4.45 (d, J=5.76 Hz, 2H) 5.78 (s, 2H) 7.03 (d, J=6.44 Hz, 1H) 7.27–7.32 (m, 2H) 7.38 (d, J=8.48 Hz, 2H) 7.51 (s, 1H) 7.60 (d, J=8.48 Hz, 2H) 7.73 (s, 1H) 7.81 (d, J=6.10 Hz, 2H) 7.98 (s, 1H) 8.75 (d, J=5.76 Hz, 2H) 8.96 (s, 2H) 9.41 (t, J=5.42 Hz, 1H); MS (ESI(+)) m/e 553 (M+H)$^+$.

EXAMPLE 638

N-[3-(4-amino-3-{4-[({[2-fluoro-5-(trifluoromethyl)phenyl]amino}carbonyl)amino]phenyl}thieno[3,2-c]pyridin-7-yl)prop-2-ynyl]isonicotinamide The desired product was prepared by substituting example 635 and 1-fluoro-2-isocyanato-4-(trifluoromethyl)benzene for example 121B and 1-fluoro-2-isocyanato-4-(trifluoromethyl)benzene in example 122. $^1$H NMR (300 MHz, DMSO-$D_6$) δ ppm 4.46 (d, J=5.43 Hz, 2H) 5.78 (s, 2H) 7.41 (d, J=8.48 Hz, 3H) 7.47–7.55 (m, 2H) 7.62 (d, J=8.48 Hz, 2H) 7.82 (d, J=5.76 Hz, 2H) 7.99 (s, 1H) 8.63 (d, J=7.46 Hz, 1H) 8.76 (d, J=6.10 Hz, 2H) 8.97 (d, J=2.71 Hz, 1H) 9.37 (s, 1H) 9.41 (t, J=5.59 Hz, 1H); MS (ESI(+)) m/e 605 (M+H)$^+$.

Example 639

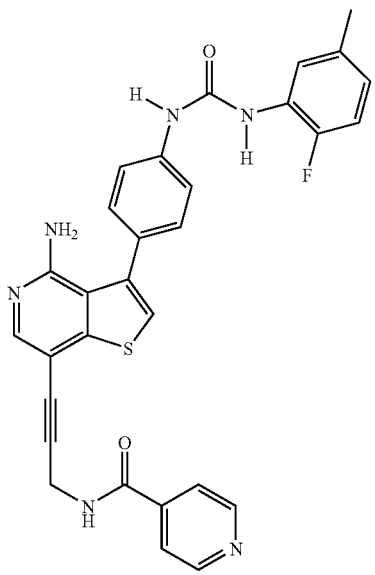

EXAMPLE 639

N-(3-{4-amino-3-[4-({[(2-fluoro-5-methylphenyl)amino]carbonyl}amino)phenyl]thieno[3,2-c]pyridin-7-yl}prop-2-ynyl)isonicotinamide The desired product was prepared by substituting example 635 and 1-fluoro-2-isocyanato-4-methylbenzene for example 121B and 1-fluoro-2-isocyanato-4-(trifluoromethyl)benzene in example 122. $^1$H NMR (300 MHz, DMSO-D$_6$) δ ppm 2.28 (s, 3H) 4.45 (d, J=5.43 Hz, 2H) 5.78 (s, 2H) 6.78–6.85 (m, 1H) 7.05–7.16 (m, 1H) 7.39 (d, J=8.48 Hz, 2H) 7.52 (s, 1H) 7.60 (d, J=8.48 Hz, 2H) 7.82 (d, J=6.10 Hz, 2H) 7.96–8.02 (m, 2H) 8.55 (d, J=2.37 Hz, 1H) 8.76 (d, J=5.76 Hz, 2H) 9.26 (s, 1H) 9.41 (t, J=5.26 Hz, 1H); MS (ESI(+)) m/e 551 (M+H)$^+$.

EXAMPLE 640

N-[3-(4-amino-3-{4-[({[3-(trifluoromethyl)phenyl]amino}carbonyl)amino]phenyl}thieno[3,2-c]pyridin-7-yl)prop-2-ynyl]isonicotinamide The desired product was prepared by substituting example 635 and 1-isocyanato-3-(trifluoromethyl)benzene for example 121B and 1-fluoro-2-isocyanato-4-(trifluoromethyl)benzene in example 122. $^1$H NMR (300 MHz, DMSO-D$_6$) δ ppm 4.46 (d, J=5.43 Hz, 2H) 5.79 (s, 2H) 7.33 (d, J=7.46 Hz, 1H) 7.39 (d, J=8.48 Hz, 2H) 7.49–7.57 (m, 2H) 7.62 (d, J=8.82 Hz, 3H) 7.82 (d, J=6.10 Hz, 2H) 7.98 (s, 1H) 8.04 (s, 1H) 8.76 (d, J=6.10 Hz, 2H) 9.03 (s, 1H) 9.15 (s, 1H) 9.41 (t, J=5.43 Hz, 1H); MS (ESI(+) m/e 587 (M+H)$^+$.

EXAMPLE 641

N-{3-[4-amino-3-(4-aminophenyl)thieno[3,2-c]pyridin-7-yl]prop-2-ynyl}methanesulfonamide The desired product was prepared by substituting example 77B and N-prop-2-ynylmethanesulfonamide for example 144A and 3-butyn-1-ol in example 144B. $^1$H NMR (300 MHz, DMSO-D$_6$) δ ppm 3.06 (s, 3H) 4.15 (d, J=6.10 Hz, 2H) 5.38 (s, 2H) 5.86 (s, 2H) 6.67 (d, J=8.48 Hz, 2H) 7.08 (d, J=8.14 Hz, 2H) 7.38 (s, 1H) 7.69 (t, J=6.10 Hz, 1H) 7.96 (s, 1H); MS (ESI(+)) m/e 373 (M+H)$^+$.

EXAMPLE 642

N-(3-{4-amino-3-[4-({[(3-methylphenyl)amino]carbonyl}amino)phenyl]thieno[3,2-c]-pyridin-7-yl}prop-2-ynyl)methanesulfonamide The desired product was prepared by substituting example 641 and 1-isocyanato-3-methylbenzene for example 121B and 1-fluoro-2-isocyanato-4-(trifluoromethyl)benzene in example 122. $^1$H NMR (300 MHz, DMSO-D$_6$) δ ppm 2.29 (s, 3H) 3.07 (s, 3H) 4.17 (d, J=5.43 Hz, 2H) 5.83 (s, 2H) 6.81 (d, J=6.44 Hz, 1H) 7.17 (t, J=7.63 Hz, 1H) 7.22–7.29 (m, 1H) 7.32 (s, 1H) 7.38 (d, J=8.48 Hz, 2H) 7.53 (s, 1H) 7.60 (d, J=8.14 Hz, 2H) 7.70 (t, J=5.76 Hz, 1H) 8.00 (s, 1H) 8.66 (s, 1H) 8.86 (s, 1H); ); MS (ESI(+)) m/e 506 (M+H)$^+$.

EXAMPLE 643

N-(3-{4-amino-3-[4-({[(2-fluoro-5-methylphenyl)amino]carbonyl}amino)phenyl]thieno[3,2-c]pyridin-7-yl}prop-2-ynyl)methanesulfonamide The desired product was prepared by substituting example 641 and 1-fluoro-2-isocyanato-4-methylbenzene for example 121B and 1-fluoro-2-isocyanato-4-(trifluoromethyl)benzene in example 122. $^1$H NMR (300 MHz, DMSO-D$_6$) δ ppm 2.28 (s, 3H) 3.07 (s, 3H) 4.17 (d, J=6.10 Hz, 2H) 5.82 (s, 2H) 6.76–6.87 (m, 1H) 7.04–7.16 (m, 1H) 7.39 (d, J=8.48 Hz, 2H) 7.53 (s, 1H) 7.61 (d, J=8.48 Hz, 2H) 7.70 (t, J=5.93 Hz, 1H) 8.00 (s, 2H) 8.55 (s, 1H) 9.26 (s, 1H); MS (ESI(+)) m/e 524 (M+H)$^+$.

EXAMPLE 644

N-(3-{4-amino-3-[4-({[(3-chlorophenyl)amino]carbonyl}amino)phenyl]thieno[3,2-c]pyridin-7-yl}prop-2-ynyl)methanesulfonamide The desired product was prepared by substituting example 641 and 1-chloro-3-isocyanatobenzene for example 121B and 1-fluoro-2-isocyanato-4-(trifluoromethyl)benzene in example 122. $^1$H NMR (300 MHz, DMSO-D$_6$) δ ppm 3.07 (s, 3H) 4.17 (d, J=6.10 Hz, 2H) 5.82 (s, 2H) 7.01–7.07 (m, 1H) 7.29–7.33 (m, 2H) 7.39 (d, J=8.48 Hz, 2H) 7.53 (s, 1H) 7.61 (d, J=8.82 Hz, 2H) 7.67–7.71 (m, 1H) 7.73 (t, J=2.03 Hz, 1H) 8.00 (s, 1H) 8.97 (s, 2H); MS (ESI(+)) m/e 526 (M+H)$^+$.

EXAMPLE 645

N-[3-(4-amino-3-{4-[({[3-(trifluoromethyl)phenyl]amino}carbonyl)amino]phenyl}thieno[3,2-c]pyridin-7-yl)prop-2-ynyl]methanesulfonamide The desired product was prepared by substituting example 641 and 1-isocyanato-3-(trifluoromethyl)benzene for example 121B and 1-fluoro-2-isocyanato-4-(trifluoromethyl)benzene in example 122. $^1$H NMR (300 MHz, DMSO-D$_6$) δ ppm 3.07 (s, 3H) 4.17 (d, J=6.10 Hz, 2H) 5.82 (s, 2H) 7.33 (d, J=7.80 Hz, 1H) 7.40 (d, J=8.48 Hz, 2H) 7.49–7.57 (m, 2H) 7.59 (s, 1H) 7.63 (d, J=8.48 Hz, 2H) 7.70 (t, J=5.93

Hz, 1H) 8.00 (s, 1H) 8.04 (s, 1H) 9.01 (s, 1H) 9.13 (s, 1H); MS (ESI(+)) m/e 560 (M+H)$^+$.

EXAMPLE 646

N-[3-(4-amino-3-{4-[({[2-fluoro-5-(trifluoromethyl)phenyl]amino}carbonyl)amino]phenyl}thieno[3,2-c]pyridin-7-yl)prop-2-ynyl]methanesulfonamide The desired product was prepared by substituting example 641 for example 121B in example 122. $^1$H NMR (300 MHz, DMSO-D$_6$) δ ppm 3.07 (s, 3H) 4.17 (d, J=6.10 Hz, 2H) 5.82 (s, 2H) 7.41 (d, J=8.48 Hz, 3H) 7.50 (d, J=10.85 Hz, 1H) 7.54 (s, 1H) 7.62 (d, J=8.48 Hz, 2H) 7.70 (t, J=5.93 Hz, 1H) 8.01 (s, 1H) 8.63 (d, J=7.12 Hz, 1H) 8.97 d, J=2.71 Hz, 1H) 9.38 (s, 1H); MS (ESI(+)) m/e 578 (M+H)$^+$.

EXAMPLE 647

N-[4-(4-amino-7-pyrimidin-5-ylthieno[3,2-c]pyridin-3-yl)phenyl]-N'-(2-fluoro-5-methylphenyl)urea The desired product was prepared by substituting example 136A and 1-fluoro-2-isocyanato-4-methyl-benzene for example 121B and 1-fluoro-2-isocyanato-4-(trifluoromethyl)benzene in example 122. $^1$H NMR (300 MHz, DMSO-D$_6$) δ ppm 2.29 (s, 3H) 5.74 (s, 2H) 6.78–6.86 (m, 1H) 7.10 (d, J=8.14 Hz, 1H) 7.14 (d, J=8.14 Hz, 1H) 7.42 (d, J=8.81 Hz, 2H) 7.55 (s, 1H) 7.63 (d, J=8.48 Hz, 2H) 8.00 (dd, J=7.80, 2.03 Hz, 1H) 8.04 (s, 1H) 8.56 (d, J=2.71 Hz, 1H) 9.14 (s, 1H) 9.23 (s, 1H) 9.28 (s, 1H); MS (ESI(+)) m/e 471 (M+H)$^+$.

EXAMPLE 648

N-[4-(4-amino-7-pyrimidin-5-ylthieno[3,2-c]pyridin-3-yl)phenyl]-N'-(3-fluorophenyl)urea The desired product was prepared by substituting example 136A and 1-fluoro-3-isocyanatobenzene for example 121B and 1-fluoro-2-isocyanato-4-(trifluoromethyl)benzene in example 122. $^1$H NMR (300 MHz, DMSO-D$_6$) δ ppm 5.74 (s, 2H) 6.75–6.85 (m, 1H) 7.15 (d, J=9.16 Hz, 1H) 7.26–7.37 (m, 1H) 7.42 (d, J=8.48 Hz, 2H) 7.48–7.56 (m, 2H) 7.63 (d, J=8.48 Hz, 2H) 8.04 (s, 1H) 8.99 (d, J=6.44 Hz, 2H) 9.14 (s, 2H) 9.23 (s, 1H); MS (ESI(+)) m/e 457 (M+H)$^+$.

EXAMPLE 649

N-[4-(4-amino-7-pyrimidin-5-ylthieno[3,2-c]pyridin-3-yl)phenyl]-N'-(3-fluoro-4-methylphenyl)urea The desired product was prepared by substituting example 136A and 1-fluoro-4-isocyanato-2-methyl-benzene for example 121B and 1-fluoro-2-isocyanato-4-(trifluoromethyl)benzene in example 122. $^1$H NMR (300 MHz, DMSO-D$_6$) δ ppm 2.18 (s, 3H) 5.74 (s, 2H) 7.02–7.10 (m, 1H) 7.18 (t, J=8.65 Hz, 1H) 7.41 (d, J=8.48 Hz, 3H) 7.54 (s, 1H) 7.62 (d, J=8.48 Hz, 2H) 8.04 (s, 1H) 8.86 (s, 1H) 8.93 (s, 1H) 9.14 (s, 2H) 9.23 (s, 1H); MS (ESI(+)) m/e 470 (M+H)$^+$.

EXAMPLE 650

N-[4-(4-amino-7-thien-3-ylthieno[3,2-c]pyridin-3-yl)phenyl]-N'-(3-chlorophenyl)urea The desired product was prepared by substituting example 126 and 1-chloro-3-isocyanatobenzene for example 121B and 1-fluoro-2-isocyanato-4-(trifluoromethyl)benzene in example 122. $^1$H NMR (300 MHz, DMSO-D$_6$) δ ppm 5.53 (s, 2H) 7.00–7.07 (m, 1H) 7.28–7.34 (m, 2H) 7.41 (d, J=8.48 Hz, 2H) 7.52 (s, 1H) 7.57 (d, J=6.10 Hz, 1H) 7.62 (d, J=8.48 Hz, 2H) 7.73 (t, J=3.73 Hz, 2H) 7.81 (d, J=3.73 Hz, 1H) 8.09 (s, 1H) 8.97 (s, 2H); MS (ESI(+)) m/e 478 (M+H)$^+$.

EXAMPLE 651

N-[4-(4-amino-7-thien-3-ylthieno[3,2-c]pyridin-3-yl)phenyl]-N'-[2-fluoro-5-(trifluoromethyl)phenyl]urea The desired product was prepared by substituting example 126 for example 121B in example 122. $^1$H NMR (300 MHz, DMSO-D$_6$) δ ppm 5.53 (s, 2H) 7.43 (d, J=8.48 Hz, 3H) 7.48–7.54 (m, 2H) 7.57 (d, J=3.39 Hz, 1H) 7.63 (d, J=8.48 Hz, 2H) 7.74 (dd, J=5.09, 2.71 Hz, 1H) 7.81 (d, J=4.07 Hz, 1H) 8.09 (s, 1H) 8.64 (d, J=5.43 Hz, 1H) 8.98 (s, 1H) 9.38 (s, 1H); MS (ESI(+)) m/e 529 (M+H)$^+$.

EXAMPLE 652

N-[4-(4-amino-7-thien-3-ylthieno[3,2-c]pyridin-3-yl)phenyl]-N'-[3-(trifluoromethyl)phenyl]urea The desired product was prepared by substituting example 126 and 1-isocyanato-3-(trifluoromethyl)benzene for example 121B and 1-fluoro-2-isocyanato-4-(trifluoromethyl)benzene in example 122. $^1$H NMR (300 MHz, DMSO-D$_6$) δ ppm 5.53 (s, 2H) 7.33 (d, J=7.46 Hz, 1H) 7.42 (d, J=8.48 Hz, 2H) 7.52 (s, 2H) 7.55–7.61 (m, 2H) 7.61–7.67 (m, 2H) 7.73 (dd, J=5.09, 3.05 Hz, 1H) 7.81 (dd, J=2.71, 1.36 Hz, 1H) 8.04 (s, 1H) 8.09 (s, 1H) 9.01 (s, 1H) 9.13 (s, 1H); MS (ESI(+)) m/e 511 (M+H)$^+$.

EXAMPLE 653

N-[4-(4-amino-7-thien-3-ylthieno[3,2-c]pyridin-3-yl)phenyl]-N'-(3-fluorophenyl)urea The desired product was prepared by substituting example 126 and 1-fluoro-3-isocyanatobenzene for example 121B and 1-fluoro-2-isocyanato-4-(trifluoromethyl)benzene in example 122. $^1$H NMR (300 MHz, DMSO-D$_6$) δ ppm 5.53 (s, 2H) 6.74–6.85 (m, 1H) 7.15 (d, J=8.14 Hz, 1H) 7.27–7.38 (m, 1H) 7.41 (d, J=8.48 Hz, 2H) 7.47–7.55 (m, 2H) 7.57 (d, J=3.73 Hz, 1H) 7.62 (d, J=8.48 Hz, 2H) 7.73 (dd, J=5.09, 2.71 Hz, 1H) 7.78–7.84 (m, 1H) 8.09 (s, 1H) 8.96 (s, 1H) 8.99 (s, 1H); MS (ESI(+)) m/e 461 (M+H)$^+$.

EXAMPLE 654

N-[4-(4-amino-7-thien-3-ylthieno[3,2-c]pyridin-3-yl)phenyl]-N'-(2-fluoro-5-methylphenyl)urea The desired product was prepared by substituting example 126 and 1-fluoro-2-isocyanato-4-methylbenzene for example 121B and 1-fluoro-2-isocyanato-4-(trifluoromethyl)benzene in example 122. $^1$H NMR (300 MHz, DMSO- D$_6$) δ ppm 2.28 (s, 3H) 5.53 (s, 2H) 6.77–6.86 (m, 1H) 7.12 (dd, J=11.36, 8.31 Hz, 1H) 7.41 (d, J=8.48 Hz, 2H) 7.52 (s, 1H) 7.57 (dd, J=4.92, 1.19 Hz, 1H) 7.62 (d, J=8.48 Hz, 2H) 7.69–7.76 (m, 1H) 7.78–7.84 (m, 1H) 7.92–8.07 (m, 1H) 8.09 (s, 1H) 8.55 (d, J=2.71 Hz, 1H) 9.27 (s, 1H); MS (ESI(+)) m/e 475 (M+H)$^+$.

EXAMPLE 655

3-(4-aminophenyl)-7-[3-(diisopropylamino)prop-1-ynyl]thieno[3,2-c]pyridin-4-amine

EXAMPLE 655A

N,N-diisopropyl-N-prop-2-ynylamine

The desired product was prepared by substituting diisopropylamine for pyrrolidine in example 506A.

EXAMPLE 655B 3-(4-aminophenyl)-7-[3-(diisopropylamino)prop-1-ynyl]thieno[3,2-c]pyridin-4-amine The desired product was prepared by substituting example 77B and example 655A for example 144A and 3-butyn-1-ol in example 144B. $^1$H NMR (300 MHz, DMSO-D$_6$) δ ppm 1.11 (d, J=6.44 Hz, 12H) 3.14–3.29 (m, 2H) 3.68 (s, 2H) 5.37 (s, 2H) 5.75 (s, 2H) 6.67 (d, J=8.48 Hz, 2H) 7.08 (d, J=8.48 Hz, 2H) 7.35 (s, 1H) 7.88 (s, 1H); MS (ESI(+) m/e 379 (M+H)$^+$.

EXAMPLE 656

N-(4-{4-amino-7-[3-(diisopropylamino)prop-1-ynyl]thieno[3,2-c]pyridin-3-yl}phenyl)-N'-(3-methylphenyl)urea The desired product was prepared by substituting example 655B and 1-isocyanato-3-methylbenzene for example 121B and 1-fluoro-2-isocyanato-4-(trifluoromethyl)benzene in example 122. $^1$H NMR (300 MHz, DMSO-D$_6$) δ ppm 1.12 (d, J=6.44 Hz, 12H) 2.29 (s, 3H) 3.18–3.30 (m, 2H) 3.69 (s, 2H) 5.72 (s, 2H) 6.80 (d, J=7.46 Hz, 1H) 7.17 (t, J=7.80 Hz, 1H) 7.22–7.29 (m, 1H) 7.31 (s, 1H) 7.37 (d, J=8.48 Hz, 2H) 7.50 (s, 1H) 7.60 (d, J=8.82 Hz, 2H) 7.92 (s, 1H) 8.66 (s, 1H) 8.86 (s, 1H); MS (ESI(+)) m/e 512 (M+H)$^+$.

EXAMPLE 657

N-(4-{4-amino-7-[3-(diisopropylamino)prop-1-ynyl]thieno[3,2-c]pyridin-3-yl}phenyl)-N'-(3-fluorophenyl)urea The desired product was prepared by substituting example 655B and 1-fluoro-3-isocyanatobenzene for example 121B and 1-fluoro-2-isocyanato-4-(trifluoromethyl)benzene in example 122. $^1$H NMR (300 MHz, DMSO-D$_6$) δ ppm 1.12 (d, J=6.44 Hz, 12H) 3.17–3.28 (m, 2H) 3.69 (s, 2H) 5.72 (s, 2H) 6.76–6.84 (m, 1H) 7.14 (d, J=9.15 Hz, 1H) 7.27–7.34 (m, 1H) 7.38 (d, J=8.48 Hz, 2H) 7.47–7.55 (m, 2H) 7.60 (d, J=8.48 Hz, 2H) 7.91 (s, 1H) 8.95 (s, 1H) 8.98 (s, 1H); MS (ESI(+)) m/e 516 (M+H)$^+$.

EXAMPLE 658

N-(4-{4-amino-7-[3-(diisopropylamino)prop-1-ynyl]thieno[3,2-c]pyridin-3-yl}phenyl)-N'-[3-(trifluoromethyl)phenyl]urea The desired product was prepared by substituting example 655B and 1-isocyanato-3-(trifluoromethyl)benzene for example 121B and 1-fluoro-2-isocyanato-4-(trifluoromethyl)benzene in example 122. $^1$H NMR (300 MHz, DMSO-D$_6$) δ ppm 1.12 (d, J=6.44 Hz, 12H) 3.18–3.28 (m, 2H) 3.69 (s, 2H) 5.72 (s, 2H) 7.33 (d, J=7.46 Hz, 1H) 7.39 (d, J=8.48 Hz, 2H) 7.51 (s, 1H) 7.54 (d, J=7.46 Hz, 1H) 7.59 (s, 1H) 7.62 (d, J=8.48 Hz, 2H) 7.92 (s, 1H) 8.03 (s, 1H) 9.01 (s, 1H) 9.12 (s, 1H); MS (ESI(+)) m/e 566 (M+H)$^+$.

EXAMPLE 659

N-(4-{4-amino-7-[3-(diisopropylamino)prop-1-ynyl]thieno[3,2-c]pyridin-3-yl}phenyl)-N'-[2-fluoro-5-(trifluoromethyl)phenyl]urea The desired product was prepared by substituting example 655B for example 121B in example 122. $^1$H NMR (300 MHz, DMSO-D$_6$) δ ppm 1.12 (d, J=6.78 Hz, 12H) 3.17–3.28 (m, 2H) 3.70 (s, 2H) 5.72 (s, 2H) 7.37–7.44 (m, 3H) 7.46–7.56 (m, 2H) 7.62 (d, J=8.48 Hz, 2H) 7.92 (s, 1H) 8.64 (dd, J=7.12, 2.03 Hz, 1H) 8.97 (d, J=2.71 Hz, 1H) 9.38 (s, 1H; MS (ESI(+)) m/e 584 (M+H)$^+$.

EXAMPLE 660

N-(4-{4-amino-7-[3-(diisopropylamino)prop-1-ynyl]thieno[3,2-c]pyridin-3-yl}phenyl)-N'-(3-chlorophenyl)urea The desired product was prepared by substituting example 655B and 1-chloro-3-isocyanatobenzene for example 121B and 1-fluoro-2-isocyanato-4-(trifluoromethyl)benzene in example 122. $^1$H NMR (300 MHz, DMSO-D$_6$) δ ppm 1.12 (d, J=6.78 Hz, 12H) 3.17–3.29 (m, 2H) 3.70 (s, 2H) 5.72 (s, 2H) 7.00–7.07 (m, 1H) 7.28–7.33 (m, 2H) 7.38 (d, J=8.48 Hz, 2H) 7.50 (s, 1H) 7.61 (d, J=8.48 Hz, 2H) 7.68–7.75 (m, 1H) 7.92 (s, 1H) 8.97 (d, J=1.70 Hz, 2H); MS (ESI(+)) m/e 532 (M+H)$^+$.

EXAMPLE 661

N-(4-{4-amino-7-[3-(diisopropylamino)prop-1-ynyl]thieno[3,2-c]pyridin-3-yl}phenyl)-N'-(2-fluoro-5-methylphenyl)urea The desired product was prepared by substituting example 655B and 1-fluoro-2-isocyanato-4-methylbenzene for example 121B and 1-fluoro-2-isocyanato-4-(trifluoromethyl)benzene in example 122. $^1$H NMR (300 MHz, DMSO-D$_6$) δ ppm 1.12 (d, J=6.44 Hz, 12H) 2.28 (s, 3H) 3.16–3.29 (m, 2H) 3.69 (s, 2H) 5.72 (s, 2H) 6.82 (dd, J=7.29, 6.61 Hz, 1H) 7.12 (dd, J=11.53, 8.48 Hz, 1H) 7.38 (d, J=8.48 Hz, 2H) 7.50 (s, 1H) 7.60 (d, J=8.48 Hz, 2H) 7.92 (s, 1H) 7.99 (d, J=8.14 Hz, 1H) 8.54 (d, J=2.37 Hz, 1H) 9.26 (s, 1H); MS (ESI(+)) m/e 530 (M+H)$^+$.

EXAMPLE 662

3-(4-aminophenyl)-7-(3-furyl)thieno[3,2-c]pyridin-4-amine

The desired product was prepared by substituting Example 77B and 3-furylboronic acid for Example 1B and 4-phenoxyphenylboronic acid in Example 10A. $^1$H NMR (300 MHz, DMSO-D$_6$) δ ppm 5.37 (s, 2H) 5.58 (s, 2H) 6.68 (d, J=8.48 Hz, 2H) 7.01–7.04 (m, 1H) 7.10 (d, J=8.48 Hz, 2H) 7.38 (s, 1H) 7.79–7.85 (m, 1H) 8.06 (s, 1H) 8.08–8.11 (m, 1H); MS (ESI(+)) m/e 308 (M+H)$^+$.

EXAMPLE 663

N-{4-[4-amino-7-(3-furyl)thieno[3,2-c]pyridin-3-yl]phenyl}-N'-(3-chlorophenyl)urea The desired product was prepared by substituting example 662 and 1-chloro-3-isocyanatobenzene for example 121B and 1-fluoro-2-isocyanato-4-(trifluoromethyl)benzene in example 122. $^1$H NMR (300 MHz, DMSO-D$_6$) δ ppm 5.52 (s, 2H) 7.01–7.06 (m, 2H) 7.28–7.33 (m, 2H) 7.41 (d, J=8.48 Hz, 2H) 7.53 (s, 1H) 7.62 (d, J=8.48 Hz, 2H) 7.73 (t, J=2.03 Hz, 1H) 7.84 (t, J=1.70 Hz, 1H) 8.10 (s, 1H) 8.11–8.14 (m, 1H) 8.96 (s, 2H); MS (ESI(+)) m/e 460 (M+H)$^+$.

EXAMPLE 664

N-{4-[4-amino-7-(3-furyl)thieno[3,2-c]pyridin-3-yl]phenyl}-N'-(3-fluorophenyl)urea The desired product was prepared by substituting example 662 and 1-fluoro-3-isocyanatobenzene for example 121B and 1-fluoro-2-isocyanato-4-(trifluoromethyl)benzene in example 122. $^1$H NMR (300 MHz, DMSO-D$_6$) δ ppm 5.53 (s, 2H) 6.73–6.86 (m, 1H) 7.05 (s, 1H) 7.15 (d, J=8.48 Hz, 1H) 7.25–7.38 (m, 1H) 7.41 (d, J=8.14 Hz, 2H) 7.48–7.56 (m, 2H) 7.62 (d, J=8.48 Hz, 2H) 7.84 (s, 1H) 8.07–8.17 (m, 2H) 8.97 (d, J=8.82 Hz, 2H); MS (ESI(+)) m/e 445 (M+H)$^+$.

EXAMPLE 665

N-{4-[4-amino-7-(3-furyl)thieno[3,2-c]pyridin-3-yl]phenyl}-N'-[3-(trifluoromethyl)phenyl]urea The desired product was prepared by substituting example 662 and 1-isocyanato-3-(trifluoromethyl)benzene for example 121B and 1-fluoro-2-isocyanato-4-(trifluoromethyl)benzene in example 122. $^1$H NMR (300 MHz, DMSO-D$_6$) δ ppm 5.53 (s, 2H) 6.94–7.11 (m, 1H) 7.33 (d, J=7.46 Hz, 1H) 7.41 (d, J=8.48 Hz, 2H) 7.49–7.57 (m, 2H) 7.59 (s, 1H) 7.63 (d, J=8.81 Hz, 2H) 7.84 (t, J=1.70 Hz, 1H) 8.04 (s, 1H) 8.10 (s, 1H) 8.12 (s, 1H) 9.01 (s, 1H) 9.12 (s, 1H); MS (ESI(+)) m/e 495 (M+H)$^+$.

EXAMPLE 666

N-{4-[4-amino-7-(3-furyl)thieno[3,2-c]pyridin-3-yl]phenyl}-N'-(2-fluoro-5-methylphenyl)urea The desired product was prepared by substituting example 662 and 1-fluoro-2-isocyanato-4-methylbenzene for example 121B and 1-fluoro-2-isocyanato-4-(trifluoromethyl)benzene in example 122. $^1$H NMR (300 MHz, DMSO-D$_6$) δ ppm 2.28 (s, 3H) 5.52 (s, 2H) 6.75–6.87 (m, 1H) 7.05 (s, 1H) 7.12 (dd, J=11.36, 8.31 Hz, 1H) 7.41 (d, J=8.14 Hz, 2H) 7.53 (s, 1H) 7.61 (d, J=8.48 Hz, 2H) 7.84 (s, 1H) 8.00 (d, J=6.10 Hz, 1H) 8.07–8.16 (m, 2H) 8.54 (s, 1H) 9.26 (s, 1H); MS (ESI(+)) m/e 459 (M+H)$^+$.

EXAMPLE 667

N-{4-[4-amino-7-(3-furyl)thieno[3,2-c]pyridin-3-yl]phenyl}-N'-(2-fluorophenyl)urea The desired product was prepared by substituting example 662 and 1-fluoro-2-isocyanatobenzene for example 121B and 1-fluoro-2-isocyanato-4-(trifluoromethyl)benzene in example 122. $^1$H NMR (300 MHz, DMSO-D$_6$) δ ppm 5.52 (s, 2H) 7.00–7.07 (m, 2H) 7.16 (t, J=7.80 Hz, 1H) 7.26 (dd, J=11.70, 7.97 Hz, 1H) 7.41 (d, J=8.48 Hz, 2H) 7.53 (s, 1H) 7.62 (d, J=8.81 Hz, 2H) 7.84 (t, J=1.70 Hz, 1H) 8.08–8.14 (m, 2H) 8.18 (t, J=8.31 Hz, 1H) 8.62 (d, J=2.37 Hz, 1H) 9.28 (s, 1H); MS (ESI(+)) m/e 445 (M+H)$^+$.

EXAMPLE 668

N-{4-[4-amino-7-(3-fluoropyridin-4-yl)thieno[3,2-c]pyridin-3-yl]phenyl}-N'-[2-fluoro-5-(trifluoromethyl)phenyl]urea

EXAMPLE 668A 3-(4-aminophenyl)-7-(3-fluoropyridin-4-yl)thieno[3,2-c]pyridin-4-amine The desired product was prepared by substituting 3-fluoro-4-pyridineboronic acid and example 77B for Example 1B and 4-phenoxyphenylboronic acid in example 10A,

EXAMPLE 668B

N-{4-[4-amino-7-(3-fluoropyridin-4-yl)thieno[3,2-c]pyridin-3-yl]phenyl}-N'-[2-fluoro-5-(trifluoromethyl)phenyl]urea The desired product was prepared by substituting example 668A for example 121B in example 122. $^1$H NMR (300 MHz, DMSO-D$_6$) δ ppm 5.79 (s, 2H) 7.38–7.42 (m, 1H) 7.45 (d, J=8.48 Hz, 2H) 7.51 (d, J=10.85 Hz, 1H) 7.54–7.56 (m, 1H) 7.64 (d, J=8.48 Hz, 2H) 7.74 (dd, J=6.61, 4.92 Hz, 1H) 7.98 (d, J=1.70 Hz, 1H) 8.57 (d, J=5.43 Hz, 1H) 8.64 (dd, J=7.12, 2.03 Hz, 1H) 8.74 (d, J=2.03 Hz, 1H) 8.98 (d, J=3.05 Hz, 1H) 9.39 (s, 1H). MS (ESI(+)) m/e 542 (M+H)$^+$.

EXAMPLE 669

N-(4-{4-amino-7-[3-(4-methylpiperazin-1-yl)prop-1-ynyl]thieno[3,2-c]pyridin-3-yl}phenyl)-N'-(2-fluoro-5-methylphenyl)urea The desired product was prepared by substituting example 557B and 1-fluoro-2-isocyanato-4-methylbenzene for example 121B and 1-fluoro-2-isocyanato-4-(trifluoromethyl)benzene in example 122. $^1$H NMR (300 MHz, DMSO-D$_6$) δ ppm 2.17 (s, 3H) 2.28 (s, 3H) 2.37 (s, 4H) 2.59 (s, 4H) 3.61 (s, 2H) 5.76 (s, 2H) 6.75–6.87 (m, 1H) 7.12 (dd, J=11.36, 8.31 Hz, 1H) 7.39 (d, J=8.48 Hz, 2H) 7.52 (s, 1H) 7.61 (d, J=8.48 Hz, 2H) 7.97 (s, 1H) 8.00 (d, J=6.10 Hz, 1H) 8.54 (s, 1H) 9.26 (s, 1H); MS (ESI(+)) m/e 529 (M+H)$^+$.

EXAMPLE 670

N-(4-{4-amino-7-[3-(4-methylpiperazin-1-yl)prop-1-ynyl]thieno[3,2-c]pyridin-3-yl}phenyl)-N'-[3-(trifluoromethyl)phenyl]urea The desired product was prepared by substituting example 557B and 1-isocyanato-3-(trifluoromethyl)benzene for example 121B and 1-fluoro-2-isocyanato-4-(trifluoromethyl)benzene in example 122. $^1$H NMR (500 MHz, DMSO-D$_6$) δ ppm 2.17 (s, 3H) 2.37 (s, 4H) 2.60 (s, 4H) 3.61 (s, 2H) 5.75 (s, 2H) 7.33 (d, J=7.49 Hz, 1H) 7.40 (d, J=8.42 Hz, 2H) 7.49–7.56 (m, 2H) 7.62 (t, J=8.73 Hz, 3H) 7.97 (s, 1H) 8.03 (s, 1H) 9.00 (s, 1H) 9.12 (s, 1H); MS (ESI(+)) m/e 565 (M+H)$^+$.

EXAMPLE 671

N-(4-{4-amino-7-[3-(4-methylpiperazin-1-yl)prop-1-ynyl]thieno[3,2-c]pyridin-3-yl}phenyl)-N'-[2-fluoro-5-(trifluoromethyl)phenyl]urea The desired product was prepared by substituting example 557B for example 121B in example 122. $^1$H NMR (300 MHz, DMSO-D$_6$) δ ppm 2.17 (s, 3H) 2.39 (s, 4H) 2.60 (s, 4H) 3.61 (s, 2H) 5.76 (s, 2H) 7.41 (d, J=8.48 Hz, 3H) 7.46–7.57 (m, 2H) 7.63 (d, J=8.82 Hz, 2H) 7.97 (s, 1H) 8.64 (dd, J=7.29, 2.20 Hz, 1H) 8.98 (s, 1H) 9.38 (s, 1H); MS (ESI(+)) m/e 583 (M+H)$^+$.

EXAMPLE 672

N-(4-{4-amino-7-[3-(4-methylpiperazin-1-yl)prop-1-ynyl]thieno[3,2-c]pyridin-3-yl}phenyl)-N'-(3-fluorophenyl)urea The desired product was prepared by substituting example 557B and 1-fluoro-3-isocyanatobenzene for example 121B and 1-fluoro-2-isocyanato-4-(trifluoromethyl)benzene in example 122. $^1$H NMR (300 MHz, DMSO-D$_6$) δ ppm 2.17 (s, 3H) 2.37 (s, 4H) 2.59 (s, 4H) 3.61 (s, 2H) 5.76 (s, 2H) 6.75–6.85 (m, 1H) 7.15 (d, J=7.12 Hz, 1H) 7.27–7.34 (m, 1H) 7.39 (d, J=8.48 Hz, 2H) 7.46–7.54 (m, 2H) 7.61 (d, J=8.82 Hz, 2H) 7.97 (s, 1H) 8.96 (s, 1H) 8.99 (s, 1H); MS (ESI(+)) m/e 515 (M+H)$^+$.

EXAMPLE 673

N-[4-(4-amino-7-{3-[(4-methylpiperazin-1-yl)methyl]phenyl}thieno[3,2-c]pyridin-3-yl)phenyl]-N'-(3-methylphenyl)urea

EXAMPLE 673A

[3-(4-amino-3-bromothieno[3,2-c]pyridin-7-yl)phenyl]methanol

The desired product was prepared by substituting example 21A and 3-hydroxymethylphenylboronic acid for example 77A and 4-pyridylboronic acid in example 121A. MS (ESI (+) m/e 334.7, 336.7 (M+H)$^+$.

EXAMPLE 673B 3-bromo-7-[3-(chloromethyl)phenyl]thieno[3,2-c]pyridin-4-amine

A solution of example 673A (550 mg, 1.64 mmol) in CHCl$_3$ (5 mL) was treated with SOCl$_2$ (5 mL), stirred at room temperature for 3 hours then concentrated to give the title compound. MS (ESI (+)) m/e 352.7, 354.7 (M+H)$^+$.

EXAMPLE 673C 3-bromo-7-{3-[(4-methylpiperazin-1-yl)methyl]phenyl}thieno[3,2-c]pyridin-4-amine A solution of example 673B (200 mg, 0.5 mmol) in DMF (2.5 mL) was treated with N-methylpiperazine (0.3 mL, 2.7 mmol) and K$_2$CO$_3$ (350 mg, 2.5 mmol), heated at 70° C. for 1 hour, allowed to cool to room temperature, and partitioned between water and CH$_2$Cl$_2$. The organic extract was dried (Na$_2$SO$_4$), filtered, and the filtrate was concentrated under reduced pressure. The residue was purified via silica gel chromatography eluting with 10% MeOH in CH$_2$Cl$_2$: 0.1% NH$_4$OH to give 135 mg of the title compound (63% yield). MS (ESI (+)) m/e 416.8, 418.8 (M+H)$^+$.

EXAMPLE 673D

N-[4-(4-amino-7-{3-[(4-methylpiperazin-1-yl)methyl]phenyl}thieno[3,2-c]pyridin-3-yl)phenyl]-N'-(3-methylphenyl)urea The desired product was prepared by substituting example 673C and 66D for 77A and 4-pyridylboronic acid in example 121A. $^1$H NMR (300 MHz, DMSO-D$_6$) δ ppm 2.29 (s, 3H), 2.38–2.51 (m, 2H), 2.80 (s, 3H), 2.97–3.14 (m, 4H), 3.34–3.48 (m, 2H), 3.77 (s, 2H), 6.81 (d, J=7.1 Hz, 1H), 7.17 (t, J=7.8 Hz, 1H), 7.28 (d, J=8.5 Hz, 1H), 7.33 (s, 1H), 7.46 (d, J=8.8 Hz, 2H), 7.49 (d, J=8.8 Hz, 1H), 7.59 (t, J=7.5 Hz, 1H), 7.63–7.74 (m, 4H), 7.88 (s, 1H), 7.98 (s, 1H), 8.90 (s, 1H), 9.17 (s, 1H) MS (ESI(+)) m/e 563.0 (M+H)$^+$.

EXAMPLE 674

N-(4-{4-amino-7-[3-(pyrrolidin-1-ylmethyl)phenyl]thieno[3,2-c]pyridin-3-yl}phenyl)-N'-(3-methylphenyl)urea The desired product was prepared using the procedures described in examples 673C and 673D substituting pyrrolidine for N-methylpiperazine in example 673C. $^1$H NMR (400 MHz, DMSO-D$_6$) δ ppm 2.11 (dd, J=6.3, 5.1 Hz, 2H), 2.23–2.31 (m, 2H), 2.49 (s, 3H), 3.32–3.42 (m, 2H), 3.61–3.70 (m, 2H), 4.67 (s, 2H), 7.01 (d, J=7.4 Hz, 1H), 7.37 (t, J=7.8 Hz, 1H), 7.48 (d, J=8.3 Hz, 1H), 7.54 (s, 1H), 7.65 (d, J=8.6 Hz, 2H), 7.83–7.93 (m, 4H), 8.01 (dt, J=6.8, 1.8 Hz, 1H), 8.06–8.07 (m, 2H), 8.20 (s, 1H), 9.23 (s, 1H), 9.50 (s, 1H) MS (ESI(+)) m/e 534.0 (M+H)$^+$.

EXAMPLE 675

N-[4-(4-amino-7-{3-[(diethylamino)methyl]phenyl}thieno[3,2-c]pyridin-3-yl)phenyl]-N'-(3-methylphenyl)urea The desired product was prepared using the procedures described in examples 673C and 673D substituting diethylamine for N-methylpiperazine in example 673C. $^1$H NMR (400 MHz, DMSO-D$_6$) δ ppm 1.47 (t, J=7.2 Hz, 6H), 2.49 (s, 3H), 3.32–3.40 (m, 4H), 4.63 (d, J=4.0 Hz, 2H), 7.01 (d, J=7.7 Hz, 1H), 7.04–7.24 (m, 2H), 7.37 (t, J=7.8 Hz, 1H), 7.54 (s, 1H), 7.65 (d, J=8.3 Hz, 2H), 7.86–7.93 (m, 4H), 8.01–8.08 (m, 3H), 8.19 (s, 1H), 9.17 (s, 1H), 9.44 (s, 1H), 9.79 (s, 1H) MS (ESI(+)) m/e 536.0 (M+H)$^+$.

EXAMPLE 676

N-[4-(4-amino-7-{4-[(4-methylpiperazin-1-yl)methyl]phenyl}thieno[3,2-c]pyridin-3-yl)phenyl]-N'-(3-methylphenyl)urea The desired product was prepared using the procedures described in examples 673A through 673D substituting 4-hydroxymethylphenylboronic acid for 3-hydroxymethylphenylboronic acid in example 673A. $^1$H NMR (400 MHz, DMSO-D$_6$) δ ppm 2.16 (s, 3H), 2.29 (s, 3H), 2.31–2.45 (m, 8H), 3.52 (s, 2H), 5.51 (s, 2H), 6.81 (d, J=7.7 Hz, 1H), 7.17 (t, J=7.7 Hz, 1H), 7.26 (d, J=8.3 Hz, 1H), 7.32 (s, 1H), 7.40 (d, J=8.6 Hz, 2H), 7.43 (d, J=8.3 Hz, 2H), 7.47 (s, 1H), 7.60–7.63 (m, 4H), 7.90 (s, 1H), 8.66 (s, 1H), 8.86 (s, 1H) MS (ESI(+)) m/e 501.5 (M+H)$^+$.

EXAMPLE 677

N-[4-(4-amino-7-{4-[(diethylamino)methyl]phenyl}thieno[3,2-c]pyridin-3-yl)phenyl]-N'-(3-methylphenyl)urea The desired product was prepared using the procedures described in examples 673A through 673D substituting 4-hydroxymethylphenylboronic acid for 3-hydroxymethylphenylboronic acid in example 673A and substituting diethylamine for N-methylpiperazine in examples 673C. $^1$H NMR (300 MHz, DMSO-D$_6$) δ ppm 1.02 (t, J=7.1 Hz, 6H), 2.29 (s, 3H), 2.51 (q, J=7.1 Hz, 4H), 3.59 (s, 2H), 5.51 (s, 2H), 6.81 (d, J=7.8 Hz, 1H), 7.17 (t, J=7.6 Hz, 1H), 7.26 (d, J=8.5 Hz, 1H), 7.32 (s, 1H), 7.40 (d, J=8.8 Hz, 2H), 7.45 (d, J=8.1 Hz, 2H), 7.47 (s, 1H), 7.59–7.64 (m, 4H), 7.90 (s, 1H), 8.68 (s, 1H), 8.88 (s, 1H) MS (ESI(+)) m/e 536.3 (M+H)$^+$.

EXAMPLE 678

N-(4-{4-amino-7-[4-(pyrrolidin-1-ylmethyl)phenyl]thieno[3,2-c]pyridin-3-yl}phenyl)-N'-(3-methylphenyl)urea The desired product was prepared using the procedures described in examples 673A through 673D substituting 4-hydroxymethylphenylboronic acid for 3-hydroxymethylphenylboronic acid in example 673A and substituting pyrrolidine for N-methylpiperazine in examples 673C. $^1$H NMR (300 MHz, DMSO-D$_6$) δ ppm 1.72 (s, 4H), 2.29 (s, 3H), 3.64 (s, 2H), 5.52 (s, 2H), 6.81 (d, J=7.5 Hz, 1H), 7.17 (t, J=8.0 Hz, 1H), 7.26 (d, J=8.1 Hz, 1H), 7.32 (s, 1H), 7.40 (d, J=8.5 Hz, 2H), 7.44 (d, J=8.1 Hz, 2H), 7.47 (s, 1H), 7.59–7.64 (m, 4H), 7.90 (s, 1H), 8.67 (s, 1H), 8.86 (s, 1H) MS (ESI(+)) m/e 534.0 (M+H)$^+$.

EXAMPLE 679

N-(4-{4-amino-3-[4-({[(3-methylphenyl)amino]carbonyl}amino)phenyl]thieno[3,2-c]pyridin-7-yl}phenyl)-3-piperidin-1-ylpropanamide The desired product was prepared by substituting 3-piperidin-1-ylpropionic acid and example 460 for example 11B and 2-piperazinone in example 11C. $^1$H NMR (300 MHz, DMSO-D$_6$) δ ppm 1.38–1.43 (m, 2H), 1.49–1.57 (m, 4H), 2.29 (s, 3H), 2.36–2.45 (m, 4H), 2.62 (t, J=7.0 Hz, 2H), 5.50 (s, 2H), 6.81 (d, J=7.1 Hz, 1H), 7.17 (t, J=7.6 Hz, 1H), 7.26 (d, J=8.1 Hz, 1H), 7.32 (s, 1H), 7.40 (d, J=8.5 Hz, 2H), 7.47 (s, 1H), 7.59 (d, J=8.8 Hz, 2H), 7.61 (d, J=8.5 Hz, 2H), 7.72 (d, J=8.5 Hz, 2H), 7.87 (s, 1H), 8.67 (s, 1H), 8.86 (s, 1H), 10.31 (s, 1H) MS (ESI(+)) m/e 605.1 (M+H)$^+$.

EXAMPLE 680

N-(4-{4-amino-3-[4-({[(3-methylphenyl)amino]carbonyl}amino)phenyl]thieno[3,2-c]pyridin-7-yl}phenyl)-4-(dimethylamino)butanamide The desired product was prepared by substituting 4-dimethylaminobutyric acid and example 460 for example 11B and 2-piperazinone in example 11C. $^1$H NMR (300 MHz, DMSO-D$_6$) δ ppm 1.73–1.84 (m, 2H), 2.29 (s, 9H), 2.35–2.46 (m, 4H), 5.50 (s, 2H), 6.81 (d, J=7.8 Hz, 1H), 7.17 (t, J=7.6 Hz, 1H), 7.26 (d, J=8.8 Hz, 1H), 7.32 (s, 1H), 7.39 (d, J=8.5 Hz, 2H), 7.47 (s, 1H), 7.57–7.63 (m, 4H), 7.73 (d, J=8.8 Hz, 2H), 7.87 (s, 1H), 8.69 (s, 1H), 8.89 (s, 1H), 10.06 (s, 1H) MS (ESI(+)) m/e 579.0 (M+H)$^+$.

EXAMPLE 681

N-(4-{4-amino-3-[4-({[(3-methylphenyl)amino]carbonyl}amino)phenyl]thieno[3,2-c]pyridin-7-yl}phenyl)-2-(dimethylamino)acetamide The desired product was prepared by substituting dimethylaminoacetic acid and example 460 for example 11B and 2-piperazinone in example 11C. $^1$H NMR (300 MHz, DMSO-D$_6$) δ ppm 2.29 (s, 3H), 2.30 (s, 6H), 3.11 (s, 2H), 5.50 (s, 2H), 6.81 (d, J=7.1 Hz, 1H), 7.17 (t, J=7.8 Hz, 1H), 7.26 (d, J=7.8 Hz, 1H), 7.32 (s, 1H), 7.40 (d, J=8.5 Hz, 2H), 7.48 (s, 1H), 7.56–7.66 (m, 4H), 7.81 (d, J=8.5 Hz, 2H), 7.88 (s, 1H), 8.68 (s, 1H), 8.88 (s, 1H), 9.85 (s, 1H) MS (ESI(+)) m/e 551.0 (M+H)$^+$.

EXAMPLE 682

N-(4-{4-amino-3-[4-({[(3-methylphenyl)amino]carbonyl}amino)phenyl]thieno[3,2-c]pyridin-7-yl}phenyl)-3-(dimethylamino)propanamide The desired product was prepared by substituting 3-dimethylaminopropanoic acid and example 460 for example 11B and 2-piperazinone in example 11C. $^1$H NMR (300 MHz, DMSO-D$_6$) δ ppm 2.21 (s, 6H), 2.29 (s, 3H), 2.46–2.52 (m, 2H), 2.61 (t, J=7.0 Hz, 2H), 5.50 (s, 2H), 6.81 (d, J=7.5 Hz, 1H), 7.17 (t, J=7.8 Hz, 1H), 7.22–7.29 (m, J=8.5 Hz, 1H), 7.32 (s, 1H), 7.39 (d, J=8.8 Hz, 2H), 7.47 (s, 1H), 7.57–7.63 (m, 4H), 7.72 (d, J=8.5 Hz, 2H), 7.87 (s, 1H), 8.67 (s, 1H), 8.87 (s, 1H), 10.17 (s, 1H) MS (ESI(+)) m/e 565.0 (M+H)$^+$.

EXAMPLE 683

N-(3-{4-amino-3-[4-({[(3-methylphenyl)amino]carbonyl}amino)phenyl]thieno[3,2-c]pyridin-7-yl}phenyl)-3-piperidin-1-ylpropanamide The desired product was prepared by substituting 3-piperidin-1-ylpropionic acid and example 461 for example 11B and 2-piperazinone in example 11C. $^1$H NMR (300 MHz, DMSO-D$_6$) δ ppm 1.36–1.43 (m, 2H), 1.47–1.56 (m, 4H), 2.29 (s, 3H), 2.37–2.43 (m, 4H), 2.46–2.50 (m, 2H), 2.61 (t, J=6.6 Hz, 2H), 5.55 (s, 2H), 6.81 (d, J=7.5 Hz, 1H), 7.17 (t, J=7.8 Hz, 1H), 7.26 (d, J=8.8 Hz, 1H), 7.30–7.34 (m, 2H), 7.40 (d, J=8.5 Hz, 2H), 7.44 (t, J=7.8 Hz, 1H), 7.49 (s, 1H), 7.57–7.63 (m, 3H), 7.88 (s, 1H), 7.97 (s, 1H), 8.67 (s, 1H), 8.87 (s, 1H), 10.34 (s, 1H) MS (ESI(+)) m/e 605.1 (M+H)$^+$.

EXAMPLE 684

N-(3-{4-amino-3-[4-({[(3-methylphenyl)amino]carbonyl}amino)phenyl]thieno[3,2-c]pyridin-7-yl}phenyl)-2-(dimethylamino)acetamide The desired product was prepared by substituting dimethylaminoacetic acid and example 461 for example 11B and 2-piperazinone in example 11C. $^1$H NMR (300 MHz, DMSO-D$_6$) δ ppm 2.29 (s, 3H), 2.30 (s, 6H), 3.10 (s, 2H), 5.55 (s, 2H), 6.81 (d, J=7.5 Hz, 1H), 7.17 (t, J=7.6 Hz, 1H), 7.23–7.28 (m, 1H), 7.32 (s, 1H), 7.35 (ddd, J=7.9, 1.4, 1.2 Hz, 1H), 7.38–7.47 (m, 3H), 7.48 (s, 1H), 7.61 (d, J=8.8 Hz, 2H), 7.67 (ddd, J=8.1, 2.0, 1.4 Hz, 1H), 7.89 (s, 1H), 8.05 (t, J=1.7 Hz, 1H), 8.67 (s, 1H), 8.87 (s, 1H), 9.85 (s, 1H) MS (ESI(+)) m/e 551.0 (M+H)$^+$.

EXAMPLE 685

N-(3-{4-amino-3-[4-({[(3-methylphenyl)amino]carbonyl}amino)phenyl]thieno[3,2-c]pyridin-7-yl}phenyl)-3-(dimethylamino)propanamide The desired product was prepared by substituting 3-dimethylaminopropanoic acid and example 461 for example 11B and 2-piperazinone in example 11C. $^1$H NMR (300 MHz, DMSO-D$_6$) δ ppm 2.23 (s, 6H), 2.29 (s, 3H), 2.49–2.53 (m, 2H), 2.64 (t, J=7.0 Hz, 2H), 5.55 (s, 2H), 6.81 (d, J=7.1 Hz, 1H), 7.17 (t, J=7.8 Hz, 1H), 7.26 (d, J=8.5 Hz, 1H), 7.30–7.35 (m, 2H), 7.37–7.47 (m, 3H), 7.49 (s, 1H), 7.58–7.64 (m, 3H), 7.88 (s, 1H), 7.98 (t, J=1.7 Hz, 1H), 8.69 (s, 1H), 8.89 (s, 1H), 10.19 (s, 1H) MS (ESI(+)) m/e 565.0 (M+H)$^+$.

EXAMPLE 686

N-(3-{4-amino-3-[4-({[(3-methylphenyl)amino]carbonyl}amino)phenyl]thieno[3,2-c]pyridin-7-yl}phenyl)-4-(dimethylamino)butanamide The desired product was prepared by substituting 4-dimethylaminobutyric acid and example 461 for example 11B and 2-piperazinone in example 11C. $^1$H NMR (300 MHz, DMSO-D$_6$) δ ppm 1.76–1.87 (m, 2H), 2.29 (s, 3H), 2.38 (s, 6H), 2.38–2.43 (m, 2H), 2.54–2.60 (m, 2H), 5.55 (s, 2H), 6.81 (d, J=7.5 Hz, 1H), 7.17 (t, J=7.8 Hz, 1H), 7.26 (d, J=8.5 Hz, 1H), 7.30–7.34 (m, 2H), 7.40 (d, J=8.5 Hz, 2H), 7.43 (t, J=7.8 Hz, 1H), 7.49 (s, 1H), 7.58–7.64 (m, 3H), 7.87 (s, 1H), 8.00 (t, J=1.9 Hz, 1H), 8.77 (s, 1H), 8.98 (s, 1H), 10.09 (s, 1H) MS (ESI(+)) m/e 579.0 (M+H)$^+$.

EXAMPLE 687

N-{4-[4-amino-7-(2-methyl-1,3-benzothiazol-5-yl)thieno[3,2-c]pyridin-3-yl]phenyl}-N'-(3-chlorophenyl)urea

EXAMPLE 687A 3-(4-aminophenyl)-7-(2-methyl-1,3-benzothiazol-5-yl)thieno[3,2-c]pyridin-4-amine The desired product was prepared by substituting 2-methyl-5-(4,4,5,5-tetramethyl-[1,3,2]dioxaborolan-2-yl)benzothiazole and example 77B for 4-phenoxyphenylboronic acid and example 1B in example 10A. MS (ESI(+) m/e 389 (M+H)$^+$.

EXAMPLE 687B

N-{4-[4-amino-7-(2-methyl-1,3-benzothiazol-5-yl)thieno[3,2-c]pyridin-3-yl]phenyl}-N'-(3-chlorophenyl)urea The desired product was prepared by substituting example 687A and 1-chloro-3-isocyanatobenzene for example 121B and 1-fluoro-2-isocyanato-4-(trifluoromethyl)benzene in example 122. $^1$H NMR (300 MHz, DMSO-D$_6$) δ ppm 2.85 (s, 3H) 5.57 (s, 2H) 7.01–7.06 (m, 1H) 7.29–7.33 (m, 2H) 7.43 (d, J=8.48 Hz, 2H) 7.50 (s, 1H) 7.63 (d, J=8.81 Hz, 2H) 7.69 (dd, J=8.48, 1.70 Hz, 1H) 7.72–7.75 (m, 1H) 7.99 (s, 1H) 8.17 (dd, J=4.92, 2.88 Hz, 2H) 8.97 (s, 2H); MS (ESI(+)) m/e 542 (M+H)$^+$.

EXAMPLE 688

N-{4-[4-amino-7-(2-methyl-1,3-benzothiazol-5-yl)thieno[3,2-c]pyridin-3-yl]phenyl}-N'-(3-fluorophenyl)urea The desired product was prepared by substituting example 687A and 1-fluoro-3-isocyanatobenzene for example 121B and 1-fluoro-2-isocyanato-4-(trifluoromethyl)benzene in example 122. $^1$H NMR (300 MHz, DMSO-D$_6$) δ ppm 2.85 (s, 3H) 5.57 (s, 2H) 6.76–6.85 (m, 1H) 7.16 (dd, J=8.31, 1.86 Hz, 1H) 7.28–7.37 (m, 1H) 7.43 (d, J=8.48 Hz, 2H) 7.49–7.56 (m, 2H) 7.63 (d, J=8.82 Hz, 2H) 7.69 (dd, J=8.48, 1.70 Hz, 1H) 7.99 (s, 1H) 8.17 (dd, J=5.09, 2.71 Hz, 2H) 8.96 (s, 1H) 8.99 (s, 1H); MS (ESI(+)) m/e 526 (M+H)$^+$.

EXAMPLE 689

N-{4-[4-amino-7-(2-methyl-1,3-benzothiazol-5-yl)thieno[3,2-c]pyridin-3-yl]phenyl}-N'-(2-fluoro-5-methylphenyl)urea The desired product was prepared by substituting example 687A and 1-fluoro-2-isocyanato-4-methylbenzene for example 121B and 1-fluoro-2-isocyanato-4-(trifluoromethyl)benzene in example 122. $^1$H NMR (300 MHz, DMSO-D$_6$) δ ppm 2.29 (s, 3H) 2.85 (s, 3H) 5.57 (s, 2H) 6.76–6.87 (m, 1H) 7.12 (dd, J=11.19, 8.48 Hz, 1H) 7.43 (d, J=8.14 Hz, 2H) 7.50 (s, 1H) 7.62 (d, J=8.48 Hz, 2H) 7.69 (d, J=7.46 Hz, 1H) 7.96–8.04 (m, 2H) 8.13–8.21 (m, 2H) 8.56 (s, 1H) 9.27 (s, 1H); ); MS (ESI(+)) m/e 540 (M+H)$^+$.

EXAMPLE 690

N-(3-{4-amino-3-[4-({[(3-methylphenyl)amino]carbonyl}amino)phenyl]thieno[3,2-c]pyridin-7-yl}prop-2-ynyl)-2-methylpropanamide The desired product was prepared by substituting example 77B and 2-methyl-N-prop-2-ynylpropanamide for example 144A and 3-butyn-1-ol in example 144B. $^1$H NMR (300 MHz, DMSO-D$_6$) δ ppm 1.04 (d, J=6.78 Hz, 6H) 2.28 (s, 3H) 2.37–2.47 (m, 1H) 4.19 (d, J=5.43 Hz, 2H) 5.77 (s, 2H) 6.80 (d, J=7.80 Hz, 1H) 7.16 (t, J=7.63 Hz, 1H), 7.22–7.28 (m, 1H) 7.32 (s, 1H) 7.37 (d, J=8.48 Hz, 2H) 7.51 (s, 1H) 7.60 (d, J=8.48 Hz, 2H) 7.96 (s, 1H) 8.33 (t, J=5.43 Hz, 1H) 8.69 (s, 1H) 8.90 (s, 1H); MS (ESI(+)) m/e 498 (M+H)$^+$.

EXAMPLE 691

N-{4-[4-amino-7-(3-morpholin-4-ylprop-1-ynyl)thieno[3,2-c]pyridin-3-yl]phenyl}-N'-(3-methylphenyl)urea The desired product was prepared by substituting example 77B and 4-prop-2-ynylmorpholine for example 144A and 3-butyn-1-ol in example 144B. $^1$H NMR (300 MHz, DMSO-D$_6$) δ ppm 2.29 (s, 3H) 2.51 (s, 4H) 3.65 (s, 6H) 5.77 (s, 2H) 6.81 (d, J=7.12 Hz, 1H) 7.17 (t, J=7.63 Hz, 1H) 7.22–7.29 (m, 1H) 7.31 (s, 1H) 7.37 (d, J=8.48 Hz, 2H) 7.51 (s, 1H) 7.60 (d, J=8.48 Hz, 2H) 7.98 (s, 1H) 8.65 (s, 1H) 8.86 (s, 1H); MS (ESI(+)) m/e 498 (M+H)$^+$.

EXAMPLE 692

N-(4-{4-amino-7-[3-(cyclopropylmethoxy)prop-1-ynyl]thieno[3,2-c]pyridin-3-yl}phenyl)-N'-(3-methylphenyl)urea The desired product was prepared by substituting example 77B and [(prop-2-ynyloxy)methyl]cyclopropane for example 144A and 3-butyn-1-ol in example 144B. $^1$H NMR (300 MHz, DMSO-D$_6$) δ ppm 0.18–0.29 (m, 2H) 0.45–0.58 (m, 2H) 0.97–1.14 (m, 1H) 2.29 (s, 3H) 3.41 (d, J=6.78 Hz, 2H) 4.47 (s, 2H) 5.81 (s, 2H) 6.81 (d, J=7.46 Hz, 1H) 7.17 (t, J=7.80 Hz, 1H) 7.22–7.28 (m, 1H) 7.31 (s, 1H) 7.38 (d, J=8.48 Hz, 2H) 7.52 (s, 1H) 7.60 (d, J=8.48 Hz, 2H) 8.00 (s, 1H) 8.66 (s, 1H) 8.86 (s, 1H); MS (ESI(+)) m/e 483 (M+H)$^+$.

EXAMPLE 693

N-{4-[4-amino-7-(phenylethynyl)thieno[3,2-c]pyridin-3-yl]phenyl}-N'-(3-methylphenyl)urea The desired product was prepared by substituting example 77B and ethynylbenzene for example 144A and 3-butyn-1-ol in example 144B. $^1$H NMR (300 MHz, DMSO-D$_6$) δ ppm 2.29 (s, 3H) 5.87 (s, 2H) 6.81 (d, J=7.46 Hz, 1H) 7.17 (t, J=7.80 Hz, 1H) 7.22–7.29 (m, 1H) 7.32 (s, 1H) 7.40 (d, J=8.48 Hz, 2H) 7.45 (d, J=7.46 Hz, 3H) 7.54–7.58 (m, 2H) 7.62 (d, J=8.48 Hz, 3H) 8.11 (s, 1H) 8.66 (s, 1H) 8.87 (s, 1H); MS (ESI(+)) m/e 475 (M+H)$^+$.

EXAMPLE 694

N'-[4-(4-aminothieno[3,2-c]pyridin-3-yl)phenyl]-N-methyl-N-(3-methylphenyl)urea

Example 17A (100 mg, 0.41 mmol) in THF (3 mL) was treated with Et$_3$N (0.064 mL, 0.45 mmol) and 4-nitrophenylchloroformate (95 mg, 0.45 mmol) at 0° C. After stirring at 0° C. for 45 minutes, the mixture was treated with N-methyl toluidine (0.062 mL, 0.5 mmol) and heated to reflux for 1 hour. The mixture was cooled to room temperature, concentrated under reduced pressure and the residue was purified via silica gel chromatography eluting with 2 to 5% MeOH in CH$_2$Cl$_2$ to give 28 mg of the title compound. $^1$H NMR (300 MHz, DMSO-D$_6$) δ ppm 2.34 (s, 3H) 3.27 (s, 3H) 5.41 (s, 2H) 6.93 (d, J=9.16 Hz, 1H) 7.11 (dd, J=13.73, 7.63 Hz, 1H) 7.18 (s, 1H) 7.24 (d, J=5.43 Hz, 1H) 7.31 (d, J=8.48 Hz, 2H) 7.39 (s, 1H) 7.58 (d, J=8.48 Hz, 2H) 7.82 (d, J=5.43 Hz, 1H) 8.12 (d, J=9.16 Hz, 1H) 8.28 (s, 1H); MS (ESI(+)) m/e 389 (M+H)$^+$.

EXAMPLE 695

N-{4-[4-amino-7-(pyridin-4-ylethynyl)thieno[3,2-c]pyridin-3-yl]phenyl}-N'-[2-fluoro-5-(trifluoromethyl)phenyl]urea

EXAMPLE 695A 3-(4-aminophenyl)-7-(pyridin-4-ylethynyl)thieno[3,2-c]pyridin-4-amine The desired product was prepared by substituting example 77B and 4-ethynylpyridine for example 144A and 3-butyn-1-ol in example 144B. MS (ESI(+)) m/e 343 (M+H)$^+$.

EXAMPLE 695B

N-{4-[4-amino-7-(pyridin-4-ylethynyl)thieno[3,2-c]pyridin-3-yl]phenyl}-N'-[2-fluoro-5-(trifluoromethyl)phenyl]urea The desired product was prepared by substituting example 695A for example 121B in example 122. $^1$H NMR (300 MHz, DMSO-D$_6$) δ ppm 6.00 (s, 2H) 7.44 (d, J=8.48 Hz, 3H) 7.53 (d, J=4.41 Hz, 3H) 7.60 (s, 1H) 7.64 (d, J=8.82 Hz, 2H) 8.19 (s, 1H) 8.64 (d, J=6.10 Hz, 3H) 8.98 (d, J=2.37 Hz, 1H) 9.39 (s, 1H); MS (ESI(+)) m/e 548 (M+H)$^+$.

EXAMPLE 696

N-{4-[4-amino-7-(pyridin-4-ylethynyl)thieno[3,2-c]pyridin-3-yl]phenyl}-N'-(2-fluoro-5-methylphenyl)urea The desired product was prepared by substituting example 695A and 1-fluoro-2-isocyanato-4-methylbenzene for example 121B and 1-fluoro-2-isocyanato-4-(trifluoromethyl)benzene in example 122. $^1$H NMR (300 MHz, DMSO-D$_6$) δ ppm 2.28 (s, 3H) 6.00 (s, 2H) 6.78–6.86 (m, 1H) 7.12 (dd, J=11.36, 8.31 Hz, 1H) 7.42 (d, J=8.48 Hz, 2H) 7.53 (d, J=6.10 Hz, 2H) 7.60 (d, J=4.41 Hz, 2H) 7.63 (s, 1H) 8.00 (d, J=7.80 Hz, 1H) 8.18 (s, 1H) 8.55 (d, J=2.37 Hz, 1H) 8.64 (d, J=5.76 Hz, 2H) 9.27 (s, 1H); MS (ESI(+)) m/e 494 (M+H)$^+$.

EXAMPLE 697

N-{4-[4-amino-7-(pyridin-4-ylethynyl)thieno[3,2-c]pyridin-3-yl]phenyl}-N'-(3-chlorophenyl)urea The desired product was prepared by substituting example 695A and 1-chloro-3-isocyanatobenzene for example 121B and 1-fluoro-2-isocyanato-4-(trifluoromethyl)benzene in example 122. $^1$H NMR (300 MHz, DMSO-D$_6$) δ ppm 6.01 (s, 2H) 7.00–7.07 (m, 1H) 7.29–7.33 (m, 2H) 7.42 (d, J=8.48 Hz, 2H) 7.53 (d, J=4.41 Hz, 2H) 7.60 (d, J=6.10 Hz, 2H) 7.64 (s, 1H) 7.73 (s, 1H) 8.18 (s, 1H) 8.64 (d, J=6.10 Hz, 2H) 8.98 (d, J=2.71 Hz, 2H); MS (ESI(+)) m/e 496 (M+H)$^+$.

EXAMPLE 698

N-{4-[4-amino-7-(pyridin-4-ylethynyl)thieno[3,2-c]pyridin-3-yl]phenyl}-N'-[3-(trifluoromethyl)phenyl]urea The desired product was prepared by substituting example 695A and 1-isocyanato-3-trifluoromethyl-benzene for example 121B and 1-fluoro-2-isocyanato-4-(trifluoromethyl)benzene in example 122. $^1$H NMR (300 MHz, DMSO-D$_6$) δ ppm 6.01 (s, 2H) 7.33 (d, J=7.46 Hz, 1H) 7.42 (d, J=8.48 Hz, 2H) 7.49–7.57 (m, 3H) 7.59 (s, 2H) 7.62–7.67 (m, 2H) 8.04 (s, 1H) 8.18 (s, 1H) 8.64 (d, J=5.76 Hz, 2H) 9.03 (s, 1H) 9.13 (s, 1H); MS (ESI(+)) m/e 530 (M+H)$^+$.

EXAMPLE 699

N-[4-(4-aminothieno[3,2-c]pyridin-3-yl)phenyl]-N'-(3-methylphenyl)thiourea

Example 17A (116 mg, 0.48 mmol) in DMF (3 mL) at –30° C. was treated with 1-isothiocyanato-3-methylbenzene (0.071 mL, 0.51 mmol), stirred at –30° C. for 15 minutes, and allowed to warm up to room temperature. The mixture was concentrated under reduced pressure and the residue was purified via silica gel chromatography eluting with 3% MeOH in CH$_2$Cl$_2$ to give 119 mg of the title compound. $^1$H NMR (300 MHz, DMSO-D$_6$) δ ppm 2.30 (s, 3H) 5.46 (s, 2H) 6.97 (d, J=7.12 Hz, 1H) 7.18–7.24 (m, 1H) 7.26 (d, J=5.76 Hz, 2H) 7.29 (s, 1H) 7.41 (d, J=8.48 Hz, 2H) 7.45 (s, 1H) 7.62 (d, J=8.48 Hz, 2H) 7.83 (d, J=5.76 Hz, 1H) 9.83 (s, 1H) 9.92 (s, 1H); (ESI(+)) m/e 391 (M+H)$^+$.

EXAMPLE 700

N-[4-(4-amino-2-methylthieno[3,2-c]pyridin-3-yl)phenyl]-N'-(2-fluoro-5-methylphenyl)urea

EXAMPLE 700A 3-(4-aminophenyl)-2-methylthieno[3,2-c]pyridin-4-amine

The desired product was prepared by substituting example 67A and 4-(4,4,5,5-tetramethyl-[1,3,2]dioxaborolan-2-yl)phenylamine for example 1B and 4-phenoxyphenylboronic acid in example 10A. $^1$H NMR (300 MHz, DMSO-D$_6$) δ ppm 2.24 (s, 3H) 5.21–5.46 (m, 4H) 6.69 (d, J=8.48 Hz, 2H) 6.98 (d, J=8.48 Hz, 2H) 7.13 (d, J=5.76 Hz, 1H) 7.71 (d, J=5.43 Hz, 1H).

EXAMPLE 700B

N-[4-(4-amino-2-methylthieno[3,2-c]pyridin-3-yl)phenyl]-N'-(2-fluoro-5-methylphenyl)urea The desired product was prepared by substituting example 700A and 1-fluoro-2-isocyanato-4-methylbenzene for example 121B and 1-fluoro-2-isocyanato-4-(trifluoromethyl)benzene in example 122. $^1$H NMR (300 MHz, DMSO-D$_6$) δ ppm 2.27 (d, J=6.44 Hz, 6H) 5.17 (s, 2H) 6.77–6.87 (m, 1H) 7.07–7.14 (m, 1H) 7.16 (d, J=5.76 Hz, 1H) 7.29 (d, J=8.48 Hz, 2H) 7.62 (d, J=8.48 Hz, 2H) 7.75 (d, J=5.43 Hz, 1H) 8.00 (dd, J=7.80, 1.70 Hz, 1H) 8.55 (d, J=2.37 Hz, 1H) 9.26 (s, 1H); MS (ESI(+)) m/e 407 (M+H)$^+$.

EXAMPLE 701

N-[4-(4-amino-2-methylthieno[3,2-c]pyridin-3-yl)phenyl]-N'-[2-fluoro-5-(trifluoromethyl)phenyl]urea The desired product was prepared by substituting example 700A for example 121B in example 122. $^1$H NMR (300 MHz, DMSO-D$_6$) δ ppm 2.26 (s, 3H) 5.16 (s, 2H) 7.16 (d, J=5.42 Hz, 1H) 7.31 (d, J=8.48 Hz, 2H) 7.37–7.45 (m, 1H) 7.46–7.58 (m, 1H) 7.64 (d, J=8.48 Hz, 2H) 7.76 (d, J=5.76 Hz, 1H) 8.64 (d, J=9.49 Hz, 1H) 8.98 (d, J=2.71 Hz, 1H) 9.38 (s, 1H); MS (ESI(+)) m/e 461 (M+H)$^+$.

EXAMPLE 702

N-[4-(4-amino-2-methylthieno[3,2-c]pyridin-3-yl)phenyl]-N'-[3-(trifluoromethyl)phenyl]urea The desired product was prepared by substituting example 700A and 1-isocyanato-3-trifluoromethylbenzene for example 121B and 1-fluoro-2-isocyanato-4-(trifluoromethyl)benzene in example 122. $^1$H NMR (300 MHz, DMSO-D$_6$) δ ppm 2.26 (s, 3H) 5.18 (s, 2H) 7.16 (d, J=5.43 Hz, 1H) 7.31 (t, J=8.82 Hz, 3H) 7.56 (s, 1H) 7.63 (t, J=9.16 Hz, 3H) 7.75 (d, J=5.43 Hz, 1H) 8.04 (s, 1H) 9.01 (s, 1H) 9.13 (s, 1H); MS (ESI(+)) m/e 443 (M+H)$^+$.

EXAMPLE 703

N-{4-[4-amino-7-(1H-pyrazol-4-yl)thieno[3,2-c]pyridin-3-yl]phenyl}-N'-(3-methylphenyl)urea The desired product was prepared by substituting 4-(4,4,5,5-tetramethyl[1,3,2]dioxaborolan-2-yl)-1H-pyrazole and example 144A for 4-phenoxyphenylboronic acid and example 1B in example 10A. $^1$H NMR (300 MHz, DMSO-D$_6$) δ ppm 2.29 (s, 3H) 5.42 (s, 2H) 6.81 (d, J=7.46 Hz, 1H) 7.17 (t, J=7.80 Hz, 1H) 7.21–7.29 (m, 1H) 7.32 (s, 1H) 7.39 (d, J=8.48 Hz, 2H) 7.49 (s, 1H) 7.61 (d, J=8.48 Hz, 2H) 7.95 (s, 1H) 8.06 (s, 1H) 8.16 (s, 1H) 8.66 (s, 1H) 8.86 (s, 1H) 13.09 (s, 1H); MS (ESI(+)) m/e 441 (M+H)$^+$.

EXAMPLE 704

4-[4-amino-3-(2-methyl-1H-indol-5-yl)thieno[3,2-c]pyridin-7-yl]benzonitrile

EXAMPLE 704A 4-(4-amino-3-bromothieno[3,2-c]pyridin-7-yl)benzonitrile

The desired product was prepared by substituting Example 21A, 4-(4,4,5,5-tetramethyl-[1,3,2]dioxaborolan-2-yl)benzonitrile, and PdCl$_2$(dppf) for Example 1B, 4-phenoxyphenylboronic acid, and Pd(PPh$_3$)$_4$ in Example 10A.

EXAMPLE 704B

4-[4-amino-3-(2-methyl-1H-indol-5-yl)thieno[3,2-c]pyridin-7-yl]benzonitrile

The desired product was prepared by substituting Example 704A and example 467A for Example 21B and 4-chlorophenylboronic acid in Example 21C. $^1$H NMR (300 MHz, DMSO-D$_6$) δ ppm 2.42 (s, 3H), 5.66 (br. s, 2H), 6.21 (s, 1H), 7.06 (dd, J=8.5, 1.7 Hz, 1H), 7.41 (d, J=8.1 Hz, 1H), 7.46 (s, 1H), 7.48 (d, J=1.0 Hz, 1H), 7.91 (d, J=8.5 Hz, 2H), 7.95–8.02 (m, 3H), 11.17 (s, 1H) MS (ESI(+)) m/e 380.9 (M+H)$^+$.

EXAMPLE 705

7-(4-aminophenyl)-3-(2-methyl-1,3-benzothiazol-5-yl)thieno[3,2-c]pyridin-4-amine The desired product was prepared by substituting examples 492A and 482A for example 21B and 4-chlorophenylboronic acid in example 21C. $^1$H NMR (300 MHz, DMSO-D$_6$) δ ppm 2.85 (s, 3H), 5.25 (s, 2H), 5.28 (s, 2H), 6.70 (d, J=8.8 Hz, 2H), 7.32 (d, J=8.5 Hz, 2H), 7.50 (dd, J=8.3, 1.2 Hz, 1H), 7.57 (s, 1H), 7.80 (s, 1H), 7.99 (s, 1H), 8.18 (d, J=8.5 Hz, 1H) MS (ESI(+)) m/e 388.9 (M+H)$^+$.

EXAMPLE 706

N-{4-[4-amino-3-(1-benzofuran-2-yl)thieno[3,2-c]pyridin-7-yl]phenyl}acetamide

EXAMPLE 706A

N-[4-(4-amino-3-bromothieno[3,2-c]pyridin-7-yl)phenyl]acetamide

The desired product was prepared by substituting Example 21A and 4'-(4,4,5,5-tetramethyl-1,3,2-dioxaborolan-2-yl)acetanilide for Example 1B and 4-phenoxyphenylboronic acid in Example 10A. MS ESI(+)) m/e 361.8, 363.7 (M+H)$^+$.

EXAMPLE 706B

N-{4-[4-amino-3-(1-benzofuran-2-yl)thieno[3,2-c]pyridin-7-yl]phenyl}acetamide

The desired product was prepared by substituting example 706A and benzofuran-2-ylboronic acid for 21B and 4-chlorophenylboronic acid in example 21C. $^1$H NMR (300 MHz, DMSO-D$_6$) δ ppm 2.10 (s, 3H), 7.33–7.46 (m, 3H), 7.63 (d, J=8.8 Hz, 2H), 7.72 (d, J=7.8 Hz, 1H), 7.75–7.80 (m, 4H), 7.98 (s, 1H), 8.34 (s, 1H); MS (ESI(+)) m/e 400.1 (M+H)$^+$.

EXAMPLE 707

N-{4-[4-amino-3-(2,3-dihydro-1H-indol-5-yl)thieno[3,2-c]pyridin-7-yl]phenyl}acetamide The desired product was prepared by substituting examples 706A and 489B for example 21B and 4-chlorophenylboronic acid in example 21C, then deprotecting as in example 76C. $^1$H NMR (300 MHz, DMSO-D$_6$) δ ppm 2.08 (s, 3H), 2.98 (t, J=8.5 Hz, 2H), 3.50 (t, J=7.8 Hz, 2H), 5.56 (s, 2H), 5.77 (s, 1H), 6.60 (d, J=7.8 Hz, 1H), 6.98 (d, J=7.1 Hz, 1H), 7.10 (s, 1H), 7.33 (s, 1H), 7.58 (d, J=8.5 Hz, 2H), 7.70 (d, J=8.5 Hz, 2H), 7.83 (s, 1H), 10.05 (s, 1H); MS (ESI(+)) m/e 401.1 (M+H)$^+$.

EXAMPLE 708

N-{4-[4-amino-3-(2-methyl-1,3-benzothiazol-5-yl)thieno[3,2-c]pyridin-7-yl]phenyl}acetamide The desired product was prepared by substituting examples 706A and 482A for example 21B and 4-chlorophenylboronic acid in example 21C. $^1$H NMR (300 MHz, DMSO-D$_6$) δ ppm 2.09 (s, 3H), 2.85 (s, 3H), 5.41 (s, 2H), 7.50 (dd, J=8.1, 1.7 Hz, 1H), 7.60 (d, J=8.5 Hz, 2H), 7.60 (s, 1H), 7.73 (d, J=8.5 Hz, 2H), 7.90 (s, 1H), 8.00 (d, J=1.7 Hz, 1H), 8.19 (d, J=8.1 Hz, 1H), 10.07 (s, 1H) MS (ESI(+)) m/e 431.1 (M+H)$^+$.

EXAMPLE 709

3-(2-methyl-1H-indol-5-yl)-7-[4-(methylsulfonyl)phenyl]thieno[3,2-c]pyridin-4-amine

EXAMPLE 709A 3-bromo-7-[4-(methylsulfonyl)phenyl]thieno[3,2-c]pyridin-4-amine The desired product was prepared by substituting Example 21A, 4-methanesulfonylphenylboronic acid, and PdCl$_2$(dppf) for Example 1B, 4-phenoxyphenylboronic acid, and Pd(PPh$_3$)$_4$ in Example 10A.

EXAMPLE 709B 3-(2-methyl-1H-indol-5-yl)-7-[4-(methylsulfonyl)phenyl]thieno[3,2-c]pyridin-4-amine The desired product was prepared by substituting Example 709A and 467A for Example 21B and 4-chlorophenylboronic acid in Example 21C. $^1$H NMR (300 MHz, DMSO-D$_6$) δ ppm 2.43 (s, 3H), 3.32 (s, 3H), 6.23 (s, 1H), 7.11 (dd, J=8.1, 1.7 Hz, 1H), 7.45 (d, J=8.1 Hz, 1H), 7.54 (d, J=1.4 Hz, 1H), 7.76 (s, 1H), 8.00 (d, J=8.8 Hz, 2H), 8.05 (s, 1H), 8.12 (d, J=8.8 Hz, 2H), 11.24 (s, 1H) MS (ESI(+)) m/e 433.8 (M+H)$^+$.

EXAMPLE 710

7-[4-(ethylsulfonyl)phenyl]-3-(2-methyl-1H-indol-5-yl)thieno[3,2-c]pyridin-4-amine

EXAMPLE 710A 3-bromo-7-[4-(ethylsulfonyl)phenyl]thieno[3,2-c]pyridin-4-amine The desired product was prepared by substituting Example 21A, 4-ethanesulfonylphenylboronic acid, and PdCl$_2$(dppf) for Example 1B, 4-phenoxyphenylboronic acid, and Pd(PPh$_3$)$_4$ in Example 10A.

EXAMPLE 710B

7-[4-(ethylsulfonyl)phenyl]-3-(2-methyl-1H-indol-5-yl)thieno[3,2-c]pyridin-4-amine The desired product was prepared by substituting Example 710A and 467A for Example 21B and 4-chlorophenylboronic acid in Example 21C. $^1$H NMR (300 MHz, DMSO-D$_6$) δ ppm 1.17 (t, J=7.5 Hz, 3H), 2.42 (s, 3H), 3.37 (q, J=7.2 Hz, 2H), 5.66 (s, 2H), 6.20–6.22 (m, 1H), 7.07 (dd, J=8.1, 1.7 Hz, 1H), 7.41 (d, J=8.1 Hz, 1H), 7.47 (s, 1H), 7.48 (d, J=1.4 Hz, 1H), 7.99–8.01 (m, 5H), 11.17 (s, 1H) MS (ESI(+)) m/e 448.1 (M+H)$^+$.

EXAMPLE 711

N-{4-[4-amino-3-(1-benzofuran-2-yl)thieno[3,2-c]pyridin-7-yl]phenyl}methanesulfonamide

EXAMPLE 711A

N-[4-(4-amino-3-bromothieno[3,2-c]pyridin-7-yl)phenyl]methanesulfonamide

The desired product was prepared by substituting example 21A and 4-(methylsulfonylamino)phenylboronic acid for example 1B and 4-phenoxyphenylboronic acid in example 10A. MS (ESI(+) m/e 397.6, 399.6 (M+H)$^+$.

EXAMPLE 711B

N-{4-[4-amino-3-(1-benzofuran-2-yl)thieno[3,2-c]pyridin-7-yl]phenyl}methanesulfonamide The desired product was prepared by substituting examples 711A and benzofuran-2-ylboronic acid for example 21B and 4-chlorophenylboronic acid in example 21C. $^1$H NMR (300 MHz, DMSO-D$_6$) δ ppm 3.10 (s, 3H), 7.33–7.46 (m, 5H), 7.67 (d, J=8.5 Hz, 2H), 7.70–7.73 (m, 1H), 7.75–7.78 (m, 1H), 7.98 (s, 1H), 8.34 (s, 1H), 10.03 (s, 1H) MS (ESI(+)) m/e 435.8 (M+H)$^+$.

EXAMPLE 712

N-{4-[4-amino-3-(7-fluoro-1H-indol-5-yl)thieno[3,2-c]pyridin-7-yl]phenyl}methanesulfonamide The desired product was prepared by substituting examples 711A and Example 468C for example 21B and 4-chlorophenylboronic acid in example 21C. $^1$H NMR (300 MHz, DMSO-D$_6$) δ ppm 3.10 (s, 3H), 6.64 (td, J=3.2, 1.7 Hz, 1H), 7.12 (dd, J=11.9, 1.4 Hz, 1H), 7.40 (d, J=8.8 Hz, 2H), 7.54–7.58 (m, 2H), 7.68 (d, J=8.5 Hz, 2H), 7.86 (s, 1H), 7.92 (s, 1H), 10.06 (s, 1H), 11.92 (s, 1H) MS (ESI(+)) m/e 452.8 (M+H)$^+$.

EXAMPLE 713

N-{4-[4-amino-3-(2-methyl-1,3-benzothiazol-5-yl)thieno[3,2-c]pyridin-7-yl]phenyl}methanesulfonamide The desired product was prepared by substituting examples 711A and Example 482A for example 21B and 4-chlorophenylboronic acid in example 21C. $^1$H NMR (300 MHz, DMSO-D$_6$) δ ppm 2.86 (s, 3H), 3.10 (s, 3H), 7.40 (d, J=8.8 Hz, 2H), 7.54 (dd, J=8.3, 1.9 Hz, 1H), 7.68 (d, J=8.5 Hz, 2H), 7.93–7.94 (m, 2H), 8.07 (d, J=1.0 Hz, 1H), 8.23 (d, J=8.8 Hz, 1H), 10.05 (s, 1H) MS (ESI(+)) m/e 466.8 (M+H)$^+$.

EXAMPLE 714

N-{4-[4-amino-3-(1H-indol-5-yl)thieno[3,2-c]pyridin-7-yl]phenyl}methanesulfonamide The desired product was prepared by substituting examples 711A and 1H-indol-5-ylboronic acid for example 21B and 4-chlorophenylboronic acid in example 21C. $^1$H NMR (300 MHz, DMSO-D$_6$) δ ppm 3.11 (s, 3H), 6.55 (ddd, J=3.0, 1.9, 0.8 Hz, 1H), 7.21 (dd, J=8.5, 1.7 Hz, 1H), 7.40 (d, J=8.8 Hz, 2H), 7.50–7.52 (m, 1H), 7.59 (d, J=8.5 Hz, 1H), 7.67–7.71 (m, 3H), 7.82 (s, 1H), 7.91 (s, 1H), 10.06 (s, 1H), 11.41 (s, 1H) MS (ESI(+)) m/e 434.8 (M+H)$^+$.

EXAMPLE 715

N-{4-[4-amino-3-(2,3-dihydro-1H-indol-5-yl)thieno[3,2-c]pyridin-7-yl]phenyl}methanesulfonamide The desired product was prepared by substituting examples 711A and Example 489B for example 21B and 4-chlorophenylboronic acid in example 21C, followed by deprotection as in example 76C. $^1$H NMR (300 MHz, DMSO-D$_6$) δ ppm 3.01 (t, J=8.8 Hz, 2H), 3.10 (s, 3H), 3.54 (t, J=8.8 Hz, 2H), 6.64 (d, J=7.8 Hz, 1H), 7.04–7.08 (m, 1H), 7.17 (s, 1H), 7.39 (d, J=8.5 Hz, 2H), 7.67 (d, J=8.5 Hz, 2H), 7.76 (s, 1H), 7.90 (s, 1H), 10.07 (s, 1H) MS (ESI(+)) m/e 436.9 (M+H)$^+$.

EXAMPLE 716

N-{4-[4-amino-3-(2-methyl-1,3-benzoxazol-5-yl)thieno[3,2-c]pyridin-7-yl]phenyl}methanesulfonamide The desired product was prepared by substituting examples 711A and 2-methyl-5-(4,4,5,5-tetramethyl-[1,3,2]dioxaborolan-2-yl)benzoxazole for example 21B and 4-chlorophenylboronic acid in example 21C. $^1$H NMR (300 MHz, DMSO-D$_6$) δ ppm 2.67 (s, 3H), 3.07 (s, 3H), 5.40 (s, 2H), 7.35 (d, J=8.5 Hz, 2H), 7.44 (dd, J=8.1, 1.7 Hz, 1H), 7.56 (s, 1H), 7.65 (d, J=8.5 Hz, 2H), 7.76 (d, J=1.7 Hz, 1H), 7.81 (d, J=8.5 Hz, 1H), 7.89 (s, 1H), 9.90 (s, 1H) MS (ESI(+)) m/e 451.1 (M+H)$^+$.

EXAMPLE 717

N-(4-{4-amino-3-[4-(dimethylamino)phenyl]thieno[3,2-c]pyridin-7-yl}phenyl)methanesulfonamide The desired product was prepared by substituting examples 711A and 4-dimethylaminophenylboronic acid for example 21B and 4-chlorophenylboronic acid in example 21C. $^1$H NMR (300 MHz, DMSO-D$_6$) δ ppm 2.98 (s, 6H), 3.06 (s, 3H), 5.55 (s, 2H), 6.85 (d, J=8.8 Hz, 2H), 7.28 (d, J=8.5 Hz, 2H), 7.34 (d, J=8.8 Hz, 2H), 7.37 (s, 1H), 7.63 (d, J=8.5 Hz, 2H), 7.85 (s, 1H), 9.89 (s, 1H) MS (ESI(+)) m/e 439.1 (M+H)$^+$.

EXAMPLE 718

N-{4-[4-amino-3-(2-methyl-1H-indol-5-yl)thieno[3,2-c]pyridin-7-yl]phenyl}methanesulfonamide The desired product was prepared by substituting examples 711A and example 467A for example 21B and 4-chlorophenylboronic acid in example 21C. $^1$H NMR (300 MHz, DMSO-D$_6$) 2.42 (s, 3H), 3.06 (s, 3H), 5.46 (s, 2H), 6.20 (s, 1H), 7.06 (dd, J=8.1, 1.7 Hz, 1H), 7.34 (d, J=8.8 Hz, 2H), 7.39–7.42 (m, 2H), 7.47 (d, J=1.4 Hz, 1H), 7.64 (d, J=8.5 Hz, 2H), 7.85 (s, 1H), 9.89 (s, 1H), 11.16 (s, 1H); MS (ESI(+)) m/e 448.9 (M+H)$^+$.

EXAMPLE 719

3-(2-methyl-1H-indol-5-yl)-7-[3-(methylsulfonyl)phenyl]thieno[3,2-c]pyridin-4-amine

EXAMPLE 719A 3-bromo-7-[3-(methylsulfonyl)phenyl]thieno[3,2-c]pyridin-4-amine The desired product was prepared by substituting Example 21A, 3-(methanesulfonyl)phenylboronic acid, and PdCl$_2$(dppf) for Example 1B, 4-phenoxyphenylboronic acid, and Pd(PPh$_3$)$_4$ in Example 10A.

EXAMPLE 719B 3-(2-methyl-1H-indol-5-yl)-7-[3-(methylsulfonyl)phenyl]thieno[3,2-c]pyridin-4-amine The desired product was prepared by substituting Example 719A and 467A for Example 21B and 4-chlorophenylboronic acid in Example 21C. $^1$H NMR (300 MHz, DMSO-D$_6$) δ ppm 2.43 (s, 3H), 3.31 (s, 3H), 5.63 (s, 2H), 6.21 (s, 1H), 7.07 (dd, J=8.5, 1.7 Hz, 1H), 7.41 (d, J=8.5 Hz, 1H), 7.46 (s, 1H), 7.48 (d, J=1.4 Hz, 1H), 7.81 (t, J=7.8 Hz, 1H), 7.93–7.97 (m, 1H), 8.01 (s, 1H), 8.06 (dt, J=7.7, 1.4 Hz, 1H), 8.22 (t, J=1.9 Hz, 1H), 11.17 (s, 1H) MS (ESI(+)) m/e 433.8 (M+H)$^+$.

EXAMPLE 720

N-[4-(4-aminofuro[3,2-c]pyridin-3-yl)phenyl]-N'-(3,5-dimethylphenyl)urea

The desired product was prepared by substituting Example 543C and 1-isocyanato-3,5-dimethylbenzene for Example 1C and 1-isocyanato-3-methylbenzene in Example 1D. $^1$H NMR (500 MHz, DMSO-D$_6$) δ ppm 2.24 (s, 6H), 6.63 (s, 1H), 7.10 (s, 2H), 7.25 (s, 2H), 7.38 (d, J=6.86 Hz, 1H), 7.44 (d, J=8.42 Hz, 2H), 7.65 (d, J=8.42 Hz, 2H), 7.99 (d, J=7.17 Hz, 1H), 8.27 (s, 1H), 8.75 (s, 1H), 9.06 (s, 1H); MS DCI(+)) m/e 373 (M+H)$^+$.

EXAMPLE 721

N-[4-(4-aminofuro[3,2-c]pyridin-3-yl)phenyl]-N'-(3,5-difluorophenyl)urea

The desired product was prepared by substituting Example 543C and 3,5-difluoro-1-isocyanatobenzene for Example 1C and 1-isocyanato-3-methylbenzene in Example 1D. $^1$H NMR (300 MHz, DMSO-D$_6$) δ ppm $^1$H NMR (500 MHz, DMSO-D$_6$) δ ppm 6.77–6.84 (m, 1H), 7.08–7.14 (m, 2H), 7.22 (dd, J=9.98, 2.18 Hz, 2H), 7.36 (d, J=7.18 Hz, 1H), 7.47 (d, J=8.73 Hz, 2H), 7.65 (d, J=8.42 Hz, 2H), 7.98 (d, J=7.18 Hz, 1H), 8.26 (s, 1H), 9.24 (s, 1H), 9.33 (s, 1H); MS DCI(+)) m/e 381 (M+H)$^+$.

EXAMPLE 722

N-(3-acetylphenyl)-N'-[4-(4-aminofuro[3,2-c]pyridin-3-yl)phenyl]urea

The desired product was prepared by substituting Example 543C and 1-(3-isocyanatophenyl)ethanone for Example 1C and 1-isocyanato-3-methylbenzene in Example 1D. $^1$H NMR (500 MHz, DMSO-D$_6$) δ ppm 2.57 (s, 3H), 7.25 (s, 2H), 7.38 (d, J=6.86 Hz, 1H), 7.43–7.48 (m, 3H), 7.60 (d, J=7.80 Hz, 1H), 7.66–7.73 (m, 3H), 7.99 (d, J=6.86 Hz, 1H), 8.12 (t, J=1.87 Hz, 1H), 8.28 (s, 1H), 9.18 (s, 1H), 9.19 (s, 1H); MS DCI(+) m/e 387 (M+H)$^+$.

EXAMPLE 723

N-[4-(4-aminofuro[3,2-c]pyridin-3-yl)phenyl]-N'-cyclopentylurea

The desired product was prepared by substituting Example 543C and isocyanatocyclopentane for Example 1C and 1-isocyanato-3-methylbenzene in Example 1D. $^1$H NMR (500 MHz, DMSO-D$_6$) δ ppm 1.34–1.42 (m, 2H), 1.50–1.57 (m, 2H), 1.60–1.69 (m, 2H), 1.81–1.89 (m, 2H), 3.84–4.04 (m, 1H), 7.18 (s, 2H), 7.32–7.42 (m, 3H), 7.36 (s, 1H), 7.56 (d, J=8.73 Hz, 2H), 7.97 (d, J=7.18 Hz, 1H), 8.24 (s, 1H), 8.56 (s, 1H),; MS DCI(+) m/e 383 (M+H)$^+$.

EXAMPLE 724

N-[4-(4-aminofuro[3,2-c]pyridin-3-yl)phenyl]-N'-(3-cyanophenyl)urea

The desired product was prepared by substituting Example 543C and 3-isocyanatobenzonitrile for Example 1C and 1-isocyanato-3-methylbenzene in Example 1D. $^1$H NMR (500 MHz, DMSO-D$_6$) δ ppm 7.27 (s, 2H), 7.39 (d, J=7.18 Hz, 1H), 7.42–7.45 (m, 1H), 7.47 (d, J=8.73 Hz, 2H), 7.51 (t, J=7.96 Hz, 1H), 7.67 (d, J=8.42 Hz, 2H), 7.69–7.73 (m, 1H), 7.99 (d, J=7.18 Hz, 1H), 8.02 (t, J=1.72 Hz, 1H), 8.28 (s, 1H), 9.37 (s, 1H), 9.41 (s, 1H); MS DCI(+) m/e 387 (M+H)$^+$.

EXAMPLE 725

N-[4-(4-aminofuro[3,2-c]pyridin-3-yl)phenyl]-N'-2-naphthylurea

The desired product was prepared by substituting Example 543C and 2-isocyanatonaphthalene for Example 1C and 1-isocyanato-3-methylbenzene in Example 1D. $^1$H NMR (500 MHz, DMSO-D$_6$) δ ppm 7.21 (s, 2H), 7.34–7.41 (m, 2H), 7.43–7.50 (m, 3H), 7.53 (dd, J=8.73, 2.18 Hz, 1H), 7.70 (d, J=8.73 Hz, 2H), 7.77–7.84 (m, J=14.19, 8.27 Hz, 2H), 7.85 (d, J=9.05 Hz, 1H), 7.99 (d, J=6.86 Hz, 1H), 8.13 (d, J=1.87 Hz, 1H), 8.28 (s, 1H), 9.12 (s, 1H), 9.16 (s, 1H); MS DCI(+)) m/e 395 (M+H)$^+$.

EXAMPLE 726

4-{4-amino-3-[4-({[(3-methylphenyl)amino]carbonyl}amino)phenyl]furo[3,2-c]pyridin-7-yl}-N-methylbenzamide The desired product was prepared by substituting example 547D and 4-N-methylaminocarbonylphenylboronic acid for example 10B and 4-pyridylboronic acid in example 10C. $^1$H NMR (300 MHz, DMSO-D$_6$) δ ppm 2.30 (d, 3H), 2.83 (d, 3H), 6.81 (d, J=7.46 Hz, 1H), 6.91 (s, 2H), 7.17 (t, J=7.80 Hz, 1H), 7.22–7.29 (m, 1H), 7.32 (s, 1H), 7.48 (d, J=8.48 Hz, 2H), 7.63–7.70 (m, 2H), 7.89–7.96 (m, 2H), 7.96–8.03 (m, 2H), 8.28 (s, 1H), 8.31 (s, 1H), 8.48–8.58 (m, 1H), 8.69 (s, 1H), 8.93 (s, 1H); MS DCI(+)) m/e 492 (M+H)$^+$.

EXAMPLE 727

N-{4-[4-amino-7-(4-cyanophenyl)furo[3,2-c]pyridin-3-yl]phenyl}-N'-(3-methylphenyl)urea The desired product was prepared by substituting example 547D and 4-cyanophenylboronic acid for example 10B and 4-pyridylboronic acid in example 10C. $^1$H NMR (300 MHz, DMSO-D$_6$) δ ppm 2.54 (s, 3H), 6.70–6.89 (m, 3H), 7.17 (t, J=7.63 Hz, 1H), 7.23–7.28 (m, 1H), 7.32 (s, 1H), 7.47 (d, J=8.48 Hz, 2H), 7.65 (d, J=8.82 Hz, 2H), 7.97–8.10 (m, 4H), 8.28 (s, 1H), 8.33 (s, 1H), 8.68 (s, 1H), 8.91 (s, 1H); MS ESI(+)) m/e 460 (M+H)$^+$.

EXAMPLE 728

N-{4-[4-amino-7-(1,3-benzodioxol-5-yl)furo[3,2-c]pyridin-3-yl]phenyl}-N'-(3-methylphenyl)urea The desired product was prepared by substituting example 547D and benzo[1,3]dioxol-5-ylboronic acid for example 10B and 4-pyridylboronic acid in example 10C. $^1$H NMR (500 MHz, DMSO-D$_6$) δ ppm 2.26–2.31 (m, 3H), 6.12 (s, 2H), 6.81 (d, J=7.63 Hz, 1H), 7.11 (d, J=8.24 Hz, 1H), 7.17 (t, J=7.78 Hz, 1H), 7.21 (s, 2H), 7.27 (d, J=8.54 Hz, 1H), 7.30–7.35 (m, 2H), 7.38 (d, J=1.83 Hz, 1H), 7.47 (d, J=8.54 Hz, 2H), 7.67 (d, J=8.54 Hz, 2H), 8.15 (s, 1H), 8.33 (s, 1H), 8.92 (s, 1H), 9.17 (s, 1H); MS ESI(+)) m/e 479 (M+H)$^+$.

EXAMPLE 729

N-(4-{4-amino-7-[4-(methylsulfonyl)phenyl]furo[3,2-c]pyridin-3-yl}phenyl)-N'-(3-methylphenyl)urea The desired product was prepared by substituting example 547D and 4-methanesulfonylphenylboronic acid for example 10B and 4-pyridylboronic acid in example 10C. $^1$H NMR (500 MHz, DMSO-D$_6$) δ ppm 2.29 (s, 3H), 3.27–3.31 (m, 3H), 6.81 (d, J=7.32 Hz, 1H), 7.10–7.15 (m, 1H), 7.15–7.18 (m, 1H), 7.18–7.22 (m, 1H), 7.26 (d, J=6.71 Hz, 1H), 7.33 (s, 1H), 7.48 (d, J=8.54 Hz, 2H), 7.67 (d, J=8.54 Hz, 2H), 8.08–8.13 (m, 4H), 8.33 (s, 1H), 8.34 (s, 1H), 8.79 (s, 1H), 9.04 (s, 1H); MS ESI(+)) m/e 513 (M+H)$^+$.

EXAMPLE 730

N-(4-{4-amino-3-[4-({[(3-methylphenyl)amino]carbonyl}amino)phenyl]furo[3,2-c]pyridin-7-yl}phenyl)acetamide The desired product was prepared by substituting example 547D and 4-acetamidophenylboronic acid for example 10B and 4-pyridylboronic acid in example 10C. $^1$H NMR (400 MHz, DMSO-D$_6$) δ ppm 2.09 (s, 3H), 2.29 (s, 3H), 6.81 (d, J=7.36 Hz, 1H), 7.11 (s, 2H), 7.17 (t, J=7.82 Hz, 1H), 7.26 (d, J=8.29 Hz, 1H), 7.32 (s, 1H), 7.48 (d, J=8.59 Hz, 2H), 7.66 (d, J=8.59 Hz, 2H), 7.74–7.78 (m, 4H), 8.17 (s, 1H), 8.34 (s, 1H), 8.78 (s, 1H), 9.03 (s, 1H), 10.13 (s, 1H); MS ESI(+)) m/e 492 (M+H)$^+$.

EXAMPLE 731

N-{4-[4-amino-7-(2-methyl-1,3-benzothiazol-5-yl)furo[3,2-c]pyridin-3-yl]phenyl}-N'-(3-methylphenyl)urea The desired product was prepared by substituting example 547D and Example 482A for example 10B and 4-pyridylboronic acid in example 10C. $^1$H NMR (400 MHz, DMSO-D$_6$) δ ppm 2.29 (s, 3H), 2.85 (s, 3H), 6.78–6.84 (m, 1H), 7.12 (s, 2H), 7.17 (s, 1H), 7.24–7.29 (m, 1H), 7.33 (s, 1H), 7.50 (d, J=8.29 Hz, 2H), 7.67 (d, J=8.59 Hz, 2H), 7.84 (dd, J=1.84 Hz, 1H), 8.22 (d, J=8.29 Hz, 1H), 8.32 (s, 1H), 8.36 (s, 1H), 8.37 (d, J=1.53 Hz, 1H), 8.79 (s, 1H), 9.04 (s, 1H); MS ESI(+)) m/e 506 (M+H)$^+$.

EXAMPLE 732

N-{4-[4-amino-7-(2-methyl-1,3-benzoxazol-5-yl)furo[3,2-c]pyridin-3-yl]phenyl}-N'-(3-methylphenyl)urea The desired product was prepared by substituting 547D and 2-methyl-5-(4,4,5,5-tetramethyl-[1,3,2]dioxaborolan-2-yl)benzoxazole for example 10B and 4-pyridylboronic acid in example 10C. $^1$H NMR (500 MHz, DMSO-D$_6$) δ ppm 2.14 (s, 3H), 2.29 (s, 3H), 6.81 (d, J=7.49 Hz, 1H), 7.04 (d, J=8.42 Hz, 1H), 7.11–7.20 (m, J=7.80, 7.80 Hz, 3H), 7.27 (d, J=7.80 Hz, 1H), 7.33 (s, 1H), 7.46–7.50 (m, 2H), 7.64–7.69 (m, 2H), 8.07 (s, 1H), 8.25 (s, 1H), 8.34 (s, 1H), 8.85 (s, 1H), 9.10 (s, 1H), 9.38 (s, 1H); MS ESI(+)) m/e 490 (M+H)$^+$.

EXAMPLE 733

4-{4-amino-3-[4-({[(3-methylphenyl)amino]carbonyl}amino)phenyl]furo[3,2-c]pyridin-7-yl}benzamide The desired product was prepared by substituting example 547D and 4-aminocarbonylphenylboronic acid for example 10B and 4-pyridylboronic acid in example 10C. $^1$H NMR (400 MHz, DMSO-D$_6$) δ ppm 2.29 (s, 3H), 6.81 (d, J=7.67

Hz, 1H), 7.02 (s, 2H), 7.17 (t, J=7.82 Hz, 1H), 7.26 (d, J=8.29 Hz, 1H), 7.32 (s, 1H), 7.44 (s, 2H), 7.48 (d, J=8.29 Hz, 2H), 7.66 (d, J=8.59 Hz, 2H), 7.92 (d, J=8.29 Hz, 2H), 8.04 (d, J=8.59 Hz, 2H), 8.30 (s, 1H), 8.32 (s, 1H), 8.75 (s, 1H), 8.99 (s, 1H); MS ESI(+)) m/e 478 (M+H)$^+$.

EXAMPLE 734

N-{4-[4-amino-7-(1-benzothien-5-yl)furo[3,2-c]pyridin-3-yl]phenyl}-N'-(3-methylphenyl)urea The desired product was prepared by substituting example 547D and benzothiophen-5-ylboronic acid for example 10B and 4-pyridylboronic acid in example 10C. $^1$H NMR (500 MHz, DMSO-D$_6$) δ ppm 2.28 (none, 1H), 2.29 (s, 3H), 6.81 (d, J=7.49 Hz, 1H), 7.13 (s, 2H), 7.17 (t, J=7.80 Hz, 1H), 7.27 (d, J=7.80 Hz, 1H), 7.33 (s, 1H), 7.50 (d, J=8.74 Hz, 2H), 7.59 (d, J=5.30 Hz, 1H), 7.68 (d, J=8.42 Hz, 2H), 7.79 (dd, J=8.42, 1.56 Hz, 1H), 7.88 (d, J=5.30 Hz, 1H), 8.20 (d, J=8.42 Hz, 1H), 8.28 (s, 1H), 8.34 (d, J=1.25 Hz, 1H), 8.36 (s, 1H), 8.80 (s, 1H), 9.06 (s, 1H); MS ESI(+)) m/e 491 (M+H)$^+$.

EXAMPLE 735

N-{4-[4-amino-7-(3-morpholin-4-ylprop-1-ynyl)furo[3,2-c]pyridin-3-yl]phenyl}-N'-(3-methylphenyl)urea The desired product was prepared by substituting example 547D and 4-prop-2-ynylmorpholine for example 144A and 3-butyn-1-ol in example 144B. $^1$H NMR (500 MHz, DMSO-D$_6$) δ ppm 2.29 (s, 3H), 3.24–3.41 (m, 4H), 3.76–3.92 (m, 4H), 4.43 (s, 2H), 6.63 (s, 2H), 6.80 (d, J=7.49 Hz, 1H), 7.16 (t, J=7.80 Hz, 1H), 7.26 (d, J=8.11 Hz, 1H), 7.33 (s, 1H), 7.43 (d, J=8.74 Hz, 2H), 7.64 (d, J=8.73 Hz, 2H), 8.14 (s, 1H), 8.20 (s, 1H), 8.85 (s, 1H), 9.08 (s, 1H); MS ESI(+)) m/e 482 (M+H)$^+$.

EXAMPLE 736

N-(3-{4-amino-3-[4-({[(3-methylphenyl)amino]carbonyl}amino)phenyl]furo[3,2-c]pyridin-7-yl}prop-2-ynyl)methanesulfonamide The desired product was prepared by substituting example 547D and N-prop-2-ynylmethanesulfonamide for example 144A and 3-butyn-1-ol in example 144B. $^1$H NMR (400 MHz, DMSO-D$_6$) δ ppm 2.29 (s, 3H), 3.06 (s, 3H), 4.13 (s, 2H), 5.91 (s, 2H), 6.80 (d, J=7.36 Hz, 1H), 7.17 (t, J=7.67 Hz, 1H), 7.23–7.27 (m, 1H), 7.31 (s, 1H), 7.43 (d, J=8.29 Hz, 2H), 7.55–7.69 (m, 3H), 8.00 (s, 1H), 8.01 (s, 1H), 8.63 (s, 1H), 8.83 (s, 1H); MS ESI(+)) m/e 490 (M+H)$^+$.

EXAMPLE 737

N-(3-{4-amino-3-[4-({[(3-methylphenyl)amino]carbonyl}amino)phenyl]furo[3,2-c]pyridin-7-yl}prop-2-ynyl)-2-methylpropanamide The desired product was prepared by substituting example 547D and 2-methyl-N-prop-2-ynylpropanamide for example 144A and 3-butyn-1-ol in example 144B. $^1$H NMR (400 MHz, DMSO-D$_6$) δ ppm 1.03 (d, J=6.75 Hz, 6H), 2.29 (s, 3H), 2.36–2.47 (m, 1H), 4.18 (d, J=5.52 Hz, 2H), 5.87 (s, 2H), 6.80 (d, J=7.36 Hz, 1H), 7.17 (t, J=7.82 Hz, 1H), 7.22–7.29 (m, 1H), 7.32 (s, 1H), 7.43 (d, J=8.59 Hz, 2H), 7.61 (d, J=8.29 Hz, 2H), 7.98 (d, J=4.30 Hz, 2H), 8.29 (t, J=5.22 Hz, 1H), 8.64 (s, 1H), 8.84 (s, 1H); MS ESI(+)) m/e 482 (M+H)$^+$.

EXAMPLE 738

N-{4-[4-amino-7-(3-amino-3-methylbut-1-ynyl)furo[3,2-c]pyridin-3-yl]phenyl}-N'-(3-methylphenyl)urea The desired product was prepared by substituting example 547D and Example 552A for example 144A and 3-butyn-1-ol in example 144B, followed by deprotection as in example 76C. $^1$H NMR (500 MHz, DMSO-D$_6$) δ ppm 1.67 (s, 6H), 2.29 (s, 3H), 6.02 (s, 2H), 6.80 (d, J=7.49 Hz, 1H), 7.16 (t, J=7.80 Hz, 1H), 7.25 (d, J=8.11 Hz, 1H), 7.31 (s, 1H), 7.42 (d, J=8.74 Hz, 2H), 7.62 (d, J=8.73 Hz, 2H), 8.04 (d, J=6.55 Hz, 2H), 8.50–8.61 (m, 4H), 8.69 (s, 1H), 8.90 (s, 1H); MS ESI(+)) m/e 440 (M+H)$^+$.

EXAMPLE 739

N-{4-[4-amino-7-(2-methoxypyrimidin-5-yl)thieno[3,2-c]pyridin-3-yl]phenyl}-N'-(3-methylphenyl)urea The desired product was prepared by substituting 1-isocyanato-3-methylbenzene and Example 440 for 1-fluoro-2-isocyanato-4-(trifluoromethyl)benzene and Example 121B in Example 122. $^1$H NMR (300 MHz, DMSO-D$_6$) δ ppm 2.29 (s, 3H) 4.00 (s, 3H) 5.65 (s, 2H), 6.81 (d, J=7.46 Hz, 1H) 7.17 (t, J=7.63 Hz, 1H) 7.23–7.28 (m, 1H) 7.32 (s, 1H), 7.39 (d, J=8.81 Hz, 2H) 7.52 (s, 1H) 7.62 (d, J=8.48 Hz, 2H) 7.94 (s, 1H) 8.67 (s, 1H), 8.87 (s, 1H) 8.90 (s, 2H); MS (ESI(+)) m/e 483 (M+H)$^+$.

EXAMPLE 740

N-{4-[4-amino-7-(2-methoxypyrimidin-5-yl)thieno[3,2-c]pyridin-3-yl]phenyl}-N'-(3-chlorophenyl)urea The desired product was prepared by substituting 1-isocyanato-3-chlorobenzene and Example 440 for 1-fluoro-2-isocyanato-4-(trifluoromethyl)benzene and Example 121B in Example 122. $^1$H NMR (300 MHz, DMSO-D$_6$) δ ppm 4.00 (s, 3H) 5.64 (s, 2H) 7.01–7.06 (m, 1H) 7.28–7.34 (m, 2H) 7.41 (d, J=8.48 Hz, 2H) 7.52 (s, 1H) 7.62 (d, J=8.48 Hz, 2H) 7.73 (s, 1H) 7.94 (s, 1H) 8.90 (s, 2H) 8.98 (d, J=2.71 Hz, 2H); MS (ESI(+)) m/e 503 (M+H)$^+$.

EXAMPLE 741

3-(4-aminophenyl)-7-(1-benzothien-2-yl)thieno[3,2-c]pyridin-4-amine

The desired product was prepared by substituting example 77B and benzothiophen-2-ylboronic acid for example 1B and 4-phenoxyphenylboronic acid in example 10A. $^1$H NMR (500 MHz, DMSO-D$_6$) δ ppm 6.76 (d, J=8.4 Hz, 2H) 7.20 (d, J=8.4 Hz, 2H) 7.38–7.54 (m, 2H) 7.76 (s, 1H) 7.91 (s, 1H) 7.94–8.00 (m, 1H) 8.07 (d, J=7.5 Hz, 1H) 8.21 (s, 1H); MS ESI(+) m/e 374 (M+H)$^+$.

EXAMPLE 742

N-[4-(4-aminothieno[3,2-c]pyridin-3-yl)phenyl]-2-(3-methylphenyl)acetamide

The desired product was prepared by substituting m-tolylacetyl chloride for acetyl chloride in example 17B. $^1$H NMR (400 MHz, DMSO-D$_6$) δ ppm 2.31 (s, 3H) 3.63 (s, 2H) 5.34 (s, 2H) 7.03–7.10 (m, 1H) 7.12–7.19 (m, J=5.5 Hz, 2H) 7.21 (d, J=7.4 Hz, 1H) 7.25 (d, J=5.8 Hz, 1H) 7.34–7.44 (m, 3H) 7.74 (d, J=8.3 Hz, 2H) 7.82 (d, J=5.5 Hz, 1H) 10.31 (s, 1H); MS ESI(+) m/e 374 (M+H)$^+$.

EXAMPLE 743

2-[4-(4-aminothieno[3,2-c]pyridin-3-yl)phenyl]-N-(3-methylphenyl)acetamide

The desired product was prepared by substituting 2-[4-(4,4,5,5-tetramethyl-[1,3,2]dioxaborolan-2-yl)-phenyl]-N-m-tolyl-acetamide (prepared by reacting [4-(4,4,5,5-tetramethyl-[1,3,2]dioxaborolan-2-yl)-phenyl]-acetic acid with 3-methylaniline as in example 11C) for 4-phenoxyphenylboronic acid in example 10A. $^1$H NMR (300 MHz, DMSO-D$_6$) δ ppm 2.27 (s, 3H) 3.73 (s, 2H) 5.38 (br s, 2H) 6.87 (d, J=7.5 Hz, 1H) 7.18 (t, J=7.8 Hz, 1H) 7.27 (d, J=5.4 Hz, 1H) 7.36–7.51 (m, 7H) 7.83 (d, J=5.4 Hz, 1H) 10.14 (s, 1H); MS ESI(+) m/e 374 (M+H)$^+$.

EXAMPLE 744

N-[4-(4-aminothieno[3,2-c]pyridin-3-yl)phenyl]-N'-cyclopentylurea

The desired product was prepared by substituting example 17A and isocyanatocyclopentane for example 121B and 1-fluoro-2-isocyanato-4-(trifluoromethyl)benzene, respectively in example 122. $^1$H NMR (300 MHz, DMSO-D$_6$) δ ppm 1.28–1.48 (m, 2H) 1.47–1.75 (m, 4H) 1.75–2.00 (m, 2H) 3.79–4.13 (m, 1H) 5.41 (br s, 2H) 6.23 (d, J=7.1 Hz, 1H) 7.24 (d, J=5.8 Hz, 1H) 7.30 (d, J=8.5 Hz, 2H) 7.38 (s, 1H) 7.51 (d, J=8.5 Hz, 2H) 7.81 (d, J=5.4 Hz, 1H) 8.45 (s, 1H); MS ESI(+) m/e 353 (M+H)$^+$.

EXAMPLE 745

N-[4-(4-aminothieno[3,2-c]pyridin-3-yl)phenyl]-N'-cyclohexylurea

The desired product was prepared by substituting example 17A and isocyanatocyclohexane for example 121B and 1-fluoro-2-isocyanato-4-(trifluoromethyl)benzene in example 122. $^1$H NMR (300 MHz, DMSO-D$_6$) δ ppm 1.04–1.45 (m, 5H) 1.47–163 (s, 1H) 1.65–169 (m, 2H) 1.80–184 (m, 2H) 3.40–3.60 (m, 1H) 5.41 (s, 2H) 6.14 (d, J=7.8 Hz, 1H) 7.24 (d, J=5.8 Hz, 1H) 7.30 (d, J=8.5 Hz, 2H) 7.38 (s, 1H) 7.51 (d, J=8.5 Hz, 2H) 7.81 (d, J=5.8 Hz, 1H) 8.50 (s, 1H); MS ESI(+) m/e 367 (M+H)$^+$.

EXAMPLE 746

N-[4-(4-aminothieno[3,2-c]pyridin-3-yl)phenyl]-N'-1-naphthylurea

The desired product was prepared by substituting example 17A and 1-isocyanatonaphthalene for example 121B and 1-fluoro-2-isocyanato-4-(trifluoromethyl)benzene in example 122. $^1$H NMR (300 MHz, DMSO-D$_6$) δ ppm 5.45 (br s, 2H) 7.26 (d, J=5.8 Hz, 1H) 7.36–7.71 (m, 9H) 7.83 (d, J=5.8 Hz, 1H) 7.95 (d, J=7.5 Hz, 1H) 8.03 (d, J=7.5 Hz, 1H) 8.15 (d, J=8.1 Hz, 1H) 8.85 (s, 1H) 9.26 (s, 1H); MS ESI(+) m/e 411 (M+H)$^+$.

EXAMPLE 747

N-[4-(4-aminothieno[3,2-c]pyridin-3-yl)phenyl]-N'-2-naphthylurea

The desired product was prepared by substituting example 17A and 2-isocyanatonaphthalene for example 121B and 1-fluoro-2-isocyanato-4-(trifluoromethyl)benzene in example 122. $^1$H NMR (300 MHz, DMSO-D$_6$) δ ppm 5.44 (br s, 2H) 7.26 (d, J=5.4 Hz, 1H) 7.33–7.49 (m, 5H) 7.52 (dd, J=8.8, 2.03 Hz, 1H) 7.64 (d, J=8.8 Hz, 2H) 7.76–7.90 (m, 4H) 8.13 (d, J=2.0 Hz, 1H) 8.97 (s, 2H); MS ESI(+) m/e example 461 for example 11B and 2-piperazinone in example 11C. $^1$H NMR (300 MHz, DMSO-D$_6$) δ ppm 2.23 (s, 6H), 2.29 (s, 3H), 2.49–2.53 (m, 2H), 2.64 (t, J=7.0 Hz, 2H), 5.55 (s, 2H), 6.81 (d, J=7.1 Hz, 1H), 7.17 (t, J=7.8 Hz, 1H), 7.26 (d, J=8.5 Hz, 1H), 7.30–7.35 (m, 2H), 7.37–7.47 (m, 3H), 7.49 (s, 1H), 7.58–7.64 (m, 3H), 7.88 (s, 1H), 7.98 (t, J=1.7 Hz, 1H), 8.69 (s, 1H), 8.89 (s, 1H), 10.19 (s, 1H) MS (ESI(+)) m/e 565.0 (M+H)$^+$.

EXAMPLE 686

N-(3-{4-amino-3-[4-({[(3-methylphenyl)amino]carbonyl}amino)phenyl]thieno[3,2-c]pyridin-7-yl}phenyl)-4-(dimethylamino)butanamide The desired product was prepared by substituting 4-dimethylaminobutyric acid and example 461 for example 11B and 2-piperazinone in example 11C. $^1$H NMR (300 MHz, DMSO-D$_6$) δ ppm 1.76–1.87 (m, 2H), 2.29 (s, 3H), 2.38 (s, 6H), 2.38–2.43 (m, 2H), 2.54–2.60 (m, 2H), 5.55 (s, 2H), 6.81 (d, J=7.5 Hz, 1H), 7.17 (t, J=7.8 Hz, 1H), 7.26 (d, J=8.5 Hz, 1H), 7.30–7.34 (m, 2H), 7.40 (d, J=8.5 Hz, 2H), 7.43 (t, J=7.8 Hz, 1H), 7.49 (s, 1H), 7.58–7.64 (m, 3H), 7.87 (s, 1H), 8.00 (t, J=1.9 Hz, 1H), 8.77 (s, 1H), 8.98 (s, 1H), 10.09 (s, 1H) MS (ESI(+)) m/e 579.0 (M+H)$^+$.

EXAMPLE 687

N-{4-[4-amino-7-(2-methyl-1,3-benzothiazol-5-yl)thieno[3,2-c]pyridin-3-yl]phenyl}-N'-(3-chlorophenyl)urea

EXAMPLE 687A 3-(4-aminophenyl)-7-(2-methyl-1,3-benzothiazol-5-yl)thieno[3,2-c]pyridin-4-amine The desired product was prepared by substituting 2-methyl-5-(4,4,5,5-tetramethyl-[1,3,2]dioxaborolan-2-yl)benzothiazole and example 77B for 4-phenoxyphenylboronic acid and example 1B in example 10A. MS (ESI(+) m/e 389 (M+H)$^+$.

EXAMPLE 687B

N-{4-[4-amino-7-(2-methyl-1,3-benzothiazol-5-yl)thieno[3,2-c]pyridin-3-yl]phenyl}-N'-(3-chlorophenyl)urea 3-(2-methyl-1H-indol-5-yl)-7-phenylthieno[3,2-c]pyridin-4-amine

EXAMPLE 749A 3-bromo-7-phenylthieno[3,2-c]pyridin-4-amine

The desired product was prepared by substituting Example 21A, phenylboronic acid, and PdCl$_2$(dppf) for Example 1B, 4-phenoxyphenylboronic acid, and Pd(PPh$_3$)$_4$ in Example 10A.

EXAMPLE 749B 3-(2-methyl-1H-indol-5-yl)-7-phenylthieno[3,2-c]pyridin-4-amine The desired product was prepared by substituting example 749A and example 467A for Example 21B and 4-chlorophenylboronic acid in Example 21C. $^1$H NMR (300 MHz, DMSO-D$_6$) 2.42 (s, 3H), 5.49 (s, 2H), 6.20 (s, 1H), 7.06 (dd, J=8.1, 1.7 Hz, 1H), 7.38–7.44 (m, 3H), 7.48 (d, J=1.4 Hz, 1H), 7.53 (t, J=7.6 Hz, 2H), 7.68 (d, J=7.1 Hz, 2H), 7.88 (s, 1H), 11.16 (s, 1H); MS (ESI(+)) m/e 355.9 (M+H)$^+$.

EXAMPLE 750

N-(4-{4-amino-7-[(4-methylpiperazin-1-yl)methyl]thieno[3,2-c]pyridin-3-yl}phenyl)-N'-(3-methylphenyl)urea

EXAMPLE 750A 3-bromo-7-[(4-methylpiperazin-1-yl)methyl]thieno[3,2-c]pyridin-4-amine The desired product was prepared by substituting N-methylpiperazine for morpholine in examples 278B.

EXAMPLE 750B

N-(4-{4-amino-7-[(4-methylpiperazin-1-yl)methyl]thieno[3,2-c]pyridin-3-yl}phenyl)-N'-(3-methylphenyl)urea The desired product was prepared by substituting Example 750A and Example 66D for Example 1B and 4-phenoxyphenylboronic acid respectively, in Example 10A. $^1$H NMR (300 MHz, DMSO-D$_6$) 2.16 (s, 3H), 2.29 (s, 3H), 2.30–2.45 (m, 8H), 3.58 (s, 2H), 5.34 (s, 2H), 6.80 (d, J=7.8 Hz, 1H), 7.17 (t, J=7.8 Hz, 1H), 7.25 (d, J=8.1 Hz, 1H) 7.31 (s, 1H), 7.36 (d, J=8.5 Hz, 2H), 7.39 (s, 1H), 7.58 (d, J=8.5 Hz, 2H), 7.68 (s, 1H), 8.66 (s, 1H), 8.84 (s, 1H) MS (ESI(+)) m/e 487.1 (M+H)$^+$.

EXAMPLE 751

N-(4-{4-amino-3-[4-({[(3-methylphenyl)amino]carbonyl}amino)phenyl]thieno[3,2-c]pyridin-7-yl}phenyl)methanesulfonamide The desired product was prepared by substituting example 458 and 1-isocyanato-3-methylbenzene for 121B and 1-fluoro-2-isocyanato-4-(trifluoromethyl)benzene in example 122. $^1$H NMR (300 MHz, DMSO-D$_6$) 2.29 (s, 3H), 3.10 (s, 3H), 6.82 (d, J=6.8 Hz, 1H), 7.18 (t, J=7.8 Hz, 1H), 7.27 (d, J=7.8 Hz, 1H), 7.32 (s, 1H), 7.39 (d, J=8.5 Hz, 2H), 7.45 (d, J=8.5 Hz, 2H), 7.63–7.70 (m, 4H), 7.83 (s, 1H), 7.93 (s, 1H), 8.73 (s, 1H), 8.98 (s, 1H), 10.06 (s, 1H). MS (ESI(+)) m/e 544.0 (M+H)$^+$.

EXAMPLE 752

3-(4-aminophenyl)-7-[2-(1H-benzimidazol-2-yl)vinyl]thieno[3,2-c]pyridin-4-amine

EXAMPLE 752A tert-butyl 3-(4-amino-3-bromothieno[3,2-c]pyridin-7-yl)acrylate The desired product was prepared by substituting example 21A for example 10B in example 11A.

EXAMPLE 752B 3-(4-amino-3-bromothieno[3,2-c]pyridin-7-yl)acrylic acid

The desired product was prepared by substituting 752A for example 11A in example 11B.

EXAMPLE 752C

7-[2-(1H-benzimidazol-2-yl)vinyl]-3-bromothieno[3,2-c]pyridin-4-amine

Example 752B (200 mg, 0.39 mmol) in polyphosphoric acid (0.5 mL0 was treated with benzene-1,2-diamine (45 mg, 0.42 mmol) and heated at 170° C. for 3 hours. The mixture was cooled to room temperature and diluted with ice and concentrated NH$_4$OH. The resulting solid was collected via filtration to give 125 mg of the title compound. MS (ESI(+)) m/e 370.8, 372.8 (M+H)$^+$.

EXAMPLE 752D 3-(4-aminophenyl)-7-[2-(1H-benzimidazol-2-yl)vinyl]thieno[3,2-c]pyridin-4-amine The desired product was prepared by substituting example 752C and 4-(4,4,5,5-tetramethyl-[1,3,2]dioxaborolan-2-yl)phenylamine for example 21B and 4-chlorophenylboronic acid in example 21C. $^1$H NMR (300 MHz, DMSO-D$_6$) 5.40 (s, 2H), 5.91 (s, 2H), 6.70 (d, J=8.5 Hz, 2H), 7.09–7.21 (m, 5H), 7.46–7.50 (m, 2H), 7.57–7.60 (m, 1H), 7.81 (d, J=16.6 Hz, 1H), 8.17 (s, 1H), 12.63 (s, 1H) MS (ESI(+)) m/e 383.9 (M+H)$^+$.

EXAMPLE 753

7-(4-aminophenyl)-3-(1H-indol-5-yl)thieno[3,2-c]pyridin-4-amine

The desired product was prepared by substituting example 492A and 1H-indol-5-ylboronic acid for example 21B and 4-chlorophenylboronic acid in example 21C. $^1$H NMR (300 MHz, DMSO-D$_6$) 5.23 (s, 2H), 5.31 (s, 2H), 6.50–6.52 (m, 1H), 6.69 (d, J=8.5 Hz, 2H), 7.15 (dd, J=8.5, 1.7 Hz, 1H), 7.32 (d, J=8.5 Hz, 2H), 7.39 (s, 1H), 7.45–7.48 (m, 1H), 7.53 (d, J=8.1 Hz, 1H), 7.62 (s, 1H), 7.76 (s, 1H), 11.32 (s, 1H); MS (ESI(+)) m/e 356.9 (M+H)$^+$.

EXAMPLE 754

N-{3-[4-amino-3-(2-methyl-1H-indol-5-yl)thieno[3,2-c]pyridin-7-yl]phenyl}methanesulfonamide

EXAMPLE 754A

N-[3-(4-amino-3-bromothieno[3,2-c]pyridin-7-yl)phenyl]methanesulfonamide

The desired product was prepared by substituting Example 21A, 3-(methylsulfonylamino)phenylboronic acid, and PdCl$_2$(dppf) for Example 1B, 4-phenoxyphenylboronic acid, and Pd(PPh$_3$)$_4$ in Example 10A.

EXAMPLE 754B

N-{3-[4-amino-3-(2-methyl-1H-indol-5-yl)thieno[3,2-c]pyridin-7-yl]phenyl}methanesulfonamide The desired product was prepared by substituting example 755A and example 467A for Example 21B and 4-chlorophenylboronic acid in Example 21C. $^1$H NMR (300 MHz, DMSO-D$_6$) 2.42 (s, 3H), 3.08 (s, 3H), 5.52 (s, 2H), 6.20 (s, 1H), 7.06 (dd, J=8.1, 1.7 Hz, 1H), 7.23 (ddd, J=7.9, 2.1, 0.8 Hz, 1H), 7.37–7.51 (m, 5H), 7.55 (t, J=1.9 Hz, 1H), 7.87 (s, 1H), 9.92 (s, 1H), 11.16 (s, 1H); MS (ESI(+)) m/e 449.0 (M+H)$^+$.

EXAMPLE 755

N-{4-[4-amino-3-(2-methyl-1H-indol-5-yl)thieno[3,2-c]pyridin-7-yl]phenyl}acetamide

EXAMPLE 755A

N-[4-(4-amino-3-bromothieno[3,2-c]pyridin-7-yl)phenyl]acetamide

The desired product was prepared by substituting Example 21A, 4-acetamidophenylboronic acid, and PdCl$_2$(dppf) for Example 1B, 4-phenoxyphenylboronic acid, and Pd(PPh$_3$)$_4$ in Example 10A.

EXAMPLE 755B

N-{4-[4-amino-3-(2-methyl-1H-indol-5-yl)thieno[3,2-c]pyridin-7-yl]phenyl}acetamide The desired product was prepared by substituting example 755A and example 467A for Example 21B and 4-chlorophenylboronic acid in Example 21C. $^1$H NMR (300 MHz, DMSO-D$_6$) 2.08 (s, 3H), 2.42 (s, 3H), 5.44 (s, 2H), 6.19–6.21 (m, 1H), 7.06 (dd, J=8.5, 1.7 Hz, 1H), 7.40 (d, J=8.1 Hz, 1H), 7.41 (s, 1H), 7.47 (d, J=1.4 Hz, 1H), 7.60 (d, J=8.8 Hz, 2H), 7.71 (d, J=8.8 Hz, 2H), 7.85 (s, 1H), 10.06 (s, 1H), 11.15 (s, 1H); MS (ESI(+)) m/e 412.9 (M+H)$^+$.

EXAMPLE 756

N-[4-(4-amino-7-pyridin-4-ylthieno[3,2-c]pyridin-3-yl)phenyl]-N'-(3-fluorophenyl)urea The desired product was prepared by substituting 1-fluoro-3-isocyanatobenzene for 1-fluoro-2-isocyanato-4-(trifluoromethyl)benzene in example 122. $^1$H NMR (300 MHz, DMSO-D$_6$) δ ppm 5.74 (s, 2H) 6.74–6.86 (m, 1H) 7.15 (d, J=8.14 Hz, 1H) 7.26–7.37 (m, 1H) 7.42 (d, J=8.48 Hz, 2H) 7.47–7.56 (m, 2H) 7.63 (d, J=8.81 Hz, 2H) 7.73 (d, J=6.10 Hz, 2H) 8.09 (s, 1H) 8.69 (d, J=6.10 Hz, 2H) 8.98 (d, J=7.46 Hz, 2H); MS (ESI(+)) m/e 456 (M+H)$^+$.

EXAMPLE 757

N-[4-(4-amino-7-pyridin-4-ylthieno[3,2-c]pyridin-3-yl)phenyl]-N'-(3-chlorophenyl)urea The desired product was prepared by substituting 1-chloro-3-isocyanatobenzene for 1-fluoro-2-isocyanato-4-(trifluoromethyl)benzene in example 122. $^1$H NMR (300 MHz, DMSO-D$_6$) δ ppm 5.74 (s, 2H) 7.01–7.07 (m, 1H) 7.29–7.34 (m, 2H) 7.42 (d, J=8.48 Hz, 2H) 7.54 (s, 1H) 7.63 (d, J=8.48 Hz, 2H) 7.70–7.76 (m, 3H) 8.09 (s, 1H) 8.69 (d, J=6.44 Hz, 2H) 8.98 (d, J=2.71 Hz, 2H); MS (ESI(+)) m/e 472 (M+H)$^+$.

EXAMPLE 758

N-[4-(4-amino-7-pyridin-4-ylthieno[3,2-c]pyridin-3-yl)phenyl]-N'-[3-(trifluoromethyl)phenyl]urea The desired product was prepared by substituting 1-isocyanato-3-(trifluoromethyl)benzene for 1-fluoro-2-isocyanato-4-(trifluoromethyl)benzene in example 122. $^1$H NMR (300 MHz, DMSO-D$_6$) δ ppm 5.75 (s, 2H) 7.33 (d, J=7.46 Hz, 1H) 7.42 (d, J=8.48 Hz, 2H) 7.52–7.58 (m, 2H) 7.63 (t, J=8.99 Hz, 3H) 7.73 (d, J=6.44 Hz, 2H) 8.04 (s, 1H) 8.09 (s, 1H) 8.69 (d, J=6.10 Hz, 2H) 9.03 (s, 1H) 9.14 (s, 1H); MS (ESI(+)) m/e 506 (M+H)$^+$.

EXAMPLE 759

N-[4-(4-amino-7-pyridin-4-ylthieno[3,2-c]pyridin-3-yl)phenyl]-N'-1,3-benzodioxol-5-ylurea The desired product was prepared by substituting 5-isocyanato-1,3-benzodioxole for 1-fluoro-2-isocyanato-4-(trifluoromethyl)benzene in example 122. $^1$H NMR (300 MHz, DMSO-D$_6$) δ ppm 5.74 (s, 2H) 5.98 (s, 2H) 6.75–6.81 (m, 1H) 6.82–6.87 (m, 1H) 7.22 (d, J=2.03 Hz, 1H) 7.40 (d, J=8.48 Hz, 2H) 7.53 (s, 1H) 7.60 (d, J=8.48 Hz, 2H) 7.72 (d, J=6.10 Hz, 2H) 8.09 (s, 1H) 8.63 (s, 1H) 8.68 (d, J=6.10 Hz, 2H) 8.83 (s, 1H); MS (ESI(+)) m/e 482 (M+H)$^+$.

EXAMPLE 760

N-[4-(4-amino-7-pyridin-4-ylthieno[3,2-c]pyridin-3-yl)phenyl]-N'-thien-3-ylurea

The desired product was prepared by substituting 3-isocyanatothiophene for 1-fluoro-2-isocyanato-4-(trifluoromethyl)benzene in example 122. $^1$H NMR (300 MHz, DMSO-D$_6$) δ ppm 5.75 (s, 2H) 7.08 (d, J=6.44 Hz, 1H) 7.31 (dd, J=3.05, 1.36 Hz, 1H) 7.40 (d, J=8.48 Hz, 2H) 7.45 (dd, J=5.09, 3.05 Hz, 1H) 7.53 (s, 1H) 7.62 (d, J=8.48 Hz, 2H) 7.72 (d, J=6.10 Hz, 2H) 8.09 (s, 1H) 8.69 (d, J=6.10 Hz, 2H) 8.86 (s, 1H) 9.02 (s, 1H); MS (ESI(+)) m/e 444 (M+H)$^+$.

EXAMPLE 761

N-[4-(4-aminothieno[3,2-c]pyridin-3-yl)phenyl]-N'-thien-3-ylurea

The desired product was prepared by substituting example 17A and 3-isocyanatothiophene for example 121B and 1-fluoro-2-isocyanato-4-(trifluoromethyl)benzene in example 122. $^1$H NMR (300 MHz, DMSO-D$_6$) δ ppm 5.42 (s, 2H) 7.07 (dd, J=5.09, 1.36 Hz, 1H) 7.25 (d, J=5.43 Hz, 1H) 7.31 (dd, J=3.22, 1.19 Hz, 1H) 7.36 (d, J=8.48 Hz, 2H) 7.42 (s, 1H) 7.45 (dd, J=5.09, 3.05 Hz, 1H) 7.60 (d, J=8.82 Hz, 2H) 7.82 (d, J=5.43 Hz, 1H) 8.83 (s, 1H) 9.01 (s, 1H); MS (ESI(+)) m/e 367 (M+H)$^+$.

EXAMPLE 762

N-(4-{4-amino-7-[3-(4-methylpiperazin-1-yl)prop-1-ynyl]furo[3,2-c]pyridin-3-yl}phenyl)-N'-(3-methylphenyl)urea The desired product was prepared by substituting example 547D and 1-methyl-4-prop-2-ynylpiperazine for example 144A and 3-butyn-1-ol in example 144B. $^1$H NMR (500 MHz, DMSO-D$_6$) δ ppm 2.49 (s, 3H), 2.68 (s, 3H), 2.84–2.94 (m, 4H), 2.96–3.07 (m, 4H), 3.85 (s, 2H), 6.07 (s, 2H), 7.01 (d, J=7.18 Hz, 1H), 7.37 (t, J=7.80 Hz, 1H), 7.46 (d, J=8.42 Hz, 1H), 7.52 (s, 1H), 7.63 (d, J=8.42 Hz, 2H), 7.82 (d, J=8.42 Hz, 2H), 8.20 (s, 1H), 8.20 (s, 1H), 8.93 (s, 1H), 9.13 (s, 1H); MS ESI(+)) m/e 495 (M+H)$^+$.

EXAMPLE 763

N-(4-{7-[(4-acetylpiperazin-1-yl)carbonyl]-4-aminothieno[3,2-c]pyridin-3-yl}phenyl)-N'-(3-methylphenyl)urea The desired product was prepared by substituting example 602 and 1-acetylpiperazine for example 11B and 2-piperazinone in example 11C. $^1$H NMR (300 MHz, DMSO-D$_6$) δ ppm 2.04 (s, 3H), 2.29 (s, 3H), 3.50–3.66 (m, 8H), 5.86 (s, 2H), 6.81 (d, J=7.5 Hz, 1H), 7.17 (t, J=7.6 Hz, 1H), 7.25 (d, J=8.1 Hz, 1H), 7.32 (s, 1H), 7.38 (d, J=8.5 Hz, 2H), 7.50 (s, 1H), 7.60 (d, J=8.5 Hz, 2H), 8.02 (s, 1H), 8.66 (s, 1H), 8.86 (s, 1H) MS (ESI(+)) m/e 528.8 (M+H)$^+$.

EXAMPLE 764

N-(4-{4-amino-7-[(4-isopropylpiperazin-1-yl)carbonyl]thieno[3,2-c]pyridin-3-yl}phenyl)-N'-(3-methylphenyl)urea The desired product was prepared by substituting example 602 and 1-isopropylpiperazine for example 11B and 2-piperazinone in example 11C. $^1$H NMR (300 MHz, DMSO-D$_6$) δ ppm 0.99 (d, J=6.4 Hz, 6H), 2.29 (s, 3H), 2.46–2.52 (m, 4H), 2.65–2.74 (m, 1H), 3.55–3.60 (m, 4H), 5.81 (s, 2H), 6.81 (d, J=7.5 Hz, 1H), 7.17 (t, J=7.8 Hz, 1H), 7.25 (d, J=8.5 Hz, 1H), 7.31 (s, 1H), 7.37 (d, J=8.8 Hz, 2H), 7.49 (s, 1H), 7.60 (d, J=8.5 Hz, 2H), 7.95 (s, 1H), 8.67 (s, 1H), 8.87 (s, 1H) MS (ESI(+)) m/e 528.9 (M+H)$^+$.

EXAMPLE 765

N-(4-{4-amino-7-[(4-pyrimidin-2-ylpiperazin-1-yl)carbonyl]thieno[3,2-c]pyridin-3-yl}phenyl)-N'-(3-methylphenyl)urea The desired product was prepared by substituting example 602 and 2-piperazin-1-ylpyrimidine for example 11B and 2-piperazinone in example 11C. $^1$H NMR (300 MHz, DMSO-D$_6$) δ ppm 2.29 (s, 3H), 3.69 (dd, J=6.4, 3.4 Hz, 4H), 3.84 (dd, J=6.4, 3.4 Hz, 4H), 5.85 (s, 2H), 6.68 (t, J=4.7 Hz, 1H), 6.81 (d, J=7.5 Hz, 1H), 7.17 (t, J=7.8 Hz, 1H), 7.25 (d, J=7.1 Hz, 1H), 7.32 (s, 1H), 7.38 (d, J=8.5 Hz, 2H), 7.50 (s, 1H), 7.61 (d, J=8.5 Hz, 2H), 8.04 (s, 1H), 8.40 (d, J=4.7 Hz, 2H), 8.66 (s, 1H), 8.86 (s, 1H); MS (ESI(+)) m/e 564.5 (M+H)$^+$.

EXAMPLE 766

N-(4-{4-amino-7-[(4-phenylpiperazin-1-yl)carbonyl]thieno[3,2-c]pyridin-3-yl}phenyl)-N'-(3-methylphenyl)urea The desired product was prepared by substituting example 602 and 1-phenylpiperazine for example 11B and 2-piperazinone in example 11C. $^1$H NMR (300 MHz, DMSO-D$_6$) δ ppm 2.29 (s, 3H), 3.20–3.25 (m, 4H), 3.72–3.78 (m, 4H), 5.85 (s, 2H), 6.82 (t, J=7.3 Hz, 2H), 6.98 (d, J=8.1 Hz, 2H), 7.17 (t, J=7.8 Hz, 1H), 7.21–7.28 (m, 3H), 7.32 (s, 1H), 7.38 (d, J=8.5 Hz, 2H), 7.50 (s, 1H), 7.61 (d, J=8.8 Hz, 2H), 8.03 (s, 1H), 8.66 (s, 1H), 8.86 (s, 1H) MS (ESI(+)) m/e 562.7 (M+H)$^+$.

EXAMPLE 767

N-(4-{4-amino-7-[(4-pyridin-4-ylpiperazin-1-yl)carbonyl]thieno[3,2-c]pyridin-3-yl}phenyl)-N'-(3-methylphenyl)urea The desired product was prepared by substituting example 602 and 1-pyridin-4-ylpiperazine for example 11B and 2-piperazinone in example 11C. $^1$H NMR (300 MHz, DMSO-D$_6$) δ ppm 2.29 (s, 3H), 3.45 (dd, J=5.8, 4.1 Hz, 4H), 3.73 (dd, J=5.8, 4.1 Hz, 4H), 5.86 (s, 2H), 6.81 (d, J=7.5 Hz, 1H), 6.84 (d, J=6.8 Hz, 2H), 7.17 (t, J=7.6 Hz, 1H), 7.26 (d, J=8.8 Hz, 1H), 7.32 (s, 1H), 7.38 (d, J=8.8 Hz, 2H), 7.51 (s, 1H), 7.61 (d, J=8.5 Hz, 2H), 8.05 (s, 1H), 8.19 (d, J=6.4 Hz, 2H), 8.66 (s, 1H), 8.86 (s, 1H) MS (ESI(+)) m/e 563.6 (M+H)$^+$.

EXAMPLE 768

N-(4-{4-amino-7-[(4-ethylpiperazin-1-yl)carbonyl]thieno[3,2-c]pyridin-3-yl}phenyl)-N'-(3-methylphenyl)urea The desired product was prepared by substituting example 602 and 1-ethylpiperazine for example 11B and 2-piperazinone in example 11C. $^1$H NMR (300 MHz, DMSO-D$_6$) δ ppm 1.02 (t, J=7.3 Hz, 3H), 2.29 (s, 3H), 2.36 (q, J=7.1 Hz, 2H), 2.39–2.43 (m, 4H), 3.56–3.61 (m, 4H), 5.82 (s, 2H), 6.81 (d, J=7.8 Hz, 1H), 7.17 (t, J=7.8 Hz, 1H), 7.26 (d, J=8.5 Hz, 1H), 7.32 (s, 1H), 7.37 (d, J=8.5 Hz, 2H), 7.49 (s, 1H), 7.60 (d, J=8.8 Hz, 2H), 7.95 (s, 1H), 8.68 (s, 1H), 8.87 (s, 1H) MS (ESI(+)) m/e 514.9 (M+H)$^+$.

EXAMPLE 769

N-{4-[4-amino-7-({4-[2-(dimethylamino)ethyl]piperazin-1-yl}carbonyl)thieno[3,2-c]pyridin-3-yl]phenyl}-N'-(3-methylphenyl)urea The desired product was prepared by substituting example 602 and N,N-dimethyl-N-(2-piperazin-1-ylethyl)amine for example 11B and 2-piperazinone in example 11C. $^1$H NMR (300 MHz, DMSO-D$_6$) δ ppm 2.14 (s, 6H), 2.29 (s, 3H), 2.32–2.48 (m, 8H), 3.54–3.60 (m, 4H), 5.82 (s, 2H), 6.80 (d, J=7.5 Hz, 1H), 7.17 (t, J=7.6 Hz, 1H), 7.26 (d, J=8.5 Hz, 1H), 7.31 (s, 1H), 7.37 (d, J=8.8 Hz, 2H), 7.49 (s, 1H), 7.60 (d, J=8.5 Hz, 2H), 7.94 (s, 1H), 8.87 (s, 1H), 9.10 (s, 1H) m/e 557.8 (M+H)$^+$.

EXAMPLE 770

N-[4-(4-amino-7-pyridin-4-ylthieno[3,2-c]pyridin-3-yl)phenyl]-N'-thien-2-ylurea

The desired product was prepared by substituting 2-isocyanatothiophene for 1-fluoro-2-isocyanato-4-(trifluoromethyl)benzene in example 122. $^1$H NMR (300 MHz, DMSO-D$_6$) δ ppm 5.74 (s, 2H) 6.59 (d, J=5.09 Hz, 1H) 6.79–6.85 (m, 1H) 6.86–6.94 (m, 1H) 7.41 (d, J=8.48 Hz, 2H) 7.54 (s, 1H) 7.63 (d, J=8.82 Hz, 2H) 7.72 (d, J=6.10 Hz, 2H) 8.09 (s, 1H) 8.68 (d, J=6.10 Hz, 2H) 8.96 (s, 1H) 9.71 (s, 1H); MS (ESI(+)) m/e 444 (M+H)$^+$.

EXAMPLE 771

N-[4-(4-aminothieno[3,2-c]pyridin-3-yl)phenyl]-N'-thien-2-ylurea

The desired product was prepared by substituting example 17A and 2-isocyanatothiophene for example 121B and 1-fluoro-2-isocyanato-4-(trifluoromethyl)benzene in example 122. $^1$H NMR (300 MHz, DMSO-D$_6$) δ ppm 5.41 (s, 2H) 6.59 (dd, J=3.73, 1.36 Hz, 1H) 6.80–6.85 (m, 1H) 6.87–6.91 (m, 1H) 7.26 (d, J=5.42 Hz, 1H) 7.38 (d, J=8.81 Hz, 2H) 7.42 (s, 1H) 7.60 (d, J=8.48 Hz, 2H) 7.82 (d, J=5.42 Hz, 1H) 8.93 (s, 1H) 9.70 (s, 1H); MS (ESI(+)) m/e 367 (M+H)$^+$.

General Procedure A

A mixture of a boronate ester or a boronic acid (1–5 equivalents, preferably 1–1.5 equivalents), a halide (for example a bromide or an iodide, preferably an iodide) (preferably 1.0 equivalent) and a base (for example, sodium carbonate or cesium carbonate, preferably sodium carbonate) (1–10 equivalents, preferably 2–3 equivalents) is heated in a mixture of an organic solvent (for example, ethylene glycol dimethyl ether, N,N-dimethylformamide, or toluene, preferably ethylene glycol dimethyl ether) and water at about 20–150° C. (preferably about 80–95° C.). A palladium catalyst (for example, palladium(II) acetate, tris(dibenzylideneacetone)dipalladium(0), tetrakis(triphenylphosphine)palladium(0), preferably tetrakis(triphenylphosphine)-palladium(0)) (0.01–0.2 equivalents, preferably 0.05–0.09 equivalents) is added and the reaction mixture is allowed to stir for about 1–48 hours (preferably about 2–18 hours) under an inert atmosphere. The mixture is allowed to cool to ambient temperature and the solvents are removed under reduced pressure. The residue is partitioned between water and an organic solvent, the organic layer is separated and the aqueous layer is further extracted with organic solvent. The combined organic extracts are dried over a desiccant. The solvents are evaporated under reduced pressure to afford the product that can be further purified by crystallization or chromatography.

EXAMPLE 780

N-(4-{4-amino-7-[3-(dimethylamino)phenyl]thieno[3,2-c]pyridin-3-yl}-2-methoxyphenyl)-1-methyl-1H-indole-2-carboxamide A mixture of 1-Methyl-1H-indole-2-carboxylic acid [4-(4-amino-7-iodo-thieno[3,2-c]pyridin-3-yl)-2-methoxyphenyl]-amide (0.100 g, 0.18 mmol) in 1,2-dimethoxyethane (3 mL) and water (1.5 mL) was reacted with 3-(dimethylamino)phenylboronic acid (0.045 g, 0.27 mmol), sodium carbonate (0.06 g, 0.54 mmol) and tetrakis triphenylphosphine palladium (0) (0.017 g, 0.01 mmol) at reflux for two hours. The solvent was removed in vacuo and the residue was purified by preparative RP-HPLC (Hypersil-HS 100 A, C18, 8 μm, 100 Å, 25 cm; 5% acetonitrile—0.1M ammonium acetate 5–100% acetonitrile—0.1M ammonium acetate over 25 min, 21 ml/min). The acetonitrile was removed in vacuo and the aqueous mixture was lyophilized to provide the title compound (20 mg) as an off-white powder. $^1$H NMR (DMSO-d$_6$, 400 MHz) δ 9.52 (s, 1H), 8.01 (t, 1H), 7.94 (s, 1H), 7.72 (d, 1H), 7.58 (m, 2H), 7.34 (m, 3H), 7.23 (s, 1H), 7.16 (t, 1H), 7.10 (d, 1H), 6.97 (s, 1H), 6.95 (d, 1H), 6.79 (d, 1H), 5.56 (bs, 2H), 4.04 (s, 3H), 3.92 (s, 3H), 2.97 (s, 6H); LCMS (Conditions b), Rt=6.22 min, MS m/e: 548 (M+H)$^+$.

General Procedure B

To a suspension of the appropriate aldehyde or ketone substrate and a primary or secondary amine (1–10 eq, preferably 1–4 equvalents) in an organic solvent (for example dichloromethane, ethyl acetate, N,N-dimethylformamide or dichloroethane, preferably dichloroethane) was added sodium triacetoxy borohydride (1–10 equivalents, preferably 1–2 equivalents). The resulting solution was allowed to stir at room temperature for 2–20 hours. Acetic acid (catalytic—10 equivalents, preferably 1 drop to 4 equivalents) was added to progress the reaction when necessary. Upon completion, the reaction solution was treated with an aqueous solution of an appropriate base (sodium hydroxide, sodium bicarbonate, or sodium carbonate preferably sodium bicarbonate) and dichloromethane. The layers were separated and the organic layer was concentrated under reduced pressure. When a Boc protected amine was used the group was removed by treating the residue with 2:1 acetone/6 N HCl for 2 hours at ambient temperature to give the title compound. The resulting crude product was purified by either trituration with an appropriate solvent (for example water, dichloromethane, ethyl acetate, toluene or ethanol) or by chromatography.

EXAMPLE 781

1-{(2E)-3-[4-amino-3-(3-methoxy-4-{[(1-methyl-1H-indol-2-yl)carbonyl]amino}phenyl)thieno[3,2-c]pyridin-7-yl]prop-2-enyl}azetidine-3-carboxylic acid diacetate A mixture of N-(4-{4-amino-7-[(1E)-3-oxoprop-1-enyl]thieno[3,2-c]pyridin-3-yl}-2-methoxyphenyl)-1-methyl-1H-indole-2-carboxamide (0.05 g, 0.104 mmol) and azetidine-3-carboxylic acid (0.207 mmol, 2 eq.) in 1,2-dichloroethane (3 mL) was stirred fifteen minutes, at ambient temperature, and then reacted with sodium triacetoxyborohydride (0.044 g, 0.207 mmol) and acetic acid (1 drop) at ambient temperature for eighteen hours. The solvent was removed in vacuo and the residue was partitioned between dichloromethane (5 mL) and 5 N aqueous sodium hydroxide (10 mL). The layers were separated and the aqueous layer was extracted with dichloromethane (3×5 mL). The residue was purified by preparative RP-HPLC (Hypersil-HS C18, 8 μm, 100 Å, 25 cm; 5–100% acetonitrile—0.1M ammonium acetate over 25 min, 21 ml/min). The acetonitrile was removed in vacuo and the aqueous mixture was lyophilized to give the title compound as a white solid. $^1$H NMR (DMSO-d$_6$, 400 MHz) δ 9.51 (s, 1H), 7.98 (d, 1H), 7.96 (s, 1H), 7.69 (d, 1H), 7.62 (s, 1H), 7.58 (d, 1H), 7.33 (m, 2H), 7.20 (d, 1H), 7.15 (d, 1H), 7.07 (dd, 1H), 6.67 (d, 1H), 6.11 (m, 1H), 5.6 (bs, 2H), 4.04 (s, 3H), 3.91 (s, 3H), 3.43 (t, 2H), 3.1–3.25 (m, 5H), 1.89 (s, 6H); LCMS (Conditions a), R$_t$ 1.93 min.; MS: MH$^+$ 568.

General Procedure C

To a suspension of the appropriate amine substrate (1.0 equivalent) and ketone/aldehyde (1–10 equivalents, preferably 1.2–1.5 equivalents) in an organic solvent such as 1,2-dichloroethane, dichloromethane, N,N,-dimethylformamide, or ethyl acetate (preferably 1,2-dichloroethane) was added sodiumtriacetoxy borohydride (1–10 equivalents, preferably 1.4–2.0 equivalents). The resulting solution was allowed to stir at room temperature for 2–20 hours. Acetic acid (catalytic—10 eq., preferably 1 drop to 4 eq.) was added to progress the reaction when necessary. Upon completion, the reaction solution was treated with an aqueous solution of an appropriate base (sodium hydroxide, sodium bicarbonate, or sodium carbonate, preferably sodium bicarbonate) and dichloromethane. The two layers were stirred for 15 minutes, followed by separation of the two layers, and removal of the organic solvent. The resulting crude product was purified by either trituration with an appropriate solvent (water, ethanol, toluene, or ethyl acetate, preferably ethanol) or by chromatography

EXAMPLE 782 ethyl 4-({(2E)-3-[4-amino-3-(3-methoxy-4-{[(1-methyl-1H-indol-2-yl)carbonyl]amino}phenyl)thieno[3,2-c]pyridin-7-yl]prop-2-enyl}amino)piperidine-1-carboxylate To a suspension of N-(4-{4-amino-7-[(1E)-3-aminoprop-1-enyl]thieno[3,2-c]pyridin-3-yl}-2-methoxyphenyl)-1-methyl-1H-indole-2-carboxamide (0.050 g, 0.104 mmol) and ethyl 4-oxo-1-piperidinecarboxylate (0.017 g, 0.087 mmol) in dichloroethane (1.5 mL) was added sodiumtriacetoxy borohydride (0.036 g, 0.173 mmol). The resulting solution was allowed to stir at room temperature for 12 hours. Upon completion, the reaction solution was treated with an aqueous solution of 10% sodium hydroxide (3 mL) and dichloromethane (3 mL). The two layers were stirred for 15 minutes, followed by filtration through an Empore™ cartridge, and removal of the solvent. The resulting crude product was purified by trituration of the residue in ethanol and collection of the title compound (0.030 g, 45%) as a white powder. LCMS (Conditions a) R$_t$ 3.57 minutes, 639.4 (MH+); $^1$H NMR (400 MHz, DMSO-d$_6$) δ 9.51 (s, 1H), 8.01 (dd, J=8.2 Hz, J=7.8 Hz, 1H), 7.95 (s, 1H), 7.71 (d, J=8.2 Hz, 1H), 7.62 (s, 1H), 7.59 (d, J=8.2 Hz, 1H), 7.35 (s, 1H), 7.32 (d, J=8.5 Hz, 1H), 7.21 (d, J=1.9 Hz, 1H), 7.15 (t, J=7.8 Hz, 1H), 7.08 (dd, J=8.2 Hz, 1.9 Hz, 1H), 6.67 (d, J=16.0 Hz, 1H), 6.29 (td, J=16.4 Hz, J=5.9 Hz, 1H), 5.61 (s (br), 1H), 4.04 (s, 3H), 4.02 (q, J=7.02 Hz, 2H), 3.91 (s, 3H), 3.88 (m, 2H), 3.42 (d, J=5.5 Hz, 2H), 2.87 (m, 2H), 2.67 (m, 1H), 1.83 (m, 2H), 1.19 (m, 2H), 1.18 (t, J=7.02 Hz, 3H).

General Procedure D

An acid (1 equivalent) was combined with a peptide coupling reagent [such as O-benzotriazol-1-yl-N,N,N',N'-tetramethyluronium hexafluorophosphate/1-hydroxybenzotriazole hydrate, O-(7-azabenzotriazol-1-yl-N,N,N',N'-tetramethyluronium hexafluorophosphate, EEDQ, EDCI, or 1,3-dicyclohexylcarbodiimide/1-hydroxybenzotriazole hydrate, but preferably O-benzotriazol-1-yl-N,N,N',N'-tetramethyluronium hexafluorophosphate (0.1–5 equivalents, preferably 1.2 equivalents), 1-hydroxybenzotriazole hydrate (0.1–5 equivalents, preferably 1.2 equivalents)] and an organic solvent such as N,N-dimethylformamide, dichloromethane, ethylene glycol dimethyl ether, ethyl acetate, or toluene (preferably N,N-dimethylformamide). To the suspension was added an organic base such as diisopropylethylamine, N-methylmorpholine, triethylamine, or pyridine (preferably diisopropylethylamine) (0.5–10 equivalents, preferably 4–5 equivalents), and the appropriate amine (0.1–10 equivalents, preferably 1.1–1.2 equivalents). The vial was flushed with nitrogen gas prior to capping, and the reaction mixture was shaken at room temperature for 30 minutes-40 hours (preferably 1–16 hours). Upon completion of the reaction, methylene chloride and an aqueous base (saturated sodium bicarbonate, sodium hydroxide, or sodium carbonate, preferably saturated sodium bicarbonate) were added. The layers were shaken together, separated, and the organic solvent removed under reduced pressure. The crude products were purified by either trituration from the appropriate solvent (preferably water, diethyl ether, or ethanol/water), or chromatography.

EXAMPLE 783

4-amino-N-{2-[bis(2-hydroxyethyl)amino]ethyl}-3-(3-methoxy-4-{[(1-methyl-1H-indol-2-yl)carbonyl]amino}phenyl)thieno[3,2-c]pyridine-7-carboxamide A 20 mL scintillation vial was charged with 4-amino-3-(3-methoxy-4-{[(1-methyl-1H-indol-2-yl)carbonyl]amino}phenyl)thieno[3,2-c]pyridine-7-carboxylic acid (0.070 g, 0.148 mmol), O-benzotriazol-1-yl-N,N,N',N'-tetramethyluronium hexafluorophosphate (0.067 g, 0.177 mmol), 1-hydroxybenzotriazole hydrate (0.024 g, 0.177 mmol) and N,N-dimethylformamide (1.5 mL). To the suspension was added diisopropylethylamine (0.100 mL, 0.592 mmol) and 2-[(2-aminoethyl)(2-hydroxyethyl)amino]ethanol (0.024 mg, 0.162 mmol). The vial was flushed with nitrogen gas prior to capping, and the reaction mixture was shaken at room temperature for 12 hours. Upon completion of the reaction, methylene chloride (2 mL) and saturated sodium bicarbonate solution (2 mL) were added. The solution was filtered through an Empore™ cartridge, and the solvents removed under reduced pressure. The residues were taken up in a minimal amount of methanol and eluted (gravity) through a Si-carbonate™ cartridge (2 gram, 6 mL). The organic solution obtained was concentrated and the resulting residue triturated with water to give N7-2-[di(2-hydroxyethyl)amino]ethyl-4-amino-3-(3-methoxy-4-[(1-methyl-1H-2-indolyl)carbonyl]aminophenyl)thieno[3,2-c]pyridine-7-carboxamide as a precipitate. The title compound was collected and dried by vacuum filtration (15 mg, 14%). LCMS (Conditions a) $R_t$ 2.62 min., 603.4 (MH+); $^1$H NMR (400 MHz, DMSO-$d_6$) δ 9.51 (s, 1H), 8.51 (s, 1H), 8.39 (t, J=5.5 Hz, 1H), 7.99 (dd, J=7.8 Hz, 8.2 Hz, 1H), 7.70 (d, J=8.2 Hz, 1H), 7.59 (d, J=7.2 Hz, 1H), 7.58 (s, 1H), 7.35 (s, 1H), 7.32 (d, J=8.2 Hz, 1H), 7.20 (d, J=1.6 Hz, 1H), 7.15 (dd, J=7.8 Hz, 7.2 Hz, 1H), 7.07 (dd, J=8.2 Hz, 1.6 Hz, 1H), 4.41 (t, J=5.8 Hz, 1H), 4.04 (s, 3H), 3.91 (s, 3H), 3.44 (q, J=5.8 Hz, 4H), 3.34 (m, 2H), 2.68 (t, J=7.2 Hz, 2H), 2.61 (t, J=5.8 Hz, 4H).

General Procedure E

A mixture of amine (preferably one equivalent), a halide (for example a chloride, bromide or iodide) (0.1–2 equivalents, preferably 1–1.2 equvalents) and a base (for example, sodium carbonate, cesium carbonate or potassium carbonate, preferably potassium carbonate) (0.5–10 equivalents, preferably 1–2 equivalents) in a solvent (for example water, ethanol, ethyl acetate, THF or N,N-dimethylformamide, preferably N,N-dimethylformamide) was stirred at 20–120° C. (preferably 20–45° C.) for about 1–48 hours (preferably for about 12hours). The residue is partitioned between water and an organic solvent, the organic layer is separated and the aqueous layer is further extracted with organic solvent. The solvents are evaporated under reduced pressure to afford the product that can be further purified by crystallization or chromatography.

EXAMPLE 784

4-amino-N-{[1-(2-amino-2-oxoethyl)pyrrolidin-2-yl]methyl}-3-(3-methoxy-4-{[(1-methyl-1H-indol-2-yl)carbonyl]amino}phenyl)thieno[3,2-c]pyridine-7-carboxamide triacetate A mixture of 4-amino-3-(3-methoxy-4-{[(1-methyl-1H-indol-2-yl)carbonyl]amino}phenyl)-N-(pyrrolidin-2-ylmethyl)thieno[3,2-c]pyridine-7-carboxamide (0.100 g, 0.18 mmol), 2-bromoacetamide (0.03 g, 0.217 mmol) and potassium carbonate (0.05 g, 0.36 mmol) in N,N-dimethylformamide (2 mL) was stirred at ambient temperature for 18 hours. The solvent was removed in vacuo and the residue was purified by preparative RP-HPLC (Hypersil-HS C18, 8 μm, 100 Å, 25 cm; 5–100% acetonitrile—0.1M ammonium acetate over 25 min, 21 ml/min). The acetonitrile was removed in vacuo and the aqueous mixture was lyophilized to give the title compound as a white solid.: $^1$H NMR (DMSO-$d_6$, 400 MHz) δ 9.50(s, 1H), 8.56 (s, 1H), 8.44 (t, 1H), 7.98 (d, 1H), 7.69 (d, 1H), 7.58 (d, 1H), 7.58 (s, 1H), 7.35 (m, 3H), 7.15 (m, 3H), 7.06 (d, 1H), 6.0 (bs, 2H), 4.04 (s, 3H), 3.91 (s, 3H), 3.42 (m, 1H), 3.38 (d, 1H), 3.24 (m, 1H), 3.04 (m, 1H), 2.86 (d, 1H), 2.79 (m, 1H), 2.27 (m, 1H), 1.86 (s, 9H), 1.85 (m, 1H), 1.68 (m, 3H); LCMS (Conditions a), $R_t$ 2.88 min.; MS: MH+ 612.

General Procedure F

A mixture of an amine (preferably one equivalent), an acid chloride (0.1–3 equivalents, preferably 1–1.5 equivalents) and a base (for example triethyl amine, pyridine or N,N-diisopropylethyl amine, preferably N,N-diisopropylethyl amine) in a solvent (example water, N,N-dimethyl formamide, ethyl acetate, THF or dichloromethane, preferably dichloromethane) was stirred at ambient temperature for 1 hour-4 days (preferably 1–2 hours). The solvents are removed under reduced pressure. The residue is partitioned between water and an organic solvent, the organic layer is separated and the aqueous layer is further extracted with organic solvent. The organic solvents are evaporated under reduced pressure to afford the product that can be further purified by crystallization or chromatography.

EXAMPLE 785

4-amino-N-({1-[2-(dimethylamino)-2-oxoethyl]pyrrolidin-2-yl}methyl)-3-(3-methoxy-4-{[(1-methyl-1H-indol-2-yl)carbonyl]amino}phenyl)thieno[3,2-c]pyridine-7-carboxamide A mixture of 4-amino-3-(3-methoxy-4-{[(1-methyl-1H-indol-2-yl)carbonyl]amino}phenyl)-N-(pyrrolidin-2-ylmethyl)thieno[3,2-c]pyridine-7-carboxamide (0.100 g, 0.18 mmol), dimethylaminoacetyl chloride hydrochloride (0.035 g, 0.217 mmol) and N,N-diisopropylethyl amine (0.046 g, 0.360 mmol) in dichloromethane (2 mL) was stirred at ambient temperature for 1 hour. The mixture was diluted with dichloromethane then extracted with 2N aqueous sodium hydroxide. The layers were separated and the organic solution was concentrated and the residue was purified by flash chromatography on silica gel to provide the title compound: $^1$H NMR (DMSO-$d_6$, 400 MHz) δ 9.49 (s, 1H), 8.69 (t, 1H), 8.53 (d, 1H), 8.01 (m, 1H), 7.72 (d, 1H), 7.58 (m, 2H), 7.35 (m, 2H), 7.19 (s, 1H), 7.15 (t, 1H), 7.08 (d, 1H), 6.02 (bs, 2H), 4.25 (m, 1H), 4.04 (s, 3H), 3.91 (s, 3H), 3.48 (m, 2H), 3.10 (m, 2H), 2.26 (s, 6H), 1.7–2 (m, 4H); LCMS (Conditions a), $R_t$ 2.75 min.; MS: MH+ 640

General Procedure G

To a solution of an appropriate amine (1.0 equivalent) in an organic solvent (for example pyridine, dichloromethane, 1,2-dichloroethane; preferably pyridine or dichloromethane) was added the appropriately substituted sulfonyl chloride (0.5–5 equivalents, preferably 1.0–1.2 equivalents), and the mixture was stirred at ambient temperature for 1–24 hours (preferably 2–17 hours). The reaction mixture was diluted with an aqueous base such as sodium carbonate, sodium bicarbonate, or sodium hydroxide (preferably sodium bicarbonate) and the resulting mixture was extracted with dichloromethane. The layers were separated and the organic solvent removed under reduced pressure. The crude products were purified by chromatography to yield the pure products.

EXAMPLE 786

4-amino-3-(3-methoxy-4-{[(1-methyl-1H-indol-2-yl)carbonyl]amino}phenyl)-N-[1-(methylsulfonyl)piperidin-3-yl]thieno[3,2-c]pyridine-7-carboxamide A mixture of 4-amino-3-(3-methoxy-4-{[(1-methyl-1H-indol-2-yl)carbonyl]amino}phenyl)-N-piperidin-3-ylthieno[3,2-c]pyridine-7-carboxamide (150 mg, 0.270 mmol), methanesulfonyl chloride (26 µL, 0.32 mmol) and N,N-diisopropylethyl amine (0.15 mL, 0.81 mmol) in dichloromethane (5 mL) was stirred at room temperature for 2 hours. Saturated sodium bicarbonate (2 mL) was added. The layers were separated and the organic solvent was removed. The residue was purified by flash column chromatography on silica using dichloromethane/methanol/ammonium hydroxide (28–30% solution) (90:10:0.05) mixture as the mobile phase to give the title compound. $^1$H NMR (DMSO, d$_6$) δ 1.58 (m, 2H), 1.91 (m, 2H), 2.58 (m, 1H), 2.71 (m, 1H), 3.50(m, 1H), 3.73 (m, 1H), 3.91 (s, 3H), 3.99 (m 1H), 4.04 (m, 3H), 7.07 (d, 1H), 7.15 (t, 1H), 7.19 (s, 1H), 7.33 (t, 1H), 7.35 (s, 1H), 7.58 (m, 2H), 7.71 (d, 1H), 7.99 (d, 1H), 8.34 (d, 1H), 8.61 (s, 1H), 9.50 (s, 1H). LCMS (Conditions a) R$_t$=3.22 min., 633.0 (MH+).

General Procedure H

To a solution of an appropriate N-Boc amine in an organic solvent such as methylene chloride, 1,2-dichloroethane, ethyl acetate, or toluene (preferably dichloromethane) was added a solution of trifluoroacetic acid in that same organic solvent yielding a 10–50% (preferably 20%) solution of trifluoroacetic acid in the previously described solvent. The reaction solution was stirred at ambient temperature for 1–16 hours (preferably 2–3 hours) followed by removal of the solvents under reduced pressure. The resulting residue was dissolved in methylene chloride and washed with aqueous base (such as sodium hydroxide, sodium carbonate, sodium bicarbonate, preferably sodium hydroxide) to ensure that the free base was obtained. The organic layer was separated and the solvent removed under reduced pressure to give the free amine as an off-white/tan powder. If necessary, trituration from an appropriate solvent (preferably water, ethanol, toluene, diethyl ether, or ethyl acetate) or chromatography was carried out to purify the final products.

EXAMPLE 787

4-amino-3-(3-methoxy-4-{[(1-methyl-1H-indol-2-yl)carbonyl]amino}phenyl)-N-(piperidin-4-ylmethyl)thieno[3,2-c]pyridine-7-carboxamide To a solution of tert-butyl 4-[({[4-amino-3-(3-methoxy-4-{[(1-methyl-1H-indol-2-yl)carbonyl]amino}phenyl)thieno[3,2-c]pyridin-7-yl]carbonyl}amino)methyl]piperidine-1-carboxylate (0.066 g, 0.099 mmol) in dichloromethane (1.5 mL) was added a solution of trifluoroacetic acid (0.3 mL) in dicloromethane (0.3 mL) yielding a 20% solution of trifluoroacetic acid. The reaction solution was stirred at ambient temperature for 3 hours, followed by removal of the solvents under reduced pressure. The resulting residue was dissolved in methylene chloride and washed with a 0.5 N solution of sodium hydroxide to ensure that the free base was obtained. The organic layer was separated and the solvent removed under reduced pressure to give the title compound as an off-white/tan powder (0.032 g, 57%). LCMS (Conditions a), R$_t$ 2.92 minutes, 569.1 (MH+); $^1$H NMR (DMSO-d$_6$) δ 9.50 (s, 1H), 8.57 (s, 1H), 8.46 (t, J=5.9 Hz, 1H), 7.99 (d, J=7.8 Hz, 1H), 7.70 (d, J=8.2 Hz, 1H), 7.58 (d, J=8.8 Hz, 1H), 7.58 (s, 1H), 7.35 (s, 1H), 7.32 (d, J=8.2 Hz, 1H), 7.18 (s, 1H), 7.15 (dd, J=7.8, 7.0 Hz, 1H), 7.06 (d, J=8.2 Hz, 1H), 4.04 (s, 3H), 3.91 (s, 3H), 3.15 (m, 2H), 2.91 (m, 2H), 2.39 (m, 2H), 1.60 (m, 2H), 1.35 (m, 1H), 1.05 (m, 2H).

General Procedure I

Round bottom flasks were charged with a stir bar and an appropriate tosylate(1.0 equivalent). The appropriate amines (1–12 equivalents, preferably 2–8 eq) were added neat or with an appropriate organic solvent, preferably tetrahydrofuran or N,N-dimethylformamide. The reaction mixtures were stirred for 5–60 hours (preferably 15–48 hours) at 25–60° C., preferably 55–60° C. The solvents were removed under reduced pressure and the crude material was purified by chromatography.

EXAMPLE 788

(A-832021.15)

tert-butyl 1-{(3E)-4-[4-amino-3-(3-methoxy-4-{[(1-methyl-1H-indol-2-yl)carbonyl]amino}phenyl)thieno[3,2-c]pyridin-7-yl]but-3-enyl}piperidin-4-ylcarbamate A solution of (3E)-4-[4-amino-3-(3-methoxy-4-{[(1-methyl-1H-indol-2-yl)carbonyl]amino}phenyl)thieno[3,2-c]pyridin-7-yl]but-3-enyl 4-methylbenzenesulfonate (0.10 g, 0.15 mmol) in tetrahydrofuran (2 mL) was treated with 4-Boc-aminopiperidine (0.122 g, 0.612 mmol). The reaction mixture was stirred at 55° C. for 48 hours. The solvent was removed under reduced pressure and was purified by preparative HPLC chromatography to give 0.063 g (61%) of the title compound as a monoacetate salt. $^1$H NMR (DMSO-d$_6$, 400 MHz) δ 9.49 (s, 1H), 8.00 (d, 1H), 7.89 (s, 1H), 7.70 (d, 1H), 7.58 (m, 2H), 7.33 (m, 2H), 7.18 (m, 1H), 7.15 (m, 1H), 7.10 (m, 1H), 6.80 (d, 1H), 6.60 (d, 1H), 6.20 (m, 1H), 5.60 (s, 2H), 4.02 (s, 3H), 3.89 (s, 3H), 3.20 (m, 1H), 2.85 (m, 2H), 2.40 (m, 4H), 2.98 (t, 2H), 1.70 (m, 2H), 1.35 (s, 9H); LCMS (Conditions a): R$_t$ 3.50 min (100%), M$^+$ 681.4.

General Procedure J

In a 3-necked round bottom flask were combined an aryl halide (aryl bromide or iodide, preferably an iodide, 1.0 equivalent) and a suitable catalyst [for example trans-dichloro[bis(triphenylphosphine)]palladium (II) or tetrakis(triphenylphosphine) palladium (0), preferably trans-dichloro[bis(triphenylphosphine)]palladium (II)] (0.01–10 mol %, preferably 5–10 mol %). The flask was filled and evacuated with nitrogen gas 4 times, followed by the addition of an organic solvent (such as N,N-dimethylformamide, N-methyl pyrrolidinone, or ethylene glycol dimethyl ether, preferably N,N-dimethylformamide), an organic base (for example triethylamine, N-methylmorpholine, pyridine, or diisopropylethylamine, preferably triethylamine) (1–10 equivalents, preferably 2 equivalents) and the appropriate amine substrate (1–5 equivalents, preferably 1.5–2.0 equivalents). The flask was then filled and evacuated with carbon monoxide gas (large excess) 3 times and the reaction mixture heated to 60–100° C. (preferably 80–90° C.) under an atmosphere of carbon monoxide for 1–24 hours (preferably 3–15 hours). The reaction mixture was cooled to room temperature, the solvents removed under reduced pressure, and the resulting solid dissolved with an organic solvent (preferably dichloromethane), and washed with water and brine. The organic layer was separated and the solvents were removed under reduced pressure. The crude products were purified by chromatography or trituration from an appropriate solvent (for example water, methanol, ethanol, diethyl ether, preferably ethanol).

EXAMPLE 789

4-amino-N-[2-(dimethylamino)ethyl]-3-(3-methoxy-4-{[(1-methyl-1H-indol-2-yl)carbonyl]amino}phenyl)thieno[3,2-c]pyridine-7-carboxamide In a 3-necked round bottom flask were combined 4-amino-3-(3-methoxy-4-{[(1-methyl-1H-indol-2-yl)carbonyl]amino}phenyl)thieno[3,2-c]pyridine-7-carboxylic acid (0.100 g, 0.180 mmol) and trans-dichloro[bis(triphenylphosphine)]palladium (II) (0.012 g, 0.018 mmol). The flask was filled and evacuated with nitrogen gas 4 times, followed by the addition of N,N-dimethylformamide (2.5 mL), triethylamine (0.050 mL, 0.361 mmol), and the appropriate amine (0.032 mg, 0.361 mmol). The flask was then filled and evacuated with carbon monoxide gas 3 times and the reaction mixture heated to 90° C. under an atmosphere of carbon monoxide for 4 hours. The reaction was cooled to room temperature, diluted with methylene chloride (50 mL), and washed with water and brine (50 mL each). The organic layer was separated and dried over magnesium sulfate, filtered, and the solvents removed. The crude product was purified by trituration with ethanol to give the title compound (0.034 mg, 36%) as a tan powder. LCMS (Conditions a): $R_t$ 3.00 minutes, 543.3 (MH+); $^1$H NMR DMSO-$d_6$ δ 9.50 (s, 1H), 8.54 (s, 1H), 8.43 (t, J=5.9 Hz, 1H), 8.00 (d, J=8.2 Hz, 1H), 7.70 (d, J=7.8 Hz, 1H), 7.59 (d, J=8.6 Hz, 1H), 7.58 (s, 1H), 7.35 (s, 1H), 7.32 (d, J=8.6 Hz, 1H), 7.19 (s, 1H), 7.15 (t, J=7.0 Hz, 1H), 7.06 (d, J=7.0 Hz, 1H), 4.04 (s, 3H), 3.91 (s, 3H), 3.40 (m, 2H), 2.43 (m, 2H), 2.20 (s, 6H).

General Procedure K

A mixture of an amine (preferably one equivalent) and an acrylic acid or an acrylic acid derivative such as an amide or ester (preferably an amide) (0.5–1.5 equivalents, preferably 1 equivalent) in an organic solvent (for example dichloromethane, 1,2-dichlorethane or ethyl alcohol, preferably dichlormethane) was stirred at 20–50° C. for 2 to 18 hours. The organic solvent was removed and the residue purified by column chromatography.

EXAMPLE 790

4-amino-N-{1-[3-(dimethylamino)-3-oxopropyl]piperidin-3-yl}-3-(3-methoxy-4-{[(1-methyl-1H-indol-2-yl)carbonyl]amino}phenyl)thieno[3,2-c]pyridine-7-carboxamide A mixture of 4-amino-3-(3-methoxy-4-{[(1-methyl-1H-indol-2-yl)carbonyl]amino}phenyl)-N-piperidin-3-ylthieno[3,2-c]pyridine-7-carboxamide (150 mg, 0.270 mmol) and N,N-dimethyl-acrylamide (28 mg, 0.283 mmol) in dichloromethane (5 mL) was stirred at room temperature for 2 hours. N,N-dimethylacrylamide (28 mg, 0.283 mmol) was added every 2 hour three times. The organic solvent was removed. The residue was purified by flash column chromatography on silica using dichloromethane/methanol/ammonium hydroxide (28–30% solution) (80:20:0.05) mixture as the mobile phase to give the title compound. $^1$H NMR (DMSO, $d_6$) δ 1.39 (m, 1H), 1.51(m, 1H), 1.70 (m, 1H), 1.81 (m, 1H), 1.98 (m, 2H), 2.48 (m, 2H), 2.58 (m, 2H), 2.76 (m, 1H), 2.81 (s, 3H), 2.91 (m, 1H), 2.99 (s, 3H), 3.91 (s, 3H), 3.99 (m 1H), 4.04 (m, 3H), 7.07 (d, 1H), 7.15 (t, 1H), 7.18 (s, 1H), 7.33 (t, 1H), 7.35 (s, 1H), 7.60 (m, 2H), 7.71 (d, 1H), 7.99 (d, 1H), 8.16 (d, 1H), 8.59 (s, 1H), 9.50 (s, 1H). LCMS (Conditions a): MH+=654.1, $R_t$=2.55 min.

General Procedure L

A schlenck tube was charged with 3-(4-amino-3-methoxy-phenyl)-7-iodo-thieno[3,2-c]pyridin-4-ylamine (199 mg,0.5 mmol), 3-pyrrolidin-1-yl-propionamide (0.6 mmol), copper(I) iodide (4.8 mg, 0.025 mmol), potassium phosphate (225 mg, 1.06 mmol). Evacuated and back filled with nitrogen. The appropriate amide (6.5 uL, 0.05 mmol) and 1,4-dioxane (1 mL) were then added. The reaction tube was sealed and heated at about 110° C. overnight. The solvent was removed and the crude product was used in the next reaction without further purification.

General Procedure M

The formamidine (1.0 equivalent) was dissolved in an organic solvent (preferably dioxane) and aqueous 6N hydrochloric acid (excess) was added. The mixture was stirred at ambient temperature at 60° C. (preferably 50° C.) for 2–24 hours (preferably 13 hours), cooled to ambient temperature, and quenched with an aqueous base (preferably sodium carbonate, sodium hydroxide, or sodium bicarbonate). The mixture was extracted with an organic solvent [preferably methanol/dichloromethane (1:9)], and the combined organic fractions were dried over magnesium sulfate, filtered, and concentrated. Purification of the crude products by flash column chromatography on silica gel which had been deactivated with triethylamine (10% by volume of silica gel used) afforded the products.

EXAMPLE 791

N-(4-{4-amino-7-[(thien-2-ylsulfonyl)amino]thieno[3,2-c]pyridin-3-yl}-2-methoxyphenyl)-1-methyl-1H-indole-2-carboxamide N-(4-{4-{[(1E)-(dimethylamino)methylene]amino}-7-[(thien-2-ylsulfonyl)amino]thieno[3,2-c]pyridin-3-yl}-2-methoxyphenyl)-1-methyl-1H-indole-2-carboxamide (prepared by reaction of N-[4-(7-amino-4-{[(1E)-(dimethylamino)methylene]amino}thieno[3,2-c]pyridin-3-yl)-2-methoxyphenyl]-1-methyl-1H-indole-2-carboxamide with 2-thiophenesulfonyl chloride according to General Procedure G) (0.021 g, 0.033 mmol) was dissolved in dioxane (1 mL), and aqueous hydrochloric acid (6 M, 1 mL) was added. The mixture was stirred at 50° C. for 13 h, cooled to ambient temperature, and quenched with aqueous sodium carbonate (1 M, 10 mL). The mixture was extracted with methanol/dichloromethane (1:9, 3×20 mL), and the combined organic fractions were dried over magnesiuin sulfate, filtered, and concentrated. Purification of the residue by flash column chromatography on silica gel which had been deactivated with triethylamine (10% by volume of silica gel used) afforded the title compound as a white foam (0.0085 g, 45%): $^1$H NMR (DMSO-$d_6$, 400 MHz) δ 9.70 (br, 1H), 9.49 (s, 1H), 7.97 (d, 1H), 7.80 (m, 1H), 7.70 (d, 1H), 7.58 (d, 1H), 7.47 (s, 1H), 7.40 (m, 1H), 7.37 (s, 1H), 7.34 (m, 2H), 7.17 (s 1H), 7.14 (d, 1H), 7.07 (m, 2H), 5.35 (br, 2H), 4.03 (s, 3H), 3.09 (s, 3H); MS: (M–H)⁻ 588.

General Procedure N

To a solution of N-[4-(7-amino-4-{[(dimethylamino)methylene]amino}thieno[3,2-c]pyridin-3-yl)-2-methoxyphenyl]-1-methyl-1H-indole-2-carboxamide (1.0 equivalent) in an organic solvent such as dichloromethane or pyridine (preferably pyridine) at 0° C. was added the appropriately substituted isocyanate (0.5–5.0 equivalents, preferably 1.0 equivalent). The mixture was allowed to warm to ambient temperature, and was stirred at ambient temperature for 2–20 hours (preferably 12 hours). The reaction mixture was concentrated, and the residue was purified by flash column chromatography on silica gel, which had been deactivated with triethylamine (10% by volume of silica gel used), using methanol/dichloromethane as the mobile phase, to afford an intermediate that was then subjected to General Procedure M for formamidine hydrolysis.

EXAMPLE 792

N-(4-{4-amino-7-[(anilinocarbonyl)amino]thieno[3,2-c]pyridin-3-yl}-2-methoxyphenyl)-1-methyl-1H-indole-2-carboxamide To a solution of N-[4-(7-amino-4-{[(1E)-(dimethylamino)methylene]amino}thieno[3,2-c]pyridin-3-yl)-2-methoxyphenyl]-1-methyl-1H-indole-2-carboxamide (0.020 g, 0.040 mmol) in pyridine (1.1 mL) at 0° C. was added phenyl isocyanate (0.0043 mL, 0.040 mmol). The mixture was allowed to warm to ambient temperature, and was stirred at ambient temperature for 12 h. The reaction mixture was concentrated, and the residue was purified by flash column chromatography on silica gel, which had been deactivated with triethylamine (10% by volume of silica gel used), using methanol/dichloromethane as the mobile phase, to afford an intermediate that was then subjected to General Procedure M for formamidine hydrolysis to yield the title compound (0.007 g, 32%) as an off-white foam: $^1$H NMR (DMSO-$d_6$, 400 MHz) δ 9.52 (s, 1H), 9.07 (s, 1H), 8.58 (s, 1H), 8.09 (s, 1H), 8.06 (d, 1H), 7.73 (m, 2H), 7.60 (d, 1H), 7.49 (d, 2H), 7.36 (s, 1H), 7.30 (m, 4H), 7.14 (m, 2H), 7.00 (t, 1H), 6.10 (br, 2H), 4.04 (s, 3H), 3.93 (s, 3H); MS: (MH)⁺ 563.

General Procedure O

N-[4-(7-Amino-4-{[(1E)-(dimethylamino)methylene]amino}thieno[3,2-c]pyridin-3-yl)-2-methoxyphenyl]-1-methyl-1H-indole-2-carboxamide (1.0 equivalent) was dissolved in an organic solvent (preferably pyridine). Methyl chlorothiolformate (0.5–3 equivalents, preferably 1.1 equivalents) was added, and the solution was stirred at ambient temperature for 0.5–10 hours (preferably 1.5 hours), at which point a clean conversion of the 7-amino group to the thiocarbamic acid S-methyl ester had occurred. N,O-Dimethylhydroxylamine hydrochloride (1–10 equivalents, preferably 5 equivalents) was added, and the solution was stirred at 25–60° C. (preferably 50° C.) for 1–8 hours (preferably 4 hours), at which point the 4-(dimethylaminomethyleneamino) group had been cleaved. The reaction mixture was cooled to ambient temperature, and an organic base (such as N,N-diisopropylethylamine, triethylamine, N-methylmorpholine, or N-methylpiperidine, preferably N,N-diisopropylethylamine) (2–10 equivalents, preferably 6 equivalents) and the appropriate amine (1–10 equivalents, preferably 7.0 equivalents) were added. The mixture was stirred at 25–100° C. (preferably 70° C.) for 3–20 hours (preferably 12 hours), then was cooled to ambient temperature and concentrated. The residue was diluted with an aqueous base such as sodium carbonate, sodium hydroxide, or sodium bicarbonate (preferably sodium carbonate) and the mixture was extracted with dichloromethane. The organic fractions were combined, dried over magnesium sulfate, and concentrated. Purification of the residue on silica gel which had been deactivated with triethylamine (10% by volume of silica gel used) afforded the urea product.

EXAMPLE 793

N-{4-[4-amino-7-({[4-(2-hydroxyethyl)piperazin-1-yl]carbonyl}amino)thieno[3,2-c]pyridin-3-yl]-2-methoxyphenyl}-1-methyl-1H-indole-2-carboxamide N-[4-(7-Amino-4-{[(1E)-(dimethylamino)methylene]amino}thieno[3,2-c]pyridin-3-yl)-2-methoxyphenyl]-1-methyl-1H-indole-2-carboxamide (0.108 g, 0.217 mmol) was dissolved in pyridine (3 mL). Methyl chlorothiolformate (0.020 mL, 0.233 mmol) was added, and the solution was stirred at ambient temperature for 1.5 hours, at which point LCMS analysis indicated that a clean conversion of the 7-amino group to the thiocarbamic acid S-methyl ester had occurred. N,O-Dimethylhydroxylamine hydrochloride (0.106 g, 1.09 mmol) was added, and the solution was stirred at 50° C. for 4 h, at which point LCMS analysis indicated that the 4-(dimethylaminomethyleneamino) group had been cleaved. The reaction mixture was cooled to ambient temperature, and N,N-diisopropylethylamine (0.264 mL, 1.30 mmol) and 1-(2-hydroxyethyl)piperazine (0.057 mL, 1.52 mmol) were added. The mixture was stirred at 70° C. for 12 h, then was cooled to ambient temperature and concentrated. The residue was diluted with aqueous sodium carbonate (0.5 M, 10 mL), and the mixture was extracted with dichloromethane (3×20 mL). The organic fractions were combined, dried over magnesium sulfate, and concentrated. Purification of the residue on silica gel which had been deactivated with triethylamine (10% by volume of silica gel used) afforded the title compound as an off-white powder: $^1$H NMR (DMSO-$d_6$, 400 MHz) δ 9.51 (s, 1H), 8.48 (s, 1H), 7.99 (d, 1H), 7.71 (d, 1H), 7.64 (s, 1H), 7.59 (d, 1H), 7.50 (s, 1H), 7.35 (s, 1H), 7.33 (t, 1H), 7.20 (s, 1H), 7.15 (t, 1H), 7.08 (d, 1H), 5.40 (br, 2H), 4.47 (br, 1H), 4.04 (s, 3H), 3.91 (s, 3H), 3.55 (m, 2H), 3.46 (m, 4H), 2.45 (m, 6H); MS: (MH)⁺ 600.

HPLC Conditions:

Solvent A=50 mM ammonium acetate buffered to pH 4.5
Solvent B=Acetonitrile a) Thermoquest AQA single-quad MS, (Genesis C18 column, 3 mm particle size, 33×4.6 mm; 30–95% B over 3 min, then isocratic 95% B for 1.5 min, 0.8 mL/min)

b) Thermoquest AQA single-quad MS, (Genesis C18 column, 3 mm particle size, 33×4.6 mm; 30% to 95% B over 6 min, 0.8 mL/min)

c) Thermoquest AQA single-quad MS, (Genesis C18 column, 3 mm particle size, 33×4.6 mm; 10–40% B over 5 min, then 40–80% B over 1 min, 0.8 mL/min)

d) Delta Pak C18, 5 μm, 300 Å, 15 cm, 50%-100% B over 10 min, 1 mL/min e) Delta Pak C18, 5 μm, 300 Å, 15 cm, 5%-100% B over 15 min, 1 mL/min f) Delta Pak C18, 5 μm, 300 Å, 15 cm; 5%-95% B over 10 min, then isocratic 3 min, 1 mL/min g) Delta Pak C18, 5 μm, 300 Å, 15 cm; 50%-100% B over 30 min, 1 mL/min h) Finnigan Advantage LCQ-MS (Genesis C18 column, 3 μm particle size, 30×4.6 mm; 30%-95% B over 3.0 min, 95% B for 1.5 min then 95% -30% B over 0.5 min, 30% B for 1 min, 0.8 ml/min)

i) 5% to 95% B over 25 minutes, 1 ml/min, Hypersil HS 100 Å, C18, 5 μm, 250×4.6 column j) 5% to 95% B over 10 minutes, 1 ml/min, Hypersil HS 100 Å, C18, 5 μm, 250×4.6 column k) 5% to 95% B over 5 minutes, 1 ml/min, Hypersil HS 100 Å, C18, 5 μm, 250×4.6 column l) Thermoquest AQA single-quad MS, (Genesis C18 column, 3 mm particle size, 33×4.6 mm; 30% to 95% B over 5 min, then isocratic 95% B for 7 min, 0.8 mL/min)

EXAMPLE 794

2-(but-3-ynyloxy)tetrahydro-2H-pyran

A solution of but-3-yn-1-ol (10.00 g, 143 mmol) in dichloromethane (310 mL) was treated with dihyropyran (18.10 g, 215 mmol) and pyridinium p-toluene sulfonate (3.60 g, 14.30 mmol). The reaction mixture was stirred at room temperature for 4 days. Water was added and the layers were partitioned. The organic layer was washed with brine, dried over magnesium sulfate, filtered and evaporated under reduced pressure. The crude material was purified by flash chromatography on silica gel using 1:1 ethyl acetate:heptane to give 21.57 g (98%) of the title compound. $^1$H NMR (CDCl$_3$, 400 MHz) δ 4.65 (m, 1H), 3.90–3.80 (m, 2H), 3.60–3.50 (m, 2H), 2.50–2.45 (m, 2H), 1.95 (m, 1H), 1.90–1.80 (m, 1H), 1.79–1.10 (m, 1H), 1.65–1.50 (m, 4H).

EXAMPLE 795

4,4,5,5-Tetramethyl-2-[(E)-4-(1-propoxy-propoxy)-but-1-enyl]-[1,2,3]dioxaborolane A solution of 2-(but-3-ynyloxy)tetrahydro-2H-pyran (0.25 g, 1.62 mmol) in dichloromethane (1 mL) was treated with pinacolborane (0.22 g, 1.70 mmol). The reaction mixture was cooled to 0° C. The solution was added to solid bis(cyclopentadienyl)zirconium chloride hydride (0.02 g, 0.08 mmol) at 0° C. The reaction mixture was stirred at 0° C. for 30 minutes and at room temperature for 4 days. Diethyl ether was added and was washed with water. The organic layer was dried over magnesium sulfate, filtered and evaporated under reduced pressure. The crude material was purified by flash chromatography on silica gel using 10% ethyl acetate in heptane to give 0.198 g (43%) the title compound. $^1$H NMR (CDCl$_3$, 400 MHz) δ 6.67–6.59 (m, 1H), 5.55–5.49 (m, 1H), 4.60–4.58 (m, 1H), 3.90–3.80 (m, 2H), 3.55–3.49 (m, 2H), 2.50–2.40 (m, 2H), 1.90–1.79 (m, 1H), 1.75–1.65 (m, 1H), 1.60–1.50 (m, 4H), 1.25 (s, 12H).

EXAMPLE 796

(3E)-4-[4-amino-3-(3-methoxy-4-{[(1-methyl-1H-indol-2-yl)carbonyl]amino}phenyl)thieno[3,2-c]pyridin-7-yl]but-3-enyl 4-methylbenzenesulfonate A solution of N-(4-{4-amino-7-[(1E)-4-hydroxybut-1-enyl]thieno[3,2-c]pyridin-3-yl}-2-methoxyphenyl)-1-methyl-1H-indole-2-carboxamide (0.20 g, 0.40 mmol) in dichloromethane (10 mL) was treated with p-toluene sulfonyl chloride (0.100 g, 0.521 mmol), triethyl amine (0.08 g, 0.80 mmol), and dimethyl amino pyridine (0.003 g, 0.02 mmol). The reaction mixture was stirred at room temperature for 24 hours. No workup was used. The compound was purified by flash chromatography on silica gel using 1:1 ethyl acetate:heptane then 100% ethyl acetate to give 0.075 g (29%) the title compound. $^1$H NMR (CDCl$_3$, 400 MHz) δ 8.70 (m, 1H), 8.60 (d, 1H), 7.90 (s, 1H), 7.80 (d, 1H), 7.70 (d, 1H), 7.45 (m, 1H), 7.40 (m, 1H), 7.30 (m, 2H), 7.21 (m, 2H), 7.19 (m, 1H), 7.10 (m, 1H), 7.05 (m, 1H), 6.60–6.50 (d, 2H), 6.15–6.10 (m, 1H), 4.95 (s, 2H), 4.20 (t, 2H), 4.12 (s, 3H), 3.98 (s, 3H), 2.70 (q, 2H), 2.39 (s, 3H); LCMS (conditions a) R$_t$ 4.28 min (95%), M$^+$ 653.4.

EXAMPLE 797

3-Bromo-4-chlorofuro[3,2-c]pyridine

A solution of 4-chlorofuro[3,2-c]pyridine (10.60 g, 69 mmol, 1.0 eq) in carbon tetrachloride (135 mL) was cooled to −15° C. and bromine (12.13 g, 80 mmol, 1.2 eq) was added drop-wise over a fifteen minute time period. The mixture was stirred at ambient temperature for eighteen hours. The solvent was removed in vacuo, and the residue was dissolved in methanol (250 mL). A solution of 20% aqueous sodium hydroxide (35 mL) was added and the mixture was stirred 1 hour at ambient temperature. The methanol was removed in vacuo, and the residue was partitioned between water (100 mL) and dichloromethane (50 mL). The layers were separated and the aqueous phase was extracted with dichloromethane (50 mL). The combined organic layers were dried over anhydrous magnesium sulfate and the solvent was removed in vacuo to give the title compound (15.45 g, 96%) as a solid. $^1$H NMR (DMSO-d$_6$, 400 MHz) δ 8.54 (s, 1H), 8.37 (d, 1H), 7.87 (d, 1H); RP-HPLC (Conditions f) R$_t$ 11.46 min.; MS: MH$^+$ 232, 234.

EXAMPLE 798

3-Bromofuro[3,2-c]pyridin-4-amine

A mixture of 3-bromo-4-chlorofuro[3,2-c]pyridine (7.0 g, 22 mmol), 38 wt % aqueous ammonium hydroxide (75 mL) and dioxane (75 mL) in a Parr mini-reactor was stirred at 150° C. for two days. The solvent was removed in vacuo and water (200 mL) was added to the residue.The mixture was adjusted to pH 12 with 2N NaOH (aq) extracted with ethyl acetate (5×100 mL). The combined organic layers were dried over anhydrous magnesium sulfate and the solvent was removed in vacuo to give the title compound (4.6 g, 71%). $^1$H NMR (DMSO-d$_6$, 400 MHz) 8.13 (s, 1H), 7.85 (d, 1H), 6.92 (d, 1H), 6.17–6.27 (bs, 2H); RP-HPLC (Conditions d) R$_t$ 8.02 min.; MS: MH$^+$ 213, 215.

EXAMPLE 799 tert-butyl 4-(4-aminofuro[3,2-c]pyridin-3-yl)-2-methoxyphenylcarbamate

A mixture of 3-bromofuro[3,2-c]pyridin-4-amine (0.443 g, 2.1 mmol) in 1,2-dimethoxyethane (16 mL) and water (8 mL) was treated with tert-butyl N-[2-methoxy-4-(4,4,5,5-tetramethyl-1,3,2-dioxaborolan-2-yl)phenyl]carbamate (0.872 g, 2.5 mmol,), sodium carbonate (0.749 g, 7.1 mmol) and tetrakis triphenylphosphine palladium (0) (0.144 g, 0.12 mmol) at 80° C. for 18 hours. The organic solvent was removed in vacuo and the aqueous mixture was extracted with ethyl acetate (3×10 mL). The combined organic phases were dried over anhydrous magnesium sulfate and the solvent was removed in vacuo. The residue was purified by flash column chromatography on silica gel using heptane/ethyl acetate (4:1) followed by ethyl acetate as an eluents to give the title compound (0.734 g, 85%) as a tan solid. $^1$H NMR (DMSO-$d_6$, 400 MHz) δ 8.07 (s, 1H), 7.96 (s, 1H), 7.87 (d, 1H), 7.84 (d, 1H), 7.14 (d, 1H), 7.05 (dd, 1H), 6.94 (d, 1H), 5.55–5.62 (bs, 2H), 3.87 (s, 3H), 1.48 (s, 9H); RP-HPLC (Conditions f) $R_t$ 12.13 min.; MS: MH$^+$ 356.

EXAMPLE 800 tert-butyl 4-(4-amino-7-iodofuro[3,2-c]pyridin-3-yl)-2-methoxyphenylcarbamate

N-Iodosuccinimide (0.333 g, 1.48 mmol) was added to a solution of tert-butyl 4-(4-aminofuro[3,2-c]pyridin-3-yl)-2-methoxyphenylcarbamate (0.439 g, 1.24 mmol) in N,N-dimethylformamide (10 mL) at ambient temperature. The reaction suspension was stirred for 18 hours, at which time no starting material remained. An aqueous solution of 10% sodium thiosulfate (10 mL) was added to the suspension and stirred for 30 minutes. The precipitate was collected by vacuum filtration and washed with water. The solid was dried in vacuo to give the title compound (0.501 g, 84%) as a tan solid. $^1$H NMR (DMSO-$d_6$, 400 MHz) δ 8.08 (s, 1H), 8.07 (s, 1H), 8.06 (s, 1H), 7.85 (d, 1H), 7.13 (d, 1H), 7.04, (dd, 1H), 5.73–5.80 (bs, 2H), 3.86 (s, 3H), 1.48 (s, 9H); RP-HPLC (Conditions d) $R_t$ 8.49 min.; MS: MH$^+$ 482.

EXAMPLE 801

3-(4-amino-3-methoxyphenyl)-7-iodofuro[3,2-c]pyridin-4-amine

Tert-butyl 4-(4-amino-7-iodofuro[3,2-c]pyridin-3-yl)-2-methoxyphenylcarbamate (3.98 g, 8.28 mmol) was added to a 20% solution of trifluoroacetic acid in dichloro-methane (150 mL). The mixture was stirred for two hours and then the solvent was removed in vacuo. To the residue was added water (15 mL) and dichloromethane (25 mL). The mixture was adjusted to pH 12 with 1 N aqueous sodium hydroxide and the layers were separated. The aqueous layer was extracted with dichloromethane (2×10 mL) and the combined organic layers were dried over anhydrous magnesium sulfate. The solvent was removed in vacuo to give the title compound (2.534 g, 80%). $^1$H NMR (DMSO-$d_6$, 400 MHz) □ 8.03 (s, 1H), 7.94 (s, 1H), 6.91 (d, 1H), 6.82 (dd, 1H), 6.75 (d, 1H), 5.69–5.77 (bs, 2H), 4.96–5.05(bs, 2H), 3.81 (s, 3H); RP-HPLC (Conditions f) $R_t$ 11.22 min.; MS: MH$^+$ 382.

EXAMPLE 802

N-[4-(4-amino-7-iodofuro[3,2-c]pyridin-3-yl)-2-methoxyphenyl]-1-methyl-1H-indole-2-carboxamide A solution of 3-(4-amino-3-methoxyphenyl)-7-iodofuro[3,2-c]pyridin-4-amine (2.53 g, 6.65 mmol) in pyridine (30 mL) was cooled to 0° C. and 1-methyl-1H-2-indolecarbonyl chloride (2.57 g, 13.3 mmol) was added. The mixture was stirred for 15 minutes at 0° C. and then allowed to rise to ambient temperature over an 18 hour time period. The solvent was removed in vacuo and the residue was dissolved in water (50 mL) and brought to pH 12 with 0.1 N aqueous sodium hydroxide, at which point a precipitate formed. The suspension was extracted with dichloromethane (4×25 mL) and the combined organic layers were washed with brine (25 mL) and dried over anhydrous magnesium sulfate. The solvent was removed in vacuo to give the title compound (3.21 g, 89%) as a yellow solid. $^1$H NMR (DMSO-$d_6$, 400 MHz) δ 9.48 (s, 1H), 8.14 (s, 1H), 8.08 (s, 1H), 8.04 (t, 1H), 7.71 (d, 1H), 7.59 (d, 1H), 7.30–7.37 (m, 2H), 7.25 (d, 1H), 7.11–7.18 (m, 2H), 5.75–5.83 (bs, 2H), 4.04 (s, 3H), 3.93 (s, 3H); RP-HPLC (Conditions d) $R_t$ 8.73 min.; MS: MH$^+$ 539.

EXAMPLE 803

N-[4-(4-amino-7-iodofuro[3,2-c]pyridin-3-yl)-2-methoxyphenyl]-1-methyl-1H-benzimidazole-2-carboxamide A solution of 3-(4-amino-3-methoxyphenyl)-7-iodofuro[3,2-c]pyridin-4-amine (1.50 g, 3.94 mmol) in pyridine (18 mL) was cooled to 0° C. and 1-methyl-1H-benzo[d]imidazole-2-carbonyl chloride (0.874 g, 3.33 mmol) was added. The mixture was stirred for 15 minutes at 0° C. and then allowed to rise to ambient temperature over an eighteen hour time period. The solvent was removed in vacuo and the residue was suspended in water (50 mL) and brought to pH 12 with 0.1 N aqueous sodium hydroxide. The suspension was extracted with dichloromethane (4×25 mL) and the combined organic layers were washed with brine (25 mL) and dried over anhydrous magnesium sulfate. The solvent was removed in vacuo to give the title compound (1.90 g, 90%) as a yellow solid. $^1$H NMR (DMSO-$d_6$, 400 MHz.)δ 10.18 (s, 1H), 8.49 (d, 1H), 8.14 (s, 1H), 8.08 (s, 1H), 7.85 (d, 1H), 7.76 (d, 1H), 7.46 (t, 1H), 7.39 (t, 1H), 7.30 (s, 1H), 7.19 (d, 1H), 5.77–5.89 (b, 2H), 4.24 (s, 3H), 4.03 (s, 3H); RP-HPLC (Conditions d) $R_t$ 11.89 min.; MS: MH$^+$ 540.

EXAMPLE 804

2-[(E)-3,3-diethoxy-1-propenyl]-4,4,5,5-tetramethyl-1,3,2-dioxaborolane

A mixture of 3,3-diethoxy-1-propyne (18.5 g, 0.144 mol), 4,4,5,5-tetramethyl-1,3,2-dioxaborolane (27.6 g, 0.216 mol) and bis(cyclopentadienyl)zirconium chloride hydride (1.9 g, 0.007 mol) in tetrahydrofuran (75 mL) was heated at 50° C. for 2 days. Triethylamine (2 mL) was added and the solvent was removed in vacuo. The residue was distilled at 90° C. at 10 torr. The residue was purified by column chromatography on neutral alumina using 89:10:1 dichloromethane:ethyl acetate:triethylamine as an eluent. The solvent was removed in vacuo to give the title compound (15.9 g, 53%) as a brown oil. $^1$H NMR (DMSO-$d_6$, 400 MHz) δ 6.48 (dd, 1H), 5.75 (d, 1H), 4.85 (d, 1H), 3.55–3.67 (m, 2H), 3.40–3.52 (m, 2H), 1.22 (s, 12H), 1.17 (t, 6H).

EXAMPLE 805

N-(4-{4-amino-7-[(1E)-3-oxoprop-1-enyl]furo[3,2-c]pyridin-3-yl}-2-methoxyphenyl)-1-methyl-1H-indole-2-carboxamide A mixture of N-[4-(4-amino-7-iodofuro[3,2-c]pyridin-3-yl)-2-methoxyphenyl]-1-methyl-1H-indole-2-carboxamide (3.16 g, 5.86 mmol) in 1,2-dimethoxyethane (40 mL) and water (20 mL) was reacted 2-[(E)-3,3-diethoxy-1-propenyl]-4,4,5,5-tetramethyl-1,3,2-dioxaborolane (2.87 g, 7.03 mmol,), sodium carbonate (1.55 g, 14.66 mmol) and tetrakis triphenylphosphine palladium (0) (0.68 g, 0.59 mmol) at 80° C. for eighteen hours. The solvent was removed in vacuo and the residue was partitioned between ethyl acetate (15 mL) and water (30 mL). The layers were separated and the aqueous layer was extracted with ethyl acetate (2×15 mL). The combined organic layers were dried over anhydrous magnesium sulfate and the solvent was removed in vacuo. The residue was purified by flash column chromatography on silica gel using 10% methanol in dichloromethane as an eluent to give a mixture of diethyl acetal, methyl ethyl acetal, and aldehyde. This mixture was reacted with p-toluenesulfonic acid monohydrate (0.10 g, 0.53 mmol) in acetone (100 mL) and water (10 mL) at ambient temperature for eighteen hours. The acetone was removed in vacuo and the precipitate was filtered, washing with water. The precipitate was triturated with 2-propanol (30 mL) for 1 hour. The solid was filtered and dried in vacuo to give the title compound (1.690 g, 62%) as a yellow solid. $^1$H NMR (DMSO-$d_6$, 400 MHz) 9.64 (d, 1H), 9.49 (s, 1H), 8.26 (s, 1H), 8.22 (s, 1H), 8.06 (t, 1H), 7.79 (d, 1H), 7.71 (d, 1H), 7.59 (d, 1H), 7.30–7.38 (m, 2H), 7.27 (d, 1H), 7.12–7.20 (m, 2H), 6.94 (dd, 1H), 6.33–6.59 (b, 2H), 4.04 (s, 3H), 3.94 (s, 3H); RP-HPLC (Conditions d) $R_t$ 7.36 min.; MS: MH$^+$ 467.

EXAMPLE 806

N-(4-{4-amino-7-[(1E)-3-oxoprop-1-enyl]furo[3,2-c]pyridin-3-yl}-2-methoxyphenyl)-1-methyl-1H-benzimidazole-2-carboxamide A mixture of N-[4-(4-amino-7-iodofuro[3,2-c]pyridin-3-yl)-2-methoxyphenyl]-1-methyl-1H-benzimidazole-2-carboxamide (1.50 g, 2.78 mmol) in 1,2-dimethoxyethane (30 mL) and water (15 mL) was reacted 2-[(E)-3,3-diethoxy-1-propenyl]-4,4,5,5-tetramethyl-1,3,2-dioxaborolane (1.42 g, 5.56 mmol,), sodium carbonate (1.17 g, 11.12 mmol) and tetrakis triphenylphosphine palladium (0) (0.19 g, 0.17 mmol) at 80° C. for 18 hours. Additional 2-[(E)-3,3-diethoxy-1-propenyl]-4,4,5,5-tetramethyl-1,3,2-dioxaborolane (1.00 g, 3.90 mmol,), sodium carbonate (0.508 g, 4.80 mmol) and tetrakis triphenylphosphine palladium (0) (0.19 g, 0.17 mmol) was added and the mixture was heated for another 24 hours. Additional tetrakis triphenylphosphine palladium (0) (0.32 g, 0.27 mmol) was added and the mixture was heated for another 24 hours after which time all starting material was consumed. The solvent was removed in vacuo and the residue was triturated with water (30 mL) for 3 hours. The solid was collected by filtration and dried in vacuo. The crude product was suspended in acetone (60 mL) and water (8 mL) and reacted with p-toluenesulfonic acid monohydrate (0.10 g, 0.52 mmol) at ambient temperature for eighteen hours. The acetone was removed in vacuo and the precipitate was filtered, washing with water. The precipitate was triturated with 2-propanol (30 mL) for 1 hour. The solvent was removed an the residue was partitioned between dichloromethane (20 mL) and water (40 mL). The organic layer was dried over anhydrous magnesium sulfate and the solvent was removed in vacuo to give the title compound (0.48 g, 31%) as a yellow solid. $^1$H NMR (DMSO-$d_6$, 400 MHz) δ 10.19 (s, 1H), 9.64 (d, 1H), 8.52 (dd, 1H), 8.26 (s, 1H), 8.21 (s, 1H), 7.86 (d, 1H), 7.75–7.82 (m, 2H), 7.47 (t, 1H), 7.39 (t, 1H), 7.32 (d, 1H), 7.21 (dd, 1H), 6.93 (dd, 1H), 4.25 (s, 3H), 4.04 (s, 3H), 1.86 (s, 3H); RP-HPLC (Conditions g) $R_t$ 12.21 min.; MS: MH$^+$ 468.

EXAMPLE 807

(2E)-3-(4-amino-3-bromothieno[3,2-c]pyridin-7-yl)acrylonitrile

To a solution of 3-bromo-7-iodothieno[3,2-c]pyridin-4-ylamine (430 mg, 1.21 mmol), triphenylphosphine (128 mg, 0.48 mmol) and sodium carbonate (257 mg, 2.42 mmol) in N,N-dimethylformamide (6 ml) was added acrylonitrile (0.32 ml, 4.84 mmol) followed by palladium(II) acetate (56 mg, 0.24 mmol). The reaction was heated at 77° C. for 18 hours under an atmosphere of nitrogen. The mixture was allowed to cool to ambient temperature and solvents were removed under reduced pressure. The residue was purified by flash chromatography on silica gel using ethyl acetate as the mobile phase to give the title compound (300 mg, 88%) as an off-white solid used directly in the following Suzuki coupling step. LCMS (Conditions g); $R_t$ 2.28; MS: MH$^+$ 280.

Examples 808–811, shown in Table 1, were prepared from N-[4-(4-amino-7-iodothieno[3,2-c]pyridin-3-yl)-2-methoxyphenyl]-1-methyl-1H-indole-2-carboxamide and the approriate boronic acid or vinyl boronate using General Procedure A. When a Boc protected amine was used the Boc group was removed by treatment with 6N HCl/acetone for 2 hours at ambient temperature.

TABLE 1

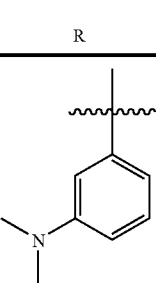

| R | Example | HPLC RT (min.) | m/z (M + H)$^+$ |
|---|---|---|---|
| 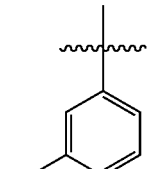 | 808 | 6.22 (b) | 548 |
| 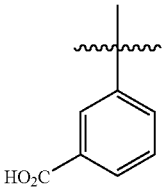 | 809 | 4.92 (b) | 520 |
|  | 810 | 3.02 (b) | 549 |

TABLE 1-continued

| | | HPLC RT | |
|---|---|---|---|
| R | Example | (min.) | m/z (M + H)+ |
| (tetrahydropyridine structure) | 811 | 2.71 (a) | 510 |

EXAMPLE 812

N-{4-[4-amino-7-(3-formyl-2-furyl)thieno[3,2-c]pyridin-3-yl]-2-methoxyphenyl}-1-methyl-1H-indole-2-carboxamide The title compound was prepared using N-[4-(4-amino-7-iodothieno[3,2-c]pyridin-3-yl)-2-methoxyphenyl]-1-methyl-1H-indole-2-carboxamide (0.120 g, 0.217 mmol), 3-formyl-2-furylboronic acid (0.247 mmol) and the procedure described in General Procedure A. $^1$H NMR (DMSO-d$_6$, 400 MHz) δ 9.48 (s, 1H), 7.96 (d, 1H), 7.82 (d, 1H), 7.68 (d, 1H), 7.57 (m, 2H), 7.51 (s, 1H), 7.33 (s, 1H), 7.29 (m, 1H), 7.26 (d, 1H), 7.17 (m, 1H), 7.13 (t, 1H), 7.05 (m, 1H), 4.04 (s, 3H), 3.91 (s, 3H); MS: (M–H)$^-$ 521.

EXAMPLE 813

N-{4-[4-amino-7-(4-formylphenyl)thieno[3,2-c]pyridin-3-yl]-2-methoxyphenyl}-1-methyl-1H-indole-2-carboxamide The title compound was prepared using N-[4-(4-amino-7-iodothieno[3,2-c]pyridin-3-yl)-2-methoxyphenyl]-1-methyl-1H-indole-2-carboxamide (0.120 g, 0.217 mmol), 4-formylphenylboronic acid (0.247 mmol) and the procedure described in General Procedure A. $^1$H NMR (DMSO-d6, 400 MHz) δ 10.12 (s, 1H), 9.53 (s, 1H), 8.03 (s, 1H), 7.97 (d, 1H), 7.78 (t, 1H), 7.71 (d, 1H), 7.64 (m, 2H), 7.62 (s, 1H), 7.55 (m, 3H), 7.36 (s, 1H), 7.24 (m, 1H), 7.16 (d, 1H), 7.12 (d, 1H), 5.72 (br, 2H), 4.05 (s, 3H), 3.93 (s, 3H); MS: (M–H)– 531.

EXAMPLE 814

N-{4-[4-amino-7-(5-formyl-2-furyl)thieno[3,2-c]pyridin-3-yl]-2-methoxyphenyl}-1-methyl-1H-indole-2-carboxamide The title compound was prepared using N-[4-(4-amino-7-iodothieno[3,2-c]pyridin-3-yl)-2-methoxyphenyl]-1-methyl-1H-indole-2-carboxamide (0.120 g, 0.217 mmol), 5-formyl-2-furylboronic acid (0.247 mmol) and the procedure described in General Procedure A.

EXAMPLE 815

N-{4-[4-amino-7-(5-{[[3-(dimethylamino)propyl](methyl)amino]methyl}-2-furyl)thieno[3,2-c]pyridin-3-yl]-2-methoxyphenyl}-1-methyl-1H-indole-2-carboxamide The title compound was prepared using N-{4-[4-amino-7-(5-formyl-2-furyl)thieno[3,2-c]pyridin-3-yl]-2-methoxyphenyl}-1-methyl-1H-indole-2-carboxamide, N,N,N'-trimethylpropane-1,3-diamine and the procedure described in General Procedure B. $^1$H NMR (DMSO-d$_6$, 400 MHz) δ 9.53 (s, 1H), 8.31 (s, 1H), 8.01 (d, 1H), 7.71 (d, 1H), 6.67 (s, 1H), 7.59 (d, 1H), 7.36 (s, 1H), 7.32 (m, 1H), 7.22 (s, 1H), 7.15 (m, 1H), 7.11 (m, 1H), 6.80 (m, 1H), 6.49 (m, 1H), 5.63 (br, 2H), 4.04 (s, 3H), 3.92 (s, 3H), 3.66 (s, 2H), 2.43 (m, 2H), 2.35 (s, 6H), 2.26 (s, 3H), 2.19 (m, 2H), 1.96 (m, 2H); MS: (M–H)$^-$ 621.

EXAMPLE 816

N-(4-{4-amino-7-[4-(hydroxymethyl)phenyl]thieno[3,2-c]pyridin-3-yl}-2-methoxyphenyl)-1-methyl-1H-indole-2-carboxamide N-{4-[4-amino-7-(4-formylphenyl)thieno[3,2-c]pyridin-3-yl]-2-methoxyphenyl}-1-methyl-1H-indole-2-carboxamide (Example 2, 0.030 g, 0.056 mmol) was dissolved in N,N-dimethylformamide (0.5 mL). Sodium borohydride (0.006 g, 0.167 mmol) and methanol (0.5 mL) were added, and the reaction mixture was stirred at ambient temperature for 16 h. The mixture was diluted with aqueous sodium carbonate (1 M, 10 mL) and the product was extracted with methanol/dichloromethane (1:33, 3×20 mL). The organic fractions were combined, dried over magnesium sulfate, filtered, and concentrated. The residue was purified by flash column chromatography on silica gel, using ethyl acetate-heptane (3:1) as the mobile phase, to afford the title compound (0.011 g, 0.020 mmol) as a white powder. $^1$H NMR (DMSO-d$_6$, 400 MHz) δ 9.53 (s, 1H), 8.00 (d, 1H), 7.92 (s, 1H), 7.71 (s, 1H), 7.62 (m, 1H), 7.49 (t, 1H), 7.36 (s, 1H), 7.32 (m, 3H), 7.16 (d, 1H), 7.12 (m, 1H), 5.61 (br, 2H), 5.31 t, 1H), 4.61 (d, 2H), 4.05 (s, 3H), 3.92 (s, 3H); MS: (M–H)$^-$ 533.

Examples 817–823, shown in Table 2, were prepared using 3-bromo-7-iodothieno[3,2-c]pyridin-4-amine, the appropriate boronic acid, and the procedure described in General Procedure A.

TABLE 2

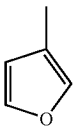

| R | Example | HPLC RT (min.) | m/z (M + H)+ |
|---|---------|----------------|--------------|
| 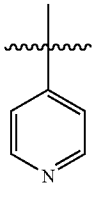 | 817 | 11.50 (f) | 295, 297 |
| 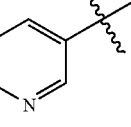 | 818 | 9.77 (f) | 306, 308 |
| 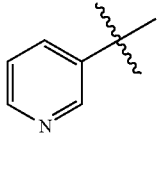 | 819 | 9.84 (f) | 306, 308 |
| 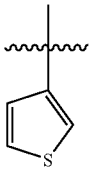 | 820 | 12.09 (f) | 311, 313 |
| 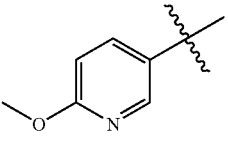 | 821 | 7.48 (d) | 311, 313 |
| 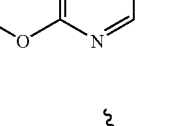 | 822 | 6.60 (d) | 336, 338 |
| | 823 | 7.65 (d) | 394, 396 |

Examples 824–833, shown in Table 3, were prepared using N-[4-(4-amino-7-iodothieno[3,2-c]pyridin-3-yl)-2-methoxyphenyl]-1-methyl-1H-indole-2-carboxamide, the appropriate boronic acid, and the procedure described in General Procedure A. Examples 831, 832, and 833 additional manipulations as described below.

EXAMPLE 831

N-{4-[4-amino-7-(1H-pyrrol-2-yl)thieno[3,2-c]pyridin-3-yl]-2-methoxyphenyl}-1-methyl-1H-indole-2-carboxamide The title compound was prepared using tert-butyl 2-[4-amino-3-(3-methoxy-4-{[(1-methyl-1H-indol-2-yl)carbonyl]amino}phenyl)thieno[3,2-c]pyridin-7-yl]-1H-pyrrole-1-carboxylate and the procedure described in General Procedure H to provide the title compound (4.4 mg, 4%) as a white solid.

EXAMPLE 832

N-{4-[4-amino-7-(1H-pyrrol-2-yl)thieno[3,2-c]pyridin-3-yl]-2-methoxyphenyl}-1-methyl-1H-indole-2-carboxamide The title compound was prepared using N-{4-[4-Amino-7-(5-formyl-2-furyl)thieno[3,2-c]pyridin-3-yl]-2-methoxyphenyl}-1-methyl-1H-indole-2-carboxamide, diethylamine, and the procedure described in General Procedure B.

EXAMPLE 833

N-(4-{4-amino-7-[5-(hydroxymethyl)-2-furyl]thieno[3,2-c]pyridin-3-yl}-2-methoxyphenyl)-1-methyl-1H-indole-2-carboxamide A mixture of N-{4-[4-amino-7-(5-formyl-2-furyl)thieno[3,2-c]pyridin-3-yl]-2-methoxyphenyl}-1-methyl-1H-indole-2-carboxamide (0.060 g, 0.12 mmol) and sodium borohydride (0.013 g, 0.344 mmol) in N,N-dimethylformamide (4 mL) and methanol (4 mL) was stirred at ambient temperature for 18 hours. The solvent was removed in vacuo and the residue was partitioned between dichloromethane (10 mL) and 0.1 N hydrochloric acid (10 mL). The layers were separated and the aqueous layer was extracted with dichloromethane (3×10 mL). The combined organic layers were dried over anhydrous magnesium sulfate and the solvent was removed in vacuo. The residue was purified by preparative RP-HPLC (Rainin C18, 8 mm, 300 Å, 25 cm; 40% acetonitrile—0.1M ammonium acetate isocratic for 5 minutes, then 40–100% acetonitrile—0.1M ammonium acetate over 30 min, 21 ml/min). The acetonitrile was removed in vacuo and the aqueous mixture was lyophilized to give the title compound (2.1 mg, 0.004 mmol) as a white solid.

TABLE 3

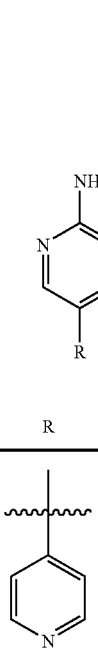

| R | Example | HPLC RT (min.) | m/z (M + H)+ |
|---|---|---|---|
|  | 824 | 3.95 (a) | 506 |
| 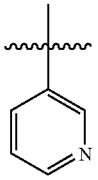 | 825 | 8.75 (d) | 495 |
| 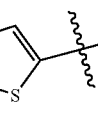 | 826 | 8.50 (d) | 506 |
| 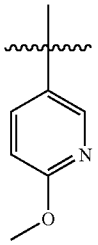 | 827 | 9.61 (d) | 511 |
|  | 828 | 9.30 (d) | 536 |
| 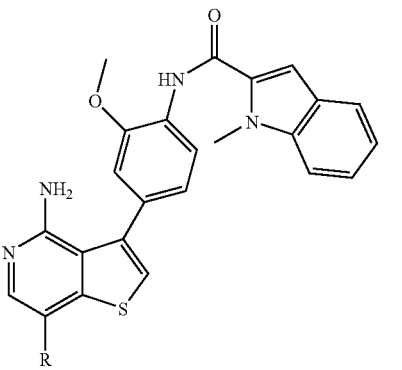 | 829 | 11.82 (d) | 511 |

TABLE 3-continued

| R | Example | HPLC RT (min.) | m/z (M + H)+ |
|---|---|---|---|
| 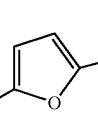 | 830 | 10.15 (d) | 523 |
| 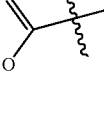 | 831 | 8.23 (d) | 494 |
| | 832 | 5.07 (a) | 580 |
| | 833 | 7.93 (a) | 525 |

EXAMPLE 834

N-{4-[4-amino-7-(2-formylthien-3-yl)thieno[3,2-c]pyridin-3-yl]-2-methoxyphenyl}-1-methyl-1H-indole-2-carboxamide N-[4-(4-amino-7-iodothieno[3,2-c]pyridin-3-yl)-2-methoxyphenyl]-1-methyl-1H-indole-2-carboxamide and 3-(4,4,5,5-tetramethyl-1,3,2-dioxaborolan-2-yl)thiophene-2-carbaldehyde were reacted together according to general procedure A to furnish the title compound. LCMS (Conditions a): MH+=539.0, RT=4.10 minutes; $^1$H NMR (DMSO-d$_6$, 400 MHz) δ 9.77 (s, 1H), 9.53 (s, 1H), 8.29 (d, J=5.3 Hz, 1H), 7.98 (m, 2H), 7.63 (m, 6H), 7.36 (m, 1H), 7.24 (s, 1H), 7.15 (m, 1H), 5.85 (br, 2H), 4.04 (s, 3H), 3.92 (s, 3H).

EXAMPLE 835

N-(4-{4-amino-7-[2-(hydroxymethyl)thien-3-yl]thieno[3,2-c]pyridin-3-yl}-2-methoxyphenyl)-1-methyl-1H-indole-2-carboxamide Sodium borohydride (9.4 mg, 0.223 mmol) was added to a mixture of N-{4-[4-amino-7-(2-formylthien-3-yl)thieno[3,2-c]pyridin-3-yl]-2-methoxyphenyl}-1-methyl-1H-indole-2-carboxamide (40.0 mg, 0.0743 mmol) in N, N-dimethylformamide (5 mL) under an atmosphere of nitrogen gas. The solution was stirred for 20 hours at room temperature after which it was diluted with methylene chloride and was washed with water (10 mL) and brine (10 mL). The organics were dried over magnesium sulfate and the solvent was removed in vacuo. The product was purified via flash chromatography to furnish the title compound as a yellow powder (12.0 mg, 0.0222 mmol). LCMS (Conditions a): (MH+)=541.0, RT=3.70 minutes; $^1$H NMR (DMSO-$d_6$, 400 MHz) δ 9.51 (s, 1H), 7.99 (d, J=8.2 Hz, 1H), 7.81 (s, 1H), 7.70 (d, J=7.8 Hz, 1H), 7.60 (d, J=5.1 Hz, 1H), 7.57 (d, J=8.6 Hz, 1H), 7.55 (s, 1H), 7.35–7.32 (m, 2H), 7.24 (d, J=5.1 Hz, 1H), 7.21 (d, J=1.56 Hz, 1H), 7.13 (m, 1H), 7.09 (dd, J=8.2, 1.56 Hz, 1H), 5.58 (br, 2H), 4.57 (d, J=5.5 Hz, 2H), 4.02 (s, 3H), 3.90 (s, 3H).

Examples 836–838, shown in Table 4, were prepared using N-{4-[4-amino-7-(2-formylthien-3-yl)thieno[3,2-c]pyridin-3-yl]-2-methoxyphenyl}-1-methyl-1H-indole-2-carboxamide, the appropriate amine, and the procedure described in General Procedure B.

TABLE 4

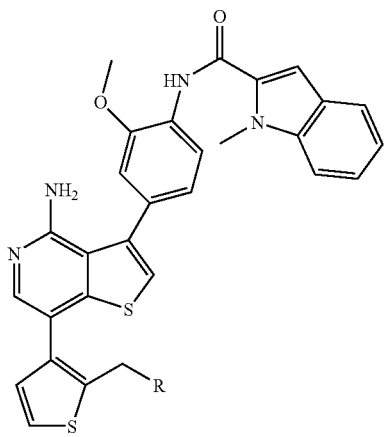

| R | Example o | RT (min.) | m/z (MH+) |
|---|---|---|---|
| Morpholine | 836 | 4.32[a] | 610 |
| Diethylene | 837 | 5.19[a] | 596 |
| N,N,N'-trimethylpropane-1,3-diamine | 838 | 3.79[a] | 639 |

EXAMPLE 839

N-(4-{4-amino-7-[5-(morpholin-4-ylmethyl)thien-2-yl]thieno[3,2-c]pyridin-3-yl}-2-methoxyphenyl)-1-methyl-1H-indole-2-carboxamide N-{4-[4-amino-7-(5-formylthien-2-yl)thieno[3,2-c]pyridin-3-yl]-2-methoxyphenyl}-1-methyl-1H-indole-2-carboxamide (80.0 mg, 0.149 mmol) and morpholine (51.7 μL, 0.595 mmol) were reacted according to General Procedure B followed by flash chromatography purification to furnish the title compound as a light yellow powder. (1.3 mg, 0.0021 mmol): LCMS (Conditions a): MH–=608.0, RT =4.35 minutes; $^1$H NMR (DMSO-$d_6$, 400 MHz) δ 9.50 (s, 1H), 8.08 (s, 1H), 8.00 (d, J=8.2 Hz, 1H), 7.70 (d, J=8.0 Hz, 1H), 7.63 (s, 1H), 7.59 (dd, J=8.5, 0.70 Hz, 1H), 7.34 (m, 1H), 7.31 (m, 1H), 7.22 (d, J=1.8 Hz, 1H), 7.14 (d, J=7.8 Hz, 2H), 7.08–7.12 (m, 1H), 7.05 (d, J=3.5 Hz, 1H), 5.69 (br, 2H), 4.04 (s, 3H), 3.92 (s, 3H), 3.72 (s, 2H), 3.61 (t, J=4.5 Hz, 4H), 2.46 (m, 4H).

EXAMPLE 839

N-(4-{4-amino-7-[4-methyl-5-(morpholin-4-ylmethyl)thien-2-yl]thieno[3,2-c]pyridin-3-yl}-2-methoxyphenyl)-1-methyl-1H-indole-2-carboxamide N-{4-[4-amino-7-(5-formyl-4-methylthien-2-yl)thieno[3,2-c]pyridin-3-yl]-2-methoxyphenyl}-1-methyl-1H-indole-2-carboxamide (70.0 mg, 0.127 mmol) and morpholine (44.2 μL, 0.507 mmol) were reacted according to General Procedure B followed by HPLC purification to give the title compound as a light yellow powder. (3.2 mg, 0.0051 mmol): LCMS (Conditions a): MH–=622, RT=4.73 minutes; $^1$H NMR (DMSO-$d_6$, 400 MHz) δ 9.50 (s, 1H), 8.06 (s, 1H), 8.00 (d, J=8.0 Hz, 1H), 7.70 (d, J=8.0 Hz, 1H), 7.63 (s, 1H), 7.58 (dd, J=8.4, 0.80 Hz, 1H), 7.34 (m, 1H), 7.32 (m, 1H), 7.22 (d, J=2.0 Hz, 1H), 7.20 (s, 1H), 7.12–7.16 (m, 1H), 7.09 (dd, J=8.0, 2.0 Hz, 1H), 5.69 (br, 2H), 4.04 (s, 3H), 3.91 (s, 3H), 3.63 (s, 2H), 3.60 (t, J=4.6 Hz, 4H), 2.46 (m, 4H), 2.22 (s, 3H).

Examples 840–847, shown in Table 5, were prepared using N-{4-[4-amino-7-(3-formylphenyl)thieno[3,2-c]pyridin-3-yl]-2-methoxyphenyl}-1-methyl-1H-indole-2-carboxamide, the appropriate amine, and the procedure described in General Procedure B.

TABLE 5

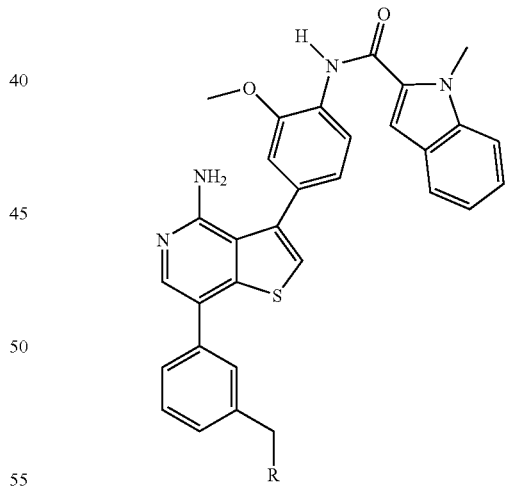

| R | Example | RT (min.) | m/z (MH+) |
|---|---|---|---|
| 4-Piperidinopiperidine | 840 | 4.45[1] | 685 |
| 1-(2-Dimethylaminoethyl)piperazine | 841 | 3.90[a] | 674 |
| (3S)-(−)-3-(Dimethylamino)pyrrolidine | 842 | 5.22[1] | 631 |
| 3-Diethylaminopropylamine | 843 | 4.87[1] | 647 |
| N-(3'-Aminopropyl)2-pyrrolidinone | 844 | 2.97[1] | 659 |
| N,N,N'-Trimethyl-1,3-propanediamine | 845 | 4.85[1] | 633 |

TABLE 5-continued

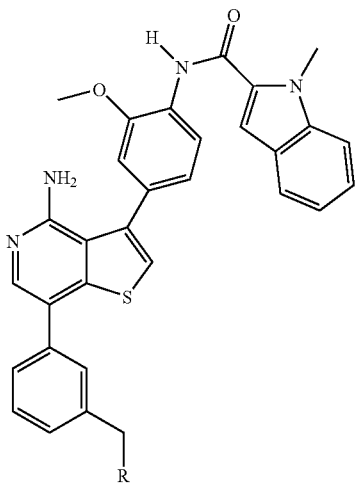

| R | Example | RT (min.) | m/z (MH+) |
|---|---|---|---|
| N',N'-Diethyl-pentane-1,4-diamine | 846 | 4.32[a] | 675 |
| N',N'-Diethyl-butane-1,4-diamine | 847 | 3.63[a] | 661 |

Examples 848–851, shown in Table 6, were prepared using N-[4-(4-amino-7-iodothieno[3,2-c]pyridin-3-yl)-2-methoxyphenyl]-1-methyl-1H-indole-2-carboxamide, the appropriate boronic acid, and the procedure described in General Procedure A.

TABLE 6

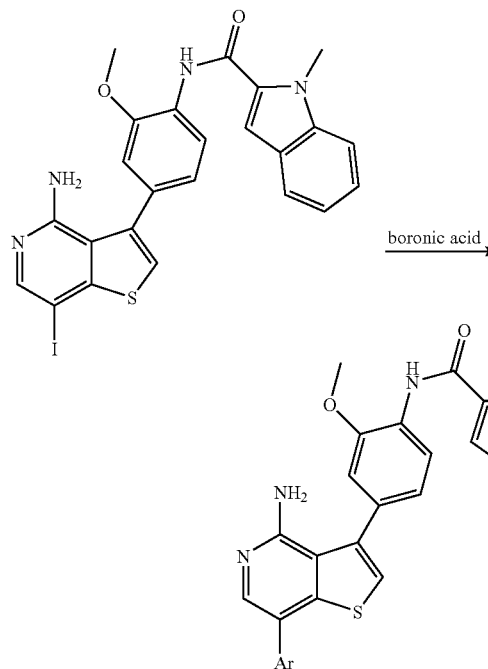

| Boronic Acid | Example | RT (min.) | m/z (MH−) |
|---|---|---|---|
| (3-AMINOMETHYLPHENYL) BORONIC ACID, HCl | 848 | 10.9 (j) | 532.3 |

TABLE 6-continued

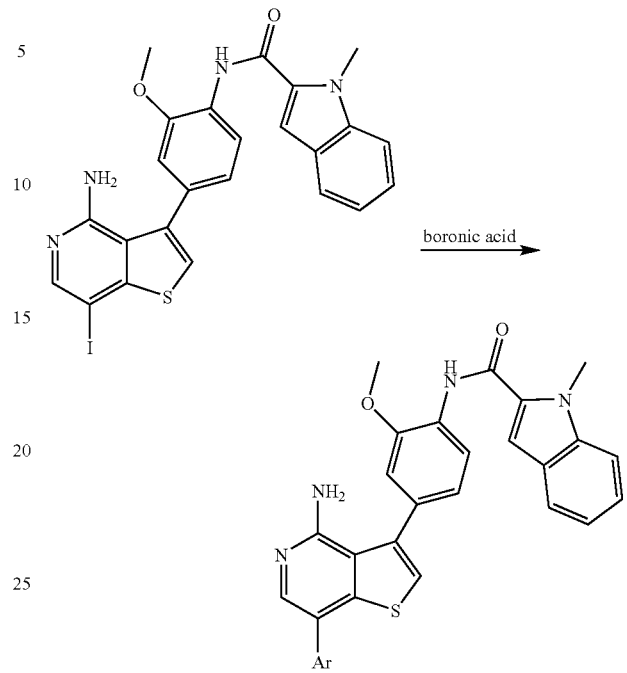

| Boronic Acid | Example | RT (min.) | m/z (MH−) |
|---|---|---|---|
| 2-(N,N-DIMETHYLAMINOMETHYL) PHENYLBORONIC ACID | 849 | 12.0 (j) | 560.3 |
| 3-(2-CARBOXYVINYL) BENZENEBORONIC ACID | 850 | 22.6 (j) | 573.1 |
| 3-(METHYLSULFONYLAMINO) PHENYLBORONIC ACID | 851 | 23.1 (i) | 596.3 |

Examples 855–863, shown in Table 7, were prepared using 4-amino-3-(3-methoxy-4-{[(1-methyl-1H-indol-2-yl)carbonyl]amino}phenyl)thieno[3,2-c]pyridine-7-carboxylic acid, the appropriate amine, and the procedure described in General Procedure D.

TABLE 7

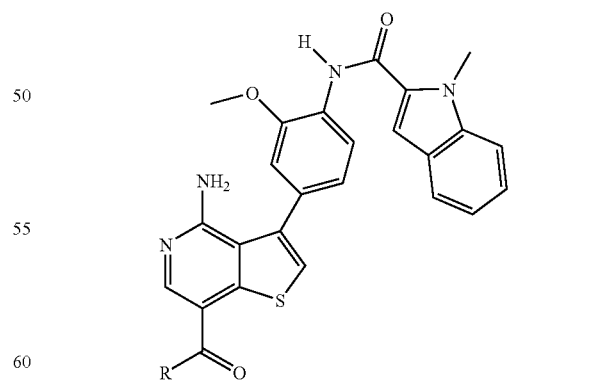

| R | Example | LCMS RT (m+/z) |
|---|---|---|
| (+/−)-3-Amino-1-N-Boc piperidine | 855 | 3.97 min (655.3) |
| 3-Aminomethyl-1-N-Boc piperidine | 856 | 4.03 min (669.3) |

TABLE 7-continued

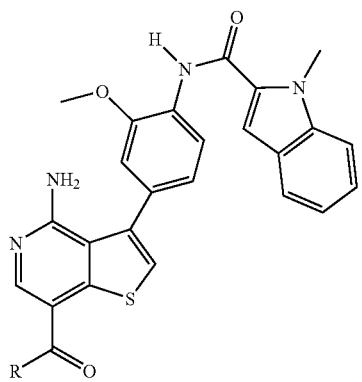

| R | Example | LCMS RT (m+/z) |
|---|---|---|
| N,2,2-Tetramethyl-1,3-propanediamine | 857 | 3.32 min (585.1) |
| tert-butyl-N-(3-aminopropyl) carbamate | 858 | 3.68 min (629.1) |
| tert-butyl N-(2-aminoethyl) carbamate | 859 | 3.53 min (615.1) |
| N-(3-aminopropyl)-N-methyl carbamic acid tert-butyl ester | 860 | 3.90 min (643.1) |

TABLE 7-continued

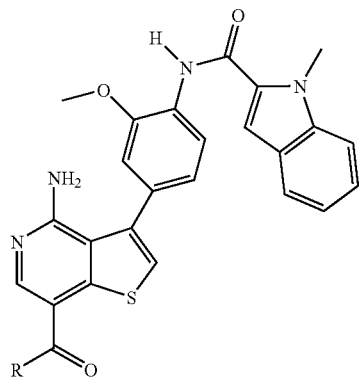

| R | Example | LCMS RT (m+/z) |
|---|---|---|
| N-(2-aminoethyl)-N-methyl carbamic acid tert-butyl ester | 861 | 3.77 min (629.1) |
| R-3-Amino-1-N-Boc Piperidine | 862 | 3.75 min (655.1) |
| S-3-Amino-1-N-Boc Piperidine | 863 | 3.76 min (655.1) |

Examples 864–871, in Table 8, were prepared using a compound from Table 7 and the procedure described in General Procedure H.

TABLE 8

| Product | Example | LCMS RT (m+/z) |
|---|---|---|
| 4-amino-3-(3-methoxy-4-{[(1-methyl-1H-indol-2-yl)carbonyl]amino}phenyl)-N-piperidin-3-ylthieno[3,2-c]pyridine-7-carboxamide | 864 | 2.83 min (555.2) |
| 4-amino-3-(3-methoxy-4-{[(1-methyl-1H-indol-2-yl)carbonyl]amino}phenyl)-N-(piperidin-3-ylmethyl)thieno[3,2-c]pyridine-7-carboxamide | 865 | 2.95 min (569.2) |
| 4-amino-3-(3-methoxy-4-{[(1-methyl-1H-indol-2-yl)carbonyl]amino}phenyl)-N-[3-(methylamino)propyl]thieno[3,2-c]pyridine-7-carboxamide | 866 | 2.88 min (543.1) |
| 4-amino-N-(3-aminopropyl)-3-(3-methoxy-4-{[(1-methyl-1H-indol-2-yl)carbonyl]amino}phenyl)thieno[3,2-c]pyridine-7-carboxamide | 867 | 2.8 min (529.1) |
| 4-amino-3-(3-methoxy-4-{[(1-methyl-1H-indol-2-yl)carbonyl]amino}phenyl)-N-[2-(methylamino)ethyl]thieno[3,2-c]pyridine-7-carboxamide | 868 | 2.96 min (529.1) |
| 4-amino-N-(2-aminoethyl)-3-(3-methoxy-4-{[(1-methyl-1H-indol-2-yl)carbonyl]amino}phenyl)thieno[3,2-c]pyridine-7-carboxamide | 869 | 2.75 min (515.1) |
| 4-amino-3-(3-methoxy-4-{[(1-methyl-1H-indol-2-yl)carbonyl]amino}phenyl)-N-[(3R)-piperidin-3-yl]thieno[3,2-c]pyridine-7-carboxamide | 870 | 2.57 min (555.1) |
| 4-amino-3-(3-methoxy-4-{[(1-methyl-1H-indol-2-yl)carbonyl]amino}phenyl)-N-[(3S)-piperidin-3-yl]thieno[3,2-c]pyridine-7-carboxamide | 871 | 2.68 min (555.1) |

Examples 872–887, shown in Table 9, were prepared using N-[4-(4-amino-7-iodothieno[3,2-c]pyridin-3-yl)-2-methoxyphenyl]-1-methyl-1H-indole-2-carboxamide, the appropriate amine, and the procedure described in General Procedure J.

TABLE 9

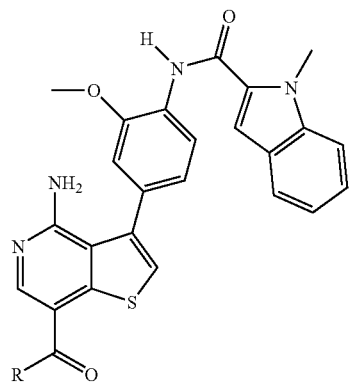

| R | Example | HPLC RT min. | m/z (M+H)+ |
|---|---|---|---|
| 3-aminopyridine | 872 | 3.42 (a) | 549.2 |
| 4-aminopyridine | 873 | 3.45 (a) | 549.2 |
| Thiazol-2-ylamine | 874 | 3.75 (a) | 555.2 |
| 5-Methyl-isoxazol-3-ylamine | 875 | 3.72 (a) | 553.3 |
| 3-Amino-1H-pyrazole-4-carbonitrile | 876 | 3.02 (a) | 563.1 |
| (2-Amino-thiazol-4-yl)-acetic acid ethyl ester | 877 | 3.93 (a) | 641.0 |
| 2-Amino-4-methyl-thiazole-5-carboxylic acid dimethylamide | 878 | 3.33 (a) | 640.0 |
| 2-Ethyl-2H-pyrazol-3-ylamine | 879 | 3.32 (a) | 566.1 |
| Isoxazol-3-ylamine | 880 | 3.58 (a) | 539.1 |
| Pyridine-2,6-diamine | 881 | 3.07 (a) | 592.1 |
| 6-Amino-nicotinamide | 882 | 3.60 (a) | 564.1 |
| Pyrimidin-4-ylamine | 883 | 3.55 (a) | 550.2 |
| Pyrazin-2-ylamine | 884 | 3.53 (a) | 550.2 |
| 1-Methyl-1H-pyrazol-3-ylamine | 885 | 3.35 (a) | 552.1 |
| 4-Piperidin-1-ylmethyl-thiazol-2-ylamine | 886 | 4.03 (a) | 652.0 |
| 2-Aminopyridine | 887 | 3.90 (a) | 549.3 |

Examples 888–891, shown in Table 10, were prepared using 4-amino-3-(3-methoxy-4-{[(1-methyl-1H-indol-2-yl)carbonyl]amino}phenyl)thieno[3,2-c]pyridine-7-carboxylic acid, the appropriate amine, and the procedure described in General Procedure D.

TABLE 10

| R | Example | HPLC RT min. | m/z (M + H)+ |
|---|---|---|---|
| (S)-5-Amino-piperidin-2-one | 888 | 2.65 (a) | 569.1 |
| (S)-(1-Aza-bicyclo[2.2.2]oct-3-yl)amine | 889 | 2.98 (a) | 581.0 |
| (R)-(1-Aza-blcyclo[2.2.2]oct-3-yl)amine | 890 | 2.98 (a) | 581.0 |
| 1-ethylpiperidin-3-ylamine | 891 | 2.98 (a) | 583.1 |

Examples 895–902, 904, and 905, shown in Table 11, were prepared using 4-amino-3-(3-methoxy-4-{[(1-methyl-1H-indol-2-yl)carbonyl]amino}phenyl)thieno[3,2-c]pyridine-7-carboxylic acid, the appropriate amine, and the procedure described in General Procedure D.

Example 892–894 and 903, shown in Table 11, were prepared using N-[4-(4-amino-7-iodothieno[3,2-c]pyridin-3-yl)-2-methoxyphenyl]-1-methyl-1H-indole-2-carboxamide, the appropriate amine, and the procedure described in General Procedure J.

TABLE 11

| R | Example | RT (min.) | m/z (MH+) |
|---|---|---|---|
| 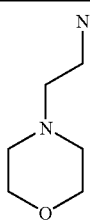 | 892 | 2.62 | 585.5 |

TABLE 11-continued

[Structure: thieno-pyridine core with NH2, methoxy-phenyl-N-methylindole carboxamide, and R-C(O)- substituent]

| R | Example | RT (min.) | m/z (MH+) |
|---|---|---|---|
| methoxyethylamine (CH3-O-CH2-CH2-NH2) | 893 | 2.68 | 530.4 |
| 1-methylpyrrolidin-2-yl ethylamine | 894 | 2.42 | 583.4 |
| 2-(pyridin-3-yl)ethylamine | 895 | 3.05 | 577.4 |
| 2-(piperidin-1-yl)ethylamine | 896 | 3.15 | 583.4 |
| 2-(diethylamino)ethylamine | 897 | 3.10 | 571.3 |
| 1-(2-aminoethyl)pyrrolidin-2-one | 898 | 2.95 | 597.3 |

TABLE 11-continued

[Same core structure]

| R | Example | RT (min.) | m/z (MH+) |
|---|---|---|---|
| 4-hydroxypiperidine | 899 | 2.73 | 556.2 |
| 1-(2-hydroxyethyl)piperazine | 890 | 2.47 | 585.4 |
| N,N-bis(2-hydroxyethyl)ethylenediamine | 891 | 2.62 | 603.4 |
| 2-amino-1,3-propanediol (serinol) | 892 | 2.52 | 546.2 |
| 3-(pyrrolidin-1-yl)propylamine | 893 | 3.03 | 583.3 |
| cyclopropylamine | 894 | 3.27 | 512.3 |

TABLE 11-continued

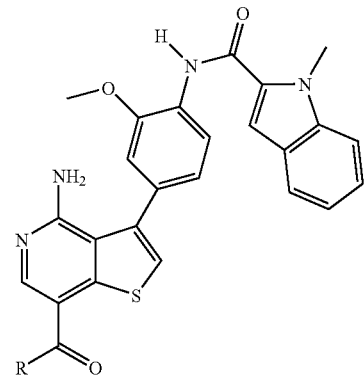

| R | Example | RT (min.) | m/z (MH+) |
|---|---|---|---|
| piperazine-acetyl | 895 | 2.77 | 583.3 |
| 2-aminoethoxyethanol | 896 | 2.73 | 560.2 |
| 4-ethylpiperazine | 897 | 3.13 | 569.4 |
| N,N-dimethylethylenediamine | 898 | 3.00 | 543.3 |
| N-methyl-N'-ethyl-N'-ethyl-ethylenediamine | 899 | 3.15 | 585.3 |
| 2-(pyrrolidin-1-yl)ethylamine | 900 | 3.11 | 569.3 |

TABLE 11-continued

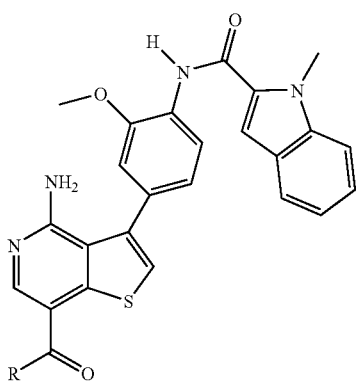

| R | Example | RT (min.) | m/z (MH+) |
|---|---|---|---|
| 3-amino-propyl-2-methylpiperidine | 901 | 3.55 | 611.1 |
| 3-amino-propyl-piperazine | 902 | 3.25 | 612.1 |
| aminomethyl-piperazine-acetic acid | 903 | 2.82 | 598 |
| β-alanine | 904 | 2.10 | 544 |
| N-(2-dimethylaminoethyl)-β-alaninamide | 905 | 2.77 | 614 |

Examples 906–912, shown in Table 12, were prepared using 4-amino-3-(3-methoxy-4-{[(1-methyl-1H-indol-2-yl)carbonyl]amino}phenyl)thieno[3,2-c]pyridine-7-carboxylic acid, the appropriate amine, and the procedure described in General Procedure D. LCMS conditions: Conditions a.

TABLE 12

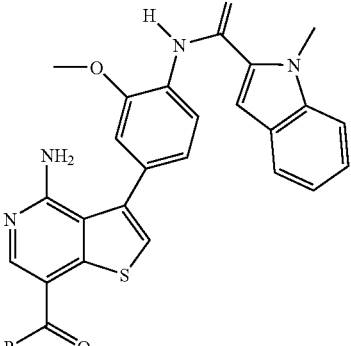

| R | Example | RT (min.) | m/z (MH+) |
|---|---|---|---|
| 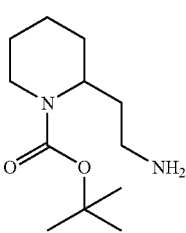 | 906 | 4.05 | 669.1 |
| 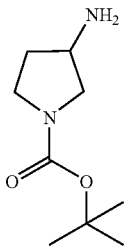 | 907 | 4.43 | 683.2 |
| 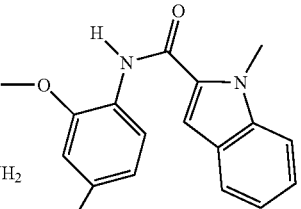 | 908 | 3.85 | 641.0 |

TABLE 12-continued

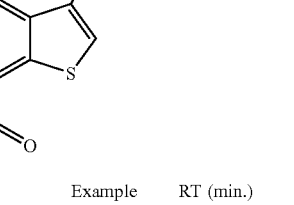

| R | Example | RT (min.) | m/z (MH+) |
|---|---|---|---|
| 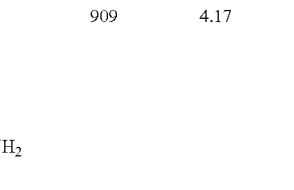 | 909 | 4.17 | 655.1 |
| 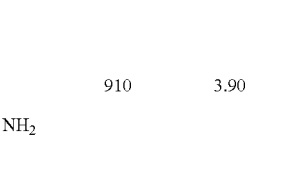 | 910 | 3.90 | 655.0 |
| 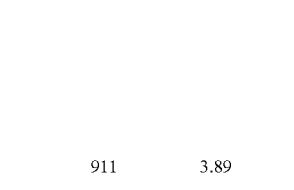 | 911 | 3.89 | 669.2 |
|  | 912 | 3.77 | 655.0 |

Examples 913–919, shown in Table 13, were prepared by treating the compounds from Table 12 according to General Procedure H. LCMS: Condidions a.

TABLE 13

| R | Example | RT (min) | m/z (MH+) |
|---|---------|----------|-----------|
| (piperidin-4-ylmethyl)amino | 913 | 2.92 | 569.1 |
| 2-(piperidin-2-yl)ethylamino | 914 | 3.22 | 583.1 |
| (piperidin-2-ylmethyl)amino | 915 | 3.30 | 569.1 |
| pyrrolidin-3-ylamino | 916 | 3.02 | 541.0 |
| (pyrrolidin-2-ylmethyl)amino | 917 | 3.22 | 555.0 |

TABLE 13-continued

| R | Example | RT (min) | m/z (MH+) |
|---|---------|----------|-----------|
| piperidin-4-ylamino | 918 | 2.73 | 555.0 |
| (pyrrolidin-3-ylmethyl)amino | 919 | 2.97 | 555.0 |

Examples 920–941, shown in Table 14, were prepared using 4-amino-3-(3-methoxy-4-{[(1-methyl-1H-indol-2-yl)carbonyl]amino}phenyl)thieno[3,2-c]pyridine-7-carboxylic acid, the appropriate amine, and the procedure described in General Procedure D.

TABLE 14

| R | Example | RT (min.) | m/z (MH+) |
|---|---------|-----------|-----------|
| 2-Ethylsulfanyl ethylamine | 920 | 3.73[a] | 560 |
| 3-(4H-Imidazol-1-yl) propylamine | 921 | 3.00[a] | 580 |

TABLE 14-continued

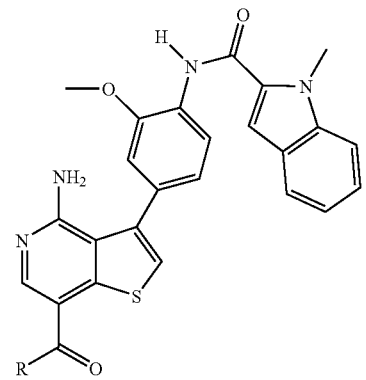

| R | Example | RT (min.) | m/z (MH+) |
|---|---|---|---|
| 4-Amino butan-1-ol | 922 | 2.90[a] | 544 |
| Pyridin-2-yl methylamine | 923 | 3.28[a] | 563 |
| Aminoacetic acid methyl ester | 924 | 3.25[a] | 544 |
| 2-Thiophen-2-yl ethylamine | 925 | 3.87[a] | 582 |
| (Tetrahydro-furan-2-yl)methylamine | 926 | 3.37[a] | 556 |
| 2-Ethoxyethylamine | 927 | 3.38[a] | 544 |
| Furan-2-yl methylamine | 928 | 3.58[a] | 552 |
| 1-(2-Aminoethyl) imidazolidin-2-one | 929 | 2.77[a] | 584 |
| 2-Pyridin-2-yl ethylamine | 930 | 3.28[a] | 577 |
| 1-Aminobutan-2-ol | 931 | 3.12[a] | 544 |
| 1-(3-Aminopropyl) pyrrolidin-2-one | 932 | 2.98[a] | 597 |
| 2-(1H-Imidazol-4-yl) ethylamine | 933 | 2.75[a] | 566 |
| 2-Pyridin-4-yl ethylamine | 934 | 3.12[a] | 577 |
| Pyridin-3-yl methylamine | 935 | 3.10[a] | 563 |
| 2-(1-Methyl-1H-pyrrol-2-yl) ethylamine | 936 | 3.68[a] | 579 |
| (Tetrahydro-pyran-4-yl)methylamine | 937 | 3.25[a] | 556 |
| (2,2-Dimethyl-[1,3] dioxolan-4-yl) methylamine | 938 | 3.45[a] | 586 |
| Pyridin-4-yl methylamine | 939 | 3.08[a] | 563 |
| 2-(3-Methyl-3H-imidazol-4-yl) ethylamine | 940 | 2.88[a] | 580 |
| 1-Amino-propan-2-ol | 941 | 2.88[a] | 530 |

EXAMPLE 942

({[4-amino-3-(3-methoxy-4-{[(1-methyl-1H-indol-2-yl)carbonyl]amino}phenyl)thieno[3,2-c]pyridin-7-yl]carbonyl}amino)acetic acid To a mixture of methyl ({[4-amino-3-(3-methoxy-4-{[(1-methyl-1H-indol-2-yl)carbonyl]amino}phenyl)thieno[3,2-c]pyridin-7-yl]carbonyl}amino)acetate (0.130 g, 0.239 mmol) in 1,4 dioxane (10 mL) was added 2M sodium hydroxide in water (0.260 mL, 0.521 mmol). The resulting solution was heated at 50° C. for 3 hours. 1M hydrochloric acid was added until pH of the mixture was 4 and solvent was removed under reduced pressure. The resulting white solid was washed with water (2 mL) and filtered and dried to furnish the title compound (64 mg, 0.121 mmol): LCMS (Conditions b): MH+=530 RT=2.03 min; $^1$H NMR (DMSO-$d_6$, 400 MHz) δ 12.65 (1H), 9.50 (1H), 8.95 (1H), 8.60 (1H), 8.02 (1H), 7.71 (2H), 7.58 (1H), 7.35 (2H), 7.21 (1H), 7.15 (1H), 7.09 (1H), 6.29 (2H), 4.04 (3H), 3.97 (2H), 3.92 (3H).

EXAMPLE 943

4-amino-3-(3-methoxy-4-{[(1-methyl-1H-indol-2-yl) carbonyl]amino}phenyl)thieno[3,2-c]pyridine-7-carboxamide N2-[4-(4-amino-7-cyanothieno[3,2-c]pyridin-3-yl)-2-methoxyphenyl]-1-methyl-1H-2-indolecarboxamide (A-825289.0, 50 mg, 0.11 mmol), potassium carbonate (61 mg, 0.44 mmol), and hydrogen peroxide (0.150 mL, 30% aqueous) were heated in dimethylsulfoxide (1 mL) for 25 minutes at 150° C. in a microwave. The mixture was evaporated, diluted in dimethylformamide, filtered, and the filtrate was purified by RP-HPLC to yield the title compound (2 mg, 4% yield): $^1$H NMR (DMSO-$d_6$, 400 MHz) δ 9.50 (s, 1H), 8.57 (s, 1H), 8.00 (d, 1H), 7.71 (d, 1H), 7.58–7.62 (m, H), 7.06–7.35 (m, 5H), 4.04 (s, 3H); RP-HPLC (Conditions i) $R_t$ 11.7 min. MS: 470.0 MH−.

Examples 943–951, shown in Table 15, were prepared using 4-amino-3-(3-methoxy-4-{[(1-methyl-1H-indol-2-yl)carbonyl]amino}phenyl)thieno[3,2-c]pyridine-7-carboxylic acid, the appropriate amine, and the procedure described in General Procedure D.

TABLE 15

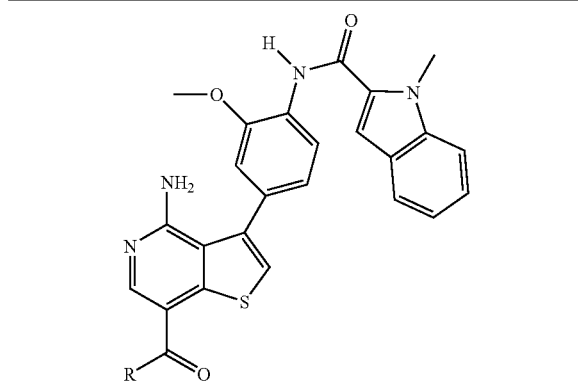

| R | Example | RT (min.) | m/z (MH−) |
|---|---|---|---|
| 2-Amino-ethanol | 943 | 11.0 (j) | 516.1 (+) |
| N-ACETYLPUTRESCINE HYDROCHLORIDE | 944 | 2.6 (a) | 583.3 |
| 2-THIOPHENE METHYLAMINE | 945 | 3.7 (a) | 566.3 |
| 2-[1,2,4]Triazol-1-yl ethyl-ammonium; bromide | 946 | 2.8 (a) | 565.3 |
| GLYCINAMIDE HYDROCHLORIDE | 947 | 2.6 (a) | 527.0 |
| 3-AMINO-1-PROPANOL | 948 | 2.8 (a) | 583.0 |
| 2-AMINOETHYL ISOPROPYL ETHER | 949 | 13.7 (j) | 558.0 (+) |
| 3-AMINO-2,2-DIMETHYL-1-PROPANOL | 950 | 13.1 (j) | 558.0 (+) |

TABLE 15-continued

| R | Example | RT (min.) | m/z (MH−) |
|---|---|---|---|
| 3-(2-AMINOETHYL)-2,4-THIAZOLIDINEDIONE HYDROCHLORIDE | 951 | 3.25 (a) | 615.0 (+) |

EXAMPLE 952

4-amino-N-(2,2-dimethoxyethyl)-3-(3-methoxy-4-{[(1-methyl-1H-indol-2-yl)carbonyl]amino}phenyl)thieno[3,2-c]pyridine-7-carboxamide 4-amino-3-(3-methoxy-4-{[(1-methyl-1H-indol-2-yl)carbonyl]amino}phenyl)thieno[3,2-c]pyridine-7-carboxylic acid (1.0 g, 2.1 mmol) and 2,2-dimethoxy-1-ethanamine (252 uL, 2.3 mmol) were reacted according to General Procedure D. MP-carbonate resin (5 g) was added, and the mixture was shaken for 2 hours. The resin was filtered from the mixture and the filtrate was concentrated in vacuo to yield 1.5 g crude material. Isopropyl alcohol (35 mL) was added and the crude product was triturated and filtered to yield the title compound (830 mg, 71% yield): $^1$H NMR (DMSO, 400 MHz) δ 9.48 (s, 1H), 8.56 (s, 2H), 7.98 (d, 1H), 7.69 (d, 1H), 7.56–7.58 (m, 2H), 7.31–7.33 (m, 2H), 7.04–7.17 (m, 3H), 4.54 (t, 1H), 4.02 (s, 3H), 3.89 (s, 3H), 3.37 (t, 2H), 3.31 (s, 6H), 2.51 (t, 2H); RP-HPLC (Conditions j) $R_t$ 12.2 min. MS: 560.0 MH$^+$.

EXAMPLE 953

4-amino-3-(3-methoxy-4-{[(1-methyl-1H-indol-2-yl)carbonyl]amino}phenyl)-N-(2-oxoethyl)thieno[3,2-c]pyridine-7-carboxamide 4-Amino-N-(2,2-dimethoxyethyl)-3-(3-methoxy-4-{[(1-methyl-1H-indol-2-yl)carbonyl]amino}phenyl)thieno[3,2-c]pyridine-7-carboxamide (100 mg, 0.18 mmol), trifluoroacetic acid (2 mL), and water (4 mL) were combined at ambient temperature for 2 hours. Mixture was diluted with a solution of saturated sodium bicarbonate (50 mL) and filtered to yield the title compound (65 mg, 70% yield): $^1$H NMR (DMSO, 400 MHz) δ 9.59 (s, 1H), 9.50 (s, 1H), 9.13 (m, 1H), 8.61 (s, 2H), 8.08 (d, 1H), 7.79 (s, 1H), 7.65 (dd, 2H), 7.32–7.35 (m, 2H), 7.25 (s, 1H), 7.10–7.16 (m, 2H), 4.16 (d, 2H), 4.04 (s, 3H), 3.92 (s, 3H); RP-HPLC (5% to 95% acetonitrile over 5 minutes, 1 ml/min, 254 nm, betasil HS 100 Å, C18, 5 μm, 50×2.1 column) $R_t$ 3.54 min. MS: 531.0 MH$^+$.

Examples 954–968, shown in Table 16, were prepared using 4-amino-3-(3-methoxy-4-{[(1-methyl-1H-indol-2-yl)carbonyl]amino}phenyl)-N-(2-oxoethyl)thieno[3,2-c]pyridine-7-carboxamide, the appropriate amine, and the procedure described in General Procedure B.

TABLE 16

| R | Example | RT (min.) | m/z (MH−) |
|---|---|---|---|
| 3-PYRROLIDINOL | 954 | 2.7 (a) | 583.9 |
| 3-AMINO-1-PROPANOL | 955 | 9.8 (j) | 573.1 (+) |
| 2-(ETHYLAMINO) | 956 | 10.4 (j) | 587.1 (+) |
| AZETIDINE HYDROCHLORIDE | 957 | 2.9 (a) | 553.1 |
| 2-METHOXY ETHYLAMINE | 958 | 10.4 (j) | 573.0 (+) |
| ETHANOLAMINE | 959 | 2.5 (a) | 559.0 (+) |
| D-PROLINOL | 960 | 3.4 (k) | 599.1 (+) |
| 2-METHYL PYRROLIDINE | 961 | 2.9 (a) | 583.1 (+) |
| CYCLOPROPYLAMINE | 962 | 17.9 (j) | 543.0 (+) |
| N,N-DIMETHYL ETHYLENEDIAMINE | 963 | 17.1 (j) | 586.0 (+) |
| (3R)-(+)-3-(DIMETHYLAMINO) PYRROLIDINE | 964 | 17.4 (i) | 612.1 (+) |
| Pyrrolidin-3-ylamine | 965 | 16.5 (i) | 684.1 (+) |
| (S)-(+)-2-(METHOXYMETHYL) PYRROLIDINE | 966 | 3.2 (a) | 613.1 (+) |
| 1-AMINO-2-PROPANOL | 967 | 9.9 (j) | 573.1 (+) |
| CYCLOPROPYLAMINE | 968 | 2.9 (a) | 555.0 (+) |

Examples 969–981, shown in Table 17, were prepared using 4-amino-3-(3-methoxy-4-{[(1-methyl-1H-indol-2-yl)carbonyl]amino}phenyl)-N-(pyrrolidin-2-ylmethyl)thieno[3,2-c]pyridine-7-carboxamide and the appropriate aldehyde, alkyl halide or acyl chloride according to General Procedures C, E or F respectively.

TABLE 17
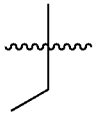
| R | Example | HPLC RT (min.) | m/z (M + H)+ |
|---|---|---|---|
| 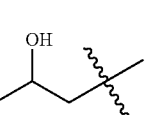 | 969 | 2.72 (a) | 583 |
| 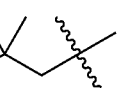 | 970 | 2.52 (a) | 629 |
| 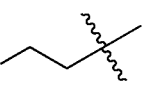 | 971 | 3.92 (a) | 625 |
| 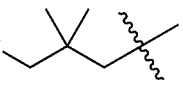 | 972 | 3.12 (a) | 613 |
| 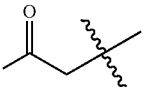 | 973 | 3.57 (a) | 668 |
| 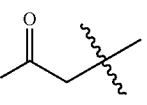 | 974 | 2.88 (a) | 612 |
| 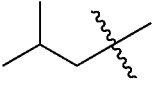 | 975 | 2.3 (a) | 613 |
TABLE 17-continued
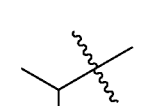
| R | Example | HPLC RT (min.) | m/z (M + H)+ |
|---|---|---|---|
| 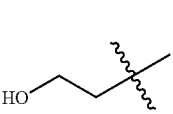 | 976 | 3.63 (a) | 611 |
| 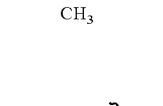 | 977 | 3.34 (a) | 597 |
| 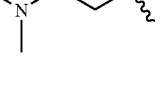 | 978 | 2.65 (a) | 599 |
| CH₃ | 979 | 2.96 (a) | 569 |
| 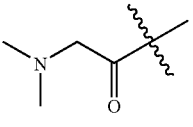 | 980 | 3.38 (a) | 626 |
|  | 981 | 2.75 (a) | 640 |
Examples 983–987, shown in Table 18, were prepared using 4-amino-3-(3-methoxy-4-{[(1-methyl-1H-indol-2-yl)carbonyl]amino}phenyl)-N-piperidin-3-ylthieno[3,2-c]pyridine-7-carboxamide and the appropriate alkyl halide according to General Procedure E.

TABLE 18

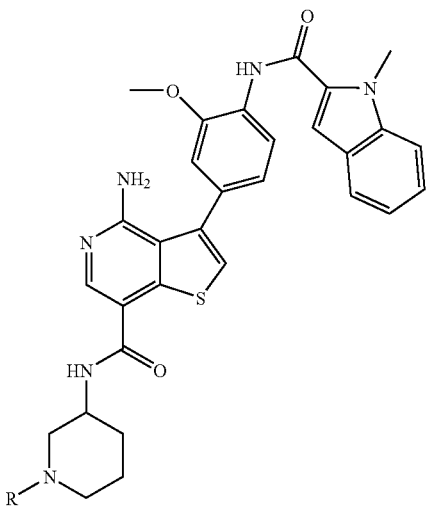

| alkyl halide | Example | HPLC RT min. | m/z (M + H)+ |
|---|---|---|---|
| 1-Bromo-2-methoxyethane | 983 | 3.12 (a) | 613.0 |
| 2-Bromo-acetamide | 984 | 2.85 (a) | 612.0 |
| 3-Bromo-propionamide | 985 | 2.22 (a) | 626.0 |
| 2-Chloro-ethylamine hydrochloride salt | 986 | 2.42 (a) | 598.0 |
| 2-Bromoethanol | 987 | 2.72 (a) | 599.1 |

Examples 988–992, shown in Table 19, were prepared using 4-amino-3-(3-methoxy-4-{[(1-methyl-1H-indol-2-yl)carbonyl]amino}phenyl)-N-piperidin-3-ylthieno[3,2-c]pyridine-7-carboxamide and the appropriate aldehyde or ketone according to General Procedure C.

TABLE 19

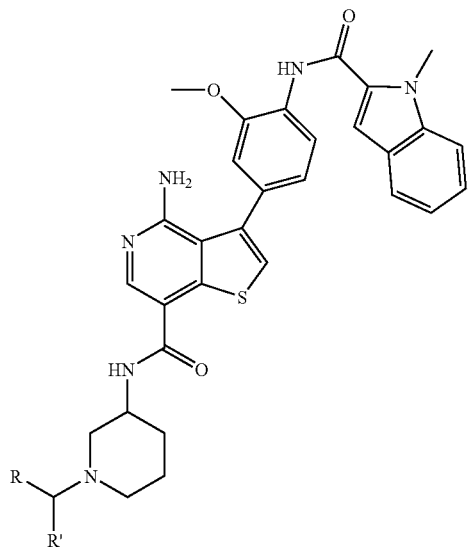

| aldehyde or ketone | Example | HPLC RT min. | m/z (M + H)+ |
|---|---|---|---|
| 2-Methyl-propionaldehyde | 988 | 3.73 (a) | 611.0 |
| 2,2-Dimethyl-propionaldehyde | 989 | 4.93 (a) | 625.1 |

TABLE 19-continued

| aldehyde or ketone | Example | HPLC RT min. | m/z (M + H)+ |
|---|---|---|---|
| 3-Dimethylamino-2,2-dimethylpropionaldehyde | 990 | 3.45 (a) | 668.1 |
| Acetone | 991 | 3.05 (a) | 597.0 |
| Formaldehyde | 992 | 3.02 (a) | 569.1 |

Examples 993–996, shown in Table 20, were prepared using 4-amino-3-(3-methoxy-4-{[(1-methyl-1H-indol-2-yl)carbonyl]amino}phenyl)-N-piperidin-3-ylthieno[3,2-c]pyridine-7-carboxamide and the appropriate acylating reagent according to General Procedure F or G.

TABLE 20

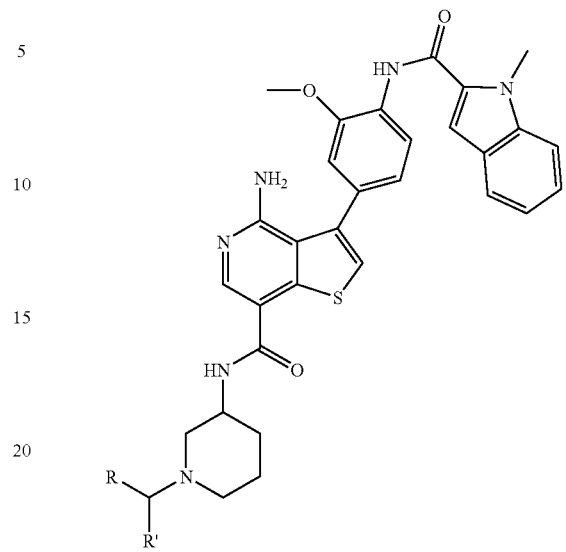

| acylating reagent | Example | HPLC RT min. | m/z (M + H)+ |
|---|---|---|---|
| Acetic anhydride | 993 | 2.70 (a) | 597.0 |
| Dimethylsulfamoyl chloride | 994 | 3.48 (a) | 662.0 |
| Dimethylaminoacetyl chloride hydrochloride salt | 995 | 2.70 (a) | 640.1 |
| Methanesulfonyl chloride | 996 | 3.22 (a) | 633.0 |

EXAMPLE 997

4-amino-N-{1-[3-(dimethylamino)-3-oxopropyl]
piperidin-3-yl}-3-(3-methoxy-4-{[(1-methyl-1H-
indol-2-yl)carbonyl]amino}phenyl)thieno[3,2-c]
pyridine-7-carboxamide A mixture of 4-amino-3-(3-methoxy-4-{[(1-methyl-1H-indol-2-yl)carbonyl]amino}phenyl)-N-piperidin-3-ylthieno[3,2-c]pyridine-7-carboxamide (150 mg, 0.270 mmol) and N,N-dimethylacrylamide (28 mg, 0.283 mmol, 3 portions at 2 hour intervals) were reacted according to General Procedure K. The residue was purified by flash column chromatography on silica using dichloromethane/methanol/ammonium hydroxide (28–30% solution) (80:20:0.05) mixture as the mobile phase to give the title compound. $^1$H NMR (400 MHz, DMSO-$d_6$) δ 1.39 (m, 1H), 1.51(m, 1H), 1.70 (m, 1H), 1.81 (m, 1H), 1.98 (m, 2H), 2.48 (m, 2H), 2.58 (m, 2H), 2.76 (m, 1H), 2.81 (s, 3H), 2.91 (m, 1H), 2.99 (s, 3H), 3.91 (s, 3H), 3.99 (m, 1H), 4.04 (m, 3H), 7.07 (d, 1H), 7.15 (t, 1H), 7.18 (s, 1H), 7.33 (t, 1H), 7.35 (s, 1H), 7.60 (m, 2H), 7.71 (d, 1H), 7.99 (d, 1H), 8.16 (d, 1H), 8.59 (s, 1H), 9.50 (s, 1H). LCMS (Conditions a): MH$^+$=654.1, R$_f$=2.55 min.

Examples 998–1012, shown in Table 21, were prepared using 4-amino-3-(3-methoxy-4-{[(1-methyl-1H-indol-2-yl)carbonyl]amino}phenyl)-N-(piperidin-3-ylmethyl)thieno[3,2-c]pyridine-7-carboxamide and the appropriate aldehyde, ketone, carboxylic acid, alkyl halide, acyl chloride, or sulfonyl chloride according to General Procedures C, D, E, F, and G.

TABLE 21

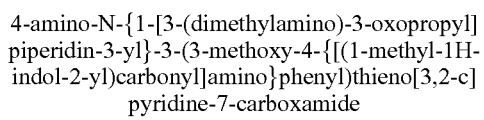

| R | Example | HPLC RT (min.) | m/z (M + H)$^+$ |
|---|---|---|---|
| isobutyl | 998 | 11.02 (g) | 625 |
| H$_2$N-C(O)-CH(CH$_3$)- | 999 | 9.25 (g) | 626 |
| (CH$_3$)$_2$N-CH$_2$-C(CH$_3$)$_2$- | 1000 | 9.58 (d) | 682 |

TABLE 21-continued

| R | Example | HPLC RT (min.) | m/z (M + H)$^+$ |
|---|---|---|---|
| MeO-CH$_2$CH$_2$- | 1001 | 6.55 (g) | 627 |
| ethyl | 1002 | 7.96 (d) | 597 |
| HO-CH$_2$-CH(OH)-CH$_2$- | 1003 | 5.02 (d) | 643 |
| (CH$_3$)$_3$C-CH$_2$- | 1004 | 8.56 (d) | 639 |
| CH$_3$-C(O)-CH(CH$_3$)- | 1005 | 7.12 (d) | 611 |
| CH$_3$-SO$_2$-C(CH$_3$)$_2$- | 1006 | 8.36 (d) | 647 |
| methyl | 1007 | 6.24 (d) | 583 |
| imidazolylmethyl | 1008 | 5.45 (d) | 649 |
| (CH$_3$)$_2$N-SO$_2$-C(CH$_3$)$_2$- | 1009 | 9.56 (d) | 676 |
| isopropyl | 1010 | 7.04 (d) | 611 |
| (CH$_3$)$_2$N-CH$_2$-C(O)-C(CH$_3$)$_2$- | 1011 | 7.84 (g) | 6.54 |
| HO-CH$_2$CH$_2$-C(CH$_3$)$_2$- | 1012 | 6.87 (g) | 613 |

Examples 1013–1015, shown in Table 22, were prepared using 4-amino-3-(3-methoxy-4-{[(1-methyl-1H-indol-2-yl)carbonyl]amino}phenyl)-N-(piperidin-2-ylmethyl)thieno[3,2-c]pyridine-7-carboxamide and the appropriate aldehyde according to General Procedure C. LCMS: Conditions a

TABLE 22

| Aldehyde | Example | RT (min) | m/z (MH+) |
| --- | --- | --- | --- |
| acetaldehyde | 1013 | 2.90 | 597.2 |
| isobutyraldehyde | 1014 | 3.70 | 625.0 |
| formaldehyde | 1015 | 3.07 | 583.0 |

Examples 1016–1018, shown in Table 23, were prepared using 4-amino-3-(3-methoxy-4-{[(1-methyl-1H-indol-2-yl)carbonyl]amino}phenyl)-N-(piperidin-2-ylmethyl)thieno[3,2-c]pyridine-7-carboxamide and the appropriate alkyl halide according to General Procedure E. LCMS: Conditions a

TABLE 23

| alkyl halide | Example | RT (min) | m/z (MH+) |
| --- | --- | --- | --- |
| 2-bromoacetamide | 1016 | 3.08 | 626.1 |
| 2-bromoethanol | 1017 | 2.80 | 613.0 |
| 3-bromopropionamide | 1018 | 2.85 | 640.0 |

EXAMPLE 1019

N-[(1-acetylpiperidin-2-yl)methyl]-4-amino-3-(3-methoxy-4-{[(1-methyl-1H-indol-2-yl)carbonyl]amino}phenyl)thieno[3,2-c]pyridine-7-carboxamide 4-Amino-3-(3-methoxy-4-{[(1-methyl-1H-indol-2-yl)carbonyl]amino}phenyl)-N-(piperidin-2-ylmethyl)thieno[3,2-c]pyridine-7-carboxamide (0.090 g, 0.16 mmol) and acetic acid (0.012 g, 0.17 mmol) were treated according to General Procedure D to provide the title compound. LCMS Conditions a: 3.11 minute, 611.1 (MH+).

Examples 1020 and 1021, shown in Table 24, were prepared using 4-amino-3-(3-methoxy-4-{[(1-methyl-1H-indol-2-yl)carbonyl]amino}phenyl)-N-(piperidin-2-ylmethyl)thieno[3,2-c]pyridine-7-carboxamide and the appropriate sulfonyl chloride according to General Procedure G. LCMS: Conditions a

TABLE 24

| sulfonyl chloride | Example | RT (min) | m/z (MH+) |
| --- | --- | --- | --- |
| methanesulfonyl chloride | 1020 | 3.40 | 646.9 |
| dimethylsulfamoyl chloride | 1021 | 3.68 | 675.9 |

EXAMPLE 1022

4-amino-N-[3-(dimethylamino)-2-oxo-1-piperidin-2-ylpropyl]-3-(3-methoxy-4-{[(1-methyl-1H-indol-2-yl)carbonyl]amino}phenyl)thieno[3,2-c]pyridine-7-carboxamide 4-Amino-3-(3-methoxy-4-{[(1-methyl-1H-indol-2-yl)carbonyl]amino }phenyl)-N-(piperidin-2-ylmethyl)thieno[3,2-c]pyridine-7-carboxamide (0.056 g, 0.098 mmol) and dimethylamino acetal chloride hydrochloride (0.019 g, 0.12 mmol) were reacted according to General Procedure F. LCMS Conditions a: RT=3.02 minutes, 654.0 (MH+).

Examples 1023–1029, shown in Table 25, were prepared using 4-amino-3-(3-methoxy-4-{[(1-methyl-1H-indol-2-yl)carbonyl]amino }phenyl)-N-pyrrolidin-3-ylthieno[3,2-c]pyridine-7-carboxamide and the appropriate aldehyde or ketone according to General Procedure C.

TABLE 25

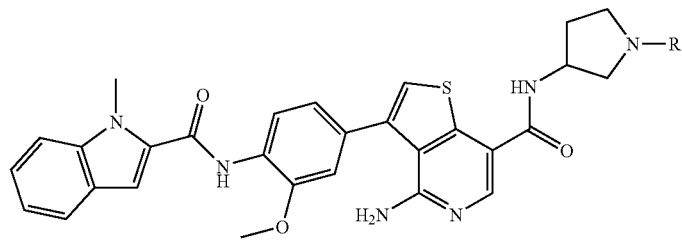

| Aldehyde or Ketone | Example | RT (min) | m/z (MH+) |
|---|---|---|---|
| 2-Methyl-propionaldehyde | 1023 | 3.25$^a$ | 597 |
| 1H-Imidazole-4-carbaldehyde | 1024 | 2.57$^a$ | 621 |
| 3-Dimethylamino-2,2-dimethyl propionaldehyde | 1025 | 2.82$^a$ | 569 |
| Oxo-acetic acid | 1026 | 2.25$^a$ | 599 |
| 2,2-Dimethyl-propionaldehyde | 1027 | 3.78$^a$ | 611 |
| Formaldehyde | 1028 | 3.03$^a$ | 555 |
| Propan-2-one | 1029 | 2.87$^a$ | 583 |

EXAMPLE 1030

N-(1-acetylpyrrolidin-3-yl)-4-amino-3-(3-methoxy-4-{[(1-methyl-1H-indol-2-yl)carbonyl]amino}phenyl)thieno[3,2-c]pyridine-7-carboxamide 4-Amino-3-(3-methoxy-4-{[(1-methyl-1H-indol-2-yl)carbonyl]amino}phenyl)-N-pyrrolidin-3-ylthieno[3,2-c]pyridine-7-carboxamide (100 mg, 0.185 mmol) and acetic acid (9.6 μL, 0.168 mmol) were treated according to General Procedure D. MP-carbonate (184 mg, 0.504 mmol) was added and mixture placed on shaker for 20 hours. The mixture was then filtered and solvent removed in vacuo. The product was purified via flash chromatography to furnish the title compound as a off-white powder. (3.2 mg, 0.0051 mmol): LCMS (Conditions b): MH+=583, R$_f$=2.85 minutes;

$^1$H NMR (DMSO-d$_6$, 400 MHz) δ 9.50 (1H), 8.62 (1H), 8.54 (1H), 8.00 (1H), 7.71 (1H), 7.59 (2H), 7.35 (2H), 7.19 (1H), 7.15 (1H), 7.06 (1H), 6.04 (2H), 4.46–4.56 (1H), 4.04 (3H), 3.91 (3H), 3.91 (3H), 3.80 (1H), 3.61 (1H), 3.50 (1H), 3.39 (1H), 2.00–2.22 (2H), 1.96 (3H).

Examples 1031–1035, shown in Table 26, were prepared using 4-amino-3-(3-methoxy-4-{[(1-methyl-1H-indol-2-yl)carbonyl]amino}phenyl)-N-pyrrolidin-3-ylthieno[3,2-c]pyridine-7-carboxamide and the appropriate chloride or bromide according to General Procedure E.

TABLE 26

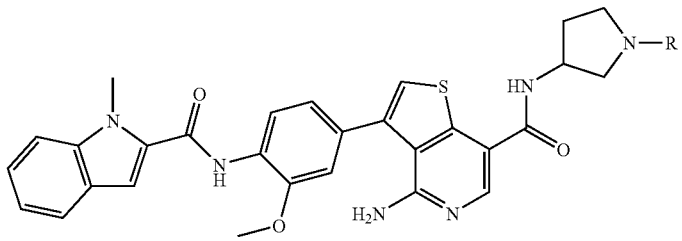

| Bromide or Chloride | Example | RT (min.) | m/z (MH+) |
|---|---|---|---|
| 2-Bromoacetamide | 1031 | 2.65$^a$ | 598 |
| 1-Bromo-2-methoxyethane | 1032 | 2.93$^a$ | 599 |
| Dimethylsulfamoylchloride | 1033 | 3.37$^a$ | 648 |
| 2-Bromoethanol | 1034 | 2.75$^a$ | 585 |
| 3-Bromopropionamide | 1035 | 2.07$^a$ | 612 |

Examples 1036 and 1037, shown in Table 27, were prepared using 4-amino-3-(3-methoxy-4-{[(1-methyl-1H-indol-2-yl)carbonyl]amino}phenyl)-N-(piperidin-4-ylmethyl)thieno[3,2-c]pyridine-7-carboxamide and the appropriate aldehyde according to General Procedure C.

TABLE 27

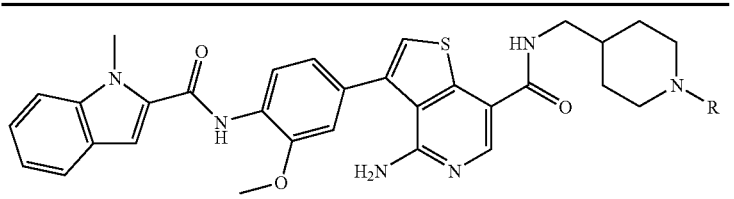

| Aldehyde | Example | RT (min.) | m/z (MH+) |
|---|---|---|---|
| ACETALDEHYDE | 1036 | 18.2 (i) | 597.0 |
| ISOBUTYRALDEHYDE | 1037 | 19.7 (i) | 625.1 |

Examples 1038 and 1039, shown in Table 28, were prepared using 4-amino-3-(3-methoxy-4-{[(1-methyl-1H-indol-2-yl)carbonyl]amino}phenyl)-N-(piperidin-4-ylmethyl)thieno[3,2-c]pyridine-7-carboxamide and the appropriate alkyl halide according to General Procedure E.

TABLE 28

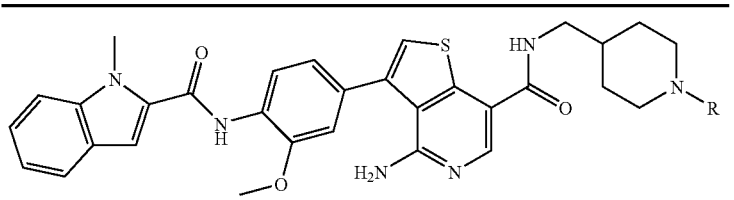

| Alkyl halide | Example | RT (min.) | m/z (MH−) |
|---|---|---|---|
| 2-BROMOACETAMIDE | 1038 | 2.7 (a) | 566.9 |
| 2-BROMOETHYL METHYL ETHER | 1039 | 2.7 (a) | 567.1 |

Examples 1040–1047, shown in Table 29, were prepared using N-(4-{4-amino-7-[(1E)-3-oxoprop-1-enyl]thieno[3,2-c]pyridin-3-yl}-2-methoxyphenyl)-1-methyl-1H-indole-2-carboxamide and the appropriate amine according to General Procedure B.

TABLE 29

| R | Example | HPLC RT (min.) | m/z (M+H)+ |
|---|---|---|---|
| HO—⌬—NH2 | 1040 | 3.55 (a) | 583 |
| N-methylpyrrolidin-3-amine | 1041 | 3.42 (b) | 581 |
| 1-methylpyrrolidin-3-amine | 1042 | 4.02 (b) | 595 |
| HOOC—⌬—NH2 | 1043 | 1.50 (a) | 610 |

TABLE 29-continued

[Structure: core scaffold with R group]

| R | Example | HPLC RT (min.) | m/z (M+H)+ |
|---|---|---|---|
| [azetidine-3-carboxylic acid, HO-] | 1044 | 1.93 (a) | 568 |
| [N-acetyl-1,4-diaminobutane] | 1045 | 1.58 (a) | 597 |
| [trans-N-Boc-1,4-diaminocyclohexane] | 1046 | 3.68 (b) | 581 |
| [(3-aminomethyl)-N-Boc-pyrrolidine] | 1047 | 4.48 (b) | 567 |

EXAMPLE 1048

N-(4-{4-amino-7-[(1Z)-3-(diethylamino)prop-1-enyl]thieno[3,2-c]pyridin-3-yl}-2-methoxyphenyl)-1-methyl-1H-indole-2-carboxamide A solution of N-(4-{4-amino-7-[3-(diethylamino)prop-1-ynyl]thieno[3,2-c]pyridin-3-yl}-2-methoxyphenyl)-1-methyl-1H-indole-2-carboxamide (0.135 g, 0.251 mmol) in ethanol/pyridine (15 mL/10 mL) was treated with Lindlar's catalyst (0.027 g), quinoline (0.05 g, 0.38 mmol), and hydrogen (55 psi) in a Parr Hydrogenator. The reaction mixture was shaken for 1H. The catalyst was filtered through celite. The solvent was removed under reduced pressure. The crude material was purified by preparative HPLC to afford 0.051 g (38%) of the title compound. $^1$H NMR (DMSO-d$_6$, 400 MHz) δ 9.50 (s, 1H), 8.00–7.98 (d, 1H), 7.81 (s, 1H), 7.71–7.69 (d, 1H), 7.60–7.57 (m, 2H), 7.35–7.33 (m, 2H), 7.21–7.21 (m, 1H), 7.17–7.13 (t, H), 7.10–7.08 (d, 1H), 6.56–6.53 (d, 1H), 5.90–5.88 (dt, 1H), 5.60 (brs, 2H), 4.04 (s, 3H), 3.91 (s, 3H), 3.30–3.28 (m, 2H), 2.49–2.44 (q, 4H), 0.93–0.89 (t, 6H); LCMS (conditions a) R$_t$ 3.28 min (95%), MH$^+$ 540.3.

EXAMPLE 1049

N-(4-{4-amino-7-[(1E)-4-(tetrahydro-2H-pyran-2-yloxy)but-1-enyl]thieno[3,2-c]pyridin-3-yl}-2-methoxyphenyl)-1-methyl-1H-indole-2-carboxamide N-[4-(4-Amino-7-iodothieno[3,2-c]pyridin-3-yl)-2-methoxyphenyl]-1-methyl-1H-indole-2-carboxamide (0.178 g, 0.32 mmol) and 4,4,5,5-tetramethyl-2-[(E)-4-(1-propoxypropoxy)-but-1-enyl]-[1,2,3]dioxaborolane (0.10 g, 0.35 mmol) were treated according to General Procedure A. The crude material was purified by flash chromatography on silica gel using 1:1 ethyl acetate:heptane to afford 0.10 g (53%) of the title compound. $^1$H NMR (DMSO-d$_6$, 400 MHz) δ 9.46 (s, 1H), 7.97–7.93 (m, 1H), 7.88 (s, 1H), 7.67–7.62 (m, 1H), 7.57–7.52 (m, 2H), 7.35–7.26 (m, 2H), 7.15 (s, 1H), 7.12–7.10 (m, 1H), 7.08–7.02 (m, 1H), 6.59–6.55 (m, 1H), 6.27–6.20 (m, 1H), 5.55 (brs, 2H), 4.60 (m, 1H), 3.94 (s, 3H), 3.86 (s, 3H), 3.75 (m, 2H), 3.50–3.40 (m, 2H), 2.46–2.44 (m, 2H), 1.71–1.70 (m, 1H), 1.68–1.60 (m, 1H), 1.56–1.40 (m, 4H); LCMS (conditions a) R$_t$ 4.83 min (100%), M$^+$ 583.6.

EXAMPLE 1050

N-(4-{4-amino-7-[(1E)-4-hydroxybut-1-enyl]thieno[3,2-c]pyridin-3-yl}-2-methoxyphenyl)-1-methyl-1H-indole-2-carboxamide A suspension of N-(4-{4-amino-7-[(1E)-4-(tetrahydro-2H-pyran-2-yloxy)but-1-enyl]thieno[3,2-c]pyridin-3-yl}-2-methoxyphenyl)-1-methyl-1H-indole-2-carboxamide (0.05 g, 0.09 mmol) in methanol (3 mL) was treated with p-toluene sulfonic acid monohydrate (0.002 g, 0.0095 mmol). The reaction mixture was stirred for 15 hours at room temperature. Solvent was removed under reduced pressure. The crude material was purified by flash chromatography on silica gel using 10% methanol in dichloromethane to give 0.033 g (77%) of the title compound. $^1$H NMR (DMSO-d$_6$, 400 MHz) δ 9.51 (s, 1H), 8.00–7.98 (m, 1H), 7.93 (s, 1H), 7.71–7.69 (m, 1H), 7.61–7.58 (m, 2H), 7.35–7.33 (m, 2H), 7.20 (m, 1H), 7.15–7.15 (m, 1H), 709–7.07 (m, 1H), 6.59–6.55 (m, 1H), 6.35–6.20 (m, 1H), 5.58 (brs, 2H), 4.65 (m, 1H), 4.04 (s, 3H), 3.91 (s, 3H), 3.57–3.54 (m, 2H), 2.42 (m, 2H); LCMS (conditions a) R$_t$ 3.42 min (96%), M$^+$ 499.3.

Examples 1051–1064, shown in Table 30, were prepared using (3E)-4-[4-amino-3-(3-methoxy-4-{[(1-methyl-1H-indol-2-yl)carbonyl]amino}phenyl)thieno[3,2-c]pyridin-7-yl]but-3-enyl 4-methylbenzenesulfonate and the appropriate amine according to General Procedure I. LCMS conditions (a).

TABLE 30

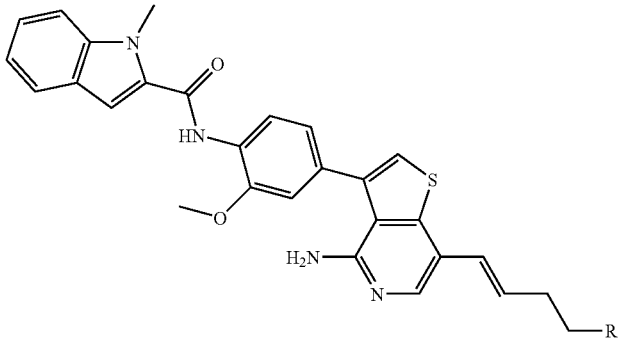

| Amine | Example | LCMS RT (m+/z) |
|---|---|---|
| 2M dimethylamine in THF | 1051 | 4.22 min (526.4) |
| potassium phthalimide | 1052 | 4.15 min (628.4) |
| piperazine | 1053 | 2.50 min (567.4) |
| diethyl amine | 1054 | 2.72 min (554.4) |
| N-Boc-trans-1,4-cyclohexanediamine | 1055 | 3.00 min (695.4) |
| N-acetyl piperazine | 1056 | 1.88 min (609.4) |
| 4-BOC-aminopiperidine | 1057 | 3.50 min (681.4) |
| 4-BOC-aminomethylpiperidine | 1058 | 3.57 min (695.5) |
| 3-amino-N-BOC-pyrrolidine | 1059 | 2.88 min (667.5) |
| 2-(2-aminoethyl)-1-methylpyrrolidine | 1060 | 2.83 min (609.4) |
| 4-piperidine ethanol | 1061 | 2.75 min (610.4) |
| 1-methylpiperazine | 1062 | 3.67 min (581.4) |
| 2M ethylamine in THF | 1063 | 3.00 min (526.4) |
| 2M methylamine in THF | 1064 | 2.43 min (512.3) |

EXAMPLE 1065

N-(4-{4-amino-7-[(1E)-4-aminobut-1-enyl]thieno[3,2-c]pyridin-3-yl}-2-methoxyphenyl)-1-methyl-1H-indole-2-carboxamide tetraacetate A suspension of N-(4-{4-amino-7-[(1E)-4-(1,3-dioxo-1,3-dihydro-2H-isoindol-2-yl)but-1-enyl]thieno[3,2-c]pyridin-3-yl}-2-methoxyphenyl)-1-methyl-1H-indole-2-carboxamide (0.024 g, 0.038 mmol) in ethanol (5 mL) was treated with anhydrous hydrazine (0.01 g, 0.30 mmol). The reaction mixture was stirred at room temperature for 15 hours. The solvent was removed and the crude material was purified by preparative HPLC chromatography to give 0.001 g (1%) of the title compound as a tetraacetate salt. $^1$H NMR (DMSO-$d_6$, 400 MHz) δ 9.55 (s, 1H), 8.05 (d, 1H), 8.03 (s, 1H), 7.70 (d, 1H), 7.60 (m, 2H), 7.35 (m, 2H), 7.20 (m, 1H), 7.15 (m, 1H), 7.10 (m, 1H), 6.60 (d, 1H), 6.30–6.20 (m, 1H), 5.60 (s, 3H), 4.05 (s, 3H), 3.95 (s, 3H), 2.75 (t, 2H), 2.40 (q, 2H); LCMS (conditions a) $R_t$ 2.38 min (95%), M$^+$ 498.3.

EXAMPLE 1066

N-(4-{4-amino-7-[(1E)-4-(4-aminopiperidin-1-yl)but-1-enyl]thieno[3,2-c]pyridin-3-yl}-2-methoxyphenyl)-1-methyl-1H-indole-2-carboxamide Tert-butyl 1-{(3E)-4-[4-amino-3-(3-methoxy-4-{[(1-methyl-1H-indol-2-yl)carbonyl]amino}phenyl)thieno[3,2-c]pyridin-7-yl]but-3-enyl}piperidin-4-ylcarbamate (0.058 g, 0.085 mmol) was reacted according to General Procedure H. Dichloromethane and MP-carbonate resin were added and stirred for 15 hours. The resin was filtered and the solvent removed under reduced pressure to give 0.016 g (33%) of the title compound. $^1$H NMR (DMSO-$d_6$, 400 MHz) δ 9.50 (s, 1H), 8.00–7.98 (d, 1H), 7.91 (s, 1H), 7.71–7.69 (d, 1H), 7.60–7.58 (m, 2H), 7.35–7.31 (m, 2H), 7.20 (m, 1H), 7.15 (t, 1H), 7.09–7.06 (m, 1H), 6.59–6.55 (d, 1H), 6.30–6.20 (m, 1H), 5.57 (brs, 2H), 4.04 (s, 3H), 3.91 (s, 2H), 2.97–2.94 (m, 1H), 2.85–2.82 (m, 2H), 2.44–2.38 (m, 4H), 1.95 (t, 2H), 1.68–1.65 (m, 2H), 1.24–1.22 (m, 2H); LCMS (conditions a) $R_t$ 2.07 min (100%), M$^+$ 581.4.

EXAMPLE 1067

N-[4-(4-amino-7-{(1E)-4-[4-(aminomethyl)piperidin-1-yl]but-1-enyl}thieno[3,2-c]pyridin-3-yl)-2-methoxyphenyl]-1-methyl-1H-indole-2-carboxamide Tert-butyl (1-{(3E)-4-[4-amino-3-(3-methoxy-4-{[(1-methyl-1H-indol-2-yl)carbonyl]amino}phenyl)thieno[3,2-c]pyridin-7-yl]but-3-enyl}piperidin-4-yl)methylcarbamate (0.08 g, 0.112 mmol) was reacted according to General Procedure H. Dichloromethane and MP-carbonate resin were added and shaken overnight. The resin was filtered and the solvent evaporated under reduced pressure to give 0.02 g (29%) of the title compound. $^1$H NMR (DMSO-$d_6$, 400 MHz) δ 9.51 (s, 1H), 8.01–7.99 (d, 1H), 7.92 (s, 1H), 7.71–7.69 (d, 1H), 7.60–7.57 (m, 2H), 7.35–7.31 (m, 2H), 7.19 (m, 1H), 7.15 (m, 1H), 7.13–7.07 (m, 1H), 6.59–6.55 (d, 1H), 6.27–6.23 (m, 1H), 5.58 (brs, 2H), 4.04 (s, 3H), 3.91 (s, 3H), 2.94–2.91 (m, 3H), 2.44 (m, 6H), 1.92–1.87 (t, 2H), 1.69–1.66 (d, 1H), 1.23 (m, 1H), 1.16–1.11 (m, 2H); LCMS (conditions a) $R_t$ 2.37 min (100%), M$^+$ 595.4.

EXAMPLE 1068

N-(4-{4-amino-7-[-3-(4-methyl-3-oxopiperazin-1-yl)prop-1-enyl]thieno[3,2-c]pyridin-3-yl}-2-methoxyphenyl)-1-methyl-1H-indole-2-carboxamide The title compound was prepared using N-(4-{4-amino-7-[(1Z)-3-oxoprop-1-enyl]thieno[3,2-c]pyridin-3-yl}-2- methoxyphenyl)-1-methyl-1H-indole-2-carboxamide, 1-methyl-piperazin-2-one (trifluoroacetic acid salt), and General Procedure B. ¹H NMR (DMSO-d₆, 400 MHz) δ 9.51 (s, 1H), 7.99 (m, 1H), 7.97 (s, 1H), 7.70 (d, 1H), 7.60 (s, 1H), 7.58 (d, 1H), 7.33 (s, 1H), 7.31 (t, 1H), 7.19 (s, 1H), 7.11 (t, 1H), 7.07 (d, 1H), 6.71 (d, 1H), 6.22 (m, 1H), 5.65 (br, 2H), 4.02 (s, 3H), 3.89 (s, 3H); 3.30 (m, 4H), 3.03 (s, 2H), 2.81 (s, 3H), 2.72 (m, 2H); MS: (MH)⁺ 581.

EXAMPLE 1069

N-(4-{4-amino-7-[(1Z)-3-(4-methyl-5-oxo-1,4-diazepan-1-yl)prop-1-enyl]thieno[3,2-c]pyridin-3-yl }-2-methoxyphenyl)-1-methyl-1H-indole-2-carboxamide The title compound was prepared using N-(4-{4-amino-7-[(1Z)-3-oxoprop-1-enyl]thieno[3,2-c]pyridin-3-yl }-2-methoxyphenyl)-1-methyl-1H-indole-2-carboxamide, 4-methyl-1,4-diazepan-5-one (trifluoroacetic acid salt), and General Procedure B. ¹H NMR (DMSO-d₆, 400 MHz) δ 9.51 (s, 1H), 8.01 (m, 1H), 7.98 (s, 1H), 7.70 (d, 1H), 7.62 (s, 1H), 7.59 (d, 1H), 7.36 (s, 1H), 7.32 (d, 1H), 7.20 (m, 1H), 7.15 (t, 1H), 7.08 (d, 1H), 6.69 (d, 1H), 6.21 (m, 1H), 5.65 (br, 2H), 4.04 (s, 3H), 3.91 (s, 3H); 3.47 (m, 2H), 3.32 (m, 2H), 3.02 (m, 2H), 2.85 (s, 3H), 2.58 (m, 4H); MS: (M–H)⁻ 593.

EXAMPLE 1070

N-[4-(4-amino-7-{3-[(diethylamino)methyl]phenyl}thieno[3,2-c]pyridin-3-yl)-2-methoxyphenyl]-1-methyl-1H-indole-2-carboxamide The title compound was prepared using N-{4-[4-amino-7-(3-formylphenyl)thieno[3,2-c]pyridin-3-yl]-2-methoxyphenyl}-1-methyl-1H-indole-2-carboxamide, N,N-diethylamine, and General Procedure B. ¹H NMR (DMSO-d₆, 400 MHz) δ 9.53 (s, 1H), 8.02 (d, 1H), 7.92 (s, 1H), 7.71 (d, 1H), 7.67 (s, 1H), 7.64 (m, 2H), 7.60 (s, 1H), 7.52 (m, 1H), 7.47 (t, 1H), 7.35 (m, 1H), 7.32 (m, 1H), 7.24 (m, 1H), 7.15 (m, 1H), 7.12 (m, 1H), 5.62 (br, 2H), 4.05 (s, 3H), 3.92 (s, 3H), 3.62 (s, 2H), 2.53 (qt, 4H), 1.02 (t, 6H); MS: (MH)⁺ 590.

EXAMPLE 1071

N-{4-[4-amino-7-(3-{[[3-(dimethylamino)propyl](methyl)amino]methyl}phenyl)thieno[3,2-c]pyridin-3-yl]-2-methoxyphenyl}-1-methyl-1H-indole-2-carboxamide The title compound was prepared using N-{4-[4-amino-7-(3-formylphenyl)thieno[3,2-c]pyridin-3-yl]-2-methoxyphenyl}-1-methyl-1H-indole-2-carboxamide, N,N,N'-trimethyl-1,3-propanediamine, and General Procedure B. ¹H NMR (DMSO-d₆, 400 MHz) δ 9.53 (s, 1H), 8.01 (d, 1H), 7.93 (s, 1H), 7.71 (d, 1H), 7.63 (m, 1H), 7.61 (m, 1H), 7.60 (s, 1H), 7.58 (m, 1H), 7.57 (m, 1H), 7.49 (t, 1H), 7.36 (s, 1H), 7.33 (m, 1H), 7.22 (m, 1H), 7.16 (d, 1H), 7.12 (m, 1H), 5.63 (br, 2H), 4.05 (s, 3H), 3.92 (s, 3H), 3.57 (s, 2H), 2.43 (m, 2H), 2.32 (s, 6H), 2.26 (s, 3H), 1.96 (m, 2H), 1.63 (m, 2H); MS: (MH)⁺ 633.

Examples 1072–1095, shown in Table 31, were prepared using N-(4-{4-amino-7-[(1E)-3-oxoprop-1-enyl]thieno[3,2-c]pyridin-3-yl}-2-methoxyphenyl)-1-methyl-1H-indole-2-carboxamide and the appropriate amine according to General Procedure B.

TABLE 31

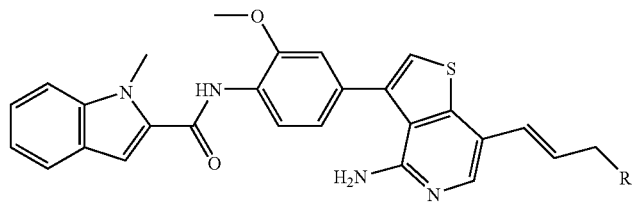

| R | Example | HPLC RT (min.) | m/z (M+H)⁺ |
|---|---|---|---|
| HO—⟨piperidine-CH₂CH₂⟩—N— | 1073 | 2.13 (a) | 580 |
| CH₃—N⟨piperazine⟩N— | 1074 | 2.28 (a) | 551 |
| HO—CH₂CH₂—N(Et)— | 1075 | 5.88 (d) | 540 |

TABLE 31-continued
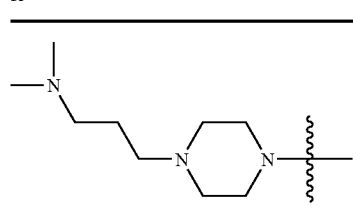
| R | Example | HPLC RT (min.) | m/z (M+H)+ |
|---|---|---|---|
| 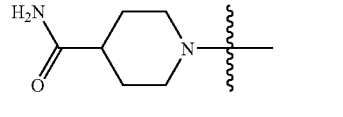 | 1076 | 2.32 (a) | 622 |
| 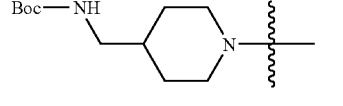 | 1077 | 5.16 (d) | 579 |
| 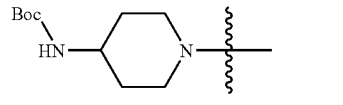 | 1078 | 3.02 (a) | 665 |
| 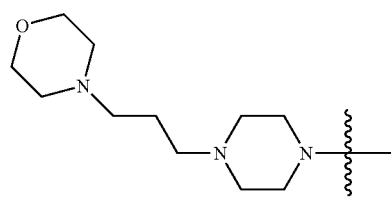 | 1079 | 2.57 (a) | 649 (M−H)+ |
| 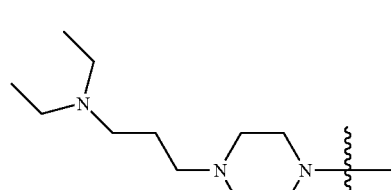 | 1080 | 3.60 (a) | 664 |
| 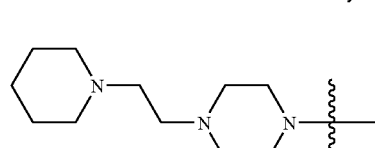 | 1081 | 4.33 (a) | 650 |
| 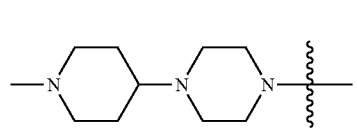 | 1082 | 4.12 (a) | 648 |
|  | 1083 | 4.25 (a) | 634 |

TABLE 31-continued

| R | Example | HPLC RT (min.) | m/z (M+H)+ |
|---|---|---|---|
| pyrrolidine-propyl-piperazinyl | 1084 | 4.28 (a) | 648 |
| dimethylamine | 1085 | 3.77 (a) | 496 |
| dimethylaminoethyl-methylamino | 1086 | 2.87 (a) | 553 |
| N-methylpiperidin-4-yl-methylamino | 1087 | 3.00 (a) | 451 |
| 4-(2-hydroxyethyl)piperazinyl | 1088 | 3.03 (a) | 581 |
| 1-methylpyrrolidin-3-yl-methylamino | 1089 | 4.43 (a) | 565 |
| 4-methyl-1,4-diazepan-1-yl | 1090 | 3.23 (a) | 565 |
| 4-aminopiperidin-1-yl | 1091 | 4.17 (a) | 551 |
| 4-hydroxypiperidin-1-yl | 1092 | 3.32 (a) | 552 |
| trans-4-aminocyclohexylamino | 1093 | 2.26 (h) | 565 |

TABLE 31-continued

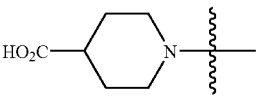

| R | Example | HPLC RT (min.) | m/z (M+H)+ |
|---|---|---|---|
| 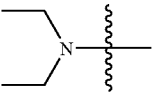 | 1094 | 2.05 (h) | 580 |
| 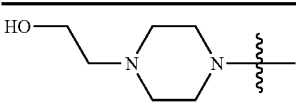 | 1095 | 3.13 (h) | 524 |

Examples 1096–1098, shown in Table 32, were prepared using N-(4-{4-amino-7-[(1E)-3-oxoprop-1-enyl]furo[3,2-c]pyridin-3-yl}-2-methoxyphenyl)-1-methyl-1H-benzimidazole-2-carboxamide and the appropriate amine according to General Procedure B.

TABLE 32

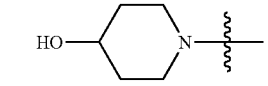

| R | Example | HPLC RT (min.) | m/z (M+H)+ |
|---|---|---|---|
| 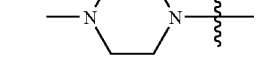 | 1096 | 12.17 (e) | 582 |
| 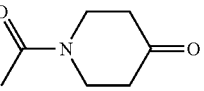 | 1097 | 4.79 (d) | 553 |
| 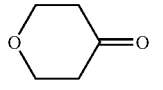 | 1098 | 6.41 (d) | 552 |

Examples 1099–1113, shown in Table 33, were prepared using N-(4-{4-amino-7-[(1E)-3-aminoprop-1-enyl]thieno[3,2-c]pyridin-3-yl}-2-methoxyphenyl)-1-methyl-1H-indole-2-carboxamide and the appropriate aldehyde or ketone according to General Procedure C. LCMS conditions: Conditions a.

TABLE 33

| aldehyde or ketone | Example | RT (min.) | m/z (MH+) |
|---|---|---|---|
| 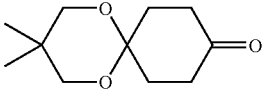 | 1099 | 2.88 | 609.5 |
| 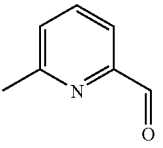 | 1100 | 3.01 | 568.1 |
| | 1101 | 3.14 | 624.3 |
| | 1102 | 3.22 | 666.3 |
| | 1103 | 3.30 | 589.5 |

TABLE 33-continued

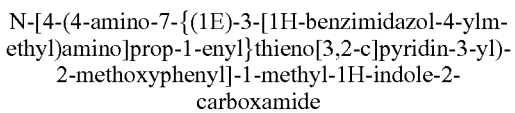

| aldehyde or ketone | Example | RT (min.) | m/z (MH+) |
|---|---|---|---|
| | 1104 | 2.38 | 558.1 |
| | 1105 | 3.52 | 609.7 |
| | 1106 | 3.57 | 639.4 |
| | 1107 | 3.35 | 584.4 |
| | 1108 | 4.47 | 609.5 |
| | 1109 | 3.90 | 595.4 |
| | 1110 | 4.02 | 566.4 |
| | 1111 | 3.58 | 623.5 |
| | 1112 | 4.02 | 667.4 |
| | 1113 | 3.42 | 581.2 |

EXAMPLE 1114

N-[4-(4-amino-7-{(1E)-3-[1H-benzimidazol-4-ylm-ethyl)amino]prop-1-enyl}thieno[3,2-c]pyridin-3-yl)-2-methoxyphenyl]-1-methyl-1H-indole-2-carboxamide In a round bottom flask was combined N-(4-{4-amino-7-[(1E)-3-oxoprop-1-enyl]thieno[3,2-c]pyridin-3-yl}-2-methoxyphenyl)-1-methyl-1H-indole-2-carboxamide (0.050 g, 0.104 mmol), 4-formylimidazole (0.0083 g, 0.086 mmol), and toluene (1.5 mL). The flask was flushed with nitrogen gas, followed by the addition of titanium (IV) isopropoxide (0.061 g, 0.215 mmol). The mixture was heated under a nitrogen atmosphere to 50° C. for 16 hours. The reaction mixture was cooled to room temperature and treated with methanol (1 mL) and sodium borohydride (0.010 g, 0.263 mmol). The resulting mixture was stirred for 12 hours at room temperature, followed by the addition of a 10% aqueous solution of sodium hydroxide (5 mL) and methylene chloride (5 mL). The mixture was filtered through an Empore™ cartridge, the solvents removed, and the product purified by preparative RP-HPLC (Rainin C18, 8 mm, 300 Å, 25 cm; 5% acetonitrile—0.1M ammonium acetate isocratic for 5 minutes, then 5–100% acetonitrile—0.1M ammonium acetate over 30 min, 21 ml/min). The acetonitrile was removed and the aqueous solution was lyophilized to give the title compound as an off-white solid: 0.012 g (24%): LCMS (Conditions b): MH+=467.3, RT=2.35 minutes; $^1$H NMR (DMSO-$d_6$, 400 MHz) δ 9.52 (s, 1H), 7.99 (d, J=8.2 Hz, 1H), 7.95 (s, 1H), 7.70 (d, J=8.2 Hz, 1H), 7.62 (s, 1H), 7.59 (d, J=8.6 Hz, 1H), 7.55 (s, 1H), 7.35 (s, 1H), 7.32 (d, J=8.6 Hz, 1H), 7.21 (d, J=1.6 Hz, 1H), 7.15 (dd, J=7.8 Hz, 7.0 Hz, 1H), 7.08 (dd, J=7.8 Hz, 1.6 Hz, 1H), 6.88 (s (br), 1H), 6.67 (d, J=16.0 Hz, 1H), 6.30 (td, J=16.4 Hz, 5.5 Hz, 1H), 5.61 (s (br), 1H), 4.04 (s, 3H), 3.91 (s, 3H), 3.67 (s, 2H), 3.39 (d, J=5.5 Hz, 2H), 2.78 (s, 15H, acetate)

EXAMPLE 1115

N-(4-{4-amino-7-[(1E)-3-(3,3-dimethyl-5-oxopiper-azin-1-yl)prop-1-enyl]thieno[3,2-c]pyridin-3-yl}-2-methoxyphenyl)-l1-methyl-1H-indole-2-carboxamide N-(4-{4-Amino-7-[(1E)-3-oxoprop-1-enyl]thieno[3,2-c]pyridin-3-yl}-2-methoxyphenyl)-1-methyl-1H-indole-2-carboxamide (60.0 mg, 0.125 mmol) and 6,6-dimethyl-piperazin-2-one (75.7 mg, 0.498 mmol) were reacted according to General Procedure B. The product was purified via flash chromatography to furnish the title compound as a yellow powder. (5.0 mg, 0.0084 mmol): LCMS (Conditions a): MH+=595.0, R$_t$=3.58 minutes; $^1$H NMR (DMSO-$d_6$, 400 MHz) δ 9.52 (s, 1H), 7.98 (m, 2H), 7.80 (s, 1H), 7.71 (d, J=7.8 Hz, 1H), 7.62 (s, 1H), 7.58 (d, J=8.2 Hz, 1H), 7.35 (m, 1H), 7.31 (m, 1H), 7.20 (m, 1H), 7.15 (t, J=7.8 Hz, 1H), 7.09 (dd, J=8.2, 1.56 Hz, 1H), 6.74 (d, J=16.0 Hz, 1H), 6.23 (m, 1H), 5.66 (br, 2H), 4.04 (s, 3H), 3.91 (s, 3H), 3.24 (m, 2H), 2.95 (s, 2H), 2.42 (s, 2H), 1.20 (s, 6H).

EXAMPLE 1116

N-(4-{4-amino-7-[(1E)-3-(3-aminopyrrolidin-1-yl)prop-1-enyl]thieno[3,2-c]pyridin-3-yl}-2-methoxyphenyl)-1-methyl-1H-indole-2-carboxamide N-(4-{4-Amino-7-[(1E)-3-oxoprop-1-enyl]thieno[3,2-c]pyridin-3-yl}-2-methoxyphenyl)-1-methyl-1H-indole-2- carboxamide (100 mg, 0.207 mmol) and tert-butyl pyrrolidin-3-ylcarbamate (115.7 mg, 0.621 mmol) were reacted according to General Procedure B. The crude product (135 mg, 0.207 mmol) was dissolved in methanol (1 mL) and treated with 6.0 M hydrochloric acid in 1,4 dioxane (0.518 mL, 2.07 mmol) and heated to 55 degrees Celsius for 4 hours. The mixture was cooled to room temperature then 1M sodium carbonate solution (5 mL) was added and product was extracted with ethyl acetate (3×10 mL). The organic layer was separated, dried over magnesium sulfate, filtered, and the solvent was removed under reduced pressure. The product was purified via flash chromatography to furnish the title compound as an ivory powder (22.5 mg, 0.0408 mmol): LCMS (Conditions a): MH−=551 RT=3.62 minutes; $^1$H NMR (DMSO-$d_6$, 400 MHz) δ 9.51 (1H), 7.97 (2H), 7.72 (1H), 7.63 (2H), 7.36 (2H), 7.21 (1H), 7.15 (1H), 7.07 (1H), 6.70 (1H), 6.26 (1H), 5.65 (1H), 4.04 (3H), 3.91 (3H), 3.51 (1H), 3.29 (2H), 2.71 (2H), 2.45 (2H), 2.10 (1H), 1.53 (1H).

EXAMPLE 1117

N-(4-{4-amino-7-[(1E)-3-(3-aminopiperidin-1-yl)prop-1-enyl]thieno[3,2-c]pyridin-3-yl}-2-methoxyphenyl)-1-methyl-1H-indole-2-carboxamide N-(4-{4-Amino-7-[(1E)-3-oxoprop-1-enyl]thieno[3,2-c]pyridin-3-yl}-2-methoxyphenyl)-1-methyl-1H-indole-2-carboxamide (100 mg, 0.207 mmol) and tert-butyl piperidin-3-ylcarbamate (124 mg, 0.621 mmol), were reacted according to General Procedure B. The crude product (137 mg, 0.206 mmol) was dissolved in methanol (1 mL) and treated with 6.0 M hydrochloric acid in 1,4 dioxane (0.514 mL, 2.06 mmol) and heated to 55 degrees Celsius for 20 hours. The mixture was cooled to room temperature then 1M sodium carbonate solution (5 mL) was added and product was extracted with ethyl acetate (3×10 mL). The organic layer was separated, dried over magnesium sulfate, filtered, and the solvent was removed under reduced pressure. The product was purified via HPLC preparation to furnish the title compound as an ivory powder (23.0 mg, 0.0406 mmol): LCMS (Conditions a): MH−=565 RT=3.35 minutes; $^1$H NMR (DMSO-$d_6$, 400 MHz) δ 9.45 (1H), 7.91 (2H), 7.65 (1H), 7.28 (3H), 7.10 (3H), 7.01 (1H), 6.64 (1H), 6.15 (1H), 5.59 (1H), (1H), 2.62 (1H), 2.16 (1H), 2.03 (1H), 1.66 (1H), 1.42 (1H), 1.15 (1H).

Examples 1118–1120, shown in Table 34, were prepared using N-(4-{4-amino-7-[(1E)-3-oxoprop-1-enyl]thieno[3,2-c]pyridin-3-yl}-2-methoxyphenyl)-1-methyl-1H-indole-2-carboxamide and the appropriate amine according to General Procedure B.

TABLE 34

| Amine | Example | RT (min.) | m/z (MH+) |
|---|---|---|---|
| Piperidin-4-ol | 1118 | 2.55$^a$ | 553 |
| 1-Methylpiperazine | 1119 | 2.84$^a$ | 553 |
| 2-Piperazin-1-ylethanol | 1120 | 2.60$^a$ | 583 |

Examples 1121–1138, shown in Table 35, were prepared using N-(4-{4-amino-7-[(1E)-3-oxoprop-1-enyl]thieno[3,2-c]pyridin-3-yl}-2-methoxyphenyl)-1-methyl-1H-indole-2-carboxamide and the appropriate amine according to General Procedure B.

TABLE 35

| Amine | Example | RT (min.) | m/z (MH$^+$) |
|---|---|---|---|
| 4-amino-1-boc-piperidine | 1121 | 9.8 (j) | 565.3 (−) |
| 3-(aminomethyl)-1-n-boc-piperidine | 1122 | 12.6 (j) | 579.5 |
| Dimethyl amine | 1123 | 11.1 (j) | 512.3 |
| 3-amino-1-n-boc-azetidine | 1124 | 13.6 (i) | 539.2 |
| 3-piperazine-1-yl proprionic acid | 1125 | 9.4 (i) | 623.7 (−) |
| 3-amino-1-n-boc pyrrolidine | 1126 | 12.7 (i) | 553.0 |
| N,N-dimethyl-1,3-propanediamine | 1127 | 9.2 (i) | 569.0 |
| N,N-dimethyenediamine | 1128 | 10.8 (i) | 553.4 |
| Guavacine Hydrochloride | 1129 | 9.4 (j) | 594.4 |
| Isoguavacine Hydrochloride | 1130 | 16.3 (i) | 594.3 |
| N,N-DIETHYLNIPECOTAMIDE | 1131 | 10.7 (j) | 649.4 (−) |
| 3-PIPERIDINEMETHANOL | 1132 | 12.1 (j) | 580.4 (−) |
| TETRAHYDROFURFURYLAMINE | 1133 | 19.9 (i) | 566.4 (−) |
| 2-AMINO-1,3-PROPANEDIOL | 1134 | 10.1 (i) | 556.4 (−) |
| NIPECOTAMIDE | 1135 | 17.8 (i) | 593.5 (−) |
| ETHANOL AMINE | 1136 | 17.5 (i) | 526.4 (−) |
| 3-AMINO-1-PROPANOL | 1137 | 17.6 (i) | 540.4 (−) |
| GYLCINAMIDE HYDROCHLORIDE | 1138 | 28.7 (i) | 539.4 (−) |

Examples 1139–1143, shown in Table 36, were prepared using N-(4-{4-amino-7-[(1E)-3-oxoprop-1-enyl]thieno[3,2-c]pyridin-3-yl}-2-methoxyphenyl)-1-methyl-1H-indole-2-carboxamide and the appropriate amine according to general procedure B. The organics were combined, concentrated, treated with lithium hydroxide monohydrate in dioxane/water (4:1, 2 mL). The mixture was treated with microwave radiation at 150° C. for 600 s. The material was diluted with dichloromethane/methanol (9:1, 10 mL) and the aqueous layer was washed with dichloromethane. The combined organics were dried over magnesium sulfate and concentrated in vacuo. The residue was purified by preparative RP-HPLC. The acetonitrile was removed in vacuo and the aqueous mixture was lyophilized to give the following compounds in Table 36.

TABLE 36

| Amine | Example | RT (min.) | m/z (MH$^+$) |
|---|---|---|---|
| DIETHYL IMINODIACETATE | 1139 | 8.9 (j) | 600.5 |
| ETHYL 4-AMINOBUTYRATE HYDROCHLORIDE | 1140 | 13.0 (j) | 592.0 (−) |
| BETA-ALANINE ETHYL ESTER HYDROCHLORIDE | 1141 | 9.4 (j) | 556.4 |

TABLE 36-continued

Amine | Example | RT (min.) | m/z (MH+)
---|---|---|---
SARCOSINE ETHYL ESTER HYDROCHLORIDE | 1142 | 9.8 (j) | 556.3
GLYCINE METHYL ESTER HYDROCHLORIDE | 1143 | 9.4 (i) | 542.4

Examples 1144–1146, shown in Table 37, were prepared using N-(4-{4-amino-7-[(1E)-3-oxoprop-1-enyl]thieno[3,2-c]pyridin-3-yl}-2-methoxyphenyl)-1-methyl-1H-benzimidazole-2-carboxamide and the appropriate amine according to General Procedure B.

TABLE 37

Amine | Example | RT (min.) | m/z (MH−)
---|---|---|---
2-Piperazin-1-ylethanol | 1144 | 16.7 (i) | 596.9
Piperidin-4-ol | 1145 | 8.9 (j) | 567.4
1-Methylpiperazine | 1146 | 4.6 (a) | 566.2

EXAMPLE 1147

N-(4-{4-amino-7-[(E)-2-cyanovinyl]thieno[3,2-c]pyridin-3-yl}-2-methoxyphenyl)-1-methyl-1H-benzimidazole-2-carboxamide (2E)-3-(4-Amino-3-bromothieno[3,2-c]pyridin-7-yl)acrylonitrile (300 mg, 1.07 mmol) and N-2-[(2-methoxy)-5-(4,4,5,5-tetramethyl-1,3,2-dioxaborolan-2-yl)phenyl]-1-methyl-1H-benzo[d]imidazole-2-carboxamide (430 mg, 1.07 mmol) in 1,2-dimethoxyethane (6 ml) was added a solution of sodium carbonate (340 mg, 3.21 mmol) in water (3 ml) followed by tetrakis(triphenylphosphine)palladium (0) (120 mg, 0.11 mmol). The reaction was heated at 95° C. for 18 hours under an atmosphere of nitrogen. The mixture was allowed to cool to ambient temperature and solvents were removed under reduced pressure. Ethyl acetate (15 ml) was added to the residue and the precipitate was filtered to give crude product (120 mg), which was purified by RP-HPLC (Hyperprep HS C18, 8 μm, 250×21.2 mm; 20% acetonitrile—50 mM ammonium acetate over 1 min, 20–100% acetonitrile—50 mM ammonium acetate over 24 min, 100% acetonitrile over 5 min, 20 ml/min). The acetonitrile was removed under reduced pressure and the aqueous mixture was lyophilized to give the title compound (15 mg, 3%) as a white solid. $^1$H NMR (400 MHz, DMSO-d$_6$) δ 9.51 (s, 1H), 8.23 (s, 1H), 8.03 (d, 1H), 7.75 (m, 2H), 7.70 (d, 1H), 7.58 (d, 1H), 7.35 (m, 2H), 7.22 (d, 1H), 7.15 (t, 1H), 7.10 (dd, 1H), 6.09 (dd, 1H), 4.03 (s, 3H), 3.91 (s, 3H); LCMS (Conditions h); R$_t$ 3.37; MS: MH+ 480.

EXAMPLE 1148

1-Methyl-1H-indole-2-carboxylic acid {4-[4-amino-7-(6-hex-1-ynyl)-thieno[3,2-c]pyridine-3-yl-2-methyoxy-phenyl}-amide A solution of N-(4-{4-amino-7-[6-(1,3-dioxo-1,3-dihydro-2H-isoindol-2-yl)hex-1-ynyl]thieno[3,2-c]pyridin-3-yl}-2-methoxyphenyl)-1-methyl-1H-indole-2-carboxamide (0.078 g, 0.119 mmol) in ethanol (5 mL) was treated with hydrazine monohydrate (0.048 g, 0.955 mmol). The reaction mixture was stirred for 15 hours at 50° C. The solvent was removed under reduced pressure. The compound was purified by preparative HPLC to afford 0.007 g (10%) the title compound. $^1$H NMR (DMSO-d$_6$, 400 MHz) δ 9.463 (s, 1H), 8.05–7.98 (m, 1H), 7.94 (s, 1H), 7.65–7.6 (m, 1H), 7.561–7.519 (m, 2H), 7.304–7.265 9 (m, 2H), 7.124 (s, 1H), 7.104–7.084 (m, 1H), 7.046–7.021 (m, 1H), 5.736 (brs, 2H), 3.99 (s, 3H), 3.867 (s, 3H), 2.7–2.6 (m, 2H), 2.58–2.5 (m, 2H), 1.6 (m, 4H); LCMS (Conditions a) R$_t$ 3.45 min (95%), M+ 524.6.

Examples 1149–1153, shown in Table 38, were prepared using N-{4-[4-amino-7-(3-aminoprop-1-ynyl)thieno[3,2-c]pyridin-3-yl]-2-methoxyphenyl}-1-methyl-1H-benzimidazole-2-carboxamide and the appropriate ketone according to General Procedure C.

TABLE 38

Ketone | Example | LCMS RT (m+/z)
---|---|---
1-acetyl-4-piperidone | 1149 | 2.85 min (607.12)
tetrahydro-4-pyran-one | 1150 | 3.28 min (566.19)
N-methyl-piperidin-4-one | 1151 | 3.02 min (579.10)
1,4-cyclohexanedione monoethylene ketal | 1152 | 3.49 min (622.13)
BOC-piperidone | 1153 | 4.02 min (655.18)

EXAMPLE 1154

N-[4-(4-amino-7-{3-[(4-oxocyclohexyl)amino]prop-1-ynyl}thieno[3,2-c]pyridin-3-yl)-2-methoxyphenyl]-1-methyl-1H-indole-2-carboxamide N-(4-{4-Amino-7-[3-(1,4-dioxaspiro[4.5]dec-8-ylamino)prop-1-ynyl]thieno[3,2-c]pyridin-3-yl}-2-methoxyphenyl)-1-methyl-1H-indole-2-carboxamide (0.062 g, 0.099 mmol) in acetone was treated with 5N hydrochloric acid (5 mL). The reaction mixture was stirred for 15 hours at room temperature. Solid sodium carbonate and water were added to basify reaction mixture to pH 7. Ethyl acetate was added and the layers were partitioned. The aqueous layer was extracted with ethyl acetate. The organic layers were combined and dried over magnesium sulfate, filtered and evaporated under reduced pressure to give 0.024 g (41%) of the title compound. $^1$H NMR (DMSO-d$_6$, 400 MHz) δ 9.51 (s, 1H), 8.01–7.98 (m, 2H), 7.70 (m, 1H), 7.62 (m, 2H), 7.35 (m, 2H), 7.21 (m, 1H), 7.19 (m, 1H), 7.10 (m, 1H), 5.85 (brs, 2H), 4.03 (s, 3H), 3.91 (s, 3H), 3.73 (s, 2H), 3.15 (m, 1H), 2.40–2.20 (m, 4H), 2.10 (m, 2H), 1.70 (m, 2H); LCMS (Conditions a) $R_t$ 3.50 min (95%), $M^+$ 578.4.

The amides listed below were prepared from acrylamide and the appropriate amine according to General Procedure K
3-Pyrrolidin-1-yl-propionamide
3-Morpholin-4-yl-propionamide
3-(4-Methyl-piperazin-1-yl)-propionamide
3-(4-Hydroxy-piperidin-1-yl)-propionamide
3-Diethylamino-propionamide
3-[(3-Dimethylamino-propyl)-methyl-amino]-propionamide The compounds on the following list were prepared from 3-(4-amino-3-methoxyphenyl)-7-iodothieno[3,2-c]pyridin-4-amine and the appropriate amides according to General Procedure L.
N-[4-Amino-3-(4-amino-3-methoxy-phenyl)-thieno[3,2-c]pyridin-7-yl]-3-pyrrolidin-1-yl-propionamide
N-[4-Amino-3-(4-amino-3-methoxy-phenyl)-thieno[3,2-c]pyridin-7-yl]-3-morpholin-4-yl-propionamide
N-[4-Amino-3-(4-amino-3-methoxy-phenyl)-thieno[3,2-c]pyridin-7-yl]-3-(4-methyl-piperazin-1-yl)-propionamide
N-[4-Amino-3-(4-amino-3-methoxy-phenyl)-thieno[3,2-c]pyridin-7-yl]-3-(4-hydroxy-piperidin-1-yl)-propionamide
N-[4-Amino-3-(4-amino-3-methoxy-phenyl)-thieno[3,2-c]pyridin-7-yl]-3-diethylamino-propionamide
N-[4-Amino-3-(4-amino-3-methoxy-phenyl)-thieno[3,2-c]pyridin-7-yl]-3-[(3-dimethylamino-propyl)-methyl-amino]-propionamide

EXAMPLE 1155

N-(4-{4-amino-7-[(3-pyrrolidin-1-ylpropanoyl)amino]thieno[3,2-c]pyridin-3-yl}-2-methoxyphenyl)-1-methyl-1H-indole-2-carboxamide 1-Methyl-1H-indole-2-carbonyl chloride (109 mg, 0.6 mmol) in dichloromethane (2 mL) was added to N-[4-amino-3-(4-amino-3-methoxyphenyl)thieno[3,2-c]pyridin-7-yl]-3-pyrrolidin-1-ylpropanamide (0.5 mmol) in pyridine (3 mL) at about 0° C. The ice-water bath was removed and the reaction mixture was stirred at room temperature overnight. The solvent was removed and residue was purified by reverse phase preparative HPLC to give the title compound as the acetate salt (116 mg, 37%). $^1$H NMR (DMSO, $d_6$) δ 1.75 (m, 4H), 1.90 (s, 3H), 2.55 (m, 6H), 2.77 (t, 2H), 3.91 (s, 3H), 4.04 (s, 3H), 5.44 (s, 2H), 7.08 (d, 1H), 7.15 (t, 1H), 7.20 (s, 1H), 7.33(t, 1H), 7.35 (s, 1H), 7.55 (s, 1H), 7.59 (d, 1H), 7.71 (d, 1H), 7.91 (s, 1H), 7.99 (d, 1H), 9.51 (s, 1H), 10.14 (s, 1H). LCMS: $MH^+$=567.3, $R_t$ =2.579 min. (a).

EXAMPLE 1156

N-(4-{4-amino-7-[(3-morpholin-4-ylpropanoyl)amino]thieno[3,2-c]pyridin-3-yl}-2-methoxyphenyl)-1-methyl-1H-indole-2-carboxamide The title compound was prepared using 1-methyl-1H-indole-2-carbonyl chloride, N-[4-amino-3-(4-amino-3-methoxyphenyl)thieno[3,2-c]pyridin-7-yl]-3-morpholin-4-ylpropanamide, and the procedure described in General Procedure F. m/z $(M+H)^+$ 585.4.

EXAMPLE 1157

N-[4-(4-amino-7-{[3-(4-methylpiperazin-1-yl)propanoyl]amino}thieno[3,2-c]pyridin-3-yl)-2-methoxyphenyl]-1-methyl-1H-indole-2-carboxamide The title compound was prepared using 1-methyl-1H-indole-2-carbonyl chloride, N-[4-amino-3-(4-amino-3-methoxyphenyl)thieno[3,2-c]pyridin-7-yl]-3-(4-methylpiperazin-1-yl)propanamide, and the procedure described in General Procedure F. m/z $(M+H)^+$598.4.

EXAMPLE 1158

N-[4-(4-amino-7-{[3-(4-hydroxypiperidin-1-yl)propanoyl]amino}thieno[3,2-c]pyridin-3-yl)-2-methoxyphenyl]-1-methyl-1H-indole-2-carboxamide The title compound was prepared using 1-methyl-1H-indole-2-carbonyl chloride, N-[4-Amino-3-(4-amino-3-methoxyphenyl)-thieno[3,2-c]pyridin-7-yl]-3-(4-hydroxypiperidin-1-yl)propionamide, and the procedure described in General Procedure F. m/z $(M+H)^+$ 599.4.

EXAMPLE 1159

N-[4-(4-amino-7-{[3-(diethylamino)propanoyl]amino}thieno[3,2-c]pyridin-3-yl)-2-methoxyphenyl]-1-methyl-1H-indole-2-carboxamide The title compound was prepared using 1-methyl-1H-indole-2-carbonyl chloride, N-[4-Amino-3-(4-amino-3-methoxyphenyl)thieno[3,2-c]pyridin-7-yl]-3-diethylaminopropionamide, and the procedure described in General Procedure F. m/z $(M+H)^+$571.3.

EXAMPLE 1160

N-{4-[4-amino-7-({3-[[3-(dimethylamino)propyl](methyl)amino]propanoyl}amino)thieno[3,2-c]pyridin-3-yl]-2-methoxyphenyl}-1-methyl-1H-indole-2-carboxamide The title compound was prepared using 1-methyl-1H-indole-2-carbonyl chloride, N-[4-Amino-3-(4-amino-3-methoxyphenyl)-thieno[3,2-c]pyridin-7-yl]-3-[(3-dimethylamino-propyl)methylamino]propionamide, and the procedure described in General Procedure F. m/z $(M+H)^+$ 614.3.

The compounds below were prepared from 2-chloroacetamide and the appropriate amine according to General Procedure E.

2-Pyrrolidin-1-ylacetamide

2-Morpholin-4-ylacetamide
2-(4-Methylpiperazin-1-yl)acetamide
2-(4-Hydroxypiperidin-1-yl)acetamide
2-Diethylaminoacetamide
2-[Methyl-(3-methylamino-propyl)-amino]acetamide.

EXAMPLE 1161

N-[4-amino-3-(4-amino-3-methoxyphenyl)thieno[3,2-c]pyridin-7-yl]-2-pyrrolidin-1-ylacetamide triacetate salt A schlenck tube was charged with 3-(4-amino-3-methoxyphenyl)-7-iodothieno[3,2-c]pyridin-4-amine (199 mg, 0.5 mmol), 2-pyrrolidin-1-ylacetamide (0.6 mmol), copper(I) iodide (4.8 mg, 0.025 mmol), potassium phosphate (225 mg, 1.06 mmol). Evacuated under vacuum and back filled with nitrogen. trans-Cyclohexane-1,2-diamine (6.5 uL, 0.05 mmol) and dioxane (1 mL) was added. The reaction tube was sealed and heated at about 110° C. overnight. The solvent was removed and the crude product was purified by reverse phase preparative HPLC to give the title compound as the tri-acetate salt. LCMS (Conditions a): $MH^+$=398.2, $R_t$=1.55 min. (154 mg, 45%)

Examples 1162–1166, shown in Table 39, were prepared using 3-(4-amino-3-methoxyphenyl)-7-iodothieno[3,2-c]pyridin-4-amine and the appropriate amides according to General Procedure L.

TABLE 39

| Amide precursor | Example | HPLC RT min. | m/z M+H+ |
|---|---|---|---|
| 2-Morpholin-4-ylacetamide | 1162 | 1.63 (a) | 414.2 |
| 2-(4-Methyl-piperazin-1-yl)acetamide | 1163 | 0.92 (a) | 427.2 |
| 2-(4-Hydroxy-piperadin-1-yl)acetamide | 1164 | 1.09 (a) | 428.2 |
| 2-Diethylaminoacetamide | 1165 | 2.13 (a) | 400.2 |
| 2-[Methyl-(3-methylamino-propyl)amino]-acetamide | 1166 | 1.13 (a) | 443.3 |

Examples 1167–1173, shown in Table 40, were prepared using 1-methyl-1H-indole-2-carbonyl chloride or acetyl chloride and the appropriate acyl precursor according to General Procedure F.

TABLE 40

| Product | Example | HPLC RT min. | m/z (M+H)+ |
|---|---|---|---|
| 4-amino-3-(3-methoxy-4-{[(1-methyl-1H-indol-2-yl)carbonyl]amino}phenyl)-N-(pyrrolidin-1-ylmethyl)thieno[3,2-c]pyridine-7-carboxamide | 1167 | 3.28 (a) | 555.3 |
| 3-[4-(acetylamino)-3-methoxyphenyl]-4-N-ammo-(pyrrolidin-1-ylmethyl)thieno[3,2-c]pyridine-7-carboxamide | 1168 | 1.50 (a) | 440.3 |
| 4-amino-3-(3-methoxy-4-{[(1-methyl-1H-indol-2-yl)carbonyl]amino}phenyl)-N-(morpholin-4-ylmethyl)thieno[3,2-c]pyridine-7-carboxamide | 1169 | 3.02 (a) | 571.3 |
| 4-amino-3-(3-methoxy-4-{[(1-methyl-1H-indol-2-yl)carbonyl]amino}phenyl)-N-[(4-methylpiperazin-1-yl)methyl]thieno[3,2-c]pyridine-7-carboxamide triacetate salt | 1170 | 2.58 (a) | 584.3 |
| 4-amino-N-[(4-hydroxypipendin-1-yl)methyl]-3-(3-methoxy-4-{[(1-methyl-1H-indol-2-yl)carbonyl]amino}phenyl)thieno[3,2-c]pyridine-7-carboxamide acetate salt | 1171 | 2.68 (a) | 585.3 |
| 4-amino-N-[(diethylamino)methyl]-3-(3-methoxy-4-{[(1-methyl-1H-indol-2-yl)carbonyl]amino}phenyl)thieno[3,2-c]pyridine-7-carboxamide acetate salt | 1172 | 3.82 (a) | 557.3 |
| 4-amino-N-{[[3-(dimethylamino)propyl](methyl)amino]methyl}-3-(3-methoxy-4-{[(1-methyl-1H-indol-2-yl)carbonyl]amino}phenyl)thieno[3,2-c]pyridine-7-carboxamide | 1173 | 2.92 (a) | 600.3 |

EXAMPLE 1174

N-(4-{4-amino-7-[(diphenylmethylene)amino]thieno[3,2-c]pyridin-3-yl}-2-methoxyphenyl)-1-methyl-1H-indole-2-carboxamide A mixture of N-[4-(4-amino-7-iodothieno[3,2-c]pyridin-3-yl)-2-methoxyphenyl]-1-methyl-1H-indole-2-carboxamide (4.03 g, 7.72 mmol), tris(dibenzylideneacetone)dipalladium (0) (0.283 g, 0.31 mmol), 9,9-dimethyl-4–5-bis(diphenylphosphino)xanthene (0.536 g, 0.93 mmol), sodium tert-butoxide (1.00 g, 10.42 mmol), 18-crown-6 (2.75 g, 10.42 mmol), and benzophenone imine (1.16 mL, 6.9 mmol) were combined in N,N-dimethylformamide (100 mL), and the solution was heated at 95° C. for 12 h. The reaction mixture was cooled to ambient temperature and concentrated. The residue was diluted with brine (100 mL) and extracted with methanol/dichloromethane (1:33, 3×150 mL). The organic layers were combined, dried over magnesium sulfate, filtered, and concentrated. Purification of the residue by flash column chromatography on silica gel which had been deactivated with triethylamine (10% by volume of silica gel used), using a gradient of ethyl acetate/heptane (1:3 to 4:1) as the mobile phase afforded the title compound (2.71 g, 4.47 mmol) as a yellow foam: MS: $(MH)^+$ 608; LCMS (Conditions a), $R_t$ 2.27 min.

EXAMPLE 1175

N-[4-(4,7-diaminothieno[3,2-c]pyridin-3-yl)-2-methoxyphenyl]-1-methyl-1H-indole-2-carboxamide N-(4-{4-Amino-7-[(diphenylmethylene)amino]thieno[3,2-c]pyridin-3-yl}-2-methoxyphenyl)-1-methyl-1H-indole-2-carboxamide (0.058 g, 0.096 mmol) in tetrahydrofuran (2 mL) and aqueous hydrochloric acid (2 M, 0.225 mL) was stirred at ambient temperature for 15 h. The reaction mixture was diluted with methanol/dichloromethane (1:49, 50 mL), and the resulting solution was extracted with aqueous sodium carbonate (1 M, 10 mL). The organic layer was dried over magnesium sulfate, filtered, and concentrated. Purification of the residue by flash column chromatography on silica gel which had been deactivated with triethylamine (10% by volume of silica gel used), using a gradient of methanol/dichloromethane (1:19 to 1:9) as the mobile phase afforded the title compound (0.015 g, 0.034 mmol) as light brown flakes: $^1$H NMR (DMSO-$d_6$, 400 MHz) δ 9.49 (s, 1H), 7.96 (d, 1H), 7.70 (d, 1H), 7.58 (d, 1H), 7.39 (s, 1H), 7.35 (s, 1H), 7.33 (m, 1H), 7.17 (s, 1H), 7.15 (m, 1H), 7.06 (d, 1H), 4.77 (br, 2H), 4.71 (br, 2H), 4.04 (s, 3H), 3.91 (s, 3H); MS: (MH)$^+$ 444.

EXAMPLE 1176

N-[4-(7-amino-4-{[(dimethylamino)methylene]amino}thieno[3,2-c]pyridin-3-yl)-2-methoxyphenyl]-1-methyl-1H-indole-2-carboxamide N,N-Dimethylformamide dimethyl acetal (0.116 mL, 0.87 mmol) was added to a solution of N-(4-{4-amino-7-[(diphenylmethylene)amino]thieno[3,2-c]pyridin-3-yl}-2-methoxyphenyl)-1-methyl-1H-indole-2-carboxamide (0.156 g, 0.257 mmol) in N,N-dimethylformamide (6 mL). The solution was stirred at 95° C. for 9 h, then was cooled to ambient temperature, and the mixture was concentrated. Partial purification of the residue by flash column chromatography on silica gel which had been deactivated with triethylamine (10% by volume of silica gel used), using dichloromethane as the mobile phase afforded crude N-(4-{4-{[(dimethylamino)methylene]amino}-7-[(diphenylmethylene)amino]thieno[3,2-c]pyridin-3-yl}-2-methoxyphenyl)-1-methyl-1H-indole-2-carboxamide as a yellow foam (0.16 g, 0.24 mmol): MS: (MH)$^+$ 663.

N-(4-{4-{[(dimethylamino)methylene]amino}-7-[(diphenylmethylene)amino]thieno[3,2-c]pyridin-3-yl}-2-methoxyphenyl)-1-methyl-1H-indole-2-carboxamide (0.117 g, 0.177 mmol) was dissolved in tetrahydrofuran (5 mL), and aqueous hydrochloric acid (1 M, 0.24 mL) was added, and the mixture was stirred at ambient temperature for 12 h. The mixture was diluted with methanol/dichloromethane (1:19, 50 mL) the resulting solution was extracted with aqueous sodium bicarbonate (1 M, 10 mL). The organic layer was dried over magnesium sulfate, filtered, and concentrated. Purification of the residue by flash column chromatography on silica gel which had been deactivated with triethylamine (10% by volume of silica gel used) using methanol/dichloromethane (1:19) as the mobile phase afforded the title compound (0.085 g, 0.17 mmol) as a tan powder: $^1$H NMR (DMSO-$d_6$, 400 MHz) δ 9.40 (s, 1H), 8.13 (s, 1H), 7.79 (d, 1H), 7.70 (d, 1H), 7.58 (d, 1H), 7.56 (s, 1H), 7.49 (s, 1H), 7.33 (m, 2H), 7.15 (t, 1H), 7.06 (m, 1H), 7.01 (d, 1H), 5.07 (br, 2H), 4.04 (s, 3H), 3.88 (s, 3H), 2.94 (s, 3H), 2.47 (s, 3H); MS: (MH)$^+$ 499.

EXAMPLE 1177

N-(4-{4-amino-7-[(thien-2-ylsulfonyl)amino]thieno[3,2-c]pyridin-3-yl}-2-methoxyphenyl)-1-methyl-1H-indole-2-carboxamide The title compound was prepared using N-[4-(7-amino-4-{[(dimethylamino)methylene]amino}thieno[3,2-c]pyridin-3-yl]-2-methoxyphenyl]-1-methyl-1H-indole-2-carboxamide and 2-thiophenesulfonyl chloride using General Procedure G followed by General Procedure M. $^1$H NMR (DMSO-$d_6$, 400 MHz) δ 9.70 (br, 1H), 9.49 (s, 1H), 7.97 (d, 1H), 7.80 (m, 1H), 7.70 (d, 1H), 7.58 (d, 1H), 7.47 (s, 1H), 7.40 (m, 1H), 7.37 (s, 1H), 7.34 (m, 2H), 7.17 (s 1H), 7.14 (d, 1H), 7.07 (m, 2H), 5.35 (br, 2H), 4.03 (s, 3H), 3.90 (s, 3H); MS: (M–H)$^-$ 588.

EXAMPLE 1178

N-(4-{4-amino-7-[(phenylsulfonyl)amino]thieno[3,2-c]pyridin-3-yl}-2-methoxyphenyl)-1-methyl-1H-indole-2-carboxamide The title compound was prepared using N-[4-(7-amino-4-{[(dimethylamino)methylene]amino}thieno[3,2-c]pyridin-3-yl]-2-methoxyphenyl]-1-methyl-1H-indole-2-carboxamide and phenylsulfonyl chloride using General Procedure G followed by General Procedure M. $^1$H NMR (DMSO-$d_6$, 400 MHz) δ 9.80 (br, 1H), 9.49 (s, 1H), 7.97 (d, 1H), 7.75 (d, 2H), 7.70 (d, 1H), 7.64 (d, 1H), 7.58 (m, 3H), 7.51 (s, 1H), 7.34 (m, 2H), 7.17 (m, 2H), 7.15 (s, 1H), 7.05 (d, 1H), 5.50 (br, 2H), 4.03 (s, 3H), 3.90 (s, 3H); MS: (MH)$^+$ 584.

EXAMPLE 1179

N-(4-{4-amino-7-[(anilinocarbonyl)amino]thieno[3,2-c]pyridin-3-yl}-2-methoxyphenyl)-1-methyl-1H-indole-2-carboxamide The title compound was prepared using N-[4-(7-amino-4-{[(dimethylamino)methylene]amino}thieno[3,2-c]pyridin-3-yl]-2-methoxyphenyl]-1-methyl-1H-indole-2-carboxamide and phenyl isocyanate using General Procedure N followed by General Procedure M. $^1$H NMR (DMSO-$d_6$, 400 MHz) δ 9.52 (s, 1H), 9.07 (s, 1H), 8.58 (s, 1H), 8.09 (s, 1H), 8.06 (d, 1H), 7.73 (m, 2H), 7.60 (d, 1H), 7.49 (d, 2H), 7.36 (s, 1H), 7.30 (m, 4H), 7.14 (m, 2H), 7.00 (t, 1H), 6.10 (br, 2H), 4.04 (s, 3H), 3.93 (s, 3H); MS: (MH)$^+$ 563.

EXAMPLE 1180

N-(4-{4-amino-7-[({[4-(dimethylamino)phenyl]amino}carbonyl)amino]thieno[3,2-c]pyridin-3-yl}-2-methoxyphenyl)-1-methyl-1H-indole-2-carboxamide The title compound was prepared using N-[4-(7-amino-4-{[(dimethylamino)methylene]amino}thieno[3,2-c]pyridin-3-yl]-2-methoxyphenyl]-1-methyl-1H-indole-2-carboxamide and 4-(dimethylamino)phenyl isocyanate using General Procedure N followed by General Procedure M. $^1$H NMR (DMSO-$d_6$, 400 MHz) δ 9.52 (s, 1H), 8.48 (s, 1H), 8.11 (s, 1H), 7.99 (d, 1H), 7.95 (s, 1H), 7.71 (d, 1H), 7.59 (d, 1H), 7.55 (s, 1H), 7.35 (s, 1H), 7.29 (m, 3H), 7.21 (m, 1H), 7.15 (t, 1H), 7.08 (d, 1H), 6.70 (d, 2H), 5.39 (br, 2H), 4.04 (s, 3H), 3.92 (s, 3H), 2.83 (s, 6H); MS: (MH)$^+$ 606.

EXAMPLE 1181

N-{4-[4-amino-7-({[(3-chloropropyl)amino]carbonyl}amino)thieno[3,2-c]pyridin-3-yl]-2-methoxyphenyl}-1-methyl-1H-indole-2-carboxamide The title compound was prepared using N-[4-(7-amino-4-{[(dimethylamino)methylene]amino}thieno[3,2-c]pyridin-3-yl]-2-methoxyphenyl]-1-methyl-1H-indole-2-carboxamide and 3-chloropropyl isocyanate using General Procedure N followed by General Procedure M. $^1$H NMR (DMSO-$d_6$, 400 MHz) δ 9.50 (s, 1H), 8.69 (s, 1H), 8.19 (br, 1H), 8.13 (d, 1H), 7.94 (s, 1H), 7.71 (d, 1H), 7.60 (d, 1H), 7.35 (m, 1H), 7.29 (s, 1H), 7.16 (m, 2H), 6.08 (m, 2H), 4.04 (s, 3H), 3.93 (s, 3H), 3.71 (t, 2H), 3.25 (m, 2H), 1.93 (m, 2H); MS: (MH)+ 563.

EXAMPLE 1182

N-[4-(4-amino-7-{[(4-methylpiperazin-1-yl)carbonyl]amino}thieno[3,2-c]pyridin-3-yl)-2-methoxyphenyl]-1-methyl-1H-indole-2-carboxamide The title compound was prepared using N-[4-(7-amino-4-{[(dimethylamino)methylene]amino }thieno[3,2-c]pyridin-3-yl)-2-methoxyphenyl]-1-methyl-1H-indole-2-carboxamide and N-methyl piperazine using General Procedure O. $^1$H NMR (DMSO-d$_6$, 400 MHz) δ 9.51 (s, 1H), 8.49 (s, 1H), 7.99 (d, 1H), 7.71 (d, 1H), 7.64 (s, 1H), 7.59 (d, 1H), 7.51 (s, 1H), 7.35 (s, 1H), 7.33 (m, 1H), 7.20 (s, 1H), 7.15 (t, 1H), 7.08(d, 1H), 5.40 (br, 2H), 4.04 (s, 3H), 3.92 (s, 3H), 3.46 (m, 4H), 2.36 (m, 4H), 2.23 (s, 3H); (MH)+ 570.

EXAMPLE 1183

N-[4-(4-amino-7-{[(diethylamino)carbonyl]amino}thieno[3,2-c]pyridin-3-yl)-2-methoxyphenyl]-1-methyl-1H-indole-2-carboxamide The title compound was prepared using N-[4-(7-amino-4-{[(dimethylamino)methylene]amino }thieno[3,2-c]pyridin-3-yl)-2-methoxyphenyl]-1-methyl-1H-indole-2-carboxamide and N,N-diethylamine using General Procedure O. $^1$H NMR (DMSO-d$_6$, 400 MHz) δ 9.51 (s, 1H), 8.27 (s, 1H), 7.70 (d, 1H), 7.66 (s, 1H), 7.59 (d, 1H), 7.56 (s, 1H), 7.35 (s, 1H), 7.32 (m, 1H), 7.21 (s, 1H), 7.15 (t, 1H), 7.09 (d, 1H), 5.65 (br, 2H), 4.04 (s, 3H), 3.92 (s, 3H), 3.35 (qt, 4H), 1.15 (t, 6H); MS: (MH)+ 543.

EXAMPLE 1184

N-(4-{4-amino-7-[(pyrrolidin-1-ylcarbonyl)amino]thieno[3,2-c]pyridin-3-yl}-2-methoxyphenyl)-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and pyrrolidine using General Procedure O. $^1$H NMR (DMSO-d$_6$, 400 MHz) δ 9.51 (s, 1H), 8.22 (s, 1H), 8.03 (d, 1H), 7.72 (s, 1H), 7.71 (m, 1H), 7.61 (s, 1H), 7.61 (m, 1H), 7.35 (s, 1H), 7.34 (t, 1H), 7.22 (s, 1H), 7.15 (t, 1H), 7.11 (m, 1H), 5.84 (br, 2H), 4.04 (s, 3H), 3.92 (s, 3H), 3.39 (m, 4H), 1.89 (m, 4H); MS: (MH)+ 541.

EXAMPLE 1185

N-(4-{4-amino-7-[(morpholin-4-ylcarbonyl)amino]thieno[3,2-c]pyridin-3-yl}-2-methoxyphenyl)-1-methyl-1H-indole-2-carboxamide The title compound was prepared using N-[4-(7-amino-4-{[(dimethylamino)methylene]amino }thieno[3,2-c]pyridin-3-yl)-2-methoxyphenyl]-1-methyl-1H-indole-2-carboxamide and morpholine using General Procedure O. $^1$H NMR (DMSO-d$_6$, 400 MHz) δ 9.51 (s, 1H), 8.54 (s, 1H), 7.99 (d, 1H), 7.71 (d, 1H), 7.66 (s, 1H), 7.59 (d, 1H), 7.52 (s, 1H), 7.35 (s, 1H), 7.33 (m, 1H), 7.20 (s, 1H), 7.15 (t, 1H), 7.08 (d, 1H), 5.46 (br, 2H), 4.04 (s, 3H), 3.92 (s, 3H), 3.65 (m, 4H), 3.45 (m, 4H); MS: (MH)+ 557.

Example 1186 N-{4-[4-amino-7-({[[3-(dimethylamino)propyl](methyl)amino]carbonyl}amino)thieno[3,2-c]pyridin-3-yl]-2-methoxyphenyl}-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and N,N,N'-trimethyl-1,3-propanediamine using General Procedure O. $^1$H NMR (DMSO-d$_6$, 400 MHz) δ 9.51 (s, 1H), 8.83 (br, 1H), 7.99 (d, 1H), 7.74 (s, 1H), 7.70 (d, 1H), 7.59 (d, 1H), 7.51 (s, 1H), 7.35 (s, 1H), 7.33 (m, 1H), 7.20 (s, 1H), 7.15 (t, 1H), 7.08 (d, 1H), 5.38 (br, 2H), 4.04 (s, 3H), 3.92 (s, 3H), 3.37 (m, 2H), 2.92 (s, 3H), 2.35 (m, 2H), 2.21 (s, 6H), 1.74 (m, 2H); MS: (MH)+ 586.

EXAMPLE 1187

N-{4-[4-amino-7-({[ethyl(2-hydroxyethyl)amino]carbonyl}amino)thieno[3,2-c]pyridin-3-yl]-2-methoxyphenyl}-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and 2-(ethylamino)ethanol using General Procedure O. $^1$H NMR (DMSO-d$_6$, 400 MHz) δ 9.51 (s, 1H), 8.33 (s, 1H), 7.99 (d, 1H), 7.70 (d, 1H), 7.69 (s, 1H), 7.59 (d, 1H), 7.51 (d, 1H), 7.35 (s, 1H), 7.34 (m, 1H), 7.19 (s, 1H), 7.15 (t, 1H), 7.07 (d, 1H), 5.38 (br, 2H), 5.07 (br, 1H), 4.04 (s, 3H), 3.92 (s, 3H), 3.60 (m, 2H), 3.39 (m, 4H), 1.15 (t, 3H); MS: (MH)+ 559.

EXAMPLE 1188

N-{4-[4-amino-7-({[(2-piperidin-1-ylethyl)amino]carbonyl}amino)thieno[3,2-c]pyridin-3-yl]-2-methoxyphenyl}-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and 1-(2-aminoethyl)piperidine using General Procedure O. $^1$H NMR (DMSO-d$_6$, 400 MHz) δ 9.51 (s, 1H), 8.19 (br, 1H), 8.00 (m, 1H), 7.92 (br, 1H), 7.86 (s, 1H), 7.70 (d, 1H), 7.59 (d, 1H), 7.53 (s, 1H), 7.35 (s, 1H), 7.34 (t, 1H), 7.19 (s, 1H), 7.15 (t, 1H), 7.07 (d, 1H), 5.35 (br, 2H), 4.04 (s, 3H), 3.91 (s, 3H), 3.20 (m, 2H), 2.36 (m, 6H), 1.56 (m, 4H), 1.38 (m, 2H); MS: (MH)+ 598.

EXAMPLE 1189

N-[4-(4-amino-7-{[({[(2R)-1-ethylpyrrolidin-2-yl]methyl}amino)carbonyl]amino}thieno[3,2-c]pyridin-3-yl)-2-methoxyphenyl]-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and (R)-2-aminomethyl-1-ethylpyrrolidine using General Procedure O. $^1$H NMR (DMSO-d$_6$, 400 MHz) δ 9.51 (s, 1H), 8.22 (br, 1H), 7.98 (d, 1H), 7.88 (s, 1H), 7.70 (d, 1H), 7.59 (d, 1H), 7.53 (s, 1H), 7.35 (s, 1H), 7.33 (t, 1H), 7.19 (s, 1H), 7.15 (t, 1H), 7.07 (d, 1H), 6.19 (br, 1H), 5.33 (br, 2H), 4.04 (s, 3H), 3.91 (s, 3H), 3.08 (m, 1H), 2.97 (m, 1H), 2.83 (m, 1H), 2.46 (m, 2H), 2.17 (m, 2H), 1.70 (m, 4H), 1.05 (t, 3H); MS: (MH)⁺ 598.

EXAMPLE 1190

N-(4-{4-amino-7-[({[2-(diethylamino)ethyl]amino}carbonyl)amino]thieno[3,2-c]pyridin-3-yl}-2-methoxyphenyl)-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and N,N-diethylethylenediamine using General Procedure O. ¹H NMR (DMSO-d₆, 400 MHz) δ 9.51 (s, 1H), 8.19 (br, 1H), 7.99 (d, 1H), 7.85 (s, 1H), 7.71 (d, 1H), 7.59 (d, 1H), 7.53 (s, 1H), 7.35 (s, 1H), 7.33 (t, 1H), 7.19 (s, 1H), 7.15 (t, 1H), 7.07 (d, 1H), 6.16 (br, 1H), 5.35 (br, 2H), 4.04 (s, 3H), 3.91 (s, 3H), 3.15 (m, 2H), 2.49 (m, 6H), 0.98 (t, 6H); MS: (MH)⁺ 586.

EXAMPLE 1191

N-{4-[4-amino-7-({[4-(2-hydroxyethyl)piperazin-1-yl]carbonyl}amino)thieno[3,2-c]pyridin-3-yl]-2-methoxyphenyl}-1-methyl-1H-indole-2-carboxamide The title compound was prepared using N-[4-(7-amino-4-{[(dimethylamino)methylene]amino }thieno[3,2-c]pyridin-3-yl)-2-methoxyphenyl]-1-methyl-1H-indole-2-carboxamide and 2-piperazin-1-ylethanol using General Procedure O. ¹H NMR (DMSO-d₆, 400 MHz) δ 9.51 (s, 1H), 8.48 (s, 1H), 7.99 (d, 1H), 7.71 (d, 1H), 7.64 (s, 1H), 7.59 (d, 1H), 7.50 (s, 1H), 7.35 (s, 1H), 7.33 (t, 1H), 7.20 (s, 1H), 7.15 (t, 1H), 7.08 (d, 1H), 5.40 (br, 2H), 4.47 (br, 1H), 4.04 (s, 3H), 3.91 (s, 3H), 3.55 (m, 2H), 3.46 (m, 4H), 2.45 (m, 6H); MS: (MH)⁺ 600.

EXAMPLE 1192

N-{4-[4-amino-7-({[methoxy(methyl)amino]carbonyl}amino)thieno[3,2-c]pyridin-3-yl]-2-methoxyphenyl }-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and N,O-dimethylhydroxylamine hydrochloride using General Procedure O. ¹H NMR (DMSO-d₆, 400 MHz) 9.50 (s, 1H), 9.07 (s, 1H), 7.98 (d, 1H), 7.69 (d, 1H), 7.67 (s, 1H), 7.57 (d, 1H), 7.51 (s, 1H), 7.33 (s, 1H), 7.32 (t, 1H), 7.19 (s, 1H), 7.14 (t, 1H), 7.07 (d, 1H), 5.45 (br, 2H), 4.02 (s, 3H), 3.90 (s, 3H), 3.72 (s, 3H), 3.06 (s, 3H); MS: (MH)⁺ 531.

EXAMPLE 1193

N-{4-[4-amino-7-({[(2-pyrrolidin-1-ylethyl)amino]carbonyl}amino)thieno[3,2-c]pyridin-3-yl]-2-methoxyphenyl}-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and 2-pyrrolidin-1-ylethylamine using General Procedure O. ¹H NMR (DMSO-d₆, 400 MHz) δ 9.51 (s, 1H), 8.15 (br, 1H), 7.98 (d, 1H), 7.89 (s, 1H), 7.71 (d, 1H), 7.59 (d, 1H), 7.53 (s, 1H), 7.33 (s, 1H), 7.33 (t, 1H), 7.19 (s, 1H), 7.15 (t, 1H), 7.07 (d, 1H), 6.30 (br, 1H), 5.33 (br, 2H), 4.04(s, 3H), 3.91 (s, 3H), 3.20 (m, 2H), 2.48 (m, 6H), 1.71 (m, 4H); MS: (MH)⁺ 584.

EXAMPLE 1194

N-{4-[4-amino-7-({[(3-pyrrolidin-1-ylpropyl)amino]carbonyl}amino)thieno[3,2-c]pyridin-3-yl]-2-methoxyphenyl}-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and 3-pyrrolidin-1-ylpropylamine using General Procedure O. ¹H NMR (DMSO-d₆, 400 MHz) δ 9.51 (s, 1H), 8.00 (br, 1H), 7.98 (d, 1H), 7.84 (s, 1H), 7.71 (d, 1H), 7.59 (d, 1H), 7.53 (s, 1H), 7.35 (s, 1H), 7.33 (t, 1H), 7.18 (s, 1H), 7.15 (t, 1H), 7.07 (d, 1H), 6.32 (br, 1H), 5.36 (br, 2H), 4.04(s, 3H), 3.91 (s, 3H), 3.11 (m, 2H), 2.40 (m, 6H), 1.60 (m, 6H); MS: (MH)+ 598.

EXAMPLE 1195

A-841786.0 (Propanediamine Dimethylamine)

N-(4-{4-amino-7-[({[3-(dimethylamino)propyl]amino}carbonyl)amino]thieno[3,2-c]pyridin-3-yl}-2-methoxyphenyl)-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and N-(3-aminopropyl)-N,N-dimethylamine using General Procedure O. ¹H NMR (DMSO-d₆, 400 MHz) δ 9.51 (s, 1H), 8.00 (br, 1H), 7.99 (d, 1H), 7.84 (s, 1H), 7.71 (d, 1H), 7.59 (d, 1H), 7.53 (s, 1H), 7.35 (s, 1H), 7.33 (t, 1H), 7.18 (s, 1H), 7.15 (t, 1H), 7.07 (d, 1H), 6.35 (br, 1H), 5.36 (br, 2H), 4.04(s, 3H), 3.91 (s, 3H), 3.10 (m, 2H), 2.24 (m, 2H), 2.11 (s, 6H), 1.56 (m, 2H); MS: (MH)⁺ 572.

EXAMPLE 1196

N-(4-{4-amino-7-[({[2-(2-hydroxyethoxy)ethyl]amino}carbonyl)amino]thieno[3,2-c]pyridin-3-yl}-2-methoxyphenyl)-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and 2-(2-aminoethoxy)ethanol using General Procedure O. ¹H NMR (DMSO-d₆, 400 MHz) δ 9.51 (s, 1H), 8.10 (s, 1H), 7.99 (d, 1H), 7.89 (s, 1H), 7.71 (d, 1H), 7.59 (d, 1H), 7.53 (s, 1H), 7.35 (s, 1H), 7.34 (t, 1H), 7.19 (s, 1H), 7.15 (t, 1H), 7.07 (d, 1H), 6.36 (t, 1H), 5.34 (br, 2H), 4.64 (t, 1H), 4.04(s, 3H), 3.91 (s, 3H), 3.53 (m, 2H), 3.48 (m, 4H), 3.27 (m, 2H); MS: (MH)⁺ 575.

EXAMPLE 1197

N-{4-[4-amino-7-({[(2-morpholin-4-ylethyl)amino]carbonyl}amino)thieno[3,2-c]pyridin-3-yl)-2-yl]-2-methoxyphenyl}-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and 2-morpholin-4-ylethylamine using General Procedure O. $^1$H NMR (DMSO-d$_6$, 400 MHz) δ 9.51 (s, 1H), 8.16 (br, 1H), 7.99 (d, 1H), 7.87 (s, 1H), 7.71 (d, 1H), 7.59 (d, 1H), 7.53 (s, 1H), 7.35 (s, 1H), 7.33 (t, 1H), 7.19 (s, 1H), 7.15 (t, 1H), 7.08 (d, 1H), 6.29 (br, 1H), 5.36 (br, 2H), 4.04(s, 3H), 3.91 (s, 3H), 3.60 (m, 4H), 3.21 (m, 2H), 2.40 (m, 6H); MS: (MH)$^+$ 600.

EXAMPLE 1198

N-[4-(4-amino-7-{[(4-hydroxypiperidin-1-yl)carbonyl]amino}thieno[3,2-c]pyridin-3-yl)-2-methoxyphenyl]-1-methyl-1H-indole-2-carboxamide The title compound was prepared using N-[4-(7-amino-4-{[(dimethylamino)methylene]amino}thieno[3,2-c]pyridin-3-yl)-2-methoxyphenyl]-1-methyl-1H-indole-2-carboxamide and piperidin-4-ol using General Procedure O. $^1$H NMR (DMSO-d$_6$, 400 MHz) δ 9.51 (s, 1H), 8.47 (s, 1H), 7.99 (d, 1H), 7.71 (d, 1H), 7.59 (d, 1H), 7.50 (s, 1H), 7.35 (s, 1H), 7.33 (t, 1H), 7.19 (s, 1H), 7.15 (t, 1H), 7.08 (d, 1H), 5.39 (br, 2H), 4.77 (m, 1H), 4.04(s, 3H), 3.91 (s, 3H), 3.85 (m, 2H), 3.69 (m, 1H), 3.06 (m, 2H), 1.77 (m, 2H), 1.38 (m, 2H); MS: (MH)$^+$ 571.

EXAMPLE 1199 ethyl 2-[4-amino-3-(3-methoxy-4-{[(1-methyl-1H-indol-2-yl)carbonyl]amino}phenyl)thieno[3,2-c]pyridin-7-yl]cyclopropanecarboxylate Trimethylsulfoxonium iodide (45.1 mg, 0.205 mmol) in anhydrous methyl sulfoxide (4 mL) and 60% sodium hydride in mineral oil (16.4 mg, 0.411 mmol) was stirred for 5 minutes at room temperature and treated with a mixture of ethyl (2E)-3-[4-amino-3-(3-methoxy-4-{[(1-methyl-1H-indol-2-yl)carbonyl]amino}phenyl)thieno[3,2-c]pyridin-7-yl]acrylate (108 mg, 0.205 mmol) in methyl sulfoxide (2 mL) was added. After 4 hours the mixture was cooled to room temperature and quenched with saturated ammonium chloride solution (7 mL). The aqueous layer was extracted with dichloromethane (3×10 mL), dried over magnesium sulfate, filtered, and the solvent was removed under reduced pressure. The crude product was purified via HPLC preparative to give the title compound as a white solid (33.6 mg 0.062 mmol): LCMS (Conditions a): MH$^+$=541 R$_t$ =4.20 minutes; $^1$H NMR (DMSO-d$_6$, 400 MHz) δ 9.51 (1H), 7.99 (1H), 7.69 (2H), 7.58 (2H), 7.35 (2H), 7.18 (1H), 7.15 (1H), 7.06 (1H), 5.49 (1H), 4.18 (2H), 4.04 (3H), 3.91 (3H), 2.45 (1H), 1.86 (1H), 1.56 (1H), 1.47 (1H), 1.26 (3H).

EXAMPLE 1200

2-[4-amino-3-(3-methoxy-4-{[(1-methyl-1H-indol-2-yl)carbonyl]amino}phenyl)thieno[3,2-c]pyridin-7-yl]cyclopropanecarboxylic acid Ethyl 2-[4-amino-3-(3-methoxy-4-{[(1-methyl-1H-indol-2-yl)carbonyl]amino}phenyl)thieno[3,2-c]pyridin-7-yl]cyclopropanecarboxylate (433 mg, 0.8018 mmol) in methanol (2 mL) and 2M sodium hydroxide (1.604 mL, 3.207 mmol) was stirred for 23 hours at 50° C., cooled to room temperature, and acidified to a pH of 4 with 1M hydrochloric acid. Solids were filtered off and washed with water. The material was purified by HPLC preparative to furnish the title compound as a white solid (61 mg 0.119 mmol): LCMS (Conditions a): MH$^+$=513 R$_t$ =2.22 minutes; $^1$H NMR (DMSO-d$_6$, 400 MHz) 9.51 (1H), 7.99 (1H), 7.71 (2H), 7.57 (2H), 7.34 (2H), 7.19 (1H), 7.15 (1H), 7.07 (1H), 5.46 (1H), 4.04 (3H), 3.91 (3H), 2.39 (1H), 1.73 (1H), 1.46 (1H), 1.39

Examples 1201–1204, shown in Table 41, were prepared using 2-[4-amino-3-(3-methoxy-4-{[(1-methyl-1H-indol-2-yl)carbonyl]amino}phenyl)thieno[3,2-c]pyridin-7-yl]cyclopropanecarboxylic acid and the appropriate amine according to General Procedure D.

TABLE 41

| Amine | Example | RT (min.) | m/z (MH+) |
|---|---|---|---|
| Methylamine | 1201 | 3.07$^a$ | 526 |
| N',N'-Diethylpropane-1,3-diamine | 1202 | 3.17$^a$ | 625 |
| 2-Pyrrolidin-1-ylethylamine | 1203 | 3.18$^a$ | 609 |
| Dimethylamine | 1204 | 3.32$^a$ | 540 |

EXAMPLE 1205

N-{4-[4-amino-7-(1-methyl-4,5-dihydro-1H-pyrazol-5-yl)thieno[3,2-c]pyridin-3-yl]-2-methoxyphenyl}-1-methyl-1H-indole-2-carboxamide N-(4-{4-amino-7-[(1E)-3-oxoprop-1-enyl]thieno[3,2-c]pyridin-3-yl}-2-methoxyphenyl)-1-methyl-1H-indole-2-carboxamide (0.10 g, 0.207 mmol) was stirred with methyl hydrazine (0.5 mL) at ambient temperature for 3 hours then water (8 mL) was added and the white precipitate was collected by filtration and dried to give the title compound. Rt=3.62 min (Conditions a) MS m/e: 511 (M+H)$^+$, 509 (M−H)$^-$

EXAMPLE 1206

3-(4-phenoxyphenyl)isoxazolo[4,5-c]pyridin-4(5H)-one

The title compound was prepared from 4-phenoxybenzohydroxyiminoyl chloride, prepared using the procedure described in Jones, Raymond C. F. et al, J. Med. Chem. 2003, 46, 87–96, and ethyl (Z)-5-{[(benzyloxy)carbonyl]amino}-3-tetrahydro-1H-1-pyrrolyl-2-pentenoate, prepared using the procedure described in Natale, Nicholas, R. et al, J. Chem. Soc. Perkins Trans. I, 1999, 765–776, using a manner similar to that described in Natale, Nicholas, R. et al, J. Chem. Soc. Perkins Trans. I, 1999, 765–776 for the preparation of 3-methyl-4,5-dihydroisoxazolo[4,5-c]pyridin-4-one. $^1$H NMR (DMSO-d$_6$, 400 MHz) δ 8.31 (d, 2H), 7.66 (d, 1H), 7.46 (t, 2H), 7.22 (t, 1H), 7.1–7.15 (m, 5H), 6.82 (d, 1H); Rt=3.03 min (Conditions a), MS m/e: 303 (M−H)$^-$.

EXAMPLE 1207

3-(4-phenoxyphenyl)isoxazolo[4,5-c]pyridin-4-amine

A mixture of 3-(4-phenoxyphenyl)isoxazolo[4,5-c]pyridin-4(5H)-one (0.185 g, 0.6 mmol) and phosphorous oxylchloride (1 mL) was heated to 100° C. for 25 minutes. The mixture was concentrated then dissolved in dioxane (3 mL) and 35% aqueous ammonium hydroxide (3 mL). The mixture was heated to 120° C. in a sealed tube for 24 hours then the mixture was concentrated and the title compound was isolated by preparative RP-HPLC (Hypersil-HS C18, 8 μm, 100 Å, 25 cm; 5% acetonitrile—0.1M ammonium acetate isocratic for 5 minutes, then 5–100% acetonitrile—0.1M ammonium acetate over 30 min, 21 ml/min). The acetonitrile was removed in vacuo and the aqueous mixture was lyophilized: $^1$H NMR (DMSO-$d_6$, 400 MHz) δ 8.08 (d, 1H), 7.7 (d, 2H), 7.46 (t, 2H), 7.16–7.25 (m, 5H), 6.99 (d, 1H), 6.26 (bs, 2H); Rt=2.67 min (Conditions a), MS m/e: 304 (M+H)$^+$.

EXAMPLE 1208

7-[(1E)-3-(diethylamino)prop-1-enyl]-3-(4-phenoxyphenyl)isoxazolo[4,5-c]pyridin-4-amine

EXAMPLE 1208A 7-iodo-3-(4-phenoxyphenyl)isoxazolo[4,5-c]pyridin-4-amine 3-(4-Phenoxyphenyl)isoxazolo[4,5-c]pyridin-4-amine (0.11 g, 0.36 mmol) and N-iodosuccinimide (0.098 g, 0.43 mmol) in N,N-dimethylformamide (1.5 mL) was stirred at ambient temperature for 30 minutes. The mixture was applied to a silica gel column and eluted with dichloromethane/ethyl acetate (8:2) to provide the title compound (100 mg): $^1$H NMR (DMSO-$d_6$, 400 MHz) δ 8.26 (s, 1H), 7.71 (d, 2H), 7.46 (t, 2H), 7.15–7.25 (m, 5H), 6.45 (bs, 2H); $R_t$=3.78 min (Conditions a), MS m/e: 430 (M+H)$^+$ b)

EXAMPLE 1208B

7-[(1E)-3-(diethylamino)prop-1-enyl]-3-(4-phenoxyphenyl)isoxazolo[4,5-c]pyridin-4-amine 7-Iodo-3-(4-phenoxyphenyl)isoxazolo[4,5-c]pyridin-4-amine (0.100 g, 0.233 mmol) in 1,2-dimethoxyethane (4 mL) and water (2 mL) was reacted with an 2-[(E)-3,3-diethoxy-1-propenyl]-4,4,5,5-tetramethyl-1,3,2-dioxaborolane (0.09 g, 0.35 mmol), sodium carbonate (0.05 g, 0.47 mmol) and tetrakis triphenylphosphine palladium (0) (0.02 g, 0.014 mmol) at 90° C. for 18 hours. The solvent was removed in vacuo and the residue was dissolved in acetone/water 95:5 (10 mL) then p-toluene sulfonic acid was added. The mixture was stirred at ambient temperature for 18 hours then evaporated and the residue dissolved in 1,2-dichloroethane (4 mL). Diethylamine (100 mg) was added followed by sodium triacetoxyborohydride (100 mg). The mixture was stirred for 18 hours then the concentrated and by preparative RP-HPLC (Rainin C18, 8 mm, 100 Å, 25 cm; 20% acetonitrile—0.1M ammonium acetate isocratic for 5 minutes, then 20–80% acetonitrile—0.1M ammonium acetate over 30 min, 21 ml/min) followed by treatment with Silica-carbonate and lyophilization: $^1$H NMR (DMSO-$d_6$, 400 MHz) δ 8.08 (s, 1H), 7.7 (d, 2H), 7.46 (t, 2H), 7.16–7.25 (m, 5H), 6.6 (d, 1H), 6.49 (m, 1H), 6.33 (bs, 2H), 3.25 (d, 2H), 2.50 (q, 4H), 1.0 (t, 6H); Rt=2.90 min (Conditions a), MS m/e: 413 (M–H)$^-$.

EXAMPLE 1209

N-[4-(4-amino-7-cyanothieno[3,2-c]pyridin-3-yl)-2-methoxyphenyl]-1-methyl-1H-indole-2-carboxamide N-[4-(4-amino-7-iodothieno[3,2-c]pyridin-3-yl)-2-methoxyphenyl]-1-methyl-1H-indole-2-carboxamide (A-796259.0, 100 mg, 0.36 mmol), copper(I) cyanide (65 mg, 0.72 mmol), tetraethylammonium cyanide (28 mg, 0.18 mmol), Tris(dibenzylideneacetone)-dipalladium(0) (7 mg, 0.007 mmol), and 1,1'-bis(diphenylphosphino)ferrocene (16 mg, 0.029 mmol) were purged and heated to 110° C. in 1,4-dioxane (2 mL) for 16 hours. The mixture was evaporated in vacuo, diluted with dichloromethane/methanol (95:5, 50 mL), and washed with ammonium hydroxide (8% aqueous, 8 mL). The aqueous layer was washed with dichloromethane/methanol (95:5, 10 mL), and the combined organics were evaporated in vacuo, diluted with dimethylforamide (2.5 mL), and filtered. The precipitate was triturated in acetic acid (3 mL) and filtered to yield the title compound (20 mg, 25% yield): $^1$H NMR (DMSO, 400 MHz) δ 9.49 (s, 1H), 8.44 (s, 1H), 8.03 (d, 1H), 7.76 (s, 1H), 7.70 (d, 1H), 7.56 (d, 1H), 7.05–7.33 (m, 5H), 4.01 (s, 3H), 3.89 (s, 3H); RP-HPLC (Conditions i) $R_t$ 24.9 min. MS: 452.2 MH–.

EXAMPLE 1210

N-(4-{4-amino-7-[3-(4-hydroxypiperidin-1-yl)propyl]thieno[3,2-c]pyridin-3-yl}2-methoxyphenyl)-1-methyl-1H-indole-2-carboxamide N-(4-{4-Amino-7-[(1E)-3-(4-hydroxypiperidin-1-yl)prop-1-enyl]thieno[3,2-c]pyridin-3-yl}-2-methoxyphenyl)-1-methyl-1H-indole-2-carboxamide (130 mg, 0.23 mmol), ethanol (25 mL), and acetic acid (0.65 mL) were combined in a hydrogenation vessel, purged, and palladium hydroxide on carbon (45 mg, 50% weight dispersion in oil, 0.16 mmol) was added. 50 Psi of hydrogen was applied for 16 hours. The mixture was filtered and purified by RP-HPLC to yield the title compound (35 mg, 25% yield) after lyophilization: $^1$H NMR (DMSO, 400 MHz) δ 9.50 (s, 1H), 7.98 (d, 1H), 7.70–7.72 (m, 2H), 5.59 (d, 1H), 7.54 (s, 1H), 7.07–7.35 (m, 3H), 5.34 (bs, 2H), 4.58 (bs, 1H), 4.04 (s, 3H), 3.91 (s, 3H), 2.71 (t, 2H), 2.28 (t, 2H), 1.97 (t, 2H), 1.90 (s, 3H), 1.82 (t, 2H), 1.70 (m, 1H), 1.40 (q, 2H); RP-HPLC (Conditions i) $R_t$ 10.0 min. MS: 568.3 MH–.

EXAMPLE 1211

N-{4-[4-amino-7-(3-hydroxypropyl)thieno[3,2-c]pyridin-3-yl]-2-methoxyphenyl}-1-methyl-1H-indole-2-carboxamide N-(4-{4-Amino-7-[(1E)-3-hydroxyprop-1-enyl]thieno[3,2-c]pyridin-3-yl}-2-methoxyphenyl)-1-methyl-1H-indole-2-carboxamide (110 mg, 0.228 mmol), methanol (2 mL) and N,N-dimethylforamide (2 mL) was added sodium borohydride (26.9 mg, 0.684 mmol) under an atmosphere of nitrogen. Mixture stirred for 30 minutes at room temperature after which it was treated with 1M sodium carbonate (5 mL) and extracted with dichloromethane (3×5 mL). The organic layer was separated, dried over magnesium sulfate, and filtered, and the solvent was removed under reduced pressure. The product was purified via flash chromatography to furnish the title compound as a pale yellow powder (21.1 mg, 0.0434 mmol): LCMS (Thermoquest AQA single-quad MS, Genesis C18 column, 3 mm particle size, 33×4.6 mm; 70% 50 mM ammonium Acetate in Water to 95% Acetonitrile over 4.5 min, 0.8 mL/min): MH+=487 RT=3.23 minutes; $^1$H NMR (DMSO-$d_6$, 400 MHz) δ 9.51 (1H), 7.99 (1H), 7.70 (2H), 7.60 (1H), 7.55 (1H), 7.32–7.35 (2H), 7.21 (1H), 7.15 (1H), 7.07 (1H), 5.34 (2H), 4.04 (3H), 3.91 (3H), 3.47 (2H), 2.75 (2H), 1.83 (4H).

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

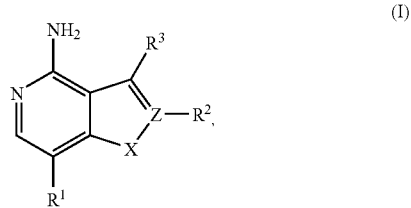

(I)

or a therapeutically acceptable salt thereof, wherein
X is selected from the group consisting of O and S;
Z is C;
$R^1$ is selected from the group consisting of $NR^aR^b$, $(NR^aR^b)$alkenyl, $(NR^aR^b)$alkyl, $(NR^aR^b)$alkynyl, $(NR^aR^b)$carbonyl, $(NR^aR^b)$carbonylalkenyl, $(NR^aR^b)$carbonylalkyl, and $(NR^aR^b)$carbonylalkynyl;
$R^2$ is selected from the group consisting of hydrogen and alkyl;
$R^3$ is aryl wherein the aryl is optionally substituted with one, two, or three substituents independently selected from the group consisting of alkoxy, alkyl, aryl, cyano, halo, haloalkoxy, haloalkyl, hydroxy, hydroxyalkyl, $LR^4$, and $NR^aR^b$; provided that at least two of the three substituents are other than $LR^4$;
L is selected from the group consisting of O, $(CH_2)_mC(O)NR^5$, $NR^5C(O)(CH_2)_m$, $NR^5SO_2$, $SO_2NR^5$, $(CH_2)_mN(R^5)C(O)N(R^6)(CH_2)_n$, and $(CH_2)_mN(R^5)C(S)N(R^6)(CH_2)_n$, wherein m and n are independently 0 or 1, and wherein each group is drawn with its right end attached to $R^4$;
$R^4$ is selected from the group consisting of aryl and arylalkyl;
$R^5$ and $R^6$ are independently selected from the group consisting of hydrogen and alkyl;
$R^a$ and $R^b$ are independently selected from the group consisting of hydrogen, alkyl, alkoxyalkyl, alkoxycarbonyl, alkoxycarbonylalkyl, alkyl, alkylcarbonyl, alkylsulfanylalkyl, alkylsulfonyl, aryl, arylalkoxycarbonyl, arylalkoxycarbonylalkyl, arylalkyl, arylcarbonyl, and arylsulfonyl, wherein the aryl and the aryl part of the arylalkoxycarbonyl, the arylalkoxycarbonylalkyl, the arylalkyl, the arylcarbonyl, and the arylsulfonyl can be further optionally substituted with one, two, three, four, or five substituents independently selected from the group consisting of alkenyl, alkoxy, alkoxycarbonyl, alkyl, alkylcarbonyl, aryl, arylalkyl, halo, haloalkoxy, haloalkyl, hydroxy, nitro, $NR^cR^d$, $(NR^cR^d)$alkyl, $(NR^cR^d)$alkylcarbonyl, $(NR^cR^d)$carbonyl, and $(NR^cR^d)$carbonylalkyl, wherein the aryl and the aryl part of the arylalkyl can be substituted with one, two, three, four, or five substituents independently selected from the group consisting of alkoxy, alkyl, cyano, halo, haloalkoxy, haloalkyl, nitro, and oxo;
$R^c$ and $R^d$ are independently selected from the group consisting of hydrogen, alkoxy, alkyl, aryl, carboxyalkyl, haloalkyl, hydroxyalkoxyalkyl, hydroxyalkyl, and $(NR^eR^f)$alkyl, wherein the aryl can be optionally substituted with one, two, three, four, or five substituents independently selected from the group consisting of alkenyl, alkoxy, alkyl, halo, haloalkoxy, haloalkyl, hydroxy, and nitro; and
$R^e$ and $R^f$ are independently selected from the group consisting of hydrogen and alkyl.

2. The compound of claim 1 wherein $R^3$ is aryl, wherein the aryl is substituted with $LR^4$ and optionally with one or two additional substituents independently selected from the group consisting of alkoxy, alkyl, aryl, cyano, halo, haloalkoxy, haloalkyl, hydroxyalkyl, and $NR^aR^b$.

3. The compound of claim 2 wherein L is O.

4. The compound of claim 2 wherein L is selected from the group consisting of $NR^5C(O)(CH_2)_m$ and $NR^5SO_2$.

5. The compound of claim 4 wherein $R^1$ is $(NR^aR^b)$alkenyl.

6. The compound of claim 2 wherein L is $(CH_2)_mN(R^5)C(O)N(R^6)(CH_2)_n$.

7. The compound of claim 6 wherein $R^1$ is $(NR^aR^b)$alkynyl.

8. The compound of claim 6 wherein $R^1$ is $(NR^aR^b)$carbonylalkenyl.

9. A compound selected from the group consisting of
N-(4-{4-amino-7-[3-(diethylamino)-1-propynyl]thieno[3,2-c]pyridin-3-yl}phenyl)-N'-(3-methylphenyl)urea; and
N-(4-{4-amino-7-[3-(methylamino)-1-propynyl]thieno[3,2-c]pyridin-3-yl}phenyl)-N'-(3-methylphenyl)urea.

* * * * *